US007642264B2

(12) United States Patent
Gatti McArthur et al.

(10) Patent No.: US 7,642,264 B2
(45) Date of Patent: Jan. 5, 2010

(54) PHENYL-SUBSTITUTED PYRIMIDINE DERIVATIVES AS MGLUR ANTAGONISTS

(75) Inventors: Silvia Gatti McArthur, Basel (CH); Erwin Goetschi, Reinach (CH); Juergen Wichmann, Steinen (DE); Thomas Johannes Woltering, Grenzach-Wyhlen (DE)

(73) Assignee: Hoffman-La Roche Inc., Nutley, NJ (US)

( * ) Notice: Subject to any disclaimer, the term of this patent is extended or adjusted under 35 U.S.C. 154(b) by 132 days.

(21) Appl. No.: 11/726,575

(22) Filed: Mar. 22, 2007

(65) Prior Publication Data

US 2007/0232583 A1 Oct. 4, 2007

(30) Foreign Application Priority Data

Mar. 29, 2006 (EP) .................................. 06111939

(51) Int. Cl.
*A01N 43/54* (2006.01)

(52) U.S. Cl. .................... 514/256; 544/242; 546/268.1; 548/131; 548/146; 548/262.2; 548/335.1; 548/373.1; 548/579; 549/59

(58) Field of Classification Search ................. 514/256; 544/242; 546/268.1; 548/131, 146, 262.2, 548/335.1, 373.1, 579; 549/59
See application file for complete search history.

(56) References Cited

U.S. PATENT DOCUMENTS

2003/0055085 A1 3/2003 Wagenen et al.

FOREIGN PATENT DOCUMENTS

| | | | |
|---|---|---|---|
| JP | 54147921 | * | 11/1979 |
| JP | 03169802 | * | 1/1991 |
| JP | 09169741 | * | 6/1997 |
| WO | WO 03/027100 | * | 4/2003 |
| WO | WO 2005/044797 A1 | | 5/2005 |

OTHER PUBLICATIONS

Jordan, V. C. Nature Reviews: Drug Discovery, 2, 2003, p. 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
D'Onofrio et al., J. Neurochem. Mar. 2003, vol. 84(6) pp. 1288-1295.
Narsaiah et al., Org. Prep. Proceed. Int. 1993, vol. 25(1) pp. 116-117.
Popic, et al., Synthesis 1991, vol. 3, pp. 195-198.
Franek, W., Monatsh. Chem. 1996, vol. 127(8-9) pp. 895-907.
Krohn et al., Angew. Chem. Int. Ed. Engl. 1993 vol. 32(8) pp. 1151-1152.
Snider et al., J. Org. Chem. 1993, vol. 58(11) pp. 3185-3187.
Joshi et al., J. Fluorine Chem. 1986 vol. 32(2) pp. 229-231.
Adkins et al., Org. Synth. Coll. 1955, vol. III, pp. 387-390.
Bruno et al., J. Am. Chem. Soc. 1953, vol. 75, pp. 626-628 & 4109-4110.
Rehberg et al., J. Am. Chem. Soc. 1941, vol. 63, p. 2785-2789.
Stetter et al., Chem. Ber. 1970, vol. 103, pp. 1088-1094.
Basu et al., J. Indian Chem. Soc. 1930, vol. 7, pp. 815-824.
Negishi et al., Tetr. Lett. 1983, vol. 24, pp. 5181-5184.
Mikolajczyk et al. J. Org. Chem. 1998, vol. 63 (24) pp. 8894-8897.
Alvarez Ibarra, C., J. Chem. Soc. Perkin T. vol. 2, 1989 pp. 503-508.
Abadi et al., Farmaco, 1999, vol. 54(4) pp. 195-201.
Klapars et al., J. Am. Chem. Soc. 2002, vol. 124(50) pp. 14844-14845.
Kronhnke, Fritz, Synthesis, pp. 1-24 (1976), XP002438390.
T. Ross Kelly, Hshiou-Ting Liu, Journal of the American Chemical Society, vol. 107, pp. 4998-4999 (1985), XP002438391.
Wenkert, et al., Journal of Organic Chemistry, vol. 50, pp. 1125-1126 (1985), XP002438392.
Funabiki, K., et al., Journal of the Chemical Society Perkin Transactions I, pp. 2578-2582 (2001), XP002438393.
Bagley, M.C., et al., Synlett 2003 Germany, No. 2, pp. 259-261 (2003), XP002438394.
Spivey Alan C., et al., Organic & Biomolecular Chemistry, vol. 1, No. 10, pp. 1638-1640 (2003), XP002438395.

* cited by examiner

*Primary Examiner*—Douglas M Willis
(74) *Attorney, Agent, or Firm*—George W. Johnston; Patricia S. Rocha-Tramaloni; Kimberly J. Prior

(57) ABSTRACT

The present invention relates to compounds of formula (Ia), a process for the manufacture thereof, pharmaceutical compositions containing them, and their use for treating CNS disorders:

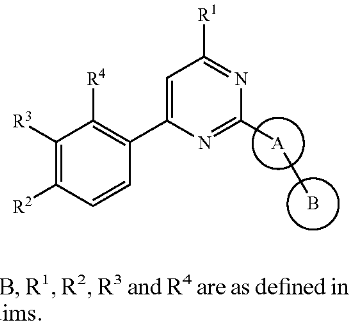

wherein A, B, $R^1$, $R^2$, $R^3$ and $R^4$ are as defined in the description and claims.

39 Claims, No Drawings

PHENYL-SUBSTITUTED PYRIMIDINE DERIVATIVES AS MGLUR ANTAGONISTS

PRIORITY TO RELATED APPLICATION(S)

This application claims the benefit of European Patent Application No. 06111939.2, filed Mar. 29, 2006, which is hereby incorporated by reference in its entirety.

BACKGROUND OF THE INVENTION

In the central nervous system (CNS) the transmission of stimuli takes place by the interaction of a neurotransmitter, which is sent out by a neuron, with a neuroreceptor.

L-glutamic acid, the most commonly occurring neurotransmitter in the CNS, plays a critical role in a large number of physiological processes. The glutamate-dependent stimulus receptors are divided into two main groups. The first main group forms ligand-controlled ion channels. The metabotropic glutamate receptors (mGluR) form the second main group and, furthermore, belong to the family of G-protein-coupled receptors.

At present, eight different members of these mGluR are known and of these some even have sub-types. On the basis of structural parameters, the different influences on the synthesis of secondary metabolites and the different affinity to low-molecular weight chemical compounds, these eight receptors can be sub-divided into three sub-groups: mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the group II can be used for the treatment or prevention of acute and/or chronic neurological disorders such as psychosis, schizophrenia, Alzheimer's disease, cognitive disorders and memory deficits. Other treatable indications in this connection are restricted brain function caused by bypass operations or transplants, poor blood supply to the brain, spinal cord injuries, head injuries, hypoxia caused by pregnancy, cardiac arrest and hypoglycemia. Further treatable indications are chronic and acute pain, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia, depressions, colon cancer, sleep disorders, disorders of circadian rhythms and glioma since mGluR2 antagonists have been found to reduce cell proliferation in human glioma cells (J. Neurochem. March 2003, 84(6): 1288-95).

SUMMARY OF THE INVENTION

The present invention provides compounds of formula (I), a process for the manufacture thereof, pharmaceutical compositions containing them, and methods for the treatment of CNS disorders.

In particular, the present invention provides compounds of general formula (I)

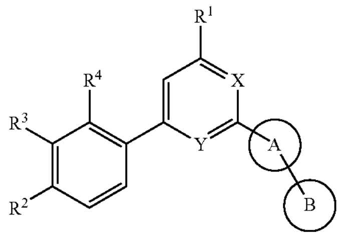

wherein either one of X or Y is N and the other is CH, or both X and Y are N;

A is aryl or 5 or 6 membered heteroaryl each of which is optionally substituted by $C_{1-6}$-alkyl;

B is H, cyano, an optionally substituted aryl, or an optionally substituted 5 or 6 membered heteroaryl, wherein the substituents are selected from the group consisting of:
- halo,
- nitro,
- $C_{1-6}$-alkyl optionally substituted by hydroxy,
- $NR^aR^b$, wherein $R^a$ and $R^b$ are independently H, $C_{1-6}$-alkyl or —(CO)—$C_{1-6}$-alkyl,
- S—$C_{1-6}$-alkyl,
- $(SO_2)$—OH,
- $(SO_2)$—$C_{1-6}$-alkyl,
- $(SO_2)$—$NR^cR^d$, wherein $R^c$ and $R^d$ are independently:
  - H,
  - $C_{1-6}$-alkyl optionally substituted by hydroxy,
  - $C_{1-6}$-haloalkyl, or
  - $C_{1-6}$-alkoxy,
- $(CO)C_{1-6}$-alkyl optionally substituted by $C_{1-6}$-alkoxy,
- $(CH_2CH_2O)_nCHR^e$, wherein $R^e$ is H or $CH_2OH$ and n is 1, 2, 3, 4, 5, 6, 7, 8, 9 or 10,
- $(CH_2)_m$-aryl, wherein m is 1 or 2 and the aryl is optionally substituted by halo or $C_{1-6}$-alkoxy,
- $(CH_2)_p$—$C_{3-6}$-cycloalkyl, wherein p is 0 or 1,
- 5 or 6-membered heterocycloalkyl,
- $(SO_2)$—$NR^fR^g$, wherein $R^f$ and $R^g$ together with the nitrogen atom to which they are attached form a 4, 5 or 6 membered heterocycloalkyl ring optionally containing a further heteroatom selected from nitrogen, oxygen, sulphur and an $SO_2$ group, wherein said 4, 5 or 6 membered heterocycloalkyl ring is optionally substituted by a substituent selected from the group consisting of hydroxy, $C_{1-6}$-alkyl, $C_{1-6}$-alkoxy which is optionally substituted by hydroxy, and 5 or 6 membered heteroaryloxy,
- $NHSO_2$—$C_{1-6}$-alkyl,
- $NHSO_2$—$NR^hR^i$ wherein $R^h$ and $R^i$ are independently H, $C_{1-6}$-alkyl, —(CO)O—$C_{1-6}$-alkyl, or $R^h$ and $R^i$ together with the nitrogen atom to which they are attached form a 4, 5 or 6 membered heterocycloalkyl ring optionally containing a further heteroatom selected from nitrogen, oxygen and sulphur, wherein said 4, 5 or 6 membered heterocycloalkyl ring is optionally substituted by $C_{1-6}$-alkyl, $R^1$ is H, halogen, $C_{1-6}$-alkyl optionally substituted by hydroxy, $C_{1-6}$-alkoxy, $C_{1-6}$-haloalkyl, or $C_{3-6}$-cycloalkyl;

$R^2$ is H, cyano, halogen, $C_{1-6}$-haloalkyl, $C_{1-6}$-alkoxy, $C_{1-6}$-haloalkoxy, $C_{1-6}$-alkyl or $C_{3-6}$-cycloalkyl;

$R^3$ is halogen, H, $C_{1-6}$-alkoxy, $C_{1-6}$-haloalkyl, $C_{1-6}$-alkyl, $C_{3-6}$-cycloalkyl, $C_{1-6}$-haloalkoxy, or is $NR^jR^k$ wherein $R^j$ and $R^k$ are independently selected from the group consisting of:

H, $C_{3-8}$-cycloalkyl, aryl, heteroaryl having from 5 to 12 ring atoms and $C_{1-6}$-alkyl which optionally substituted by one or more substituent(s) selected from the group consisting of halogen, hydroxy, $C_{3-8}$-cycloalkyl, aryl, heteroaryl having from 5 to 12 ring atoms, and —$NR^l R^m$, wherein $R^1$ and $R^m$ are independently selected from the group consisting of H and $C_{1-6}$-alkyl;

or $R^l$ and $R^m$ can, together with the nitrogen atom to which they are attached, form an optionally substituted heterocyclic group comprising 5 to 12 ring atoms optionally containing a further heteroatom selected from nitrogen, oxygen and sulphur, wherein said heterocyclic group is optionally substituted by one, two, three, four or five substituents selected from the group consisting of halogen, hydroxy, $C_{1-6}$-alkyl and $C_{1-6}$-haloalkyl;

or $R^2$ and $R^3$ can together form a dioxo bridge;

$R^4$ is H or halo;

and pharmaceutically acceptable salts thereof.

The compounds of formula (I) can also be used in form of their prodrugs. Examples are esters, N-oxides, phosphate esters, glycoamide esters, glyceride conjugates and the like. The prodrugs may add to the value of the present compounds advantages in absorption, pharmacokinetics in distribution and transport to the brain.

Compounds of formula I are metabotropic glutamate receptor antagonists. Compounds of formula I are distinguished by valuable therapeutic properties.

DETAILED DESCRIPTION OF THE INVENTION

Unless otherwise stated, the following terms used in the present description have the definitions given in the following. It must be noted that, as used in the specification and the appended claims, the singular forms "a", "an," and "the" include plural forms unless the context clearly dictates otherwise.

The term "alkyl" denotes straight-chain or branched saturated hydrocarbon residues with 1 to 6 carbon atoms ($C_{1-6}$-alkyl), preferably with 1 to 4 carbon atoms, such as methyl, ethyl, n-propyl, i-propyl, i-butyl, t-butyl, as well as those groups which are illustrated with the exemplified compounds of the invention hereinafter.

The term "$C_{1-6}$-haloalkyl" denotes a $C_{1-6}$-alkyl group as defined hereinabove, which is substituted by one or more halogen atom(s), in particular Cl, F or I, preferably three Cl or two or three F, i.e. $CCl_3$, $CHF_2$ and $CF_3$ as well as those groups which are specifically illustrated with the exemplified compounds of the invention hereinafter.

The term "$C_{1-6}$-alkoxy" denotes a $C_{1-6}$-alkyl residue as defined hereinabove bound via an oxygen atom. Examples of "$C_{1-6}$-alkoxy" residues include methoxy, ethoxy, isopropoxy, as well as those groups which are illustrated with the exemplified compounds of the invention hereinafter.

The term "$C_{1-6}$-haloalkoxy" denotes a $C_{1-6}$-alkoxy group as defined hereinabove, which is substituted by one or more halogen atom(s), in particular Cl, F or I, preferably three Cl or two or three F, i.e. $OCHF_2$ and $OCF_3$, $OCH_2CHF_2$, $OCH_2CF_3$ as well as those groups which are specifically illustrated with the exemplified compounds of the invention hereinafter.

The term "aryl" denotes a monovalent cyclic aromatic hydrocarbon radical having from 6 to 10 ring atoms, for example phenyl, naphthyl, biphenyl or indanyl.

The terms "heteroaryl" or "5 or 6-membered heteroaryl" or "heteroaryl having from 5 to 12 ring atoms" refer to a cyclic aromatic radical having 5 to 6 or 5 to 12 ring atoms which contains one or more, in particular, one, two, three, four or five heteroatoms selected from nitrogen, oxygen and sulphur. Examples of such heteroaryl groups include, but are not limited to, thiophenyl, imidazolyl, oxadiazolyl, pyrrolyl, pyrazolyl, pyridinyl, pyrazinyl, pyrimidinyl and pyridazinyl, and in particular, [1,2,4]oxadiazolyl, pyridin-2-yl, pyridin-3-yl, pyridine-4-yl, pyrimidin-5-yl, thiazol-2-yl and thiophen-2-yl as well as those groups which are illustrated with the exemplified compounds of the invention hereinafter.

The term "heteroaryloxy" denotes a heteroaryl group, including 5 or 6-membered heteroaryl or heteroaryl having from 5 to 12 ring atoms as defined hereinabove, which is connected via an oxygen atom.

The term "halogen" or "halo" embraces fluorine (F), chlorine (Cl), bromine (Br) and iodine (I).

The term "$C_{3-6}$-cycloalkyl" or "$C_{5-8}$-cycloalkyl" means a cycloalkyl group containing 3 to 6 or 5 to 8 carbon atoms, such as cyclopropyl, cyclobutyl, cyclopentyl or cyclohexyl and those groups which are illustrated with the exemplified compounds of the invention hereinafter.

The term "heterocyclic group" denotes a non aromatic ring system having 5 or 6 or 5 to 12 ring members, containing from 1 to 3 heteroatoms selected from the group consisting of N, O and S.

The term "5 or 6-membered or 5 to 12-membered heterocycloalkyl" denotes a saturated heterocyclic ring having 5 or 6 or 5 to 12 ring members comprising at least two carbon atoms as ring members and 1, 2 or 3 additional heteroatom(s) ring members selected from N, O and S, the remaining ring members being carbon atoms. Examples of 5 to 12 heterocycloalkyl rings include, but are not limited to, 1H-tetrazole; 2H-tetrazole; 1,2,3- and 1,24-triazole; imidazole; pyrrole; 1,2,3-, 1,3,4- or 1,2,5-thiadiazine; 1,4-oxazine; 1,2- or 1,4-thiazine; 4-morpholinyl; 1-pyrrolidinyl; 1-piperazinyl, preferably 4-morpholinyl; 1-pyrrolidinyl or 1-piperazinyl as well as those groups which are illustrated with the exemplified compounds of the invention hereinafter. Substituents for such 5 or 6 membered heterocyclic ring include but are not limited to halo, amino, nitro, cyano, hydroxy, $C_{1-6}$-alkyl optionally substituted by hydroxy, $C_{1-6}$-alkoxy, $C_{1-6}$-alkenyl, $C_{3-8}$-cycloalkyl, or $CF_3$, and preferably $C_{1-6}$-alkyl or $CF_3$ as well as those groups which are illustrated with the exemplified compounds of the invention hereinafter.

The term "dioxo bridge" denotes a group having the following formula:

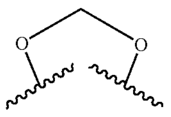

The term "optionally substituted" means that the chemical group to which it refers can be substituted by one or more of the substituents recited in this connection, for example by one, two, three, four, five, six, seven, eight, nine or ten substituents, depending on the valence and available positions of said chemical group.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable addition salt" refers to any salt derived from an inorganic or organic acid or base.

"Therapeutically effective amount" means an amount that is effective to prevent, alleviate or ameliorate symptoms of disease or prolong the survival of the subject being treated.

In all embodiments of the compounds according to the invention hereinafter and independently from each other and from the other groups, where A is aryl it is preferably phenyl optionally substituted by $C_{1-6}$-alkyl.

In all embodiments of the compounds according to the invention hereinafter and independently from each other and from the other groups, where A is phenyl optionally substituted by phenyl, the phenyl is preferably substituted by B on position metha or para.

In all embodiments of the compounds according to the invention hereinafter and independently from each other and from the other groups, where A is 5 or 6 membered heteroaryl it is preferably selected from the group consisting of imidazolyl, [1,2,4]oxadiazolyl], pyrrolyl, 1H-pyrazolyl, pyridinyl, [1,2,4]triazolyl, thiazolyl, pyrimidinyl and thiophenyl, each of which is optionally substituted by $C_{1-6}$-alkyl.

In all embodiments of the compounds according to the invention hereinafter and independently from each other and from the other groups, where A is 5 or 6 membered heteroaryl, the 5 or 6 membered heteroaryl is preferably substituted on position 3 or 4.

In all embodiments of the compounds according to the invention hereinafter and independently from each other and from the other groups, where B is an optionally substituted aryl it is preferably phenyl.

In all embodiments of the compounds according to the invention hereinafter and independently from each other and from the other groups, where B is an optionally substituted aryl, the substitution is preferably on position metha or para.

In all embodiments of the compounds according to the invention hereinafter and independently from each other and from the other groups, where B is an optionally substituted aryl, the substituents are preferably selected from the group consisting of:

halo, nitro, $C_{1-6}$-alkyl optionally substituted by hydroxy, $NR^aR^b$, wherein $R^a$ and $R^b$ are independently H or —(CO)—$C_{1-6}$-alkyl, S—$C_{1-6}$-alkyl, ($SO_2$)—OH, ($SO_2$)—$C_{1-6}$-alkyl, ($SO_2$)—$NR^cR^d$, wherein $R^c$ and $R^d$ are independently:

H, $C_{1-6}$-alkyl optionally substituted by hydroxy, $C_{1-6}$-haloalkyl, or $C_{1-6}$-alkoxy, (CO)$C_{1-6}$-alkyl optionally substituted by $C_{1-6}$-alkoxy, $(CH_2CH_2O)_nCHR^e$, wherein $R^e$ is H or $CH_2OH$ and n is 1, 2, 3, 4, 5, 6, 7, 8, 9 or 10, $(CH_2)_m$-aryl, wherein m is 1 or 2 and the aryl (e.g. phenyl) is optionally substituted by halo or $C_{1-6}$-alkoxy, $(CH_2)_p$—$C_{3-6}$-cycloalkyl, wherein p is 0 or 1, 5 or 6-membered heterocycloalkyl (e.g., ($SO_2$)—$NR^fR^g$, wherein $R^f$ and $R^g$ together with the nitrogen atom to which they are attached form a 4, 5 or 6 membered heterocycloalkyl ring optionally containing a further heteroatom selected from nitrogen, oxygen, sulphur and an $SO_2$ group, wherein said 4, 5 or 6 membered heterocycloalkyl ring is optionally substituted by a substituent selected from the group consisting of:

hydroxy, $C_{1-6}$-alkyl, $C_{1-6}$-alkoxy which is optionally substituted by hydroxy, and 5 or 6 membered heteroaryloxy (e.g. pyrimidinyloxy), $NHSO_2$—$C_{1-6}$-alkyl, and $NHSO_2$—$NR^hR^i$, wherein $R^h$ and $R^i$ are independently H, $C_{1-6}$-alkyl or —(CO)O—$C_{1-6}$-alkyl.

In all embodiments of the compounds according to the invention hereinafter and independently from each other and from the other groups, where B is an optionally substituted 5 or 6 membered heteroaryl, it is preferably selected from the group consisting of pyridinyl, pyrimidinyl, thiophenyl, thiazolyl and imidazolyl.

In all embodiments of the compounds according to the invention hereinafter and independently from each other and from the other groups, where B is an optionally substituted 5 or 6 membered heteroaryl the substituents are preferably selected from the group consisting of:

$C_{1-6}$-alkyl, $NR^aR^b$, wherein $R^a$ and $R^b$ are independently H or —(CO)—$C_{1-6}$-alkyl, ($SO_2$)—$NR^cR^d$, wherein $R^c$ and $R^d$ are independently:

H, $C_{1-6}$-alkyl optionally substituted by hydroxy, or (CO)$C_{1-6}$-alkyl optionally substituted by $C_{1-6}$-alkoxy, and $NR^hSO_2$—$NR^iR^j$, wherein $R^h$ is H and $R^i$ and $R^j$ are independently H or —(CO)O—$C_{1-6}$-alkyl.

In all embodiments of the compounds according to the invention hereinafter and independently from each other and from the other groups, $R^1$ is preferably $C_{1-6}$-alkyl or $C_{1-6}$-haloalkyl and still preferably methyl, ethyl, i-propyl), $CF_3$ or $CHF_2$.

In all embodiments of the compounds according to the invention hereinafter and independently from each other and from the other groups, $R^2$ is preferably halogen or $C_{1-6}$-haloalkyl and still preferably Cl, F or $CF_3$.

In all embodiments of the compounds according to the invention hereinafter and independently from each other and from the other groups, $R^3$ is H, halogen, $C_{1-6}$-alkoxy, $C_{1-6}$-haloalkyl, $C_{1-6}$-alkyl and $C_{1-6}$-haloalkoxy and still preferably, F, Cl, methoxy, ethoxy, $CF_3$, methyl, and trifluoroethoxy.

In all embodiments of the compounds according to the invention herein and independently from each other and from the other groups $R^4$ is H.

In a particular embodiment of the compounds of the invention, the compounds of formula (I) are those compounds wherein:

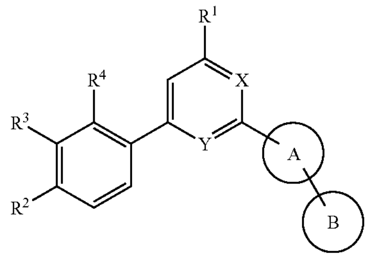

wherein either one of X or Y is N and the other is CH, or both X and Y are N;

A is aryl or 5 or 6 membered heteroaryl each of which is optionally substituted by $C_{1-6}$-alkyl;

B is H or cyano;

$R^1$ is halogen, $C_{1-6}$-alkyl optionally substituted by hydroxy, $C_{1-6}$-alkoxy, $C_{1-6}$-haloalkyl, or $C_{3-6}$-cycloalkyl;

$R^2$ is halogen, $C_{1-6}$-haloalkyl, $C_{1-6}$-alkoxy, $C_{1-6}$-haloalkoxy, $C_{1-6}$-alkyl or $C_{3-6}$-cycloalkyl;

$R^3$ is halogen, H, $C_{1-6}$-alkoxy, $C_{1-6}$-haloalkyl, $C_{1-6}$-alkyl, $C_{3-6}$-cycloalkyl, $C_{1-6}$-haloalkoxy, or is $NR^jR^k$ wherein $R^j$ and $R^k$ are independently selected from the group consisting of:

H, $C_{3-8}$-cycloalkyl, aryl, heteroaryl having from 5 to 12 ring atoms, and $C_{1-6}$-alkyl each of which is optionally substituted by one or more substituent(s) selected from the group consisting of halogen, hydroxy, $C_{3-8}$-cycloalkyl, aryl, heteroaryl having from 5 to 12 ring atoms, and —$NR^lR^m$, wherein $R^l$ and $R^m$ are independently selected from the group consisting of H and $C_{1-6}$-alkyl;

or $R^l$ and $R^m$ can, together with the nitrogen atom to which they are attached, form an optionally substituted heterocyclic group comprising 5 to 12 ring atoms optionally containing a further heteroatom selected from nitrogen, oxygen and sulphur, wherein said heteroaryl group is optionally substituted by one, two, three, four or five substituents selected from the group consisting of halogen, hydroxy, $C_{1-6}$-alkyl and $C_{1-6}$-haloalkyl;

or $R^2$ and $R^3$ can together form a dioxo bridge;

and pharmaceutically acceptable salts thereof.

In a particular embodiment of the compounds of the invention, the compounds of formula (I) are those compounds wherein:

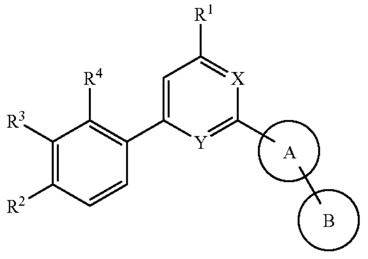

wherein either one of X or Y is N and the other is CH, or both X and Y are N;

A is aryl or 5 or 6 membered heteroaryl each of which is optionally substituted by $C_{1-6}$-alkyl;

B is an optionally substituted aryl or an optionally substituted 5 or 6 membered heteroaryl, wherein the substituents are selected from the group consisting of:

halo, nitro, $C_{1-6}$-alkyl optionally substituted by hydroxy, $NR^aR^b$, wherein $R^a$ and $R^b$ are independently H or —(CO)—$C_{1-6}$-alkyl, S—$C_{1-6}$-alkyl, $(SO_2)$—OH, $(SO_2)$—$C_{1-6}$-alkyl, $(SO_2)$—$NR^cR^d$, wherein $R^c$ and $R^d$ are independently:

H, $C_{1-6}$-alkyl optionally substituted by hydroxy, $C_{1-6}$-haloalkyl, or $C_{1-6}$-alkoxy, $(CO)C_{1-6}$-alkyl optionally substituted by $C_{1-6}$-alkoxy, $(CH_2CH_2O)_nCHR^e$, wherein $R^e$ is H or $CH_2OH$ and n is 1, 2, 3, 4, 5, 6, 7, 8, 9 or 10, $(CH_2)_m$-aryl, wherein m is 1 or 2 and the aryl is optionally substituted by halo or $C_{1-6}$-alkoxy, $(CH_2)_p$—$C_{3-6}$-cycloalkyl, wherein p is 0 or 1, 5 or 6-membered heterocycloalkyl, $(SO_2)$—$NR^fR^g$, wherein $R^f$ and $R^g$ together with the nitrogen atom to which they are attached form a 4, 5 or 6 membered heterocycloalkyl ring optionally containing a further heteroatom selected from nitrogen, oxygen, sulphur and an $SO_2$ group, wherein said 4, 5 or 6 membered heterocycloalkyl ring is optionally substituted by a substituent selected from the group consisting of hydroxy, $C_{1-6}$-alkyl, $C_{1-6}$-alkoxy which is optionally substituted by hydroxy, and 5 or 6 membered heteroaryloxy, $NHSO_2$—$C_{1-6}$-alkyl, and $NHSO_2$—$NR^hR^i$ wherein $R^h$ and $R^i$ are independently H, $C_{1-6}$-alkyl, —(CO)O—$C_{1-6}$-alkyl, or $R^h$ and $R^i$ together with the nitrogen atom to which they are attached form a 4, 5 or 6 membered heterocycloalkyl ring optionally containing a further heteroatom selected from nitrogen, oxygen or sulphur, wherein said 4, 5 or 6 membered heterocycloalkyl ring is optionally substituted by $C_{1-6}$-alkyl;

$R^1$ is halogen, $C_{1-6}$-alkyl optionally substituted by hydroxy, $C_{1-6}$-alkoxy, $C_{1-6}$-haloalkyl, or $C_{3-6}$-cycloalkyl;

$R^2$ is halogen, $C_{1-6}$-haloalkyl, $C_{1-6}$-alkoxy, $C_{1-6}$-haloalkoxy, $C_{1-6}$-alkyl or $C_{3-6}$-cycloalkyl;

$R^3$ is halogen, H, $C_{1-6}$-alkoxy, $C_{1-6}$-haloalkyl, $C_{1-6}$-alkyl, $C_{3-6}$-cycloalkyl, $C_{1-6}$-haloalkoxy, or is $NR^jR^k$ wherein $R^j$ and $R^k$ are independently selected from the group consisting of: H, $C_{3-8}$-cycloalkyl, aryl, heteroaryl having from 5 to 12 ring atoms, and $C_{1-6}$-alkyl each of which is optionally substituted by one or more substituent(s) selected from the group consisting of halogen, hydroxy, $C_{3-8}$-cycloalkyl, aryl, heteroaryl having from 5 to 12 ring atoms, and —$NR^lR^m$, wherein $R^l$ and $R^m$ are independently selected from the group consisting of H and $C_{1-6}$-alkyl;

or $R^l$ and $R^m$ can, together with the nitrogen atom to which they are attached, form an optionally substituted heterocyclic group comprising 5 to 12 ring atoms optionally containing a further heteroatom selected from nitrogen, oxygen and sulphur, wherein said heteroaryl group is optionally substituted by one, two, three, four or five substituents selected from the group consisting of halogen, hydroxy, $C_{1-6}$-alkyl and $C_{1-6}$-haloalkyl;

or $R^2$ and $R^3$ can together form a dioxo bridge;

and pharmaceutically acceptable salts thereof.

In a particular embodiment of the compounds of the invention, the compounds of formula (I) are those compounds wherein:

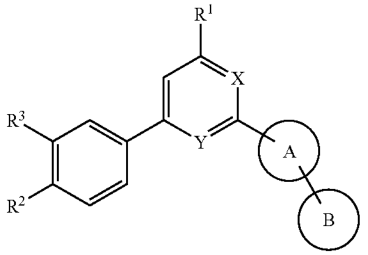

wherein either one of X or Y is N and the other is CH, or both X and Y are N;

A is aryl or 5 or 6 membered heteroaryl;

B is H or an optionally substituted aryl or an optionally substituted 5 or 6 membered heteroaryl, wherein the substituents are selected from the group consisting of:

$C_{1-6}$-alkyl, $NR^aR^b$ wherein $R^a$ and $R^b$ are independently H, $C_{1-6}$-alkyl, or —(CO)—$C_{1-6}$-alkyl, $(SO_2)$—$NR^cR^d$ wherein $R^c$ and $R^d$ are independently H, $C_{1-6}$-alkyl, or —(CO)—$C_{1-6}$-alkyl;

$R^1$ is H, halogen, $C_{1-6}$-alkyl, $C_{1-6}$-alkoxy, $C_{1-6}$-haloalkyl, or $C_{3-6}$-cycloalkyl;

$R^2$ is H, halogen, $C_{1-6}$-haloalkyl, $C_{1-6}$-alkyl or $C_{3-6}$-cycloalkyl;

$R^3$ is halogen, H, $C_{1-6}$-alkoxy, $C_{1-6}$-haloalkyl, $C_{1-6}$-alkyl, $C_{3-6}$-cycloalkyl, $C_{1-6}$-haloalkoxy, or is $NR^eR^f$ wherein $R^e$ and $R^f$ are independently selected from the group consisting of:

H, $C_{3-8}$-cycloalkyl, aryl, heteroaryl having from 5 to 12 ring atoms, and $C_{1-6}$-alkyl each of which is optionally substituted by one or more substituent(s) selected from the group consisting of halogen, hydroxy, $C_{3-8}$-cycloalkyl, aryl, heteroaryl having from 5 to 12 ring atoms and —$NR^gR^h$, wherein $R^h$ and $R^h$ are independently selected from the group consisting of H and $C_{1-6}$-alkyl;

or $R^b$ and $R^c$ can, together with the nitrogen atom to which they are attached, form an optionally substituted heterocyclic group comprising 5 to 12 ring atoms, wherein the substituents are selected from the group consisting of halogen, hydroxy, $C_{1-6}$-alkyl and $C_{1-6}$-haloalkyl;

and pharmaceutically acceptable salts thereof.

Also encompassed by the compounds of formula (I) according to the invention are the compounds of formula (I-a):

(Ia)

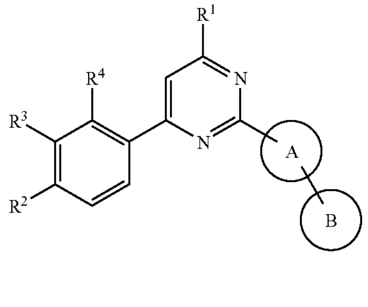

wherein A, B, $R^1$, $R^2$, $R^3$ and $R^4$ are as defined for formula (I) hereinabove.

In a certain embodiment of the invention, the compounds of formula (Ia) are those compounds wherein:

A is aryl or 5 or 6 membered heteroaryl, each of which is optionally substituted by $C_{1-6}$-alkyl;

B is H or cyano;

$R^1$ is $C_{1-6}$-alkyl or $C_{1-6}$-haloalkyl;

$R^2$ is halogen or $C_{1-6}$-haloalkyl;

$R^3$ is H, halogen, $C_{1-6}$-alkoxy, $C_{1-6}$-haloalkyl, $C_{1-6}$-alkyl or $C_{1-6}$-haloalkoxy;

$R^4$ is H or halo;

and pharmaceutically acceptable salts thereof.

In a certain embodiment of the invention, the compounds of formula (Ia) are these compounds wherein:

A is aryl or 5 or 6 membered heteroaryl;

B is an optionally substituted aryl or an optionally substituted 5 or 6 membered heteroaryl, wherein the substituents are selected from the group consisting of:

$C_{1-6}$-alkyl optionally substituted by hydroxy, $NR^aR^b$, wherein $R^a$ and $R^b$ are independently H or —(CO)—$C_{1-6}$-alkyl, $(SO_2)$—$C_{1-6}$-alkyl, $(SO_2)$—$NR^cR^d$, wherein $R^c$ and $R^d$ are independently:

H, or $C_{1-6}$-alkyl optionally substituted by hydroxy, $(CO)C_{1-6}$-alkyl optionally substituted by $C_{1-6}$-alkoxy, $(CH_2CH_2O)_nCHR^e$, wherein $R^e$ is H or $CH_2OH$ and n is 1, 2, 3, 4, 5, 6, 7, 8, 9 or 10, $(CH_2)_m$-aryl, wherein m is 1 or 2, $(CH_2)_p$—$C_{3-6}$-cycloalkyl, wherein p is 0 or 1, $(SO_2)$—$NR^fR^g$, wherein $R^f$ and $R^g$ together with the nitrogen atom to which they are attached form a 4, 5 or 6 membered heterocycloalkyl ring optionally containing a further heteroatom selected from nitrogen, oxygen, sulphur and an $SO_2$ group, wherein said 4, 5 or 6 membered heterocycloalkyl ring is optionally substituted by a substituent selected from the group consisting of hydroxyl and $C_{1-6}$-alkyl, $NHSO_2$—$C_{1-6}$-alkyl, and $NHSO_2$—$NR^hR^i$ wherein $R^h$ and $R^i$ are independently H, $C_{1-6}$-alkyl;

$R^1$ is $C_{1-6}$-alkyl or $C_{1-6}$-haloalkyl;

$R^2$ is halogen or $C_{1-6}$-haloalkyl;

$R^3$ is H, halogen, $C_{1-6}$-alkoxy, $C_{1-6}$-haloalkyl, $C_{1-6}$-alkyl or $C_{1-6}$-haloalkoxy;

$R^4$ is H or halo;

and pharmaceutically acceptable salts thereof.

Encompassed by the compounds of formula (I) according to the invention are the compound of formula (I-a1):

(Ia1)

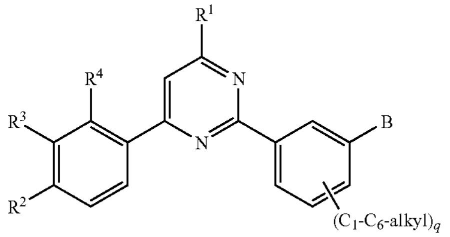

wherein B, $R^1$, $R^2$, $R^3$ and $R^4$ are as defined hereinabove for formulae (I) and (Ia) and q is 0, 1, 2, 3, or 4.

In a certain embodiment of the invention, the compounds of formula (Ia1) are these compounds wherein:

B is H or cyano;

$R^1$ is $C_{1-6}$-alkyl or $C_{1-6}$-haloalkyl;

$R^2$ is halogen or $C_{1-6}$-haloalkyl;

$R^3$ is H, halogen, $C_{1-6}$-alkoxy, $C_{1-6}$-haloalkyl, $C_{1-6}$-alkyl or $C_{1-6}$-haloalkoxy;

$R^4$ is H or halo;

and pharmaceutically acceptable salts thereof.

In a certain embodiment of the invention, the compounds of formula (Ia1) are these compounds wherein:

B is an optionally substituted aryl or an optionally substituted 5 or 6 membered heteroaryl, wherein the substituents are selected from the group consisting of:

$C_{1-6}$-alkyl optionally substituted by hydroxy, and $NR^aR^b$, wherein $R^a$ and $R^b$ are independently H, $(SO_2)$—$C_{1-6}$-alkyl, $(SO_2)$—$NR^cR^d$, wherein $R^c$ and $R^d$ are independently: H, $C_{1-6}$-alkyl optionally substituted by hydroxy, $NHSO_2$—$C_{1-6}$-alkyl, and $NHSO_2$—$NR^hR^i$ wherein $R^h$ and $R^i$ are independently H, $C_{1-6}$-alkyl;

$R^1$ is $C_{1-6}$-allyl or $C_{1-6}$-haloalkyl;

$R^2$ is halogen or $C_{1-6}$-haloalkyl;

$R^3$ is H, halogen, $C_{1-6}$-alkoxy, $C_{1-6}$-haloalkyl, $C_{1-6}$-alkyl or $C_{1-6}$-haloalkoxy;

$R^4$ is H or halo;

and pharmaceutically acceptable salts thereof.

In a certain embodiment of the invention, the compounds of formula (Ia1) are those compounds wherein B is an unsubstituted aryl or an unsubstituted 5 or 6 membered heteroaryl, for example the following compounds:

2-(3-Pyridin-3-yl-phenyl)-4-trifluoromethyl-6-(4-trifluoromethyl-phenyl)-pyrimidine;

4-(4-Chloro-phenyl)-2-(3-pyridin-3-yl-phenyl)-6-trifluoromethyl-pyrimidine; and

4-[4-(4-Chloro-phenyl)-6-trifluoromethyl-pyrimidin-2-yl]-[2,3']bipyridinyl.

In a certain embodiment of the invention, the compounds of formula (Ia1) are those compounds wherein B is an optionally substituted aryl or an optionally substituted 5 or 6 membered heteroaryl, wherein the substituents are selected from the group consisting of $C_{1-6}$-alkyl optionally substituted by hydroxy, for example 2-[3-(2,6-Dimethyl-pyridin-4-yl)-phenyl]-4-trifluoromethyl-6-(4-trifluoromethyl-phenyl)pyrimidine; and {3'-[4-Trifluoromethyl-6-(4-trifluoromethyl-phenyl)-pyrimidin-2-yl]-biphenyl-4-yl}-methanol.

In a certain embodiment of the invention, the compounds of formula (Ia1) are those compounds wherein B is an optionally substituted aryl or an optionally substituted 5 or 6 membered heteroaryl, wherein the substituents are selected from the group consisting of $NR^aR^b$, wherein $R^a$ and $R^b$ are independently H, for example the following compounds:

5-{3-[4-Trifluoromethyl-6-(4-trifluoromethyl-phenyl)-pyrimidin-2-yl]-phenyl}-pyridin-2-ylamine;

5-{3-[4-(4-Chloro-phenyl)-6-trifluoromethyl-pyrimidin-2-yl]-phenyl}-pyridin-2-ylamine;

5-{3-[4-Difluoromethyl-6-(4-trifluoromethyl-phenyl)-pyrimidin-2-yl]-phenyl}-pyridin-2-ylamine;

5-{3-[4-(3-Ethoxy-4-trifluoromethyl-phenyl)-6-trifluoromethyl-pyrimidin-2-yl]-phenyl}-pyridin-2-ylamine;

5-{3-[4-(3-Fluoro-4-trifluoromethyl-phenyl)-6-trifluoromethyl-pyrimidin-2-yl]-phenyl}-pyridin-2-ylamine;

5-{3-[4-(3,4-Dichloro-phenyl)-6-trifluoromethyl-pyrimidin-2-yl]-phenyl}-pyridin-2-ylamine;

5-{3-[4-(4-Chloro-3-methyl-phenyl)-6-trifluoromethyl-pyrimidin-2-yl]-phenyl}-pyridin-2-ylamine;

5-{3-[4-(4-Chloro-phenyl)-6-methyl-pyrimidin-2-yl]-phenyl}-pyridin-2-ylamine

5-{3-[4-(4-Chloro-phenyl)-6-methyl-pyrimidin-2-yl]-phenyl}-pyrimidin-2-ylamine;

5-{3-[4-Methyl-6-(4-trifluoromethyl-phenyl)-pyrimidin-2-yl]-phenyl}-pyrimidin-2-ylamine;

5-{3-[4-Methyl-6-(4-trifluoromethyl-phenyl)-pyrimidin-2-yl]-phenyl}-pyridin-2-ylamine;

3'-[4-Trifluoromethyl-6-(4-trifluoromethyl-phenyl)-pyrimidin-2-yl]-biphenyl-4-ylamine;

5-{3-[4-(3-Methyl-4-trifluoromethyl-phenyl)-6-trifluoromethyl-pyrimidin-2-yl]-phenyl}-pyridin-2-ylamine;

5-{3-[4-(3-Methyl-4-trifluoromethyl-phenyl)-6-trifluoromethyl-pyrimidin-2-yl]-phenyl}-pyrimidin-2-ylamine;

5-{3-[4-Methyl-6-(3-methyl-4-trifluoromethyl-phenyl)-pyrimidin-2-yl]-phenyl}-pyridin-2-ylamine;

5-(3-{4-[3-(2,2,2-Trifluoro-ethoxy)-4-trifluoromethyl-phenyl]-6-trifluoromethyl-pyrimidin-2-yl}-phenyl)-pyridin-2-ylamine;

5-(3-{4-[3-(2,2,2-Trifluoro-ethoxy)-4-trifluoromethyl-phenyl]-6-trifluoromethyl-pyrimidin-2-yl}-phenyl)-pyrimidin-2-ylamine;

5-{3-[4-Trifluoromethyl-6-(3-trifluoromethyl-phenyl)-pyrimidin-2-yl]-phenyl}-pyridin-2-ylamine;

5-{3-[4-(3,4-Dichloro-phenyl)-6-methyl-pyrimidin-2-yl]-phenyl}-pyridin-2-ylamine;

3'-[4-Trifluoromethyl-6-(4-trifluoromethyl-phenyl)-pyrimidin-2-yl]-biphenyl-3-ylamine; and 5-{3-[4-(4-Chloro-3-methyl-phenyl)-6-methyl-pyrimidin-2-yl]-phenyl}-pyridin-2-ylamine.

In a certain embodiment of the invention, the compounds of formula (Ia1) are those compounds wherein B is an optionally substituted aryl or an optionally substituted 5 or 6 membered heteroaryl, wherein the substituents are selected from the group consisting of —$(SO_2)$—$C_{1-6}$-alkyl or —$(SO_2)$—$NR^cR^d$, wherein $R^c$ and $R^d$ are independently H or $C_{1-6}$-alkyl optionally substituted by hydroxy, for example the following compounds:

3'-[4-Trifluoromethyl-6-(4-trifluoromethyl-phenyl)-pyrimidin-2-yl]-biphenyl-3-sulfonic acid tert-butylamide;

3'-[4-Trifluoromethyl-6-(4-trifluoromethyl-phenyl)-pyrimidin-2-yl]-biphenyl-3-sulfonic acid amide;

5-{3-[4-Trifluoromethyl-6-(4-trifluoromethyl-phenyl)-pyrimidin-2-yl]-phenyl}-thiophene-2-sulfonic acid amide;

3'-[4-Methyl-6-(4-trifluoromethyl-phenyl)-pyrimidin-2-yl]-biphenyl-3-sulfonic acid tert-butylamide;

3'-[4-(4-Chloro-phenyl)-6-methyl-pyrimidin-2-yl]-biphenyl-3-sulfonic acid amide;

3'-[4-Methyl-6-(4-trifluoromethyl-phenyl)-pyrimidin-2-yl]-biphenyl-3-sulfonic acid amide;

5-{3-[4-(4-Chloro-phenyl)-6-trifluoromethyl-pyrimidin-2-yl]-phenyl}-thiophene-2-sulfonic acid tert-butylamide;

5-{3-[4-Methyl-6-(4-trifluoromethyl-phenyl)-pyrimidin-2-yl]-phenyl}-thiophene-2-sulfonic acid amide;

5-{3-[4-(4-Chloro-phenyl)-6-methyl-pyrimidin-2-yl]-phenyl}-thiophene-2-sulfonic acid amide;

5-{3-[4-(4-Chloro-phenyl)-6-trifluoromethyl-pyrimidin-2-yl]-phenyl}-thiophene-2-sulfonic acid amide;

3'-[4-(4-Chloro-phenyl)-6-trifluoromethyl-pyrimidin-2-yl]-biphenyl-3-sulfonic acid amide;

3'-[4-(3,4-Dichloro-phenyl)-6-methyl-pyrimidin-2-yl]-biphenyl-3-sulfonic acid amide;

5-{3-[4-(3,4-Dichloro-phenyl)-6-methyl-pyrimidin-2-yl]-phenyl}-thiophene-2-sulfonic acid amide;

3'-[4-(3,4-Dichloro-phenyl)-6-trifluoromethyl-pyrimidin-2-yl]-biphenyl-3-sulfonic acid amide;

5-{3-[4-(3,4-Dichloro-phenyl)-6-trifluoromethyl-pyrimidin-2-yl]-phenyl}-thiophene-2-sulfonic acid amide;

3'-[4-(3-Methyl-4-trifluoromethyl-phenyl)-6-trifluoromethyl-pyrimidin-2-yl]-biphenyl-3-sulfonic acid amide;

5-{3-[4-(3-Methyl-4-trifluoromethyl-phenyl)-6-trifluoromethyl-pyrimidin-2-yl]-phenyl}-thiophene-2-sulfonic acid amide;

2-(3'-Methanesulfonyl-biphenyl-3-yl)-4-trifluoromethyl-6-(4-trifluoromethyl-phenyl)pyrimidine;

3'-[4-(4-Chloro-3-methyl-phenyl)-6-methyl-pyrimidin-2-yl]-biphenyl-3-sulfonic acid amide;

5-{3-[4-(4-Chloro-3-methyl-phenyl)-6-methyl-pyrimidin-2-yl]-phenyl}-thiophene-2-sulfonic acid amide;

5-{3-[4-(3,4-Difluoro-phenyl)-6-trifluoromethyl-pyrimidin-2-yl]-phenyl}-thiophene-2-sulfonic acid amide;

3'-[4-Trifluoromethyl-6-(4-trifluoromethyl-phenyl)-pyrimidin-2-yl]-biphenyl-3-sulfonic acid (2-hydroxy-ethyl)-amide;

3'-[4-Trifluoromethyl-6-(4-trifluoromethyl-phenyl)-pyrimidin-2-yl]-biphenyl-3-sulfonic acid bis-(2-hydroxy-ethyl)-amide;

3'-[4-(3,4-Difluoro-phenyl)-6-trifluoromethyl-pyrimidin-2-yl]-biphenyl-3-sulfonic acid amide;

3'-[4-(4-Fluoro-phenyl)-6-trifluoromethyl-pyrimidin-2-yl]-biphenyl-3-sulfonic acid amide;

5-{3-[4-(4-Fluoro-phenyl)-6-trifluoromethyl-pyrimidin-2-yl]-phenyl}-thiophene-2-sulfonic acid amide;

3'-[4-(2,4-Dichloro-phenyl)-6-trifluoromethyl-pyrimidin-2-yl]-biphenyl-3-sulfonic acid amide;

5-{3-[4-(2,4-Dichloro-phenyl)-6-trifluoromethyl-pyrimidin-2-yl]-phenyl}-thiophene-2-sulfonic acid amide;

3'-[4-(2-Fluoro-4-trifluoromethyl-phenyl)-6-trifluoromethyl-pyrimidin-2-yl]-biphenyl-3-sulfonic acid amide;

5-{3-[4-(2-Fluoro-4-trifluoromethyl-phenyl)-6-trifluoromethyl-pyrimidin-2-yl]-phenyl}-thiophene-2-sulfonic acid amide;

3'-[4-Methyl-6-(3-methyl-4-trifluoromethyl-phenyl)-pyrimidin-2-yl]-biphenyl-3-sulfonic acid amide;

5-{3-[4-Methyl-6-(3-methyl-4-trifluoromethyl-phenyl)-pyrimidin-2-yl]-phenyl}-thiophene-2-sulfonic acid amide;

3'-[4-Difluoromethyl-6-(4-trifluoromethyl-phenyl)-pyrimidin-2-yl]-biphenyl-3-sulfonic acid amide;

5-{3-[4-Difluoromethyl-6-(4-trifluoromethyl-phenyl)-pyrimidin-2-yl]-phenyl}-thiophene-2-sulfonic acid amide;

3'-[4-(3-Fluoro-4-trifluoromethyl-phenyl)-6-trifluoromethyl-pyrimidin-2-yl]-biphenyl-3-sulfonic acid amide; and 5-{3-[4-(3-Fluoro-4-trifluoromethyl-phenyl)-6-trifluoromethyl-pyrimidin-2-yl]-phenyl}-thiophene-2-sulfonic acid amide.

In a certain embodiment of the invention, the compounds of formula (Ia1) are those compounds wherein B is an optionally substituted aryl or an optionally substituted 5 or 6 membered heteroaryl, wherein the substituents is $NHSO_2$—$C_{1-6}$-alkyl, for example the following compound: N-{3'-[4-Trifluoromethyl-6-(4-trifluoromethyl-phenyl)-pyrimidin-2-yl]-biphenyl-3-yl}-methanesulfonamide.

In a certain embodiment of the invention, the compounds of formula (Ia1) are these compounds wherein B is an optionally substituted aryl or an optionally substituted 5 or 6 membered heteroaryl, wherein the substituents are $NHSO_2$—$NR^hR^i$ wherein $R^h$ and $R^i$ are independently H or $C_{1-6}$-alkyl, for example the following compounds:

N-{3'-[4-Trifluoromethyl-6-(4-trifluoromethyl-phenyl)-pyrimidin-2-yl]-biphenyl-3-yl}-sulfamide and N-{3'-[4-Trifluoromethyl-6-(4-trifluoromethyl-phenyl)-pyrimidin-2-yl]-biphenyl-3-yl}-N',N'-dimethyl-sulfamide.

Encompassed by the compounds of formula (I) according to the invention are compounds of formula (I-a2):

(Ia2)

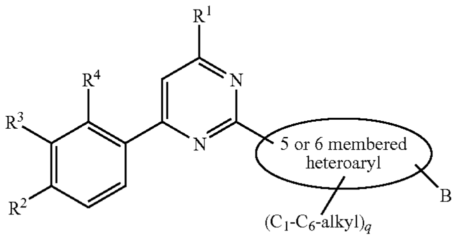

wherein B, $R^1$, $R^2$, $R^3$ and $R^4$ are as defined hereinabove for formula (I) and q is 0, 1, 2, 3, or 4.

The 5 or 6 membered heteroaryl can be selected from the group consisting of: imidazolyl, [1,2,4]oxadiazolyl], pyrrolyl, 1H-pyrazolyl, pyridinyl, [1,2,4]triazolyl, thiazolyl, pyrimidinyl and thiophenyl and preferably, imidazolyl, [1,2,4]oxadiazolyl], pyrrolyl, 1H-pyrazolyl, pyridinyl and [1,2,4]triazolyl.

In a certain embodiment of the invention, the compounds of formula (Ia2) are those compounds wherein:

B is H or cyano;

$R^1$ is $C_{1-6}$-alkyl or $C_{1-6}$-haloalkyl;

$R^2$ is halogen or $C_{1-6}$-haloalkyl;

$R^3$ is H, halogen, $C_{1-6}$-alkoxy, $C_{1-6}$-haloalkyl, $C_{1-6}$-alkyl or $C_{1-6}$-haloalkoxy;

$R^4$ is H or halo;

and pharmaceutically acceptable salts thereof.

In a certain embodiment of the invention, the compounds of formula (Ia2) are those compounds wherein B is H, for example the following compounds:

4-(4-Chloro-phenyl)-2-imidazol-1-yl-6-trifluoromethyl-pyrimidine;

2-Imidazol-1-yl-4-trifluoromethyl-6-(4-trifluoromethyl-phenyl)-pyrimidine;

2-Pyrrol-1-yl-4-trifluoromethyl-6-(4-trifluoromethyl-phenyl)-pyrimidine;

4-(4-Chloro-phenyl)-2-pyrrol-1-yl-6-trifluoromethyl-pyrimidine;

2-Pyridin-3-yl-4-trifluoromethyl-6-(4-trifluoromethyl-phenyl)-pyrimidine;

4-Difluoromethyl-2-pyridin-4-yl-6-(4-trifluoromethyl-phenyl)-pyrimidine; and

2-Pyridin-4-yl-4-trifluoromethyl-6-(4-trifluoromethyl-phenyl)-pyrimidine.

In a certain embodiment of the invention, the compounds of formula (Ia2) are those compounds wherein:

B is an optionally substituted aryl or an optionally substituted 5 or 6 membered heteroaryl, wherein the substituents are selected from the group consisting of:

$C_{1-6}$-alkyl optionally substituted by hydroxy, $NR^aR^b$, wherein $R^a$ and $R^b$ are independently H or —(CO)—$C_{1-6}$-alkyl, $(SO_2)$—$C_{1-6}$-alkyl, $(SO_2)$—$NR^cR^d$, wherein $R^c$ and $R^d$ are independently:

H, or $C_{1-6}$-alkyl optionally substituted by hydroxy, $(CO)C_{1-6}$-alkyl optionally substituted by $C_{1-6}$-alkoxy, $(CH_2CH_2O)_nCHR^e$, wherein $R^e$ is H or $CH_2OH$ and n is 1, 2, 3, 4, 5, 6, 7, 8, 9 or 10, $(CH_2)_m$-aryl, wherein m is 1 or 2, $(CH_2)_p$—$C_{3-6}$-cycloalkyl, wherein p is 0 or 1, and $(SO_2)$—$NR^fR^g$, wherein $R^f$ and $R^g$ together with the nitrogen atom to which they are attached form a 4, 5 or 6 membered heterocycloalkyl ring optionally containing a further heteroatom selected from nitrogen, oxygen, sulphur and an $SO_2$ group, wherein said 4, 5 or 6 membered heterocycloalkyl ring is optionally substituted by a substituent selected from the group consisting of hydroxy or $C_{1-6}$-alkyl;

$R^1$ is $C_{1-6}$-alkyl or $C_{1-6}$-haloalkyl;

$R^2$ is halogen or $C_{1-6}$-haloalkyl;

$R^3$ is H, halogen, $C_{1-6}$-alkoxy, $C_{1-6}$-haloalkyl, $C_{1-6}$-alkyl or $C_{1-6}$-haloalkoxy;

$R^4$ is H or halo;

and pharmaceutically acceptable salts thereof.

In a certain embodiment of the invention, the compounds of formula (Ia2) are those compounds wherein B is unsubstituted aryl or unsubstituted 5 or 6 membered heteroaryl, for example the following compounds:

2-(4-Pyridin-3-yl-imidazol-1-yl)-4-trifluoromethyl-6-(4-trifluoromethyl-phenyl)-pyrimidine;

4-(4-Chloro-phenyl)-2-(4-pyridin-3-yl-imidazol-1-yl)-6-trifluoromethyl-pyrimidine;

4-(4-Chloro-phenyl)-2-(4-pyridin-4-yl-imidazol-1-yl)-6-trifluoromethyl-pyrimidine;

4-(4-Chloro-phenyl)-2-(3-pyridin-4-yl-[1,2,4]oxadiazol-5-yl)-6-trifluoromethyl-pyrimidine;

4-(4-Chloro-phenyl)-2-(3-pyridin-3-yl-[1,2,4]oxadiazol-5-yl)-6-trifluoromethyl-pyrimidine;

4-(4-Chloro-phenyl)-6-methyl-2-(4-pyridin-3-yl-imidazol-1-yl)-pyrimidine;

4-Methyl-2-(4-pyridin-3-yl-imidazol-1-yl)-6-(4-trifluoromethyl-phenyl)-pyrimidine;

4-[4-Trifluoromethyl-6-(4-trifluoromethyl-phenyl)-pyrimidin-2-yl]-[2,3']bipyridinyl;

4-[4-(4-Chloro-phenyl)-6-trifluoromethyl-pyrimidin-2-yl]-[2,4']bipyridinyl;

2-(3-Pyridin-4-yl-[1,2,4]triazol-1-yl)-4-trifluoromethyl-6-(4-trifluoromethyl-phenyl)pyrimidine; and 2-(3-Pyridin-3-yl-[1,2,4]triazol-1-yl)-4-trifluoromethyl-6-(4-trifluoromethyl-phenyl)pyrimidine.

In a certain embodiment of the invention, the compounds of formula (Ia2) are those compounds wherein B is optionally substituted aryl or an optionally substituted 5 or 6 membered heteroaryl, wherein the substituent is $NR^aR^b$, wherein $R^a$ and $R^b$ are independently H or —(CO)—$C_{1-6}$-alkyl, for example the following compounds:

4-{5-[4-(4-Chloro-phenyl)-6-trifluoromethyl-pyrimidin-2-yl]-[1,2,4]oxadiazol-3-yl}-pyridin-2-ylamine;

5-{5-[4-(4-Chloro-phenyl)-6-trifluoromethyl-pyrimidin-2-yl]-[1,2,4]oxadiazol-3-yl}-pyridin-2-ylamine;

5-{5-[4-Trifluoromethyl-6-(4-trifluoromethyl-phenyl)-pyrimidin-2-yl]-[1,2,4]oxadiazol-3-yl}-pyridin-2-ylamine;

4-{5-[4-Trifluoromethyl-6-(4-trifluoromethyl-phenyl)-pyrimidin-2-yl]-[1,2,4]oxadiazol-3-yl}-pyridin-2-ylamine;

5-{1-[4-Trifluoromethyl-6-(4-trifluoromethyl-phenyl)-pyrimidin-2-yl]-1H-imidazol-4-yl}-pyridin-2-ylamine;

5-{1-[4-(4-Chloro-phenyl)-6-trifluoromethyl-pyrimidin-2-yl]-1H-imidazol-4-yl}-pyridin-2-ylamine;

5-{1-[4-Trifluoromethyl-6-(4-trifluoromethyl-phenyl)-pyrimidin-2-yl]-1H-pyrazol-4-yl}-pyridin-2-ylamine;

5-{5-[4-Trifluoromethyl-6-(4-trifluoromethyl-phenyl)-pyrimidin-2-yl]-[1,2,4]oxadiazol-3-yl}-pyrimidin-2-ylamine;

5-{3-[4-Trifluoromethyl-6-(4-trifluoromethyl-phenyl)-pyrimidin-2-yl]-[1,2,4]oxadiazol-5-yl}-pyridin-2-ylamine;

5-{3-[4-(4-Chloro-phenyl)-6-trifluoromethyl-pyrimidin-2-yl]-[1,2,4]oxadiazol-5-yl}-pyridin-2-ylamine;

4-[4-(4-Chloro-phenyl)-6-trifluoromethyl-pyrimidin-2-yl]-[2,3']bipyridinyl-6'-ylamine;

4-[4-Trifluoromethyl-6-(4-trifluoromethyl-phenyl)-pyrimidin-2-yl]-[2,3']bipyridinyl-6'-ylamine;

5-{1-[4-Difluoromethyl-6-(4-trifluoromethyl-phenyl)-pyrimidin-2-yl]-1H-imidazol-4-yl}-pyridin-2-ylamine;

5-{5-[4-Difluoromethyl-6-(4-trifluoromethyl-phenyl)-pyrimidin-2-yl]-[1,2,4]oxadiazol-3-yl}-pyridin-2-ylamine;

5-{1-[4-(4-Chloro-phenyl)-6-methyl-pyrimidin-2-yl]-1H-imidazol-4-yl}-pyridin-2-ylamine;

5-{1-[4-(4-Chloro-phenyl)-6-methyl-pyrimidin-2-yl]-1H-imidazol-4-yl}-pyrimidin-2-ylamine;

5-{1-[4-Methyl-6-(4-trifluoromethyl-phenyl)-pyrimidin-2-yl]-1H-imidazol-4-yl}-pyridin-2-ylamine;

5-{1-[4-Methyl-6-(4-trifluoromethyl-phenyl)-pyrimidin-2-yl]-1H-imidazol-4-yl}-pyrimidin-2-ylamine;

5-{1-[4-(4-Chloro-phenyl)-6-cyclopropyl-pyrimidin-2-yl]-1H-imidazol-4-yl}-pyridin-2-ylamine;

5-{1-[4-(4-Chloro-phenyl)-6-cyclopropyl-pyrimidin-2-yl]-1H-imidazol-4-yl}-pyrimidin-2-ylamine;

5-{1-[4-(4-Chloro-phenyl)-pyrimidin-2-yl]-1H-imidazol-4-yl}-pyridin-2-ylamine;

5-{1-[4-Trifluoromethyl-6-(3-trifluoromethyl-phenyl)-pyrimidin-2-yl]-1H-imidazol-4-yl}-pyridin-2-ylamine;

5-{1'-[4-(3-Ethoxy-4-trifluoromethyl-phenyl)-6-trifluoromethyl-pyrimidin-2-yl]-1H-imidazol-4-yl}-pyridin-2-ylamine;

4-[4-Difluoromethyl-6-(4-trifluoromethyl-phenyl)-pyrimidin-2-yl]-[2,3']bipyridinyl-6'-ylamine;

5-{5-[4-(3-Ethoxy-4-trifluoromethyl-phenyl)-6-trifluoromethyl-pyrimidin-2-yl]-[1,2,4]oxadiazol-3-yl}-pyridin-2-ylamine;

4-[4-(3-Ethoxy-4-trifluoromethyl-phenyl)-6-trifluoromethyl-pyrimidin-2-yl]-[2,3']bipyridinyl-6'-ylamine;

5-{1-[4-(3-Fluoro-4-trifluoromethyl-phenyl)-6-trifluoromethyl-pyrimidin-2-yl]-1H-imidazol-4-yl}-pyridin-2-ylamine;

N-(5-{1-[4-Trifluoromethyl-6-(4-trifluoromethyl-phenyl)-pyrimidin-2-yl]-1H-imidazol-4-yl}-pyridin-2-yl)-acetamide;

5-{5-[4-(3,4-Dichloro-phenyl)-6-trifluoromethyl-pyrimidin-2-yl]-[1,2,4]oxadiazol-3-yl}-pyridin-2-ylamine;

5-[6-Trifluoromethyl-4-(4-trifluoromethyl-phenyl)-[2,4']bipyrimidinyl-2'-yl]-pyridin-2-ylamine;

5-{1-[4-(3,4-Dichloro-phenyl)-6-trifluoromethyl-pyrimidin-2-yl]-1H-imidazol-4-yl}-pyridin-2-ylamine;

4-[4-(3,4-Dichloro-phenyl)-6-trifluoromethyl-pyrimidin-2-yl]-[2,3']bipyridinyl-6'-ylamine;

5-{1-[4-(4-Chloro-3-methyl-phenyl)-6-trifluoromethyl-pyrimidin-2-yl]-1H-imidazol-4-yl}-pyridin-2-ylamine;

5-{5-[4-(4-Chloro-3-methyl-phenyl)-6-trifluoromethyl-pyrimidin-2-yl]-[1,2,4]oxadiazol-3-yl}-pyridin-2-ylamine;

4-[4-(4-Chloro-3-methyl-phenyl)-6-trifluoromethyl-pyrimidin-2-yl]-[2,3']bipyridinyl-6'-ylamine;

4-{1-[4-Trifluoromethyl-6-(4-trifluoromethyl-phenyl)-pyrimidin-2-yl]-1H-imidazol-4-yl}-phenylamine;

4-[4-(4-Chloro-phenyl)-6-methyl-pyrimidin-2-yl]-[2,3']bipyridinyl-6'-ylamine;

4-[4-Methyl-6-(4-trifluoromethyl-phenyl)-pyrimidin-2-yl]-[2,3']bipyridinyl-6'-ylamine;

5-{1-[4-(3-Methyl-4-trifluoromethyl-phenyl)-6-trifluoromethyl-pyrimidin-2-yl]-1H-imidazol-4-yl}-pyridin-2-ylamine;

4-[4-(3-Methyl-4-trifluoromethyl-phenyl)-6-trifluoromethyl-pyrimidin-2-yl]-[2,3']bipyridinyl-6'-ylamine;

5-{1-[4-Methyl-6-(3-methyl-4-trifluoromethyl-phenyl)-pyrimidin-2-yl]-1H-imidazol-4-yl}-pyridin-2-ylamine;

5-{1-[4-Methyl-6-(3-methyl-4-trifluoromethyl-phenyl)-pyrimidin-2-yl]-1H-imidazol-4-yl}-pyrimidin-2-ylamine;

5-{1-[4-(3-Methyl-4-trifluoromethyl-phenyl)-6-trifluoromethyl-pyrimidin-2-yl]-1H-imidazol-4-yl}-pyrimidin-2-ylamine;

5-{5-[4-Methyl-6-(4-trifluoromethyl-phenyl)-pyrimidin-2-yl]-[1,2,4]oxadiazol-3-yl}-pyridin-2-ylamine;

5-{5-[4-(3-Methyl-4-trifluoromethyl-phenyl)-6-trifluoromethyl-pyrimidin-2-yl]-[1,2,4]oxadiazol-3-yl}-pyridin-2-ylamine;

4-[4-Methyl-6-(3-methyl-4-trifluoromethyl-phenyl)-pyrimidin-2-yl]-[2,3']bipyridinyl-6'-ylamine;

5-(1-{4-[3-(2,2,2-Trifluoro-ethoxy)-4-trifluoromethyl-phenyl]-6-trifluoromethyl-pyrimidin-2-yl}-1H-imidazol-4-yl)-pyridin-2-ylamine;

4-{4-[3-(2,2,2-Trifluoro-ethoxy)-4-trifluoromethyl-phenyl]-6-trifluoromethyl-pyrimidin-2-yl}-[2,3']bipyridinyl-6'-ylamine;

5-{5-[4-(4-Chloro-phenyl)-6-methyl-pyrimidin-2-yl]-[1,2,4]oxadiazol-3-yl}-pyridin-2-ylamine;

5-{1-[4-Trifluoromethyl-6-(3-trifluoromethyl-phenyl)-pyrimidin-2-yl]-1H-imidazol-4-yl}-pyrimidin-2-ylamine;

4-[4-Trifluoromethyl-6-(3-trifluoromethyl-phenyl)-pyrimidin-2-yl]-[2,3']bipyridinyl-6'-ylamine;

5-{2-Methyl-1-[4-trifluoromethyl-6-(4-trifluoromethyl-phenyl)-pyrimidin-2-yl]-1H-imidazol-4-yl}-pyridin-2-ylamine;

5-{2-Methyl-1-[4-trifluoromethyl-6-(4-trifluoromethyl-phenyl)-pyrimidin-2-yl]-1H-imidazol-4-yl}-pyrimidin-2-ylamine;

5-{1-[4-(3,4-Dichloro-phenyl)-6-methyl-pyrimidin-2-yl]-1H-imidazol-4-yl}-pyrimidin-2-ylamine;

5-{1-[4-(3,4-Dichloro-phenyl)-6-methyl-pyrimidin-2-yl]-1H-imidazol-4-yl}-pyridin-2-ylamine;

4-[4-(3,4-Dichloro-phenyl)-6-methyl-pyrimidin-2-yl]-[2,3']bipyridinyl-6'-ylamine 5-{2-Methyl-1-[4-methyl-6-(4-trifluoromethyl-phenyl)-pyrimidin-2-yl]-1H-imidazol-4-yl}-pyridin-2-ylamine;

5-{1-[4-Methyl-6-(4-trifluoromethyl-phenyl)-pyrimidin-2-yl]-1H-[1,2,4]triazol-3-yl}-pyridin-2-ylamine;

5-{1-[4-Isopropyl-6-(4-trifluoromethyl-phenyl)-pyrimidin-2-yl]-1H-imidazol-4-yl}-pyridin-2-ylamine;

5-{1-[4-Isopropyl-6-(4-trifluoromethyl-phenyl)-pyrimidin-2-yl]-1H-imidazol-4-yl}-pyrimidin-2-ylamine;

5-{5-Methyl-1-[4-trifluoromethyl-6-(4-trifluoromethyl-phenyl)-pyrimidin-2-yl]-1H-imidazol-4-yl}-pyridin-2-ylamine;

5-{1-[4-(3-Chloro-phenyl)-6-trifluoromethyl-pyrimidin-2-yl]-1H-imidazol-4-yl}-pyridin-2-ylamine;

5-{1-[4-(3-Chloro-phenyl)-6-trifluoromethyl-pyrimidin-2-yl]-1H-imidazol-4-yl}-pyrimidin-2-ylamine;

5-{1-[4-(4-Fluoro-phenyl)-6-trifluoromethyl-pyrimidin-2-yl]-1H-imidazol-4-yl}-pyridin-2-ylamine;

5-{1-[4-(4-Chloro-3-methyl-phenyl)-6-methyl-pyrimidin-2-yl]-1H-imidazol-4-yl}-pyridin-2-ylamine; and 5-{1-[4-(3,4-Difluoro-phenyl)-6-trifluoromethyl-pyrimidin-2-yl]-1H-imidazol-4-yl}-pyridin-2-ylamine.

In a certain embodiment of the invention, the compounds of formula (Ia2) are those compounds wherein B is optionally substituted aryl or an optionally substituted 5 or 6 membered heteroaryl, wherein the substituent is —$(SO_2)$—$C_{1-6}$-alkyl, for example the following compounds:

4-(4-Chloro-phenyl)-2-[4-(3-methanesulfonyl-phenyl)-imidazol-1-yl]-6-methyl-pyrimidine;

4-(3,4-Dichloro-phenyl)-2-[4-(3-methanesulfonyl-phenyl)-imidazol-1-yl]-6-methyl-pyrimidine;

2-[4-(3-Methanesulfonyl-phenyl)-imidazol-1-yl]-4-trifluoromethyl-6-(4-trifluoromethylphenyl)-pyrimidine; and 2-[2-(3-Methanesulfonyl-phenyl)-pyridin-4-yl]-4-trifluoromethyl-6-(4-trifluoromethyl-phenyl)pyrimidine.

In a certain embodiment of the invention, the compounds of formula (Ia2) are those compounds wherein B is optionally substituted aryl or an optionally substituted 5 or 6 membered heteroaryl, wherein the substituent is —$(SO_2)$—$NR^cR^d$, wherein $R^c$ and $R^d$ are independently

H, $C_{1-6}$-alkyl optionally substituted by hydroxy, $(CO)C_{1-6}$-alkyl optionally substituted by $C_{1-6}$-alkoxy, $(CH_2CH_2O)_nCHR^e$, wherein $R^e$ is H or $CH_2OH$ and n is 1, 2, 3, 4, 5, 6, 7, 8, 9 or 10, $(CH_2)_m$-aryl, wherein m is 1 or 2, or $(CH_2)_p$—$C_{3-6}$-cycloalkyl, wherein p is 0 or 1, for example the following compounds:

3-{3-[4-(4-Chloro-phenyl)-6-trifluoromethyl-pyrimidin-2-yl]-[1,2,4]oxadiazol-5-yl}-benzenesulfonamide;

3-{3-[4-Trifluoromethyl-6-(4-trifluoromethyl-phenyl)-pyrimidin-2-yl]-[1,2,4]oxadiazol-5-yl}-benzenesulfonamide;

4-{5-[4-Trifluoromethyl-6-(4-trifluoromethyl-phenyl)-pyrimidin-2-yl]-[1,2,4]oxadiazol-3-yl}-benzenesulfonamide;

3-{5-[4-Trifluoromethyl-6-(4-trifluoromethyl-phenyl)-pyrimidin-2-yl]-[1,2,4]oxadiazol-3-yl}-benzenesulfonamide;

4-{5-[4-(4-Chloro-phenyl)-6-trifluoromethyl-pyrimidin-2-yl]-[1,2,4]oxadiazol-3-yl}-benzenesulfonamide;

3-{5-[4-(4-Chloro-phenyl)-6-trifluoromethyl-pyrimidin-2-yl]-[1,2,4]oxadiazol-3-yl}-benzenesulfonamide;

5-{3-[4-Trifluoromethyl-6-(4-trifluoromethyl-phenyl)-pyrimidin-2-yl]-[1,2,4]oxadiazol-5-yl}-thiophene-2-sulfonic acid amide;

5-{3-[4-(4-Chloro-phenyl)-6-trifluoromethyl-pyrimidin-2-yl]-[1,2,4]oxadiazol-5-yl}-thiophene-2-sulfonic acid amide;

4-{5-[4-Difluoromethyl-6-(4-trifluoromethyl-phenyl)-pyrimidin-2-yl]-[1,2,4]oxadiazol-3-yl}-benzenesulfonamide;

3-{5-[4-Difluoromethyl-6-(4-trifluoromethyl-phenyl)-pyrimidin-2-yl]-[1,2,4]oxadiazol-3-yl}-benzenesulfonamide;

4-{5-[4-(3-Ethoxy-4-trifluoromethyl-phenyl)-6-trifluoromethyl-pyrimidin-2-yl]-[1,2,4]oxadiazol-3-yl}-benzenesulfonamide;

3-{5-[4-(3-Ethoxy-4-trifluoromethyl-phenyl)-6-trifluoromethyl-pyrimidin-2-yl]-[1,2,4]oxadiazol-3-yl}-benzenesulfonamide;

4-{5-[4-(3,4-Dichloro-phenyl)-6-trifluoromethyl-pyrimidin-2-yl]-[1,2,4]oxadiazol-3-yl}-benzenesulfonamide;

3-{5-[4-(3,4-Dichloro-phenyl)-6-trifluoromethyl-pyrimidin-2-yl]-[1,2,4]oxadiazol-3-yl}-benzenesulfonamide;

3-{5-[4-(4-Chloro-3-methyl-phenyl)-6-trifluoromethyl-pyrimidin-2-yl]-[1,2,4]oxadiazol-3-yl}-benzenesulfonamide;

4-{5-[4-Methyl-6-(4-trifluoromethyl-phenyl)-pyrimidin-2-yl]-[1,2,4]oxadiazol-3-yl}-benzenesulfonamide;

3-{5-[4-Methyl-6-(4-trifluoromethyl-phenyl)-pyrimidin-2-yl]-[1,2,4]oxadiazol-3-yl}-benzenesulfonamide;

4-{5-[4-(3-Methyl-4-trifluoromethyl-phenyl)-6-trifluoromethyl-pyrimidin-2-yl]-[1,2,4]oxadiazol-3-yl}-benzenesulfonamide;

3-{5-[4-(3-Methyl-4-trifluoromethyl-phenyl)-6-trifluoromethyl-pyrimidin-2-yl]-[1,2,4]oxadiazol-3-yl}-benzenesulfonamide;

4-{5-[4-(4-Chloro-phenyl)-6-methyl-pyrimidin-2-yl]-[1,2,4]oxadiazol-3-yl}-benzenesulfonamide;

N-tert-Butyl-3-{4-[4-trifluoromethyl-6-(4-trifluoromethyl-phenyl)-pyrimidin-2-yl]-pyridin-2-yl}-benzenesulfonamide;

3-{4-[4-Trifluoromethyl-6-(4-trifluoromethyl-phenyl)-pyrimidin-2-yl]-pyridin-2-yl}-benzenesulfonamide;

4-{1-[4-Trifluoromethyl-6-(4-trifluoromethyl-phenyl)-pyrimidin-2-yl]-1H-imidazol-4-yl}-benzenesulfonamide;

3-{1-[4-Trifluoromethyl-6-(4-trifluoromethyl-phenyl)-pyrimidin-2-yl]-1H-imidazol-4-yl}-benzenesulfonamide;

5-{4-[4-Trifluoromethyl-6-(4-trifluoromethyl-phenyl)-pyrimidin-2-yl]-pyridin-2-yl}-thiophene-2-sulfonic acid tert-butylamide;

5-{1-[4-Trifluoromethyl-6-(4-trifluoromethyl-phenyl)-pyrimidin-2-yl]-1H-imidazol-4-yl}-thiophene-2-sulfonic acid amide;

5-{4-[4-Trifluoromethyl-6-(4-trifluoromethyl-phenyl)-pyrimidin-2-yl]-pyridin-2-yl}-thiophene-2-sulfonic acid amide;

3-{4-[4-Methyl-6-(4-trifluoromethyl-phenyl)-pyrimidin-2-yl]-pyridin-2-yl}-benzenesulfonamide;

5-{4-[4-(4-Chloro-phenyl)-6-trifluoromethyl-pyrimidin-2-yl]-pyridin-2-yl}-thiophene-2-sulfonic acid amide;

5-{1-[4-(4-Chloro-phenyl)-6-trifluoromethyl-pyrimidin-2-yl]-1H-imidazol-4-yl}-thiophene-2-sulfonic acid amide;

4-{1-[4-(4-Chloro-phenyl)-6-trifluoromethyl-pyrimidin-2-yl]-1H-imidazol-4-yl}-benzenesulfonamide;

3-{1-[4-(4-Chloro-phenyl)-6-methyl-pyrimidin-2-yl]-1H-imidazol-4-yl}-benzenesulfonamide 3-{1-[4-(4-Chloro-phenyl)-6-trifluoromethyl-pyrimidin-2-yl]-1H-imidazol-4-yl}-benzenesulfonamide;

3-{4-[4-(4-Chloro-phenyl)-6-trifluoromethyl-pyrimidin-2-yl]-pyridin-2-yl}-benzenesulfonamide;

4-{1-[4-(4-Chloro-phenyl)-6-methyl-pyrimidin-2-yl]-1H-imidazol-4-yl}-benzenesulfonamide;

2-{1-[4-Trifluoromethyl-6-(4-trifluoromethyl-phenyl)-pyrimidin-2-yl]-1H-imidazol-4-yl}-thiazole-5-sulfonic acid amide;

2-{1-[4-(4-Chloro-phenyl)-6-trifluoromethyl-pyrimidin-2-yl]-1H-imidazol-4-yl}-thiazole-5-sulfonic acid amide;

4-{1-[4-Methyl-6-(4-trifluoromethyl-phenyl)-pyrimidin-2-yl]-1H-imidazol-4-yl}-benzenesulfonamide;

3-{1-[4-Methyl-6-(4-trifluoromethyl-phenyl)-pyrimidin-2-yl]-1H-imidazol-4-yl}-benzenesulfonamide;

3-{1-[4-(3-Chloro-phenyl)-6-trifluoromethyl-pyrimidin-2-yl]-1H-imidazol-4-yl}-benzenesulfonamide;

5-{1-[4-(3-Chloro-phenyl)-6-trifluoromethyl-pyrimidin-2-yl]-1H-imidazol-4-yl}-thiophene-2-sulfonic acid amide;

3-{4-[4-(4-Chloro-phenyl)-6-methyl-pyrimidin-2-yl]-pyridin-2-yl}-benzenesulfonamide;

5-{1-[4-(4-Chloro-phenyl)-6-methyl-pyrimidin-2-yl]-1H-imidazol-4-yl}-thiophene-2-sulfonic acid amide;

5-{1-[4-Methyl-6-(4-trifluoromethyl-phenyl)-pyrimidin-2-yl]-1H-imidazol-4-yl}-thiophene-2-sulfonic acid amide;

5-{4-[4-(4-Chloro-phenyl)-6-methyl-pyrimidin-2-yl]-pyridin-2-yl}-thiophene-2-sulfonic acid amide;

3-{4-[4-(3,4-Dichloro-phenyl)-6-methyl-pyrimidin-2-yl]-pyridin-2-yl}-benzenesulfonamide;

5-{4-[4-(3,4-Dichloro-phenyl)-6-methyl-pyrimidin-2-yl]-pyridin-2-yl}-thiophene-2-sulfonic acid amide;

5-{4-[4-Methyl-6-(4-trifluoromethyl-phenyl)-pyrimidin-2-yl]-pyridin-2-yl}-thiophene-2-sulfonic acid amide;

3-{1-[4-(3,4-Dichloro-phenyl)-6-methyl-pyrimidin-2-yl]-1H-imidazol-4-yl}-benzenesulfonamide;

4-{1-[4-(3,4-Dichloro-phenyl)-6-methyl-pyrimidin-2-yl]-1H-imidazol-4-yl}-benzenesulfonamide;

2-{1-[4-(4-Chloro-phenyl)-6-methyl-pyrimidin-2-yl]-1H-imidazol-4-yl}-thiazole-5-sulfonic acid amide;

2-{1-[4-(3,4-Dichloro-phenyl)-6-methyl-pyrimidin-2-yl]-1H-imidazol-4-yl}-thiazole-5-sulfonic acid amide;

3-{4-[4-(3,4-Dichloro-phenyl)-6-trifluoromethyl-pyrimidin-2-yl]-pyridin-2-yl}-benzenesulfonamide;

5-{4-[4-(3,4-Dichloro-phenyl)-6-trifluoromethyl-pyrimidin-2-yl]-pyridin-2-yl}-thiophene-2-sulfonic acid amide;

5-{1-[4-(3,4-Dichloro-phenyl)-6-trifluoromethyl-pyrimidin-2-yl]-1H-imidazol-4-yl}-thiophene-2-sulfonic acid amide;

5-{1-[4-(3-Methyl-4-trifluoromethyl-phenyl)-6-trifluoromethyl-pyrimidin-2-yl]-1H-imidazol-4-yl}-thiophene-2-sulfonic acid amide;

4-{1-[4-(3,4-Dichloro-phenyl)-6-trifluoromethyl-pyrimidin-2-yl]-1H-imidazol-4-yl}-benzenesulfonamide;

4-{1-[4-(3-Methyl-4-trifluoromethyl-phenyl)-6-trifluoromethyl-pyrimidin-2-yl]-1H-imidazol-4-yl}-benzenesulfonamide;

3-{1-[4-(3-Methyl-4-trifluoromethyl-phenyl)-6-trifluoromethyl-pyrimidin-2-yl]-1H-imidazol-4-yl}-benzenesulfonamide;

3-{1-[4-(3,4-Dichloro-phenyl)-6-trifluoromethyl-pyrimidin-2-yl]-1H-imidazol-4-yl}-benzenesulfonamide;

5-{1-[4-(3,4-Dichloro-phenyl)-6-methyl-pyrimidin-2-yl]-1H-imidazol-4-yl}-thiophene-2-sulfonic acid amide;

3-{1-[4-(4-Chloro-3-methyl-phenyl)-6-methyl-pyrimidin-2-yl]-1H-imidazol-4-yl}-benzenesulfonamide;

5-{1-[4-(4-Chloro-3-methyl-phenyl)-6-methyl-pyrimidin-2-yl]-1H-imidazol-4-yl}-thiophene-2-sulfonic acid amide;

N-tert-Butyl-3-{6-[4-trifluoromethyl-6-(4-trifluoromethyl-phenyl)-pyrimidin-2-yl]-pyridin-2-yl}-benzenesulfonamide;

3-{6-[4-Trifluoromethyl-6-(4-trifluoromethyl-phenyl)-pyrimidin-2-yl]-pyridin-2-yl}-benzenesulfonamide;

N,N-Bis-(2-{2-[2-(2-methoxy-ethoxy)-ethoxy]-ethoxy}-ethyl)-3-[6'-methyl-4'-(4-trifluoromethyl-phenyl)-[2,2']bipyridinyl-6-yl]-benzenesulfonamide;

N,N-Bis-(2-hydroxy-ethyl)-3-[6'-methyl-4'-(4-trifluoromethyl-phenyl)-[2,2']bipyridinyl-6-yl]-benzenesulfonamide;

N-(2-{2-[2-(2-Methoxy-ethoxy)-ethoxy]-ethoxy}-ethyl)-3-[6'-methyl-4'-(4-trifluoromethylphenyl)-[2,2']bipyridinyl-6-yl]-benzenesulfonamide;

N-Propionyl-3-{4-[4-trifluoromethyl-6-(4-trifluoromethyl-phenyl)-pyrimidin-2-yl]-pyridin-2-yl}-benzenesulfonamide;

5-{4-[4-Trifluoromethyl-6-(4-trifluoromethyl-phenyl)-pyrimidin-2-yl]-pyridin-2-yl}-thiophene-2-sulfonic acid propionyl-amide;

N-(2-Hydroxy-ethyl)-3-{4-[4-trifluoromethyl-6-(4-trifluoromethyl-phenyl)-pyrimidin-2-yl]-pyridin-2-yl}-benzenesulfonamide;

N-(2-Hydroxy-1,1-dimethyl-ethyl)-3-{4-[4-trifluoromethyl-6-(4-trifluoromethyl-phenyl)pyrimidin-2-yl]-pyridin-2-yl}-benzenesulfonamide;

N,N-Bis-(2-hydroxy-ethyl)-3-{4-[4-trifluoromethyl-6-(4-trifluoromethyl-phenyl)-pyrimidin-2-yl]-pyridin-2-yl}-benzenesulfonamide;

5-{1-[4-(3,4-Difluoro-phenyl)-6-trifluoromethyl-pyrimidin-2-yl]-1H-imidazol-4-yl}-thiophene-2-sulfonic acid amide;

5-{1-[4-(4-Fluoro-phenyl)-6-trifluoromethyl-pyrimidin-2-yl]-1H-imidazol-4-yl}-thiophene-2-sulfonic acid amide;

3-{1-[4-(4-Fluoro-phenyl)-6-trifluoromethyl-pyrimidin-2-yl]-1H-imidazol-4-yl}-benzenesulfonamide;

3-{1-[4-(3,4-Difluoro-phenyl)-6-trifluoromethyl-pyrimidin-2-yl]-1H-imidazol-4-yl}-benzenesulfonamide;
5-{4-[4-(4-Fluoro-phenyl)-6-trifluoromethyl-pyrimidin-2-yl]-pyridin-2-yl}-thiophene-2-sulfonic acid amide;
3-{4-[4-(4-Fluoro-phenyl)-6-trifluoromethyl-pyrimidin-2-yl]-pyridin-2-yl}-benzenesulfonamide;
5-{4-[4-(3,4-Difluoro-phenyl)-6-trifluoromethyl-pyrimidin-2-yl]-pyridin-2-yl}-thiophene-2-sulfonic acid amide;
3-{4-[4-(3,4-Difluoro-phenyl)-6-trifluoromethyl-pyrimidin-2-yl]-pyridin-2-yl}-benzenesulfonamide;
N,N-Dimethyl-3-{4-[4-trifluoromethyl-6-(4-trifluoromethyl-phenyl)-pyrimidin-2-yl]-pyridin-2-yl}-benzenesulfonamide;
N-Methyl-3-{4-[4-trifluoromethyl-6-(4-trifluoromethyl-phenyl)-pyrimidin-2-yl]-pyridin-2-yl}-benzenesulfonamide;
N-Isobutyl-N-methyl-3-{4-[4-trifluoromethyl-6-(4-trifluoromethyl-phenyl)-pyrimidin-2-yl]-pyridin-2-yl}-benzenesulfonamide;
N-Methyl-N-propyl-3-{4-[4-trifluoromethyl-6-(4-trifluoromethyl-phenyl)-pyrimidin-2-yl]-pyridin-2-yl}-benzenesulfonamide;
N-Benzyl-3-{4-[4-trifluoromethyl-6-(4-trifluoromethyl-phenyl)-pyrimidin-2-yl]-pyridin-2-yl}-benzenesulfonamide;
N-Phenethyl-3-{4-[4-trifluoromethyl-6-(4-trifluoromethyl-phenyl)-pyrimidin-2-yl]-pyridin-2-yl}-benzenesulfonamide;
N-Cyclopropylmethyl-3-{4-[4-trifluoromethyl-6-(4-trifluoromethyl-phenyl)-pyrimidin-2-yl]-pyridin-2-yl}-benzenesulfonamide;
N-Cyclopropyl-3-{4-[4-trifluoromethyl-6-(4-trifluoromethyl-phenyl)-pyrimidin-2-yl]-pyridin-2-yl}-benzenesulfonamide;
5-{4-[4-(4-Chloro-3-methyl-phenyl)-6-trifluoromethyl-pyrimidin-2-yl]-pyridin-2-yl}-thiophene-2-sulfonic acid amide;
3-{4-[4-(4-Chloro-3-methyl-phenyl)-6-trifluoromethyl-pyrimidin-2-yl]-pyridin-2-yl}-benzenesulfonamide;
N-tert-Butyl-3-{6-[4-methyl-6-(4-trifluoromethyl-phenyl)-pyrimidin-2-yl]-pyridin-2-yl}-benzenesulfonamide;
3-{6-[4-Methyl-6-(4-trifluoromethyl-phenyl)-pyrimidin-2-yl]-pyridin-2-yl}-benzenesulfonamide;
N-tert-Butyl-3-{6-[4-(4-cyano-phenyl)-6-methyl-pyrimidin-2-yl]-pyridin-2-yl}-benzenesulfonamide;
3-{6-[4-(4-Cyano-phenyl)-6-methyl-pyrimidin-2-yl]-pyridin-2-yl}-benzenesulfonamide;
3-(4-{4-[3-(2,2,2-Trifluoro-ethoxy)-4-trifluoromethyl-phenyl]-6-trifluoromethyl-pyrimidin-2-yl}-pyridin-2-yl)-benzenesulfonamide;
3-f{4-[4-Trifluoromethyl-6-(3-trifluoromethyl-phenyl)-pyrimidin-2-yl]-pyridin-2-yl}-benzenesulfonamide;
3-{4-[4-(2-Fluoro-4-trifluoromethyl-phenyl)-6-trifluoromethyl-pyrimidin-2-yl]-pyridin-2-yl}-benzenesulfonamide;
5-{4-[4-(2-Fluoro-4-trifluoromethyl-phenyl)-6-trifluoromethyl-pyrimidin-2-yl]-pyridin-2-yl}-thiophene-2-sulfonic acid amide;
3-{4-[4-(3-Ethoxy-4-trifluoromethyl-phenyl)-6-trifluoromethyl-pyrimidin-2-yl]-pyridin-2-yl}-benzenesulfonamide;
5-{4-[4-(3-Ethoxy-4-trifluoromethyl-phenyl)-6-trifluoromethyl-pyrimidin-2-yl]-pyridin-2-yl}-thiophene-2-sulfonic acid amide;
3-{4-[4-Difluoromethyl-6-(4-trifluoromethyl-phenyl)-pyrimidin-2-yl]-pyridin-2-yl}-benzenesulfonamide; and
5-{4-[4-Difluoromethyl-6-(4-trifluoromethyl-phenyl)-pyrimidin-2-yl]-pyridin-2-yl}-thiophene-2-sulfonic acid amide.

In a certain embodiment of the invention, the compounds of formula (Ia2) are those compounds wherein B is optionally substituted aryl or an optionally substituted 5 or 6 membered heteroaryl, wherein the substituent is —$(SO_2)$—$NR^fR^g$, wherein $R^f$ and $R^g$ together with the nitrogen atom to which they are attached form a 4, 5 or 6 membered heterocycloalkyl ring optionally containing a further heteroatom selected from nitrogen, oxygen, sulphur and an $SO_2$ group, wherein said 4, 5 or 6 membered heterocycloalkyl ring is optionally substituted by hydroxy or $C_{1-6}$-alkyl, for example the following compounds:

4-(3-{4-[4-Trifluoromethyl-6-(4-trifluoromethyl-phenyl)-pyrimidin-2-yl]-pyridin-2-yl}-benzenesulfonyl)-morpholine;
2-{2-[3-(4-Methyl-piperazine-1-sulfonyl)-phenyl]-pyridin-4-yl}-4-trifluoromethyl-6-(4-trifluoromethyl-phenyl)-pyrimidine;
2-{2-[3-(Pyrrolidine-1-sulfonyl)-phenyl]-pyridin-4-yl}-4-trifluoromethyl-6-(4-trifluoromethylphenyl)-pyrimidine; and
(RS)-1-(3-{4-[4-Trifluoromethyl-6-(4-trifluoromethyl-phenyl)-pyrimidin-2-yl]-pyridin-2-yl}-benzenesulfonyl)-pyrrolidin-3-ol.

Also encompassed by the compounds of formula (I) according to the invention are the compounds of formula (I-b):

(Ib)

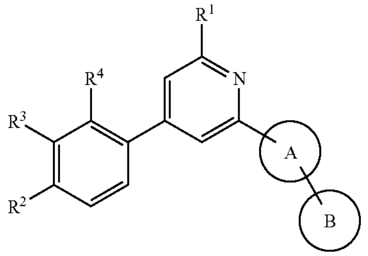

wherein A, B, $R^1$, $R^2$ and $R^3$ are as defined for formula (I) hereinabove.

In a certain embodiment of the invention, the compounds of formula (Ia2) are those compounds wherein:

A is aryl or 5 or 6 membered heteroaryl each of which is optionally substituted by $C_{1-6}$-alkyl;

B is
- H,
- cyano
- an optionally substituted aryl or an optionally substituted 5 or 6 membered heteroaryl, wherein the substituents are selected from the group consisting of:
  - halo,
  - nitro,
  - $C_{1-6}$-alkyl optionally substituted by hydroxy, and
  - $NR^aR^b$, wherein $R^a$ and $R^b$ are independently H or —(CO)—$C_{1-6}$-alkyl,
- S—$C_{1-6}$-alkyl,
- $(SO_2)$—OH,
- $(SO_2)$—$C_{1-6}$-alkyl,
- $(SO_2)$—$NR^cR^d$, wherein $R^c$ and $R^d$ are independently:
  - H,
  - $C_{1-6}$-alkyl optionally substituted by hydroxy,
  - $C_{1-6}$-haloalkyl, or
  - $C_{1-6}$-alkoxy,
- $(CO)C_{1-6}$-alkyl optionally substituted by $C_{1-6}$-alkoxy, $(CH_2CH_2O)_nCHR^e$, wherein $R^e$ is H or $CH_2OH$ and n is 1, 2, 3, 4, 5, 6, 7, 8, 9 or 10, $(CH_2)_m$-aryl, wherein m is 1 or 2 and the aryl is optionally substituted by halo or $C_{1-6}$-alkoxy, $(CH_2)_p$—$C_{3-6}$-cycloalkyl, wherein p is 0 or 1, 5 or 6-membered heterocycloalkyl, $(SO_2)$—$NR^fR^g$, wherein $R^f$ and $R^g$ together with the nitrogen atom to which they are attached form a 4, 5 or 6 membered heterocycloalkyl ring optionally containing a further heteroatom selected from nitrogen, oxygen, sulphur and an $SO_2$ group, wherein said 4, 5 or 6 membered heterocycloalkyl ring is optionally substituted by a substituent selected from the group consisting of hydroxy, $C_{1-6}$-alkyl, $C_{1-6}$-alkoxy which is optionally substituted by hydroxy, and 5 or 6 membered heteroaryloxy, $NHSO_2$—$C_{1-6}$-alkyl, and $NHSO_2$—$NR^hR^i$ wherein $R^h$ and $R^i$ are independently H, $C_{1-6}$-alkyl, —(CO)O—$C_{1-6}$-alkyl, or $R^h$ and $R^i$ together with the nitrogen atom to which they are attached form a 4, 5 or 6 membered heterocycloalkyl ring optionally containing a further heteroatom selected from nitrogen, oxygen and sulphur, wherein said 4, 5 or 6 membered heterocycloalkyl ring is optionally substituted by $C_{1-6}$-alkyl;

$R^1$ is H, halogen, $C_{1-6}$-alkyl optionally substituted by hydroxy, $C_{1-6}$-alkoxy, $C_{1-6}$-haloalkyl, or $C_{3-6}$-cycloalkyl;

$R^2$ is H, cyano, halogen, $C_{1-6}$-haloalkyl, $C_{1-6}$-alkoxy, $C_{1-6}$-haloalkoxy, $C_{1-6}$-alkyl or $C_{3-6}$-cycloalkyl;

$R^3$ is halogen, H, $C_{1-6}$-alkoxy, $C_{1-6}$-haloalkyl, $C_{1-6}$-alkyl, $C_{3-6}$-cycloalkyl, $C_{1-6}$-haloalkoxy, or is $NR^jR^k$ wherein $R^j$ and $R^k$ are independently selected from the group consisting of:

H, $C_{3-8}$-cycloalkyl, aryl, heteroaryl having from 5 to 12 ring atoms and $C_{1-6}$-alkyl each of which is optionally substituted by one or more substituent(s) selected from the group consisting of halogen, hydroxy, $C_{3-8}$-cycloalkyl, aryl, heteroaryl having from 5 to 12 ring atoms and —$NR^lR^m$, wherein $R^1$ and $R^m$ are independently selected from the group consisting of H and $C_{1-6}$-alkyl;

or $R^l$ and $R^m$ can, together with the nitrogen atom to which they are attached, form an optionally substituted heterocyclic group comprising 5 to 12 ring atoms optionally containing a further heteroatom selected from nitrogen, oxygen and sulphur, wherein said heteroaryl group is optionally substituted by one, two, three, four or five substituents are selected from the group consisting of halogen, hydroxy, $C_{1-6}$-alkyl and $C_{1-6}$-haloalkyl;

or $R^2$ and $R^3$ can together form a dioxo bridge;

$R^4$ is H or halo;

and pharmaceutically acceptable salts thereof.

In a certain embodiment of the invention, the compounds of formula (Ia2) are those compounds wherein:

A is aryl or 5 or 6 membered heteroaryl each of which is optionally substituted by $C_{1-6}$-alkyl;

B is H or cyano;

$R^1$ is H, halogen, $C_{1-6}$-alkyl optionally substituted by hydroxy, $C_{1-6}$-alkoxy, $C_{1-6}$-haloalkyl, or $C_{3-6}$-cycloalkyl;

$R^2$ is H, cyano, halogen, $C_{1-6}$-haloalkyl, $C_{1-6}$-alkoxy, $C_{1-6}$-haloalkoxy, $C_{1-6}$-alkyl or $C_{3-6}$-cycloalkyl;

$R^3$ is H, halogen, $C_{1-6}$-alkoxy, $C_{1-6}$-haloalkyl, $C_{1-6}$-alkyl or $C_{1-6}$-haloalkoxy and still preferably, F, Cl, methoxy, ethoxy, $CF_3$, methyl, or trifluoroethoxy;

or $R^2$ and $R^3$ can together form a dioxo bridge;

$R^4$ is H or halo;

and pharmaceutically acceptable salts thereof.

In a certain embodiment of the invention, the compounds of formula (Ia2) are those compounds wherein:

A is aryl or 5 or 6 membered heteroaryl each of which is optionally substituted by $C_{1-6}$-alkyl;

B is an optionally substituted aryl or an optionally substituted 5 or 6 membered heteroaryl, wherein the substituents are selected from the group consisting of:

halo, nitro, $C_{1-6}$-alkyl, $NR^aR^b$, wherein $R^a$ and $R^b$ are independently H or —(CO)—$C_{1-6}$-alkyl, S—$C_{1-6}$-alkyl, $(SO_2)$—OH, $(SO_2)$—$C_{1-6}$-alkyl, $(SO_2)$—$NR^cR^d$, wherein $R^c$ and $R^d$ are independently:

H, $C_{1-6}$-alkyl optionally substituted by hydroxy, $C_{1-6}$-haloalkyl, or $C_{1-6}$-alkoxy, $(CO)C_{1-6}$-alkyl optionally substituted by $C_{1-6}$-alkoxy, $(CH_2CH_2O)_nCHR^e$, wherein $R^e$ is H or $CH_2OH$ and n is 1, 2, 3, 4, 5, 6, 7, 8, 9 or 10, $(CH_2)_m$-aryl, wherein m is 1 or 2 and the aryl is optionally substituted by halo or $C_{1-6}$-alkoxy, $(CH_2)_p$—$C_{3-6}$-cycloalkyl, wherein p is 0 or 1, 5 or 6-membered heterocycloalkyl, $(SO_2)$—$NR^fR^g$, wherein $R^f$ and $R^g$ together with the nitrogen atom to which they are attached form a 4, 5 or 6 membered heterocycloalkyl ring optionally containing a further heteroatom selected from nitrogen, oxygen, sulphur and an $SO_2$ group, wherein said 4, 5 or 6 membered heterocycloalkyl ring is optionally substituted by a substituent selected from the group consisting of hydroxy, $C_{1-6}$-alkyl, $C_{1-6}$-alkoxy optionally substituted by hydroxy, and 5 or 6 membered heteroaryloxy, $NHSO_2$—$C_{1-6}$-alkyl, and $NHSO_2$—$NR^hR^i$ wherein $R^h$ and $R^i$ are independently H, $C_{1-6}$-alkyl or —(CO)O—$C_{1-6}$-alkyl;

$R^1$ is H, halogen, $C_{1-6}$-alkyl optionally substituted by hydroxy, $C_{1-6}$-alkoxy, $C_{1-6}$-haloalkyl, or $C_{3-6}$-cycloalkyl;

$R^2$ is H, cyano, halogen, $C_{1-6}$-haloalkyl, $C_{1-6}$-alkoxy, $C_{1-6}$-haloalkoxy, $C_{1-6}$-alkyl or $C_{3-6}$-cycloalkyl;

$R^3$ is H, halogen, $C_{1-6}$-alkoxy, $C_{1-6}$-haloalkyl, $C_{1-6}$-alkyl or $C_{1-6}$-haloalkoxy and still preferably, F, Cl, methoxy, ethoxy, $CF_3$, methyl, or trifluoroethoxy;

or $R^2$ and $R^3$ can together form a dioxo bridge;

$R^4$ is H or halo;

and pharmaceutically acceptable salts thereof.

Encompassed by the compounds of formula (I) according to the invention are the compound of formula (I-b):

(Ib1)

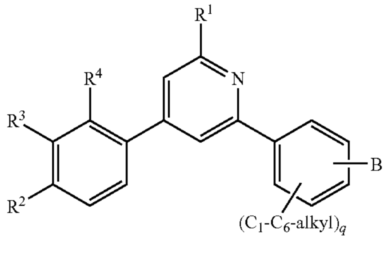

wherein B, $R^1$, $R^2$, $R^3$ and $R^4$ are as defined hereinabove for formulae (I) and (Ib) and q is 0, 1, 2, 3, or 4.

In a certain embodiment of the invention, the compounds of formula (Iab 1) are those compounds wherein B is an unsubstituted aryl or an unsubstituted 5 or 6 membered heteroaryl, for example the following compounds:

2-Methyl-6-(3-pyridin-3-yl-phenyl)-4-(4-trifluoromethyl-phenyl)-pyridine;

2-Cyclopropyl-6-(3-pyridin-3-yl-phenyl)-4-(4-trifluoromethyl-phenyl)-pyridine; and 2-Methyl-6-(3-pyridin-4-yl-phenyl)-4-(4-trifluoromethyl-phenyl)-pyridine.

In a certain embodiment of the invention, the compounds of formula (Ib1) are those compounds wherein B is an optionally substituted aryl or an optionally substituted 5 or 6 membered heteroaryl, wherein the substituent is cyano, for example the following compound:

3-[6-Methyl-4-(4-trifluoromethyl-phenyl)-pyridin-2-yl]-benzonitrile.

In a certain embodiment of the invention, the compounds of formula (Ib1) are those compounds wherein B is an optionally substituted aryl or an optionally substituted 5 or 6 membered heteroaryl, wherein the substituent is halo, for example the following compound:

4,6-Difluoro-3'-[6-methyl-4-(4-trifluoromethyl-phenyl)-pyridin-2-yl]-biphenyl-3-sulfonic acid amide.

In a certain embodiment of the invention, the compounds of formula (Ib1) are those compounds wherein B is an optionally substituted aryl or an optionally substituted 5 or 6 membered heteroaryl, wherein the substituent is $C_{1-6}$-alkyl, for example the following compound:

2-Methyl-6-[3-(4-methyl-imidazol-1-yl)-phenyl]-4-(4-trifluoromethyl-phenyl)-pyridine.

In a certain embodiment of the invention, the compounds of formula (Ib1) are those compounds wherein B is an optionally substituted aryl or an optionally substituted 5 or 6 membered heteroaryl, wherein the substituent is $NR^aR^b$, wherein $R^a$ and $R^b$ are independently H or —(CO)—$C_{1-6}$-alkyl, for example the following compounds:

5-{3-[6-Methyl-4-(4-trifluoromethyl-phenyl)-pyridin-2-yl]-phenyl}-pyridin-2-ylamine;

5-{3-[6-Cyclopropyl-4-(4-trifluoromethyl-phenyl)-pyridin-2-yl]-phenyl}-pyridin-2-ylamine;

5-{3-[6-Methyl-4-(4-trifluoromethyl-phenyl)-pyridin-2-yl]-phenyl}-pyrimidin-2-ylamine;

5-{3-[4-(4-Chloro-phenyl)-6-methyl-pyridin-2-yl]-phenyl}-pyrimidin-2-ylamine;

5-{3-[4-(4-Chloro-phenyl)-6-methyl-pyridin-2-yl]-phenyl}-pyridin-2-ylamine;

5-{3-[6-Trifluoromethyl-4-(4-trifluoromethyl-phenyl)-pyridin-2-yl]-phenyl}-pyridin-2-ylamine;

5-{3-[6-Trifluoromethyl-4-(4-trifluoromethyl-phenyl)-pyridin-2-yl]-phenyl}-pyrimidin-2-ylamine;

5-{3-[4-(4-Chloro-phenyl)-6-trifluoromethyl-pyridin-2-yl]-phenyl}-pyrimidin-2-ylamine;

5-{3-[4-(4-Chloro-phenyl)-6-trifluoromethyl-pyridin-2-yl]-phenyl}-pyridin-2-ylamine;

5-{3-[4-(3,4-Dichloro-phenyl)-6-methyl-pyridin-2-yl]-phenyl}-pyridin-2-ylamine;

5-{3-[4-(3,4-Dichloro-phenyl)-6-methyl-pyridin-2-yl]-phenyl}-pyrimidin-2-ylamine;

5-{3-[6-Ethyl-4-(4-trifluoromethyl-phenyl)-pyridin-2-yl]-phenyl}-pyrimidin-2-ylamine;

5-{3-[6-Ethyl-4-(4-trifluoromethyl-phenyl)-pyridin-2-yl]-phenyl}-pyridin-2-ylamine;

5-[3-(4-Benzo[1,3]dioxol-5-yl-6-methyl-pyridin-2-yl)-phenyl]-pyridin-2-ylamine; and 4-{3-[6-Methyl-4-(4-trifluoromethyl-phenyl)-pyridin-2-yl]-phenyl}-thiazol-2-ylamine.

In a certain embodiment of the invention, the compounds of formula (Ib1) are those compounds wherein B is an optionally substituted aryl or an optionally substituted 5 or 6 membered heteroaryl, wherein the substituent is —$(SO_2)$—$C_{1-6}$-alkyl, for example the following compound: 2-(3'-Methanesulfonyl-biphenyl-3-yl)-6-methyl-4-(4-trifluoromethyl-phenyl)pyridine.

In a certain embodiment of the invention, the compounds of formula (Ib1) are those compounds wherein B is an optionally substituted aryl or an optionally substituted 5 or 6 membered heteroaryl, wherein the substituent is —$(SO_2)$—$NR^c R^d$, wherein $R^c$ and $R^d$ are independently:

H, $C_{1-6}$-alkyl optionally substituted by hydroxy, $C_{1-6}$-haloalkyl, $C_{1-6}$-alkoxy, $(CO)C_{1-6}$-alkyl optionally substituted by $C_{1-6}$-alkoxy, —

—$(CH_2CH_2O)_nCHR^e$ wherein $R^e$ is H or $CH_2OH$ and n is 1, 2, 3, 4, 5, 6, 7, 8, 9 or 10, $(CH_2)_m$-aryl, wherein m is 1 or 2 and the aryl is optionally substituted by halo or $C_{1-6}$-alkoxy, $(CH_2)_p$—$C_{3-6}$-cycloalkyl, wherein p is 0 or 1 or 5 or 6-membered heterocycloalkyl, for example the following compounds:

3'-[6-Trifluoromethyl-4-(4-trifluoromethyl-phenyl)-pyridin-2-yl]-biphenyl-3-sulfonic acid amide;

5-{3-[6-Trifluoromethyl-4-(4-trifluoromethyl-phenyl)-pyridin-2-yl]-phenyl}-pyridine-3-sulfonic acid amide;

5-{3-[6-Methyl-4-(4-trifluoromethyl-phenyl)-pyridin-2-yl]-phenyl}-pyridine-3-sulfonic acid amide;

5-{3-[6-Methyl-4-(4-trifluoromethyl-phenyl)-pyridin-2-yl]-phenyl}-pyridine-3-sulfonic acid (2-hydroxy-1,1-dimethyl-ethyl)-amide;

3'-[6-Methyl-4-(4-trifluoromethyl-phenyl)-pyridin-2-yl]-biphenyl-3-sulfonic acid methoxy-amide;

3'-[6-Methyl-4-(4-trifluoromethyl-phenyl)-pyridin-2-yl]-biphenyl-3-sulfonic acid (2-hydroxy-1,1-dimethyl-ethyl)-amide;

3'-[6-Ethyl-4-(4-trifluoromethyl-phenyl)-pyridin-2-yl]-biphenyl-3-sulfonic acid tert-butylamide;

3'-[6-Ethyl-4-(4-trifluoromethyl-phenyl)-pyridin-2-yl]-biphenyl-3-sulfonic acid amide;

4,6-Difluoro-3'-[6-methyl-4-(4-trifluoromethyl-phenyl)-pyridin-2-yl]-biphenyl-3-sulfonic acid amide;

5-{3-[6-Methyl-4-(4-trifluoromethyl-phenyl)-pyridin-2-yl]-phenyl}-thiophene-2-sulfonic acid amide;

3'-[6-Methyl-4-(4-trifluoromethyl-phenyl)-pyridin-2-yl]-biphenyl-3-sulfonic acid amide; and N-(tert-Butoxycarbonyl)-N'-(4-{3-[6-methyl-4-(4-trifluoromethyl-phenyl)-pyridin-2-yl]-phenyl}-thiazol-2-yl)-sulfamide.

Encompassed by the compounds of formula (I) according to the invention are the compound of formula (I-b11):

(Ib11)

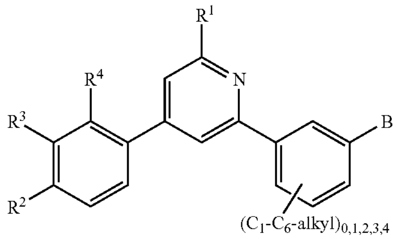

wherein B, $R^1$, $R^2$, $R^3$ and $R^4$ are as defined hereinabove for formulae (I), (Ib) and (Ib1).

Encompassed by the compounds of formula (I) according to the invention are the compound of formula (I-b2):

(Ib2)

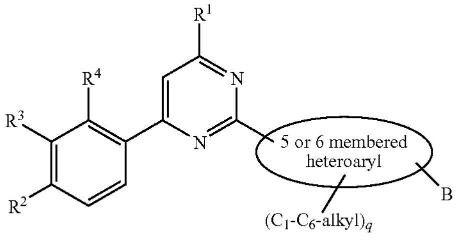

wherein B, $R^1$, $R^2$, $R^3$ and $R^4$ are as defined hereinabove for formula (I) and q is 0, 1, 2, 3, or 4.

The 5 or 6 membered heteroaryl can be selected from the group consisting of: imidazolyl, [1,2,4]oxadiazolyl], pyrrolyl, 1H-pyrazolyl, pyridinyl, [1,2,4]triazolyl, thiazolyl, pyrimidinyl and thiophenyl and preferably, thiazolyl, imidazolyl, [1,2,4]oxadiazolyl], pyridinyl, pyrimidinyl, thiophenyl and [1,2,4]triazolyl.

In a certain embodiment of the invention, the compounds of formula (Ib2) are those compounds wherein:

B is H or cyano, preferably H;

$R^1$ is $C_{1-6}$-alkyl or $C_{1-6}$-haloalkyl;

$R^2$ is halogen or $C_{1-6}$-haloalkyl;

$R^3$ is H, halogen, $C_{1-6}$-alkoxy, $C_{1-6}$-haloalkyl, $C_{1-6}$-alkyl or $C_{1-6}$-haloalkoxy;

$R^4$ is H or halo;

and pharmaceutically acceptable salts thereof.

In a certain embodiment of the invention, the compounds of formula (Ib2) are those compounds wherein B is H, for example the following compounds:

2-Imidazol-1-yl-6-methyl-4-(4-trifluoromethyl-phenyl)-pyridine;

4-(3,4-Dichloro-phenyl)-2-imidazol-1-yl-6-methyl-pyridine; and

2-Methyl-6-thiazol-2-yl-4-(4-trifluoromethyl-phenyl)-pyridine.

In a certain embodiment of the invention, the compounds of formula (Ia3) are those compounds wherein B is an optionally substituted aryl or an optionally substituted 5 or 6 membered heteroaryl, wherein the substituents are selected from the group consisting of:

nitro, $C_{1-6}$-alkyl optionally substituted by hydroxy, $C_{1-6}$-haloalkyl, $NR^aR^b$, wherein $R^a$ and $R^b$ are independently H or —(CO)—$C_{1-6}$-alkyl, S—$C_{1-6}$-alkyl, $NHSO_2$—$C_{1-6}$-alkyl, —$NHSO_2$—$NR^hR^i$ wherein $R^h$ and $R^i$ are independently H, $C_{1-6}$-alkyl or —(CO)O—$C_{1-6}$-alkyl —($SO_2$)—$C_{1-6}$-alkyl, ($SO_2$)—OH, ($SO_2$)—$NR^cR^d$, wherein $R^c$ and $R^d$ are independently:

H, or $C_{1-6}$-alkyl optionally substituted by hydroxy or halo, (CO)$C_{1-6}$-alkyl optionally substituted by $C_{1-6}$-alkoxy, $(CH_2CH_2O)_nCHR^e$, wherein $R^e$ is H or $CH_2OH$ and n is 1, 2, 3, 4, 5, 6, 7, 8, 9 or 10, $(CH_2)_m$-aryl, wherein m is 1 or 2 and the aryl is optionally substituted by halo or $C_{1-6}$-alkoxy, $(CH_2)_p$—$C_{3-6}$-cycloalkyl, wherein p is 0 or 1, 5 or 6-membered heterocycloalkyl, and ($SO_2$)—$NR^fR^g$, wherein $R^f$ and $R^g$ together with the nitrogen atom to which they are attached form a 4, 5 or 6 membered heterocycloalkyl ring optionally containing a further heteroatom selected from nitrogen, oxygen, sulphur and an $SO_2$ group, wherein said 4, 5 or 6 membered heterocycloalkyl ring is optionally substituted by a substituent selected from the group consisting of hydroxy, $C_{1-6}$-alkyl, $C_{1-6}$-alkoxy optionally substituted by hydroxy, and heteroaryloxy, $R^1$ is $C_{1-6}$-alkyl or $C_{1-6}$-haloalkyl;

$R^2$ is halogen or $C_{1-6}$-haloalkyl;

$R^3$ is H, halogen, $C_{1-6}$-alkoxy, $C_{1-6}$-haloalkyl, $C_{1-6}$-alkyl or $C_{1-6}$-haloalkoxy;

$R^4$ is H or halo;

and pharmaceutically acceptable salts thereof.

In a certain embodiment of the invention, the compounds of formula (Ia2) are those compounds wherein B is an optionally substituted aryl or an optionally substituted 5 or 6 membered heteroaryl, wherein the substituent is nitro, for example the following compounds: 6-Methyl-2'-(3-nitro-phenyl)-4-(4-trifluoromethyl-phenyl)-[2,4']bipyridinyl and 4-[6-Methyl-4-(4-trifluoromethyl-phenyl)-pyridin-2-yl]-2-(3-nitro-phenyl)-pyrimidine.

In a certain embodiment of the invention, the compounds of formula (Ia2) are those compounds wherein B is an optionally substituted aryl or an optionally substituted 5 or 6 membered heteroaryl, wherein the substituent is $NR^aR^b$, wherein $R^a$ and $R^b$ are independently H or —(CO)—$C_{1-6}$-alkyl, for example the following compounds:

5-{1-[6-Cyclopropyl-4-(4-trifluoromethyl-phenyl)-pyridin-2-yl]-1H-imidazol-4-yl}-pyridin-2-ylamine;

5-{1-[6-Methyl-4-(4-trifluoromethyl-phenyl)-pyridin-2-yl]-1H-imidazol-4-yl}-pyridin-2-ylamine;

6-Methyl-4-(4-trifluoromethyl-phenyl)-[2,3';5',3"]terpyridin-6"-ylamine;

5-[6-Methyl-4-(4-trifluoromethyl-phenyl)-[2,3']bipyridinyl-5'-yl]-pyrimidin-2-ylamine;

6-Cyclopropyl-4-(4-trifluoromethyl-phenyl)-[2,3';5',3"]terpyridin-6"-ylamine;

6-Methyl-4-(4-trifluoromethyl-phenyl)-[2,2';6',3"]terpyridin-6"-ylamine;

5-[6'-Methyl-4'-(4-trifluoromethyl-phenyl)-[2,2']bipyridinyl-6-yl]-pyrimidin-2-ylamine;

6-Methyl-4-(4-trifluoromethyl-phenyl)-[2,4';2',3"]terpyridin-6"-ylamine;

5-[6-Methyl-4-(4-trifluoromethyl-phenyl)-[2,4']bipyridinyl-2'-yl]-pyrimidin-2-ylamine;

6-Cyclopropyl-4-(4-trifluoromethyl-phenyl)-[2,4';2',3"]terpyridin-6"-ylamine;

5-[6-Cyclopropyl-4-(4-trifluoromethyl-phenyl)-[2,4']bipyridinyl-2'-yl]-pyrimidin-2-ylamine;

5-{1-[4-(4-Chloro-phenyl)-6-methyl-pyridin-2-yl]-1H-imidazol-4-yl}-pyridin-2-ylamine;

4-(4-Chloro-phenyl)-6-methyl-[2,3';5',3"]terpyridin-6"-ylamine;

5-{2-[6-Methyl-4-(4-trifluoromethyl-phenyl)-pyridin-2-yl]-thiazol-4-yl}-pyridin-2-ylamine;

5-{2-[6-Methyl-4-(4-trifluoromethyl-phenyl)-pyridin-2-yl]-thiazol-4-yl}-pyrimidin-2-ylamine;

5-{5-[6-Methyl-4-(4-trifluoromethyl-phenyl)-pyridin-2-yl]-[1,2,4]oxadiazol-3-yl}-pyridin-2-ylamine;

5-{5-[4-Trifluoromethyl-6-(4-trifluoromethyl-phenyl)-pyridin-2-yl]-[1,2,4]oxadiazol-3-yl}-pyridin-2-ylamine;

5-{4-[6-Methyl-4-(4-trifluoromethyl-phenyl)-pyridin-2-yl]-pyrimidin-2-yl}-pyridin-2-ylamine;

4-[6-Methyl-4-(4-trifluoromethyl-phenyl)-pyridin-2-yl]-[2,5']bipyrimidinyl-2'-ylamine;

5-{2-[6-Methyl-4-(4-trifluoromethyl-phenyl)-pyridin-2-yl]-pyrimidin-4-yl}-pyridin-2-ylamine;

5-{1-[4-(3,4-Dichloro-phenyl)-6-methyl-pyridin-2-yl]-1H-imidazol-4-yl}-pyridin-2-ylamine;

5-{5-[6-Methyl-4-(4-trifluoromethyl-phenyl)-pyridin-2-yl]-thiophen-2-yl}-pyridin-2-ylamine;

5-{5-[6-Methyl-4-(4-trifluoromethyl-phenyl)-pyridin-2-yl]-thiophen-2-yl}-pyrimidin-2-ylamine;

5-{5-[4-(3,4-Dichloro-phenyl)-6-methyl-pyridin-2-yl]-thiophen-2-yl}-pyridin-2-ylamine;

5-{5-[4-(3,4-Dichloro-phenyl)-6-methyl-pyridin-2-yl]-thiophen-2-yl}-pyrimidin-2-ylamine;

5-{5-[6-Methyl-4-(4-trifluoromethyl-phenyl)-pyridin-2-yl]-thiophen-3-yl}-pyridin-2-ylamine;

3-[6-Methyl-4-(4-trifluoromethyl-phenyl)-[2,4']bipyridinyl-2'-yl]-phenylamine;

3-{4-[6-Methyl-4-(4-trifluoromethyl-phenyl)-pyridin-2-yl]-pyrimidin-2-yl}-phenylamine;

3-[6'-Methyl-4'-(4-trifluoromethyl-phenyl)-[2,2']bipyridinyl-6-yl]-phenylamine;

N-(3-{4-[6-Methyl-4-(4-trifluoromethyl-phenyl)-pyridin-2-yl]-pyrimidin-2-yl}-phenyl)acetamide;

N-{3-[6'-Methyl-4'-(4-trifluoromethyl-phenyl)-[2,2']bipyridinyl-6-yl]-phenyl}-acetamide;

6-Methyl-4-(4-trifluoromethyl-phenyl)-[2,2';6',4"]terpyridin-2"-ylamine;

4-{4-[6-Methyl-4-(4-trifluoromethyl-phenyl)-pyridin-2-yl]-pyrimidin-2-yl}-pyridin-2-ylamine; and 3-[4-Methyl-6-(4-trifluoromethyl-phenyl)-[2,4']bipyridinyl-2'-yl]-phenylamine.

In a certain embodiment of the invention, the compounds of formula (Ia2) are those compounds wherein B is an optionally substituted aryl or an optionally substituted 5 or 6 membered heteroaryl, wherein the substituent is —S—$C_{1-6}$-alkyl, for example the following compound: 6-Methyl-6'-(3-methylsulfanyl-phenyl)-4-(4-trifluoromethyl-phenyl)-[2,2']bipyridinyl.

In a certain embodiment of the invention, the compounds of formula (Ia2) are those compounds wherein B is an optionally substituted aryl or an optionally substituted 5 or 6 membered heteroaryl, wherein the substituent is $S(O)_2$—$C_{1-6}$-alkyl for example the following compounds: 2-(3-Methanesulfonyl-phenyl)-4-[6-methyl-4-(4-trifluoromethyl-phenyl)-pyridin-2-yl]-pyrimidine and 6'-(3-Methanesulfonyl-phenyl)-6-methyl-4-(4-trifluoromethyl-phenyl)-[2,2']bipyridinyl.

In a certain embodiment of the invention, the compounds of formula (Ia2) are those compounds wherein B is an optionally substituted aryl or an optionally substituted 5 or 6 membered heteroaryl, wherein the substituent is —$(SO_2)$—$NR^cR^d$, wherein $R^c$ and $R^d$ are independently:

H, $C_{1-6}$-alkyl optionally substituted by hydroxyl or halo, $(CO)C_{1-6}$-alkyl optionally substituted by $C_{1-6}$-alkoxy, $(CH_2CH_2O)_nCHR^e$, wherein $R^e$ is H or $CH_2OH$ and n is 1, 2, 3, 4, 5, 6, 7, 8, 9 or 10, $(CH_2)_m$-aryl optionally substituted by halo, or $C_{1-6}$-alkoxy, wherein m is 1 or 2 and the aryl is optionally substituted by halo or $C_{1-6}$-alkoxy, $(CH_2)_p$—$C_{3-6}$-cycloalkyl, wherein p is 0 or 1 or 5 or 6-membered heterocycloalkyl, for example the following compounds:

4-[6'-Methyl-4'-(4-trifluoromethyl-phenyl)-[2,2']bipyridinyl-6-yl]-benzenesulfonamide;

3-{5-[6-Methyl-4-(4-trifluoromethyl-phenyl)-pyridin-2-yl]-[1,2,4]oxadiazol-3-yl}-benzenesulfonamide;

N-tert-Butyl-3-[6'-methyl-4'-(4-trifluoromethyl-phenyl)-[2,2']bipyridinyl-6-yl]-benzenesulfonamide;

N-tert-Butyl-3-{4-[6-methyl-4-(4-trifluoromethyl-phenyl)-pyridin-2-yl]-pyrimidin-2-yl}-benzenesulfonamide;

N-tert-Butyl-3-{2-[6-methyl-4-(4-trifluoromethyl-phenyl)-pyridin-2-yl]-thiazol-4-yl}-benzenesulfonamide;

3-[6'-Methyl-4'-(4-trifluoromethyl-phenyl)-[2,2']bipyridinyl-6-yl]-benzenesulfonamide;

3-{4-[6-Methyl-4-(4-trifluoromethyl-phenyl)-pyridin-2-yl]-pyrimidin-2-yl}-benzenesulfonamide;

3-{2-[6-Methyl-4-(4-trifluoromethyl-phenyl)-pyridin-2-yl]-thiazol-4-yl}-benzenesulfonamide;

N-tert-Butyl-3-[6-methyl-4-(4-trifluoromethyl-phenyl)-[2,4']bipyridinyl-2'-yl]-benzenesulfonamide;

N-tert-Butyl-3-[6-methyl-4-(4-trifluoromethyl-phenyl)-[2,3']bipyridinyl-5'-yl]-benzenesulfonamide;

3-[6-Methyl-4-(4-trifluoromethyl-phenyl)-[2,4']bipyridinyl-2'-yl]-benzenesulfonamide;

N-tert-Butyl-3-{1-[6-trifluoromethyl-4-(4-trifluoromethyl-phenyl)-pyridin-2-yl]-1H-imidazol-4-yl}-benzenesulfonamide;

3-[6-Methyl-4-(4-trifluoromethyl-phenyl)-[2,3']bipyridinyl-5'-yl]-benzenesulfonamide;

3-{1-[6-Trifluoromethyl-4-(4-trifluoromethyl-phenyl)-pyridin-2-yl]-1H-imidazol-4-yl}-benzenesulfonamide;

4-Methyl-2-{1-[6-trifluoromethyl-4-(4-trifluoromethyl-phenyl)-pyridin-2-yl]-1H-imidazol-4-yl}-thiazole-5-sulfonic acid tert-butylamide;

5-{1-[6-Trifluoromethyl-4-(4-trifluoromethyl-phenyl)-pyridin-2-yl]-1H-imidazol-4-yl}-thiophene-2-sulfonic acid tert-butylamide;

2-{1-[6-Trifluoromethyl-4-(4-trifluoromethyl-phenyl)-pyridin-2-yl]-1H-imidazol-4-yl}-thiazole-5-sulfonic acid tert-butylamide;

5-{4-[6-Methyl-4-(4-trifluoromethyl-phenyl)-pyridin-2-yl]-pyrimidin-2-yl}-thiophene-2-sulfonic acid tert-butylamide;

5-[6-Methyl-4-(4-trifluoromethyl-phenyl)-[2,4']bipyridinyl-2'-yl]-thiophene-2-sulfonic acid tert-butylamide;

5-[6'-Methyl-4'-(4-trifluoromethyl-phenyl)-[2,2']bipyridinyl-6-yl]-thiophene-2-sulfonic acid tert-butylamide;

4-Methyl-2-{1-[6-trifluoromethyl-4-(4-trifluoromethyl-phenyl)-pyridin-2-yl]-1H-imidazol-4-yl}-thiazole-5-sulfonic acid amide;

2-{1-[6-Trifluoromethyl-4-(4-trifluoromethyl-phenyl)-pyridin-2-yl]-1H-imidazol-4-yl}-thiazole-5-sulfonic acid amide;

5-{1-[6-Trifluoromethyl-4-(4-trifluoromethyl-phenyl)-pyridin-2-yl]-1H-imidazol-4-yl}-thiophene-2-sulfonic acid amide;

5-{4-[6-Methyl-4-(4-trifluoromethyl-phenyl)-pyridin-2-yl]-pyrimidin-2-yl}-thiophene-2-sulfonic acid amide;

5-[6-Methyl-4-(4-trifluoromethyl-phenyl)-[2,4']bipyridinyl-2'-yl]-thiophene-2-sulfonic acid amide;

5-[6'-Methyl-4'-(4-trifluoromethyl-phenyl)-[2,2']bipyridinyl-6-yl]-thiophene-2-sulfonic acid amide;

5-{2-[6-Methyl-4-(4-trifluoromethyl-phenyl)-pyridin-2-yl]-thiazol-4-yl}-thiophene-2-sulfonic acid tert-butylamide;

5-{2-[6-Methyl-4-(4-trifluoromethyl-phenyl)-pyridin-2-yl]-thiazol-4-yl}-thiophene-2-sulfonic acid amide;

4-{4-[6-Methyl-4-(4-trifluoromethyl-phenyl)-pyridin-2-yl]-pyrimidin-2-yl}-benzenesulfonamide;

4-[6-Methyl-4-(4-trifluoromethyl-phenyl)-[2,4']bipyridinyl-2'-yl]-benzenesulfonamide;

N-tert-Butyl-3-[4-(3-methoxy-4-trifluoromethyl-phenyl)-6-methyl-[2,4']bipyridinyl-2'-yl]-benzenesulfonamide;

5-[4-(3-Methoxy-4-trifluoromethyl-phenyl)-6-methyl-[2,4']bipyridinyl-2'-yl]-thiophene-2-sulfonic acid tert-butylamide;

3-[4-(3-Methoxy-4-trifluoromethyl-phenyl)-6-methyl-[2,4']bipyridinyl-2'-yl]-benzenesulfonamide;

5-[4-(3-Methoxy-4-trifluoromethyl-phenyl)-6-methyl-[2,4']bipyridinyl-2'-yl]-thiophene-2-sulfonic acid amide;

N-(2-Hydroxy-ethyl)-3-[6-methyl-4-(4-trifluoromethyl-phenyl)-[2,4']bipyridinyl-2'-yl]-benzenesulfonamide;

N-(2-Hydroxy-1,1-dimethyl-ethyl)-3-[6-methyl-4-(4-trifluoromethyl-phenyl)-[2,4']bipyridinyl-2'-yl]-benzenesulfonamide;

3-[6'-Methyl-4'-(4-trifluoromethyl-phenyl)-[2,2']bipyridinyl-6-yl]-N-propionyl-benzenesulfonamide;

N-(2-Hydroxy-ethyl)-3-[6'-methyl-4'-(4-trifluoromethyl-phenyl)-[2,2']bipyridinyl-6-yl]-benzenesulfonamide;

N-(2-Hydroxy-1,1-dimethyl-ethyl)-3-[6'-methyl-4'-(4-trifluoromethyl-phenyl)-[2,2']bipyridinyl-6-yl]-benzenesulfonamide;

N-(2-Methoxy-ethyl)-3-[6'-methyl-4'-(4-trifluoromethyl-phenyl)-[2,2']bipyridinyl-6-yl]-benzenesulfonamide;

N-[2-(2-Hydroxy-ethoxy)-ethyl]-3-[6'-methyl-4'-(4-trifluoromethyl-phenyl)-[2,2']bipyridinyl-6-yl]-benzenesulfonamide;

N-[2-(2-Methoxy-ethoxy)-ethyl]-3-[6'-methyl-4'-(4-trifluoromethyl-phenyl)-[2,2']bipyridinyl-6-yl]-benzenesulfonamide;

N-{2-[2-(2-Methoxy-ethoxy)-ethoxy]-ethyl}-3-[6'-methyl-4'-(4-trifluoromethyl-phenyl)-[2,2']bipyridinyl-6-yl]-benzenesulfonamide;

N-Methyl-3-[6'-methyl-4'-(4-trifluoromethyl-phenyl)-[2,2']bipyridinyl-6-yl]-benzenesulfonamide;

N,N-Dimethyl-3-[6'-methyl-4'-(4-trifluoromethyl-phenyl)-[2,2']bipyridinyl-6-yl]-benzenesulfonamide;

N-Cyclopropyl-3-[6'-methyl-4'-(4-trifluoromethyl-phenyl)-[2,2']bipyridinyl-6-yl]-benzenesulfonamide;

N-Cyclopropyl-N-methyl-3-[6'-methyl-4'-(4-trifluoromethyl-phenyl)-[2,2']bipyridinyl-6-yl]-benzenesulfonamide;

N-Benzyl-3-[6'-methyl-4'-(4-trifluoromethyl-phenyl)-[2,2']bipyridinyl-6-yl]-benzenesulfonamide;

N-(4-Methoxy-benzyl)-3-[6'-methyl-4'-(4-trifluoromethyl-phenyl)-[2,2']bipyridinyl-6-yl]-benzenesulfonamide;

N-(4-Fluoro-benzyl)-3-[6'-methyl-4'-(4-trifluoromethyl-phenyl)-[2,2']bipyridinyl-6-yl]-benzenesulfonamide;

N-tert-Butyl-3-[6'-methyl-4'-(4-trifluoromethoxy-phenyl)-[2,2']bipyridinyl-6-yl]-benzenesulfonamide;

3-[6'-Methyl-4'-(4-trifluoromethoxy-phenyl)-[2,2']bipyridinyl-6-yl]-benzenesulfonamide;

N-tert-Butyl-3-[6'-methyl-4'-(3-methyl-4-trifluoromethyl-phenyl)-[2,2']bipyridinyl-6-yl]-benzenesulfonamide;

3-[6'-Hydroxymethyl-4'-(4-trifluoromethyl-phenyl)-[2,2']bipyridinyl-6-yl]-benzenesulfonamide;

3-[6'-Methyl-4'-(3-methyl-4-trifluoromethyl-phenyl)-[2,2']bipyridinyl-6-yl]-benzenesulfonamide;

N-Acetyl-3-[6'-methyl-4'-(4-trifluoromethyl-phenyl)-[2,2']bipyridinyl-6-yl]-benzenesulfonamide;

3-[6'-Methyl-4'-(4-trifluoromethyl-phenyl)-[2,2']bipyridinyl-6-yl]-N-(tetrahydro-pyran-4-yl)benzenesulfonamide;

3-[6'-Methyl-4'-(4-trifluoromethyl-phenyl)-[2,2']bipyridinyl-6-yl]-N-(2,2,2-trifluoro-ethyl)benzenesulfonamide;

N-Ethyl-3-[6'-methyl-4'-(4-trifluoromethyl-phenyl)-[2,2']bipyridinyl-6-yl]-benzenesulfonamide;

N-Butyryl-3-[6'-methyl-4'-(4-trifluoromethyl-phenyl)-[2,2']bipyridinyl-6-yl]-benzenesulfonamide; and N-Isobutyryl-3-[6'-methyl-4'-(4-trifluoromethyl-phenyl)-[2,2']bipyridinyl-6-yl]-benzenesulfonamide.

In a certain embodiment of the invention, the compounds of formula (Ia2) are those compounds wherein B is an optionally substituted aryl or an optionally substituted 5 or 6 membered heteroaryl, wherein the substituent is $NHSO_2$—$C_{1-6}$-alkyl, for example the following compounds:

N-{3-[6-Methyl-4-(4-trifluoromethyl-phenyl)-[2,4']bipyridinyl-2'-yl]-phenyl}-methanesulfonamide;

N-(3-{4-[6-Methyl-4-(4-trifluoromethyl-phenyl)-pyridin-2-yl]-pyrimidin-2-yl}-phenyl)methanesulfonamide; and N-{3-[6'-Methyl-4'-(4-trifluoromethyl-phenyl)-[2,2']bipyridinyl-6-yl]-phenyl}-methanesulfonamide.

In a certain embodiment of the invention, the compounds of formula (Ia2) are those compounds wherein B is an optionally substituted aryl or an optionally substituted 5 or 6 membered heteroaryl, wherein the substituent is —$SO_2$—OH, for example the following compound: 3-[6'-Methyl-4'-(4-trifluoromethyl-phenyl)-[2,2']bipyridinyl-6-yl]-benzenesulfonic acid.

In a certain embodiment of the invention, the compounds of formula (Ia2) are those compounds wherein B is an optionally substituted aryl or an optionally substituted 5 or 6 membered heteroaryl, wherein the substituent is $NHSO_2$—$NR^hR^i$ wherein $R^h$ and $R^i$ are independently H, $C_{1-6}$-alkyl or —(CO)O—$C_{1-6}$-alkyl, for example the following compounds:

N-(tert-Butoxycarbonyl)-N'-{3-[6'-methyl-4'-(4-trifluoromethyl-phenyl)-[2,2']bipyridinyl-6-yl]-phenyl}-sulfamide;

N-(tert-Butoxycarbonyl)-N'-(3-{4-[6-methyl-4-(4-trifluoromethyl-phenyl)-pyridin-2-yl]-pyrimidin-2-yl}-phenyl)-sulfamide;

N-{3-[6'-Methyl-4'-(4-trifluoromethyl-phenyl)-[2,2']bipyridinyl-6-yl]-phenyl}-sulfamide;

N-(3-{4-[6-Methyl-4-(4-trifluoromethyl-phenyl)-pyridin-2-yl]-pyrimidin-2-yl}-phenyl)sulfamide; and N,N-(Dimethyl)-N'-{3-[6'-methyl-4'-(4-trifluoromethyl-phenyl)-[2,2']bipyridinyl-6-yl]-phenyl}-sulfamide.

In a certain embodiment of the invention, the compounds of formula (Ia2) are those compounds wherein B is an optionally substituted aryl or an optionally substituted 5 or 6 membered heteroaryl, wherein the substituent is —$(SO_2)$—$NR^fR^g$, wherein $R^f$ and $R^g$ together with the nitrogen atom to which they are attached form a 4, 5 or 6 membered heterocycloalkyl ring optionally containing a further heteroatom selected from nitrogen, oxygen, sulphur and an $SO_2$ group, wherein said 4, 5 or 6 membered heterocycloalkyl ring is optionally substituted by a substituent selected from the group consisting of hydroxy, $C_{1-6}$-alkyl, $C_{1-6}$-alkoxy optionally substituted by hydroxy, and heteroaryloxy, for example the following compounds:

6-Methyl-2'-[3-(morpholine-4-sulfonyl)-phenyl]-4-(4-trifluoromethyl-phenyl)-[2,4']bipyridinyl 6-Methyl-2'-[3-(thiomorpholine-4-sulfonyl)-phenyl]-4-(4-trifluoromethyl-phenyl)-[2,4']bipyridinyl 6-Methyl-2'-[3-(4-methyl-piperazine-1-sulfonyl)-phenyl]-4-(4-trifluoromethyl-phenyl)-[2,4']bipyridinyl Morpholine-4-sulfonic acid {3-[6'-methyl-4'-(4-trifluoromethyl-phenyl)-[2,2']bipyridinyl-6-yl]-phenyl}-amide 6'-[3-(1,1-Dioxo-1×6-thiomorpholine-4-sulfonyl)-phenyl]-6-methyl-4-(4-trifluoromethylphenyl)-[2,2']bipyridinyl 6-Methyl-6'-[3-(pyrrolidine-1-sulfonyl)-phenyl]-4-(4-trifluoromethyl-phenyl)-[2,2']bipyridinyl 6-Methyl-6'-[3-(4-methyl-piperazine-1-sulfonyl)-phenyl]-4-(4-trifluoromethyl-phenyl)-[2,2']bipyridinyl 6-Methyl-6'-[3-(morpholine-4-sulfonyl)-phenyl]-4-(4-trifluoromethyl-phenyl)-[2,2']bipyridinyl 6'-[3-(Azetidine-1-sulfonyl)-phenyl]-6-methyl-4-(4-trifluoromethyl-phenyl)-[2,2']bipyridinyl 1-{3-[6'-Methyl-4'-(4-trifluoromethyl-phenyl)-[2,2']bipyridinyl-6-yl]-benzenesulfonyl}-piperidin-4-ol 1-{3-[6'-Methyl-4'-(4-trifluoromethyl-phenyl)-[2,2']bipyridinyl-6-yl]-benzenesulfonyl}-azetidin-3-ol 6'-[3-(4-Methoxy-piperidine-1-sulfonyl)-phenyl]-6-methyl-4-(4-trifluoromethyl-phenyl)-[2,2']bipyridinyl 2-(1-{3-[6'-Methyl-4'-(4-trifluoromethyl-phenyl)-[2,2']bipyridinyl-6-yl]-benzenesulfonyl}-piperidin-4-yloxy)-ethanol 6-Methyl-6'-{3-[4-(pyridin-4-yloxy)-piperidine-1-sulfonyl]-phenyl}-4-(4-trifluoromethylphenyl)-[2,2']bipyridinyl; and 6-Methyl-6'-{3-[4-(pyrimidin-2-yloxy)-piperidine-1-sulfonyl]-phenyl}-4-(4-trifluoromethylphenyl)-[2,2']bipyridinyl.

Also encompassed by the compounds of formula (I) according to the invention are the compounds of formula (I-c):

(Ic)

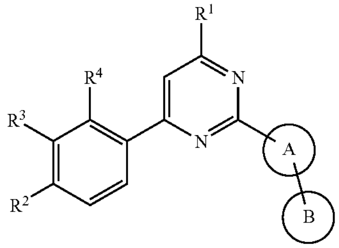

wherein A, B, $R^1$, $R^2$ and $R^3$ are as defined for formula (I) hereinabove.

In a certain embodiment, the compounds of formula (Ic) according to the invention are those compounds wherein:

A is aryl or 5 or 6 membered heteroaryl each of which is optionally substituted by $C_{1-6}$-alkyl;

B is H or cyano;

$R^1$ is halogen, $C_{1-6}$-alkyl optionally substituted by hydroxy, $C_{1-6}$-alkoxy, $C_{1-6}$-haloalkyl, or $C_{3-6}$-cycloalkyl;

$R^2$ is halogen, $C_{1-6}$-haloalkyl, $C_{1-6}$-alkoxy, $C_{1-6}$-haloalkoxy, $C_{1-6}$-alkyl or $C_{3-6}$-cycloalkyl;

$R^3$ is halogen, H, $C_{1-6}$-alkoxy, $C_{1-6}$-haloalkyl, $C_{1-6}$-alkyl, $C_{3-6}$-cycloalkyl, $C_{1-6}$-haloalkoxy, or is $NR^jR^k$ wherein $R^j$ and $R^k$ are independently selected from the group consisting of:

H, $C_{3-8}$-cycloalkyl, aryl, heteroaryl having from 5 to 12 ring atoms, and $C_{1-6}$-alkyl each of which is optionally substituted by one or more substituent(s) selected from the group consisting of halogen, hydroxy, $C_{3-8}$-cycloalkyl, aryl, heteroaryl having from 5 to 12 ring atoms, and —$NR^lR^m$, wherein $R^l$ and $R^m$ are independently selected from the group consisting of H and $C_{1-6}$-alkyl;

or $R^l$ and $R^m$ can, together with the nitrogen atom to which they are attached, form an optionally substituted heterocyclic group comprising 5 to 12 ring atoms optionally containing a further heteroatom selected from nitrogen, oxygen and sulphur, wherein said heteroaryl group is optionally substituted by one, two, three, four or five substituents selected from the group consisting of halogen, hydroxy, $C_{1-6}$-alkyl and $C_{1-6}$-haloalkyl;

or $R^2$ and $R^3$ can together form a dioxo bridge;

and pharmaceutically acceptable salts thereof.

In a certain embodiment, the compounds of formula (Ic) according to the invention are those compounds wherein:

A is aryl or 5 or 6 membered heteroaryl each of which is optionally substituted by $C_{1-6}$-alkyl;

B is an optionally substituted aryl or an optionally substituted 5 or 6 membered heteroaryl, wherein the substituents are selected from the group consisting of:

halo, nitro, $C_{1-6}$-alkyl optionally substituted by hydroxy, $NR^aR^b$, wherein $R^a$ and $R^b$ are independently H or —(CO)—$C_{1-6}$-alkyl, S—$C_{1-6}$-alkyl, $(SO_2)$—OH, $(SO_2)$—$C_{1-6}$-alkyl, $(SO_2)$—$NR^cR^d$, wherein $R^c$ and $R^d$ are independently:

H, $C_{1-6}$-alkyl optionally substituted by hydroxy, $C_{1-6}$-haloalkyl, or $C_{1-6}$-alkoxy, $(CO)C_{1-6}$-alkyl optionally substituted by $C_{1-6}$-alkoxy, $(CH_2CH_2O)_nCHR^e$, wherein $R^e$ is H or $CH_2OH$ and n is 1, 2, 3, 4, 5, 6, 7, 8, 9 or 10, $(CH_2)_m$-aryl, wherein m is 1 or 2 and the aryl is optionally substituted by halo or $C_{1-6}$-alkoxy, $(CH_2)_p$—$C_{3-6}$-cycloalkyl, wherein p is 0 or 1, 5 or 6-membered heterocycloalkyl, $(SO_2)$—$NR^fR^g$, wherein $R^f$ and $R^g$ together with the nitrogen atom to which they are attached form a 4, 5 or 6 membered heterocycloalkyl ring optionally containing a further heteroatom selected from nitrogen, oxygen, sulphur and an $SO_2$ group, wherein said 4, 5 or 6 membered heterocycloalkyl ring is optionally substituted by a substituent selected from the group consisting of hydroxy, $C_{1-6}$-alkyl, $C_{1-6}$-alkoxy optionally substituted by hydroxy, and 5 or 6 membered heteroaryloxy, $NHSO_2$—$C_{1-6}$-alkyl, and $NHSO_2$—$NR^hR^i$ wherein $R^h$ and $R^i$ are independently H, $C_{1-6}$-alkyl, —(CO)O—$C_{1-6}$-alkyl, or $R^h$ and $R^i$ together with the nitrogen atom to which they are attached form a 4, 5 or 6 membered heterocycloalkyl ring optionally containing a further heteroatom selected from nitrogen, oxygen and sulphur, wherein said 4, 5 or 6 membered heterocycloalkyl ring is optionally substituted by $C_{1-6}$-alkyl;

$R^1$ is halogen, $C_{1-6}$-alkyl optionally substituted by hydroxy, $C_{1-6}$-alkoxy, $C_{1-6}$-haloalkyl, or $C_{3-6}$-cycloalkyl;

$R^2$ is halogen, $C_{1-6}$-haloalkyl, $C_{1-6}$-alkoxy, $C_{1-6}$-haloalkoxy, $C_{1-6}$-alkyl or $C_{3-6}$-cycloalkyl;

$R^3$ is halogen, H, $C_{1-6}$-alkoxy, $C_{1-6}$-haloalkyl, $C_{1-6}$-alkyl, $C_{3-6}$-cycloalkyl, $C_{1-6}$-haloalkoxy, or is $NR^jR^k$ wherein $R^j$ and $R^k$ are independently selected from the group consisting of:

H, $C_{3-8}$-cycloalkyl, aryl, heteroaryl having from 5 to 12 ring atoms and $C_{1-6}$-alkyl which optionally substituted by one or more substituent(s) selected from the group consisting of halogen, hydroxy, $C_{3-8}$-cycloalkyl, aryl, heteroaryl having from 5 to 12 ring atoms, and —$NR^l R^m$, wherein $R^l$ and $R^m$ are independently selected from the group consisting of H and $C_{1-6}$-alkyl;

or $R^l$ and $R^m$ can, together with the nitrogen atom to which they are attached, form an optionally substituted heterocyclic group comprising 5 to 12 ring atoms optionally containing a further heteroatom selected from nitrogen, oxygen and sulphur, wherein said heteroaryl group is optionally substituted by one, two, three, four or five substituents are selected from the group consisting of halogen, hydroxy, $C_{1-6}$-alkyl and $C_{1-6}$-haloalkyl;

or $R^2$ and $R^3$ can together form a dioxo bridge;

and pharmaceutically acceptable salts thereof.

Encompassed by the compounds of formula (I) according to the invention are the compounds of formula (I-c1):

(Ic1)

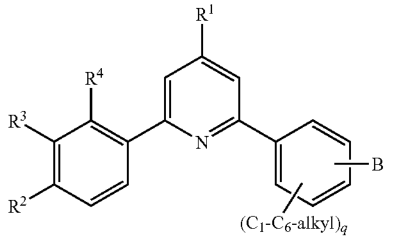

wherein B, $R^1$, $R^2$, $R^3$ and $R^4$ are as defined hereinabove for formulae (I) and (Ic) and q is 0, 1, 2, 3, or 4.

In a certain embodiment, the compounds of formula (Ic1) according to the invention are those compounds wherein B is an unsubstituted aryl or an unsubstituted 5 or 6 membered heteroaryl, for example the following compound: 2-(3-Pyridin-3-yl-phenyl)-4-trifluoromethyl-6-(4-trifluoromethyl-phenyl)-pyridine.

In a certain embodiment, the compounds of formula (Ic1) according to the invention are those compounds wherein B is an optionally substituted aryl or an optionally substituted 5 or 6 membered heteroaryl, wherein the substituents is $NR^aR^b$, wherein $R^a$ and $R^b$ are independently H or —(CO)—$C_{1-6}$-alkyl, for example the following compounds:

5-{3-[4-Trifluoromethyl-6-(4-trifluoromethyl-phenyl)-pyridin-2-yl]-phenyl}-pyridin-2-ylamine and 5-{3-[4-Methyl-6-(4-trifluoromethyl-phenyl)-pyridin-2-yl]-phenyl}-pyridine-3-sulfonic acid amide.

In a certain embodiment, the compounds of formula (Ic1) according to the invention are those compounds wherein B is an optionally substituted aryl or an optionally substituted 5 or 6 membered heteroaryl, wherein the substituent is —$(SO_2)$—$NR^cR^d$, wherein $R^c$ and $R^d$ are independently

H, $C_{1-6}$-alkyl optionally substituted by hydroxy, $C_{1-6}$-haloalkyl, $C_{1-6}$-alkoxy, —(CO)$C_{1-6}$-alkyl optionally substituted by $C_{1-6}$-alkoxy, —$(CH_2CH_2O)_nCHR^e$, wherein $R^e$ is H or $CH_2OH$ and n is 1, 2, 3, 4, 5, 6, 7, 8, 9 or 10, —$(CH_2)_m$-aryl, wherein m is 1 or 2 and the aryl is optionally substituted by halo or $C_{1-6}$-alkoxy, —$(CH_2)_p$—$C_{3-6}$-cycloalkyl, wherein p is 0 or 1, 5 or 6-membered heterocycloalkyl, for example the following compounds:

3'-[4-Trifluoromethyl-6-(4-trifluoromethyl-phenyl)-pyridin-2-yl]-biphenyl-3-sulfonic acid amide;

5-{3-[4-Methyl-6-(4-trifluoromethyl-phenyl)-pyridin-2-yl]-phenyl}-thiophene-2-sulfonic acid tert-butylamide;

5-{3-[4-Methyl-6-(4-trifluoromethyl-phenyl)-pyridin-2-yl]-phenyl}-thiophene-2-sulfonic acid amide; and 3'-[4-Methyl-6-(4-trifluoromethyl-phenyl)-pyridin-2-yl]-biphenyl-3-sulfonic acid amide.

Encompassed by the compounds of formula (I) according to the invention are the compound of formula (I-c11):

(Ic11)

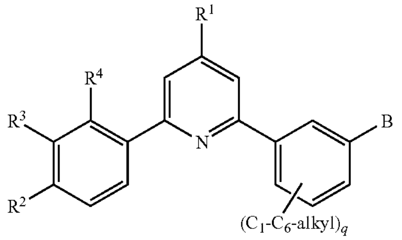

wherein B, $R^1$, $R^2$, $R^3$ and $R^4$ are as defined hereinabove for formulae (I), (Ic) and (Ic1) and q is 0, 1, 2, 3, or 4.

Encompassed by the compounds of formula (I) according to the invention are the compound of formula (I-c2):

(Ic2)

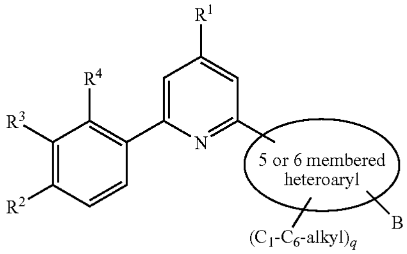

wherein B, $R^1$, $R^2$, $R^3$ and $R^4$ are as defined hereinabove for formulae (I) and (Ic) and q is 0, 1, 2, 3, or 4.

The 5 or 6 membered heteroaryl can be selected from the group consisting of: imidazolyl, [1,2,4]oxadiazolyl], pyrrolyl, 1H-pyrazolyl, pyridinyl, [1,2,4]triazolyl, thiazolyl, pyrimidinyl and thiophenyl and preferably imidazolyl, [1,2,4]oxadiazolyl], pyridinyl, pyrimidinyl and [1,2,4]triazolyl.

In a certain embodiment, the compounds of formula (Ic2) according to the invention are those compounds wherein B is an unsubstituted aryl or an unsubstituted 5 or 6 membered heteroaryl, for example the following compound: 2-(4-Chloro-phenyl)-6-(4-pyridin-3-yl-imidazol-1-yl)-4-trifluoromethyl-pyridine.

In a certain embodiment, the compounds of formula (Ic2) according to the invention are those compounds wherein B is an optionally substituted aryl or an optionally substituted 5 or 6 membered heteroaryl, wherein the substituents is $C_{1-6}$-alkyl, for example the following compound:

4-Methyl-2-{1-[4-trifluoromethyl-6-(4-trifluoromethyl-phenyl)-pyridin-2-yl]-1H-imidazol-4-yl}-thiazole-5-sulfonic acid tert-butylamide; and 4-Methyl-2-{1-[4-trifluoromethyl-6-(4-trifluoromethyl-phenyl)-pyridin-2-yl]-1H-imidazol-4-yl}-thiazole-5-sulfonic acid amide.

In a certain embodiment, the compounds of formula (Ic2) according to the invention are those compounds wherein B is an optionally substituted aryl or an optionally substituted 5 or 6 membered heteroaryl, wherein the substituent is $NR^aR^b$, wherein $R^a$ and $R^b$ are independently H or —(CO)—$C_1$-$C_6$-alkyl, for example the following compounds:

5-{1-[4-Trifluoromethyl-6-(4-trifluoromethyl-phenyl)-pyridin-2-yl]-1H-imidazol-4-yl}-pyridin-2-ylamine;

5-{1-[4-Trifluoromethyl-6-(4-trifluoromethyl-phenyl)-pyridin-2-yl]-1H-imidazol-4-yl}-pyrimidin-2-ylamine;

4-Trifluoromethyl-6-(4-trifluoromethyl-phenyl)-[2,4';2',3"]terpyridin-6"-ylamine;

5-{1-[6-(4-Chloro-phenyl)-4-trifluoromethyl-pyridin-2-yl]-1H-imidazol-4-yl}-pyridin-2-ylamine; and 5-{1-[4-Trifluoromethyl-6-(4-trifluoromethyl-phenyl)-pyridin-2-yl]-1H-[1,2,4]triazol-3-yl}-pyridin-2-ylamine.

In a certain embodiment, the compounds of formula (Ic2) according to the invention are those compounds wherein B is an optionally substituted aryl or an optionally substituted 5 or 6 membered heteroaryl, wherein the substituents is —($SO_2$)—$C_1$-$C_6$-alkyl, for example the following compounds:

2-{1-[6-Trifluoromethyl-4-(4-trifluoromethyl-phenyl)-pyridin-2-yl]-1H-imidazol-4-yl}-thiazole-5-sulfonic acid amide and 2-[4-(3-Methanesulfonyl-phenyl)-imidazol-1-yl]-4-trifluoromethyl-6-(4-trifluoromethylphenyl)-pyridine.

In a certain embodiment, the compounds of formula (Ic2) according to the invention are those compounds wherein B is an optionally substituted aryl or an optionally substituted 5 or 6 membered heteroaryl, wherein the substituents is —($SO_2$)—$NR^cR^d$, wherein $R^c$ and $R^d$ are independently

H, $C_{1-6}$-alkyl optionally substituted by hydroxy, $C_{1-6}$-haloalkyl, $C_{1-6}$-alkoxy, —(CO)$C_{1-6}$-alkyl optionally substituted by $C_{1-6}$-alkoxy, —$(CH_2CH_2O)_n$$CHR^e$, wherein $R^e$ is H or $CH_2OH$ and n is 1, 2, 3, 4, 5, 6, 7, 8, 9 or 10, —$(CH_2)_m$-aryl, wherein m is 1 or 2 and the aryl is optionally substituted by halo or $C_{1-6}$-alkoxy, —$(CH_2)_p$—$C_{3-6}$-cycloalkyl, wherein p is 0 or 1, or 5 or 6-membered heterocycloalkyl, for example the following compounds:

3-{5-[4-Trifluoromethyl-6-(4-trifluoromethyl-phenyl)-pyridin-2-yl]-[1,2,4]oxadiazol-3-yl}-benzenesulfonamide;

5-{1-[4-Trifluoromethyl-6-(4-trifluoromethyl-phenyl)-pyridin-2-yl]-1H-imidazol-4-yl}-thiophene-2-sulfonic acid tert-butylamide;

5-{1-[4-Trifluoromethyl-6-(4-trifluoromethyl-phenyl)-pyridin-2-yl]-1H-imidazol-4-yl}-thiophene-2-sulfonic acid amide;

N-tert-Butyl-3-{1-[4-trifluoromethyl-6-(4-trifluoromethyl-phenyl)-pyridin-2-yl]-1H-imidazol-4-yl}-benzene-sulfonamide;

2-{1-[4-Trifluoromethyl-6-(4-trifluoromethyl-phenyl)-pyridin-2-yl]-H-imidazol-4-yl}-thiazole-5-sulfonic acid tert-butylamide;

3-{1-[4-Trifluoromethyl-6-(4-trifluoromethyl-phenyl)-pyridin-2-yl]-1H-[1,2,4]triazol-3-yl}-benzenesulfonamide;

3-{1-[4-Trifluoromethyl-6-(4-trifluoromethyl-phenyl)-pyridin-2-yl]-1H-imidazol-4-yl}-benzenesulfonamide;

2-{1-[4-Trifluoromethyl-6-(4-trifluoromethyl-phenyl)-pyridin-2-yl]-1H-imidazol-4-yl}-thiazole-5-sulfonic acid amide;

N-tert-Butyl-3-[4-trifluoromethyl-6-(4-trifluoromethyl-phenyl)-[2,4']bipyridinyl-2'-yl]-benzenesulfonamide;

3-[4-Trifluoromethyl-6-(4-trifluoromethyl-phenyl)-[2,4']bipyridinyl-2'-yl]-benzenesulfonamide;

5-{1-[4-Trifluoromethyl-6-(4-trifluoromethyl-phenyl)-pyridin-2-yl]-1H-imidazol-4-yl}-pyridine-3-sulfonic acid amide;

N-(2-Hydroxy-1,1-dimethyl-ethyl)-3-{1-[4-trifluoromethyl-6-(4-trifluoromethyl-phenyl)pyridin-2-yl]-1H-imidazol-4-yl}-benzenesulfonamide;

4-Methyl-2-{1-[4-trifluoromethyl-6-(4-trifluoromethyl-phenyl)-pyridin-2-yl]-1H-imidazol-4-yl}-thiazole-5-sulfonic acid tert-butylamide;

4-Methyl-2-{1-[4-trifluoromethyl-6-(4-trifluoromethyl-phenyl)-pyridin-2-yl]-1H-imidazol-4-yl}-thiazole-5-sulfonic acid amide;

N-tert-Butyl-3-[4-methyl-6-(4-trifluoromethyl-phenyl)-[2,4']bipyridinyl-2'-yl]-benzenesulfonamide;

N-tert-Butyl-3-{1-[6-(4-chloro-phenyl)-4-methyl-pyridin-2-yl]-1H-imidazol-4-yl}-benzenesulfonamide;

N-tert-Butyl-3-[4'-methyl-6'-(4-trifluoromethyl-phenyl)-[2,2']bipyridinyl-6-yl]-benzenesulfonamide;

3-{4-[4-Methyl-6-(4-trifluoromethyl-phenyl)-pyridin-2-yl]-pyrimidin-2-yl}-benzenesulfonamide;

3-[4-Methyl-6-(4-trifluoromethyl-phenyl)-[2,4']bipyridinyl-2'-yl]-benzenesulfonamide;

3-[4'-Methyl-6'-(4-trifluoromethyl-phenyl)-[2,2']bipyridinyl-6-yl]-benzenesulfonamide;

3-{1-[6-(4-Chloro-phenyl)-4-methyl-pyridin-2-yl]-1H-imidazol-4-yl}-benzenesulfonamide;

5-[4-Trifluoromethyl-6-(4-trifluoromethyl-phenyl)-[2,4']bipyridinyl-2'-yl]-thiophene-2-sulfonic acid tert-butylamide;

5-[4-Methyl-6-(4-trifluoromethyl-phenyl)-[2,4']bipyridinyl-2'-yl]-thiophene-2-sulfonic acid tert-butylamide;

5-[4-Methyl-6-(4-trifluoromethyl-phenyl)-[2,4']bipyridinyl-2'-yl]-thiophene-2-sulfonic acid amide; and 5-[4-Trifluoromethyl-6-(4-trifluoromethyl-phenyl)-[2,4']bipyridinyl-2'-yl]-thiophene-2-sulfonic acid amide.

The invention further relates to a process for the preparation of a compound of formula (I), (I-a), (I-b) or (I-c) and to a compound of formula (I), (I-a), (I-b) or (I-c) prepared by such process.

In a certain embodiment, the process for the preparation of a compound of formula (I), (I-a), (I-b) or (I-c) according to the invention wherein A is an oxadiazole group (hereafter designed as compounds of formula (XIII) comprises reacting a compound of formula (VIII):

(VIII)

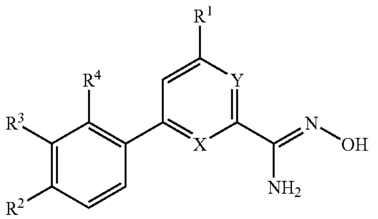

with a compound of formula (XI):

(XI)

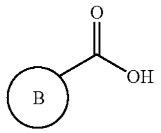

to obtain a compound of formula (XIII):

(XIII)

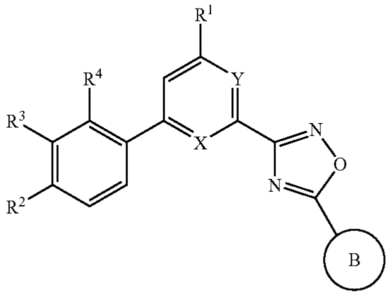

wherein B, $R^1$, $R^2$ and $R^3$ are as defined for formula (I), (I-a), (I-b) or (I-c) hereinabove.

In another embodiment, the process for the preparation of a compound of formula (I), (I-a), (I-b) or (I-c) according to the invention wherein A is an oxadiazole group (hereafter designed as compounds of formula (XIV) comprises reacting a compound of formula (IV):

(IV)

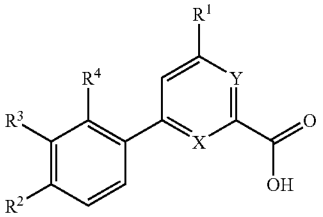

with a compound of formula (XII):

(XII)

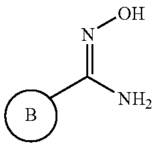

to obtain a compound of formula (XIV):

(XIV)

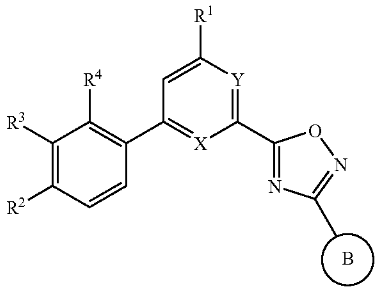

wherein B, $R^1$, $R^2$ and $R^3$ are as defined for formula (I), (I-a), (I-b) or (I-c) hereinabove.

In yet another embodiment, the process for the preparation of a compound of formula (I), (I-a), (I-b) or (I-c) according to the invention wherein A is as defined for formula (I), (I-a), (I-b) or (I-c) hereinabove but is different from an oxadiazole group (hereafter designed as compounds of formula (XV) comprises reacting a compound of formula (X):

(X)

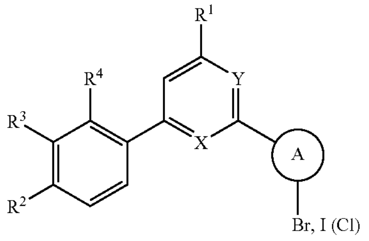

with a boronic acid derivative of formula B—$B(OH)_2$ to obtain the compound of formula (XV):

(XV)

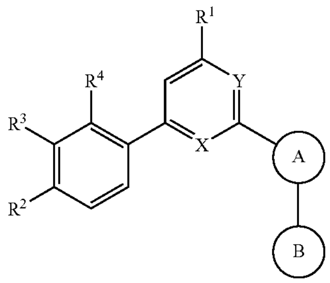

wherein B, $R^1$, $R^2$ and $R^3$ are as defined for formula (I), (I-a), (I-b) or (I-c) hereinabove.

Synthesis of 2-chloro-, 2-iodo and 2-methanesulfonyl-pyrimidines as Useful Intermediates for the Preparation of Compounds According to the Invention General procedure I

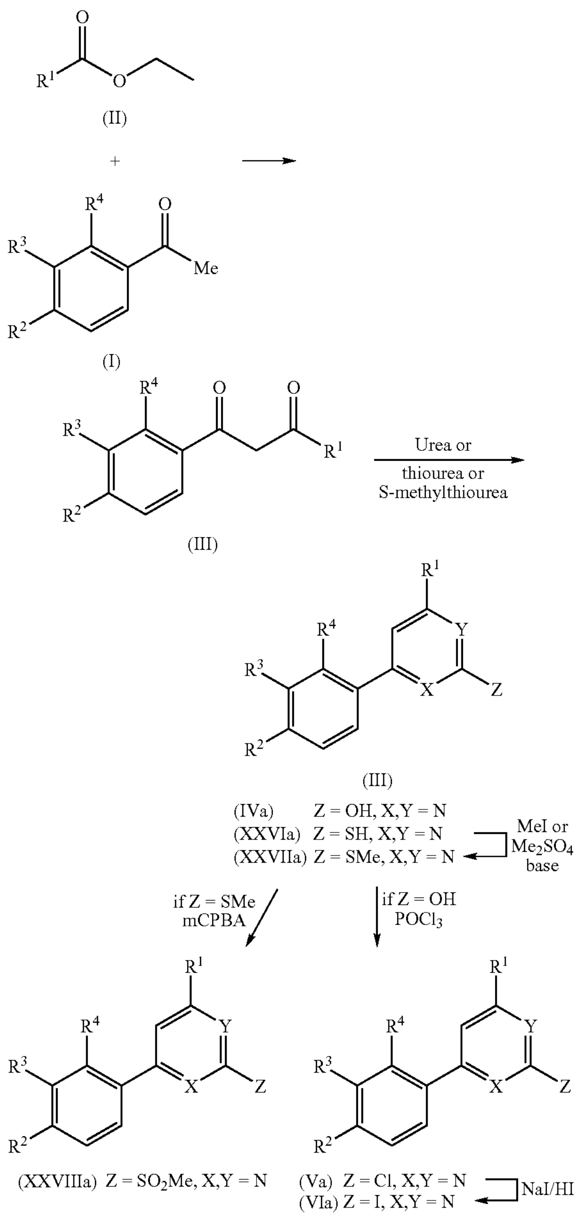

(II)

(I)

(III)

(III)

(IVa) Z = OH, X,Y = N
(XXVIa) Z = SH, X,Y = N
(XXVIIa) Z = SMe, X,Y = N (XXVIIIa) Z = $SO_2Me$, X,Y = N (Va) Z = Cl, X,Y = N
(VIa) Z = I, X,Y = N

Urea Route:

Step 1: To a stirred solution of compound of formula (I) (either commercially available or prepared as described hereinafter) in an organic solvent (e.g. tert-butyl-methyl-ether) is added at room temperature a solution of sodium methanolate in methanol followed by a solution of a compound of formula (II) in an organic solvent (e.g. tert-butyl-methyl-ether). The reaction mixture is stirred at room temperature for about 19 h, cooled, acidified and extracted (e.g. with diethyl ether). The combined organic layers are washed and dried (e.g. $MgSO_4$) and evaporated to give crude the compound of formula (III) which can be used without further purification.

Step 2: To a stirred solution of a compound of formula III (1 eq) and urea (2 eq) in an organic solvent (e.g. MeOH) is added conc. HCl (e.g. MeOH/HCl 10:1). The reaction mixture is heated under reflux conditions for about 40 h, water is added and the mixture is stirred at 0° C. for 1 h. The precipitate is collected by filtration, washed with water and recrystallized (e.g. diethyl ether/hexane) to yield the compound of formulae IVa.

Step 3: To a stirred solution of a compound of formulae IVa in phosphoryl chloride is added DMF (5-10 drops) and the reaction mixture is stirred at 115° C. for around 16 h, evaporated and ice-water is added. The water layer is extracted twice (e.g. with diethyl ether), the combined organic layer washed (water followed by brine), dried (e.g. $MgSO_4$) and evaporated to yield the compound of formulae Va.

Step 4: To a stirred solution of a compound of formulae Va (1 eq) in an organic solvent (e.g. 2-butanone) is added sodium iodide (3.5 eq) and hydroiodic acid (57% in water, 1 eq). The reaction mixture is heated under reflux conditions for 16 to 72 h, cooled and poured into ice/sat. sodium bicarbonate solution. The water layer is extracted twice (e.g. with diethyl ether), the combined organic layer washed (water followed by brine), dried (e.g. $MgSO_4$) and evaporated. Further purification by column chromatography on silica gel (e.g. toluene) yields the compound of formulae VIa.

Thiourea Route:

Step 1: same as step 1 in the urea route to produce compounds of general formula III.

Step 2: (Protocol a, with S-methylthiourea): A stirred solution of a compound of formula III (1 eq) and S-methylthiourea sulfate (1 eq) in an organic solvent (e.g. EtOH) is heated under reflux conditions for about 48 h, water is added and the mixture is stirred at 0° C. for 1 h. The precipitate is collected by filtration, washed with water and recrystallized (e.g. diethyl ether/hexane) to yield the compound of formula XXVIIa.

Step 2: (Protocol b, with thiourea): 1.) To a stirred solution of a compound of formula III (1 eq) and thiourea (1 eq) and catalytic amount (0.1 to 0.5 eq.) of a mineral acid (e.g. sulfuric acid) in an organic solvent (e.g. EtOH) is heated under reflux conditions for about 48 h, water is added and the mixture is stirred at 0° C. for 1 h. The precipitate is collected by filtration, washed with water and recrystallized (e.g. diethyl ether/hexane) to yield the compound of formula XXVIa. 2.) To a stirred mixture of a compound of formula XXVIa (1 eq.) and a base (1.2 to 1.3 eq.) (e.g. $NaHCO_3$ or $Na_2CO_3$) in an organic solvent (e.g. DMF) is added a methylating reagent (1 eq.) (e.g. iodomethane or dimethyl sulfate) and the mixture is stirred at ambient temperatures for 2 to 24 h. Diluted with EtOAc, the organic layer is washed with water and brine, finally dried over $Na_2SO_4$. Removal of the solvent left a crude residue, which is either recrystallized (e.g. diethyl ether/heptane) or purified by silica gel column chromatography (ethyl acetate/heptane) to yield the compound of the formula XXVIIa.

Step 3: To a stirred solution of a compound of the formula XXVIIa (1 eq.) in an organic solvent (e.g. dichloromethane) is added an oxidizing reagent (2 eq.) (e.g. mCPBA) and the mixture is stirred at ambient temperature for around 16 h. Poured into sat. $NaHCO_3$-sol., extracted with dichloromethane, dried the organic layer over $Na_2SO_4$. Removal of the solvent in vacuum left a crude product, which is recrystallized (e.g. diethyl ether/heptane) to give the pure compound of the formula XXVIIIa.

Synthesis of 2-chloro-, 2-bromo-, 2-iodo- and 2-trifluoromethanesulfonyloxy-4-aryl- and -6-aryl-pyridines as Useful Intermediates for the Preparation of Compounds According to the Invention General procedure Ia Method a ($R^1$ = alkyl, $CF_3$)

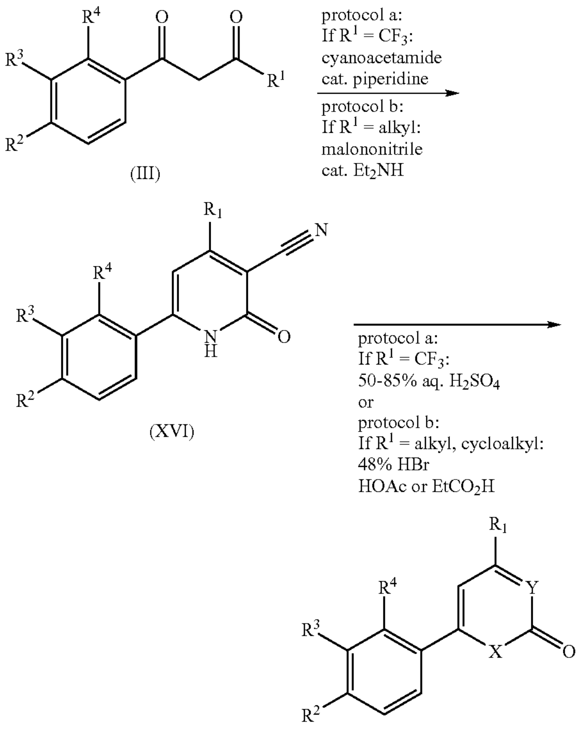

(III)

(XVI)

(IVb) X = NH, Y = CH

General procedure Ib

Method b ($R^1$ = alkyl, cycloalkyl)

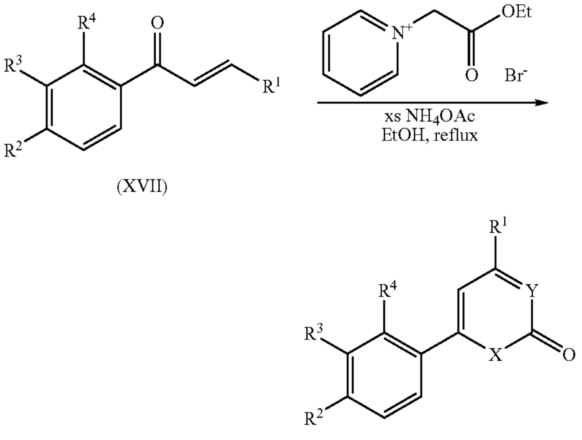

(XVII)

(IVb) X = NH, Y = CH

-continued

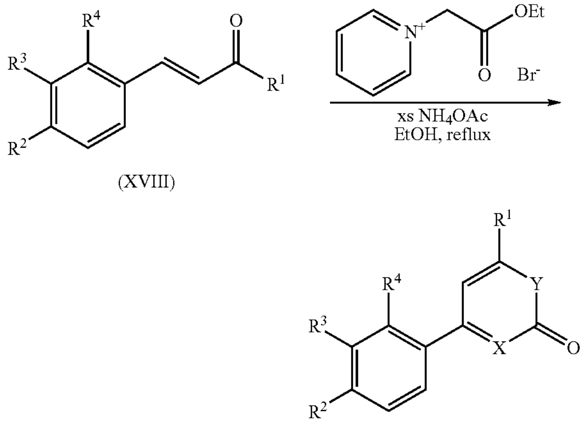

(XVIII)

(IVc) X = CH, Y = NH

General procedure Ic

Method c ($R^1$ = alkyl, cycloalkyl)

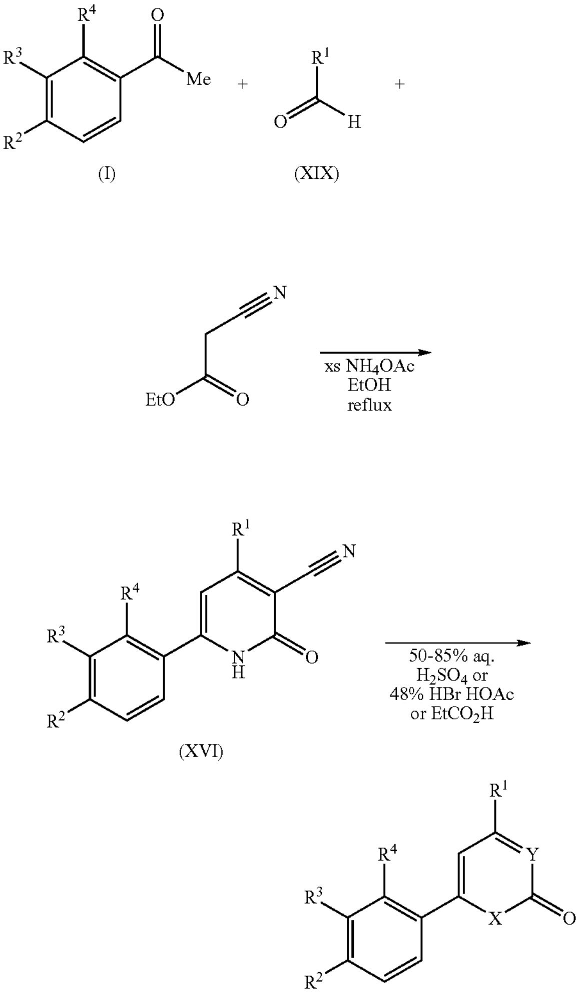

(I)

(XIX)

(XVI)

(IVb) X = NH, Y = CH

General procedure Id

Method d ($R^1$ = alkyl, cycloalkyl or $CF_3$)

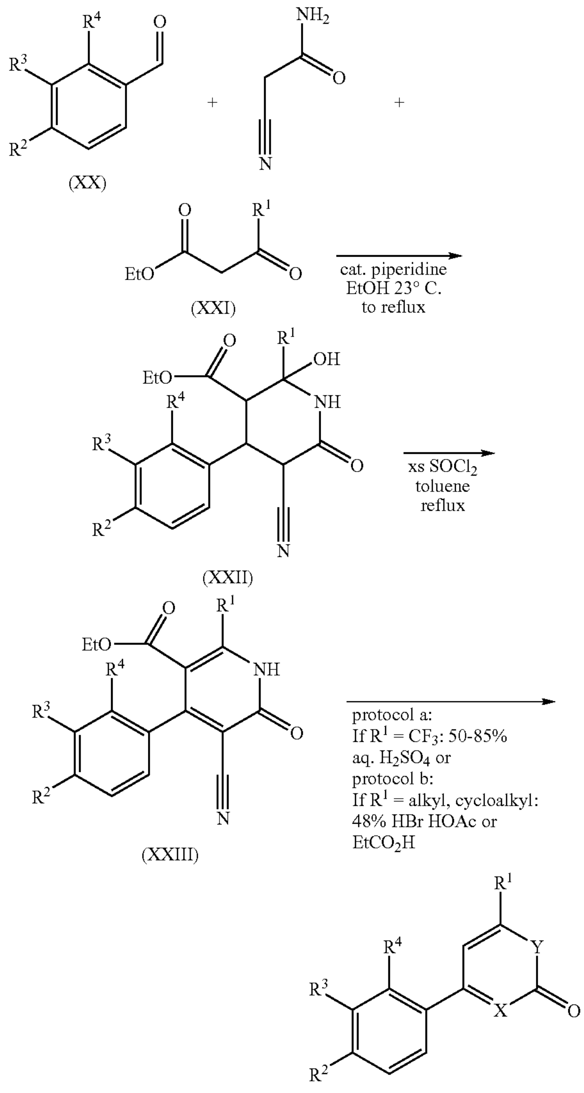

(XX) (XXI) (XXII) (XXIII)

(IVc) X = CH, Y = NH

Method a ($R^1$=alkyl, $CF_3$);

Step 1 protocol a ($R^1$ is $CF_3$): To a mixture of a 1,3-diketo-compound of formula III (wherein $R^1$ is $CF_3$; prepared as described under general procedure I step 1) and cyanoacetamide in a protic solvent (e.g. ethanol) is added at room temperature a catalytic amount (ca. 0.1 eq.) of piperidine and the mixture stirred at reflux temperature for 16 to 24 h. The reaction mixture is concentrated in vacuum, then treated with ice-water and acidified with 1M aqueous hydrochloric acid to achieve pH 1, the precipitate is filtered off, washed with water and dried in air at 60 to 70° C. to give the crude compounds of formula XVI, which can be used without further purification (according to *Org. Prep. Proced. Int.* 1993, 25(1), 116-117).

Step 1 protocol b ($R^1$ is alkyl): To a mixture of a 1,3-diketo-compound of formula III (wherein $R^1$ is alkyl; prepared from the corresponding acetophenone of general formula I and the $R^1$-carboxylic acid derivative under conditions as e.g. described in general procedure I step 1, *Synthesis* 1991, (3), 195; *Monatsh. Chem.* 1996, 127-(8-9), 895-907; *Angew. Chem. Int. Ed. Engl.* 1993, 32(8), 1151-1152; *J. Org. Chem.* 1993, 58(11), 3185-3187; *J. Fluorine Chem.* 1986, 32(2), 229-231; *Org. Synth. Coll. Vol. III,* 387; *J. Am. Chem. Soc.* 1953, 75, 626 and 4109; *J. Am. Chem. Soc.* 1941, 63, 2785; *Chem. Ber.* 1970, 103, 1088) and malononitrile (1.33 eq.) in a protic solvent (e.g. ethanol) at ambient temperature is added a catalytic amount of diethylamine (0.2 eq.) and the mixture was stirred at 20 to 25° C. for around 3 h. Then the mixture was heated under reflux conditions for around 16 to 48 h. After cooling to room temperature, the mixture was diluted with 1M aqueous HCl, stirred for 30 min, the precipitate was filtered off, washed with ethanol and was dried in air at 60° C. overnight to give the crude product, which was purified by trituration with ethanol/diethyl ether/acidic acid to give the pure product (according to *J. Indian Chem. Soc.* 1930, 7, 815).

Step 2:

Protocol a (if $R^2$ or $R^3$ are not $CF_3$): A mixture of a compound of formula XVI in 50 to 85% aqueous sulfuric acid is heated with stirring to 150 to 180° C. for 16 to 24 h. After cooling to room temperature the reaction mixture was poured onto ice-water, the precipitate was filtered off, washed thoroughly with water and dried in air at 60 to 70° C. to give the crude compounds of formula IVb, which can be used without further purification.

Protocol b (if $R^2$ or $R^3$ are $CF_3$): A mixture of a compound of formula XIV in 48% aqueous hydrobromic acid and acetic or propionic acid (3:2) is heated with stirring to 140° C. for 4 to 12 days. After cooling to room temperature the reaction mixture was poured onto ice-water, the precipitate was filtered off, washed thoroughly with water, dissolved in a minimum amount of THF, diluted with ethyl acetate, the organic phase is washed twice with sat. $NaHCO_3$-sol., then with brine and finally dried over $MgSO_4$. Filtration and removal of the solvent in vacuum gave the crude compounds of formula IVb, which can be used without further purification.

Method b ($R^1$=alkyl, cycloalkyl):

Step 1: A stirred mixture of 1-aryl-prop-2-en-1-one-compound of formula XVII (wherein R1 is alkyl; prepared e.g. from the corresponding aryl zinc chloride and the R1-substituted acrylic acid chloride under conditions as e.g. described in *Tetr. Lett.* 1983, 24, 5181—or e.g. from the corresponding aryl carboxylic acid ester and the R1-carboxaldeyde by the following sequence: 1.) conversion of the aryl carboxylic acid ester into the 2-oxo-2-aryl-ethyl-phosphonic acid dimethyl ester by reaction with dimethyl methylphosphonate and n-BuLi as described in *J. Org. Chem.* 1998, 63(24), 8894-8897. 2.) Horner-Emmons-Wadsworth reaction of the phosphonate with the R1-carboxaldehyde with cesium carbonate as described in *J. Chem. Soc. Perkin T2* 1989, 503) and commercially available 1-ethoxycarbonylmethyl-pyridinium bromide [CAS-No. 17282-40-5] (1.1 eq.) and ammonium acetate (5 eq.) in a protic solvent (e.g. ethanol) was heated under reflux conditions for around 16 to 48 h. After cooling to room temperature, the mixture was diluted with 1M aqueous HCl (until pH 1 was achieved) and water, stirred for 30 min, the precipitate was filtered off, washed with water and was dried in air at 60° C. overnight to give the crude product, which was purified by trituration with diethyl ether/heptane to give the pure product of general formula IVb.

Method c ($R^1$=alkyl, cycloalkyl):

Step 1: A stirred mixture of the acetophenone of general formula I, R1-carboxaldehyde of general formula XIX, ethyl cyanoacetate (all 1.0 eq.) and ammonium acetate (8 eq.) in a protic solvent (e.g. ethanol) was heated under reflux conditions and ambient atmosphere for around 16 to 48 h. After cooling to room temperature, the mixture was diluted with 1M aqueous HCl (until pH 1 was achieved) and water, stirred for 30 min, the precipitate was filtered off, washed with water and was dried in air at 60° C. overnight to give the crude product, which was purified by trituration with diethyl ether/heptane to give the pure product of general formula XVI (according to *Farmaco* 1999, 54(4), 195-201).

Step 3: Performed in complete analogy to general procedure Ia method a, protocols a or b to produce from the cyanopyridiones of general formula XVI the pyridones of general formula IVb.

Method d ($R^1$=alkyl, cycloalkyl and $CF_3$:

Step 1: To stirred mixture of the benzaldehyde of general formula XX and cyanoacetamide (1.02 eq) in a protic solvent (e.g. EtOH) at 30° C. was added piperidine (0.2 eq) stirring was continued at 30° C. for around 3 to 5 h (almost complete conversion to the Knovenagel-condensation product). Then the 3-(R1)-3-oxo-3-propionic acid ester of general formula XXI (1.05 eq.) was added and the reaction was stirred at reflux for around 1 to 2 h. The EtOH was removed in vacuum, the residue was dissolved in EtOAc, washed with brine containing 1N HCl, dried over $Na_2SO_4$. Removal of the solvent in vacuum and drying in high vacuum at 60° C. left the compound of general formula XXII as a light yellow foam which was used without further purification.

Step 2: To the above prepared compound of the general formula XXII in toluene at 23° C. was added thionyl chloride (6 eq.), resulting in a suspension and the mixture was stirred at 80° C. for around 1 to 2 h, then at 115° C. for around 4 to 5 h. Cooled to 100° C., added slowly heptane (one to six times the volume of the toluene) to the stirred hot solution, allowed to slowly cool to 23° C. overnight while stirring, cooled with stirring to 5° C., filtered the precipitate off, washed with heptane and dried in air at 60° C. to give the crude product of the general formula XXIII as a brown solid which was used without further purification.

Step 3: Performed in complete analogy to general procedure Ia method a, protocols a or b to produce from the alkyl cyanopyridione carboxylic acid esters of general formula XXIII the pyridones of general formula IVc.

Preparation of Chlorides, Bromides, Iodides and Triflates as Useful Intermediates for the Preparation of Compounds According to the Invention

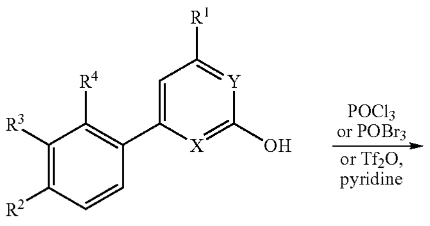

(IV)

-continued

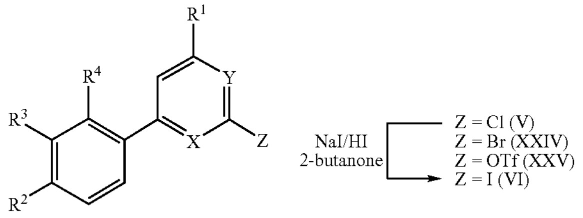

For all general methods Ia, Ib, Ic and Id, the following preparations of chlorides, bromides, iodides and triflates do apply:

Preparation of chlorides/bromides: To a stirred mixture of a compound of formula IV in phosphoryl chloride or phosphoryl bromide (some additional toluene can be added in the case of $POBr_3$ to facilitate stirring) is added DMF (0.3 to 0.4 eq.) and the reaction mixture is stirred at 105° C. for around 16 h, evaporated and ice-water is added. The precipitated solid is filtered off, dissolved in an organic solvent (e.g. tert-butyl methyl ether or ethyl acetate), the organic layer is washed with sat. $NaHCO_3$-sol., then with brine and finally dried over $MgSO_4$. Filtration and removal of the solvent in vacuum gave the crude material, which is either used without further purification or is purified by silica gel column chromatography to give the pure compounds of formula V or XXIV where Z is either Cl or Br.

Preparation of iodides: Performed in complete analogy to general procedure I step 4 to produce from compounds of formula V where Z is Cl (1 eq.) the compounds of formula VI where Z is I. Alternatively the iodides of formula VI where Z is I can be prepared from the compounds of formula V where Z is Br by treatment with sodium iodide (2.0 eq.), copper(I) iodide (0.05 eq.) and N,N'-dimethylethylenediamine (0.1 eq.) in 1,4-dioxane at 110° C. for ca. 1-2 h according to a procedure in *J. Am. Chem. Soc.* 2002, 124(50), 14844.

Preparation of Triflates: To a stirred mixture of compounds of the general formula IV in pyridine or ethyldiisopropyl amine/methylene chloride at temperatures between −15 and 0° C. was added trifluoromethansulfonic anhydride (1.0 to 2.0 eq.) and stirring was continued at 0° C. for 0.5 to 16 h. Poured into ice-water, extracted with ethyl acetate, washed with ice cold 1 M sulfuric acid, saturated $NaHCO_3$-sol. and brine, dried over $Na_2SO_4$. Removal of the solvent in vacuum left the crude product as a brown solid which can be purified by silica gel column chromatography with heptane/EtOAc to give the pure triflates of general formula XXV.

Preparation of Triflates: To a stirred mixture of compounds of the general formula IV in pyridine at −15° C. was added trifluoromethansulfonic anhydride (1.0 eq.) and stirring was continued at 0° C. for 0.5 to 16 h. Poured into ice-water, extracted with ethyl acetate, washed with brine and dried over $Na_2SO_4$. Removal of the solvent in vacuum left the crude product as a brown solid which can be purified by silica gel column chromatography with heptane/EtOAc to give the pure triflates of general formula XXV.

Synthesis of Compounds of Formulae (I), (I-a), (I-b) and (I-c) According to the Invention, wherein A is an Oxadiazole Group: General Procedure V:

In the following schemes the compounds of formulae (XIII) and (XIV) are compounds of formulae (I), (I-a), (I-b) and (I-c) wherein A is an oxadiazole and $R^1$, $R^2$, $R^3$ and $R^4$ and B are as defined as for formula (I), (I-a), (I-b) or (I-c) hereinabove.

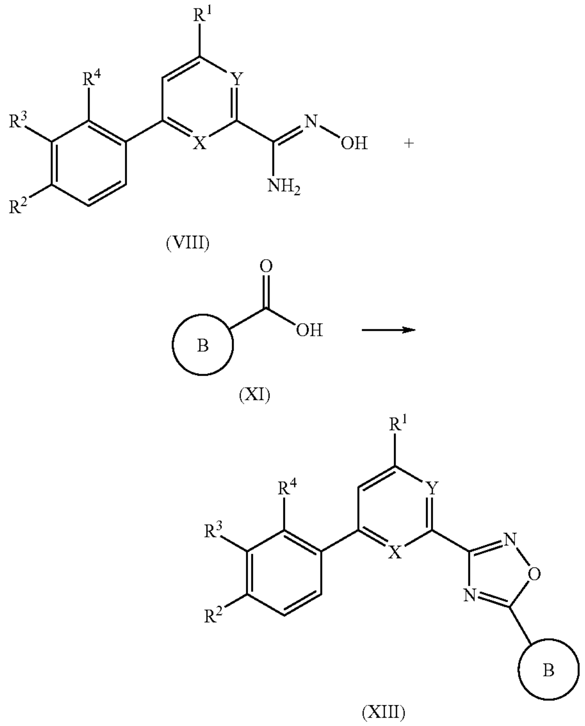

(VIII)

(XI)

(XIII)

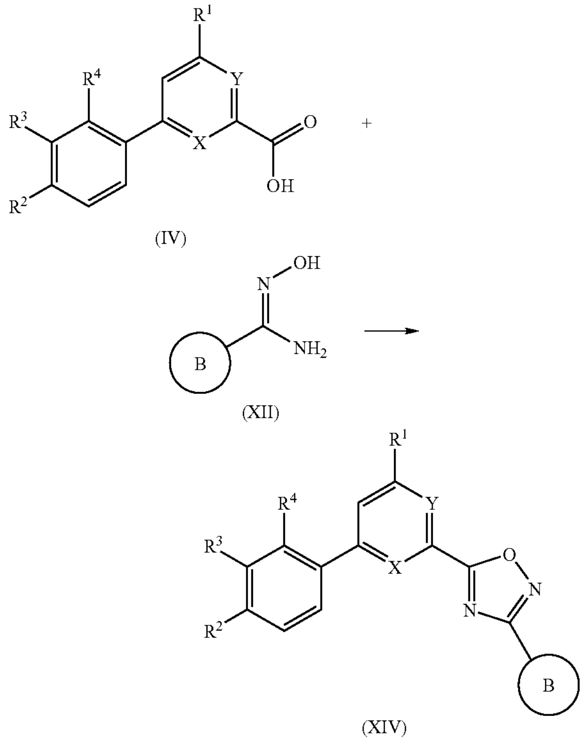

(IV)

(XII)

(XIV)

To a stirred solution of a carboxylic acid of formulae XI or IV (1 eq) in an organic solvent (e.g. DMF) is added at room temperature 1,1'-carbonyl-diimidazol (1.5 eq) and the reaction mixture was allowed to stir at room temperature for around 2 h. The corresponding N-hydroxyamidine of formulae VIII or XII (1.5 eq.) is added, the reaction mixture is stirred at 80° C. for around 15 h and evaporated to dryness. Acetic acid is added, the stirred reaction mixture heated under reflux conditions for around 4 h, cooled and evaporated. Purification by chromatography on silica gel and crystallization yielded the final product of formula XIII or XIV.

Synthesis of Compounds of Formulae (I), (I-a), (I-b) and (I-c) Wherein A is Other than an Oxadiazole Group: General Procedure VI In the following schemes the compound of formula (XIV) is a compound of formula (I), (I-a), (I-b) or (I-c) wherein A is defined as for formula (I), (I-a), (I-b) or (I-c) hereinabove but is other than an oxadiazole group and wherein $R^1$, $R^2$, $R^3$ and B are as defined as for formula (I), (I-a), (I-b) or (I-c) hereinabove.

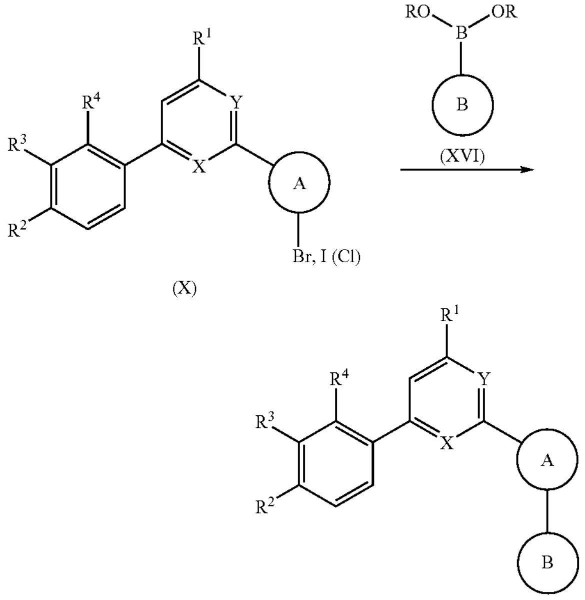

(X)

(XVI)

(XV)

To a stirred mixture of a compound of formula X (1 eq.), a boronic acid derivative of formula XVI (1.0 to 1.5 eq.) and tetrakis(triphenylphosphine)palladium (0.02 to 0.1 eq.) in an organic solvent (e.g. DME or dioxane) is added at room temperature 1M aqueous sodium carbonate solution (2 to 3 eq.), the reaction mixture is heated under reflux conditions for around 18 h, cooled, poured into ice-water and extracted two times with ethyl acetate. The combined organic layers are washed two times with brine, dried (e.g. $MgSO_4$) and evaporated. The crude product is further purified by column chromatography on silica gel (e.g. $MeCl_2$/MeOH/$NH_4OH$ 20:1:0.1) and crystallization (e.g. dichloromethane/MeOH/hexane) to give a compound of formulae XV.

As mentioned hereinabove, the invention also provides pharmaceutical compositions containing a compound of formula (I), (I-a), (I-b) or (I-c) and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like; depending on the nature of the active substance no carriers are, however, usually required in the case of soft gelatin capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The compounds of formula (I) and their pharmaceutically acceptable salts are metabotropic glutamate receptor antagonists and can be used for the treatment or prevention of acute and/or chronic neurological disorders, such as psychosis, schizophrenia, Alzheimer's disease, cognitive disorders and memory deficits. Other treatable indications are restricted brain function caused by bypass operations or transplants, poor blood supply to the brain, spinal cord injuries, head injuries, hypoxia caused by pregnancy, cardiac arrest and hypoglycemia. Further treatable indications are acute and chronic pain, Huntington's chorea, ALS, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, nicotine addiction, psychoses, opiate addiction, anxiety, vomiting, dyskinesia, depression, colon cancer, sleep disorders, disorders of circadian rhythms and glioma.

The dosage at which compounds of the invention can be administered can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

The compounds of the present invention are group II mGlu receptor antagonists. The compounds show activities, as measured in the assay described below, of 0.250 μM or less, typically 0.100 μM or less, and ideally of 0.010 μM or less. In the table below are described some specific Ki values of some preferred compounds.

| | Ex. No. | | | | | | | | | |
|---|---|---|---|---|---|---|---|---|---|---|
| | 1 | 2 | 3 | 5 | 8 | 10 | 11 | 26 | 33 | 34 |
| $K_i$ mGlu2 (μM) | 0.074 | 0.028 | 0.072 | 0.047 | 0.100 | 0.025 | 0.0216 | 0.014 | 0.017 | 0.047 |
| | Ex. No. | | | | | | | | | |
| | 35 | 39 | 42 | 54 | 55 | 56 | 59 | 60 | 61 | 62 |
| $K_i$ mGlu2 (μM) | 0.031 | 0.0395 | 0.140 | 0.060 | 0.096 | 0.009 | 0.0583 | 0.032 | 0.013 | 0.003 |
| | Ex. No. | | | | | | | | | |
| | 63 | 65 | 70 | 71 | 72 | 73 | 74 | 90 | 114 | 138 |
| $K_i$ mGlu2 (μM) | 0.029 | 0.006 | 0.044 | 0.001 | 0.056 | 0.019 | 0.010 | 0.055 | 0.006 | 0.028 |
| | Ex. No. | | | | | | | | | |
| | 148 | 155 | 187 | 210 | 218 | 221 | 222 | 223 | 227 | 237 |
| $K_i$ mGlu2 (μM) | 0.049 | 0.0084 | 0.0137 | 0.023 | 0.003 | 0.007 | 0.0124 | 0.013 | 0.034 | 0.004 |
| | Ex. No. | | | | | | | | | |
| | 242 | 243 | 244 | 247 | 249 | 270 | 271 | 272 | 274 | 275 |
| $K_i$ mGlu2 (μM) | 0.042 | 0.003 | 0.005 | 0.041 | 0.009 | 0.006 | 0.003 | 0.080 | 0.004 | 0.087 |

-continued

| | Ex. No. | | | | | | | | | |
|---|---|---|---|---|---|---|---|---|---|---|
| | 277 | 280 | 292 | 294 | 306 | 313 | 318 | 320 | 322 | 330 |
| $K_i$ mGlu2 (μM) | 0.071 | 0.003 | 0.028 | 0.013 | 0.038 | 0.018 | 0.004 | 0.016 | 0.009 | 0.004 |

| | Ex. No. | | | | | | | | | |
|---|---|---|---|---|---|---|---|---|---|---|
| | 334 | 338 | 345 | 346 | 350 | 353 | 355 | 356 | 357 | 360 |
| $K_i$ mGlu2 (μM) | 0.011 | 0.001 | 0.0007 | 0.004 | 0.022 | 0.003 | 0.001 | 0.001 | 0.039 | 0.005 |

| | Ex. No. | | | | | |
|---|---|---|---|---|---|---|
| | 377 | 384 | 390 | 394 | 445 | 452 |
| $K_i$ mGlu2 (μM) | 0.007 | 0.032 | 0.021 | 0.003 | 0.003 | 0.016 |

[$^3$H]-LY354740 Binding on mGlu2 Transfected CHO Cell Membranes.

Transfection and Cell Culture cDNA encoding the rat mGlu2 receptor protein in pBluescript II was subcloned into the eukaryotic expression vector pcDNA I-amp from Invitrogen Ltd (Paisley, UK). This vector construct (pcD1mGR2) was co-transfected with a psvNeo plasmid encoding the gene for neomycin resistance, into CHO cells by a modified calcium phosphate method described by Chen & Okayama (1988). The cells were maintained in Dulbecco's Modified Eagle medium with reduced L-glutamine (1 mM final concentration), 36 mg/L L-Proline and 10% dialysed foetal calf serum from Gibco-Invitrogen; the medium was supplemented with 500 microM α-methyl-4-carboxyphenylglycine (MCPG). Selection was made in the presence of G-418 (300 ug/ml final concentration). Clones were identified by reverse transcription of 5 μg total RNA, followed by PCR using mGlu2 receptor specific primers 5'-atcactgcttgggtttctggcactg-3' and 5'-agcatcactgtgggtggcataggagc-3' in 60 mM Tris HCl (pH 10), 15 mM $(NH4)_2SO_4$, 2 mM $MgCl_2$, 25 units/ml Taq Polymerase with 30 cycles annealing at 60° C. for 1 min., extention at 72° C. for 30 s, and 1 min. 95° C. denaturation.

Membrane Preparation

Cells, cultured as above, were harvested and washed three times with cold PBS and frozen at −80° C. The pellet was resuspended in cold 20 mM HEPES-NaOH buffer containing 10 mM EDTA (pH 7.4), and homogenised with a polytron (Kinematica, AG, Littau, Switzerland) for 10 s at 10 000 rpm. After centrifugation for 30 min. at 4° C., the pellet was washed once with cold 20 mM HEPES-NaOH buffer containing 0.1 mM EDTA, (pH 7.4). After a second centrifugation for 30 min. at 4° C. the pellet was resuspended in cold 20 mM HEPES-NaOH buffer containing 0.1 mM EDTA, (pH 7.4). Protein content was measured using the Micro BCA method from Pierce-Perbio (Rockford, Ill., USA) using bovine serum albumin as standard.

[$^3$H]-LY354740 Binding

After thawing, the membranes were resuspended in cold 50 mM Tris-HCl buffer containing 2 mM $MgCl_2$ (pH 7.4) (binding buffer). The final concentration of the membranes in the assays was 25 μg protein/ml. Inhibition experiments were performed with membranes incubated with 10 nM [$^3$H]-LY354740 at room temperature, for 1 hour, in presence of various concentrations of the compound to be tested. Following the incubations, membranes were filtered onto Whatmann GF/B glass fiber filters or onto GF/B Unifilter plates and washed 5 times with cold binding buffer. Non specific binding was measured in the presence of 10 μM (2S,2'R,3'R)-2-(2'3'-Dicarboxycyclopropyl)glycine (DCG IV from Tocris, Ellisville, Mo. USA). After transfer of the filters into plastic vials containing 10 ml of Ultima-gold scintillation fluid from Perkin-Elmer (Boston, Mass., USA), the radioactivity was measured by liquid scintillation in a Tri-Carb 2500 TR counter (Packard, Zürich, Switzerland). For 96-Unifilter plates the radioactivity was measured after addition of Microscint 40 scintillation fluid (Perkin Elmer, Boston Mass.) using a Top-Count NXT (Packard)

Data Analysis.

The inhibition curves were fitted with a four parameter logistic equation giving $IC_{50}$ values, and Hill coefficients.

EXAMPLE A.1

2-Chloro-4-(4-chloro-phenyl)-6-trifluoromethyl-pyrimidine 1) 4-(4-Chloro-phenyl)-6-trifluoromethyl-1H-pyrimidin-2-one: The compound was prepared from commercially available ethyl trifluoroacetate, commercially available 4-chloro-acetophenone and urea according to the general procedure I. Obtained as a light yellow solid (60%). MS (EI) 274.1 [$(M)^+$]; mp 200° C.

2) The title compound was prepared from 4-(4-chloro-phenyl)-6-trifluoromethyl-1H-pyrimidin-2-one (6.96 g, 25.3 mmol) and phosphoryl chloride (80 mL) according to the general procedure I. Obtained as an off-white solid (7.35 g, 99%). MS (EI) 292.0 [$(M)^+$]; mp 108° C.

EXAMPLE A.2

2-Chloro-4-trifluoromethyl-6-(4-trifluoromethyl-phenyl)-pyrimidine 1) 6-Trifluoromethyl-4-(4-trifluoromethyl-phenyl)-1H-pyrimidin-2-one: The compound was prepared from commercially available ethyl trifluoroacetate, commercially available 4-trifluoromethyl-acetophenone and urea according to the general procedure I. Obtained as a white solid (57%). MS (ISP) 309.0 [$(M+H)^+$]; mp 136° C.

2) The title compound was prepared from 6-trifluoromethyl-4-(4-trifluoromethylphenyl)-1H-pyrimidin-2-one (8.72 g, 28.3 mmol) and phosphoryl chloride (80 mL) according to the general procedure I. Obtained as a light brown solid (9.13 g, 98%). MS (EI) 326.0 [(M)$^+$]; mp 71.5° C.

EXAMPLE A.3

4-(4-Chloro-phenyl)-2-iodo-6-trifluoromethyl-pyrimidine

The title compound was prepared from 2-chloro-4-(4-chloro-phenyl)-6-trifluoromethyl-pyrimidine (example A.1) (1.0 g, 3.41 mmol) according to the general procedure I. Obtained as a light green solid (1.27 g, 97%). MS (ISP) 385.0 [(M+H)$^+$]; mp 73° C.

EXAMPLE A.4

2-Iodo-4-trifluoromethyl-6-(4-trifluoromethyl-phenyl)-pyrimidine

The title compound was prepared from 2-chloro-4-trifluoromethyl-6-(4-trifluoromethylphenyl)-pyrimidine (example A.2) (1.31 g, 4.01 mmol) according to the general procedure I. Obtained as a light yellow solid (1.62 g, 97%). MS (ISP) 419.1 [(M+H)$^+$]; mp 96° C.

EXAMPLE A.5

2-Chloro-4-difluoromethyl-6-(4-trifluoromethyl-phenyl)-pyrimidine 1) 4-(4-Chloro-phenyl)-6-difluoromethyl-1H-pyrimidin-2-one: The compound was prepared from commercially available ethyl difluoroacetate, commercially available 4-trifluoromethyl-acetophenone and urea according to the general procedure I. Obtained as a white solid (49%). MS (EI) 290.2 [(M)$^+$]; mp 210° C.

2) The title compound was prepared from 4-(4-chloro-phenyl)-6-difluoromethyl-1H-pyrimidin-2-one (5.09 g, 17.5 mmol) and phosphoryl chloride (55 mL) according to the general procedure I. Obtained as a light brown solid (5.11 g, 94%). MS (EI) 308.1 [(M)$^+$]; mp 63° C.

EXAMPLE A.6

2-Chloro-4-(3-fluoro-4-trifluoromethyl-phenyl)-6-trifluoromethyl-pyrimidine 1) 4-(3-Fluoro-4-trifluoromethyl-phenyl)-6-trifluoromethyl-1H-pyrimidin-2-one: The compound was prepared from commercially available ethyl trifluoroacetate, commercially available 3-fluoro-4-trifluoromethyl-acetophenone and urea according to the general procedure I. Obtained as a white solid (56%) MS (EI) 326.1 [(M)$^+$]; mp 150° C.

2) The title compound was prepared from 4-(3-fluoro-4-trifluoromethyl-phenyl)-6-trifluoromethyl-1H-pyrimidin-2-one (4.08 g, 12.5 mmol) and phosphoryl chloride (40 mL) according to the general procedure I. Obtained as a yellow solid (4.26 g, 99%). MS (EI) 344.0 [(M)$^+$]; mp 41° C.

EXAMPLE A.7

2-Chloro-4-(3,4-dichloro-phenyl)-6-trifluoromethyl-pyrimidine 1) 4-(3,4-Dichloro-phenyl)-6-trifluoromethyl-1H-pyrimidin-2-one: The compound was prepared from commercially available ethyl trifluoroacetate, commercially available 3,4-dichloro-acetophenone and urea according to the general procedure I. Obtained as a white solid (38%). MS (EI) 308.0 [(M)$^+$]; mp 180° C.

2) The title compound was prepared from 4-(3,4-dichloro-phenyl)-6-trifluoromethyl-1H-pyrimidin-2-one (5.72 g, 18.5 mmol) and phosphoryl chloride (60 mL) according to the general procedure I. Obtained as a white solid (6.04 g, 99%). MS (EI) 326.0 [(M)$^+$]; mp 82° C.

EXAMPLE A.8

2-Chloro-4-(4-chloro-3-methyl-phenyl)-6-trifluoromethyl-pyrimidine 1) 4-(4-Chloro-3-methyl-phenyl)-6-trifluoromethyl-1H-pyrimidin-2-one: The compound was prepared from commercially available ethyl trifluoroacetate, commercially available 4-chloro-3-methyl-acetophenone and urea according to the general procedure I. Obtained as a white solid (42%). MS (EI) 288.1 [(M)$^+$]; mp 201° C.

2) The title compound was prepared from 4-(4-chloro-3-methyl-phenyl)-6-trifluoromethyl-1H-pyrimidin-2-one (9.07 g, 31.4 mmol) and phosphoryl chloride (100 mL) according to the general procedure I. Obtained as a white solid (8.68 g, 99%). MS (EI) 306.1 [(M)$^+$]; mp 90° C.

EXAMPLE A.9

4-Difluoromethyl-2-iodo-6-(4-trifluoromethyl-phenyl)-pyrimidine

The title compound was prepared from 2-chloro-4-difluoromethyl-6-(4-trifluoromethylphenyl)-pyrimidine (example A.5) (0.5 g, 1.62 mmol) according to the general procedure I. Obtained as a green solid (0.43 g, 66%). MS (ISP) 399.0 [(M−H)$^-$]; mp 85° C.

EXAMPLE A.10

2-Chloro-4-(3-ethoxy-4-trifluoromethyl-phenyl)-6-trifluoromethyl-pyrimidine 1) 4-(3-Ethoxy-4-trifluoromethyl-phenyl)-6-trifluoromethyl-1H-pyrimidin-2-one: The compound was prepared from commercially available ethyl trifluoroacetate, 3-ethoxy-4-trifluoromethyl-acetophenone [CAS-No. 851263-21-3] and urea according to the general procedure I. Obtained as an off-white solid (54%). MS (EI) 352.1 [(M)$^+$]; mp 217° C.

2) The title compound was prepared from 4-(3-ethoxy-4-trifluoromethyl-phenyl)-6-trifluoromethyl-1H-pyrimidin-2-one (3.74 g, 10.6 mmol) and phosphoryl chloride (35 mL) according to the general procedure I. Obtained as a light brown solid. MS (EI) 370.0 [(M)$^+$]; mp 89° C.

EXAMPLE A.11

2-Chloro-4-(4-chloro-phenyl)-6-methyl-pyrimidine 1) 4-(4-Chloro-phenyl)-6-methyl-1H-pyrimidin-2-one: The compound was prepared from 1-(4-chloro-phenyl)-butane-1,3-dione and urea according to step 2 of the general procedure I. Obtained as a light red solid (85%). MS (ISP) 221.1 [(M+H)$^+$]; mp 236-239° C.

2). The title compound was prepared from 4-(4-chloro-phenyl)-6-methyl-1H-pyrimidin-2-one (11.0 g, 50.0 mmol) and phosphoryl chloride (20 mL) according to step 3 of the general procedure I. Obtained as an off-white solid (6.8 g, 57%). MS (ISP) 239.0 [(M+H)$^+$]; mp 116-117° C.

EXAMPLE A.12

2-Chloro-4-methyl-6-(4-trifluoromethyl-phenyl)-pyrimidine 1) 6-Methyl-4-(4-trifluoromethyl-phenyl)-1H-pyrimidin-2-one: The compound was prepared from 1-(4-trifluoromethyl-phenyl)-butane-1,3-dione and urea according to step 2 of the general procedure I. Obtained as a light yellow solid (14%). MS (ISP) 255.3 [(M+H)$^+$]; mp 250-252° C.

2) The title compound was prepared from 6-methyl-4-(4-trifluoromethyl-phenyl)-1H-pyrimidin-2-one (5.1 g, 20.0 mmol) and phosphoryl chloride (10 mL) according to step 3 of the general procedure I. Obtained as a light brown solid (4.1 g, 75%). MS (ISP) 273.1 [(M+H)$^+$]; mp 82-83° C.

EXAMPLE A.13

2-Chloro-4-(4-chloro-phenyl)-6-cylopropyl-pyrimidine 1) 2,4-Dichloro-6-(4-chloro-phenyl)-pyrimidine: A mixture of 2,4,6-trichloropyrimidine (10.1 g, 55 mmol), 4-chlorophenylboronic acid (8.6 g, 55 mmol), sodium carbonate (18.1 g, 171 mmol), palladium acetate (0.61 g, 2.7 mmol), and triphenylphosphine (1.44 g, 5.5 mmol) in dimethoxyethane (0.5 L)/$H_2O$ (0.1 L) was heated to 80° C. for 18 h. The cooled mixture was poured onto ice-water and the product was extracted with diethyl ether. The organic layer was washed with brine, dried and evaporated. The crude product was purified by trituration with diethyl ether/dichloromethane (9:1) to give 2,4-dichloro-6-(4-chloro-phenyl)-pyrimidine as an off-white solid (5.0 g, 35%). mp 130-132° C.

2) To a solution of 2,4-dichloro-6-(4-chloro-phenyl)-pyrimidine (2.6 g, 10.0 mmol) and tetrakis(triphenylphosphine) palladium (0.69 g, 0.6 mmol) in THF (10 mL) was added at 20° C. a 0.25 M cyclopropylzinc chloride/THF solution (120 mL, 30 mmol; freshly prepared by stirring a mixture of 60 mL of 0.5 M cyclopropylmagnesium bromide/THF and 60 mL of 0.5 M zinc chloride/THF for 1 h at 0° C., followed by 1 h at 20° C.) and the mixture was refluxed in an atmosphere of argon for 3 h. After the slow addition of sat. aqueous $NH_4Cl$ solution (20 mL) at 0° C. the mixture was partitioned between AcOEt and 10% sodium chloride solution. The organic layer was dried ($Na_2SO_4$) and evaporated in vacuo. The residue was chromatographed on silica gel using AcOEt/cyclohexane (1:19 v/v) as eluent to give 2-chloro-4-(4-chloro-phenyl)-6-cyclopropyl-pyrimidine (1.12 g, 42%) as a light yellow solid. MS (ISP) 265.1 [(M+H)$^+$]; mp 70-72° C.

EXAMPLE A.14

2-Chloro-4-(4-chloro-phenyl)-pyrimidine

1) A mixture of 2,4-dichloropyrimidine (3.1 g, 20 mmol), 4-chlorophenylboronic acid (3.0 g, 20 mmol), and tetrakis (triphenylphosphine)palladium (0.69 g, 0.6 mmol) in dimethoxyethane (200 mL)/sat. $Na_2CO_3$ solution (34 mL) was heated to 80° C. for 20 h. The cooled mixture was poured into ice-water and the product was extracted with ethyl acetate. The organic layer was washed with brine, dried and evaporated. The crude product was purified by chromatography on silica gel using ethyl acetate/cyclohexane (1:2, v/v) as eluent to give the title compound (1.82 g, 40%) as white solid. NMR (DMSO-$d_6$) δ 7.67 (d, 2H, J=7 Hz), 8.19 (d, 2H, J=5 Hz), 8.23 (d, 2H, J=7 Hz), 8.86 (d, 2H, J=5 Hz) ppm; mp 290-292° C.

EXAMPLE A.15

2-Methanesulfonyl-4-trifluoromethyl-6-(3-trifluoromethyl-phenyl)-pyrimidine 1) 2-Methylsulfanyl-4-trifluoromethyl-6-(3-trifluoromethyl-phenyl)-pyrimidine: The compound was prepared from commercially available ethyl trifluoroacetate, commercially available 3-trifluoromethyl-acetophenone and commercially available S-methylthiourea sulfate according to the general procedure I step 1 and step 2 (thiourea route, protocol a). Obtained as a white solid (98%). MS (ISP) 339.0 [(M+H)$^+$].

2) The title compound was prepared from 2-methylsulfanyl-4-trifluoromethyl-6-(3-trifluoromethyl-phenyl)-pyrimidine (1.88 g, 6 mmol) with m-CPBA (3.365 g, 11 mmol) according to general procedure I step 3 (thiourea route). Obtained as a white solid (1.8 g, 87%). MS (ISP) 370.9 [(M+H)$^+$].

EXAMPLE A.16

2-Chloro-6-(4-chloro-phenyl)-4-trifluoromethyl-pyridine 1) 6-(4-Chloro-phenyl)-2-oxo-4-trifluoromethyl-1,2-dihydro-pyridine-3-carbonitrile: The compound was prepared from commercially available ethyl trifluoroacetate, commercially available 4-chloro-acetophenone and commercially available cyanoacetamide according to the general procedure I step 1 and Ia step 1. Obtained as a yellow solid (82%). MS (ISP) 299.1 [(M+H)$^+$] and 301 [(M+2+H)$^+$]; mp 287° C.

2) 6-(4-Chloro-phenyl)-4-trifluoromethyl-1H-pyridin-2-one: The compound was prepared from 6-(4-chloro-phenyl)-2-oxo-4-trifluoromethyl-1,2-dihydro-pyridine-3-carbonitrile (26.68 g, 89 mmol) and 85% aqueous $H_2SO_4$ according to general procedure Ia, step 2 protocol a. Obtained as a white solid (22.28 g, 91%). MS (ISN) 272.1 [(M−H)$^-$] and 274.0 [(M+2−H)$^-$]; mp 220-221° C.

3) The title compound was prepared from 6-(4-chloro-phenyl)-4-trifluoromethyl-1H-pyridin-2-one (10.0 g, 37 mmol) and phosphoryl chloride (16.75 mL, 183 mmol) according to the general procedure Ia to d preparation of chlorides. Obtained as a light brown solid (10.14 g, 95%). MS (ISP) 292.1 [(M+H)$^+$], 294 [(M+2+H)$^+$] and 296 [(M+4+H)$^+$].

EXAMPLE A.17

2-Chloro-4-trifluoromethyl-6-(4-trifluoromethyl-phenyl)-pyridine 1) 2-Oxo-4-trifluoromethyl-6-(4-trifluoromethyl-phenyl)-1,2-dihydro-pyridine-3-carbonitrile: The compound was prepared from commercially available ethyl trifluoroacetate, commercially available 4-trifluoromethyl-acetophenone and commercially available cyanoacetamide according to the general procedure I step 1 and Ia step 1. Obtained as a light yellow solid (69%). MS (ISN) 331 [(M−H)$^-$]; mp 197° C.

2) 4-Trifluoromethyl-6-(4-trifluoromethyl-phenyl)-1H-pyridin-2-one: The compound was prepared from 2-oxo-4-trifluoromethyl-6-(4-trifluoromethyl-phenyl)-1,2-dihydro-pyridine-3-carbonitrile (42 g, 126 mmol) and 48% aqueous HBr in propionic acid according to general procedure Ia, step 2 protocol b. Obtained as a white solid (52.98 g, 88%). MS (ISP) 308.3 [(M+H)$^+$]; mp 203-204° C.

3) The title compound was prepared from 4-trifluoromethyl-6-(4-trifluoromethylphenyl)-1H-pyridin-2-one (51.5 g, 168 mmol) and phosphoryl chloride (50 mL) according to the general procedure Ia to d preparation of chlorides. Obtained as an off-white solid (53.4 g, 98%). MS (ISN) 384.1 [(M+OAc)$^-$], 386.0 [(M+2+OAc)$^-$]; mp 39-40° C.

EXAMPLE A.18

2-Bromo-6-(4-chloro-phenyl)-4-trifluoromethyl-pyridine

The title compound was prepared from 6-(4-chloro-phenyl)-4-trifluoromethyl-1H-pyridin-2-one (example A.16 step 2) (7.38 g, 27 mmol) and phosphoryl bromide (25 g, 87 mmol) according to the general procedure Ia to d preparation of bromides. Obtained as a brown solid (8.92 g, 98%). MS (EI) 334.8 [(M)$^+$], 336.7 [(M+2)$^+$], 338.8 [(M+4)$^+$] and 339.8 [(M+6)$^+$]; mp 51-53° C.

EXAMPLE A.19

2-Bromo-4-trifluoromethyl-6-(4-trifluoromethyl-phenyl)-pyridine

The title compound was prepared from 4-trifluoromethyl-6-(4-trifluoromethyl-phenyl)-1H-pyridin-2-one (example A.17 step 2) (15 g, 49 mmol) and phosphoryl bromide (42 g, 146 mmol) according to the general procedure Ia to d preparation of bromides. Obtained as a brown solid (18 g, quant.). MS (EI) 368.9 [(M)$^+$] and 370.8 [(M+2)$^+$]; mp 35-37° C.

EXAMPLE A.20

6-(4-Chloro-phenyl)-2-iodo-4-trifluoromethyl-pyridine

The title compound was prepared from 2-chloro-6-(4-chloro-phenyl)-4-trifluoromethyl-pyridine (example A.16) (4.97 g, 17 mmol) according to the general procedure Ia to d preparation of iodides. Obtained as a brown solid (5.39 g, 79%). MS (ISP) 384.0 [(M+H)$^+$] and 386 [(M+2+H)$^+$].

EXAMPLE A.21

2-Iodo-4-trifluoromethyl-6-(4-trifluoromethyl-phenyl)-pyridine

The title compound was prepared from 2-chloro-4-trifluoromethyl-6-(4-trifluoromethylphenyl)-pyridine (example A.17) (37.12 g, 114 mmol) according to the general procedure Ia to d preparation of iodides. Obtained as a light yellow solid (33.37 g, 70%). MS (ISP) 418.0 [(M+H)$^+$].

EXAMPLE A.22

2-Bromo-6-(4-chloro-phenyl)-4-methyl-pyridine 1) 6-(4-Chloro-phenyl)-4-methyl-2-oxo-1,2-dihydro-pyridine-3-carbonitrile: The compound was prepared from commercially available ethyl acetate, commercially available 4-chloro-acetophenone and commercially available malononitrile according to the general procedure Ia step 1 protocol b. Obtained as a yellow solid (56%). MS (ISP) 245.5 [(M+H)$^+$] and 247 [(M+2+H)$^+$].

2) 6-(4-Chloro-phenyl)-4-methyl-1H-pyridin-2-one: The compound was prepared from 6-(4-chloro-phenyl)-4-methyl-2-oxo-1,2-dihydro-pyridine-3-carbonitrile (7.26 g, 30 mmol) and 85% aqueous $H_2SO_4$ at 180° C. according to general procedure Ia, step 2 protocol a. Obtained as a white solid (4.66 g, 72%). MS (ISP) 220.1 [(M+H)$^+$] and 222 [(M+2+H)$^+$]; mp 220-221° C.

3) The title compound was prepared from 6-(4-chloro-phenyl)-4-methyl-1H-pyridin-2-one (1.1 g, 5 mmol) and phosphoryl bromide (4.63 g, 16 mmol) in toluene (9.5 mL) according to the general procedure Ia to d preparation of bromides. Obtained as a light brown solid (1.0 g, quant., 74% purity). MS (ISP) 282.0 [(M+H)$^+$], 284.0 [(M+2+H)$^+$] and 286.0 [(M+4+H)$^+$].

EXAMPLE A.23

2-Chloro-4-methyl-6-(4-trifluoromethyl-phenyl)-pyridine Starting material: (E)-1-(4-Trifluoromethyl-phenyl)-but-2-en-1-one [CAS-No. 201164-24-1]

To a solution of commercially available 4-iodobenzotrifluoride (11.76 mL, 80 mmol) in THF (70 mL) at −40° C. was added isopropylmagnesium chloride (2 M in THF, 41.2 mL, 88 mmol) within 5 min keeping the internal temperature below −20° C., stirring was continued at −20 to 0° C. for 40 min. $ZnCl_2$ (1M in THF, 88 mL, 88 mmol) was added, the cooling bath was removed and replaced with a water bath, the mixture was allowed to reach 23° C. and stirred at 23° C. for 45 min resulting in a light yellow suspension. $Pd(PPh_3)_4$ (924 mg, 1 mol %) and trans-crotonyl chloride (90%, 9.38 mL, 88 mmol) were added dropwise at 23° C. (exothermic reaction (!), keeping the internal temperature at ~35° C. by water bath cooling) and stirring was continued at 23° C. for 1 h. Poured into icecold 0.5 N HCl, extracted with EtOAc, washed with sat. $NaHCO_3$-sol. and brine, dried over $MgSO_4$. Removal of the solvent in vacuum left a red oil which was purified with chromatography with heptane to heptane:TBME (9:1) to give the (E)-1-(4-trifluoromethyl-phenyl)-but-2-en-1-one as a yellow liquid (18.37 g, quant., 93% purity).

1) 4-Methyl-6-(4-trifluoromethyl-phenyl)-1H-pyridin-2-one: The compound was prepared from the above described (E)-1-(4-trifluoromethyl-phenyl)-but-2-en-1-one (18.35 g, ca. 80 mmol), commercially available 1-ethoxycarbonylmethyl-pyridinium bromide [CAS-No. 17282-40-5] (21.57 g, 88 mmol) and ammonium acetate (30.71 g, 398 mmol) in ethanol (80 mL) was according to the general procedure Ib step 1. Obtained as a light red solid (11.43 g, 57%). MS (ISN) 252.1 [(M−H)$^-$].

2) 2-Chloro-4-methyl-6-(4-trifluoromethyl-phenyl)-pyridine: The compound was prepared from 4-methyl-6-(4-trifluoromethyl-phenyl)-1H-pyridin-2-one (13.64 g, 54 mmol) and phosphoryl chloride (14.8 mL, 162 mmol) according to the general procedure Ia to d preparation of chlorides. Obtained as a brown solid (13.77 g, 94%). MS (ISP) 272.2 [(M+H)$^+$] and 274.0 [(M+2+H)$^+$].

EXAMPLE A.24

2-Chloro-4-cyclopropyl-6-(4-trifluoromethyl-phenyl)-pyridine Starting material: (E)-3-Cyclopropyl-1-(4-trifluoromethyl-phenyl)-propenone Step a) [2-Oxo-2-(4-trifluoromethyl-phenyl)-ethyl]-phosphonic acid dimethyl ester [CAS-No. 51638-15-4]: To a solution of commercially available dimethyl methylphosphonate (26.8 mL, 247 mmol) in THF (500 mL) was added n-BuLi (1.6 M in hexane) (153.1 mL, 245 mmol) keeping the internal temperature below −65° C. Stirring was continued for 15 min, then a solution of commercially available methyl 4-(trifluoromethyl)benzoate (25.0 g, 122 mmol) in THF (70 mL) was added, keeping the temperature below −70° C. The mixture was stirred for additional 30 min at −78° C., then was allowed to warm to 0° C. The mixture was quenched by addition of 1N HCl saturated with solid NaCl, extracted with TBME, dried over $MgSO_4$. Removal of the solvent in vacuum left a light yellow oil and the dimethyl methylphosphonate was removed by Kugelrohr distillation at 120° C. (0.94 mbar) to give the [2-oxo-2-(4-trifluoromethyl-phenyl)ethyl]-phosphonic acid dimethyl ester as a light yellow liquid (35.1 g, 97%). MS (ISN) 295.3 $[(M-H)^-]$.

Step b) (E)-3-Cyclopropyl-1-(4-trifluoromethyl-phenyl)-propenone: A mixture of the above prepared [2-oxo-2-(4-trifluoromethyl-phenyl)-ethyl]-phosphonic acid dimethyl ester (11.85 g, 40 mmol), cyclopropanecarboxaldehyde (2.99 mL, 40 mmol) and cesium carbonate (13.68 g, 42 mmol) in dioxane (80 mL) and water (1 mL) was stirred at 70° C. for 30 min. Cooled to 23° C., added 1N HCl until pH 1 was reached, extracted with TBME, washed the organic layer with sat. $NaHCO_3$-sol. and brine, dried over $Na_2SO_4$. Removal of the solvent in vacuum left a yellow oil which was purified by silica gel column chromatography with heptane/EtOAc 2:1 to give the (E)-3-cyclopropyl-1-(4-trifluoromethyl-phenyl)-propenone as a yellow solid (7.38 g, 77%). MS (EI) 240.0 $[(M)^+]$; mp 47-52° C.

1) 4-Cyclopropyl-6-(4-trifluoromethyl-phenyl)-1H-pyridin-2-one: The compound was prepared from the above described (E)-1-(4-trifluoromethyl-phenyl)-but-2-en-1-one (2.642 g, 11 mmol), commercially available 1-ethoxycarbonylmethyl-pyridinium bromide [CAS-No. 17282-40-5] (3.249 g, 13 mmol) and ammonium acetate (4.24 g, 55 mmol) in ethanol (20 mL) was according to the general procedure Ib step 1. Obtained as a light brown solid (0.91 g, 30%). MS (ISP) 280.1 $[(M+H)^+]$.

2) 2-Chloro-4-cylopropyl-6-(4-trifluoromethyl-phenyl)-pyridine: The compound was prepared from 4-cyclopropyl-6-(4-trifluoromethyl-phenyl)-1H-pyridin-2-one (0.9 g, 3.2 mmol) and phosphoryl chloride (1.0 mL, 11 mmol) according to the general procedure Ia to d preparation of chlorides. Obtained as an off-white solid (530 g, 55%). MS (ISP) 298.2 $[(M+H)^+]$ and 300 $[(M+2+H)^+]$; mp 89-93° C.

EXAMPLE A.25

2-Chloro-4-(4-chloro-phenyl)-6-trifluoromethyl-pyridine 1) 4-(4-Chloro-phenyl)-5-cyano-2-hydroxy-6-oxo-2-trifluoromethyl-piperidine-3-carboxylic acid ethyl ester: The compound was prepared from commercially available 4-chlorobenzaldehyde (28.3 g, 201 mmol), commercially available cyanoacetamide (17.3 g, 206 mmol), commercially available ethyl 4,4,4-trifluoroacetoacetate (31.0 mL, 210 mmol) and piperidine (4 mL, 0.2 eq.) in EtOH (250 mL) according to the general procedure Id step 1. Obtained as a yellow foam (80.57 g, quant.). MS (ISN) 389.1 $[(M-H)^-]$ and 391 $[(M+2-H)^-]$.

2) 4-(4-Chloro-phenyl)-5-cyano-6-oxo-2-trifluoromethyl-1,6-dihydro-pyridine-3-carboxylic acid ethyl ester: The compound was prepared from 4-(4-chloro-phenyl)-5-cyano-2-hydroxy-6-oxo-2-trifluoromethyl-piperidine-3-carboxylic acid ethyl ester (80.5 g, 200 mmol) and thionyl chloride (90 mL, 1241 mmol) according to general procedure Id step 2. Obtained as a brown solid (46.14 g, 63%). MS (ISN) 369.1 $[(M-H)^-]$ and 371.0 $[(M+2-H)^-]$.

3) 4-(4-Chloro-phenyl)-6-trifluoromethyl-1H-pyridin-2-one: The compound was prepared from 4-(4-chloro-phenyl)-5-cyano-6-oxo-2-trifluoromethyl-1,6-dihydro-pyridine-3-carboxylic acid ethyl ester (45.0 g, 121 mmol) and 48% hydrobromic acid (400 mL) in acetic acid (250 mL) at 140° C. for 11 days according to general procedure Id step 3. Obtained as a light brown solid (29.43 g, 89%, 85% purity). MS (ISN) 272.2 $[(M-H)^-]$ and 274.1 $[(M+2-H)^-]$.

4) The title compound was prepared from 4-(4-chloro-phenyl)-6-trifluoromethyl-1H-pyridin-2-one (29.5 g, 108 mmol) and phosphoryl chloride (49.2 mL, 539 mmol) according to the general procedure Ia to d preparation of chlorides. Obtained as a light brown solid (19.7 g, 62%). MS (ISP) 292.1 $[(M+H)^+]$, 294 $[(M+2+H)^+]$ and 296 $[(M+4+H)^+]$.

EXAMPLE A.26

2-Chloro-6-trifluoromethyl-4-(4-trifluoromethyl-phenyl)-pyridine 1) 5-Cyano-2-hydroxy-6-oxo-2-trifluoromethyl-4-(4-trifluoromethyl-phenyl)-piperidine-3-carboxylic acid ethyl ester: The compound was prepared from commercially available 4-trifluoromethylbenzaldehyde (28.9 mL, 200 mmol), commercially available cyanoacetamide (17.5 g, 208 mmol), commercially available ethyl 4,4,4-trifluoroacetoacetate (30.5 mL, 207 mmol) and piperidine (4 mL, 0.2 eq.) in EtOH (100 mL) according to the general procedure Id step 1. Obtained as yellow foam (90.44 g, 98%, 92% purity). MS (ISN) 423.1 $[(M-H)^-]$.

2) 5-Cyano-6-oxo-2-trifluoromethyl-4-(4-trifluoromethyl-phenyl)-1,6-dihydro-pyridine-3-carboxylic acid ethyl ester: The compound was prepared from 5-cyano-2-hydroxy-6-oxo-2-trifluoromethyl-4-(4-trifluoromethyl-phenyl)-piperidine-3-carboxylic acid ethyl ester (94.12 g, ca. 210 mmol) and thionyl chloride (95 mL, 1305 mmol) according to general procedure Id step 2. Obtained as a brown solid (70.98 g, 81%). MS (ISN) 403.1 $[(M-H)^-]$.

3) 6-Trifluoromethyl-4-(4-trifluoromethyl-phenyl)-1H-pyridin-2-one: The compound was prepared from 5-cyano-6-oxo-2-trifluoromethyl-4-(4-trifluoromethyl-phenyl)-1,6-dihydro-pyridine-3-carboxylic acid ethyl ester (70.9 g, 175 mmol) and 48% hydrobromic acid (400 mL) in acetic acid (250 mL) at 140° C. for 12 days according to general procedure Id step 3. Obtained as a brown solid (23.7 g, 44%, 84% purity). MS (ISN) 306.2 $[(M-H)^-]$.

4) The title compound was prepared from 6-trifluoromethyl-4-(4-trifluoromethylphenyl)-1H-pyridin-2-one (23.7 g, 77 mmol) and phosphoryl chloride (35.2 mL, 386 mmol) according to the general procedure Ia to d preparation of chlorides. Obtained as an off-white solid (16.5 g, 66%). MS (ISP) 326.1 [$(M+H)^+$] and 328 [$(M+2+H)^+$].

EXAMPLE A.27

2-Chloro-4-(4-chloro-phenyl)-6-methyl-pyridine 1) 4-(4-Chloro-phenyl)-6-methyl-1H-pyridin-2-one [CAS-No. 24452-07-1]: The compound was prepared from commercially available 4-(4-chloro-phenyl)-but-3-en-2-one [CAS-No. 3160-40-5] (44.15 g, 244 mmol), commercially available 1-ethoxycarbonylmethyl-pyridinium bromide [CAS-No. 17282-40-5] (66.17 g, 269 mmol) and ammonium acetate (100 g, 1297 mmol) in EtOH (300 mL) according to general procedure Ib step 1. Obtained as a yellow solid (52.61 g, 98%, 96% purity). MS (ISP) 220.2 [$(M+H)^+$] and 222 [$(M+2+H)^+$]; mp 212° C.

2) The title compound was prepared from 4-(4-chloro-phenyl)-6-methyl-1H-pyridin-2-one (15 g, 68 mmol) and phosphoryl chloride (31.1 mL, 341 mmol) according to the general procedure Ia to d preparation of chlorides. Obtained as a brown solid (12.3 g, 75%). MS (ISP) 238.1 [$(M+H)^+$], 240 [$(M+2+H)^+$] and 242 [$(M+4+H)^+$].

EXAMPLE A.28

2-Bromo-4-(4-chloro-phenyl)-6-methyl-pyridine [CAS-No. 23148-57-4]

The title compound was prepared from 4-(4-chloro-phenyl)-6-methyl-1H-pyridin-2-one (example A.27 step 1) (4.00 g, 18.2 mmol) and phosphoryl bromide (15.66 g, 54.6 mmol) according to the general procedure Ia to d preparation of bromides. Obtained as a light brown solid (2.95 g, 57%). MS (ISP) 282 [$(M+H)^+$], 284 [$(M+2+H)^+$] and 286 [$(M+4+H)^+$]; mp 92° C.

EXAMPLE A.29

4-(4-Chloro-phenyl)-2-iodo-6-methyl-pyridine

The title compound was prepared from 2-chloro-4-(4-chloro-phenyl)-6-methyl-pyridine (example A.27) (10.0 g, 42 mmol) according to the general procedure Ia to d preparation of iodides. Obtained as a white solid (9.4 g, 68%). MS (ISP) 329.9 [$(M+H)^+$] and 331 [$(M+2+H)^+$].

EXAMPLE A.30

2-Chloro-6-methyl-4-(4-trifluoromethyl-phenyl)-pyridine [CAS-No. 697739-23-4]

1) 6-Methyl-4-(4-trifluoromethyl-phenyl)-1H-pyridin-2-one: The compound was prepared from commercially available 4-(4-trifluoromethyl-phenyl)-but-3-en-2-one [CAS-No. 80992-93-4] (47.64 g, 222 mmol), commercially available 1-ethoxycarbonylmethyl-pyridinium bromide [CAS-No. 17282-40-5] (60.21 g, 245 mmol) and ammonium acetate (85.7 g, 1112 mmol) in EtOH (275 mL) according to general procedure Ib step 1. Obtained as an off-white solid (48.79 g, 87%). MS (ISP) 254.2 [$(M+H)^+$].

2) The title compound was prepared from 6-methyl-4-(4-trifluoromethyl-phenyl)-1H-pyridin-2-one (20 g, 79 mmol) and phosphoryl chloride (36.0 mL, 395 mmol) according to the general procedure Ia to d preparation of chlorides. Obtained as an off-white solid (17.35 g, 81%). NMR (DMSO-$d_6$) δ 7.71 (s, 1H), 7.73 (s, 1H), 7.88 (d, 2H, J=8.1 Hz), 8.05 (d, 2H, J=8.1 Hz) ppm.

EXAMPLE A.31

2-Iodo-6-methyl-4-(4-trifluoromethyl-phenyl)-pyridine

The title compound was prepared from 2-chloro-6-methyl-4-(4-trifluoromethyl-phenyl)-pyridine (example A.30) (2.72 g, 10 mmol) according to the general procedure Ia to d preparation of iodides. Obtained as a light yellow solid (3.42 g, 94%). MS (ISP) 364.0 [$(M+H)^+$]; mp 87-91° C.

Alternatively the title compound was prepared from 2-bromo-6-methyl-4-(4-trifluoromethyl-phenyl)-pyridine (example A.48) (101.0 g, 320 mmol), sodium iodide (91.04 g, 608 mmol), copper(I) iodide (2.89 g, 5 mol %) and N,N'-dimethylethylenediamine (3.31 mL, 11 mol %) in dioxane (304 mL) according to the general procedure Ia to d preparation of iodides. Obtained as a light yellow solid (112.5 g, 100%). MS (ISP) 364.0 [$(M+H)^+$]; mp 91-93° C.

EXAMPLE A.32

Trifluoro-methanesulfonic acid 6-methyl-4-(4-trifluoromethyl-phenyl)-pyridin-2-yl ester The title compound was prepared from 6-methyl-4-(4-trifluoromethyl-phenyl)-1H-pyridin-2-one (example A.30 step 1) (20.0 g, 79 mmol) according to the general procedure Ia to d preparation of triflates. Obtained as an off-white solid (28.13 g, 92%). MS (ISP) 386.0 [$(M+H)^+$].

EXAMPLE A.33

2-Chloro-6-cyclopropyl-4-(4-trifluoromethyl-phenyl)-pyridine

Starting material: (E)-1-Cyclopropyl-3-(4-trifluoromethyl-phenyl)-propenone [CAS-No. 72881-74-4]

To a solution of commercially available 4-trifluoromethyl-benzaldehyde (20.6 mL, 150 mmol) and commercially available cyclopropylmethylketone (14.1 mL, 150 mmol) in MeOH (30 mL) was added NaOMe-sol. (5.4 M in MeOH, 5.55 mL, 30 mmol) (slightly exothermic reaction) and the mixture was stirred at 23° C. for 16 h. Poured onto ice, acidified with 1 N HCl (150 mL), saturated with solid NaCl, extracted with TBME, dried over MgSO4. Removal of the solvent in vacuum left a light yellow semisolid (35.47 g, quant.), which was used without further purification. MS (EI) 240.2 [$(M)^+$].

1) 6-Cyclopropyl-4-(4-trifluoromethyl-phenyl)-1H-pyridin-2-one: The compound was prepared from the above described (E)-1-cyclopropyl-3-(4-trifluoromethyl-phenyl)-propenone [CAS-No. 72881-74-4] (35.09 g, 146 mmol), commercially available 1-ethoxycarbonylmethyl-pyridinium bromide [CAS-No. 17282-40-5] (43.14 g, 175 mmol) and ammonium acetate (56.3 g, 730 mmol) in EtOH (350 mL) according to general procedure Ib step 1. Obtained as a light red solid (30.17 g, 74%). MS (ISP) 280.3 [$(M+H)^+$].

2) The title compound was prepared from 6-cyclopropyl-4-(4-trifluoromethyl-phenyl)-1H-pyridin-2-one (5.0 g, 18 mmol) and phosphoryl chloride (8.2 mL, 90 mmol) according to the general procedure Ia to d preparation of chlorides. Obtained as an off-white solid (4.73 g, 88%). MS (ISP) 298.2 [$(M+H)^+$] and 300 [$(M+2+H)^+$].

EXAMPLE A.34

Trifluoro-methanesulfonic acid 6-cyclopropyl-4-(4-trifluoromethyl-phenyl)-pyridin-2-yl ester The title compound was prepared from 6-cyclopropyl-4-(4-trifluoromethyl-phenyl)-1H-pyridin-2-one (example A.33 step 1) (10.0 g, 36 mmol) according to the general procedure Ia to d preparation of triflates. Obtained as an orange oil (13.85 g, 94%). MS (ISP) 412.2 [$(M+H)^+$].

EXAMPLE A.35

4-(3-Ethoxy-4-trifluoromethyl-phenyl)-2-iodo-6-trifluoromethyl-pyrimidine

The title compound was prepared from 2-chloro-4-(3-ethoxy-4-trifluoromethyl-phenyl)-6-trifluoromethyl-pyrimidine (example A.10) (0.74 g, 2.0 mmol) according to the general procedure I. Obtained as a green solid (0.92 g, 100%). MS (ISP) 461.0 [$(M-H)^-$]; mp 81.5° C.

EXAMPLE A.36

4-(3,4-Dichloro-phenyl)-2-iodo-6-trifluoromethyl-pyrimidine

The title compound was prepared from 2-chloro-4-(3,4-dichloro-phenyl)-6-trifluoromethyl-pyrimidine (example A.7) (0.5 g, 1.53 mmol) according to the general procedure I. Obtained as an off-white solid (0.24 g, 38%). MS (EI) 417.9 [$(M)^+$]; mp 85° C.

EXAMPLE A.37

4-(4-Chloro-3-methyl-phenyl)-2-iodo-6-trifluoromethyl-pyrimidine

The title compound was prepared from 2-chloro-4-(4-chloro-3-methyl-phenyl)-6-trifluoromethyl-pyrimidine (example A.8) (4.9 g, mmol) according to the general procedure I. Obtained as a light grey solid (0.99 g, 51%). MS (EI) 397.9 [$(M)^+$]; mp 88.5° C.

EXAMPLE A.38

2-Chloro-4-(3-methyl-4-trifluoromethyl-phenyl)-6-trifluoromethyl-pyrimidine 1) 4-(3-Methyl-4-trifluoromethyl-phenyl)-6-trifluoromethyl-1H-pyrimidin-2-one: The compound was prepared from commercially available ethyl trifluoroacetate, 3-methyl-4-trifluoromethyl-acetophenone [CAS-No. 851262-60-7] (7.26 g, 24.3 mmol) and urea according to the general procedure I. Obtained as a white solid (5.42 g, 69%). MS (EI) 322.1 [$(M)^+$]; mp 182° C.

2) The title compound was prepared from 4-(3-methyl-4-trifluoromethyl-phenyl)-6-trifluoromethyl-1H-pyrimidin-2-one (4.31 g, 13.4 mmol) and phosphoroxychloride (40 mL) according to the general procedure I. Obtained as a light yellow solid (4.47 g, 98%). MS (EI) 340.1 [$(M)^+$]; Mp 53° C.

EXAMPLE A.39

2-Chloro-4-[3-(2,2,2-trifluoro-ethoxy)-4-trifluoromethyl-phenyl]-6-trifluoromethyl-pyrimidine 1) 6-[3-(2,2,2-Trifluoro-ethoxy)-4-trifluoromethyl-phenyl]-4-trifluoromethyl-1H-pyrimidin-2-one: The compound was prepared from commercially available ethyl trifluoroacetate, 3-(2,2,2-trifluoro-ethoxy)-4-trifluoromethyl-acetophenone [CAS-No. 851264-00-1] and urea according to the general procedure I. Obtained as an off-white solid (3.89 g, 58%). MS (ISN) 405.2 [$(M-H)^-$]; mp 228° C.

2) The title compound was prepared from 6-[3-(2,2,2-trifluoro-ethoxy)-4-trifluoromethyl-phenyl]-4-trifluoromethyl-1H-pyrimidin-2-one (3.74 g, 9.21 mmol) and phosphoroxychloride (30 mL) according to the general procedure I. Obtained as a brown solid (3.75 g, 96%). MS (EI) 424.0 [$(M)^+$]; mp 44° C.

EXAMPLE A.40

2-Chloro-4-(3-methyl-4-trifluoromethyl-phenyl)-6-methyl-pyrimidine 1) 4-(3-Methyl-4-trifluoromethyl-phenyl)-6-methyl-1H-pyrimidin-2-one: The compound was prepared from commercially available ethyl acetate, 3-methyl-4-trifluoromethyl-acetophenone [CAS-No. 851262-60-7] (5 g, 24.7 mmol) and urea according to the general procedure I. Obtained as a light yellow solid (1.84 g, 28%). MS (EI) 268.2 [$(M)^+$]; mp 202° C. (dec.).

2) The title compound was prepared from 4-(3-methyl-4-trifluoromethyl-phenyl)-6-methyl-1H-pyrimidin-2-one (1.73 g, 6.45 mmol) and phosphoroxychloride (20 mL) according to the general procedure I. Obtained as a brown solid (1.4 g, 76%). MS (EI) 286.1 [$(M)^+$]; mp 101° C.

EXAMPLE A.41

2-Chloro-4-(3,4-dichloro-phenyl)-6-methyl-pyrimidine 1) 4-(3,4-Dichloro-phenyl)-6-methyl-1H-pyrimidin-2-one: The compound was prepared from commercially available ethyl acetate, commercially available 3,4-dichloro-acetophenone (5 g, 26.4 mmol) and urea according to the general procedure I. Obtained as a light yellow solid (2.64 g, 40%). MS (EI) 254.1 [$(M)^+$]; mp 277° C. (dec.).

2) The title compound was prepared from 4-(3,4-dichloro-phenyl)-6-methyl-1H-pyrimidin-2-one (2.51 g, 9.84 mmol) and phosphoroxychloride (35 mL) according to the general procedure I. Obtained as a brown solid (1.55 g, 58%). MS (EI) 272.1 [$(M)^+$]; mp 123° C. (dec.).

EXAMPLE A.42

2-Chloro-4-trifluoromethyl-6-(3-trifluoromethyl-phenyl)-pyrimidine 1) 6-Trifluoromethyl-4-(3-trifluoromethyl-phenyl)-1H-pyrimidin-2-one: The compound was prepared from commercially available ethyl trifluoroacetate, commercially available 3-trifluoromethyl-acetophenone and urea according to the general procedure I. Obtained as a white solid (7.95 g, 53%). MS (ISP) 309.0 [$(M+H)^+$]; mp 167° C.

2) The title compound was prepared from 6-trifluoromethyl-4-(3-trifluoromethylphenyl)-1H-pyrimidin-2-one (7.85 g, 25.5 mmol) and phosphoroxychloride (85 mL) according to the general procedure I. Obtained as a yellow solid (5.33 g, 64%). MS (EI) 326.1 [(M)$^+$]; mp 65° C.

EXAMPLE A.43

2-Chloro-4-isopropyl-6-(4-trifluoromethyl-phenyl)-pyrimidine 1) 6-Isopropyl-4-(3-trifluoromethyl-phenyl)-1H-pyrimidin-2-one: The compound was prepared from commercially available ethyl isopropylacetate, commercially available 3-trifluoromethyl-acetophenone and urea according to the general procedure I. Obtained as a white solid (5.28 g, 42%). MS (ISP) 283.4 [(M+H)$^+$]; mp 234° C. (dec.).

2) The tide compound was prepared from 6-isopropyl-4-(3-trifluoromethyl-phenyl)-1H-pyrimidin-2-one (5.13 g, 18.2 mmol) and phosphoroxychloride (61 mL) according to the general procedure I. Obtained as a light yellow oil (3.54 g, 65%). MS (ISP) 301.1 [(M+H)$^+$].

EXAMPLE A.44

2-Chloro-4-(3-chloro-phenyl)-6-trifluoromethyl-pyrimidine 1) 4-(3-Chloro-phenyl)-6-trifluoromethyl-1H-pyrimidin-2-one: The compound was prepared from commercially available ethyl trifluoroacetate, commercially available 3-chloro-acetophenone and urea according to the general procedure I. Obtained as an off-white solid (4.94 g, 56%). MS (ISP) 275.0 [(M+H)$^+$]; mp 195° C.

2) The title compound was prepared from 4-(3-chloro-phenyl)-6-trifluoromethyl-1H-pyrimidin-2-one (2.44 g, 8.88 mmol) and phosphoroxychloride (25 mL) according to the general procedure I. Obtained as a white solid (1.62 g, 62%). MS (EI) 292.0 [(M)$^+$]; mp 89.5° C.

EXAMPLE A.45

2-Chloro-4-(4-fluoro-phenyl)-6-trifluoromethyl-pyrimidine 1) 4-(4-Fluoro-phenyl)-6-trifluoromethyl-1H-pyrimidin-2-one: The compound was prepared from commercially available ethyl trifluoroacetate, commercially available 4-fluoro-acetophenone and urea according to the general procedure I. Obtained as a white solid (15.5 g, 82%). MS (ISP) 259.1 [(M+H)$^+$]; mp 213° C.

2) The title compound was prepared from 4-(4-fluoro-phenyl)-6-trifluoromethyl-1H-pyrimidin-2-one (15.5 g, 0.06 mol) and phosphoroxychloride (155 mL) according to the general procedure I. Obtained as a light yellow solid (16.5 g, 99%). MS (EI) 276.1 [(M)$^+$]; mp 67° C.

EXAMPLE A.46

2-Chloro-4-(3,4-difluoro-phenyl)-6-trifluoromethyl-pyrimidine 1) 4-(3,4-difluoro-phenyl)-6-trifluoromethyl-1H-pyrimidin-2-one: The compound was prepared from commercially available ethyl trifluoroacetate, commercially available 3,4-difluoro-acetophenone and urea according to the general procedure I. Obtained as a white solid (14.7 g, 84%). MS (ISP) 277.0 [(M+H)$^+$]; mp 171° C.

2) The title compound was prepared from 4-(3,4-difluoro-phenyl)-6-trifluoromethyl-1H-pyrimidin-2-one (14.7 g, 0.053 mol) and phosphoroxychloride (148 mL) according to the general procedure I. Obtained as a light brown solid (15.6 g, 99%). MS (EI) 294.0 [(M)$^+$]; mp 53° C.

EXAMPLE A.47

2-Chloro-4-(4-chloro-3-methyl-phenyl)-6-methyl-pyrimidine 1) 4-(4-Chloro-3-methyl-phenyl)-6-methyl-1H-pyrimidin-2-one: The compound was prepared from commercially available ethyl acetate, commercially available 4-chloro-3-methyl-acetophenone (25 g, 0.15 mol) and urea according to the general procedure I. Obtained as an off-white solid (9.78 g, 28%). MS (ISN) 233.3 [(M−H)$^-$]; mp 255° C. (dec.).

2) The title compound was prepared from 4-(4-chloro-3-methyl-phenyl)-6-methyl-1H-pyrimidin-2-one (9.78 g, 41.7 mmol) and phosphoroxychloride (98 mL) according to the general procedure I. Obtained as an off-white solid (7.38 g, 70%). MS (ISP) 253.1 [(M+H)$^+$]; mp 131° C.

EXAMPLE A.48

2-Bromo-6-methyl-4-(4-trifluoromethyl-phenyl)-pyridine

The title compound was prepared from 6-methyl-4-(4-trifluoromethyl-phenyl)-1H-pyridin-2-one (example A.30 step 1) (118.1 g, 466.4 mmol) and phosphoryl bromide (267.4 g, 933 mmol) according to the general procedure Ia to d preparation of bromides. Obtained as an off-white solid (109.67 g, 74%). MS (ISP) 316.0 [(M+H)$^+$] and 318.0 [(M+2+H)$^+$]; mp 74-76° C.

EXAMPLE A.49

2-Iodo-6-trifluoromethyl-4-(4-trifluoromethyl-phenyl)-pyridine

The title compound was prepared 2-chloro-6-trifluoromethyl-4-(4-trifluoromethylphenyl)-pyridine (example A.26) (10.0 g, 30.7 mmol) according to the general procedure Ia to d preparation of iodides. Obtained as a white solid (6.6 g, mixture of 41% starting material and 59% product). MS (ISP) 418.0 [(M+H)$^+$].

EXAMPLE A.50

4-(4-Chloro-phenyl)-2-iodo-6-trifluoromethyl-pyridine

The title compound was prepared from 2-chloro-4-(4-chloro-phenyl)-6-trifluoromethyl-pyridine (example A.25) (10.0 g, 34.2 mmol) according to the general procedure Ia to d preparation of iodides. Obtained as a white solid (5.9 g, 55% product, 45% starting material) and mother liquor (9 g, 35% product). MS (ISP) 384.0 [(M+H)$^+$] and 386 [(M+2+H)$^+$].

EXAMPLE A.51

2-Chloro-4-(3,4-dichloro-phenyl)-6-methyl-pyridine 1) (E)-4-(3,4-Dichloro-phenyl)-but-3-en-2-one [CAS-No. 55420-70-7]: To an ice cooled mixture of commercially available 3,4-dichlorbenzaldehyde (22.5 g, 119 mmol) and dimethyl-2-oxopropylphosphonate (25 g, 143 mmol) was portionwise added a solution of $K_2CO_3$ (32.9 g, 238 mmol) in water (30.0 mL) and stirring was continued at 5° C. for 15 min. The mixture was poured onto sat. $NaHCO_3$-sol., extracted twice with TBME, the organic layers were washed with brine, dried over $MgSO_4$, filtered and the solvents were evaporated to give the crude (E)-4-(3,4-dichloro-phenyl)-but-3-en-2-one (26.7 g, 104%) as a light yellow solid, which was used without further purification. MS (ISP) 215.2 [$(M+H)^+$], 217.1 [$(M+2+H)^+$] and 219 [$(M+4+H)^+$].

2) 4-(3,4-Dichloro-phenyl)-6-methyl-1H-pyridin-2-one: The compound was prepared from the above described (E)-4-(3,4-dichloro-phenyl)-but-3-en-2-one (26.7 g, 124 mmol), commercially available 1-ethoxycarbonylmethyl-pyridinium bromide [CAS-No. 17282-40-5] (33.6 g, 137 mmol) and ammonium acetate (47.8 g, 621 mmol) in EtOH (150 mL) according to general procedure Ib step 1. Obtained as a light brown solid (25.4 g, 81%). MS (ISP) 254.1 [$(M+H)^+$], 256.2 [$(M+2+H)^+$] and 258.0 [$(M+4+H)^+$]0.3) The title compound was prepared from the above described 4-(3,4-dichloro-phenyl)-6-methyl-1H-pyridin-2-one (25.4 g, 100 mmol) and phosphoryl chloride (45.6 mL, 500 mmol) according to the general procedure Ia to d preparation of chlorides. Obtained as an off-white solid (23.7 g, 87%). MS (ISP) 272.1 [$(M+H)^+$], 274.0 [$(M+2+H)^+$], 276.0 [$(M+4+H)^+$] and 278.0 [$(M+6+H)^+$].

EXAMPLE A.52

4-(3,4-Dichloro-phenyl)-2-iodo-6-methyl-pyridine

The title compound was prepared from 2-chloro-4-(3,4-dichloro-phenyl)-6-methylpyridine (example A.51) (20.0 g, 73.4 mmol) according to the general procedure Ia to d preparation of iodides. Obtained as a white solid (17.2 g, 80% product, 20% starting material) and a second crop (6.0 g, 60% product). MS (ISP) 364.0 [$(M+H)^+$], 366 [$(M+2+H)^+$] and 368 [$(M+4+H)^+$].

EXAMPLE A.53

2-Chloro-6-ethyl-4-(4-trifluoromethyl-phenyl)-pyridine 1) (E)-1-(4-Trifluoromethyl-phenyl)-pent-1-en-3-one [CAS-No. 863970-08-5]: To a mixture of 4-(trifluoromethyl) benzaldehyde (2.74 mL, 20 mmol) and 2-butanone (8.97 mL, 100 mmol) in EtOH (20 mL) and $H_2O$ (0.8 mL) was added $Ba(OH)_2.H_2O$ (100 mg, 2.6 mol %) and the mixture was refluxed for 1 h. Poured into ice water, acidified with 1N HCl to pH 1, extracted with TBME, washed the organic layer with sat. $NaHCO_3$-sol. and brine, dried over $MgSO_4$. Removal of the solvent in vacuum left the crude (E)-1-(4-trifluoromethyl-phenyl)-pent-1-en-3-one as a yellow semisolid (4.65 g, 102%), which was used without further purification.

2) 6-Ethyl-4-(4-trifluoromethyl-phenyl)-1H-pyridin-2-one: The compound was prepared from the above described (E)-1-(4-trifluoromethyl-phenyl)-pent-1-en-3-one (4.65 g, 20.4 mmol), commercially available 1-ethoxycarbonylmethyl-pyridinium bromide [CAS-No. 17282-40-5] (5.52 g, 22.4 mmol) and ammonium acetate (7.85 g, 102 mmol) in EtOH (25 mL) according to general procedure Ib step 1. Obtained as a white solid (1.15 g, 21%, and additional 3.6 g, 66% light brown residue). MS (ISP) 268.3 [$(M+H)^+$].

3) The title compound was prepared from the above described 6-ethyl-4-(4-trifluoromethyl-phenyl)-1H-pyridin-2-one (4.6 g, 17.2 mmol) and phosphoryl chloride (7.85 mL, 86.1 mmol) according to the general procedure Ia to d preparation of chlorides. Obtained as a light yellow solid (2.2 g, 44%). MS (ISP) 286.1 [$(M+H)^+$] and 288.0 [$(M+2+H)^+$].

EXAMPLE A.54

2-Ethyl-6-iodo-4-(4-trifluoromethyl-phenyl)-pyridine

The title compound was prepared from 2-chloro-6-ethyl-4-(4-trifluoromethyl-phenyl)pyridine (example A.53) (2.2 g, 7.7 mmol) according to the general procedure Ia to d preparation of iodides. Obtained as a light brown solid (2.1 g, 62% product, 38% starting material). MS (ISP) 378.0 [$(M+H)^+$].

EXAMPLE A.55

Trifluoro-methanesulfonic acid 4-methyl-6-(4-trifluoromethyl-phenyl)-pyridin-2-yl ester The title compound was prepared from 4-methyl-6-(4-trifluoromethyl-phenyl)-1H-pyridin-2-one (example A.23 step 1) (6.33 g, 25 mmol) and trifluoromethanesulfonic anhydride (5.0 mL, 30 mmol) according to the general procedure Ia to d preparation of triflates. Obtained as an off-white solid (1.61 g, 17%). MS (ISP) 386.0 [$(M+H)^+$].

EXAMPLE A.56

Trifluoro-methanesulfonic acid 4-benzo[1,3]dioxol-5-yl-6-methyl-pyridin-2-yl ester 1) 4-Benzo[1,3]dioxol-5-yl-6-methyl-1H-pyridin-2-one: The compound was prepared from commercially available 3,4-(methylenedioxy)benzylideneacetone (25 g, 131.4 mmol), commercially available 1-ethoxycarbonylmethyl-pyridinium bromide [CAS-No. 17282-40-5] (35.58 g, 144.6 mmol) and ammonium acetate (50.7 g, 657 mmol) in EtOH (150 mL) according to general procedure Ib step 1. Obtained as a brown solid (1.2 g, 4%). MS (ISP) 230.1 [$(M+H)^+$].

2) The title compound was prepared from the above described 4-benzo[1,3]dioxol-5-yl-6-methyl-1H-pyridin-2-one (1.2 g, 5.23 mmol) and trifluoromethanesulfonic anhydride (1.04 mL, 6.28 mmol) according to the general procedure Ia to d preparation of triflates. Obtained as a light brown solid (1.13 g, 60%). MS (ISP) 362.1 [$(M+H)^+$].

EXAMPLE A.57

2-Bromo-4-methyl-6-(4-trifluoromethyl-phenyl)-pyridine

The title compound was prepared from 4-methyl-6-(4-trifluoromethyl-phenyl)-1H-pyridin-2-one (example A.23 step 1) (25.32 g, 100 mmol) and phosphoryl bromide (86.0 g, 300 mmol) according to the general procedure Ia to d preparation of bromides. Obtained as a light yellow solid (29.27 g, 93%). MS (ISP) 316.0 [$(M+H)^+$] and 318.0 [$(M+2+H)^+$].

EXAMPLE A.58

2-Iodo-4-methyl-6-(4-trifluoromethyl-phenyl)-pyridine

The title compound was prepared from 2-bromo-4-methyl-4-(4-trifluoromethylphenyl)-pyridine (example A.57) (29.0 g, 92 mmol), sodium iodide (27.5 g, 183 mmol), copper(I)

iodide (0.874 g, 5 mol %) and N,N'-dimethylethylenediamine (1.3 mL, 10 mol %) in dioxane (150 mL) according to the general procedure Ia to d preparation of iodides. Obtained as alight yellow solid (32.72 g, 98%). MS (ISP) 364.2 [$(M+H)^+$].

EXAMPLE A.59

Trifluoro-methanesulfonic acid 4-(3-methoxy-4-trifluoromethyl-phenyl)-6-methyl-pyridin-2-yl ester 1) 5-Methoxy-2-nitro-4-trifluoromethyl-phenylamine [CAS-no. 473537-32-5]: Commercially available 5-chloro-2-nitro-4-trifluoromethyl-phenylamine (30.0 g, 125 mmol) was dissolved in DMSO (250 mL) and MeOH (125 mL), then potassium hydroxide (85%, 18.1 g, 274 mmol) was added and the resulting deep red solution was stirred at 23° C. for 7 days. The mixture was poured onto 1 N HCl (350 mL) and water (1500 mL), this suspension was stirred for 1 h, then the precipate was filtered off, washed with cold water and the crystals were dried in air at 60° C. overnight to get 5-methoxy-2-nitro-4-trifluoromethyl-phenylamine (28.98 g, 98%) as a yellow solid. MS (ISN) 235.1 [$(M-H)^-$]; mp 56° C.

2) 1-Bromo-5-methoxy-2-nitro-4-trifluoromethyl-benzene: The above prepared 5-methoxy-2-nitro-4-trifluoromethyl-phenylamine (28.9 g, 122 mmol) was portionwise added to a rapidly stirred mixture of tert-butyl nitrite (24.4 mL, 206 mmol) and $CuBr_2$ (41.0 g, 184 mmol) in MeCN (200 mL) at 65°. After the addition was completed, stirring was continued at 65° C. for 1 h. The reaction mixture was cooled to rt and poured onto 1N HCl (300 mL) extracted twice with TBME, the organic layers were washed with brine, dried over $MgSO_4$, filtrated and evaporated to get a brown oil, which crystallized to give the 1-bromo-5-methoxy-2-nitro-4-trifluoromethyl-benzene (36.34 g, 99%) as a light brown solid, which was used without further purification.

3) 5-Methoxy-2-nitro-4-trifluoromethyl-benzonitrile: A mixture of the above prepared 1-bromo-5-methoxy-2-nitro-4-trifluoromethyl-benzene (17.1 g, 57 mmol) and CuCN (5.36 g, 60 mmol) in NMP (60 mL) were heated up to 150° C. and stirred for 30 minutes under argon atmosphere. The mixture was cooled to rt and poured onto 1N HCl, extracted with TBME, washed with brine, dried over $MgSO_4$, filtrated and evaporated to get the crude 5-methoxy-2-nitro-4-trifluoromethyl-benzonitrile (14.76 g, 105%) as a brown solid, which was directly used for the next step. MS (ISP) 264.1 [$(M+NH_4^+)^+$].

4) 2-Amino-5-methoxy-4-trifluoromethyl-benzonitrile: Iron powder (14.7 g, 263 mol) was added in small portions to a stirred suspension of the above prepared finely ground 5-methoxy-2-nitro-4-trifluoromethyl-benzonitrile (14.53 g, 59 mmol) in MeOH (75 mL) and HCl 37% (100 mL). The internal temperature was kept between 40 and 60° C. by waterbath cooling. The resulting brown solution was stirred at 50° C. for 1 h. The mixture was poured into icecold water (200 mL). The precipitated solid was filtered off and washed with water, dissolved in boiling EtOH (140 mL), charcoal (3 scoops) was added and the mixture was refluxed for 30 min. The hot solution was filtered and the EtOH was evaporated to leave the 2-amino-5-methoxy-4-trifluoromethyl-benzonitrile (7.35 g, 58%) as a brown solid, which was used without further purification. MS (ISP) 217.2 [$(M+H^+)^+$].

5) 3-Methoxy-4-trifluoromethyl-benzonitrile [CAS-no. 447-93-8]: The above prepared 2-amino-5-methoxy-4-trifluoromethyl-benzonitrile (7.08 g, 33 mmol) was dissolved in DMF (75 mL) heated up to 95° C., then slowly added isopentyl nitrite (6.75 mL, 49 mmol) dropwise by using a syringe, whereby the reaction temperature rose up to 106° C. (exothermic reaction). The reaction mixture was stirred for another 15 min at 95° C., then cooled rt, extracted with water and TBME, dried the organic layer over $MgSO_4$, filtered and the solvents evaporated. Purification by vacuum destillation at 1.6 mbar and 120° C. left a light yellow liquid, which still contained isoamyl alcohol and DMF and was therefore was purified by flash chromatography with n-heptane and ethyl acetate to give the 3-methoxy-4-trifluoromethyl-benzonitrile (4.0 g, 61%) as a colorless liquid. MS (EI) 201.1 [$M^+$].

6) 3-Methoxy-4-trifluoromethyl-benzaldehyde: To a solution of the above prepared 3-methoxy-4-trifluoromethyl-benzonitrile (3.95 g, 20 mmol) in toluene (60 mL) at −10° C. was added dropwise DIBAH (20% in toluene, ca. 1.2 M, 17.7 mL; 22 mmol) keeping the temperature below −5° C. Stirring was continued at −5° C. to 0° C. for 1 h. Poured into 2 M HCl, diluted with EtOAc, shaken vigorously for 3 min, brine added, shaken again, the phases separated and the organic layer dried over $Na_2SO_4$, filtered off and evaporated totally to give the 3-methoxy-4-trifluoromethyl-benzaldehyde (3.76 g, 91%) as a light yellow liquid, which was used without further purification. MS (EI) 204.2 [$M^+$].

5) (E)-4-(3-Methoxy-4-trifluoromethyl-phenyl)-but-3-en-2-one: A mixture of the above prepared 3-methoxy-4-trifluoromethyl-benzaldehyde (3.76 g, 18 mmol) and commercially available dimethyl-2-oxopropylphosphonate (3.2 mL, 22 mmol) was cooled at 0° C., then a mixture of $K_2CO_3$ (5.09 g, 37 mmol) in water (20 mL) was added and the mixture was stirred at 0° C. or 2 h. Poured onto sat. $NaHCO_3$-sol. and extracted twice with EtOAc, washed with brine and dried over $Na_2SO_4$, filtered off and evaporated totally to give the (E)-4-(3-methoxy-4-trifluoromethyl-phenyl)-but-3-en-2-one (4.06 g, 90%) as a light yellow solid, which was used without further purification. MS (EI) 244.2 [$M^+$].

6) 4-(3-Methoxy-4-trifluoromethyl-phenyl)-6-methyl-1H-pyridin-2-one: A mixture of the above prepared (E)-4-(3-methoxy-4-trifluoromethyl-phenyl)-but-3-en-2-one (4.03 g, 16.5 mmol), commercially available 1-ethoxycarbonylmethyl-pyridinium bromide [CAS-No. 17282-40-5] (4.47 g, 18.1 mmol) and ammonium acetate (6.36 g, 82.5 mmol) in EtOH (20 mL) according to general procedure Ib step 1. Obtained as a yellow solid (3.6 g, 77%). MS (ISP) 284.1 [$(M+H)^+$].

7) The title compound was prepared from the above described 4-(3-methoxy-4-trifluoromethyl-phenyl)-6-methyl-1H-pyridin-2-one (2.66 g, 9.0 mmol) and trifluoromethanesulfonic anhydride (1.9 mL, 10.8 mmol) according to the general procedure Ia to d preparation of triflates. Obtained as a white solid (3.25 g, 83%). MS (ISN) 474.1 [$(M+OAc^-)^-$].

EXAMPLE A.60

2-Chloro-4-(2-fluoro-4-trifluoromethyl-phenyl)-6-trifluoromethyl-pyrimidine 1) 4-(2-Fluoro-4-trifluoromethyl-phenyl)-6-trifluoromethyl-1H-pyrimidin-2-one: The compound was prepared from commercially available ethyl trifluoroacetate, commercially available 2-fluoro-4-trifluoromethyl-acetophenone and urea according to the general procedure I. Obtained as a white solid (9.95 g, 90%). MS (ISP) 327.1 [$(M+H)^+$]; mp 132.5° C.

2) The title compound was prepared from 4-(2-fluoro-4-trifluoromethyl-phenyl)-6-trifluoromethyl-1H-pyrimidin-2-one (9.84 g, 0.03 mol) and phosphoroxychloride (50 ml) according to the general procedure I. Obtained as a light yellow solid (9.99 g, 96%). MS (ISN) 341.2 [$(M-H)^-$]; mp 47° C.

EXAMPLE A.61

2-Chloro-4-(2,4-dichloro-phenyl)-6-trifluoromethyl-pyrimidine 1) 4-(2,4-dichloro-phenyl)-6-trifluoromethyl-1H-pyrimidin-2-one: The compound was prepared from commercially available ethyl trifluoroacetate, commercially available 2,4-dichloro-acetophenone and urea according to the general procedure I. Obtained as a white solid (10.3 g, 90%). MS (ISP) 309.1 [$(M+H)^+$]; mp 164° C.

2) The title compound was prepared from 4-(2,4-dichloro-phenyl)-6-trifluoromethyl-1H-pyrimidin-2-one (10.2 g, 0.033 mol) and phosphoroxychloride (50 ml) according to the general procedure I. Obtained as a light yellow solid (10.6 g, 98%). MS (ISP) 327.0 [$(M+H)^+$]; mp 69.5° C.

EXAMPLE A.62

Trifluoro-methanesulfonic acid 4-methyl-6-(4-trifluoromethyl-phenyl)-pyrimidin-2-yl ester The title compound was prepared from 6-methyl-4-(4-trifluoromethyl-phenyl)-1H-pyrimidin-2-one (example A.12, step 1) (3.0 g, 12 mmol), trifluoromethanesulfonic anhydride (2.4 ml, 14 mmol) and diisopropylethylamine (4.1 ml, 24 mmol) in DCM (24 ml) according to the general procedure Ia to d preparation of triflates. Obtained as a brown solid (4.42 g, 97%). MS (ISP) 387.1 [$(M+H)^+$]; mp 74.5° C.

EXAMPLE A.63

Trifluoro-methanesulfonic acid 6-methyl-4-(4-trifluoromethoxy-phenyl)-pyridin-2-yl ester 1) (E)-4-(4-Trifluoromethoxy-phenyl)-but-3-en-2-one: A mixture of commercially available 4-trifluoromethoxy-benzaldehyde [CAS-no. 659-28-9] (20 g, 95 mmol, 95% purity) and commercially available dimethyl-2-oxopropylphosphonate (16.5 mL, 114 mmol) was cooled at 0° C., then a mixture of $K_2CO_3$ (26.17 g, 189 mmol) in water (100 mL) was added and the mixture was stirred at 0° C. or 2 h. Poured onto sat. $NaHCO_3$-sol. and extracted twice with EtOAc, washed with brine and dried over $Na_2SO_4$, filtered off and evaporated totally to give the (E)-4-(4-trifluoromethoxy-phenyl)-but-3-en-2-one (19.35 g, 69%, 77% purity) as a light yellow liquid, which was used without further purification. MS (ISP) 231.1 [$(M+H)^+$].

2) 6-Methyl-4-(4-trifluoromethoxy-phenyl)-1H-pyridin-2-one: A mixture of the above described (E)-4-(4-trifluoromethoxy-phenyl)-but-3-en-2-one (19.0 g, 64 mmol, 77% purity), commercially available 1-ethoxycarbonylmethyl-pyridinium bromide [CAS-No. 17282-40-5] (17.3 g, 70 mmol) and ammonium acetate (24.6 g, 319 mmol) in EtOH (80 mL) according to general procedure Ib step 1. Obtained as a light yellow solid (13.56 g, 79%). MS (ISP) 270.3 [$(M+H)^+$].

3) The title compound was prepared from the above described 6-methyl-4-(4-trifluoromethoxy-phenyl)-1H-pyridin-2-one (3.23 g, 12 mmol), diisopropylethylamine (4.1 ml, 24 mmol) and trifluoromethanesulfonic anhydride (2.4 mL, 14 mmol) according to the general procedure Ia to d preparation of triflates. Obtained as a light brown oil (4.47 g, 93%). MS (ISP) 402.2 [$(M+H)^+$].

EXAMPLE A.64

Trifluoro-methanesulfonic acid 6-methyl-4-(3-methyl-4-trifluoromethyl-phenyl)-pyridin-2-yl ester 1) 3-Methyl-4-trifluoromethyl-benzaldehyde: To a solution of 3-methyl-4-trifluoromethyl-benzonitrile [CAS-no. 871571-28-7] (9.2 g, 49.7 mmol) in toluene (130 ml) at −10° C. was added dropwise diisobutylaluminum hydride (20% in toluene, ca. 1.2 M, 44.8 ml, 54.2 mmol) keeping the internal temperature below −5° C. and stirring was continued at −5° C. to 0° C. for 1 h. Poured into 2 M HCl, diluted with ethyl acetate, shaken vigorously for 3 min, added brine, shaken again, separated phases, the organic layer was dried over $Na_2SO_4$, filtered off and evaporated totally. The crude product was filtered through a small silica gel column with ethyl acetate to give the 3-methyl-4-trifluoromethyl-benzaldehyde (9.1 g, 97%) as a light yellow liquid.

2) (E)-4-(3-Methyl-4-trifluoromethyl-phenyl)-but-3-en-2-one: A mixture of the above described 3-methyl-4-trifluoromethyl-benzaldehyde (9.1 g, 48.3 mmol) and commercially available dimethyl-2-oxopropylphosphonate (8.46 mL, 58.0 mmol) was cooled at 0° C., then a mixture of $K_2CO_3$ (13.37 g, 96.7 mmol) in water (16 mL) was added and the mixture was stirred at 0° C. or 2 h. Poured onto sat. $NaHCO_3$-sol. and extracted twice with EtOAc, washed with brine and dried over $Na_2SO_4$, filtered off and evaporated totally to give the (E)-4-(3-methyl-4-trifluoromethyl-phenyl)-but-3-en-2-one (12.7 g, 115%, ca. 80% purity) as a light yellow liquid, which was used without further purification. MS (ISP) 229.2 [$(M+H)^+$].

3) 6-Methyl-4-(3-methyl-4-trifluoromethyl-phenyl)-1H-pyridin-2-one: A mixture of the above described (E)-4-(3-methyl-4-trifluoromethyl-phenyl)-but-3-en-2-one (12.7 g, 55.7 mmol, ca. 80% purity), commercially available 1-ethoxycarbonylmethyl-pyridinium bromide [CAS-No. 17282-40-5] (15.07 g, 61.2 mmol) and ammonium acetate (21.45 g, 278 mmol) in EtOH (60 mL) according to general procedure Ib step 1. Obtained as an off-white solid (10.35 g, 70%). MS (ISP) 268.2 [$(M+H)^+$]0.4) The title compound was prepared from the above described 6-methyl-4-(3-methyl-4-trifluoromethyl-phenyl)-1H-pyridin-2-one (3.5 g, 13.1 mmol), pyridine (50 ml) and trifluoromethanesulfonic anhydride (2.59 mL, 15.7 mmol) according to the general procedure Ia to d preparation of triflates. Obtained as a light yellow oil (5.1 g, 98%). MS (ISP) 400.0 [$(M+H)^+$].

EXAMPLE A.65

2-Bromo-6-(tetrahydro-pyran-2-yloxymethyl)-4-(4-trifluoromethyl-phenyl)-pyridine 1) 2-Bromo-6-bromomethyl-4-(4-trifluoromethyl-phenyl)-pyridine: A mixture of 2-bromo-6-methyl-4-(4-trifluoromethyl-phenyl)-pyridine (Example A.48) (34 g, 64.5 mmol, purity 60%), N-bromosuccinimide (11.5 g, 64.5 mmol) and dibenzoylperoxide (1.04 g, 5 mol %) in $CCl_4$ (200 ml) was irradiated and refluxed with a 500 W agrolamp for 8 h. Cooled to rt, filtered the succinimide off, washed with $CH_2Cl_2$ and evaporated totally to give a brown oil (43 g, NMR revealed a mixture of starting material, product and double brominated starting material), which was directly used in the next step (HPLC purity ca. 24%).

2) Acetic acid 6-bromo-4-(4-trifluoromethyl-phenyl)-pyridin-2-ylmethyl ester: A mixture of the above described crude 2-bromo-6-bromomethyl-4-(4-trifluoromethyl-phenyl)-pyridine (43 g, purity 24%, 26.1 mmol) and sodium acetate (4.29 g, 52.3 mmol) in acetic acid (100 ml) was refluxed for 3 h. Cooled to rt, extracted with water and AcOEt, washed the organic-layer with sat. $NaHCO_3$, dried over $Na_2SO_4$, filtered off and evaporated totally to give a crude product, which was purified by silica gel column chromatography with n-heptane/AcOEt to give the acetic acid 6-bromo-4-(4-trifluoromethyl-phenyl)-pyridin-2-ylmethyl ester (6.05 g, 49%, purity 80%) as a light brown solid. MS (ISP) 374.1 $[(M+H)^+]$.

3) [6-Bromo-4-(4-trifluoromethyl-phenyl)-pyridin-2-yl]-methanol: To a solution of the above described acetic acid 6-bromo-4-(4-trifluoromethyl-phenyl)-pyridin-2-ylmethyl ester (5.0 g, 13.4 mmol, purity 80%) in methanol (10 ml) at 23° C. was added a catalytical amount of sodium methoxide solution (0.4 ml, 2.16 mmol) (pH ca. 9) and the mixture was stirred at 23° C. for 30 min. Poured on acetic acid, extracted twice with AcOEt, washed with sat. $NaHCO_3$-solution, dried over $Na_2SO_4$, filtered off and evaporated totally to give a crude product, which was purified by silica gel column chromatography with n-heptane/AcOEt to give the [6-bromo-4-(4-trifluoromethyl-phenyl)-pyridin-2-yl]-methanol (4.2 g, 95%, purity 81%) as a white solid. MS (ISP) 334.1 $[(M+H)^+]$.

4) To a solution of the above described [6-bromo-4-(4-trifluoromethyl-phenyl)-pyridin-2-yl]-methanol (4.2 g, 95%, purity 81%) and 3,4-dihydro-2H-pyran (1.4 ml, 15.4 mmol) in DCM (20 ml) at 23° C. was added a catalytic amount of p-TsOH.$H_2O$ (10 mg) and the mixture was stirred at 23° C. for 18 h. Then again 3,4-dihydro-2H-pyran (0.7 ml, 7.68 mmol) was added and stirring was continued at 23° C. for another 2 h. The entire reaction mixture was directly subjected to silica gel column chromatography with n-heptane/AcOEt to give the title compound (4.59 g, 100%, 93% purity) as a light yellow oil. MS (ISP) 418.2 $[(M+H)^+]$.

Synthesis of Nitriles

General procedure II

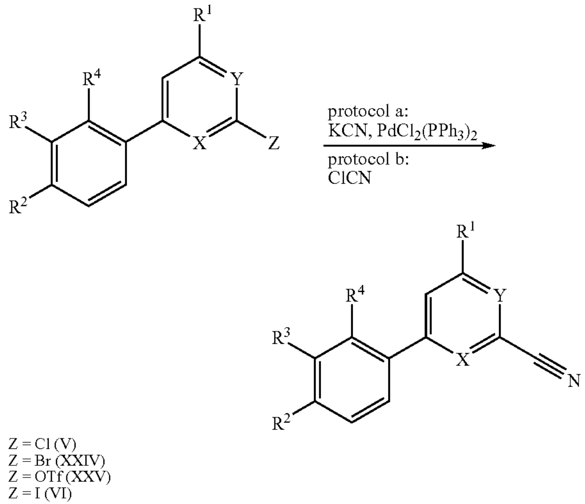

Z = Cl (V)
Z = Br (XXIV)
Z = OTf (XXV)
Z = I (VI)

Protocol a: A stirred mixture of a compound V, VI, XXIV or XXV (1 eq), potassium cyanide (2 eq) and bis-triphenylphosphine-palladiumchloride (0.02 eq.) in an organic solvent (e.g. DMF) is heated under reflux conditions for around 1 h, cooled, poured into water and extracted two times with ethyl acetate. The combined organic layers are washed with brine, dried (e.g. $MgSO_4$) and evaporated. The crude product is further purified by flash chromatography on silica gel (e.g. ethyl acetate/heptane) and crystallization (e.g. diethyl ether/hexane) to give a compound of formulae VII.

Protocol b: A stirred mixture of a compound of formula VI or XXIV (1 eq.) and copper(I) cyanide (1.03 to 1.1 eq.) in an organic solvent (e.g. DMF, DMA or NMP) is heated under argon atmosphere at temperatures of 130 to 150° C. for 2 to 16 h, cooled, diluted with water, filtered, the solid is dissolved in ethyl acetate, extracted with ethyl acetate and water/ammonia (1:1), the organic layer is washed with sat. NaCl sol., dried over $MgSO_4$, filtered and the solvents are evaporated. The crude product is purified with silica gel flash-chromatography (e.g. heptane:ethyl acetate) to give a compound of formula VII.

EXAMPLE B.1

4-(4-Chloro-phenyl)-6-trifluoromethyl-pyrimidine-2-carbonitrile

The title compound was prepared from 2-chloro-4-(4-chloro-phenyl)-6-trifluoromethyl-pyrimidine (example A.1) (1.8 g, 6.14 mmol) according to the general procedure II protocol a. Obtained as a light brown solid (1.16 g, 67%). MS (EI) 283.1 $[(M)^+]$; mp 123.5° C.

EXAMPLE B.2

4-Trifluoromethyl-6-(4-trifluoromethyl-phenyl)-pyrimidine-2-carbonitrile

The title compound was prepared from 2-chloro-4-trifluoromethyl-6-(4-trifluoromethylphenyl)-pyrimidine (example A.2) (3.0 g, 9.18 mmol) according to the general procedure II protocol a. Obtained as a light orange solid (1.96 g, 67%). MS (EI) 317.1 $[(M)^+]$; mp 70° C.

EXAMPLE B.3

4-Difluoromethyl-6-(4-trifluoromethyl-phenyl)-pyrimidine-2-carbonitrile

The title compound was prepared from 2-chloro-4-difluoromethyl-6-(4-trifluoromethylphenyl)-pyrimidine (example A.5) (1.0 g, 3.24 mmol) according to the general procedure II protocol a. Obtained as a light red liquid (0.58 g, 60%). MS (ISP) 298.1 $[(M-H)^-]$.

EXAMPLE B.4

4-(3-Ethoxy-4-trifluoromethyl-phenyl)-6-trifluoromethyl-pyrimidine-2-carbonitrile The title compound was prepared from 2-chloro-4-(3-ethoxy-4-trifluoromethyl-phenyl)-6-trifluoromethyl-pyrimidine (example A.10) (1.0 g, 2.70 mmol) according to the general procedure II protocol a. Obtained as an orange solid (0.7 g, 72%). MS (ISN) 361.2 $[(M-H)^-]$; mp 110.5° C.

EXAMPLE B.5

6-(4-Chloro-phenyl)-4-trifluoromethyl-pyridine-2-carbonitrile

The title compound was prepared from 2-bromo-6-(4-chloro-phenyl)-4-trifluoromethyl-pyridine (example A.18) (6.0 g, 18 mmol) according to the general procedure II protocol b. Obtained as a brown solid (3.67 g, 74%). MS (EI) 281.9 [$(M)^+$] and 284.0 [$(M+2)^+$]; mp 71-74° C.

EXAMPLE B.6

4-Trifluoromethyl-6-(4-trifluoromethyl-phenyl)-pyridine-2-carbonitrile

The title compound was prepared from 2-bromo-4-trifluoromethyl-6-(4-trifluoromethylphenyl)-pyridine (example A.19) (3.7 g, 10 mmol) according to the general procedure II protocol b. Obtained as a green solid (2.46 g, 78%). MS (EI) 316.1 [$(M)^+$]; mp 97-100° C.

EXAMPLE B.7

4-(3,4-Dichloro-phenyl)-6-trifluoromethyl-pyrimidine-2-carbonitrile

The title compound was prepared from 2-chloro-4-(3,4-dichloro-phenyl)-6-trifluoromethyl-pyrimidine (example A.7) (2.0 g, 6.11 mmol) according to the general procedure II. Obtained as an orange solid (1.69 g, 87%). MS (ISP) 319.1 [$(M+H)^+$]; mp 153.5° C.

EXAMPLE B.8

4-(4-Chloro-3-methyl-phenyl)-6-trifluoromethyl-pyrimidine-2-carbonitrile

The title compound was prepared from 2-chloro-4-(4-chloro-3-methyl-phenyl)-6-trifluoromethyl-pyrimidine (example A.8) (1.5 g, 4.88 mmol) according to the general procedure II. Obtained as a light yellow solid (0.92 g, 63%). MS (ISN) 296.2 [$(M-H)^-$]; mp 159.5° C.

EXAMPLE B.9

4-(4-Chloro-phenyl)-6-methyl-pyrimidine-2-carbonitrile

The title compound was prepared from 2-chloro-4-(4-chloro-phenyl)-6-methyl-pyrimidine (example A.11) (1.0 g, 4.18 mmol) according to the general procedure II. Obtained as an orange solid (0.68 g, 71%). MS (ISN) 228.1 [$(M-H)^-$]; mp 145° C.

EXAMPLE B.10

6-Methyl-4-(4-trifluoromethyl-phenyl)-pyrimidine-2-carbonitrile

The title compound was prepared from 2-chloro-4-methyl-6-(4-trifluoro-phenyl)pyrimidine (example A.12) (1.0 g, 3.67 mmol) according to the general procedure II. Obtained as a brown solid (0.66 g, 68%). MS (ISN) 262.1 [$(M-H)^-$]; mp 102° C.

EXAMPLE B.11

4-(3-Methyl-4-trifluoromethyl-phenyl)-6-trifluoromethyl-pyrimidine-2-carbonitrile The title compound was prepared from 2-chloro-4-(3-methyl-4-trifluoromethyl-phenyl)-6-trifluoromethyl-pyrimidine (example A.38) (0.2 g, 0.59 mmol) according to the general procedure II. Obtained as a light yellow solid (0.17 g, 88%). MS (EI) 331.1 [$(M)^+$]; mp 82.5° C.

EXAMPLE B.12

6-Methyl-4-(4-trifluoromethyl-phenyl)-pyridine-2-carbonitrile

The title compound was prepared from 2-iodo-6-methyl-4-(4-trifluoromethyl-phenyl)pyridine (example A.31) (2.32 g, 6.4 mmol) according to the general procedure II protocol b. Obtained as a white solid (1.28 g, 76%). MS (ISP) 263.0 [$(M+H)^+$].

EXAMPLE B.13

N-tert-Butyl-3-(6-cyano-pyridin-2-yl)-benzene-sulfonamide

The title compound was prepared from 3-(6-bromo-pyridin-2-yl)-N-tert-butyl-benzenesulfonamide (example F.6 step 1) (3.12 g, 8 mmol) according to the general procedure II protocol b. Obtained as a light brown oil (1.05 g, 39%). MS (ISP) 316.1 [$(M+H)^+$].

Synthesis of N-hydroxy-amidines

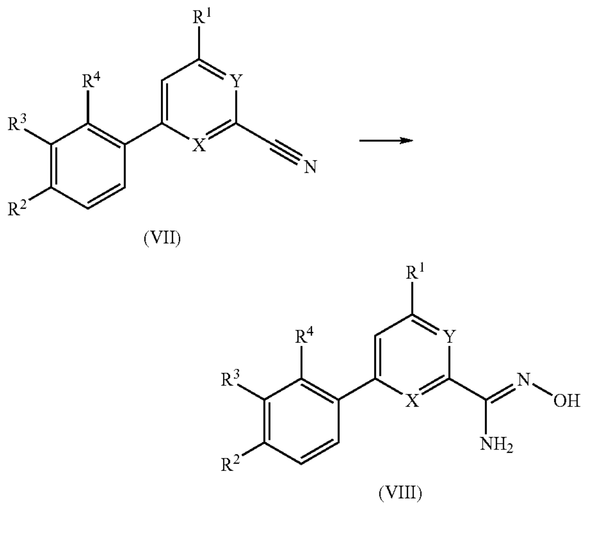

(VII)

(VIII)

EXAMPLE C.1

4-(4-Chloro-phenyl)-N-hydroxy-6-trifluoromethyl-pyrimidine-2-carboxamidine

A stirred mixture of 4-(4-chloro-phenyl)-6-trifluoromethyl-pyrimidine-2-carbonitrile (example B.1) (0.5 g, 1.76 mmol), hydroxylamine hydrochloride (0.45 g, 6.48 mol) and sodium carbonate (0.37 g, 3.53 mol) in water (10 mL) and ethanol (10 mL) was heated under reflux conditions for 2 h. The ethanol was removed partly and the mixture stirred at room temperature for 1 h. The precipitate was collected by filtration, washed with water and dried to yield the title compound (0.53 g, 94%) as a light brown solid. MS (ISP) 316.9 $[(M+H)^+]$; mp 243° C.

EXAMPLE C.2

N-Hydroxy-4-trifluoromethyl-6-(4-trifluoromethyl-phenyl)-pyrimidine-2-carboxamidine A stirred mixture of 4-trifluoromethyl-6-(4-trifluoromethyl-phenyl)-pyrimidine-2-carbonitrile (example B.2) (1.0 g, 3.15 mmol), hydroxylamine hydrochloride (0.81 g, 11.7 mol) and sodium carbonate (0.67 g, 6.32 mol) in water (15 mL) and ethanol (15 mL) was heated under reflux conditions for 2 h. The ethanol was removed partly and the mixture stirred at room temperature for 0.5 h. The precipitate was collected by filtration, washed with water and dried to yield the title compound (1.08 g, 98%) as a light brown solid. MS (ISP) 351.1 $[(M+H)^+]$; mp 224° C.

EXAMPLE C.3

6-Amino-N-hydroxy-nicotinamidine

A stirred mixture of commercially available 2-amino-5-cyano-pyridine [CAS-No. 4214-73-7] (5.0 g, 42 mmol), hydroxylamine hydrochloride (17.5 g, 0.25 mol) and sodium carbonate (31.1 g, 0.29 mol) in water (95 mL) and ethanol (21 mL) was heated under reflux conditions for 6 h. The reaction mixture was poured into water (150 mL) and extracted with ethyl acetate (4×100 mL). The combined organic layers were washed with brine (150 mL), dried ($MgSO_4$) and evaporated.

The crude product was purified by column chromatography on silica gel (ethyl acetate/MeOH/$NH_4OH$ 4:1:0.5) and crystallization (ethyl acetate/MeOH/hexane) to yield 6-amino-nicotinamide (1.39 g) and the title compound (1.42 g, 22%) as an off-white solid. MS (EI) 152.1 $[(M)^+]$; mp 300° C.

EXAMPLE C.4

2-Amino-N-hydroxy-pyrimidine-5-carboxamidine

A stirred mixture of commercially available 2-amino-5-cyano-pyrimidine [CAS-No. 1753-48-6] (1.39 g, 11.6 mmol), hydroxylamine hydrochloride (1.61 g, 23.2 mol) and potassium carbonate (4.8 g, 34.7 mol) in ethanol (57 mL) was heated under reflux conditions for 3 h. The reaction mixture was evaporated and purified by column chromatography on silica gel (dichloromethane/MeOH 9:1) to yield the title compound (1.28 g, 72%) as an off-white solid. MS (EI) 153.1 $[(M)^+]$; mp 218° C.

EXAMPLE C.5

2-Amino-N-hydroxy-pyridine-4-carboxamidine

A stirred mixture of commercially available 2-amino-4-cyano-pyridine [CAS-No. 42182-27-4] (1.0 g, 8.39 mmol), hydroxylamine hydrochloride (1.17 g, 16.8 mmol) and sodium carbonate (0.89 g, 8.39 mol) in water (8 mL) and ethanol (16 mL) was heated under reflux conditions for 3 h. The reaction mixture was evaporated, water (10 mL) was added and the mixture stirred at room temperature for 1 h. The precipitate was collected by filtration to yield the title compound (0.87 g, 68%) as an off-white solid. MS (EI) 152.0 $[(M)^+]$; mp 188° C.

EXAMPLE C.6

6-(4-Chloro-phenyl)-N-hydroxy-4-trifluoromethyl-pyridine-2-carboxamidine

A mixture of 6-(4-chloro-phenyl)-4-trifluoromethyl-pyridine-2-carbonitrile (example B.5) (3.6 g, 13 mmol), hydroxylamine-hydrochloride (3.275 g, 47 mmol) and sodium carbonate (2.7 g, 47 mmol) in EtOH (60 ml) and water (60 ml) was stirred under argon atmosphere at 100° C. for 4 h. The EtOH was evaporated, the mixture was diluted with water and stirred for 1 h at 0° C. The crude product was filtered and dried in HV to give the pure title compound as a light yellow solid (3.54 g, 88%). MS (ISP) 316.1 $[(M+H)^+]$ and 318 $[(M+2+H)^+]$; mp 180-186° C.

EXAMPLE C.7

6-(3-tert-Butylsulfamoyl-phenyl)-N-hydroxy-pyridine-2-carboxamidine

A mixture of N-tert-butyl-3-(6-cyano-pyridin-2-yl)-benzenesulfonamide (example B.13) (1.03 g, 3.27 mmol), hydroxylamine hydrochloride (794 mg, 11.4 mmol) and sodium carbonate (692 mg, 6.53 mmol) in EtOH (20 ml) and water (20 ml) was stirred under argon atmosphere at 100° C. for 2 h. The EtOH was evaporated, the mixture was diluted with water and stirred for 1 h at 0° C. The crude product was filtered and dried in HV to give the pure title compound as a white solid (850 mg, 75%). MS (ISP) 349.3 $[(M+H)^+]$.

Synthesis of carboxlic acids

General procedure III

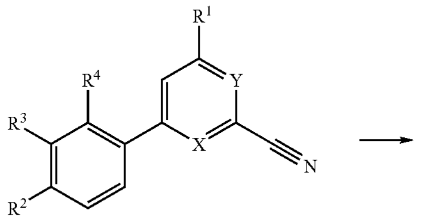

(VII)

-continued

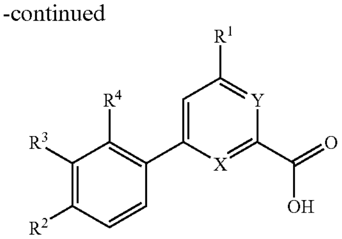

(IX)

A stirred solution of a compound VII (1 eq) in a 1:1 mixture of 37% hydrochloric acid and an organic solvent (e.g. dioxane) or alternatively in 50% aqueous sulfuric acid is heated under reflux conditions for around 2 to 18 h, cooled, poured into water and extracted three times with diethyl ether. The combined organic layers are washed with brine, dried (e.g. $MgSO_4$) and evaporated. The crude product is further purified by crystallization (e.g. diethyl ether/hexane) to give a compound of formulae IX.

EXAMPLE D.1

4-(4-Chloro-phenyl)-6-trifluoromethyl-pyrimidine-2-carboxylic acid

The title compound was prepared from 6-(4-chloro-phenyl)-4-trifluoromethyl-pyrimidine-2-carbonitrile (example B.1) (0.35 g, 1.23 mmol) according to the general procedure I. Obtained as a light yellow solid (0.31 g, 83%). MS (EI) 302.0 [$(M)^+$]; mp 133° C.

EXAMPLE D.2

4-Trifluoromethyl-6-(4-trifluoromethyl-phenyl)-pyrimidine-2-carboxylic acid

The title compound was prepared from 4-trifluoromethyl-6-(4-trifluoromethyl-phenyl)pyrimidine-2-carbonitrile (example B.2) (0.83 g, 2.62 mmol) according to the general procedure I. Obtained as a light yellow solid (0.70 g, 80%). MS (ISN) 335.3 [$(M-H)^-$]; mp 154.5° C.

EXAMPLE D.3

4-Difluoromethyl-6-(4-trifluoromethyl-phenyl)-pyrimidine-2-carboxylic acid

The title compound was prepared from 4-difluoromethyl-6-(4-trifluoromethyl-phenyl)pyrimidine-2-carbonitrile (example B.3) (0.20 g, 0.67 mmol) according to the general procedure I. Obtained as an off-white solid (0.14 g, 66%). MS (ISN) 317.1 [$(M-H)^-$]; mp 163.5° C.

EXAMPLE D.4

4-(3-Ethoxy-4-trifluoromethyl-phenyl)-6-trifluoromethyl-pyrimidine-2-carboxylic acid The title compound was prepared from 4-(3-ethoxy-4-trifluoromethyl-phenyl)-6-trifluoromethyl-pyrimidine-2-carbonitrile (example B.4) (0.66 g, 1.83 mmol) according to the general procedure I. Obtained as a light yellow solid (0.55 g, 79%). MS (ISN) 379.3 [$(M)^+$]; mp 120° C.

EXAMPLE D.5

6-(4-Chloro-phenyl)-4-trifluoromethyl-pyridine-2-carboxylic acid

The title compound was prepared from 6-(4-chloro-phenyl)-4-trifluoromethyl-pyridine-2-carbonitrile (example B.5) (0.53 g, 1.88 mmol) according to the general procedure I. Obtained as a white solid (0.484 g, 87%). MS (ISN) 300.1 [$(M-H)^-$] and 302.0 [$(M+2-H)^-$]; mp>250° C.

EXAMPLE D.6

4-(3,4-Dichloro-phenyl)-6-trifluoromethyl-pyrimidine-2-carboxylic acid

The title compound was prepared from 6-(3,4-dichloro-phenyl)-4-trifluoromethyl-pyrimidine-2-carbonitrile (example B.7) (1.61 g, 5.06 mmol) according to the general procedure I. Obtained as a yellow solid (1.25 g, 73%). MS (ISN) 335.3 [$(M-H)^-$]; mp 126° C.

EXAMPLE D.7

4-(4-Chloro-3-methyl-phenyl)-6-trifluoromethyl-pyrimidine-2-carboxylic acid

The title compound was prepared from 6-(4-chloro-3-methyl-phenyl)-4-trifluoromethyl-pyrimidine-2-carbonitrile (example B.8) (0.89 g, 2.99 mmol) according to the general procedure I. Obtained as a light yellow solid (0.85 g, 90%). MS (ISN) 315.3 [$(M-H)^-$]; mp 127° C.

EXAMPLE D.8

4-Methyl-6-(4-trifluoromethyl-phenyl)-pyrimidine-2-carboxylic acid

The title compound was prepared from 6-methyl-4-(4-trifluoromethyl-phenyl)pyrimidine-2-carbonitrile (example B.10) (0.56 g, 2.13 mmol) according to the general procedure I. Obtained as a light yellow oil (0.29 g, 48%). MS (ISN) 281.1 [$(M-H)^-$].

EXAMPLE D.9

4-(3-Methyl-4-trifluoromethyl-phenyl)-6-trifluoromethyl-pyrimidine-2-carboxylic acid The title compound was prepared from 4-(3-methyl-4-trifluoromethyl-phenyl)-6-trifluoromethyl-pyrimidine-2-carbonitrile (example B. II) (0.164 g, 0.5 mmol) according to the general procedure I. Obtained as a white solid (0.13 g, 73%). MS (ISN) 351.1 [$(M+H)^+$]; mp 130° C.

EXAMPLE D.10

4-(4-Chloro-phenyl)-6-methyl-pyrimidine-2-carboxylic acid

The title compound was prepared from 4-(4-chloro-phenyl)-6-methyl-pyrimidine-2-carbonitrile (example B.9)

(0.58 g, 2.53 mmol) according to the general procedure I. Obtained as an orange solid (0.15 g, 24%). MS (ISN) 247.3 $[(M-H)^-]$; mp 105.5° C.

EXAMPLE D.11

6-Methyl-4-(4-trifluoromethyl-phenyl)-pyridine-2-carboxylic acid

The title compound was prepared from 6-methyl-4-(4-trifluoromethyl-phenyl)-pyridine-2-carbonitrile (example B.12) (0.60 g, 2.29 mmol) according to the general procedure I. Obtained as a white solid (0.291 g, 45%). MS (ISN) 280.3 $[(M-H)^-]$.

EXAMPLE D.12

4-Trifluoromethyl-6-(4-trifluoromethyl-phenyl)-pyridine-2-carboxylic acid

The title compound was prepared from 4-trifluoromethyl-6-(4-trifluoromethyl-phenyl)pyridine-2-carbonitrile (example B.6) (0.60 g, 2.0 mmol) according to the general procedure I. Obtained as an off-white solid (0.272 g, 43%). MS (ISN) 334.3 $[(M-H)^-]$.

Synthesis of bromo- and chloro derivatives (coupling partners)

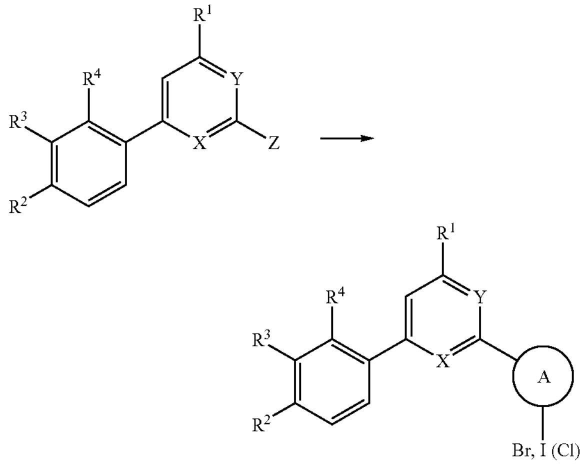

(IX)

Z = Cl (V)
Z = I (VI)
Z = Br (XXIV)
Z = OTf (XXV)
Z = $XO_2Me$ (XXVIII)

General Procedure IVa (C, N Connection)

A stirred mixture of a compound of formulae V, VI, XXIV, XXV or XXVIII (1 eq), a pyrrole, pyrazole or imidazole derivative (1.5 eq) and potassium carbonate or sodium hydride (1 eq) in an organic solvent (e.g. DMF or NMP) is heated at 130 to 150° C. until analysis (e.g. tlc or HPLC) indicated complete conversion of the compound of formula VI, cooled, poured into water and extracted three times with ethyl acetate. The combined organic layers are washed two times with brine, dried (e.g. $MgSO_4$) and evaporated. The crude product is further purified by flash chromatography on silica gel (ethyl acetate/heptane) and crystallization (e.g. ethyl acetate/hexane) to give a compound of formulae X.

General Procedure IVb (C, C Connection A—Suzuki Coupling)

To a stirred mixture of a compound of formulae V, VI, XXIV or XXV (1 eq.), a boronic acid derivative (1.1 eq.) and tetrakis(triphenylphosphine)palladium (0.03 eq.) in an organic solvent (e.g. 1,2-dimethoxy-ethane) is added at room temperature 1M sodium carbonate solution (2.5 eq.), the reaction mixture is heated at 80 to 90° C. for around 23 h, cooled, poured into ice-water and extracted two times with ethyl acetate. The combined organic layers are washed two times with brine, dried (e.g. $MgSO_4$) and evaporated. The crude product is further purified by flash chromatography on silica gel (ethyl acetate/heptane) and crystallization (e.g. dichloromethane/hexane) to give a compound of formulae X.

General Procedure IVc (C, C Connection B—Negishi Coupling)

Protocol a: To a stirred solution of a coupling partner (iodide or bromide) (1 eq.) in an organic solvent (e.g. THF) is added at −65° C. iso-propylmagnesium chloride or bromide (1 to 2M in THF, 1.05 to 1.1 eq.), the mixture is stirred at −45 to 0° C. for around 45 min and zinc chloride or bromide (1M in THF, 1.1 to 1.3 eq.) is added. The reaction mixture is stirred at room temperature for around 45 min, a compound of formulae V, VI, XXIV or XXV (1 eq.) and tetrakis(triphenylphosphine)palladium (0.01 to 0.03 eq.) are added, the reaction mixture is stirred at 50° C. for 1 to 16 h, cooled, poured into ice-saturated $NaHCO_3$ solution and extracted two times with ethyl acetate. The combined organic layers are washed with brine, dried (e.g. $MgSO_4$) and evaporated. The crude product is further purified by column chromatography on silica gel (toluene) to give a compound of formulae X.

Protocol b: To a stirred solution of compound of formula VI or XXIV (1 eq.) in an organic solvent (e.g. THF) is added at −65 to −40° C. iso-propylmagnesium chloride or bromide (1 to 2M in THF, 1.05 to 1.1 eq.), the mixture is stirred at −45 to −10° C. for around 45 min and zinc chloride or bromide (1M in THF, 1.1 to 1.3 eq.) is added. The reaction mixture is stirred at room temperature for around 45 min, a coupling partner (bromide, iodide, or triflate) (1 to 3 eq.) and tetrakis(triphenylphosphine)palladium (0.01 to 0.03 eq.) are added, the reaction mixture is stirred at 50° C. for 1 to 16 h, cooled, poured into ice-saturated $NaHCO_3$ solution and extracted two times with ethyl acetate. The combined organic layers are washed with brine, dried (e.g. $MgSO_4$) and evaporated. The crude product is further purified by column chromatography on silica gel (toluene) to give a compound of formulae X.

EXAMPLE E.1

2-(4-Bromo-imidazol-1-yl)-4-trifluoromethyl-6-(4-trifluoromethyl-phenyl)-pyrimidine The title compound was prepared from 2-chloro-4-trifluoromethyl-6-(4-trifluoromethylphenyl)-pyrimidine (example A.2) (0.98 g, 3.0 mmol) and commercially available 4-bromo-imidazole (0.66 g, 4.50 mmol) according to the general procedure IVa. Obtained as a white solid (0.78 g, 59%). MS (EI) 438.0 $[(M)^+]$; mp 184.5° C.

EXAMPLE E.2

2-(4-Bromo-imidazol-1-yl)-4-(4-chloro-phenyl)-6-trifluoromethyl-pyrimidine

The title compound was prepared from 2-chloro-4-(4-chloro-phenyl)-6-trifluoromethyl-pyrimidine (example A.1)

(1.17 g, 4.0 mmol) and commercially available 4-bromo-imidazole (0.88 g, 6.0 mmol) according to the general procedure IVa. Obtained as an off-white solid (1.23 g, 76%). MS (EI) 404.0 [$(M)^+$]; mp 247° C.

EXAMPLE E.3

2-(3-Bromo-phenyl)-4-trifluoromethyl-6-(4-trifluoromethyl-phenyl)-pyrimidine

The title compound was prepared from 2-chloro-4-trifluoromethyl-6-(4-trifluoromethylphenyl)-pyrimidine (example A.2) (0.65 g, 2.0 mmol) and commercially available 3-bromo-benzene-boronic acid (0.44 g, 2.20 mmol) according to the general procedure IVb. Obtained as a white solid (0.66 g, 73%). MS (EI) 446.0 [$(M)^+$]; mp 134° C.

EXAMPLE E.4

2-(3-Bromo-phenyl)-4-(4-chloro-phenyl)-6-trifluoromethyl-pyrimidine

The title compound was prepared from 2-chloro-4-(4-chloro-phenyl)-6-trifluoromethyl-pyrimidine (example A.1) (0.59 g, 2.0 mmol) and commercially available 3-bromo-benzeneboronic acid (0.44 g, 2.20 mmol) according to the general procedure IVa. Obtained as a white solid (0.71 g, 86%). MS (EI) 413.9 [$(M)^+$]; mp 146° C.

EXAMPLE E.5

4-(4-Chloro-phenyl)-2-(2-chloro-pyridin-4-yl)-6-trifluoromethyl-pyrimidine

The title compound was prepared from 4-(4-chloro-phenyl)-2-iodo-6-trifluoromethyl-pyrimidine (example A.3) (1.21 g, 3.15 mmol) and commercially available 2-chloro-4-iodo-pyridine [CAS No. 153034-86-7] (765 mg, 3.2 mmol) according to the general procedure IVc protocol a. Obtained as a light yellow solid (0.53 g, 45%). MS (ISP) 369.8 [$(M+H)^+$]; mp 151° C.

EXAMPLE E.6

2-(2-Chloro-pyridin-4-yl)-4-trifluoromethyl-6-(4-trifluoromethyl-phenyl)-pyrimidine The title compound was prepared from 2-iodo-4-trifluoromethyl-6-(4-trifluoromethylphenyl)-pyrimidine (example A.4) (1.47 g, 3.52 mmol) and commercially available 2-chloro-4-iodo-pyridine [CAS No. 153034-86-7] (860 mg 3.6 mmol) according to the general procedure IVc protocol a. Obtained as a light yellow solid (0.70 g, 49%). MS (ISP) 404.1 [$(M+H)^+$]; mp 144.5° C.

EXAMPLE E.7

2-(4-Bromo-imidazol-1-yl)-4-difluoromethyl-6-(4-trifluoromethyl-phenyl)-pyrimidine The title compound was prepared from 2-chloro-4-difluoromethyl-6-(4-trifluoromethylphenyl)-pyrimidine (example A.5) (1.0 g, 3.24 mmol) and commercially available 4-bromo-imidazole (0.71 g, 4.86 mmol) according to the general procedure IVa. Obtained as a light brown solid (0.98 g, 72%). MS (ISP) 420.9 [$(M+H)^+$]; mp 147° C.

EXAMPLE E.8

2-(3-Bromo-phenyl)-4-difluoromethyl-6-(4-trifluoromethyl-phenyl)-pyrimidine

The title compound was prepared from 2-chloro-4-difluoromethyl-6-(4-trifluoromethylphenyl)-pyrimidine (example A.5) (0.5 g, 1.62 mmol) and commercially available 3-bromo-benzene-boronic acid (0.42 g, 2.20 mmol) according to the general procedure IVb. Obtained as a white solid (0.54 g, 78%). MS (EI) 430.0 [$(M)^+$]; mp 98.5° C.

EXAMPLE E.9

2-(4-Bromo-imidazol-1-yl)-4-(3-ethoxy-4-trifluoromethyl-phenyl)-6-trifluoromethyl-pyrimidine The title compound was prepared from 2-chloro-4-(3-ethoxy-4-trifluoromethyl-phenyl)-6-trifluoromethyl-pyrimidine (example A.10) (0.5 g, 1.35 mmol) and commercially available 4-bromo-imidazole (0.30 g, 2.02 mmol) according to the general procedure IVa. Obtained as a white solid (0.47 g, 72%). MS (ISP) 483.0 [$(M+H)^+$]; mp 147.5° C.

EXAMPLE E.10

2-(2-Chloro-pyridin-4-yl)-4-difluoromethyl-6-(4-trifluoromethyl-phenyl)-pyrimidine The title compound was prepared from 2-iodo-4-difluoromethyl-6-(4-trifluoromethylphenyl)-pyrimidine (example A.9) (0.43 g, 1.07 mmol) and commercially available 2-chloro-4-iodo-pyridine [CAS No. 153034-86-7] (263 mg, 1.1 mmol) according to the general procedure IVc protocol a. Obtained as an off-white solid (0.20 g, 48%). MS (ISP) 386.0 [$(M+H)^+$]; mp 143.5° C.

EXAMPLE E.11

2-(4-Bromo-pyrazol-1-yl)-4-trifluoromethyl-6-(4-trifluoromethyl-phenyl)-pyrimidine The title compound was prepared from 2-chloro-4-trifluoromethyl-6-(4-trifluoromethylphenyl)-pyrimidine (example A.2) (0.98 g, 3.0 mmol) and commercially available 4-bromopyrazole (0.66 g, 4.50 mmol) according to the general procedure IVa. Obtained as a white solid (0.83 g, 59%). MS (ISP) 437.0 [$(M+H)^+$]; mp 175.5° C.

EXAMPLE E.12

2-(4-Bromo-imidazol-1-yl)-4-(4-chloro-phenyl)-6-methyl-pyrimidine

The title compound was prepared from 2-chloro-4-(4-chloro-phenyl)-6-methyl-pyrimidine (example A.11) (1.91 g, 8.0 mmol) and commercially available 4-bromo-imidazole (1.76 g, 12.0 mmol) according to the general procedure IVa. Obtained as a light brown solid (2.76 g, 98%). MS (ISP) 349.1 [$(M+H)^+$]; mp 176-178° C.

EXAMPLE E.13

2-(4-Bromo-imidazol-1-yl)-4-methyl-6-(4-trifluoromethyl-phenyl)-pyrimidine

The title compound was prepared from 2-chloro-4-methyl-6-(4-trifluoromethyl-phenyl)-pyrimidine (example A.12) (2.73 g, 10.0 mmol) and commercially available 4-bromo-imidazole (2.21 g, 15.0 mmol) according to the general procedure IVa. Obtained as a light brown solid (3.20 g, 84%). MS (ISP) 383.0 [$(M+H)^+$]; mp 166-168° C.

EXAMPLE E.14

2-(4-Bromo-imidazol-1-yl)-4-(4-chloro-phenyl)-6-cyclopropyl-pyrimidine

The title compound was prepared from 2-chloro-4-(4-chloro-phenyl)-6-cyclopropyl-pyrimidine (example A.13) (0.80 g, 3.0 mmol) and commercially available 4-bromo-imidazole (0.66 g, 4.50 mmol) according to the general procedure IVa. Obtained as a white solid (0.71 g, 63%). MS (ISP) 375.1 [$(M+H)^+$].

EXAMPLE E.15

2-(4-Bromo-imidazol-1-yl)-4-(4-chloro-phenyl)-pyrimidine

The title compound was prepared from 2-chloro-4-(4-chloro-phenyl)-pyrimidine (example A.14) (0.90 g, 4.0 mmol) and commercially available 4-bromo-imidazole (0.88 g, 6.0 mmol) according to the general procedure IVa. Obtained as a white solid (1.09 g, 81%). MS (ISP) 335.1 [$(M+H)^+$]; mp 166-168° C.

EXAMPLE E.16

2-(4-Iodo-imidazol-1-yl)-4-trifluoromethyl-6-(3-trifluoromethyl-phenyl)-pyrimidine The title compound was prepared 2-methanesulfonyl-4-trifluoromethyl-6-(3-trifluoromethyl-phenyl)-pyrimidine (example A.15) (1.1 g, 3 mmol) and commercially available 4-iodo-imidazole (0.70 g, 4 mmol) according to the general procedure IVa. Obtained as a white solid (0.96 g, 66%). MS (ISP) 485.2 [$(M+H)^+$].

EXAMPLE E.17

2-Cyclopropyl-6-(4-iodo-imidazol-1-yl)-4-(4-trifluoromethyl-phenyl)-pyridine

The title compound was prepared 2-chloro-6-cyclopropyl-4-(4-trifluoromethyl-phenyl)pyridine (example A.33) (1.0 g, 3 mmol) and commercially available 4-iodo-imidazole (0.782 g, 4 mmol) according to the general procedure IVa. Obtained as a yellow solid (1.44 g, 93%). MS (ISP) 456.2 [$(M+H)^+$].

EXAMPLE E.18

2-(4-Iodo-imidazol-1-yl)-6-methyl-4-(4-trifluoromethyl-phenyl)-pyridine

The title compound was prepared 2-chloro-6-methyl-4-(4-trifluoromethyl-phenyl)pyridine (example A.30) (1.0 g, 3.7 mmol) and commercially available 4-iodo-imidazole (0.857 g, 4.4 mmol) according to the general procedure IVa. Obtained as a yellow solid (0.98 g, 62%). MS (ISP) 430.2 [$(M+H)^+$].

EXAMPLE E.19

2-(4-Chloro-phenyl)-6-(4-iodo-imidazol-1-yl)-4-trifluoromethyl-pyridine

The title compound was prepared 2-chloro-6-(4-chloro-phenyl)-4-trifluoromethyl-pyridine (example A.16) (10.14 g, 35 mmol) and commercially available 4-iodo-imidazole (8.081 g, 42 mmol) according to the general procedure IVa. Obtained as a white solid (2.80 g, 18%). MS (ISP) 450.0 [$(M+H)^+$] and 452 [$(M+2+H)^+$].

EXAMPLE E.20

2-(3-Bromo-phenyl)-4-trifluoromethyl-6-(4-trifluoromethyl-phenyl)-pyridine

The title compound was prepared from 2-bromo-4-trifluoromethyl-6-(4-trifluoromethylphenyl)-pyridine (example A.19) (3.0 g, 8 mmol) and commercially available 3-bromo-benzeneboronic acid (1.954 g, 10 mmol) according to the general procedure IVb. Obtained as an orange oil (3.28 g, 91%). MS (ISP) 446.0 [$(M+H)^+$] and 448.0 [$(M+2+H)^+$].

EXAMPLE E.21

2-(3-Bromo-phenyl)-6-methyl-4-(4-trifluoromethyl-phenyl)-pyridine

The title compound was prepared from trifluoro-methane-sulfonic acid 6-methyl-4-(4-trifluoromethyl-phenyl)-pyridin-2-yl ester (example A.32) (1.0 g, 2.6 mmol) and commercially available 3-bromo-benzene-boronic acid (0.573 g, 2.85 mmol) according to the general procedure IVb. Obtained as an off-white solid (1.00 g, 98%). MS (ISP) 392.0 [$(M+H)^+$] and 394.0 [$(M+2+H)^+$].

EXAMPLE E.22

2-(3-Bromo-phenyl)-6-cyclopropyl-4-(4-trifluoromethyl-phenyl)-pyridine

The title compound was prepared from trifluoro-methane-sulfonic acid 6-cyclopropyl-4-(4-trifluoromethyl-phenyl)-pyridin-2-yl ester (example A.34) (1.0 g, 2.43 mmol) and commercially available 3-bromo-benzene-boronic acid (0.573 g, 2.85 mmol) according to the general procedure IVb. Obtained as a white solid (0.91 g, 89%). MS (ISP) 418.1 [$(M+H)^+$] and 420.1 [$(M+2+H)^+$].

EXAMPLE E.23

2-(4-Iodo-imidazol-1-yl)-4-trifluoromethyl-6-(4-trifluoromethyl-phenyl)-pyridine The title compound was prepared 2-bromo-4-trifluoromethyl-6-(4-trifluoromethylphenyl)-pyridine (example A.19) (2.22 g, 6 mmol) and commercially available 4-iodo-imidazole (1.28 g, 6.6 mmol) according to the general procedure IVa. Obtained as a white solid (2.70 g, 86%, 92% purity). MS (ISP) 484.2 [$(M+H)^+$].

EXAMPLE E.24

5'-Bromo-6-methyl-4-(4-trifluoromethyl-phenyl)-[2,3']bipyridinyl

The title compound was prepared from trifluoro-methane-sulfonic acid 6-methyl-4-(4-trifluoromethyl-phenyl)-pyridin-2-yl ester (example A.32) (2.0 g, 5.2 mmol) and commercially available 3-bromo-pyridine-boronic acid [CAS-No. 452972-09-07] (alternatively prepared from commercially available 3,5-dibromopyridine according to *Tetrahedron* 2002, 58(17), 3323 or *Synthesis* 2003, (7), 1035) (1.152 g, 5.7 mmol) according to the general procedure IVb. Obtained as a white solid (1.70 g, 83%). MS (ISP) 393.0 [$(M+H)^+$] and 395.0 [$(M+2+H)^+$].

EXAMPLE E.25

5'-Bromo-6-cyclopropyl-4-(4-trifluoromethyl-phenyl)-[2,3']bipyridinyl

The title compound was prepared from trifluoro-methane-sulfonic acid 6-cyclopropyl-4-(4-trifluoromethyl-phenyl)-pyridin-2-yl ester (example A.34) (2.0 g, 4.86 mmol) and commercially available 3-bromo-pyridine-boronic acid [CAS-No. 452972-09-07] (alternatively prepared from commercially available 3,5-dibromopyridine according to *Tetrahedron* 2002, 58(17), 3323 or *Synthesis* 2003, (7), 1035) (1.079 g, 5.34 mmol) according to the general procedure IVb. Obtained as a white solid (1.55 g, 76%). MS (ISP) 419.1 [$(M+H)^+$] and 421.0 [$(M+2+H)^+$].

EXAMPLE E.26

6'-Bromo-6-methyl-4-(4-trifluoromethyl-phenyl)-[2,2']bipyridinyl

The title compound was prepared from 2-iodo-6-methyl-4-(4-trifluoromethyl-phenyl)-pyridine (example A.31) (1.09 g, 3.0 mmol), i-PrMgBr/$ZnBr_2$ and commercially available 2,6-dibromopyridine (2.13 g, 9 mmol) according to the general procedure IVc protocol b. Obtained as a light yellow solid (0.826 g, 70%). MS (ISP) 393.0 [$(M+H)^+$] and 394.8 [$(M+2+H)^+$].

EXAMPLE E.27

2'-Chloro-4-trifluoromethyl-6-(4-trifluoromethyl-phenyl)-[2,4']bipyridinyl

The title compound was prepared from 2-bromo-4-trifluoromethyl-6-(4-trifluoromethylphenyl)-pyridine (example A.19) (1.11 g, 3.0 mmol), commercially available 2-chloro-4-iodo-pyridine [CAS No. 153034-86-7] (740 mg, 3.1 mmol) and i-PrMgCl/$ZnCl_2$ according to the general procedure IVc protocol a. Obtained as a white solid (0.601 g, 50%). MS (ISP) 403.3 [$(M+H)^+$] and 405.2 [$(M+2+H)^+$].

EXAMPLE E.28

2'-Chloro-6-methyl-4-(4-trifluoromethyl-phenyl)-[2,4']bipyridinyl

The title compound was prepared from trifluoro-methane-sulfonic acid 6-methyl-4-(4-trifluoromethyl-phenyl)-pyridin-2-yl ester (example A.32) (3.0 g, 7.8 mmol), commercially available 2-chloro-4-iodo-pyridine [CAS No. 153034-86-7] (1.92 g, 8.0 mmol) and i-PrMgCl/$ZnCl_2$ according to the general procedure IVc protocol a. Obtained as a white solid (1.50 g, 55%). MS (ISP) 349.2 [$(M+H)^+$] and 351 [$(M+2+H)^+$].

EXAMPLE E.29

2'-Chloro-6-cyclopropyl-4-(4-trifluoromethyl-phenyl)-[2,4']bipyridinyl

The title compound was prepared from trifluoro-methane-sulfonic acid 6-cyclopropyl-4-(4-trifluoromethyl-phenyl)-pyridin-2-yl ester (example A.34) (2.7 g, 7.0 mmol), commercially available 2-chloro-4-iodo-pyridine [CAS No. 153034-86-7] (1.62 g, 6.8 mmol) and i-PrMgCl/$ZnCl_2$ according to the general procedure IVc protocol a. Obtained as a white solid (0.75 g, 30%). MS (ISP) 375.2 [$(M+H)^+$] and 377.1 [$(M+2+H)^+$].

EXAMPLE E.30

4-(4-Chloro-phenyl)-2-(4-iodo-imidazol-1-yl)-6-methyl-pyridine

The title compound was prepared 2-chloro-4-(4-chloro-phenyl)-6-methyl-pyridine (example A.27) (2.3 g, 10 mmol) and commercially available 4-iodo-imidazole (2.248 g, 12 mmol) according to the general procedure IVa. Obtained as an off-white solid (2.1 g, 55%). MS (ISP) 396.0 [$(M+H)^+$].

EXAMPLE E.31

5'-Bromo-4-(4-chloro-phenyl)-6-methyl-[2,3']bipyridinyl

The title compound was prepared from 4-(4-chloro-phenyl)-2-iodo-6-methyl-pyridine (example A.29) (2.15 g, 6.5 mmol) and commercially available 3-bromo-pyridine-boronic acid [CAS-No. 452972-09-07] (alternatively prepared from commercially available 3,5-dibromopyridine according to *Tetrahedron* 2002, 58(17), 3323 or *Synthesis* 2003, (7), 1035) (1.448 g, 7.1 mmol) according to the general procedure IVb. Obtained as a white solid (1.35 g, 57%). MS (ISP) 358.9 [$(M+H)^+$], 360.9 [$(M+2+H)^+$] and 363.0 [$(M+4+H)^+$].

EXAMPLE E.32

2-(3-Bromo-phenyl)-4-(4-chloro-phenyl)-6-methyl-pyridine

The title compound was prepared from 4-(4-chloro-phenyl)-2-iodo-6-methyl-pyridine (example A.29) (1.5 g, 5 mmol) and commercially available 3-bromo-benzene-boronic acid (1.005 g, 5 mmol) according to the general procedure IVb. Obtained as a white solid (0.15 g, 8.4%). MS (ISP) 358.0 [$(M+H)^+$], 360.0 [$(M+2+H)^+$] and 362.2 [$(M+4+H)^+$].

EXAMPLE E.33

2-(2-Chloro-pyridin-4-yl)-4-(3-ethoxy-4-trifluoromethyl-phenyl)-6-trifluoromethyl-pyrimidine The title compound was prepared from 4-(3-ethoxy-4-trifluoromethyl-phenyl)-2-iodo-6-trifluoromethyl-pyrimidine (example A.35) (0.99 g, 2.14 mmol) according to the general procedure IVc. Obtained as a light yellow solid (0.35 g, 36%). MS (EI) 447.1 [(M)$^+$]; mp 145.5° C.

EXAMPLE E.34

2-(3-Bromo-phenyl)-4-(3-ethoxy-4-trifluoromethyl-phenyl)-6-trifluoromethyl-pyrimidine The title compound was prepared from 2-chloro-4-(3-ethoxy-4-trifluoromethyl-phenyl)-6-trifluoromethyl-pyrimidine (example A.10) (0.25 g, 0.67 mmol) and commercially available 3-bromo-benzene-boronic acid (0.17 g, 0.85 mmol) according to the general procedure IVb. Obtained as a light yellow solid (0.32 g, 97%). MS (EI) 492.0 [(M)$^+$]; mp 108° C.

EXAMPLE E.35

2-(4-Bromo-imidazol-1-yl)-4-(3-fluoro-4-trifluoromethyl-phenyl)-6-trifluoromethyl-pyrimidine The title compound was prepared from 2-chloro-4-(3-fluoro-4-trifluoromethyl-phenyl)-6-trifluoromethyl-pyrimidine (example A.6) (0.50 g, 1.45 mmol) and commercially available 4-bromo-imidazole (0.32 g, 2.18 mmol) according to the general procedure IVa. Obtained as a white solid (0.34 g, 51%). MS (EI) 455.1 [(M)$^+$]; mp 164.5° C.

EXAMPLE E.36

2-(3-Bromo-phenyl)-4-(3-fluoro-4-trifluoromethyl-phenyl)-6-trifluoromethyl-pyrimidine The title compound was prepared from 2-chloro-4-(3-fluoro-4-trifluoromethyl-phenyl)-6-trifluoromethyl-pyrimidine (example A.6) (0.50 g, 1.45 mmol) and commercially available 3-bromo-benzene-boronic acid (0.38 g, 1.89 mmol) according to the general procedure IVb. Obtained as a white solid (0.31 g, 46%). MS (EI) 464.0, 466.0 [(M)$^+$]; mp 111° C.

EXAMPLE E.37

2-(3-Bromo-phenyl)-4-(3,4-dichloro-phenyl)-6-trifluoromethyl-pyrimidine

The title compound was prepared from 2-chloro-4-(3,4-dichloro-phenyl)-6-trifluoromethyl-pyrimidine (example A.7) (0.50 g, 1.53 mmol) and commercially available 3-bromo-benzene-boronic acid (0.40 g, 1.99 mmol) according to the general procedure IVb. Obtained as a light yellow oil (0.71 g, 83%). MS (EI) 447.7 [(M)$^+$].

EXAMPLE E.38

2-(2-Chloro-pyridin-4-yl)-4-(3,4-dichloro-phenyl)-6-trifluoromethyl-pyrimidine

The title compound was prepared from 4-(3,4-dichloro-phenyl)-2-iodo-6-trifluoromethyl-pyrimidine (example A.36) (1.11 g, 2.65 mmol) according to the general procedure IVc. Obtained as a light yellow solid (0.47 g, 44%). MS (ISP) 406.1 [(M+H)$^+$]; mp 184.5° C.

EXAMPLE E.39

2-(4-Bromo-imidazol-1-yl)-4-(3,4-dichloro-phenyl)-6-trifluoromethyl-pyrimidine

The title compound was prepared from 2-chloro-4-(3,4-dichloro-phenyl)-6-trifluoromethyl-pyrimidine (example A.7) (0.50 g, 1.53 mmol) and commercially available 4-bromo-imidazole (0.34 g, 2.31 mmol) according to the general procedure IVb. Obtained as a white solid (0.38 g, 57%). MS (ISP) 439.0 [(M+H)$^+$]; mp 225.5° C.

EXAMPLE E.40

2-(4-Bromo-imidazol-1-yl)-4-(4-chloro-3-methyl-phenyl)-6-trifluoromethyl-pyrimidine The title compound was prepared from 2-chloro-4-(4-dichloro-3-methyl-phenyl)-6-trifluoromethyl-pyrimidine (example A.8) (0.50 g, 1.63 mmol) and commercially available 4-bromo-imidazole (0.36 g, 2.45 mmol) according to the general procedure IVa. Obtained as a white solid (0.52 g, 76%). MS (ISP) 419.0 [(M+H)$^+$]; mp 229.5° C.

EXAMPLE E.41

2-(3-Bromo-phenyl)-4-(4-chloro-3-methyl-phenyl)-6-trifluoromethyl-pyrimidine

The title compound was prepared from 2-chloro-4-(4-dichloro-3-methyl-phenyl)-6-trifluoromethyl-pyrimidine (example A.8) (0.50 g, 1.63 mmol) and commercially available 3-bromo-benzene-boronic acid (0.425 g, 2.12 mmol) according to the general procedure IVb. Obtained as a white solid (0.34 g, 49%). MS (ISN) 426.2 [(M−H)$^-$]; mp 95.5° C.

EXAMPLE E.42

2'-Chloro-6-trifluoromethyl-4-(4-trifluoromethyl-phenyl)-[2,4']bipyrimidinyl

The title compound was prepared from 2-iodo-4-trifluoromethyl-6-(4-trifluoromethylphenyl)-pyrimidine (example A.4) (1.0 g, 2.39 mmol) and 2,4-dichloro-pyrimidine (0.356 g, 2.39 mmol) according to the general procedure IVc. Obtained as an off-white solid (0.49 g, 50%). MS (EI) 404.1 [(M)$^+$]; mp 152° C.

EXAMPLE E.43

4-(4-Chloro-3-methyl-phenyl)-2-(2-chloro-pyridin-4-yl)-6-trifluoromethyl-pyrimidine The title compound was prepared from 4-(4-chloro-3-methyl-phenyl)-2-iodo-6-trifluoromethyl-pyrimidine (example A.37) (0.94 g, 2.36 mmol) according to the general procedure IVc. Obtained as an off-white solid (0.49 g, 54%). MS (ISP) 384.1 [(M+H)$^+$]; mp 143° C.

EXAMPLE E.44

2-(3-Bromo-phenyl)-4-(4-chloro-phenyl)-6-methyl-pyrimidine

The title compound was prepared from 2-chloro-4-(4-chloro-phenyl)-6-methyl-pyrimidine (example A.11) (1.0 g, 4.18 mmol) and commercially available 3-bromo-benzeneboronic acid (1.09 g, 5.43 mmol) according to the general procedure IVb. Obtained as an off-white solid (0.5 g, 33%). MS (ISP) 361.0 [$(M+H)^+$]; mp 123° C.

EXAMPLE E.45

4-(4-Chloro-phenyl)-2-(2-chloro-pyridin-4-yl)-6-methyl-pyrimidine

The title compound was prepared from 2-chloro-4-(4-chloro-phenyl)-6-methyl-pyrimidine (example A.11) (0.24 g, 1.0 mmol) and commercially available 2-chloro-pyridine-4-boronic acid (0.21 g, 1.3 mmol) according to the general procedure IVb. Obtained as a light yellow solid (0.23 g, 73%). MS (ISP) 316.1 [$(M+H)^+$]; mp 175° C.

EXAMPLE E.46

2-(2-Chloro-pyridin-4-yl)-4-(4-trifluoromethyl-phenyl)-6-methyl-pyrimidine

The title compound was prepared from 2-chloro-4-methyl-6-(4-trifluoromethyl-phenyl)pyrimidine (example A.12) (0.27 g, 1.0 mmol) and commercially available 2-chloro-pyridine-4-boronic acid (0.21 g, 1.3 mmol) according to the general procedure IVb. Obtained as an off-white solid (0.175 g, 50%). MS (ISP) 350.4 [$(M+H)^+$]; mp 147° C.

EXAMPLE E.47

2-(3-Bromo-phenyl)-4-(4-trifluoromethyl-phenyl)-6-methyl-pyrimidine

The title compound was prepared from 2-chloro-4-methyl-6-(4-trifluoromethyl-phenyl)pyrimidine (example A.12) (0.5 g, 1.83 mmol) and commercially available 3-bromo-benzeneboronic acid (0.48 g, 2.39 mmol) according to the general procedure IVb. Obtained as an off-white solid (0.11 g, 15%). MS (ISP) 395.0 [$(M+H)^+$]; mp 102.5° C.

EXAMPLE E.48

2-(4-Bromo-imidazol-1-yl)-4-(3-methyl-4-trifluoromethyl-phenyl)-6-trifluoromethyl-pyrimidine The title compound was prepared from 2-chloro-6-(3-methyl-4-trifluoromethyl-phenyl)-4-trifluoromethyl-pyrimidine (example A.38) (0.68 g, 2.0 mmol) and commercially available 4-bromo-imidazole (0.44 g, 3.0 mmol) according to the general procedure IVa. Obtained as an off-white solid (0.79 g, 88%). MS (ISP) 452.9 [$(M+H)^+$]; mp 191° C.

EXAMPLE E.49

2-(3-Bromo-phenyl)-4-(3-methyl-4-trifluoromethyl-phenyl)-6-trifluoromethyl-pyrimidine The title compound was prepared from 2-chloro-6-(3-methyl-4-trifluoromethyl-phenyl)-4-trifluoromethyl-pyrimidine (example A.38) (0.68 g, 2.0 mmol) and commercially available 3-bromo-benzene-boronic acid (0.44 g, 2.20 mmol) according to the general procedure IVb. Obtained as a white solid (0.23 g, 25%). MS (EI) 462.1 [$(M)^+$]; mp 102.5° C.

EXAMPLE E.50

2-(2-Chloro-pyridin-4-yl)-4-(3-methyl-4-trifluoromethyl-phenyl)-6-trifluoromethyl-pyrimidine The title compound was prepared from 2-chloro-6-(3-methyl-4-trifluoromethyl-phenyl)-4-trifluoromethyl-pyrimidine (example A.38) (0.68 g, 2.0 mmol) and commercially available 2-chloro-pyridine-4-boronic acid (0.35 g, 2.2 mmol) according to the general procedure IVb. Obtained as an off-white solid (0.33 g, 39%). MS (ISP) 418.3 [$(M+H)^+$]; mp 105.5° C.

EXAMPLE E.51

2-(4-Bromo-imidazol-1-yl)-4-methyl-6-(3-methyl-4-trifluoromethyl-phenyl)-pyrimidine The title compound was prepared from 2-chloro-4-(3-methyl-4-trifluoromethyl-phenyl)-6-methyl-pyrimidine (example A.40) (0.40 g, 1.4 mmol) and commercially available 4-bromo-imidazole (0.31 g, 2.1 mmol) according to the general procedure IVa. Obtained as a light brown solid (0.54 g, 97%). MS (ISP) 399.0 [$(M+H)^+$]; mp 157.5° C.

EXAMPLE E.52

2-(2-Chloro-pyridin-4-yl)-4-methyl-6-(3-methyl-4-trifluoromethyl-phenyl)-pyrimidine The title compound was prepared from 2-chloro-4-(3-methyl-4-trifluoromethyl-phenyl)-6-methyl-pyrimidine (example A.40) (0.401 g, 1.4 mmol) and commercially available 2-chloro-pyridine-4-boronic acid (0.286 g, 1.82 mmol) according to the general procedure IVb. Obtained as a light brown solid (0.11 g, 22%). MS (ISP) 364.1 [$(M+H)^+$]; mp 92° C.

EXAMPLE E.53

2-(3-Bromo-phenyl)-4-methyl-6-(3-methyl-4-trifluoromethyl-phenyl)-pyrimidine

The title compound was prepared from 2-chloro-4-(3-methyl-4-trifluoromethyl-phenyl)-6-methyl-pyrimidine (example A.40) (0.401 g, 1.4 mmol) and commercially available 3-bromo-benzene-boronic acid (0.366 g, 1.82 mmol) according to the general procedure IVb. Obtained as a light yellow oil (0.13 g, 23%). MS (ISP) 409.2 [$(M+H)^+$].

EXAMPLE E.54

2-(4-Bromo-imidazol-1-yl)-4-[3-(2,2,2-trifluoro-ethoxy)-4-trifluoromethyl-phenyl]-6-trifluoromethyl-pyrimidine The title compound was prepared from 2-chloro-4-[3-(2,2,2-trifluoro-ethoxy)-4-trifluoromethyl-phenyl]-6-trifluoromethyl-pyrimidine (example A.39) (0.85 g, 2.0 mmol) and commercially available 4-bromo-imidazole (0.44 g, 3.0 mmol) according to the general procedure IVa. Obtained as a light yellow solid (0.83 g, 78%). MS (ISP) 535.0 [$(M+H)^+$]; mp 159° C.

EXAMPLE E.55

2-(3-Bromo-phenyl)-4-[3-(2,2,2-trifluoro-ethoxy)-4-trifluoromethyl-phenyl]-6-trifluoromethyl-pyrimidine The title compound was prepared from 2-chloro-4-[3-(2,2,2-trifluoro-ethoxy)-4-trifluoromethyl-phenyl]-6-trifluoromethyl-pyrimidine (example A.39) (0.85 g, 2.0 mmol) and commercially available 3-bromo-benzene-boronic acid (0.44 g, 2.19 mmol) according to the general procedure IVb. Obtained as an off-white solid (0.97 g, 80%). MS (EI) 544.1 $[(M)^+]$; mp 122° C.

EXAMPLE E.56

2-(2-Chloro-pyridin-4-yl)-4-[3-(2,2,2-trifluoro-ethoxy)-4-trifluoromethyl-phenyl]-6-trifluoromethyl-pyrimidine The title compound was prepared from 2-chloro-4-[3-(2,2,2-trifluoro-ethoxy)-4-trifluoromethyl-phenyl]-6-trifluoromethyl-pyrimidine (example A.39) (0.85 g, 2.0 mmol) and commercially available 2-chloro-pyridine-4-boronic acid (0.35 g, 2.22 mmol) according to the general procedure IVb. Obtained as an off-white solid (0.71 g, 70%). MS (EI) 501.1 $[(M)^+]$; mp 138° C.

EXAMPLE E.57

2-(4-Bromo-imidazol-1-yl)-4-trifluoromethyl-6-(3-trifluoromethyl-phenyl)-pyrimidine The title compound was prepared from 2-chloro-4-trifluoromethyl-6-(3-trifluoromethylphenyl)-pyrimidine (example A.42) (0.65 g, 2.0 mmol) and commercially available 4-bromo-imidazole (0.44 g, 3.0 mmol) according to the general procedure IVa. Obtained as a light yellow solid (0.64 g, 73%). MS (ISP) 439.1 $[(M+H)^+]$; mp 158.5° C.

EXAMPLE E.58

2-(3-Bromo-phenyl)-4-trifluoromethyl-6-(3-trifluoromethyl-phenyl)-pyrimidine

The title compound was prepared from 2-chloro-4-trifluoromethyl-6-(3-trifluoromethylphenyl)-pyrimidine (example A.42) (0.65 g, 2.0 mmol) and commercially available 3-bromo-benzene-boronic acid (0.44 g, 2.2 mmol) according to the general procedure IVb. Obtained as a white solid (0.43 g, 48%). MS (EI) 448.0 $[(M)^+]$; mp 102.5° C.

EXAMPLE E.59

2-(2-Chloro-pyridin-4-yl)-4-trifluoromethyl-6-(3-trifluoromethyl-phenyl)-pyrimidine The title compound was prepared from 2-chloro-4-trifluoromethyl-6-(3-trifluoromethylphenyl)-pyrimidine (example A.42) (0.65 g, 2.0 mmol) and commercially available 2-chloro-pyridine-4-boronic acid (0.35 g, 2.22 mmol) according to the general procedure IVb. Obtained as an off-white solid (0.59 g, 73%). MS (ISP) 404.0 $[(M+H)^+]$; mp 147° C.

EXAMPLE E.60

2-(4-Bromo-2-methyl-imidazol-1-yl)-4-trifluoromethyl-6-(4-trifluoromethyl-phenyl)pyrimidine The title compound was prepared from 2-chloro-4-trifluoromethyl-6-(4-trifluoromethylphenyl)-pyrimidine (example A.2) (0.65 g, 2.0 mmol) and commercially available 4-bromo-2-methyl-imidazole (0.48 g, 3.0 mmol) according to the general procedure IVa. Obtained as a light brown solid (0.73 g, 81%). MS (ISP) 451.0 $[(M+H)^+]$; mp 174° C.

EXAMPLE E.61

2-(4-Bromo-imidazol-1-yl)-4-(3,4-dichloro-phenyl)-6-methyl-pyrimidine

The title compound was prepared from 2-chloro-4-(3,4-dichloro-phenyl)-6-methyl-pyrimidine (example A.41) (0.4 g, 1.46 mmol) and commercially available 4-bromo-imidazole (0.32 g, 2.18 mmol) according to the general procedure IVa. Obtained as a light brown solid (0.33 g, 59%). MS (ISP) 385.0 $[(M+H)^+]$; mp 219.5° C.

EXAMPLE E.62

2-(3-Bromo-phenyl)-4-(3,4-dichloro-phenyl)-6-methyl-pyrimidine

The title compound was prepared from 2-chloro-4-(3,4-dichloro-phenyl)-6-methyl-pyrimidine (example A.41) (0.4 g, 0.5 mmol) and commercially available 3-bromo-benzeneboronic acid (0.38 g, 1.89 mmol) according to the general procedure IVb. Obtained as an orange solid (0.23 g, 40%). MS (ISP) 394.9 $[(M+H)^+]$; mp 132.5° C.

EXAMPLE E.63

2-(2-Chloro-pyridin-4-yl)-4-(3,4-dichloro-phenyl)-6-methyl-pyrimidine

The title compound was prepared from 2-chloro-4-(3,4-dichloro-phenyl)-6-methyl-pyrimidine (example A.41) (0.4 g, 1.46 mmol) and commercially available 2-chloro-pyridine-4-boronic acid (0.3 g, 1.9 mmol) according to the general procedure IVb. Obtained as a light brown solid (0.15 g, 29%). MS (ISP) 350.2 $[(M+H)^+]$; mp 155° C.

EXAMPLE E.64

2-(4-Bromo-2-methyl-imidazol-1-yl)-4-methyl-6-(4-trifluoromethyl-phenyl)-pyrimidine The title compound was prepared from 2-chloro-4-methyl-6-(4-trifluoromethyl-phenyl)pyrimidine (example A.12) (0.4 g, 1.47 mmol) and commercially available 4-bromo-2-methylimidazole (0.35 g, 2.17 mmol) according to the general procedure IVa. Obtained as a light brown solid (0.41 g, 70%). MS (ISP) 399.0 $[(M+H)^+]$; mp 180° C.

EXAMPLE E.65

2-(3-Chloro-[1,2,4]triazol-1-yl)-4-methyl-6-(4-trifluoromethyl-phenyl)-pyrimidine The title compound was prepared from 2-chloro-4-methyl-6-(4-trifluoromethyl-phenyl)pyrimidine (example A.12) (0.4 g, 1.47 mmol) and commercially available 3-chloro-1H-[1,2,4]triazole (0.22 g, 2.17 mmol) according to the general procedure IVa. Obtained as a yellow solid (0.36 g, 72%). MS (ISP) 340.0 [$(M+H)^+$]; mp 137.5° C.

EXAMPLE E.66

2-(4-Bromo-imidazol-1-yl)-4-isopropyl-6-(4-trifluoromethyl-phenyl)-pyrimidine

The title compound was prepared from 2-chloro-4-isopropyl-6-(4-trifluoromethylphenyl)-pyrimidine (example A.43) (0.4 g, 1.33 mmol) and commercially available 4-bromo-imidazole (0.29 g, 2.0 mmol) according to the general procedure IVa. Obtained as an off-white solid (0.5 g, 91%). MS (ISP) 413.1 [$(M+H)^+$]; mp 185° C.

EXAMPLE E.67

2-(4-Iodo-5-methyl-imidazol-1-yl)-4-trifluoromethyl-6-(4-trifluoromethyl-phenyl)-pyrimidine The title compound was prepared from 2-chloro-4-trifluoromethyl-6-(4-trifluoromethylphenyl)-pyrimidine (example A.2) (0.33 g, 1.0 mmol) and commercially available 4-iodo-5-methyl-imidazole (0.25 g, 1.2 mmol) according to the general procedure IVa. Obtained as an off-white solid (0.43 g, 85%). MS (ISP) 498.8 [$(M+H)^+$]; mp 202° C.

EXAMPLE E.68

2-(4-Iodo-imidazol-1-yl)-4-trifluoromethyl-6-(4-trifluoromethyl-phenyl)-pyrimidine The title compound was prepared from 2-chloro-4-trifluoromethyl-6-(4-trifluoromethylphenyl)-pyrimidine (example A.2) (1.31 g, 4.0 mmol) and commercially available 4-iodo-imidazole (0.85 g, 4.4 mmol) according to the general procedure IVa. Obtained as a pink solid (1.88 g, 97%). MS (ISP) 485.3 [$(M+H)^+$]; mp 194° C.

EXAMPLE E.69

4-(4-Chloro-phenyl)-2-(4-iodo-imidazol-1-yl)-6-methyl-pyrimidine

The title compound was prepared from 2-chloro-4-(4-chloro-phenyl)-6-methyl-pyrimidine (example A.11) (1.67 g, 7.0 mmol) and commercially available 4-iodo-imidazole (2.04 g, 10.5 mmol) according to the general procedure IVa. Obtained as a light yellow solid (1.97 g, 71%). MS (ISP) 397.1 [$(M+H)^+$]; mp 184° C.

EXAMPLE E.70

4-(4-Chloro-phenyl)-2-(4-iodo-imidazol-1-yl)-6-trifluoromethyl-pyrimidine

The title compound was prepared from 2-chloro-4-(4-chloro-phenyl)-6-trifluoromethyl-pyrimidine (example A.1) (1.76 g, 6.0 mmol) and commercially available 4-iodo-imidazole (1.28 g, 6.6 mmol) according to the general procedure IVa. Obtained as an off-white (2.59 g, 96%). MS (ISP) 451.0 [$(M+H)^+$]; mp 258° C.

EXAMPLE E.71

2-(4-Iodo-imidazol-1-yl)-4-methyl-6-(4-trifluoromethyl-phenyl)-pyrimidine

The title compound was prepared from 2-chloro-4-methyl-6-(4-trifluoromethyl-phenyl)pyrimidine (example A.12) (2.34 g, 8.58 mmol) and commercially available 4-iodo-imidazole (2.50 g, 12.9 mmol) according to the general procedure IVa. Obtained as a light brown solid (2.67 g, 72%). MS (ISP) 431.1 [$(M+H)^+$]; mp 167° C.

EXAMPLE E.72

4-(3-Chloro-phenyl)-2-(4-iodo-imidazol-1-yl)-6-trifluoromethyl-pyrimidine

The title compound was prepared from 2-chloro-4-(3-chloro-phenyl)-6-trifluoromethyl-pyrimidine (example A.44) (3.12 g, 10.6 mmol) and commercially available 4-iodo-imidazole (2.27 g, 11.7 mmol) according to the general procedure IVa. Obtained as an off-white solid (4.0 g, 83%). MS (ISP) 451.0 [$(M+H)^+$]; mp 202° C.

EXAMPLE E.73

2-(4-Iodo-imidazol-1-yl)-4-(3-methyl-4-trifluoromethyl-phenyl)-6-trifluoromethyl-pyrimidine The title compound was prepared from 2-chloro-6-(3-methyl-4-trifluoromethyl-phenyl)-4-trifluoromethyl-pyrimidine (example A.38) (2.04 g, 6.0 mmol) and commercially available 4-iodo-imidazole (1.28 g, 6.6 mmol) according to the general procedure IVa. Obtained as an off-white solid (2.83 g, 95%). MS (ISP) 499.3 [$(M+H)^+$]; mp 190° C.

EXAMPLE E.74

4-(3,4-Dichloro-phenyl)-2-(4-iodo-imidazol-1-yl)-6-trifluoromethyl-pyrimidine

The title compound was prepared from 2-chloro-4-(3,4-dichloro-phenyl)-6-trifluoromethyl-pyrimidine (example A.7) (1.97 g, 6.0 mmol) and commercially available 4-iodo-imidazole (1.28 g, 6.6 mmol) according to the general procedure IVa. Obtained as an off-white solid (2.67 g, 92%). MS (ISP) 485.1 [$(M+H)^+$]; mp 223° C.

EXAMPLE E.75

4-(3,4-Dichloro-phenyl)-2-(4-iodo-imidazol-1-yl)-6-methyl-pyrimidine

The title compound was prepared from 2-chloro-4-(3,4-dichloro-phenyl)-6-methyl-pyrimidine (example A.41) (3.83 g, 14.0 mmol) and commercially available 4-iodo-imidazole (4.07 g, 21.0 mmol) according to the general procedure IVa. Obtained as a brown solid (1.41 g, 24%). MS (ISP) 431.0 [$(M+H)^+$]; mp 224.5° C.

EXAMPLE E.76

4-(4-Chloro-3-methyl-phenyl)-2-(4-iodo-imidazol-1-yl)-6-methyl-pyrimidine

The title compound was prepared from 2-chloro-4-(4-chloro-3-methyl-phenyl)-6-methyl-pyrimidine (example A.47) (3.5 g, 13.8 mmol) and commercially available 4-iodo-imidazole (2.95 g, 15.2 mmol) according to the general procedure IVa. Obtained as an off-white solid (2.67 g, 92%). MS (ISP) 485.1 [$(M+H)^+$]; mp 223° C.

EXAMPLE E.77

2-(3-Bromo-phenyl)-4-(4-chloro-3-methyl-phenyl)-6-methyl-pyrimidine

The title compound was prepared from 2-chloro-4-(4-chloro-3-methyl-phenyl)-6-methyl-pyrimidine (example A.47) (3.84 g, 15.2 mmol) and commercially available 3-bromo-benzene-boronic acid (3.2 g, 15.9 mmol) according to the general procedure IVb. Obtained as a white solid (2.87 g, 51%). MS (ISP) 375.1 [$(M+H)^+$]; mp 108° C.

EXAMPLE E.78

4-(3,4-Difluoro-phenyl)-2-(4-iodo-imidazol-1-yl)-6-trifluoromethyl-pyrimidine

The title compound was prepared from 2-chloro-4-(3,4-difluoro-phenyl)-6-trifluoromethyl-pyrimidine (example A.46) (1.50 g, 5.1 mmol) and commercially available 4-iodo-imidazole (1.48 g, 7.63 mmol) according to the general procedure IVa. Obtained as a light red solid (2.23 g, 97%). MS (ISP) 452.9 [$(M+H)^+$]; mp 206° C.

EXAMPLE E.79

4-(4-Fluoro-phenyl)-2-(4-iodo-imidazol-1-yl)-6-trifluoromethyl-pyrimidine

The title compound was prepared from 2-chloro-4-(4-fluoro-phenyl)-6-trifluoromethyl-pyrimidine (example A.45) (1.5 g, 5.4 mmol) and commercially available 4-iodo-imidazole (1.58 g, 8.15 mmol) according to the general procedure IVa. Obtained as a white solid (2.23 g, 95%). MS (ISP) 435.0 [$(M+H)^+$]; mp 235° C.

EXAMPLE E.80

2-(4-Bromo-thiazol-2-yl)-6-methyl-4-(4-trifluoromethyl-phenyl)-pyridine

The title compound was prepared from 2-iodo-6-methyl-4-(4-trifluoromethyl-phenyl)pyridine (example A.31) (4.0 g, 9.36 mmol) and commercially available 2,4-dibromo-thiazole (2.53 g, 10.41 mmol) according to the general procedure IVc protocol b. Obtained as a light yellow solid (1.22 g, 31%). MS (ISP) 399.1 [$(M+H)^+$] and 401.1 [$(M+2+H)^+$].

EXAMPLE E.81

2-(3-Bromo-phenyl)-6-trifluoromethyl-4-(4-trifluoromethyl-phenyl)-pyridine

The title compound was prepared from a mixture of 2-chloro-6-trifluoromethyl-4-(4-trifluoromethyl-phenyl)-pyridine (example A.26) (65%) and 2-iodo-6-trifluoromethyl-4-(4-trifluoromethyl-phenyl)-pyridine (example A.49) (35%) (5.5 g, 4.62 mmol) and commercially available 3-bromo-benzene-boronic acid (1.02 g, 5.1 mmol) according to the general procedure IVb. Obtained as a white solid (1.43 g, 69%). MS (ISP) 446.0 [$(M+H)^+$] and 448 [$(M+2+H)^+$]

EXAMPLE E.82

2-(3-Bromo-phenyl)-4-(4-chloro-phenyl)-6-trifluoromethyl-pyridine

The title compound was prepared from 4-(4-chloro-phenyl)-2-iodo-6-trifluoromethyl-pyridine (example A.50) (9 g, ca. 35% pure, ca. 8.2 mmol) and commercially available 3-bromo-benzene-boronic acid (1.80 g, 9 mmol) according to the general procedure IVb. Obtained as a white solid (1.7 g, 50%). MS (ISP) 412.0 [$(M+H)^+$], 414.1 [$(M+2+H)^+$] and 416.1 [$(M+4+H)^+$].

EXAMPLE E.83

2-Chloro-4-[6-methyl-4-(4-trifluoromethyl-phenyl)-pyridin-2-yl]-pyrimidine

The title compound was prepared from 2-iodo-6-methyl-4-(4-trifluoromethyl-phenyl)pyridine (example A.31) (10.89 g, 30 mmol) and commercially available 2,4-dichlorpyrimidine (4.47 g, 30 mmol) according to the general procedure IVc protocol b. Obtained as an off-white solid (7.2 g, 68%). MS (ISP) 350.2 [$(M+H)^+$] and 352 [$(M+2+H)^+$].

EXAMPLE E.84

4-(3,4-Dichloro-phenyl)-2-(4-iodo-imidazol-1-yl)-6-methyl-pyridine

The title compound was prepared from 2-chloro-4-(3,4-dichloro-phenyl)-6-methylpyridine (example A.51) (3.5 g, 12.8 mmol) and commercially available 4-iodo-imidazole (2.99 g, 15.4 mmol) according to the general procedure IVa. Obtained as a light grey solid (0.90 g, 16%). MS (ISP) 430.0 [$(M+H)^+$], 432.1 [$(M+2+H)^+$] and 434.0 [$(M+4+H)^+$].

EXAMPLE E.85

2-(3-Bromo-phenyl)-4-(3,4-dichloro-phenyl)-6-methyl-pyridine

The title compound was prepared from 4-(3,4-dichloro-phenyl)-2-iodo-6-methylpyridine (example A.52) (5.5 g, ca. 60% pure, ca. 9 mmol) and commercially available 3-bromo-benzene-boronic acid (1.82 g, 9.1 mmol) according to the general procedure IVb. Obtained as a white solid (1.3 g, 36%). MS (ISP) 391.9 [$(M+H)^+$], 394.0 [$(M+2+H)^+$], 396.0 [$(M+4+H)^+$] and 398.0 [$(M+6+H)^+$].

EXAMPLE E.86

2-(5-Bromo-thiophen-2-yl)-6-methyl-4-(4-trifluoromethyl-phenyl)-pyridine

The title compound was prepared from 2-iodo-6-methyl-4-(4-trifluoromethyl-phenyl)pyridine (example A.31) (1.00 g, 2.75 mmol) and commercially available 5-bromthiophene-2-boronic acid (0.570 g, 2.75 mmol) according to the general procedure IVb. Obtained as a light yellow solid (0.480 g, 43%). MS (ISP) 398.0 [$(M+H)^+$] and 400.0 [$(M+2+H)^+$].

EXAMPLE E.87

2-(5-Bromo-thiophen-2-yl)-4-(3,4-dichloro-phenyl)-6-methyl-pyridine

The title compound was prepared from 4-(3,4-dichloro-phenyl)-2-iodo-6-methylpyridine (example A.52) (1.0 g, ca. 80% pure, ca. 2.75 mmol) and commercially available 5-bromthiophene-2-boronic acid (0.568 g, 2.75 mmol) according to the general procedure IVb. Obtained as an off-white solid (0.480 g, 46%). MS (ISP) 397.9 [$(M+H)^+$], 400.0 [$(M+2+H)^+$], 402.1 [$(M+4+H)^+$] and 404.2 [$(M+6+H)^+$].

EXAMPLE E.88

2-(4-Bromo-thiophen-2-yl)-6-methyl-4-(4-trifluoromethyl-phenyl)-pyridine

The title compound was prepared from 2-iodo-6-methyl-4-(4-trifluoromethyl-phenyl)pyridine (example A.31) (4.0 g, 9.36 mmol) and commercially available 2,4-dibromothiophene (2.518 g, 10.41 mmol) according to the general procedure IVc protocol b. Obtained as a white solid (2.12 g, 54%). MS (ISP) 398.0 [$(M+H)^+$] and 400.0 [$(M+2+H)^+$].

EXAMPLE E.89

2-(3-Bromo-phenyl)-6-ethyl-4-(4-trifluoromethyl-phenyl)-pyridine

The title compound was prepared from 4-(3,4-dichloro-phenyl)-2-iodo-6-methylpyridine (example A.54) (2.1 g, ca. 62% pure, ca. 3.45 mmol) and commercially available 3-bromo-benzene-boronic acid (0.693 g, 3.45 mmol) according to the general procedure IVb. Obtained as a light yellow oil (1.0 g, 71%). MS (ISP) 406.2 [$(M+H)^+$] and 408.2 [$(M+2+H)^+$].

EXAMPLE E.90

2-(3-Bromo-phenyl)-4-methyl-6-(4-trifluoromethyl-phenyl)-pyridine

The title compound was prepared from trifluoro-methane-sulfonic acid 4-methyl-6-(4-trifluoromethyl-phenyl)-pyridin-2-yl ester (example A.55) (1.6 g, 4.15 mmol) and commercially available 3-bromobenzeneboronic acid (0.751 g, 3.74 mmol) according to the general procedure Iba. Obtained as a light yellow oil (1.39 g, 85%). MS (ISP) 392.0 [$(M+H)^+$] and 394.1 [$(M+2+H)^+$].

EXAMPLE E.91

4-Benzo[1,3]dioxol-5-yl-2-(3-bromo-phenyl)-6-methyl-pyridine

The title compound was prepared from trifluoro-methane-sulfonic acid 4-benzo[1,3]dioxol-5-yl-6-methyl-pyridin-2-yl ester (example A.56) (1.1 g, 3.04 mmol) and commercially available 3-bromobenzeneboronic acid (0.611 g, 3.04 mmol) according to the general procedure IVb. Obtained as a colorless gum (0.44 g, 39%). MS (ISP) 368.0 [$(M+H)^+$] and 370.0 [$(M+2+H)^+$].

EXAMPLE E.92

2-(3-Chloro-[1,2,4]triazol-1-yl)-4-trifluoromethyl-6-(4-trifluoromethyl-phenyl)-pyridine The title compound was prepared from 2-chloro-4-trifluoromethyl-6-(4-trifluoromethylphenyl)-pyridine (example A.17) (1.628 g, 5.0 mmol) and commercially available 3-chloro-1H-(1,2,4)triazole (0.776 g, 7 mmol) according to the general procedure IVa. Obtained as a white solid (1.651 g, 84%). MS (ISP) 393.1 [$(M+H)^+$] and 395 [$(M+2+H)^+$].

EXAMPLE E.93

2-(4-Iodo-imidazol-1-yl)-6-trifluoromethyl-4-(4-trifluoromethyl-phenyl)-pyridine The title compound was prepared from 2-chloro-6-trifluoromethyl-4-(4-trifluoromethylphenyl)-pyridine (example A.26) (2.0 g, 6.14 mmol) and commercially available 4-iodo-imidazole (1.31 g, 6.75 mmol) according to the general procedure IVa. Obtained as a white solid (1.90 g, 82%). MS (ISP) 484.1 [$(M+H)^+$].

EXAMPLE E.94

2'-Chloro-4-methyl-6-(4-trifluoromethyl-phenyl)-[2,4']bipyridinyl

The title compound was prepared from 2-iodo-4-methyl-6-(4-trifluoromethyl-phenyl)pyridine (example A.58) (5.45 g, 15 mmol) and commercially available 2-chloropyridine boronic acid (2.48 g, 15.75 mmol) according to the general procedure IVb. Obtained as an off-white solid (3.82 g, 73%). MS (ISP) 349.2 [$(M+H)^+$] and 351 [$(M+2+H)^+$].

EXAMPLE E.95

2-(4-Chloro-phenyl)-6-(4-iodo-imidazol-1-yl)-4-methyl-pyridine

The title compound was prepared from 2-bromo-6-(4-chloro-phenyl)-4-methyl-pyridine (example A.22) (0.94 g, 3.0 mmol) and commercially available 4-iodo-imidazole (0.71 g, 3.3 mmol) according to the general procedure IVa. Obtained as a yellow gum (0.213 g, 18%). MS (ISP) 396.0 [$(M+H)^+$].

EXAMPLE E.96

6'-Bromo-4-methyl-6-(4-trifluoromethyl-phenyl)-[2,2']bipyridinyl

The title compound was prepared from 2-iodo-4-methyl-6-(4-trifluoromethyl-phenyl)pyridine (example A.58) (5.81 g, 16 mmol), n-BuLi/$ZnBr_2$ and commercially available 2,6-dibromopyridine (5.31 g, 22.4 mmol) according to *Tetrahedron Letters* 1996, 37(15), 2537 and the general procedure IVc protocol b. Obtained as a white solid (2.34 g, 37%). MS (ISP) 393.0 [$(M+H)^+$] and 395.0 [$(M+2+H)^+$].

EXAMPLE E.97

2-Chloro-4-[4-methyl-6-(4-trifluoromethyl-phenyl)-pyridin-2-yl]-pyrimidine

The title compound was prepared from 2-iodo-4-methyl-6-(4-trifluoromethyl-phenyl)pyridine (example A.58) (2.55 g, 7.0 mmol), i-PrMgCl/$ZnCl_2$ and commercially available 2,4-dichloropyrimidine (1.08 g, 7.21 mmol) according to the general procedure IVc protocol b. Obtained as a light brown solid (0.896 g, 37%). MS (ISP) 350.3 [$(M+H)^+$] and 352 [$(M+2+H)^+$].

EXAMPLE E.98

2'-Iodo-4-trifluoromethyl-6-(4-trifluoromethyl-phenyl)-[2,4']bipyridinyl

The title compound was prepared from 2'-chloro-4-trifluoromethyl-6-(4-trifluoromethyl-phenyl)-[2,4']bipyridinyl (example E.27) (0.403 g, 1.0 mmol) according to the general procedure Ia to d preparation of iodides. Obtained as an off-white solid (0.436 g, 88%). MS (ISP) 495.1 [$(M+H)^+$].

EXAMPLE E.99

2'-Chloro-4-(3-methoxy-4-trifluoromethyl-phenyl)-6-methyl-[2,4']bipyridinyl

The title compound was prepared from trifluoro-methane-sulfonic acid 4-(3-methoxy-4-trifluoromethyl-phenyl)-6-methyl-pyridin-2-yl ester (example A.59) (2.0 g, 5.0 mmol) and commercially available 2-chloropyridine boronic acid (0.758 g, 5.0 mmol) according to the general procedure IVb; Obtained as an off-white solid (1.50 g, 82%). MS (ISP) 379.2 [$(M+H)^+$] and 381 [$(M+2+H)^+$].

EXAMPLE E.100

2-(6-Bromo-pyridin-2-yl)-4-trifluoromethyl-6-(4-trifluoromethyl-phenyl)-pyrimidine The title compound was prepared from 2-iodo-4-trifluoromethyl-6-(4-trifluoromethylphenyl)-pyrimidine (example A.4) (0.900 g, 2.15 mmol), n-BuLi/$ZnBr_2$ and commercially available 2,6-dibromopyridine (0.510 g, 2.15 mmol) according to *Tetrahedron Letters* 1996, 37(15), 2537 and the general procedure IVc protocol b. Obtained as a yellow oil (0.658 g, 60%, 88% purity). MS (ISP) 447.8 [$(M+H)^+$] and 450.0 [$(M+2+H)^+$].

EXAMPLE E.101

2-(3-Bromo-phenyl)-4-(3,4-difluoro-phenyl)-6-trifluoromethyl-pyrimidine

The title compound was prepared from 2-chloro-4-(3,4-difluoro-phenyl)-6-trifluoromethyl-pyrimidine (example A.46) (1.50 g, 5.1 mmol) and commercially available 3-bromo-benzene-boronic acid (1.23 g, 6.12 mmol) according to the general procedure IVb. Obtained as a white solid (1.23 g, 58%). MS (EI) 416.0 [$(M)^+$]; mp 103° C.

EXAMPLE E.102

2-(3-Bromo-phenyl)-4-(4-fluoro-phenyl)-6-trifluoromethyl-pyrimidine

The title compound was prepared from 2-chloro-4-(4-fluoro-phenyl)-6-trifluoromethyl-pyrimidine (example A.45) (1.50 g, 5.42 mmol) and commercially available 3-bromo-benzeneboronic acid (1.31 g, 6.52 mmol) according to the general procedure IVb. Obtained as a white solid (1.17 g, 54%). MS (EI) 395.9, 397.9 [$(M)^+$]; mp 111° C.

EXAMPLE E.103

2-(2-Chloro-pyridin-4-yl)-4-(4-fluoro-phenyl)-6-trifluoromethyl-pyrimidine

The title compound was prepared from 2-chloro-6-(4-fluoro-phenyl)-4-trifluoromethyl-pyrimidine (example A.45) (1.5 g, 5.42 mmol) and commercially available 2-chloro-pyridine-4-boronic acid (1.02 g, 6.48 mmol) according to the general procedure IVb. Obtained as a light brown solid (0.49 g, 26%). MS (ISP) 354.2 [$(M+H)^+$]; mp 138.5° C.

EXAMPLE E.104

2-(2-Chloro-pyridin-4-yl)-4-(3,4-difluoro-phenyl)-6-trifluoromethyl-pyrimidine

The title compound was prepared from 2-chloro-6-(3,4-difluoro-phenyl)-4-trifluoromethyl-pyrimidine (example A.46) (1.5 g, 5.09 mmol) and commercially available 2-chloro-pyridine-4-boronic acid (0.96 g, 6.1 mmol) according to the general procedure IVb. Obtained as a light brown solid (0.51 g, 27%). MS (ISP) 372.0 [$(M+H)^+$]; mp 151.5° C.

EXAMPLE E.105

2-(3-Bromo-phenyl)-4-(2-fluoro-4-trifluoromethyl-phenyl)-6-trifluoromethyl-pyrimidine The title compound was prepared from 2-chloro-4-(2-fluoro-4-trifluoromethyl-phenyl)-6-trifluoromethyl-pyrimidine (example A.60) (1.50 g, 4.35 mmol) and commercially available 3-bromo-benzene-boronic acid (0.96 g, 4.78 mmol) according to the general procedure IVb. Obtained as a white solid (1.23 g, 61%). MS (EI) 466.0 [$(M)^+$]; mp 109° C.

EXAMPLE E.106

2-(3-Bromo-phenyl)-4-(2,4-dichloro-phenyl)-6-trifluoromethyl-pyrimidine

The title compound was prepared from 2-chloro-4-(2,4-dichloro-4-trifluoromethylphenyl)-6-trifluoromethyl-pyrimidine (example A.61) (1.50 g, 4.58 mmol) and commercially available 3-bromo-benzene-boronic acid (1.01 g, 5.03 mmol) according to the general procedure IVb. Obtained as a white solid (1.26 g, 61%). MS (EI) 447.9 [$(M)^+$]; mp 124.5° C.

EXAMPLE E.107

2-(2-Chloro-pyridin-4-yl)-4-(2-fluoro-4-trifluoromethyl-phenyl)-6-trifluoromethyl-pyrimidine The title compound was prepared from 2-chloro-4-(2-fluoro-4-trifluoromethyl-phenyl)-6-trifluoromethyl-pyrimidine (example A.61) (1.50 g, 4.35 mmol) and commercially available 2-chloro-pyridine-4-boronic acid (0.75 g, 4.8 mmol) according to the general procedure IVb. Obtained as a light red solid (0.64 g, 35%). MS (ISP) 422.0 [$(M+H)^+$]; mp 146° C.

EXAMPLE E.108

2-(2-Chloro-pyridin-4-yl)-4-(3-ethoxy-4-trifluoromethyl-phenyl)-6-trifluoromethyl-pyrimidine The title compound was prepared from 2-chloro-4-(3-ethoxy-4-trifluoromethyl-phenyl)-6-trifluoromethyl-pyrimidine (example A.10) (0.99 g, 2.14 mmol) according to the general procedure IVc. Obtained as a light yellow solid (0.35 g, 36%). MS (EI) 447.1 [$(M)^+$]; mp 145.5° C.

EXAMPLE E.109

2-(3-Bromo-phenyl)-4-(3-fluoro-4-trifluoromethyl-phenyl)-6-trifluoromethyl-pyrimidine The title compound was prepared from 2-chloro-4-(3-fluoro-4-trifluoromethyl-phenyl)-6-trifluoromethyl-pyrimidine (example A.6) (1.79 g, 5.19 mmol) and commercially available 3-bromo-benzene-boronic acid (1.15 g, 5.73 mmol) according to the general procedure IVb. Obtained as a white solid (0.94 g, 39%). MS (EI) 464.0, 466.0 [$(M)^+$]; mp 111° C.

EXAMPLE F.1

N-tert-Butyl-5-(4,4,5,5-tetramethyl-1,3,2-dioxaborolan-2-yl)-thiophene-2-sulfonamide To a stirred solution of commercially available 5-bromo-N-tert-butyl-thiophene-2-sulfonamide (16.9 g, 56.7 mmol) and commercially available triisopropyl borate (39.4 g, 0.21 mol) in THF (500 mL) was added dropwise at −78° C. butyllithium (1.6 M in hexane, 131 mL, 0.21 mol) in a way that the temperature did not exceed −65° C. The mixture was allowed to stir for 3 h at −78° C. and afterwards water (500 mL) was added dropwise at −20° C. The layers were separated, the water phase was extracted with diethyl ether (4×200 mL) and afterwards 2N HCl was added (120 mL). The acidic water layer was extracted with ethyl acetate (3×200 mL), the combined organic layers were dried (MgSO4) and evaporated to yield a light brown gum (12.3 g, 83%), which was dissolved in toluene (400 mL). Pinacol (16.6 g, 0.14 mol) and p-toluenesulfonic acid (0.27 g, 1.41 mmol) was added, the reaction mixture was heated under reflux conditions for 3 h and evaporated to yield a light brown oil. Hexane (50 mL) was added and the mixture was stirred at room temperature for 30 min. The precipitate was collected by filtration, washed with hexane and dried to yield the title compound as an off-white solid (9.3 g, 57%). MS (EI) 345.2 [$(M)^+$]; mp 127° C.

EXAMPLE F.2

3-Sulfamoyl-benzeneboronic acid

Step 1) To a stirred solution of commercially available 3-bromobenzeneboronic acid methyldiethanolamine ester (5 g, 17.6 mmol) in THF (150 mL) was added dropwise n-BuLi (1.6 M in hexane, 11.0 mL, 17.6 mmol) over a 3 min period at −78° C. and the mixture was stirred at −78° C. for 15 min, then gaseous sulfur dioxide (ca. 7.5 g, 117 mmol) was added causing an immediate precipitation and a 40° C. increase in the internal temperature. The mixture was allowed to warm to rt and stirred for 1 h. The precipitated lithium sulfinate was isolated by filtration under nitrogen, washed with THF and dried in HV to give as a white solid (5.1 g, purity 95%, 100% yield) (according to *Bioorg. Med. Chem.* 2005, 13, 2305-2312).

Step 2) N-Chlorosuccinimide (1.015 g, 7.6 mmol) was added to a suspension of the above prepared lithium 3-(6-methyl-[1,3,6,2]dioxazaborocan-2-yl)-benzenesulfinate (2 g, 7.27 mmol) in $CH_2Cl_2$ (14 mL) and the mixture was stirred for 2 h at rt. A solution of 25% ammonium hydroxide (1.09 mL, 14.5 mmol) was added and the mixture was stirred again for 2 h at rt, then completely evaporated to give the title compound as an off-white solid (1.38 g, 94%) (according to *Bioorg. Med. Chem.* 2005, 13, 2305-2312). MS (ISP) 200.4 [$(M-H)^-$].

EXAMPLE F.3

3-Sulfamoyl-pyridine-5-boronic acid

Step 1) A mixture of 3-bromopyridine-5-boronic acid [CAS-no. 452972-09-7] (10 g, 50 mmol) and N-methyldiethanolamine (5.9 g, 50 mmol) in toluene (50 mL) was stirred at 23° C. for 24 h, then totally evaporated, triturated with heptane to give 2-(5-bromo-pyridin-3-yl)-6-methyl-[1,3,6,2]dioxazaborocane (14.1 g, 100%) as an off-white solid. MS (ISP) 285.0 [$(M+H)^+$].

Step 2) To a stirred solution of the above described 2-(5-bromo-pyridin-3-yl)-6-methyl-[1,3,6,2]dioxazaborocane (5 g, 17.6 mmol) in THF (150 mL) was added dropwise n-BuLi (1.6 M in hexane, 11.0 mL, 17.6 mmol) over a 3 min period at −78° C. and the mixture was stirred at −78° C. for 15 min, then gaseous sulfur dioxide (ca. 7.5 g, 117 mmol) was added causing an immediate precipitation and a 40° C. increase in the internal temperature. The mixture was allowed to warm to rt and stirred for 1 h. The precipitated lithium sulfinate was isolated by filtration under nitrogen, washed with THF and dried in HV to give as a white solid (5.5 g, purity 88%, 100% yield) (according to *Bioorg. Med. Chem.* 2005, 13, 2305-2312).

Step 3) N-Chlorosuccinimide (0.937 g, 7.01 mmol) was added to a suspension of the above prepared lithium 5-(6-methyl-[1,3,6,2]dioxazaborocan-2-yl)-pyridine-3-sulfinate (2 g, 7.24 mmol) in $CH_2Cl_2$ (14 mL) and the mixture was stirred for 2 h at rt. A solution of 25% ammonium hydroxide (1.00 mL, 13.4 mmol) was added and the mixture was stirred again for 2 h at rt, then completely evaporated to give the title compound as an off-white solid (1.28 g, 88%) (according to *Bioorg. Med. Chem.* 2005, 13, 2305-2312). MS (ISP) 201.4 [$(M-H)^-$].

EXAMPLE F.4

3-(2,2-Dimethyl-propyloxysulfonyl)-benzeneboronic acid

Step 1) 3-Bromo-benzenesulfonic acid 2,2-dimethyl-propyl ester: Commercially available 3-bromobenzenesulfonyl chloride (10 g, 39 mmol) and 2,2-dimethyl-1-propanol (5.18 g, 59 mmol) were cooled to 10° C., then pyridine (6.3 mL, 78 mmol) was added and the mixture was stirred at 23° C. for 18 h. The reaction mixture was extracted with ethyl acetate and citric acid (5%), the ethyl acetate layer was washed with sat. $NaHCO_3$-sol. and brine, dried over $MgSO_4$ filtered and the solvents were evaporated to give the 3-bromo-benzene-sulfonic acid 2,2-dimethyl-propyl ester (11.48 g, 96%) as an off-white solid, which was used without further purification.

Step 2) To a solution of the above prepared 3-bromo-benzenesulfonic acid 2,2-dimethyl-propyl ester (9.83 g, 32 mmol) and triisopropyl borate (13.4 mL, 58 mmol) in THF (45 mL) at −78° C. was added n-BuLi (1.6 M in hexane, 20 mL, 32 mmol) keeping the internal temperature below −65° C. Stirring was continued at −78° C. for 1 h, then more n-BuLi (4.0 mL, 6.4 mmol) was added and stirring was continued at −78° C. for 30 min. The reaction mixture was quenched with 1 M $H_2SO_4$-sol. (40 mL), allowed to quickly (waterbath) warm to ca. 20° C. and stirred for 10 min. Diluted with EtOAc, layers were separated, washed organic layer with brine and dried over $Na_2SO_4$. Removal of the solvent in vacuum left the title compound as white solid (9.00 g, 103%). MS (ISN) 271.4 $[(M-H)^-]$.

EXAMPLE F.5

2-(2,5-Dimethyl-pyrrol-1-yl)-pyridine-4-boronic acid

Step 1) 4-Bromo-2-(2,5-dimethyl-pyrrol-1-yl)-pyridine: To commercially available 2-amino-4-bromopyridine (3.254 g, 19 mmol) and acetonylacetone (2.5 mL, 21 mmol) in toluene (40 mL) was added p-toluenesulfonic acid monohydrate (36 mg, 1 mol %) and refluxed for 1 hour, then a dean stark trap was installed and refluxed for another hour. The solvent was removed in vacuum, the residue extracted three times with ethyl acetate and sat. $NaHCO_3$-sol., the organic layers were combined, washed with brine, dried over $MgSO_4$, filtered and the solvents were evaporated to get a brown liquid, which was purified by silica gel column chromatography with n-heptane and ethyl acetate to give the 4-bromo-2-(2,5-dimethyl-pyrrol-1-yl)-pyridine (2.30 g, 50%) as a yellow liquid. MS (ISP) 251.1 $[(M+H)^+]$ and 253.0 $[(M+2+H)^+]$.

Step 2) To a solution of the above prepared 4-bromo-2-(2,5-dimethyl-pyrrol-1-yl)-pyridine (1.95 g, 7.77 mmol) and triisopropyl borate (2.68 mL, 11.6 mmol) in THF (40 mL) at −78° C. was added n-BuLi (1.6 M in hexane, 4.85 mL, 7.77 mmol) keeping the internal temperature below −65° C. Stirring was continued at −78° C. for 1 h, then more triisopropyl borate (2.68 mL, 11.6 mmol) and n-BuLi (4.85 mL, 7.77 mmol) was added and stirring was continued at −78° C. for 1 h. The reaction mixture was quenched with 1 M $NaH_2PO_4$-sol., allowed to quickly (waterbath) warm to ca. 20° C. and stirred for 10 min. Diluted with EtOAc, layers were separated, washed organic layer with brine and dried over $Na_2SO_4$. Removal of the solvent in vacuum left the title compound as a yellow foam (2.1 g, 100%, 80% purity), which was used without further purification. MS (ISN) 215.3 $[(M-H)^-]$.

EXAMPLE F.6

N-tert-Butyl-3-(6-tributylstannanyl-pyridin-2-yl)-benzenesulfonamide

Step 1) 3-(6-Bromo-pyridin-2-yl)-N-tert-butyl-benzene-sulfonamide: A mixture of commercially available 3-(tert-butylsulfamoyl)-benzeneboronic acid (5.142 g, 20 mmol), commercially available 2,6-dibromopyridine (14.2 g, 60 mmol) and $Pd(PPh_3)_4$ (1.156 g, 5 mol %) in DME (80 ml) and aqueous sodium carbonate (1 M, 40 ml, 40 mmol) was stirred at 90° C. under argon atmosphere for 18 h. The reaction mixture was extracted with water and ethyl acetate, the organic layers dried over $MgSO_4$, filtered and the solvents evaporated. The crude product was purified by flash chromatography with n-heptane/ethyl acetate to give the 3-(6-bromo-pyridin-2-yl)-N-tert-butyl-benzenesulfonamide (6.60 g, 89%) as a yellow solid. MS (ISP) 369.1 $[(M+H)^+]$ and 371.0 $[(M+2+H)^+]$.

Step 2) A mixture of the above described 3-(6-bromo-pyridin-2-yl)-N-tert-butyl-benzenesulfonamide (4.6 g, 12 mmol), hexabutyldistannane (9.9 ml, 19 mmol) and $Pd(PPh_3)_4$ (144 mg, 1 mol %) in toluene (135 ml) was stirred at 80° C. for 18 h. The solvents were evaporated and the crude product directly purified by flash chromatography with n-heptane/ethyl acetate to give the title compound (1.66 g, 23%) as a yellow oil. MS (ISP) 580.7 $[(M+H)^+]$.

EXAMPLE F.7

6-(3-tert-Butylsulfamoyl-phenyl)-pyridine-2-carboxamidinium acetate

To a mixture of 6-(3-tert-butylsulfamoyl-phenyl)-N-hydroxy-pyridine-2-carboxamidine (Example C.7) (830 mg, 2.38 mmol) in acetic acid (10 ml) at 23° C. was added acetic anhydride (0.34 ml, 3.57 mmol) and the mixture was stirred at 23° C. for 10 min, then 10% Pd on charcoal (84 mg, 0.79 mmol) was added and the mixture was hydrogenated (1 bar hydrogen) at 23° C. for 24 h. The catalyst was filtered off, washed with acetic acid and the solvents were evaporated to give the title compound (1.38 g, 148%, contains excess acetic acid) as a light yellow oil, which was used without further purification (cf. *Synth. Commun.* 1996, 26(23), 4351). MS (ISP) 333.1 $[(M+H)^+]$.

EXAMPLE G.1

2-(4-Tributylstannanyl-imidazol-1-yl)-4-trifluoromethyl-6-(4-trifluoromethyl-phenyl)-pyrimidine To a stirred solution of 2-(4-iodo-imidazol-1-yl)-4-trifluoromethyl-6-(4-trifluoromethylphenyl)-pyrimidine (Example E.68) (0.48 g, 1.0 mmol) in THF (5 mL) was added at 0° C. isopropyl-magnesium chloride lithium chloride (1M in THF, 1.22 mL, 1.22 mmol). The reaction mixture was allowed to stir for 15 min at 0° C., tributyltin chloride (0.43 g, 1.33 mmol) was added, the reaction mixture was stirred at room temperature for 16 h, poured into saturated ammonium chloride solution (30 mL) and extracted with ethyl acetate (2×50 mL). The combined organic layers were washed with brine (30 mL), dried ($MgSO_4$) and evaporated. The crude product was further purified by flash chromatography on silica gel (ethylacetate/heptane) to yield the title compound (0.27 g, 42%) as a light yellow oil. MS (ISP) 649.2 $[(M+H)^+]$.

EXAMPLE G.2

4-(4-Chloro-phenyl)-2-(4-tributylstannanyl-imidazol-1-yl)-6-trifluoromethyl-pyrimidine To a stirred solution of 4-(4-chloro-phenyl)-2-(4-iodo-imidazol-1-yl)-6-trifluoromethyl-pyrimidine (Example E.70) (0.45 g, 1.0 mmol) in THF (5 mL) was added at 0° C. isopropylmagnesium chloride lithium chloride (1M in THF, 1.22 mL, 1.22 mmol). The reaction mixture was allowed to stir for 15 min at 0° C., tributyltin chloride (0.43 g, 1.33 mmol) was added, the reaction mixture was stirred at room temperature for 16 h, poured into saturated ammonium chloride solution (30 mL) and extracted with ethyl acetate (2×50 mL). The combined organic layers were washed with brine (30 mL), dried ($MgSO_4$) and evaporated. The crude product was further purified by flash chromatography on silica gel (ethylacetate/heptane) to yield the title compound (0.29 g, 47%) as a light yellow oil. MS (ISP) 615.3 [$(M+H)^+$].

EXAMPLE G.3

4-(4-Chloro-phenyl)-6-methyl-2-(4-tributylstannanyl-imidazol-1-yl)-pyrimidine

To a stirred solution of 4-(4-chloro-phenyl)-2-(4-iodo-imidazol-1-yl)-6-methyl-pyrimidine (Example E.69) (0.40 g, 1.0 mmol) in THF (7 mL) was added at 0° C. iso-propylmagnesium chloride lithium chloride (1M in THF, 1.22 mL, 1.22 mmol). The reaction mixture was allowed to stir for 15 min at 0° C., tributyltin chloride (0.43 g, 1.33 mmol) was added, the reaction mixture was stirred at room temperature for 5 h, poured into saturated ammonium chloride solution (30 mL) and extracted with ethyl acetate (2×50 mL). The combined organic layers were washed with brine (30 mL), dried ($MgSO_4$) and evaporated. The crude product was further purified by flash chromatography on silica gel (ethylacetate/heptane) to yield the title compound (0.47 g, 84%) as a light yellow oil. MS (ISP) 561.2 [$(M+H)^+$].

EXAMPLE G.4

4-(3,4-Dichloro-phenyl)-6-methyl-2-(4-tributylstannanyl-imidazol-1-yl)-pyrimidine To a stirred solution of 4-(3,4-dichloro-phenyl)-2-(4-iodo-imidazol-1-yl)-6-methyl-pyrimidine (Example E.75) (0.43 g, 1.0 mmol) in THF (7 mL) was added at 0° C. iso-propylmagnesium chloride lithium chloride (1M in THF, 1.22 mL, 1.22 mmol). The reaction mixture was allowed to stir for 15 min at 0° C., tributyltin chloride (0.43 g, 1.33 mmol) was added, the reaction mixture was stirred at room temperature for 5 h, poured into saturated ammonium chloride solution (30 mL) and extracted with ethyl acetate (2×50 mL). The combined organic layers were washed with brine (30 mL), dried ($MgSO_4$) and evaporated. The crude product was further purified by flash chromatography on silica gel (ethylacetate/heptane) to yield the title compound (0.55 g, 92%) as a light yellow oil. MS (ISP) 593.2 [$(M+H)^+$].

EXAMPLE G.5

4-Methyl-2-(4-tributylstannanyl-imidazol-1-yl)-6-(4-trifluoromethyl-phenyl)-pyrimidine To a stirred solution of 2-(4-iodo-imidazol-1-yl)-4-methyl-6-(4-trifluoromethyl-phenyl)-pyrimidine (Example E.71) (0.43 g, 1.0 mmol) in THF (7 mL) was added at 0° C. isopropylmagnesium chloride lithium chloride (1M in THF, 1.22 mL, 1.22 mmol). The reaction mixture was allowed to stir for 15 min at 0° C., tributyltin chloride (0.43 g, 1.33 mmol) was added, the reaction mixture was stirred at room temperature for 5 h, poured into saturated ammonium chloride solution (30 mL) and extracted with ethyl acetate (2×50 mL). The combined organic layers were washed with brine (30 mL), dried ($MgSO_4$) and evaporated. The crude product was further purified by flash chromatography on silica gel (ethylacetate/heptane) to yield the title compound (0.55 g, 93%) as a light yellow oil. MS (ISP) 595.3 [$(M+H)^+$].

EXAMPLE G.6

4-(3,4-Dichloro-phenyl)-2-(4-tributylstannanyl-imidazol-1-yl)-6-trifluoromethyl-pyrimidine To a stirred solution of 4-(3,4-dichloro-phenyl)-2-(4-iodo-imidazol-1-yl)-6-trifluoromethyl-pyrimidine (Example E.74) (1.46 g, 3.0 mmol) in THF (21 mL) was added at 0° C. isopropyl-magnesium chloride lithium chloride (1M in THF, 3.6 mL, 3.6 mmol). The reaction mixture was allowed to stir for 15 min at 0° C., tributyltin chloride (1.27 g, 3.9 mmol) was added, the reaction mixture was stirred at room temperature for 16 h, poured into saturated ammonium chloride solution (70 mL) and extracted with ethyl acetate (2×100 mL). The combined organic layers were washed with brine (70 mL), dried ($MgSO_4$) and evaporated. The crude product was further purified by flash chromatography on a lox (ethylacetate/heptane) to yield the title compound (0.47 g, 24%) as a light yellow oil. MS (ISP) 649.2 [$(M+H)^+$].

EXAMPLE G.7

4-(3-Methyl-4-trifluoromethyl-phenyl)-2-(4-tributylstannanyl-imidazol-1-yl)-6-trifluoromethyl-pyrimidine To a stirred solution of 2-(4-iodo-imidazol-1-yl)-6-(3-methyl-4-trifluoromethyl-phenyl)-4-trifluoromethyl-pyrimidine (Example E.73) (1.49 g, 3.0 mmol) in THF (21 mL) was added at 0° C. isopropyl-magnesium chloride lithium chloride (1M in THF, 3.6 mL, 3.6 mmol). The reaction mixture was allowed to stir for 15 min at 0° C., tributyltin chloride (1.27 g, 3.9 mmol) was added, the reaction mixture was stirred at room temperature for 16 h, poured into saturated ammonium chloride solution (70 mL) and extracted with ethyl acetate (2×100 mL). The combined organic layers were washed with brine (70 mL), dried ($MgSO_4$) and evaporated. The crude product was further purified by flash chromatography on a lox (ethylacetate/heptane) to yield the title compound (0.33 g, 17%) as a light brown oil. MS (ISP) 663.3 [$(M+H)^+$].

EXAMPLE G.8

4-(4-Chloro-3-methyl-phenyl)-6-methyl-2-(4-tributylstannanyl-imidazol-1-yl)-pyrimidine To a stirred solution of 4-(4-chloro-3-methyl-phenyl)-2-(4-iodo-imidazol-1-yl)-6-methyl-pyrimidine (Example E.76) (1.03 g, 2.51 mmol) in THF (20 mL) was added at 0° C. isopropyl-magnesium chloride lithium chloride (1M in THF, 3.05 mL, 3.05 mmol). The reaction mixture was allowed to stir for 15 min at 0° C., tributyltin chloride (1.14 g, 3.5 mmol) was added, the reaction mixture was stirred at room temperature for 15 h, poured into saturated ammonium chloride solution (30 mL) and extracted with ethyl acetate (2×50 mL). The combined organic layers were washed with brine (30 mL), dried ($MgSO_4$) and evaporated. The crude product was further purified by flash chromatography on alox (ethylacetate/heptane) to yield the title compound (1.19 g, 83%) as a yellow oil. MS (ISP) 575.3 [$(M+H)^+$].

EXAMPLE G.9

3-[6-Methyl-4-(4-trifluoromethyl-phenyl)-pyridin-2-yl]-benzeneboronic acid

To a solution of 2-(3-bromo-phenyl)-6-methyl-4-(4-trifluoromethyl-phenyl)-pyridine (example E.21) (4.00 g, 10.2 mmol) and triisopropyl borate (2.23 g, 11.8 mmol) in THF (60 mL) at −78° C. was added n-BuLi (1.6 M in hexane, 6.50 mL, 10.4 mmol) keeping the internal temperature below −65° C. Stirring was continued at −78° C. for 45 min, again triisopropyl borate (1.11 g, 5.9 mmol) and n-BuLi (1.6 M in hexane, 3.25 mL, 5.2 mmol) were added and stirring was continued at −78° C. for 30 min. A 1 M aqueous solution of $NaH_2PO_4.2H_2O$ was added, saturated with solid NaCl and extracted with EtOAc. The organic layer was dried over $Na_2SO_4$, filtered and the solvent was removed in vacuum to give the title compound as a yellow solid (4.39 g, 96%). MS (ISP) 358.2 [$(M+H)^+$]; mp 140° C. (dec.).

EXAMPLE G.10

3-[4-Methyl-6-(4-trifluoromethyl-phenyl)-pyridin-2-yl]-benzeneboronic acid

To a solution of 2-(3-bromo-phenyl)-4-methyl-6-(4-trifluoromethyl-phenyl)-pyridine (example E.90) (1.23 g, 3.13 mmol) in TBME (80 mL) at −78° C. was added n-BuLi (1.6 M in hexane, 3.2 mL, 5.0 mmol) keeping the internal temperature below −60° C. (ca. 3 min), stirring was continued at −78° C. for 25 min, then triisopropyl borate (1.5 mL, 6.27 mmol) was added quickly, causing the internal temperature to rise to −60° C., stirring was continued at −78° C. for 20 min. The mixture was quenched by addition of 1M $NaH_2PO_4.2H_2O$-solution, the cooling bath was removed and the mixture was allowed to warm to 0° C. and stirred at 0° C. for 10 min. Diluted with EtOAc and brine, extracted three times with EtOAc, dried the combined organic layers over $Na_2SO_4$. Removal of the solvent in vacuum left the title compound as a light brown foam (1.20 g, 70.5%, purity: 65.8%), which was used without further purification. MS (ISP) 358.2 [$(M+H)^+$].

EXAMPLE G.11

2-(4-Tributylstannanyl-imidazol-1-yl)-4-trifluoromethyl-6-(4-trifluoromethyl-phenyl)-pyridine To a solution of 2-(4-iodo-imidazol-1-yl)-4-trifluoromethyl-6-(4-trifluoromethylphenyl)-pyridine (example E.23) (4.83 g, 10 mmol) in THF (50 mL) at 0° C. was quickly added added i-PrMgCl.LiCl (1 M in THF, 11 mL, 11 mmol) and the mixture was stirred at 0° C. for 15 min. Then $Bu_3SnCl$ (3.25 mL, 12 mmol) was added, the cooling bath was removed and the mixture was stirred at 23° C. for 14 h. Poured into sat. $NH_4Cl$-sol., extracted with EtOAc, washed with brine and dried over $Na_2SO_4$. Removal of the solvent in vacuum left a brown oil, which was purified by quick silica gel column chromatography with heptane/EtOAc 4:1 gave a yellow oil (4.42 g, 62%, ca. 90% pure). MS (ISP) 647.3 [$(M+H)^+$].

EXAMPLE G.12

2-(4-Tributylstannanyl-imidazol-1-yl)-6-trifluoromethyl-4-(4-trifluoromethyl-phenyl)-pyridine To a solution of 2-(4-iodo-imidazol-1-yl)-6-trifluoromethyl-4-(4-trifluoromethylphenyl)-pyridine (example E.93) (1.2 g, 2.48 mmol) in THF (15 mL) at 0° C. was quickly added added i-PrMgCl.LiCl (1 M in THF, 3.0 mL, 3.0 mmol) and the mixture was stirred at 0° C. for 15 min. Then $Bu_3SnCl$ (0.94 mL, 3.48 mmol) was added, the cooling bath was removed and the mixture was stirred at 23° C. for 48 h. Poured into sat. $NH_4Cl$-sol., extracted with EtOAc, washed with brine and dried over $Na_2SO_4$. Removal of the solvent in vacuum left a brown oil, which was purified by alox (neutral) column chromatography with heptane/methylene chloride gave a yellow oil (1.7 g, 106%, ca. 90% pure). MS (ISP) 648.3 [$(M+H)^+$].

EXAMPLE G.13

4-(3,4-Difluoro-phenyl)-2-(4-tributylstannanyl-imidazol-1-yl)-6-trifluoromethyl-pyrimidine To a stirred solution of 4-(3,4-dichloro-phenyl)-2-(4-iodo-imidazol-1-yl)-6-trifluoromethyl-pyrimidine (Example E.78) (0.9 g, 2.0 mmol) in THF (14 ml) was added at 0° C. isopropyl-magnesium chloride lithium chloride (1M in THF, 2.44 ml, 2.44 mmol). The reaction mixture was allowed to stir for 15 min at 0° C., tributyltin chloride (0.87 g, 2.67 mmol) was added, the reaction mixture was stirred at room temperature for 16 h, poured into saturated ammonium chloride solution (30 ml) and extracted with ethyl acetate (2×50 ml). The combined organic layers were washed with brine (30 ml), dried ($MgSO_4$) and evaporated. The crude product was further purified by flash chromatography on silica gel (ethylacetate/heptane) to yield the title compound (0.42 g, 34%) as a light yellow oil. MS (ISP) 616.9 [$(M+H)^+$].

EXAMPLE G.14

4-(4-Fluoro-phenyl)-2-(4-tributylstannanyl-imidazol-1-yl)-6-trifluoromethyl-pyrimidine To a stirred solution of 4-(4-fluoro-phenyl)-2-(4-iodo-imidazol-1-yl)-6-trifluoromethyl-pyrimidine (Example E.79) (0.87 g, 2.0 mmol) in THF (14 ml) was added at 0° C. isopropylmagnesium chloride lithium chloride (1M in THF, 2.44 ml, 2.44 mmol). The reaction mixture was allowed to stir for 15 min at 0° C., tributyltin chloride (0.87 g, 2.67 mmol) was added, the reaction mixture was stirred at room temperature for 16 h, poured into saturated ammonium chloride solution (30 ml) and extracted with ethyl acetate (2×50 ml). The combined organic layers were washed with brine (30 ml), dried ($MgSO_4$) and evaporated. The crude product was further purified by flash chromatography on silica gel (ethylacetate/heptane) to yield the title compound (0.69 g, 58%) as a light yellow oil. MS (ISP) 598.7 [$(M+H)^+$].

EXAMPLE H.1

2-Chloro-thiazole-5-sulfonic acid tert-butylamide

To a stirred solution of commercially available tert-butylamine (5.03 g, 68.8 mmol) in saturated $NaHCO_3$ solution (35 mL) and ethyl acetate (17 mL) was added at 0° C. (ice water bath) a solution of 2-chloro-thiazole-5-sulfonyl chloride [CAS-No. 88917-11-7] (5.0 g, 22.9 mmol). The reaction mixture was stirred at room temperature for 2 h, ethyl acetate (50 mL) was added followed by extraction. The water layer was again extracted with ethyl acetate (50 mL). The combined organic layers were washed with 2N HCl solution (40 mL) and brine (40 mL), dried ($MgSO_4$) and evaporated to yield the title compound (4.9 g, 84%) as a yellow solid. MS (ISN) 253.1 [$(M-H)^-$], mp 75° C.

EXAMPLE H.2

5-Bromo-pyridine-3-sulfonic acid (2-hydroxy-1,1-dimethyl-ethyl)-amide

To a solution of commercially available 2-amino-2-methyl-1-propanol (478 mg, 5 mmol) and $Et_3N$ (0.75 mL, 5 mmol) in THF (50 mL) at 0° C. was added portionwise added 5-bromo-pyridine-3-sulfonyl chloride [CAS-No. 65001-21-0] (according to *J. Org. Chem.* 1989, 54(2), 389) (1.28 g, 5 mmol) and the mixture was stirred at 23° C. for 1 h. The reaction is worked up by neutralization with 5% citric acid, extracted with EtOAc, washed with sat. $NaHCO_3$-sol. and brine, dried over $Na_2SO_4$, filtered and concentrated to give a light brown solid, which was purified by trituration with heptane/diethyl ether gave the title compound as a white solid (1.25 g, 82%). MS (ISP) 309.2 [$(M+H)^+$], 311.1 [$(M+2+H)^+$]; mp 112° C.

EXAMPLE H.3

3-Bromo-N-methoxy-benzenesulfonamide

To a solution of commercially available methoxyamine hydrochloride (1.96 g, 23.4 mmol) and 2 M $Na_2CO_3$-solution (20 mL, 40 mmol) in THF (100 mL) at 0° C. was added dropwise added commercially available 3-bromobenzene-sulfonyl chloride (2.5 g, 9.8 mmol) and the mixture was stirred at 23° C. for 18 h. The reaction is diluted with water, extracted with EtOAc, washed with brine, dried over $Na_2SO_4$, filtered and concentrated to give a light brown solid, which was refluxed with 1 M NaOH (10 mL) in dioxane (10 mL) for 30 min to cleave disulfonylated product. Cooled to rt, diluted with water, extracted with EtOAc, washed organic layer with brine and dried over $Na_2SO_4$. Removal of the solvent in vacuum left a light brown solid, which was purified by trituration with heptane/diethyl ether gave the title compound as a light yellow solid (1.30 g, 50%). MS (ISN) 264.0 [$(M-H)^-$] and 266.0 [$(M+2-H)^-$].

EXAMPLE H.4

3-Bromo-N-(2-hydroxy-1,1-dimethyl-ethyl)-benzenesulfonamide

To a solution of commercially available 2-amino-2-methyl-1-propanol (8.91 g, 100 mmol) in dioxane (20 mL) at 5° C. was added commercially available 3-bromobenzenesulfonyl chloride (2.88 mL, 20 mmol) and the mixture was vigorously stirred at 23° C. for 1 h. Poured into 1 N HCl, diluted with EtOAc, separated phases, washed organic layer with brine, dried over $Na_2SO_4$. Removal of the solvent in vacuum left the title compound as a white solid (5.47 g, 89%). MS (ISN) 306.1 [$(M-H)^-$] and 308.2 [$(M+2-H)^-$]; mp 138° C.

EXAMPLE H.5

2-Chloro-4-methyl-thiazole-5-sulfonic acid tert-butylamide

To a stirred solution of commercially available tert-butylamine (3.76 mL, 35.5 mmol) in saturated $NaHCO_3$ solution (30 mL) and ethyl acetate (50 mL) was added at 0° C. (ice water bath) a solution of commercially available 2-chloro-4-methyl-thiazole-5-sulfonyl chloride [CAS-No. 292138-59-1] (5.0 g, 21.5 mmol). The reaction mixture was stirred at room temperature for 16 h, ethyl acetate (50 mL) was added followed by extraction. The water layer was again extracted with ethyl acetate (50 mL). The combined organic layers were washed with 2N HCl solution (40 mL) and brine (40 mL), dried ($MgSO_4$) and evaporated to yield the title compound (4.57 g, 79%) as a yellow solid. MS (ISN) 267.3 [$(M-H)^-$].

EXAMPLE I.1

3-{4-[4-Trifluoromethyl-6-(4-trifluoromethyl-phenyl)-pyrimidin-2-yl]-pyridin-2-yl}-benzenesulfonyl chloride hydrochloride 1) 3-{4-[4-Trifluoromethyl-6-(4-trifluoromethyl-phenyl)-pyrimidin-2-yl]-pyridin-2-yl}-benzenesulfonic acid 2,2-dimethyl-propyl ester was prepared from 2-(2-chloro-pyridin-4-yl)-4-trifluoromethyl-6-(4-trifluoromethyl-phenyl)-pyrimidine (example E.6) (1.0 g, 2.5 mmol) and 3-(2,2-dimethyl-propyloxysulfonyl)-benzeneboronic acid (example F.4) (1.09 g, 4.0 mmol) according to the general procedure VI. Obtained as an off-white solid (1.28 g, 86%). MS (ISP) 595.7 [$(M+H)^+$]; mp 168.5° C.

2) A stirred mixture of 3-{4-[4-trifluoromethyl-6-(4-trifluoromethyl-phenyl)-pyrimidin-2-yl]-pyridin-2-yl}-benzenesulfonic acid 2,2-dimethyl-propyl ester (1.27 g, 2.13 mmol), 37% HCl (12.5 ml) and dioxane (12.5 ml) was heated under reflux conditions for 19 h and evaporated to dryness. Diethyl ether (50 ml) was added to the crude product and the mixture was stirred at room temperature for 1 h. The precipitate was collected by filtration and dried to yield 3-{4-[4-trifluoromethyl-6-(4-trifluoromethyl-phenyl)-pyrimidin-2-yl]-pyridin-2-yl}-benzenesulfonic acid hydrochloride as a white solid (1.08 g, 90%). MS (ISN) 524.0 [$(M-H)^-$]; mp 407° C. (dec.).

3) A stirred mixture of 3-{4-[4-trifluoromethyl-6-(4-trifluoromethyl-phenyl)-pyrimidin-2-yl]-pyridin-2-yl}-benzenesulfonic acid hydrochloride (0.14 g, 0.25 mmol), thionyl chloride (2 ml) and N,N-dimethylformamide (1 drop) was heated under reflux conditions for 2 h and evaporated to dryness to yield the tile compound as a light yellow solid (0.145, 100%) which was used without further purification. MS (EI) 543.1 [$(M)^+$]; mp 171° C.

EXAMPLE I.2

3-[6'-Methyl-4'-(4-trifluoromethyl-phenyl)-[2,2']bipyridinyl-6-yl]-benzenesulfonyl chloride To a suspension of 3-[6'-methyl-4'-(4-trifluoromethyl-phenyl)-[2,2']bipyridinyl-6-yl]-benzenesulfonic acid (example 345) (2.0 g, 4.25 mmol) in DMF (20 mL) at 23° C. was added thionyl chloride (1.54 mL, 21.25 mmol) and the mixture was stirred at 23° C. for 2 h, then added again $SOCl_2$ (1.54 mL, 21.25 mmol) and the mixture was stirred at 23° C. for 1 h. Diluted with EtOAc, poured into ice cold half-sat. $NaHCO_3$-sol., separated phases, washed organic layer with brine and dried over $Na_2SO_4$. Removal of the solvent in vacuum left the title compound as an off-white solid (2.0 g, 98%), which was used without further purification. MS (ISP) 489.2 [$(M+H)^+$] and 491.1 [$(M+2+H)^+$].

EXAMPLE I.3

3'-[4-Trifluoromethyl-6-(4-trifluoromethyl-phenyl)-pyrimidin-2-yl]-biphenyl-3-sulfonyl chloride 1) 3'-[4-Trifluoromethyl-6-(4-trifluoromethyl-phenyl)-pyrimidin-2-yl]-biphenyl-3-sulfonic acid 2,2-dimethyl-propyl ester was prepared from 2-(3-bromo-phenyl)-4-trifluoromethyl-6-(4-trifluoromethyl-phenyl)-pyrimidine (example E.3) (1.35 g, 3.02 mmol) and 3-(2,2-dimethyl-propyloxysulfonyl)-benzeneboronic acid (example F.4) (1.31 g, 4.81 mmol) according to the general procedure VI. Obtained as a white solid (1.43 g, 80%). MS (ISP) 594.6 [$(M+H)^+$]; mp 157° C.

2) A stirred mixture of 3'-[4-trifluoromethyl-6-(4-trifluoromethyl-phenyl)-pyrimidin-2-yl]-biphenyl-3-sulfonic acid 2,2-dimethyl-propyl ester (1.42 g, 2.39 mmol), 2M sodium propanolate solution (3 ml, 6 mmol), 2-(diethylamino)-ethanethiol (0.37 g, 2.75 mmol) and dioxane (15 ml) was heated under reflux conditions for 24 h and evaporated. Water (40 ml) was added and the mixture was extracted with ethyl acetate (2×50 ml). The combined organic layers were washed with water (50 ml). The water layers were combined, acidified with 2N HCl and extracted with ethyl acetate (2×50 ml). The latter two organic layers were combined, washed with brine (50 ml), dried ($MgSO_4$) and evaporated to yield the crude 3'-[4-trifluoromethyl-6-(4-trifluoromethyl-phenyl)-pyrimidin-2-yl]-biphenyl-3-sulfonic acid as a brown solid (0.91 g, 51%). Thionyl chloride (20 ml) and DMF (4 drops) were added and the stirred mixture was heated under reflux conditions for 4 h, evaporated and purified by flash chromatography on silica gel (ethyl acetate/heptane) to yield the title compound as a light brown solid (0.43 g, 33%). MS (ISP) 542.2 [$(M)^+$]; mp 176° C.

EXAMPLES OF COMPOUNDS OF FORMULA I ACCORDING TO THE INVENTION

EXAMPLE 1

4-(4-Chloro-phenyl)-2-imidazol-1-yl-6-trifluoromethyl-pyrimidine

The title compound was prepared from 2-chloro-4-(4-chloro-phenyl)-6-trifluoromethyl-pyrimidine (example A.1) (0.15 g, 0.5 mmol) and commercially available imidazole (0.034 g, 0.5 mmol) according to the general procedure IVa. Obtained as an off-white solid (0.063 g, 39%). MS (EI) 324.1 [$(M)^+$]; mp 175° C.

EXAMPLE 2

3-[3-[4-(4-Chloro-phenyl)-6-trifluoromethyl-pyrimidin-2-yl]-[1,2,4]oxadiazol-5-yl]-benzenesulfonamide The title compound was prepared from 4-(4-chloro-phenyl)-N-hydroxy-6-trifluoromethyl-pyrimidine-2-carboxamidine (example C.1) (0.16 g, 0.5 mmol) and commercially available 3-sulfamoyl-benzoic acid (0.1 g, 0.5 mmol) according to the general procedure VI. Obtained as a white solid (0.1 g, 43%). MS (ISP) 482.1 [$(M+H)^+$]; mp 273° C.

EXAMPLE 3

2-Imidazol-1-yl-4-trifluoromethyl-6-(4-trifluoromethyl-phenyl)-pyrimidine

The title compound was prepared from 2-chloro-4-(4-trifluoromethyl-phenyl)-6-trifluoromethyl-pyrimidine (example A.2) (0.16 g, 0.5 mmol) and commercially available imidazole (0.034 g, 0.5 mmol) according to the general procedure IVa. Obtained as a white solid (0.07 g, 39%). MS (EI) 358.0 [$(M)^+$]; mp 162° C.

EXAMPLE 4

2-Pyrrol-1-yl-4-trifluoromethyl-6-(4-trifluoromethyl-phenyl)-pyrimidine

The title compound was prepared from 2-chloro-4-(4-trifluoromethyl-phenyl)-6-trifluoromethyl-pyrimidine (example A.2) (0.16 g, 0.5 mmol) and commercially available pyrrole (0.067 g, 1.0 mmol) according to the general procedure IVa. Obtained as an off-white solid (0.04 g, 22%). MS (EI) 357.0 [$(M)^+$]; mp 120.5° C.

EXAMPLE 5

2-(4-Pyridin-3-yl-imidazol-1-yl)-4-trifluoromethyl-6-(4-trifluoromethyl-phenyl)-pyrimidine The title compound was prepared from 2-chloro-4-(4-trifluoromethyl-phenyl)-6-trifluoromethyl-pyrimidine (example A.2) (0.16 g, 0.5 mmol) and commercially available 3-(1H-imidazol-4-yl)-pyridine [CAS-No. 51746-85-1] (0.073 g, 0.5 mmol) according to the general procedure IVa. Obtained as a light brown solid (0.11 g, 49%). MS (ISP) 436.1 [$(M)^+$]; mp 200.5° C.

EXAMPLE 6

4-(4-Chloro-phenyl)-2-pyrrol-1-yl-6-trifluoromethyl-pyrimidine

The title compound was prepared from 2-chloro-4-(4-chloro-phenyl)-6-trifluoromethyl-pyrimidine (example A.1) (0.15 g, 0.5 mmol) and commercially available pyrrole (0.067 g, 1.0 mmol) according to the general procedure IVa. Obtained as a light brown solid (0.12 g, 74%). MS (EI) 323.1 [$(M)^+$]; mp 128.5° C.

EXAMPLE 7

4-(4-Chloro-phenyl)-2-(4-pyridin-3-yl-imidazol-1-yl)-6-trifluoromethyl-pyrimidine The title compound was prepared from 2-chloro-4-(4-chloro-phenyl)-6-trifluoromethyl-pyrimidine (example A.1) (0.15 g, 0.5 mmol) and commercially available 3-(1H-imidazol-4-yl)-pyridine [CAS-No. 51746-85-1] (0.073 g, 0.5 mmol) according to the general procedure IVa. Obtained as a light brown solid (0.09 g, 45%). MS (EI) 401.1 [$(M)^+$]; mp 228° C.

EXAMPLE 8

4-{5-[4-(4-Chloro-phenyl)-6-trifluoromethyl-pyrimidin-2-yl]-[1,2,4]oxadiazol-3-yl}-pyridin-2-ylamine The title compound was prepared from 2-amino-N-hydroxy-pyridine-4-carboxamidine (example C.5) (0.11 g, 0.75 mmol) and 4-(4-chloro-phenyl)-6-trifluoromethyl-pyrimidine-2-carboxylic acid (example D.1) (0.15 g, 0.5 mmol) according to the general procedure V. Obtained as an off-white solid (0.018 g, 9%). MS (ISP) 419.0 [$(M+H)^+$]; mp 223.5° C.

EXAMPLE 9

5-{5-[4-(4-Chloro-phenyl)-6-trifluoromethyl-pyrimidin-2-yl]-[1,2,4]oxadiazol-3-yl}-pyridin-2-ylamine The title compound was prepared from 6-amino-N-hydroxy-nicotinamidine (example C.3) (0.15 g, 1.0 mmol) and 4-(4-chloro-phenyl)-6-trifluoromethyl-pyrimidine-2-carboxylic acid (example D.1) (0.15 g, 0.5 mmol) according to the general procedure V. Obtained as a light brown solid (0.05 g, 24%). MS (ISP) 419.0 [$(M+H)^+$]; mp 211° C.

EXAMPLE 10

3-{3-[4-Trifluoromethyl-6-(4-trifluoromethyl-phenyl)-pyrimidin-2-yl]-[1,2,4]oxadiazol-5-yl}-benzenesulfonamide The title compound was prepared from N-hydroxy-4-trifluoromethyl-6-(4-trifluoromethyl-phenyl)-pyrimidine-2-carboxamidine (example C.2) (0.176 g, 0.5 mmol) and commercially available 3-sulfamoyl-benzoic acid (0.1 g, 0.5 mmol) according to the general procedure V. Obtained as an off-white solid (0.11 g, 42%). MS (ISN) 514.1 [$(M-H)^-$]; mp 205° C.

EXAMPLE 11

5-{5-[4-Trifluoromethyl-6-(4-trifluoromethyl-phenyl)-pyrimidin-2-yl]-[1,2,4]oxadiazol-3-yl}-pyridin-2-ylamine The title compound was prepared from 6-amino-N-hydroxy-nicotinamidine (example C.3) (0.15 g, 1.0 mmol) and 4-(4-trifluoromethyl-phenyl)-6-trifluoromethyl-pyrimidine-2-carboxylic acid (example D.2) (0.17 g, 0.5 mmol) according to the general procedure V. Obtained as a light yellow solid (0.13 g, 24%). MS (ISP) 453.1 [$(M+H)^+$]; mp 218.5° C.

EXAMPLE 12

4-{5-[4-Trifluoromethyl-6-(4-trifluoromethyl-phenyl)-pyrimidin-2-yl]-[1,2,4]oxadiazol-3-yl}-pyridin-2-ylamine The title compound was prepared from 2-amino-N-hydroxy-pyridine-4-carboxamidine (example C.5) (0.11 g, 0.75 mmol) and 4-(4-trifluoromethyl-phenyl)-6-trifluoromethyl-pyrimidine-2-carboxylic acid (example D.2) (0.17 g, 0.5 mmol) according to the general procedure V. Obtained as an off-white solid (0.13 g, 57%). MS (ISP) 453.1 [$(M+H)^+$]; mp 223.5° C.

EXAMPLE 13

5-{1-[4-Trifluoromethyl-6-(4-trifluoromethyl-phenyl)-pyrimidin-2-yl]-1H-imidazol-4-yl}-pyridin-2-ylamine The title compound was prepared from 2-(4-bromo-imidazol-1-yl)-4-trifluoromethyl-6-(4-trifluoromethyl-phenyl)-pyrimidine (example E.1) (0.44 g, 1.0 mmol) and commercially available 2-amino-5-(4,4,5,5-tetramethyl-1,3,2-dioxaborolan-2-yl)pyridine (0.22 g, 1.0 mmol) according to the general procedure VI. Obtained as a yellow solid (0.031 g, 7%). MS (ISP) 451.0 [$(M+H)^+$]; mp 286° C.

5-{1'-[4-Trifluoromethyl-6-(4-trifluoromethyl-phenyl)-pyrimidin-2-yl]-1H-imidazol-4-yl}-pyridin-2-ylamine hydrochloride (1:2)

The salt was prepared by treatment of the base with MeOH—HCl and diethyl ether. Obtained as a light yellow solid. mp 305° C.

EXAMPLE 14

5-{1-[4-(4-Chloro-phenyl)-6-trifluoromethyl-pyrimidin-2-yl]-1H-imidazol-4-yl}-pyridin-2-ylamine The title compound was prepared from 2-(4-bromo-imidazol-1-yl)-4-(4-chloro-phenyl)-6-trifluoromethyl-pyrimidine (example E.2) (0.40 g, 1.0 mmol) and commercially available 2-amino-5-(4,4,5,5-tetramethyl-1,3,2-dioxaborolan-2-yl) pyridine (0.22 g, 1.0 mmol) according to the general procedure VI. Obtained as a yellow solid (0.095 g, 23%). MS (ISP) 417.3 [$(M+H)^+$]; mp 254° C.

5-{1-[4-(4-Chloro-phenyl)-6-trifluoromethyl-pyrimidin-2-yl]-1H-imidazol-4-yl}-pyridin-2-ylamine hydrochloride (1:2)

The salt was prepared by treatment of the base with MeOH—HCl and diethyl ether. Obtained as a white solid. mp 314° C.

EXAMPLE 15

4-{5-[4-Trifluoromethyl-6-(4-trifluoromethyl-phenyl)-pyrimidin-2-yl]-[1,2,4]oxadiazol-3-yl}-benzenesulfonamide The title compound was prepared from N-hydroxy-4-sulfamoyl-benzamidine [CAS-No. 4476-10-2] (0.16 g, 0.75 mmol) and 4-(4-trifluoromethyl-phenyl)-6-trifluoromethyl-pyrimidine-2-carboxylic acid (example D.2) (0.17 g, 0.5 mmol) according to the general procedure V. Obtained as a white solid (0.026 g, 10%). MS (ISN) 514.2 [$(M-H)^-$]; mp 302° C.

EXAMPLE 16

3-{5-[4-Trifluoromethyl-6-(4-trifluoromethyl-phenyl)-pyrimidin-2-yl]-[1,2,4]oxadiazol-3-yl}-benzenesulfonamide The title compound was prepared from N-hydroxy-3-sulfamoyl-benzamidine [CAS-No. 9000-88-7] (0.16 g, 0.75 mmol) and 4-(4-trifluoromethyl-phenyl)-6-trifluoromethyl-pyrimidine-2-carboxylic acid (example D.2) (0.17 g, 0.5 mmol) according to the general procedure V. Obtained as a white solid (0.099 g, 38%). MS (ISN) 514.1 [$(M-H)^-$]; mp 204° C.

EXAMPLE 17

4-{5-[4-(4-Chloro-phenyl)-6-trifluoromethyl-pyrimidin-2-yl]-[1,2,4]oxadiazol-3-yl}-benzenesulfonamide The title compound was prepared from N-hydroxy-4-sulfamoyl-benzamidine [CAS-No. 4476-10-2] (0.16 g, 0.75 mmol) and 4-(4-chloro-phenyl)-6-trifluoromethyl-pyrimidine-2-carboxylic acid (example D.1) (0.15 g, 0.5 mmol)

according to the general procedure V. Obtained as a white solid (0.038 g, 16%). MS (ISN) 480.1 [(M−H)$^-$]; mp 289.5° C.

EXAMPLE 18

3-{5-[4-(4-Chloro-phenyl)-6-trifluoromethyl-pyrimidin-2-yl]-[1,2,4]oxadiazol-3-yl}-benzenesulfonamide The title compound was prepared from N-hydroxy-3-sulfamoyl-benzamidine [CAS-No. 9000-88-7] (0.16 g, 0.75 mmol) and 4-(4-chloro-phenyl)-6-trifluoromethyl-pyrimidine-2-carboxylic acid (example D.1) (0.17 g, 0.5 mmol) according to the general procedure V. Obtained as a white solid (0.18 g, 75%). MS (ISN) 480.1 [(M−H)$^-$]; mp 231° C.

EXAMPLE 19

5-{1-[4-Trifluoromethyl-6-(4-trifluoromethyl-phenyl)-pyrimidin-2-yl]-1H-pyrazol-4-yl}-pyridin-2-ylamine The title compound was prepared from 2-(4-bromo-pyrazol-1-yl)-4-trifluoromethyl-6-(4-trifluoromethyl-phenyl)-pyrimidine (example E.11) (0.44 g, 1.0 mmol) and commercially available 2-amino-5-(4,4,5,5-tetramethyl-1,3,2-dioxaborolan-2-yl)pyridine (0.22 g, 1.0 mmol) according to the general procedure VI. Obtained as a yellow solid (0.027 g, 0.6%). MS (ISP) 451.1 [(M+H)$^+$]; mp 206° C.

EXAMPLE 20

5-{5-[4-Trifluoromethyl-6-(4-trifluoromethyl-phenyl)-pyrimidin-2-yl]-[1,2,4]oxadiazol-3-yl}-pyrimidin-2-ylamine The title compound was prepared from 2-amino-N-hydroxy-pyrimidine-5-carboxamidine (example C.4) (0.115 g, 0.75 mmol) and 4-(4-trifluoromethyl-phenyl)-6-trifluoromethyl-pyrimidine-2-carboxylic acid (example D.2) (0.17 g, 0.5 mmol) according to the general procedure V. Obtained as a white solid (0.14 g, 62%). MS (EI) 453.1 [(M)$^+$]; mp 216° C.

EXAMPLE 21

5-{3-[4-Trifluoromethyl-6-(4-trifluoromethyl-phenyl)-pyrimidin-2-yl]-[1,2,4]oxadiazol-5-yl}-pyridin-2-ylamine The title compound was prepared from N-hydroxy-4-trifluoromethyl-6-(4-trifluoromethyl-phenyl)-pyrimidine-2-carboxamidine (example C.2) (0.176 g, 0.5 mmol) and commercially available 6-amino-nicotinic acid (0.07 g, 0.5 mmol) according to the general procedure V. Obtained as an off-white solid (0.055 g, 24%). MS (ISP) 453.1 [(M+H)$^+$]; mp 205° C.

EXAMPLE 22

5-{3-[4-(4-Chloro-phenyl)-6-trifluoromethyl-pyrimidin-2-yl]-[1,2,4]oxadiazol-5-yl}-pyridin-2-ylamine The title compound was prepared from 4-(4-chloro-phenyl)-N-hydroxy-6-trifluoromethyl-pyrimidine-2-carboxamidine (example C.1) (0.16 g, 0.5 mmol) and commercially available 6-amino-nicotinic acid (0.07 g, 0.5 mmol according to the general procedure VI. Obtained as an off-white solid (0.059 g, 28%). MS (ISP) 418.9 [(M+H)$^+$]; mp 191° C.

EXAMPLE 23

5-{3-[4-Trifluoromethyl-6-(4-trifluoromethyl-phenyl)-pyrimidin-2-yl]-[1,2,4]oxadiazol-5-yl}-thiophene-2-sulfonic acid amide The title compound was prepared from N-hydroxy-4-trifluoromethyl-6-(4-trifluoromethyl-phenyl)-pyrimidine-2-carboxamidine (example C.2) (0.176 g, 0.5 mmol) and commercially available 2-sulfamoyl-thiophene-5-carboxylic acid [CAS-No. 7353-87-9] (0.104 g, 0.5 mmol) according to the general procedure V. Obtained as a light yellow solid (0.12 g, 46%). MS (ISN) 520.1 [(M−H)$^-$]; mp 258.5° C.

EXAMPLE 24

5-{3-[4-(4-Chloro-phenyl)-6-trifluoromethyl-pyrimidin-2-yl]-[1,2,4]oxadiazol-5-yl}-thiophene-2-sulfonic acid amide The title compound was prepared from 4-(4-chloro-phenyl)-N-hydroxy-6-trifluoromethyl-pyrimidine-2-carboxamidine (example C.1) (0.16 g, 0.5 mmol) and commercially available 2-sulfamoyl-thiophene-5-carboxylic acid [CAS-No. 7353-87-9] (104 mg, 0.5 mmol) according to the general procedure VI. Obtained as a light yellow solid (0.085 g, 35%). MS (ISN) 486.1 [(M−H)$^-$]; mp 236.5° C.

EXAMPLE 25

4-(4-Chloro-phenyl)-2-(4-pyridin-4-yl-imidazol-1-yl)-6-trifluoromethyl-pyrimidine The title compound was prepared from 2-chloro-4-(4-chloro-phenyl)-6-trifluoromethyl-pyrimidine (example A.1) (0.15 g, 0.5 mmol) and 4-(1H-imidazol-4-yl)-pyridine [CAS-No. 51746-87-3] (0.073 g, 0.5 mmol) according to the general procedure IVa. Obtained as a light red solid (0.15 g, 76%). MS (ISP) 402.3 [(M+H)$^+$]; mp 269° C.

EXAMPLE 26

5-{3-[4-Trifluoromethyl-6-(4-trifluoromethyl-phenyl)-pyrimidin-2-yl]-phenyl}-pyridin-2-ylamine The title compound was prepared from 2-(3-bromo-phenyl)-4-trifluoromethyl-6-(4-trifluoromethyl-phenyl)-pyrimidine (example E.3) (0.22 g, 0.5 mmol) and commercially available 2-amino-5-(4,4,5,5-tetramethyl-1,3,2-dioxaborolan-2-yl)pyridine (0.14 g, 0.65 mmol) according to the general procedure VI. Obtained as an off-white solid (0.124 g, 54%). MS (ISP) 461.1 [(M+H)$^+$]; mp 205° C.

EXAMPLE 27

5-{3-[4-(4-Chloro-phenyl)-6-trifluoromethyl-pyrimidin-2-yl]-phenyl}-pyridin-2-ylamine The title compound was prepared from 2-(3-bromo-phenyl)-4-(4-chloro-phenyl)-6-trifluoromethyl-pyrimidine (example E.4) (0.21 g, 0.5 mmol) and commercially available 2-amino-5-(4,4,5,5-tetramethyl-1,3,2-dioxaborolan-2-yl) pyridine (0.14 g, 0.65 mmol) according to the general procedure VI. Obtained as an off-white solid (0.14 g, 66%). MS (ISP) 427.0 [$(M+H)^+$]; mp 171° C.

EXAMPLE 28

4-(4-Chloro-phenyl)-2-(3-pyridin-4-yl-[1,2,4]oxadiazol-5-yl)-6-trifluoromethyl-pyrimidine The title compound was prepared from commercially available N-hydroxy-4-pyridinecarboxamidine [CAS-No. 1594-57-6] (0.103 g, 0.75 mmol) and 4-(4-chloro-phenyl)-6-trifluoromethyl-pyrimidine-2-carboxylic acid (example D.1) (0.15 g, 0.5 mmol) according to the general procedure V. Obtained as a light yellow solid (0.088 g, 44%). MS (ISP) 404.1 [$(M+H)^+$]; mp 187.5° C.

EXAMPLE 29

4-(4-Chloro-phenyl)-2-(3-pyridin-3-yl-[1,2,4]oxadiazol-5-yl)-6-trifluoromethyl-pyrimidine The title compound was prepared from available N-hydroxy-3-pyridinecarboxamidine [CAS-No. 1594-58-7] (0.103 g, 0.75 mmol) and 4-(4-chloro-phenyl)-6-trifluoromethyl-pyrimidine-2-carboxylic acid (example D.1) (0.15 g, 0.5 mmol) according to the general procedure V. Obtained as a yellow solid (0.092 g, 46%). MS (ISP) 404.4 [$(M+H)^+$]; mp 168.5° C.

EXAMPLE 30

4-[4-(4-Chloro-phenyl)-6-trifluoromethyl-pyrimidin-2-yl]-[2,3']bipyridinyl-6'-ylamine The title compound was prepared from 4-(4-chloro-phenyl)-2-(2-chloro-pyridin-4-yl)-6-trifluoromethyl-pyrimidine (example E.5) (0.185 g, 0.5 mmol) and commercially available 2-amino-5-(4,4,5,5-tetramethyl-1,3,2-dioxaborolan-2-yl)pyridine (0.14 g, 0.65 mmol) according to the general procedure VI. Obtained as a light yellow solid (0.18 g, 85%). MS (ISP) 428.0 [$(M+H)^+$]; mp 227° C.

EXAMPLE 31

4-[4-Trifluoromethyl-6-(4-trifluoromethyl-phenyl)-pyrimidin-2-yl]-[2,3']bipyridinyl-6'-ylamine The title compound was prepared from 2-(2-chloro-pyridin-4-yl)-4-trifluoromethyl-6-(4-trifluoromethyl-phenyl)-pyrimidine (example E.6) (0.202 g, 0.5 mmol) and commercially available 2-amino-5-(4,4,5,5-tetramethyl-1,3,2-dioxaborolan-2-yl)pyridine (0.14 g, 0.65 mmol) according to the general procedure VI. Obtained as a light yellow solid (0.18 g, 80%). MS (ISP) 462.0 [$(M+H)^+$]; mp 226° C.

EXAMPLE 32

5-{1-[4-Difluoromethyl-6-(4-trifluoromethyl-phenyl)-pyrimidin-2-yl]-1H-imidazol-4-yl}-pyridin-2-ylamine The title compound was prepared from 2-(4-bromo-imidazol-1-yl)-4-difluoromethyl-6-(4-trifluoromethyl-phenyl)-pyrimidine (example E.7) (0.21 g, 0.5 mmol) and commercially available 2-amino-5-(4,4,5,5-tetramethyl-1,3,2-dioxaborolan-2-yl)pyridine (0.14 g, 0.64 mmol) according to the general procedure VI. Obtained as a yellow solid (0.031 g, 7%). MS (ISP) 433.3 [$(M+H)^+$]; mp 253.5° C.

5-{1'-[4-Difluoromethyl-6-(4-trifluoromethyl-phenyl)-pyrimidin-2-yl]-1H-imidazol-4-yl}-pyridin-2-ylamine hydrochloride (1:2)

The salt was prepared by treatment of the base with MeOH—HCl and diethyl ether. Obtained as an off-white solid. mp 298.5° C.

EXAMPLE 33

2-(3-Pyridin-3-yl-phenyl)-4-trifluoromethyl-6-(4-trifluoromethyl-phenyl)-pyrimidine The title compound was prepared from 2-(3-bromo-phenyl)-4-trifluoromethyl-6-(4-trifluoromethyl-phenyl)-pyrimidine (example E.3) (0.22 g, 0.5 mmol) and commercially available 3-pyridineboronic acid (0.08 g, 0.65 mmol) according to the general procedure VI. Obtained as a white solid (0.154 g, 69%). MS (ISP) 446.3 [$(M+H)^+$]; mp 194° C.

EXAMPLE 34

4-(4-Chloro-phenyl)-2-(3-pyridin-3-yl-phenyl)-6-trifluoromethyl-pyrimidine

The title compound was prepared from 2-(3-bromo-phenyl)-4-(4-chloro-phenyl)-6-trifluoromethyl-pyrimidine (example E.4) (0.21 g, 0.5 mmol) and commercially available 3-pyridineboronic acid (0.08 g, 0.65 mmol) according to the general procedure VI. Obtained as a white solid (0.12 g, 57%). MS (ISP) 412.3 [$(M+H)^+$]; mp 162° C.

EXAMPLE 35

4-{5-[4-Difluoromethyl-6-(4-trifluoromethyl-phenyl)-pyrimidin-2-yl]-[1,2,4]oxadiazol-3-yl}-benzenesulfonamide The title compound was prepared from N-hydroxy-4-sulfamoyl-benzamidine [CAS-No. 4476-10-2] (0.16 g, 0.75 mmol) and 6-difluoromethyl-4-(4-trifluoromethyl-phenyl)-pyrimidine-2-carboxylic acid (example D.3) (0.16 g, 0.5 mmol) according to the general procedure V. Obtained as a white solid (0.096 g, 39%). MS (ISP) 498.3 [$(M+H)^+$]; mp 307° C.

EXAMPLE 36

5-{5-[4-Difluoromethyl-6-(4-trifluoromethyl-phenyl)-pyrimidin-2-yl]-[1,2,4]oxadiazol-3-yl}-pyridin-2-ylamine The title compound was prepared from 6-amino-N-hydroxy-nicotinamidine (example C.3) (0.15 g, 1.0 mmol) and 6-difluoromethyl-4-(4-trifluoromethyl-phenyl)-pyrimidine-2-carboxylic acid (example D.3) (0.16 g, 0.5 mmol) according to the general procedure V. Obtained as a light yellow solid (0.066 g, 30%). MS (ISP) 435.1 [$(M+H)^+$]; mp 219° C.

EXAMPLE 37

2-Pyridin-3-yl-4-trifluoromethyl-6-(4-trifluoromethyl-phenyl)-pyrimidine

The title compound was prepared from 2-chloro-4-(4-trifluoromethyl-phenyl)-6-trifluoromethyl-pyrimidine (example A.2) (0.33 g, 1.0 mmol) and commercially available 3-pyridineboronic acid (0.184 g, 1.5 mmol) according to the general procedure IVb. Obtained as a light yellow solid (0.03 g, 8%). MS (ISP) 370.1 [(M+H)$^+$]; mp 134° C.

EXAMPLE 38

4-Difluoromethyl-2-pyridin-4-yl-6-(4-trifluoromethyl-phenyl)-pyrimidine

The title compound was prepared from 2-chloro-4-(4-difluoromethyl-phenyl)-6-trifluoromethyl-pyrimidine (example A.5) (0.31 g, 1.0 mmol) and commercially available 4-pyridineboronic acid (0.184 g, 1.5 mmol) according to the general procedure IVb. Obtained as a light red solid (0.086 g, 24%). MS (ISP) 352.3 [(M+H)$^+$]; mp 132.5° C.

EXAMPLE 39

2-Pyridin-4-yl-4-trifluoromethyl-6-(4-trifluoromethyl-phenyl)-pyrimidine

The title compound was prepared from 2-chloro-4-(4-trifluoromethyl-phenyl)-6-trifluoromethyl-pyrimidine (example A.2) (0.33 g, 1.0 mmol) and commercially available 4-pyridineboronic acid (0.184 g, 1.5 mmol) according to the general procedure IVb. Obtained as a light red solid (0.034 g, 9%). MS (ISP) 370.0 [(M+H)$^+$]; mp 153.5° C.

EXAMPLE 40

3-{5-[4-Difluoromethyl-6-(4-trifluoromethyl-phenyl)-pyrimidin-2-yl]-[1,2,4]oxadiazol-3-yl}-benzenesulfonamide The title compound was prepared from N-hydroxy-3-sulfamoyl-benzamidine [CAS-No. 9000-88-7] (0.16 g, 0.75 mmol) and 6-difluoromethyl-4-(4-trifluoromethyl-phenyl)-pyrimidine-2-carboxylic acid (example D.3) (0.16 g, 0.5 mmol) according to the general procedure V. Obtained as a white solid (0.12 g, 49%). MS (ISP) 498.3 [(M+H)$^+$]; mp 217.5° C.

EXAMPLE 41

5-{3-[4-Difluoromethyl-6-(4-trifluoromethyl-phenyl)-pyrimidin-2-yl]-phenyl}-pyridin-2-ylamine The title compound was prepared from 2-(3-bromo-phenyl)-4-difluoromethyl-6-(4-trifluoromethyl-phenyl)-pyrimidine (example E.8) (0.22 g, 0.5 mmol) and commercially available 2-amino-5-(4,4,5,5-tetramethyl-1,3,2-dioxaborolan-2-yl)pyridine (0.14 g, 0.65 mmol) according to the general procedure VI. Obtained as an off-white solid (0.035 g, 16%). MS (ISP) 443.3 [(M+H)$^+$]; mp 191° C.

EXAMPLE 42

2-[3-(2,6-Dimethyl-pyridin-4-yl)-phenyl]-4-trifluoromethyl-6-(4-trifluoromethyl-phenyl)-pyrimidine The title compound was prepared from 2-(3-bromo-phenyl)-4-trifluoromethyl-6-(4-trifluoromethyl-phenyl)-pyrimidine (example E.3) (0.45 g, 1.0 mmol) and 2,6-dimethyl-4-iodo-pyridine [CAS-No. 22282-67-3] (0.23 g, 1.0 mmol) according to the general procedure IVc. Obtained as a light yellow solid (0.057 g, 12%). MS (ISP) 474.2 [(M+H)$^+$]; mp 159° C.

EXAMPLE 43

5-{1-[4-(4-Chloro-phenyl)-6-methyl-pyrimidin-2-yl]-1H-imidazol-4-yl}-pyridin-2-ylamine The title compound was prepared from 2-(4-bromo-imidazol-1-yl)-4-(4-chloro-phenyl)-6-methyl-pyrimidine (example E.12) (0.14 g, 0.4 mmol) and commercially available 2-amino-5-(4,4,5,5-tetramethyl-1,3,2-dioxaborolan-2-yl) pyridine (0.088 g, 0.4 mmol) according to the general procedure VI. Obtained as a light yellow solid (0.045 g, 31%). MS (ISP) 363.1 [(M+H)$^+$]; mp 206-208° C.

EXAMPLE 44

4-(4-Chloro-phenyl)-6-methyl-2-(4-pyridin-3-yl-imidazol-1-yl)-pyrimidine

The title compound was prepared from 2-(4-bromo-imidazol-1-yl)-4-(4-chloro-phenyl)-6-methyl-pyrimidine (example E.12) (0.14 g, 0.4 mmol) and commercially available 3-pyridylboronic acid (0.049 g, 0.4 mmol) according to the general procedure VI. Obtained as a light yellow solid (0.027 g, 19%). MS (ISN) 346.1 [(M−H)$^-$]; mp 179-181° C.

EXAMPLE 45

5-{1-[4-(4-Chloro-phenyl)-6-methyl-pyrimidin-2-yl]-1H-imidazol-4-yl}-pyrimidin-2-ylamine The title compound was prepared from 2-(4-bromo-imidazol-1-yl)-4-(4-chloro-phenyl)-6-methyl-pyrimidine (example E.12) (0.28 g, 0.8 mmol) and commercially available 2-amino-5-(4,4,5,5-tetramethyl-1,3,2-dioxaborolan-2-yl) pyrimidine (0.18 g, 0.8 mmol) according to the general procedure VI. Obtained as an off-white solid (0.04 g, 13%). MS (ISP) 364.0 [(M+H)$^+$]; mp 264-266° C.

EXAMPLE 46

5-{1-[4-Methyl-6-(4-trifluoromethyl-phenyl)-pyrimidin-2-yl]-1H-imidazol-4-yl}-pyridin-2-ylamine The title compound was prepared from 2-(4-bromo-imidazol-1-yl)-4-methyl-6-(4-trifluoromethyl-phenyl)-pyrimidine (example E.13) (0.31 g, 0.8 mmol) and commercially available 2-amino-5-(4,4,5,5-tetramethyl-1,3,2-dioxaborolan-2-yl)pyridine (0.18 g, 0.8 mmol) according to the general procedure VI. Obtained as an off-white solid (0.08 g, 26%). MS (ISP) 397.3 [(M+H)$^+$]; mp 230-232° C.

EXAMPLE 47

5-{1-[4-Methyl-6-(4-trifluoromethyl-phenyl)-pyrimidin-2-yl]-1H-imidazol-4-yl}-pyrimidin-2-ylamine The title compound was prepared from 2-(4-bromo-imidazol-1-yl)-4-methyl-6-(4-trifluoromethyl-phenyl)-pyrimidine (example E.13) (0.31 g, 0.8 mmol) and commercially available 2-amino-5-(4,4,5,5-tetramethyl-1,3,2-dioxaborolan-2-yl)pyrimidine (0.18 g, 0.8 mmol) according to the general procedure VI. Obtained as a white solid (0.093 g, 29%). MS (ISP) 398.0 [$(M+H)^+$]; mp 267-269° C.

EXAMPLE 48

4-Methyl-2-(4-pyridin-3-yl-imidazol-1-yl)-6-(4-trifluoromethyl-phenyl)-pyrimidine The title compound was prepared from 2-(4-bromo-imidazol-1-yl)-4-methyl-6-(4-trifluoromethyl-phenyl)-pyrimidine (example E.13) (0.31 g, 0.8 mmol) and commercially available 3-(4,4,5,5-tetramethyl-1,3,2-dioxaborolan-2-yl)pyridine (0.16 g, 0.8 mmol) according to the general procedure VI. Obtained as an off-white solid (0.012 g, 4%). MS (ISP) 382.3 [$(M+H)^+$]; mp 208-210° C.

EXAMPLE 49

5-{1-[4-(4-Chloro-phenyl)-6-cyclopropyl-pyrimidin-2-yl]-1H-imidazol-4-yl}-pyridin-2-ylamine The title compound was prepared from 2-(4-bromo-imidazol-1-yl)-4-(4-chloro-phenyl)-6-cyclopropyl-pyrimidine (example E.14) (0.30 g, 0.8 mmol) and commercially available 2-amino-5-(4,4,5,5-tetramethyl-1,3,2-dioxaborolan-2-yl)pyridine (0.18 g, 0.8 mmol) according to the general procedure VI. Obtained as an off-white solid (0.08 g, 26%). MS (ISP) 389.3 [$(M+H)^+$]; mp 220-222° C.

EXAMPLE 50

4-(4-Chloro-phenyl)-6-cyclopropyl-2-(4-pyridin-3-yl-imidazol-1-yl)-pyrimidine

The title compound was prepared from 2-(4-bromo-imidazol-1-yl)-4-(4-chloro-phenyl)-6-cyclopropyl-pyrimidine (example E.14) (0.15 g, 0.4 mmol) and commercially available 3-(4,4,5,5-tetramethyl-1,3,2-dioxaborolan-2-yl)pyridine (0.08 g, 0.4 mmol) according to the general procedure VI. Obtained as an off-white solid (0.015 g, 10%). MS (ISP) 374.0 [$(M+H)^+$]; mp 180-182° C.

EXAMPLE 51

5-{1-[4-(4-Chloro-phenyl)-6-cyclopropyl-pyrimidin-2-yl]-1H-imidazol-4-yl}-pyrimidin-2-ylamine The title compound was prepared from 2-(4-bromo-imidazol-1-yl)-4-(4-chloro-phenyl)-6-cyclopropyl-pyrimidine (example E.14) (0.30 g, 0.8 mmol) and commercially available 2-amino-5-(4,4,5,5-tetramethyl-1,3,2-dioxaborolan-2-yl)pyrimidine (0.18 g, 0.8 mmol) according to the general procedure VI. Obtained as a white solid (0.093 g, 37%). MS (ISP) 390.3 [$(M+H)^+$]; mp 238-240° C.

EXAMPLE 52

5-{1-[4-(4-Chloro-phenyl)-pyrimidin-2-yl]-1H-imidazol-4-yl}-pyridin-2-ylamine

The title compound was prepared from 2-(4-bromo-imidazol-1-yl)-4-(4-chloro-phenyl)pyrimidine (example E.15) (0.27 g, 0.8 mmol) and commercially available 2-amino-5-(4,4,5,5-tetramethyl-1,3,2-dioxaborolan-2-yl)pyridine (0.18 g, 0.8 mmol) according to the general procedure VI. Obtained as a light yellow solid (0.083 g, 30%). MS (ISP) 349.3 [$(M+H)^+$]; mp 188-190° C.

EXAMPLE 53

5-{1-[4-Trifluoromethyl-6-(3-trifluoromethyl-phenyl)-pyrimidin-2-yl]-1H-imidazol-4-yl}-pyridin-2-ylamine The title compound was prepared from 2-(4-iodo-imidazol-1-yl)-4-trifluoromethyl-6-(3-trifluoromethyl-phenyl)-pyrimidine (example E.16) (0.90 g, 1.86 mmol) and commercially available 2-amino-5-(4,4,5,5-tetramethyl-1,3,2-dioxaborolan-2-yl)pyridine (0.491 g, 2.23 mmol) according to the general procedure VI. Obtained as a yellow solid (0.290 g, 34%). MS (ISP) 451.1 [$(M+H)^+$]; mp 262° C.

EXAMPLE 54

5-{1-[6-Cyclopropyl-4-(4-trifluoromethyl-phenyl)-pyridin-2-yl]-1H-imidazol-4-yl}-pyridin-2-ylamine The title compound was prepared from 2-cyclopropyl-6-(4-iodo-imidazol-1-yl)-4-(4-trifluoromethyl-phenyl)-pyridine (example E.17) (1.0 g, 2.2 mmol) and commercially available 2-amino-5-(4,4,5,5-tetramethyl-1,3,2-dioxaborolan-2-yl)pyridine (0.628 g, 2.85 mmol) according to the general procedure VI. Obtained as an off-white solid (0.180 g, 46%). MS (ISP) 422.2 [$(M+H)^+$]; mp 233-235° C.

EXAMPLE 55

2-Imidazol-1-yl-6-methyl-4-(4-trifluoromethyl-phenyl)-pyridine

The title compound was obtained as a side product in the preparation of example E.18. Obtained as a white solid (0.08 g, 21%). MS (ISP) 304.1 [$(M+H)^+$]; mp 158-160° C.

EXAMPLE 56

5-{1-[6-(4-Chloro-phenyl)-4-trifluoromethyl-pyridin-2-yl]-1H-imidazol-4-yl}-pyridin-2-ylamine The title compound was prepared from 2-(4-chloro-phenyl)-6-(4-iodo-imidazol-1-yl)-4-trifluoromethyl-pyridine (example E.19) (1.35 g, 3.0 mmol) and commercially available 2-amino-5-(4,4,5,5-tetramethyl-1,3,2-dioxaborolan-2-yl)pyridine (0.792 g, 3.6 mmol) according to the general procedure VI. Obtained as a light yellow solid. (0.750 g, 60%). MS (ISP) 416.3 [$(M+H)^+$] and 418 [$(M+2+H)^+$]; mp 196° C. (dec.).

5-{1-[6-(4-Chloro-phenyl)-4-trifluoromethyl-pyridin-2-yl]-1H-imidazol-4-yl}-pyridin-2-ylamine hydrochloride (1:2)

The salt was prepared by treatment of the base with MeOH—HCl and diethyl ether. Obtained as a white solid. mp>255° C.

EXAMPLE 57

2-(4-Chloro-phenyl)-6-(4-pyridin-3-yl-imidazol-1-yl)-4-trifluoromethyl-pyridine

The title compound was prepared from 2-(4-chloro-phenyl)-6-(4-iodo-imidazol-1-yl)-4-trifluoromethyl-pyridine (example E.19) (0.45 g, 1.0 mmol) and commercially available 3-pyridineboronic acid (0.32 g, 2.6 mmol) according to the general procedure VI. Obtained as a white solid (0.011 g, 3%). MS (ISP) 401.2 [$(M+H)^+$] and 403 [$(M+2+H)^+$].

EXAMPLE 58

5-{1-[6-Methyl-4-(4-trifluoromethyl-phenyl)-pyridin-2-yl]-1H-imidazol-4-yl}-pyridin-2-ylamine The title compound was prepared from 2-(4-iodo-imidazol-1-yl)-6-methyl-4-(4-trifluoromethyl-phenyl)-pyridine (example E.18) (0.33 g, 0.77 mmol) and commercially available 2-amino-5-(4,4,5,5-tetramethyl-1,3,2-dioxaborolan-2-yl)pyridine (0.203 g, 0.92 mmol) according to the general procedure VI. Obtained as an off-white solid (0.100 g, 33%). MS (ISP) 396.1 [$(M+H)^+$]; mp 224-226° C.

EXAMPLE 59

2-(3-Pyridin-3-yl-phenyl)-4-trifluoromethyl-6-(4-trifluoromethyl-phenyl)-pyridine The title compound was prepared from 2-(3-bromo-phenyl)-4-trifluoromethyl-6-(4-trifluoromethyl-phenyl)-pyridine (example E.20) (0.525 g, 1.0 mmol) and commercially available 3-pyridineboronic acid (0.16 g, 1.3 mmol) according to the general procedure VI. Obtained as a white solid (0.083 g, 19%). MS (ISP) 445.2 [$(M+H)^+$]; mp 164-166° C.

EXAMPLE 60

5-{3-[4-Trifluoromethyl-6-(4-trifluoromethyl-phenyl)-pyridin-2-yl]-phenyl}-pyridin-2-ylamine The title compound was prepared from 2-(3-bromo-phenyl)-4-trifluoromethyl-6-(4-trifluoromethyl-phenyl)-pyridine (example E.20) (0.525 g, 1.0 mmol) and commercially available 2-amino-5-(4,4,5,5-tetramethyl-1,3,2-dioxaborolan-2-yl)pyridine (0.286 g, 1.3 mmol) according to the general procedure VI. Obtained as a white solid (0.10 g, 22%). MS (ISP) 460.2 [$(M+H)^+$]; mp 170-172° C.

EXAMPLE 61

2-Methyl-6-(3-pyridin-3-yl-phenyl)-4-(4-trifluoromethyl-phenyl)-pyridine

The title compound was prepared from 2-(3-bromo-phenyl)-6-methyl-4-(4-trifluoromethyl-phenyl)-pyridine (example E.21) (0.392 g, 1.00 mmol) and commercially available 3-pyridineboronic acid (0.122 g, 0.99 mmol) according to the general procedure VI. Obtained as a white solid (0.080 g, 27%). MS (ISP) 391.1 [$(M+H)^+$]; mp 89-106° C.

EXAMPLE 62

5-{3-[6-Methyl-4-(4-trifluoromethyl-phenyl)-pyridin-2-yl]-phenyl}-pyridin-2-ylamine The title compound was prepared from 2-(3-bromo-phenyl)-6-methyl-4-(4-trifluoromethyl-phenyl)-pyridine (example E.21) (0.300 g, 0.77 mmol) and commercially available 2-amino-5-(4,4,5,5-tetramethyl-1,3,2-dioxaborolan-2-yl)pyridine (0.219 g, 1.0 mmol) according to the general procedure VI. Obtained as a white foam (0.15 g, 48%). MS (ISP) 406.2 [$(M+H)^+$]; mp 68-90° C.

EXAMPLE 63

2-Cyclopropyl-6-(3-pyridin-3-yl-phenyl)-4-(4-trifluoromethyl-phenyl)-pyridine

The title compound was prepared from 2-(3-bromo-phenyl)-6-cyclopropyl-4-(4-trifluoromethyl-phenyl)-pyridine (example E.22) (0.392 g, 0.72 mmol) and commercially available 3-pyridineboronic acid (0.115 g, 0.93 mmol) according to the general procedure VI. Obtained as a white solid (0.120 g, 40%). MS (ISP) 417.3 [$(M+H)^+$]; mp 100-104° C.

EXAMPLE 64

5-{3-[6-Cyclopropyl-4-(4-trifluoromethyl-phenyl)-pyridin-2-yl]-phenyl}-pyridin-2-ylamine The title compound was prepared from 2-(3-bromo-phenyl)-6-cyclopropyl-4-(4-trifluoromethyl-phenyl)-pyridine (example E.22) (0.30 g, 0.55 mmol) and commercially available 2-amino-5-(4,4,5,5-tetramethyl-1,3,2-dioxaborolan-2-yl)pyridine (0.219 g, 0.94 mmol) according to the general procedure VI. Obtained as an off-white solid (0.250 g, 80%). MS (ISP) 432.3 [$(M+H)^+$]; mp 130-135° C.

EXAMPLE 65

5-{1-[4-Trifluoromethyl-6-(4-trifluoromethyl-phenyl)-pyridin-2-yl]-1H-imidazol-4-yl}-pyridin-2-ylamine The title compound was prepared from 2-(4-iodo-imidazol-1-yl)-4-trifluoromethyl-6-(4-trifluoromethyl-phenyl)-pyridine (example E.23) (0.525 g, 1.09 mmol) and commercially available 2-amino-5-(4,4,5,5-tetramethyl-1,3,2-dioxaborolan-2-yl)pyridine (0.286 g, 1.3 mmol) according to the general procedure VI. Obtained as a yellow solid (0.148 g, 33%). MS (ISP) 450.2 [$(M+H)^+$]; mp 245-247° C.

EXAMPLE 66

5-{1-[4-Trifluoromethyl-6-(4-trifluoromethyl-phenyl)-pyridin-2-yl]-1H-imidazol-4-yl}-pyrimidin-2-ylamine The title compound was prepared from 2-(4-iodo-imidazol-1-yl)-4-trifluoromethyl-6-(4-trifluoromethyl-phenyl)-pyridine (example E.23) (0.525 g, 1.09 mmol) and commercially available 2-amino-5-(4,4,5,5-tetramethyl-1,3,2-dioxaborolan-2-yl)pyrimidine (0.287 g, 1.3 mmol) according to the general procedure VI. Obtained as a yellow solid (0.100 g, 24%). MS (ISP) 451.1 [(M)$^+$]; mp>250° C.

EXAMPLE 67

6-Methyl-4-(4-trifluoromethyl-phenyl)-[2,3';5',3"]terpyridin-6"-ylamine

The title compound was prepared from 5'-bromo-6-methyl-4-(4-trifluoromethylphenyl)-[2,3']bipyridinyl (example E.24) (0.15 g, 0.38 mmol) and commercially available 2-amino-5-(4,4,5,5-tetramethyl-1,3,2-dioxaborolan-2-yl)pyridine (0.092 g, 0.42 mmol) according to the general procedure VI. Obtained as a white solid (0.085 g, 54%). MS (ISP) 407.2 [(M+H)$^+$]; mp 161-177° C.

EXAMPLE 68

5-[6-Methyl-4-(4-trifluoromethyl-phenyl)-[2,3']bipyridinyl-5'-yl]-pyrimidin-2-ylamine The title compound was prepared from 5'-bromo-6-methyl-4-(4-trifluoromethylphenyl)-[2,3']bipyridinyl (example E.24) (0.15 g, 0.38 mmol) and commercially available 2-amino-5-(4,4,5,5-tetramethyl-1,3,2-dioxaborolan-2-yl)pyrimidine (0.093 g, 0.42 mmol) according to the general procedure VI. Obtained as a white solid (0.035 g, 22%). MS (ISP) 408.3 [(M+H)$^+$]; mp 248-252° C.

EXAMPLE 69

6-Cyclopropyl-4-(4-trifluoromethyl-phenyl)-[2,3';5',3"]terpyridin-6"-ylamine

The title compound was prepared from 5'-bromo-6-cyclopropyl-4-(4-trifluoromethylphenyl)-[2,3']bipyridinyl (example E.25) (0.15 g, 0.36 mmol) and commercially available 2-amino-5-(4,4,5,5-tetramethyl-1,3,2-dioxaborolan-2-yl)pyridine (0.087 g, 0.40 mmol) according to the general procedure VI. Obtained as a white solid (0.080 g, 51%). MS (ISP) 433.3 [(M+H)$^+$]; mp 207-209° C.

EXAMPLE 70

5-{3-[6-Methyl-4-(4-trifluoromethyl-phenyl)-pyridin-2-yl]-phenyl}-pyrimidin-2-ylamine The title compound was prepared from 2-(3-bromo-phenyl)-6-methyl-4-(4-trifluoromethyl-phenyl)-pyridine (example E.21) (0.150 g, 0.39 mmol) and commercially available 2-amino-5-(4,4,5,5-tetramethyl-1,3,2-dioxaborolan-2-yl)pyrimidine (0.093 g, 0.42 mmol) according to the general procedure VI. Obtained as a white solid (0.10 g, 64%). MS (ISP) 407.3 [(M+H)$^+$]; mp 215-217° C.

EXAMPLE 71

6-Methyl-4-(4-trifluoromethyl-phenyl)-[2,2';6',3"]terpyridin-6"-ylamine

The title compound was prepared from 6'-bromo-6-methyl-4-(4-trifluoromethylphenyl)-[2,2']bipyridinyl (example E.26) (0.150 g, 0.38 mmol) and commercially available 2-amino-5-(4,4,5,5-tetramethyl-1,3,2-dioxaborolan-2-yl)pyridine (0.092 g, 0.42 mmol) according to the general procedure VI. Obtained as a white solid (0.080 g, 51%). MS (ISP) 407.3 [(M+H)$^+$]; mp 208-211° C.

EXAMPLE 72

5-[6'-Methyl-4'-(4-trifluoromethyl-phenyl)-[2,2']bipyridinyl-6-yl]-pyrimidin-2-ylamine The title compound was prepared from 6'-bromo-6-methyl-4-(4-trifluoromethylphenyl)-[2,2']bipyridinyl (example E.26) (0.150 g, 0.38 mmol) and commercially available 2-amino-5-(4,4,5,5-tetramethyl-1,3,2-dioxaborolan-2-yl)pyrimidine (0.092 g, 0.42 mmol) according to the general procedure VI. Obtained as a white solid (0.080 g, 57%). MS (ISP) 407.3 [(M+H)$^+$]; mp 219-222° C.

EXAMPLE 73

4-[6'-Methyl-4'-(4-trifluoromethyl-phenyl)-[2,2']bipyridinyl-6-yl]-benzenesulfonamide The title compound was prepared from 6'-bromo-6-methyl-4-(4-trifluoromethylphenyl)-[2,2']bipyridinyl (example E.26) (0.150 g, 0.38 mmol) and commercially available 4-(4,4,5,5-etramethyl-[1,3,2]dioxaborolan-2-yl)-benzenesulfonamide [CAS-No. 214360-51-7] (0.142 g, 0.42 mmol) according to the general procedure VI. Obtained as a white solid (0.070 g, 44%). MS (ISP) 470.0 [(M+H)$^+$]; mp 215-227° C.

EXAMPLE 74

4-Trifluoromethyl-6-(4-trifluoromethyl-phenyl)-[2,4';2',3"]terpyridin-6"-ylamine The title compound was prepared from 2'-chloro-4-trifluoromethyl-6-(4-trifluoromethyl-phenyl)-[2,4']bipyridinyl (example E.27) (0.286 g, 0.75 mmol) and commercially available 2-amino-5-(4,4,5,5-tetramethyl-1,3,2-dioxaborolan-2-yl)pyridine (0.234 g, 1.2 mmol) according to the general procedure VI. Obtained as a yellow solid (0.343 g, 97%). MS (ISP) 461.3 [(M+H)$^+$]; mp 194-196° C.

EXAMPLE 75

6-Methyl-4-(4-trifluoromethyl-phenyl)-[2,4';2',3"]terpyridin-6"-ylamine

The title compound was prepared from 2'-chloro-6-methyl-4-(4-trifluoromethylphenyl)-[2,4']bipyridinyl (example E.28) (0.300 g, 0.86 mmol) and commercially available 2-amino-5-(4,4,5,5-tetramethyl-1,3,2-dioxaborolan-2-yl)pyridine (0.246 g, 1.26 mmol) according to the general procedure VI. Obtained as a white solid (0.140 g, 40%). MS (ISP) 407.2 [(M+H)$^+$]; mp 172-190° C.

EXAMPLE 76

5-[6-Methyl-4-(4-trifluoromethyl-phenyl)-[2,4']bipyridinyl-2'-yl]-pyrimidin-2-ylamine The title compound was prepared from 2'-chloro-6-methyl-4-(4-trifluoromethylphenyl)-[2,4']bipyridinyl (example E.28) (0.300 g, 0.86 mmol) and commercially available 2-amino-5-(4,4,5,5-tetramethyl-1,3,2-dioxaborolan-2-yl)pyrimidine (0.247 g, 1.26 mmol) according to the general procedure VI. Obtained as a white solid (0.110 g, 31%). MS (ISP) 408.3 [$(M+H)^+$]; mp>245° C.

EXAMPLE 77

6-Cyclopropyl-4-(4-trifluoromethyl-phenyl)-[2,4';2',3"]terpyridin-6"-ylamine

The title compound was prepared from 2'-chloro-6-cyclopropyl-4-(4-trifluoromethylphenyl)-[2,4']bipyridinyl (example E.29) (0.300 g, 0.80 mmol) and commercially available 2-amino-5-(4,4,5,5-tetramethyl-1,3,2-dioxaborolan-2-yl)pyridine (0.229 g, 1.17 mmol) according to the general procedure VI. Obtained as a white solid (0.060 g, 17%). MS (ISP) 433.1 [$(M+H)^+$]; mp 172-174° C.

EXAMPLE 78

5-[6-Cyclopropyl-4-(4-trifluoromethyl-phenyl)-[2,4']bipyridinyl-2'-yl]-pyrimidin-2-ylamine The title compound was prepared from 2'-chloro-6-cyclopropyl-4-(4-trifluoromethylphenyl)-[2,4']bipyridinyl (example E.29) (0.300 g, 0.80 mmol) and commercially available 2-amino-5-(4,4,5,5-tetramethyl-1,3,2-dioxaborolan-2-yl)pyrimidine (0.230 g, 1.17 mmol) according to the general procedure VI. Obtained as a white solid (0.100 g, 28%). MS (ISP) 434.1 [$(M+H)^+$]; mp 242-245° C.

EXAMPLE 79

2-Methyl-6-(3-pyridin-4-yl-phenyl)-4-(4-trifluoromethyl-phenyl)-pyridine

The title compound was prepared from trifluoro-methanesulfonic acid 6-methyl-4-(4-trifluoromethyl-phenyl)-pyridin-2-yl ester (example A.32) (0.250 g, 0.65 mmol) and 3-pyridin-4-yl-benzeneboronic acid [CAS-No. 337536-25-1] (0.143 g, 0.71 mmol) according to the general procedure VI. Obtained as a white solid (0.101 g, 40%). MS (ISP) 391.1 [$(M+H)^+$]; mp 143-147° C.

EXAMPLE 80

5-{1-[4-(4-Chloro-phenyl)-6-methyl-pyridin-2-yl]-1H-imidazol-4-yl}-pyridin-2-ylamine The title compound was prepared from 4-(4-chloro-phenyl)-2-(4-iodo-imidazol-1-yl)-6-methyl-pyridine (example E.30) (0.200 g, 0.51 mmol) and commercially available 2-amino-5-(4,4,5,5-tetramethyl-1,3,2-dioxaborolan-2-yl) pyridine (0.122 g, 0.62 mmol) according to the general procedure VI. Obtained as a white solid (0.035 g, 19%). MS (ISP) 362.3 [$(M+H)^+$] and 364 [$(M+2+H)^+$]; mp 230-233° C.

EXAMPLE 81

4-(4-Chloro-phenyl)-6-methyl-[2,3';5',3"]terpyridin-6"-ylamine

The title compound was prepared from 5'-bromo-4-(4-chloro-phenyl)-6-methyl-[2,3']bipyridinyl (example E.31) (0.600 g, 1.6 mmol) and commercially available 2-amino-5-(4,4,5,5-tetramethyl-1,3,2-dioxaborolan-2-yl)pyridine (0.404 g, 1.8 mmol) according to the general procedure VI. Obtained as a white solid (0.180 g, 29%). MS (ISP) 373.2 [$(M+H)^+$] and 375 [$(M+2+H)^+$]; mp 188-192° C.

EXAMPLE 82

5-{3-[4-(4-Chloro-phenyl)-6-methyl-pyridin-2-yl]-phenyl}-pyrimidin-2-ylamine

The title compound was prepared 2-(3-bromo-phenyl)-4-(4-chloro-phenyl)-6-methylpyridine (example E.32) (0.075 g, 0.20 mmol) and commercially available 2-amino-5-(4,4,5,5-tetramethyl-1,3,2-dioxaborolan-2-yl)pyrimidine (0.051 g, 0.2 mmol) according to the general procedure VI. Obtained as a white solid (0.035 g, 45%). MS (ISP) 373.2 [$(M+H)^+$] and 375 [$(M+2+H)^+$]; mp 197-199° C.

EXAMPLE 83

3'-[4-Trifluoromethyl-6-(4-trifluoromethyl-phenyl)-pyridin-2-yl]-biphenyl-3-sulfonic acid amide The title compound was prepared from 2-(3-bromo-phenyl)-4-trifluoromethyl-6-(4-trifluoromethyl-phenyl)-pyridine (example E.20) (0.223 g, 0.5 mmol) and commercially available 3-(4,4,5,5-tetramethyl-1,3,2-dioxaborolan-2-yl)-benzenesulfonamide [CAS-No. 486422-08-6] (0.283 g, 1.0 mmol) according to the general procedure VI. Obtained as a light brown solid (0.125 g, 43%). MS (ISP) 523.3 [$(M+H)^+$]; mp 176-179° C.

EXAMPLE 84

4-[4-(4-Chloro-phenyl)-6-trifluoromethyl-pyrimidin-2-yl]-[2,3']bipyridinyl

The title compound was prepared from 4-(4-chloro-phenyl)-2-(2-chloro-pyridin-4-yl)-6-trifluoromethyl-pyrimidine (example E.5) (0.185 g, 0.5 mmol) and commercially available 3-pyridineboronic acid (0.08 g, 0.65 mmol) according to the general procedure VI. Obtained as a white solid (0.018 g, 9%). MS (ISP) 413.1 [$(M+H)^+$]; mp 226° C.

EXAMPLE 85

4-[4-Trifluoromethyl-6-(4-trifluoromethyl-phenyl)-pyrimidin-2-yl]-[2,3']bipyridinyl The title compound was prepared from 2-(2-chloro-pyridin-4-yl)-4-trifluoromethyl-6-(4-trifluoromethyl-phenyl)-pyrimidine (example E.6) (0.202 g, 0.5 mmol) and commercially available 3-pyridineboronic acid (0.08 g, 0.65 mmol) according to the general procedure VI. Obtained as a white solid (0.013 g, 6%). MS (ISP) 447.0 [$(M+H)^+$]; mp 247° C.

EXAMPLE 86

4-[4-(4-Chloro-phenyl)-6-trifluoromethyl-pyrimidin-2-yl]-[2,4']bipyridinyl

The title compound was prepared from 4-(4-chloro-phenyl)-2-(2-chloro-pyridin-4-yl)-6-trifluoromethyl-pyrimidine (example E.5) (0.185 g, 0.5 mmol) and commercially available 4-pyridineboronic acid (0.08 g, 0.65 mmol) according to the general procedure VI. Obtained as a light yellow solid (0.06 g, 29%). MS (ISP) 413.0 [$(M+H)^+$]; mp 193° C.

EXAMPLE 87

5-{1-[4-(3-Ethoxy-4-trifluoromethyl-phenyl)-6-trifluoromethyl-pyrimidin-2-yl]-1H-imidazol-4-yl}-pyridin-2-ylamine The title compound was prepared from 2-(4-bromo-imidazol-1-yl)-4-(3-ethoxy-4-trifluoromethyl-phenyl)-6-trifluoromethyl-pyrimidine (example E.9) (0.24 g, 0.5 mmol) and commercially available 2-amino-5-(4,4,5,5-tetramethyl-1,3,2-dioxaborolan-2-yl)pyridine (0.14 g, 0.65 mmol) according to the general procedure VI. Obtained as a yellow solid (0.038 g, 15%). MS (ISP) 495.3 [$(M+H)^+$]; mp 266.5° C.

EXAMPLE 88

4-[4-Difluoromethyl-6-(4-trifluoromethyl-phenyl)-pyrimidin-2-yl]-[2,3']bipyridinyl-6'-ylamine The title compound was prepared from 2-(2-chloro-pyridin-4-yl)-4-difluoromethyl-6-(4-trifluoromethyl-phenyl)-pyrimidine (example E.10) (0.19 g, 0.5 mmol) and commercially available 2-amino-5-(4,4,5,5-tetramethyl-1,3,2-dioxaborolan-2-yl)pyridine (0.14 g, 0.65 mmol) according to the general procedure VI. Obtained as a light yellow solid (0.021 g, 9%). MS (ISP) 444.4 [$(M+H)^+$]; mp 210° C.

EXAMPLE 89

4-{5-[4-(3-Ethoxy-4-trifluoromethyl-phenyl)-6-trifluoromethyl-pyrimidin-2-yl]-[1,2,4]oxadiazol-3-yl}-benzenesulfonamide The title compound was prepared from N-hydroxy-4-sulfamoyl-benzamidine [CAS-No. 4476-10-2] (0.16 g, 0.75 mmol) and 4-(3-ethoxy-4-trifluoromethyl-phenyl)-6-trifluoromethyl-pyrimidine-2-carboxylic acid (example D.4) (0.19 g, 0.5 mmol) according to the general procedure V. Obtained as a light yellow solid (0.114 g, 41%). MS (ISP) 560.2 [$(M+H)^+$]; mp 250.5° C.

EXAMPLE 90

5-{5-[4-(3-Ethoxy-4-trifluoromethyl-phenyl)-6-trifluoromethyl-pyrimidin-2-yl]-[1,2,4]oxadiazol-3-yl}-pyridin-2-ylamine The title compound was prepared from 6-amino-N-hydroxy-nicotinamidine (example C.3) (0.15 g, 1.0 mmol) and 4-(3-ethoxy-4-trifluoromethyl-phenyl)-6-trifluoromethyl-pyrimidine-2-carboxylic acid (example D.4) (0.19 g, 0.5 mmol) according to the general procedure V. Obtained as a light yellow solid (0.076 g, 31%). MS (ISP) 497.3 [$(M+H)^+$]; mp 216° C.

EXAMPLE 91

3-{5-[4-(3-Ethoxy-4-trifluoromethyl-phenyl)-6-trifluoromethyl-pyrimidin-2-yl]-[1,2,4]oxadiazol-3-yl}-benzenesulfonamide The title compound was prepared from N-hydroxy-3-sulfamoyl-benzamidine [CAS-No. 9000-88-7] (0.16 g, 0.75 mmol) and 4-(3-ethoxy-4-trifluoromethyl-phenyl)-6-trifluoromethyl-pyrimidine-2-carboxylic acid (example D.4) (0.19 g, 0.5 mmol) according to the general procedure V. Obtained as a white solid (0.05 g, 18%). MS (ISP) 560.0 [$(M+H)^+$]; mp 227° C.

EXAMPLE 92

4-[4-(3-Ethoxy-4-trifluoromethyl-phenyl)-6-trifluoromethyl-pyrimidin-2-yl]-[2,3']bipyridinyl-6'-ylamine The title compound was prepared from 2-(2-chloro-pyridin-4-yl)-4-(3-ethoxy-4-trifluoromethyl-phenyl)-6-trifluoromethyl-pyrimidine (example E.33) (0.224 g, 0.5 mmol) and commercially available 2-amino-5-(4,4,5,5-tetramethyl-1,3,2-dioxaborolan-2-yl)pyridine (0.14 g, 0.65 mmol) according to the general procedure VI. Obtained as a light yellow solid (0.155 g, 61%). MS (ISP) 506.1 [$(M+H)^+$]; mp 222° C.

EXAMPLE 93

5-{3-[4-(3-Ethoxy-4-trifluoromethyl-phenyl)-6-trifluoromethyl-pyrimidin-2-yl]-phenyl}-pyridin-2-ylamine The title compound was prepared from 2-(3-bromo-phenyl)-4-(3-ethoxy-4-trifluoromethyl-phenyl)-6-trifluoromethyl-pyrimidine (example E.34) (0.25 g, 0.5 mmol) and commercially available 2-amino-5-(4,4,5,5-tetramethyl-1,3,2-dioxaborolan-2-yl)pyridine (0.14 g, 0.65 mmol) according to the general procedure VI. Obtained as an off-white solid (0.157 g, 62%). MS (ISP) 505.3 [$(M+H)^+$]; mp 208° C.

EXAMPLE 94

5-{1-[4-(3-Fluoro-4-trifluoromethyl-phenyl)-6-trifluoromethyl-pyrimidin-2-yl]-1H-imidazol-4-yl}-pyridin-2-ylamine The title compound was prepared from 2-(4-bromo-imidazol-1-yl)-4-(3-fluoro-4-trifluoromethyl-phenyl)-6-trifluoromethyl-pyrimidine (example 35) (0.23 g, 0.5 mmol) and commercially available 2-amino-5-(4,4,5,5-tetramethyl-1,3,2-dioxaborolan-2-yl)pyridine (0.14 g, 0.65 mmol) according to the general procedure VI. Obtained as a yellow solid (0.065 g, 28%). MS (ISP) 469.2 [$(M+H)^+$]; mp 309° C.

EXAMPLE 95

N-(5-{1-[4-Trifluoromethyl-6-(4-trifluoromethyl-phenyl)-pyrimidin-2-yl]-1H-imidazol-4-yl}-pyridin-2-yl)-acetamide A stirred solution of 5-{1-[4-trifluoromethyl-6-(4-trifluoromethyl-phenyl)-pyrimidin-2-yl]-1H-imidazol-4-yl}-pyridin-2-ylamine (example 13) (0.314 g, 0.7 mmol) in acetic acid anhydride (6 ml) was heated at 120° C. for 1 h. To the cooled reaction mixture was added diethyl ether (10 ml), the precipitate was collected by filtration and dried to yield the title compound as a light yellow solid (0.29 g, 84%). MS (ISP) 493.3 [$(M+H)^+$]; mp 314° C.

EXAMPLE 96

5-{3-[4-(3-Fluoro-4-trifluoromethyl-phenyl)-6-trifluoromethyl-pyrimidin-2-yl]-phenyl}-pyridin-2-ylamine The title compound was prepared from 2-(3-bromo-phenyl)-4-(3-fluoro-4-trifluoromethyl-phenyl)-6-trifluoromethyl-pyrimidine (example E.36) (0.23 g, 0.5 mmol) and commercially available 2-amino-5-(4,4,5,5-tetramethyl-1,3, 2-dioxaborolan-2-yl)pyridine (0.14 g, 0.65 mmol) according to the general procedure VI. Obtained as a light yellow solid (0.19 g, 79%). MS (ISP) 479.0 [(M+H)$^+$]; mp 212° C.

EXAMPLE 97

5-{3-[4-(3,4-Dichloro-phenyl)-6-trifluoromethyl-pyrimidin-2-yl]-phenyl}-pyridin-2-ylamine The title compound was prepared from 2-(3-bromo-phenyl)-4-(3,4-dichloro-phenyl)-6-trifluoromethyl-pyrimidine (example E.37) (0.13 g, 0.29 mmol) and commercially available 2-amino-5-(4,4,5,5-tetramethyl-1,3,2-dioxaborolan-2-yl)pyridine (0.083 g, 0.38 mmol) according to the general procedure VI. Obtained as an off-white solid (0.07 g, 52%). MS (ISP) 461.3 [(M+H)$^+$]; mp 179° C.

EXAMPLE 98

4-{5-[4-(3,4-Dichloro-phenyl)-6-trifluoromethyl-pyrimidin-2-yl]-[1,2,4]oxadiazol-3-yl}-benzene-sulfonamide The title compound was prepared from N-hydroxy-4-sulfamoyl-benzamidine [CAS-No. 4476-10-2] (0.16 g, 0.74 mmol) and 4-(3,4-dichloro-phenyl)-6-trifluoromethyl-pyrimidine-2-carboxylic acid (example D.6) (0.17 g, 0.50 mmol) according to the general procedure V. Obtained as a light yellow solid (0.042 g, 16%). MS (ISP) 516.1 [(M+H)$^+$]; mp 302.5° C.

EXAMPLE 99

3-{5-[4-(3,4-Dichloro-phenyl)-6-trifluoromethyl-pyrimidin-2-yl]-[1,2,4]oxadiazol-3-yl}-benzene-sulfonamide The title compound was prepared from N-hydroxy-3-sulfamoyl-benzamidine [CAS-No. 9000-88-7] (0.16 g, 0.74 mmol) and 4-(3,4-dichloro-phenyl)-6-trifluoromethyl-pyrimidine-2-carboxylic acid (example D.6) (0.17 g, 0.50 mmol) according to the general procedure V. Obtained as a light yellow solid (0.055 g, 21%). MS (ISP) 516.1 [(M+H)$^+$]; mp 258° C.

EXAMPLE 100

5-{5-[4-(3,4-Dichloro-phenyl)-6-trifluoromethyl-pyrimidin-2-yl]-[1,2,4]oxadiazol-3-yl}-pyridin-2-ylamine The title compound was prepared from 2-amino-N-hydroxy-pyrimidine-5-carboxamidine (example C.4) (0.114 g, 0.75 mmol) and 4-(3,4-dichloro-phenyl)-6-trifluoromethyl-pyrimidine-2-carboxylic acid (example D.6) (0.17 g, 0.5 mmol) according to the general procedure V. Obtained as a light yellow solid (0.11 g, 49%). MS (ISP) 453.1 [(M+H)$^+$]; mp 227° C.

EXAMPLE 101

5-[6-Trifluoromethyl-4-(4-trifluoromethyl-phenyl)-[2,4']bipyrimidinyl-2'-yl]-pyridin-2-ylamine The title compound was prepared from 2'-chloro-6-trifluoromethyl-4-(4-trifluoromethyl-phenyl)-[2,4']bipyrimidinyl (example E.42) (g, 0.5 mmol) and commercially available 2-amino-5-(4,4,5,5-tetramethyl-1,3,2-dioxaborolan-2-yl) pyridine (0.14 g, 0.65 mmol) according to the general procedure VI. Obtained as a light yellow solid (0.17 g, %). MS (ISP) 463.1 [(M+H)$^+$]; mp 236.5° C.

EXAMPLE 102

5-{1-[4-(3,4-Dichloro-phenyl)-6-trifluoromethyl-pyrimidin-2-yl]-1H-imidazol-4-yl}-pyridin-2-ylamine The title compound was prepared from 2-(4-bromo-imidazol-1-yl)-4-(3,4-dichlorophenyl)-6-trifluoromethyl-pyrimidine (example E.39) (0.22 g, 0.5 mmol) and commercially available 2-amino-5-(4,4,5,5-tetramethyl-1,3,2-dioxaborolan-2-yl)pyridine (0.14 g, 0.65 mmol) according to the general procedure VI. Obtained as a yellow solid (0.022 g, 10%). MS (ISP) 451.1 [(M+H)$^+$]; mp 282.5° C.

EXAMPLE 103

4-[4-(3,4-Dichloro-phenyl)-6-trifluoromethyl-pyrimidin-2-yl]-[2,3']bipyridinyl-6'-ylamine The title compound was prepared from 4-(3,4-dichloro-phenyl)-2-(2-chloro-pyridin-4-yl)-6-trifluoromethyl-pyrimidine (example E.38) (0.20 g, 0.5 mmol) and commercially available 2-amino-5-(4,4,5,5-tetramethyl-1,3,2-dioxaborolan-2-yl)pyridine (0.14 g, 0.65 mmol) according to the general procedure VI. Obtained as a light brown solid (0.15 g, 63%). MS (ISP) 462.1 [(M+H)$^+$]; mp 224.5° C.

EXAMPLE 104

5-{1-[4-(4-Chloro-3-methyl-phenyl)-6-trifluoromethyl-pyrimidin-2-yl]-1H-imidazol-4-yl}-pyridin-2-ylamine The title compound was prepared from 2-(4-bromo-imidazol-1-yl)-4-(4-chloro-3-methyl-phenyl)-6-trifluoromethyl-pyrimidine (example E.40) (0.21 g, 0.5 mmol) and commercially available 2-amino-5-(4,4,5,5-tetramethyl-1,3,2-dioxaborolan-2-yl)pyridine (0.14 g, 0.65 mmol) according to the general procedure VI. Obtained as a yellow solid (0.096 g, 45%). MS (ISP) 431.2 [(M+H)$^+$]; mp 276° C.

EXAMPLE 105

5-{3-[4-(4-Chloro-3-methyl-phenyl)-6-trifluoromethyl-pyrimidin-2-yl]-phenyl}-pyridin-2-ylamine The title compound was prepared from 2-(3-bromo-phenyl)-4-(4-chloro-3-methylphenyl)-6-trifluoromethyl-pyrimidine (example E.41) (0.21 g, 0.5 mmol) and commercially available 2-amino-5-(4,4,5,5-tetramethyl-1,3,2-dioxaborolan-2-yl)pyridine (0.14 g, 0.65 mmol) according to the general procedure VI. Obtained as a white solid (0.13 g, 60%). MS (ISP) 441.1 [(M+H)$^+$]; mp 168.5° C.

EXAMPLE 106

3-{5-[4-(4-Chloro-3-methyl-phenyl)-6-trifluoromethyl-pyrimidin-2-yl]-[1,2,4]oxadiazol-3-yl}-benzenesulfonamide The title compound was prepared from N-hydroxy-3-sulfamoyl-benzamidine [CAS-No. 9000-88-7] (0.16 g, 0.74 mmol) and 4-(4-chloro-3-methyl-phenyl)-6-trifluoromethyl-pyrimidine-2-carboxylic acid (example D.7) (0.16 g, 0.50 mmol) according to the general procedure V. Obtained as a white solid (0.046 g, 19%). MS (ISP) 496.2 [$(M+H)^+$]; mp 246° C.

EXAMPLE 107

5-{5-[4-(4-Chloro-3-methyl-phenyl)-6-trifluoromethyl-pyrimidin-2-yl]-[1,2,4]oxadiazol-3-yl}-pyridin-2-ylamine The title compound was prepared from 2-amino-N-hydroxy-pyrimidine-5-carboxamidine (example C.4) (0.114 g, 0.75 mmol) and 4-(4-chloro-3-methyl-phenyl)-6-trifluoromethyl-pyrimidine-2-carboxylic acid (example D.7) (0.16 g, 0.5 mmol) according to the general procedure V. Obtained as a light yellow solid (0.11 g, 52%). MS (ISP) 433.2 [$(M+H)^+$]; mp 199.5° C.

EXAMPLE 108

4-[4-(4-Chloro-3-methyl-phenyl)-6-trifluoromethyl-pyrimidin-2-yl]-[2,3']bipyridinyl-6'-ylamine The title compound was prepared from 4-(4-chloro-3-methyl-phenyl)-2-(2-chloro-pyridin-4-yl)-6-trifluoromethyl-pyrimidine (example E.43) (0.19 g, 0.5 mmol) and commercially available 2-amino-5-(4,4,5,5-tetramethyl-1,3,2-dioxaborolan-2-yl)pyridine (0.14 g, 0.65 mmol) according to the general procedure VI. Obtained as a yellow solid (0.16 g, 72%). MS (ISP) 442.3 [$(M+H)^+$]; mp 207° C.

EXAMPLE 109

5-{3-[4-(4-Chloro-phenyl)-6-methyl-pyrimidin-2-yl}-phenyl]-pyridin-2-ylamine

The title compound was prepared from 2-(3-bromo-phenyl)-4-(4-chloro-phenyl)-6-methyl-pyrimidine (example E.44) (0.18 g, 0.5 mmol) and commercially available 2-amino-5-(4,4,5,5-tetramethyl-1,3,2-dioxaborolan-2-yl) pyridine (0.14 g, 0.65 mmol) according to the general procedure VI. Obtained as a white solid (0.090 g, 48%). MS (ISP) 373.0 [$(M+H)^+$]; mp 168.5° C.

EXAMPLE 110

5-{3-[4-(4-Chloro-phenyl)-6-methyl-pyrimidin-2-yl]-phenyl}-pyrimidin-2-ylamine

The title compound was prepared from 2-(3-bromo-phenyl)-4-(4-chloro-phenyl)-6-methyl-pyrimidine (example E.44) (0.18 g, 0.5 mmol) and commercially available 2-amino-5-(4,4,5,5-tetramethyl-1,3,2-dioxaborolan-2-yl) pyrimidine (0.14 g, 0.65 mmol) according to the general procedure VI. Obtained as a white solid (0.055 g, 29%). MS (ISP) 374.1 [$(M+H)^+$]; mp 228° C.

EXAMPLE 111

4-{1-[4-Trifluoromethyl-6-(4-trifluoromethyl-phenyl)-pyrimidin-2-yl]-1H-imidazol-4-yl}-phenylamine The title compound was prepared from 2-(4-bromo-imidazol-1-yl)-4-trifluoromethyl-6-(4-trifluoromethyl-phenyl)-pyrimidine (example E.1) (0.22 g, 0.5 mmol) and commercially available 4-(4,4,5,5-tetramethyl-1,3,2-dioxaborolan-2-yl)aniline (0.14 g, 0.65 mmol) according to the general procedure VI. Obtained as a brown solid (0.032 g, 14%). MS (ISP) 450.1 [$(M+H)^+$]; mp 270° C.

EXAMPLE 112

4-[4-(4-Chloro-phenyl)-6-methyl-pyrimidin-2-yl]-[2,3']bipyridinyl-6'-ylamine

The title compound was prepared from 4-(4-chloro-phenyl)-2-(2-chloro-pyridin-4-yl)-6-methyl-pyrimidine (example E.45) (0.158 g, 0.5 mmol) and commercially available 2-amino-5-(4,4,5,5-tetramethyl-1,3,2-dioxaborolan-2-yl) pyridine (0.14 g, 0.65 mmol) according to the general procedure VI. Obtained as an off-white solid (0.032 g, 17%). MS (ISP) 374.0 [$(M+H)^+$]; mp 199° C.

EXAMPLE 113

4-[4-Methyl-6-(4-trifluoromethyl-phenyl)-pyrimidin-2-yl]-[2,3']bipyridinyl-6'-ylamine The title compound was prepared from 2-(2-chloro-pyridin-4-yl)-4-methyl-6-(4-trifluoromethyl-phenyl)-pyrimidine (example E.46) (0.175 g, 0.5 mmol) and commercially available 2-amino-5-(4,4,5,5-tetramethyl-1,3,2-dioxaborolan-2-yl)pyridine (0.14 g, 0.65 mmol) according to the general procedure VI. Obtained as an off-white solid (0.021 g, 10%). MS (ISP) 408.3 [$(M+H)^+$]; mp 232° C.

EXAMPLE 114

{3'-[4-Trifluoromethyl-6-(4-trifluoromethyl-phenyl)-pyrimidin-2-yl]-biphenyl-4-yl}-methanol The title compound was prepared from 2-(3-bromo-phenyl)-4-trifluoromethyl-6-(4-trifluoromethyl-phenyl)-pyrimidine (example E.3) (0.22 g, 0.5 mmol) and commercially available 4-hydroxymethyl-phenyl-boronic acid (0.09 g, 0.6 mmol) according to the general procedure VI. Obtained as a white solid (0.199 g, 54%). MS (ISP) 475.1 [$(M+H)^+$]; mp 171° C.

EXAMPLE 115

5-{3-[4-Methyl-6-(4-trifluoromethyl-phenyl)-pyrimidin-2-yl]-phenyl}-pyrimidin-2-ylamine The title compound was prepared from 2-(3-bromo-phenyl)-4-(4-trifluoromethylphenyl)-6-methyl-pyrimidine (example E.47) (0.175 g, 0.5 mmol) and commercially available 2-amino-5-(4,4,5,5-tetramethyl-1,3,2-dioxaborolan-2-yl) pyrimidine (0.14 g, 0.65 mmol) according to the general procedure VI. Obtained as an off-white solid (0.021 g, 10%). MS (ISP) 408.3 [$(M+H)^+$]; mp 290° C.

EXAMPLE 116

5-{3-[4-Methyl-6-(4-trifluoromethyl-phenyl)-pyrimidin-2-yl]-phenyl}-pyridin-2-ylamine The title compound was prepared from 2-(3-bromo-phenyl)-4-(4-trifluoromethylphenyl)-6-methyl-pyrimidine (example E.47) (0.197 g, 0.5 mmol) and commercially available 2-amino-5-(4,4,5,5-tetramethyl-1,3,2-dioxaborolan-2-yl)

pyridine (0.14 g, 0.65 mmol) according to the general procedure VI. Obtained as an off-white solid (0.097 g, 48%). MS (ISP) 407.3 [$(M+H)^+$]; mp 224° C.

EXAMPLE 117

3'-[4-Trifluoromethyl-6-(4-trifluoromethyl-phenyl)-pyrimidin-2-yl]-biphenyl-4-ylamine The title compound was prepared from 2-(3-bromo-phenyl)-4-trifluoromethyl-6-(4-trifluoromethyl-phenyl)-pyrimidine (example E.3) (0.22 g, 0.5 mmol) and commercially available 4-(4,4,5,5-tetramethyl-1,3,2-dioxaborolan-2-yl) aniline (0.13 g, 0.59 mmol) according to the general procedure VI. Obtained as a light yellow solid (0.174 g, 76%). MS (ISP) 460.3 [$(M+H)^+$]; mp 186° C.

EXAMPLE 118

4-{5-[4-Methyl-6-(4-trifluoromethyl-phenyl)-pyrimidin-2-yl]-[1,2,4]oxadiazol-3-yl}-benzenesulfonamide The title compound was prepared from N-hydroxy-4-sulfamoyl-benzamidine [CAS-No. 4476-10-2] (0.12 g, 0.55 mmol) and 4-methyl-6-(4-trifluoromethyl-phenyl)-pyrimidine-2-carboxylic acid (example D.8) (0.104 g, 0.37 mmol) according to the general procedure V. Obtained as a white solid (0.025 g, 15%). MS (ISP) 462.4 [$(M+H)^+$]; mp 326° C.

EXAMPLE 119

5-{3-[4-(3-Methyl-4-trifluoromethyl-phenyl)-6-trifluoromethyl-pyrimidin-2-yl]-phenyl}-pyridin-2-ylamine The title compound was prepared from 2-(3-bromo-phenyl)-4-(3-methyl-4-trifluoromethyl-phenyl)-6-trifluoromethyl-pyrimidine (example E.49) (0.23 g, 0.5 mmol) and commercially available 2-amino-5-(4,4,5,5-tetramethyl-1,3,2-dioxaborolan-2-yl)pyridine (0.14 g, 0.65 mmol) according to the general procedure VI. Obtained as a light yellow solid (0.174 g, 73%). MS (ISP) 475.1 [$(M+H)^+$]; mp 207° C.

EXAMPLE 120

5-{1-[4-(3-Methyl-4-trifluoromethyl-phenyl)-6-trifluoromethyl-pyrimidin-2-yl]-1H-imidazol-4-yl}-pyridin-2-ylamine The title compound was prepared from 2-(4-bromo-imidazol-1-yl)-4-(3-methyl-4-trifluoromethyl-phenyl)-6-trifluoromethyl-pyrimidine (example E.48) (0.23 g, 0.5 mmol) and commercially available 2-amino-5-(4,4,5,5-tetramethyl-1,3,2-dioxaborolan-2-yl)pyridine (0.14 g, 0.65 mmol) according to the general procedure VI. Obtained as a yellow solid (0.084 g, 36%). MS (ISP) 465.3 [$(M+H)^+$]; mp 290° C.

EXAMPLE 121

4-[4-(3-Methyl-4-trifluoromethyl-phenyl)-6-trifluoromethyl-pyrimidin-2-yl]-[2,3']bipyridinyl-6'-ylamine The title compound was prepared from 2-(2-chloro-pyridin-4-yl)-4-(3-methyl-4-trifluoromethyl-phenyl)-6-trifluoromethyl-pyrimidine (example E.50) (0.15 g, 0.36 mmol) and commercially available 2-amino-5-(4,4,5,5-tetramethyl-1,3,2-dioxaborolan-2-yl)pyridine (0.103 g, 0.47 mmol) according to the general procedure VI. Obtained as a light yellow solid (0.144 g, 84%). MS (ISP) 476.0 [$(M+H)^+$]; mp 223° C.

EXAMPLE 122

5-{1-[4-Methyl-6-(3-methyl-4-trifluoromethyl-phenyl)-pyrimidin-2-yl]-1H-imidazol-4-yl}-pyridin-2-ylamine The title compound was prepared from 2-(4-bromo-imidazol-1-yl)-4-methyl-6-(3-methyl-4-trifluoromethyl-phenyl)-pyrimidine (example E.51) (0.20 g, 0.5 mmol) and commercially available 2-amino-5-(4,4,5,5-tetramethyl-1,3,2-dioxaborolan-2-yl)pyridine (0.14 g, 0.65 mmol) according to the general procedure VI. Obtained as a light brown solid (0.034 g, 17%). MS (ISP) 411.0 [$(M+H)^+$]; mp 247.5° C.

EXAMPLE 123

5-{1-[4-Methyl-6-(3-methyl-4-trifluoromethyl-phenyl)-pyrimidin-2-yl]-1H-imidazol-4-yl}-pyrimidin-2-ylamine The title compound was prepared from 2-(4-bromo-imidazol-1-yl)-4-methyl-6-(3-methyl-4-trifluoromethyl-phenyl)-pyrimidine (example E.51) (0.20 g, 0.5 mmol) and commercially available 2-amino-5-(4,4,5,5-tetramethyl-1,3,2-dioxaborolan-2-yl)pyrimidine (0.14 g, 0.65 mmol) according to the general procedure VI. Obtained as a light brown solid (0.022 g, 11%). MS (ISP) 412.4 [$(M+H)^+$]; mp 248° C.

EXAMPLE 124

5-{3-[4-(3-Methyl-4-trifluoromethyl-phenyl)-6-trifluoromethyl-pyrimidin-2-yl]-phenyl}-pyrimidin-2-ylamine The title compound was prepared from 2-(3-bromo-phenyl)-4-(3-methyl-4-trifluoromethyl-phenyl)-6-trifluoromethyl-pyrimidine (example E.49) (0.23 g, 0.5 mmol) and commercially available 2-amino-5-(4,4,5,5-tetramethyl-1,3,2-dioxaborolan-2-yl)pyrimidine (0.14 g, 0.65 mmol) according to the general procedure VI. Obtained as an off-white solid (0.186 g, 78%). MS (ISP) 476.1 [$(M+H)^+$]; mp 244° C.

EXAMPLE 125

5-{1-[4-(3-Methyl-4-trifluoromethyl-phenyl)-6-trifluoromethyl-pyrimidin-2-yl]-1H-imidazol-4-yl}-pyrimidin-2-ylamine The title compound was prepared from 2-(4-bromo-imidazol-1-yl)-4-(3-methyl-4-trifluoromethyl-phenyl)-6-trifluoromethyl-pyrimidine (example E.48) (0.23 g, 0.5 mmol) and commercially available 2-amino-5-(4,4,5,5-tetramethyl-1,3,2-dioxaborolan-2-yl)pyrimidine (0.14 g, 0.65 mmol) according to the general procedure VI. Obtained as a yellow solid (0.168 g, 72%). MS (ISP) 466.1 [$(M+H)^+$]; mp 297° C.

EXAMPLE 126

3-{5-[4-Methyl-6-(4-trifluoromethyl-phenyl)-pyrimidin-2-yl]-[1,2,4]oxadiazol-3-yl}-benzenesulfonamide The title compound was prepared from N-hydroxy-3-sulfamoyl-benzamidine [CAS-No. 9000-88-7] (0.16 g, 0.74 mmol) and 4-methyl-6-(4-trifluoromethyl-phenyl)-pyrimidine-2-carboxylic acid (example D.8) (0.14 g, 0.50 mmol) according to the general procedure V. Obtained as a white solid (0.097 g, 42%). MS (ISP) 462.1 [$(M+H)^+$]; mp 240.5° C.

EXAMPLE 127

5-{5-[4-Methyl-6-(4-trifluoromethyl-phenyl)-pyrimidin-2-yl]-[1,2,4]oxadiazol-3-yl}-pyridin-2-ylamine The title compound was prepared from 2-amino-N-hydroxy-pyrimidine-5-carboxamidine (example C.4) (0.15 g, 1.0 mmol) and 4-methyl-6-(4-trifluoromethyl-phenyl)pyrimidine-2-carboxylic acid (example D.8) (0.14 g, 0.5 mmol) according to the general procedure V. Obtained as a light yellow solid (0.075 g, 38%). MS (ISP) 399.3 [$(M+H)^+$]; mp 216.5° C.

EXAMPLE 128

4-{5-[4-(3-Methyl-4-trifluoromethyl-phenyl)-6-trifluoromethyl-pyrimidin-2-yl]-[1,2,4]oxadiazol-3-yl}-benzenesulfonamide The title compound was prepared from N-hydroxy-4-sulfamoyl-benzamidine [CAS-No. 4476-10-2] (0.14 g, 0.65 mmol) and 4-(3-methyl-4-trifluoromethyl-phenyl)-6-trifluoromethyl-pyrimidine-2-carboxylic acid (example D.9) (0.175 g, 0.5 mmol) according to the general procedure V. Obtained as a white solid (0.147 g, 56%). MS (ISN) 528.3 [$(M-H)^-$]; mp 261° C.

EXAMPLE 129

3-{5-[4-(3-Methyl-4-trifluoromethyl-phenyl)-6-trifluoromethyl-pyrimidin-2-yl]-[1,2,4]oxadiazol-3-yl}-benzenesulfonamide The title compound was prepared from N-hydroxy-3-sulfamoyl-benzamidine [CAS-No. 9000-88-7] (0.14 g, 0.65 mmol) and 4-(3-methyl-4-trifluoromethyl-phenyl)-6-trifluoromethyl-pyrimidine-2-carboxylic acid (example D.9) (0.175 g, 0.5 mmol) according to the general procedure V. Obtained as a white solid (0.15 g, 57%). MS (ISN) 528.3 [$(M-H)^-$]; mp 223.5° C.

EXAMPLE 130

5-{5-[4-(3-Methyl-4-trifluoromethyl-phenyl)-6-trifluoromethyl-pyrimidin-2-yl]-[1,2,4]oxadiazol-3-yl}-pyridin-2-ylamine The title compound was prepared from 2-amino-N-hydroxy-pyrimidine-5-carboxamidine (example C.4) (0.152 g, 1.0 mmol) and 4-(3-methyl-4-trifluoromethyl-phenyl)-6-trifluoromethyl-pyrimidine-2-carboxylic acid (example D.9) (0.175 g, 0.5 mmol) according to the general procedure V. Obtained as an off-white solid (0.157 g, 67%). MS (ISP) 467.1 [$(M+H)^+$]; mp 223° C.

EXAMPLE 131

4-[4-Methyl-6-(3-methyl-4-trifluoromethyl-phenyl)-pyrimidin-2-yl]-[2,3']bipyridinyl-6'-ylamine The title compound was prepared from 2-(2-chloro-pyridin-4-yl)-4-methyl-6-(3-methyl-4-trifluoromethyl-phenyl)-pyrimidine (example E.52) (0.11 g, 0.27 mmol) and commercially available 2-amino-5-(4,4,5,5-tetramethyl-1,3,2-dioxaborolan-2-yl)pyridine (0.079 g, 0.36 mmol) according to the general procedure VI. Obtained as a light brown solid (0.021 g, 18%). MS (ISP) 422.1 [$(M+H)^+$]; mp 188° C.

EXAMPLE 132

5-{3-[4-Methyl-6-(3-methyl-4-trifluoromethyl-phenyl)-pyrimidin-2-yl]-phenyl}-pyridin-2-ylamine The title compound was prepared from 2-(3-bromo-phenyl)-4-methyl-6-(3-methyl-4-trifluoromethyl-phenyl)-pyrimidine (example E.53) (0.11 g, 0.3 mmol) and commercially available 2-amino-5-(4,4,5,5-tetramethyl-1,3,2-dioxaborolan-2-yl)pyridine (0.087 g, 0.4 mmol) according to the general procedure VI. Obtained as a light brown solid (0.028 g, 22%). MS (ISP) 421.1 [$(M+H)^+$]; mp 153° C.

EXAMPLE 133

5-(3-{4-[3-(2,2,2-Trifluoro-ethoxy)-4-trifluoromethyl-phenyl]-6-trifluoromethyl-pyrimidin-2-yl}-phenyl)-pyridin-2-ylamine The title compound was prepared from 2-(3-bromo-phenyl)-4-[3-(2,2,2-trifluoroethoxy)-4-trifluoromethyl-phenyl]-6-trifluoromethyl-pyrimidine (example E.55) (0.273 g, 0.5 mmol) and commercially available 2-amino-5-(4,4,5,5-tetramethyl-1,3,2-dioxaborolan-2-yl)pyridine (0.13 g, 0.6 mmol) according to the general procedure VI. Obtained as an off-white solid (0.20 g, 73%). MS (ISP) 559.2 [$(M+H)^+$]; mp 220° C.

EXAMPLE 134

5-(1-{4-[3-(2,2,2-Trifluoro-ethoxy)-4-trifluoromethyl-phenyl]-6-trifluoromethyl-pyrimidin-2-yl}-1H-imidazol-4-yl)-pyridin-2-ylamine The title compound was prepared from 2-(4-bromo-imidazol-1-yl)-4-[3-(2,2,2-trifluoroethoxy)-4-trifluoromethyl-phenyl]-6-trifluoromethyl-pyrimidine (example E.54) (0.268 g, 0.5 mmol) and commercially available 2-amino-5-(4,4,5,5-tetramethyl-1,3,2-dioxaborolan-2-yl)pyridine (0.13 g, 0.6 mmol) according to the general procedure VI. Obtained as a yellow solid (0.056 g, 20%). MS (ISP) 549.2 [$(M+H)^+$]; mp 285° C.

EXAMPLE 135

4-{4-[3-(2,2,2-Trifluoro-ethoxy)-4-trifluoromethyl-phenyl]-6-trifluoromethyl-pyrimidin-2-yl}-[2,3']bipyridinyl-6'-ylamine The title compound was prepared from 2-(2-chloro-pyridin-4-yl)-4-[3-(2,2,2-trifluoroethoxy)-4-trifluoromethyl-phenyl]-6-trifluoromethyl-pyrimidine (example E.56) (0.25 g, 0.5 mmol) and commercially available 2-amino-5-(4,4,5,5-tetramethyl-1,3,2-dioxaborolan-2-yl)pyridine (0.13 g, 0.6 mmol) according to the general procedure VI. Obtained as a light brown solid (0.21 g, 77%). MS (ISP) 560.0 [(M+H)$^+$]; mp 223° C.

EXAMPLE 136

4-{5-[4-(4-Chloro-phenyl)-6-methyl-pyrimidin-2-yl]-[1,2,4]oxadiazol-3-yl}-benzenesulfonamide The title compound was prepared from N-hydroxy-4-sulfamoyl-benzamidine [CAS-No. 4476-10-2] (0.16 g, 0.75 mmol) and 4-(4-chloro-phenyl)-6-methyl-pyrimidine-2-carboxylic acid (example D.10) (0.124 g, 0.5 mmol) according to the general procedure V. Obtained as an off-white solid (0.032 g, 15%). MS (ISN) 426.1 [(M−H)$^-$]; mp 297° C.

EXAMPLE 137

5-{5-[4-(4-Chloro-phenyl)-6-methyl-pyrimidin-2-yl]-[1,2,4]oxadiazol-3-yl}-pyridin-2-ylamine The title compound was prepared from 2-amino-N-hydroxy-pyrimidine-5-carboxamidine (example C.4) (0.152 g, 1.0 mmol) and 4-(4-chloro-phenyl)-6-methyl-pyrimidine-2-carboxylic acid (example D.10) (0.124 g, 0.5 mmol) according to the general procedure V. Obtained as a white solid (0.024 g, 13%). MS (ISP) 365.3 [(M+H)$^+$]; mp 258° C.

EXAMPLE 138

5-(3-{4-[3-(2,2,2-Trifluoro-ethoxy)-4-trifluoromethyl-phenyl]-6-trifluoromethyl-pyrimidin-2-yl}-phenyl)-pyrimidin-2-ylamine The title compound was prepared from 2-(3-bromo-phenyl)-4-[3-(2,2,2-trifluoroethoxy)-4-trifluoromethyl-phenyl]-6-trifluoromethyl-pyrimidine (example E.55) (0.273 g, 0.5 mmol) and commercially available 2-amino-5-(4,4,5,5-tetramethyl-1,3,2-dioxaborolan-2-yl)pyrimidine (0.14 g, 0.65 mmol) according to the general procedure VI. Obtained as an off-white solid (0.19 g, 68%). MS (ISP) 560.2 [(M+H)$^+$]; mp 250° C.

EXAMPLE 139

5-{1-[4-Trifluoromethyl-6-(3-trifluoromethyl-phenyl)-pyrimidin-2-yl]-1H-imidazol-4-yl}-pyrimidin-2-ylamine The title compound was prepared from 2-(4-bromo-imidazol-1-yl)-4-(3-trifluoromethylphenyl)-6-trifluoromethyl-pyrimidine (example E.57) (0.22 g, 0.5 mmol) and commercially available 2-amino-5-(4,4,5,5-tetramethyl-1,3,2-dioxaborolan-2-yl)pyrimidine (0.13 g, 0.6 mmol) according to the general procedure VI. Obtained as a yellow solid (0.106 g, 47%). MS (ISP) 452.0 [(M+H)$^+$]; mp 223° C.

EXAMPLE 140

5-{3-[4-Trifluoromethyl-6-(3-trifluoromethyl-phenyl)-pyrimidin-2-yl]-phenyl}-pyridin-2-ylamine The title compound was prepared from 2-(3-bromo-phenyl)-4-trifluoromethyl-6-(3-trifluoromethyl-phenyl)-pyrimidine (example E.58) (0.2 g, 0.45 mmol) and commercially available 2-amino-5-(4,4,5,5-tetramethyl-1,3,2-dioxaborolan-2-yl)pyridine (0.12 g, 0.54 mmol) according to the general procedure VI. Obtained as a yellow solid (0.14 g, 68%). MS (ISP) 461.3 [(M+H)$^+$]; mp 162° C.

EXAMPLE 141

4-[4-Trifluoromethyl-6-(3-trifluoromethyl-phenyl)-pyrimidin-2-yl]-[2,3']bipyridinyl-6'-ylamine The title compound was prepared from 2-(2-chloro-pyridin-4-yl)-4-trifluoromethyl-6-(3-trifluoromethyl-phenyl)-pyrimidine (example E.59) (0.202 g, 0.5 mmol) and commercially available 2-amino-5-(4,4,5,5-tetramethyl-1,3,2-dioxaborolan-2-yl)pyridine (0.13 g, 0.6 mmol) according to the general procedure VI. Obtained as a light yellow solid (0.19 g, 81%). MS (ISP) 462.0 [(M+H)$^+$]; mp 196° C.

EXAMPLE 142

5-{2-Methyl-1-[4-trifluoromethyl-6-(4-trifluoromethyl-phenyl)-pyrimidin-2-yl]-1H-imidazol-4-yl}-pyridin-2-ylamine The title compound was prepared from 2-(4-bromo-2-methyl-imidazol-1-yl)-4-trifluoromethyl-6-(4-trifluoromethyl-phenyl)-pyrimidine (example E.60) (0.23 g, 0.5 mmol) and commercially available 2-amino-5-(4,4,5,5-tetramethyl-1,3,2-dioxaborolan-2-yl)pyridine (0.13 g, 0.6 mmol) according to the general procedure VI. Obtained as a yellow solid (0.11 g, 47%). MS (ISP) 465.3 [(M+H)$^+$]; mp 285° C.

EXAMPLE 143

5-{2-Methyl-1-[4-trifluoromethyl-6-(4-trifluoromethyl-phenyl)-pyrimidin-2-yl]-1H-imidazol-4-yl}-pyrimidin-2-ylamine The title compound was prepared from 2-(4-bromo-2-methyl-imidazol-1-yl)-4-trifluoromethyl-6-(4-trifluoromethyl-phenyl)-pyrimidine (example E.60) (0.23 g, 0.5 mmol) and commercially available 2-amino-5-(4,4,5,5-tetramethyl-1,3,2-dioxaborolan-2-yl)pyrimidine (0.13 g, 0.6 mmol) according to the general procedure VI. Obtained as a yellow solid (0.135 g, 58%). MS (ISP) 466.3 [(M+H)$^+$]; mp 286.5° C.

EXAMPLE 144

5-{1-[4-(3,4-Dichloro-phenyl)-6-methyl-pyrimidin-2-yl]-1H-imidazol-4-yl}-pyrimidin-2-ylamine The title compound was prepared from 2-(4-bromo-imidazol-1-yl)-4-(3,4-dichlorophenyl)-6-methyl-pyrimidine (example E.61) (0.16 g, 0.42 mmol) and commercially available 2-amino-5-(4,4,5,5-tetramethyl-1,3,2-dioxaborolan-2-yl) pyrimidine (0.12 g, 0.54 mmol) according to the general procedure VI. Obtained as a yellow solid (0.043 g, 26%). MS (ISP) 398.1 [(M+H)$^+$]; mp 255.5° C.

EXAMPLE 145

5-{1-[4-(3,4-Dichloro-phenyl)-6-methyl-pyrimidin-2-yl]-1H-imidazol-4-yl}-pyridin-2-ylamine The title compound was prepared from 2-(4-bromo-imidazol-1-yl)-4-(3,4-dichlorophenyl)-6-methyl-pyrimidine (example E.61) (0.16 g, 0.42 mmol) and commercially available 2-amino-5-(4,4,5,5-tetramethyl-1,3,2-dioxaborolan-2-yl)

pyridine (0.12 g, 0.54 mmol) according to the general procedure VI. Obtained as a yellow solid (0.06 g, 36%). MS (ISP) 397.1 [(M+H)$^+$]; mp 213° C.

EXAMPLE 146

4-[4-(3,4-Dichloro-phenyl)-6-methyl-pyrimidin-2-yl]-[2,3']bipyridinyl-6'-ylamine The title compound was prepared from 2-(2-chloro-pyridin-4-yl)-4-(3,4-dichlorophenyl)-6-methyl-pyrimidine (example E.63) (0.15 g, 0.43 mmol) and commercially available 2-amino-5-(4,4,5,5-tetramethyl-1,3,2-dioxaborolan-2-yl)pyridine (0.12 g, 0.54 mmol) according to the general procedure VI. Obtained as a yellow solid (0.11 g, 63%). MS (ISP) 408.4 [(M+H)$^+$]; mp 205° C.

EXAMPLE 147

5-{3-[4-(3,4-Dichloro-phenyl)-6-methyl-pyrimidin-2-yl]-phenyl}-pyridin-2-ylamine The title compound was prepared from 2-(3-bromo-phenyl)-4-(3,4-dichloro-phenyl)-6-methyl-pyrimidine (example E.62) (0.2 g, 0.5 mmol) and commercially available 2-amino-5-(4,4,5,5-tetramethyl-1,3,2-dioxaborolan-2-yl)pyridine (0.14 g, 0.65 mmol) according to the general procedure VI. Obtained as an off-white solid (0.11 g, 54%). MS (ISP) 407.4 [(M+H)$^+$]; mp 170.5° C.

EXAMPLE 148

2-(3-Pyridin-4-yl-[1,2,4]triazol-1-yl)-4-trifluoromethyl-6-(4-trifluoromethyl-phenyl)-pyrimidine The title compound was prepared from 2-chloro-4-trifluoromethyl-6-(4-trifluoromethylphenyl)-pyrimidine (example A.2) (0.16 g, 0.5 mmol) and 4-(1H-[1,2,4]-triazol-3-yl)-pyridine [CAS-No. 14803-99-7] (0.075 g, 0.51 mmol) according to the general procedure IVa. Obtained as a white solid (0.096 g, 44%). MS (ISP) 437.3 [(M+H)$^+$]; mp 248° C.

EXAMPLE 149

2-(3-Pyridin-3-yl-[1,2,4]triazol-1-yl)-4-trifluoromethyl-6-(4-trifluoromethyl-phenyl)pyrimidine The title compound was prepared from 2-chloro-4-trifluoromethyl-6-(4-trifluoromethylphenyl)-pyrimidine (example A.2) (0.16 g, 0.5 mmol) and 3-(1H-[1,2,4]-triazol-3-yl)-pyridine [CAS-No. 23195-63-3] (0.075 g, 0.51 mmol) according to the general procedure IVa. Obtained as a light brown solid (0.095 g, 44%). MS (ISP) 437.3 [(M+H)$^+$]; mp 190° C.

EXAMPLE 150

5-{2-Methyl-1-[4-methyl-6-(4-trifluoromethyl-phenyl)-pyrimidin-2-yl]-1H-imidazol-4-yl}-pyridin-2-ylamine The title compound was prepared from 2-(4-bromo-2-methyl-imidazol-1-yl)-4-methyl-6-(4-trifluoromethyl-phenyl)-pyrimidine (example E.64) (0.2 g, 0.5 mmol) and commercially available 2-amino-5-(4,4,5,5-tetramethyl-1,3,2-dioxaborolan-2-yl)pyridine (0.14 g, 0.65 mmol) according to the general procedure VI. Obtained as a light yellow solid (0.11 g, 55%). MS (ISP) 411.0 [(M+H)$^+$]; mp 227.5° C.

EXAMPLE 151

5-{1-[4-Methyl-6-(4-trifluoromethyl-phenyl)-pyrimidin-2-yl]-1H-[1,2,4]triazol-3-yl}-pyridin-2-ylamine The title compound was prepared from 2-(3-chloro-[1,2,4]triazol-1-yl)-4-methyl-6-(4-trifluoromethyl-phenyl)-pyrimidine (example E.65) (0.17 g, 0.5 mmol) and commercially available 2-amino-5-(4,4,5,5-tetramethyl-1,3,2-dioxaborolan-2-yl)pyridine (0.14 g, 0.65 mmol) according to the general procedure VI. Obtained as a light brown solid (0.032 g, 16%). MS (ISP) 398.1 [(M+H)$^+$]; mp 244° C.

EXAMPLE 152

5-{1-[4-Isopropyl-6-(4-trifluoromethyl-phenyl)-pyrimidin-2-yl]-1H-imidazol-4-yl}-pyridin-2-ylamine The title compound was prepared from 2-(4-bromo-imidazol-1-yl)-4-isopropyl-6-(4-trifluoromethyl-phenyl)-pyrimidine (example E.66) (0.21 g, 0.5 mmol) and commercially available 2-amino-5-(4,4,5,5-tetramethyl-1,3,2-dioxaborolan-2-yl)pyridine (0.14 g, 0.65 mmol) according to the general procedure VI. Obtained as a light yellow solid (0.125 g, 59%). MS (ISP) 425.3 [(M+H)$^+$]; mp 274.5° C.

EXAMPLE 153

5-{1-[4-Isopropyl-6-(4-trifluoromethyl-phenyl)-pyrimidin-2-yl]-1H-imidazol-4-yl}-pyrimidin-2-ylamine The title compound was prepared from 2-(4-bromo-imidazol-1-yl)-4-isopropyl-6-(4-trifluoromethyl-phenyl)-pyrimidine (example E.66) (0.21 g, 0.5 mmol) and commercially available 2-amino-5-(4,4,5,5-tetramethyl-1,3,2-dioxaborolan-2-yl)pyrimidine (0.14 g, 0.65 mmol) according to the general procedure VI. Obtained as an off-white solid (0.052 g, 24%). MS (ISP) 426.1 [(M+H)$^+$]; mp 277° C.

EXAMPLE 154

5-{5-Methyl-1-[4-trifluoromethyl-6-(4-trifluoromethyl-phenyl)-pyrimidin-2-yl]-1H-imidazol-4-yl}-pyridin-2-ylamine The title compound was prepared from 2-(4-iodo-5-methyl-imidazol-1-yl)-4-trifluoromethyl-6-(4-trifluoromethyl-phenyl)-pyrimidine (example E.67) (0.25 g, 0.5 mmol) and commercially available 2-amino-5-(4,4,5,5-tetramethyl-1,3,2-dioxaborolan-2-yl)pyridine (0.13 g, 0.6 mmol) according to the general procedure VI. Obtained as a yellow solid (0.12 g, 50%). MS (ISP) 465.1 [(M+H)$^+$]; mp 252° C.

EXAMPLE 155

3'-[4-Trifluoromethyl-6-(4-trifluoromethyl-phenyl)-pyrimidin-2-yl]-biphenyl-3-sulfonic acid tert-butylamide The title compound was prepared from 2-(3-bromo-phenyl)-4-trifluoromethyl-6-(4-trifluoromethyl-phenyl)-pyrimidine (example E.3) (0.45 g, 1.0 mmol) and commercially available 3-(tert.-butylsulfamoyl)-phenylboronic acid (0.31 g, 1.2 mmol) according to the general procedure VI. Obtained as a white solid (0.48 g, 83%). MS (ISP) 580.3 [(M+H)$^+$]; mp 200° C.

EXAMPLE 156

N-tert-Butyl-3-{4-[4-trifluoromethyl-6-(4-trifluoromethyl-phenyl)-pyrimidin-2-yl]-pyridin-2-yl}-benzenesulfonamide The title compound was prepared from 2-(2-chloro-pyridin-4-yl)-4-trifluoromethyl-6-(4-trifluoromethyl-phenyl)-pyrimidine (example E.6) (0.404 g, 1.0 mmol) and commercially available 3-(tert.-butylsulfamoyl)-phenylboronic acid (0.31 g, 1.2 mmol) according to the general procedure VI. Obtained as an off-white solid (0.51 g, 88%). MS (ISP) 581.3 $[(M+H)^+]$; mp 211° C.

EXAMPLE 157

3'-[4-Trifluoromethyl-6-(4-trifluoromethyl-phenyl)-pyrimidin-2-yl]-biphenyl-3-sulfonic acid amide To a cooled and stirred solution of 3'-[4-trifluoromethyl-6-(4-trifluoromethyl-phenyl)-pyrimidin-2-yl]-biphenyl-3-sulfonic acid tert-butylamide (example 155) (0.38 g, 0.65 mmol) in dichloromethane (5 mL) was added TFA (5 mL) and the reaction mixture was allowed to stir at room temperature for 15 h. The mixture was evaporated to dryness and saturated $NaHCO_3$ solution (5 mL), diethyl ether and heptane were added. The mixture was stirred at room temperature for 1 h, the precipitate was collected by filtration, washed with water and heptane and dried to yield the title compound as a white solid (0.31 g, 90%). MS (ISN) 522.3 $[(M-H)^-]$; mp 267° C.

EXAMPLE 158

3-{4-[4-Trifluoromethyl-6-(4-trifluoromethyl-phenyl)-pyrimidin-2-yl]-pyridin-2-yl}-benzenesulfonamide To a cooled and stirred solution of N-tert-butyl-3-{4-[4-trifluoromethyl-6-(4-trifluoromethyl-phenyl)-pyrimidin-2-yl]-pyridin-2-yl}-benzenesulfonamide (example 156) (0.4 g, 0.69 mmol) in dichloromethane (5 mL) was added TFA (5 mL) and the reaction mixture was allowed to stir at room temperature for 15 h. The mixture was evaporated to dryness and saturated $NaHCO_3$ solution (5 mL), diethyl ether and heptane were added. The mixture was stirred at room temperature for 1 h, the precipitate was collected by filtration, washed with water and heptane and dried to yield the title compound as an off-white solid (0.31 g, 90%). MS (ISN) 523.7 $[(M-H)^-]$; mp 237° C.

EXAMPLE 159

4-{1-[4-Trifluoromethyl-6-(4-trifluoromethyl-phenyl)-pyrimidin-2-yl]-1H-imidazol-4-yl}-benzenesulfonamide 1) N-tert-Butyl-4-{1-[4-trifluoromethyl-6-(4-trifluoromethyl-phenyl)-pyrimidin-2-yl]-1H-imidazol-4-yl}-benzenesulfonamide was prepared from 2-(4-iodo-imidazol-1-yl)-4-trifluoromethyl-6-(4-trifluoromethyl-phenyl)-pyrimidine (example E.68) (0.48 g, 1.0 mmol) and commercially available 4-(tert.-butylsulfamoyl)-phenylboronic acid (0.31 g, 1.2 mmol) according to the general procedure VI. Obtained as a light brown solid (0.043 g) which was subsequently deprotected.

2) To a cooled and stirred solution of N-tert-butyl-4-{1-[4-trifluoromethyl-6-(4-trifluoromethyl-phenyl)-pyrimidin-2-yl]-1H-imidazol-4-yl}-benzenesulfonamide (0.043 g) in dichloromethane (1.5 mL) was added TFA (1.5 mL) and the reaction mixture was allowed to stir at room temperature for 15 h. The mixture was evaporated to dryness and saturated $NaHCO_3$ solution (2 mL), diethyl ether and heptane were added. The mixture was stirred at room temperature for 1 h, the precipitate was collected by filtration, washed with water and heptane and dried to yield the title compound as an off-white solid (0.029 g, 6%). MS (ISP) 514.3 $[(M+H)^+]$; mp 292° C.

EXAMPLE 160

3-{1-[4-Trifluoromethyl-6-(4-trifluoromethyl-phenyl)-pyrimidin-2-yl]-1H-imidazol-4-yl}-benzenesulfonamide 1) N-tert-Butyl-3-{1-[4-trifluoromethyl-6-(4-trifluoromethyl-phenyl)-pyrimidin-2-yl]-1H-imidazol-4-yl}-benzenesulfonamide was prepared from 2-(4-iodo-imidazol-1-yl)-4-trifluoromethyl-6-(4-trifluoromethyl-phenyl)-pyrimidine (example E.68) (0.73 g, 1.5 mmol) and commercially available 3-(tert.-butylsulfamoyl)-phenylboronic acid (0.46 g, 1.8 mmol) according to the general procedure VI. Obtained as a light brown solid (0.128 g), which was subsequently deprotected.

2) To a cooled and stirred solution of N-tert-butyl-3-{1-[4-trifluoromethyl-6-(4-trifluoromethyl-phenyl)-pyrimidin-2-yl]-1H-imidazol-4-yl}-benzenesulfonamide (0.128 g) in dichloromethane (3 mL) was added TFA (3 mL) and the reaction mixture was allowed to stir at room temperature for 15 h. The mixture was evaporated to dryness and purified by flash chromatography (heptane/ethyl acetate) and crystallization (dichloromethane/MeOH/hexane) to yield the title compound as a white solid (0.079 g, 10%). MS (ISP) 514.3 $[(M+H)^+]$; mp 198° C.

EXAMPLE 161

5-{3-[4-Trifluoromethyl-6-(4-trifluoromethyl-phenyl)-pyrimidin-2-yl]-phenyl}-thiophene-2-sulfonic acid amide 1) N-tert-Butyl-5-{3-[4-trifluoromethyl-6-(4-trifluoromethyl-phenyl)-pyrimidin-2-yl]-phenyl}-thiophene-2-sulfonic acid amide was prepared from 2-(3-bromo-phenyl)-4-trifluoromethyl-6-(4-trifluoromethyl-phenyl)-pyrimidine (example E.3) (0.45 g, 1.0 mmol) and N-tert-butyl-5-(4,4,5,5-tetramethyl-1,3,2-dioxaborolan-2-yl)-thiophene-2-sulfonamide (example F.1) (0.41 g, 1.2 mmol) according to the general procedure VI. Obtained as a light brown solid (0.44 g), which was subsequently deprotected.

2) To a cooled and stirred solution of N-tert-butyl-5-{3-[4-trifluoromethyl-6-(4-trifluoromethyl-phenyl)-pyrimidin-2-yl]-phenyl}-thiophene-2-sulfonic acid amide (0.44 g) in dichloromethane (7 mL) was added TFA (7 mL) and the reaction mixture was allowed to stir at room temperature for 15 h. The mixture was evaporated to dryness and purified by flash chromatography (heptane/ethyl acetate) and crystallization (dichloromethane/MeOH/hexane) to yield the title compound as an off-white solid (0.2 g, 38%). MS (ISN) 528.0 $[(M-H)^-]$; mp 204° C.

EXAMPLE 162

5-{4-[4-Trifluoromethyl-6-(4-trifluoromethyl-phenyl)-pyrimidin-2-yl]-pyridin-2-yl}-thiophene-2-sulfonic acid tert-butylamide The title compound was prepared from 2-(2-chloro-pyridin-4-yl)-4-trifluoromethyl-6-(4-trifluoromethyl-phenyl)-pyrimidine (example E.6) (0.404 g, 1.0 mmol) and N-tert-butyl-5-(4,4,5,5-tetramethyl-1,3,2-dioxaborolan-2-yl)-thiophene-2-sulfonamide (example F.1) (0.41 g, 1.2 mmol) according to the general procedure VI. Obtained as an off-white solid (0.24 g, 41%). MS (ISN) 585.2 [$(M-H)^-$]; mp 237° C.

EXAMPLE 163

5-{1-[4-Trifluoromethyl-6-(4-trifluoromethyl-phenyl)-pyrimidin-2-yl]-1H-imidazol-4-yl}-thiophene-2-sulfonic acid amide 1) 5-{1-[4-Trifluoromethyl-6-(4-trifluoromethyl-phenyl)-pyrimidin-2-yl]-1H-imidazol-4-yl}-thiophene-2-sulfonic acid tert-butyl amide was prepared from 2-(4-iodo-imidazol-1-yl)-4-trifluoromethyl-6-(4-trifluoromethyl-phenyl)-pyrimidine (example E.68) (0.73 g, 1.5 mmol) and N-tert-butyl-5-(4,4,5,5-tetramethyl-1,3,2-dioxaborolan-2-yl)-thiophene-2-sulfonamide (example F.1) (0.62 g, 1.8 mmol) according to the general procedure VI. Obtained as a light brown solid (0.43 g), which was subsequently deprotected.

2) To a cooled and stirred solution of 5-{1-[4-trifluoromethyl-6-(4-trifluoromethylphenyl)-pyrimidin-2-yl]-1H-imidazol-4-yl}-thiophene-2-sulfonic acid tert-butyl amide (0.43 g) in dichloromethane (6 mL) was added TFA (6 mL) and the reaction mixture was allowed to stir at room temperature for 15 h. The mixture was evaporated to dryness and purified by flash chromatography (heptane/ethyl acetate) and crystallization (dichloromethane/MeOH/hexane) to yield the title compound as a white solid (0.062 g, 8%). MS (ISN) 518.3 [$(M-H)^-$]; mp 281° C.

EXAMPLE 164

5-{4-[4-Trifluoromethyl-6-(4-trifluoromethyl-phenyl)-pyrimidin-2-yl]-pyridin-2-yl}-thiophene-2-sulfonic acid amide To a cooled and stirred solution of 5-{4-[4-trifluoromethyl-6-(4-trifluoromethylphenyl)-pyrimidin-2-yl]-pyridin-2-yl}-thiophene-2-sulfonic acid tert-butylamide (example 162) (0.2 g, 0.34 mmol) in dichloromethane (3 mL) was added TFA (3 mL) and the reaction mixture was allowed to stir at room temperature for 15 h. The mixture was evaporated to dryness and purified by flash chromatography (heptane/ethyl acetate) to yield the title compound as an off-white solid (0.12 g, 67%). MS (ISN) 529.3 [$(M-H)^-$]; mp 262° C.

EXAMPLE 165

3'-[4-Methyl-6-(4-trifluoromethyl-phenyl)-pyrimidin-2-yl]-biphenyl-3-sulfonic acid tert-butylamide The title compound was prepared from 2-(3-bromo-phenyl)-4-(4-trifluoromethylphenyl)-6-methyl-pyrimidine (example E.47) (0.39 g, 1.0 mmol) and commercially available 3-(tert.-butylsulfamoyl)-phenylboronic acid (0.31 g, 1.2 mmol) according to the general procedure VI. Obtained as a white solid (0.4 g, 76%). MS (ISP) 526.3 [$(M+H)^+$]; mp 163° C.

EXAMPLE 166

3'-[4-(4-Chloro-phenyl)-6-methyl-pyrimidin-2-yl]-biphenyl-3-sulfonic acid amide 1) 3'-[4-(4-Chloro-phenyl)-6-methyl-pyrimidin-2-yl]-biphenyl-3-sulfonic acid tert-butylamide was prepared from 2-(3-bromo-phenyl)-4-(4-chloro-phenyl)-6-methyl-pyrimidine (example E.44) (0.11 g, 0.3 mmol) and commercially available 3-(tert.-butylsulfamoyl)-phenylboronic acid (0.09 g, 0.35 mmol) according to the general procedure VI. Obtained as a light brown solid (0.16 g), which was subsequently deprotected.

2) To a cooled and stirred solution of 3'-[4-(4-chloro-phenyl)-6-methyl-pyrimidin-2-yl]-biphenyl-3-sulfonic acid tert-butylamide (0.16 g) in dichloromethane (3 mL) was added TFA (3 mL) and the reaction mixture was allowed to stir at room temperature for 15 h. The mixture was evaporated to dryness and saturated $NaHCO_3$ solution (5 mL), diethyl ether and heptane were added. The mixture was stirred at room temperature for 1 h, the precipitate was collected by filtration, washed with water and heptane and dried to yield the title compound as an off-white solid (0.083, 63%). MS (ISP) 436.1 [$(M+H)^+$]; mp 221° C.

EXAMPLE 167

3'-[4-Methyl-6-(4-trifluoromethyl-phenyl)-pyrimidin-2-yl]-biphenyl-3-sulfonic acid amide To a cooled and stirred solution of 3'-[4-methyl-6-(4-trifluoromethyl-phenyl)-pyrimidin-2-yl]-biphenyl-3-sulfonic acid tert-butylamide (example 165) (0.3 g, 0.57 mmol) in dichloromethane (5 mL) was added TFA (5 mL) and the reaction mixture was allowed to stir at room temperature for 15 h. The mixture was evaporated to dryness and saturated $NaHCO_3$ solution (5 mL), diethyl ether and heptane were added. The mixture was stirred at room temperature for 1 h, the precipitate was collected by filtration, washed with water and heptane and dried to yield the title compound as a white solid (0.24 g, 90%). MS (ISP) 570.3 [$(M+H)^+$]; mp 224.5° C.

EXAMPLE 168

3-{4-[4-Methyl-6-(4-trifluoromethyl-phenyl)-pyrimidin-2-yl]-pyridin-2-yl}-benzenesulfonamide 1) N-tert-Butyl-3-{4-[4-methyl-6-(4-trifluoromethyl-phenyl)-pyrimidin-2-yl]-pyridin-2-yl}-benzenesulfonamide was prepared from 2-(2-chloro-pyridin-4-yl)-4-methyl-6-(4-trifluoromethyl-phenyl)-pyrimidine (example E.46) (0.29 g, 0.83 mmol) and commercially available 3-(tert.-butylsulfamoyl)-phenylboronic acid (0.26 g, 1.0 mmol) according to the general procedure VI. Obtained as a light brown solid (0.23 g), which was subsequently deprotected.

2) To a cooled and stirred solution of N-tert-butyl-3-{4-[4-methyl-6-(4-trifluoromethylphenyl)-pyrimidin-2-yl]-pyridin-2-yl}-benzenesulfonamide (0.23 g) in dichloromethane (4 mL) was added TFA (4 mL) and the reaction mixture was allowed to stir at room temperature for 15 h. The mixture was evaporated to dryness and purified by flash chromatography (heptane/ethyl acetate) and crystallization (dichloromethane/

MeOH/hexane) to yield the title compound as a white solid (0.081, 21%). MS (ISP) 471.5 [$(M+H)^+$]; mp 218.5° C.

EXAMPLE 169

5-{3-[4-(4-Chloro-phenyl)-6-trifluoromethyl-pyrimidin-2-yl]-phenyl}-thiophene-2-sulfonic acid tert-butylamide The title compound was prepared from 2-(3-bromo-phenyl)-4-(4-chloro-phenyl)-6-trifluoromethyl-pyrimidine (example E.4) (0.414 g, 1.0 mmol) and N-tert-butyl-5-(4,4,5,5-tetramethyl-1,3,2-dioxaborolan-2-yl)-thiophene-2-sulfonamide (example F.1) (0.41 g, 1.2 mmol) according to the general procedure VI. Obtained as a white solid (0.22 g, 40%). MS (ISN) 550.2 [$(M-H)^-$]; mp 197.5° C.

EXAMPLE 170

5-{4-[4-(4-Chloro-phenyl)-6-trifluoromethyl-pyrimidin-2-yl]-pyridin-2-yl}-thiophene-2-sulfonic acid amide 1) 5-{4-[4-(4-Chloro-phenyl)-6-trifluoromethyl-pyrimidin-2-yl]-pyridin-2-yl}-thiophene-2-sulfonic acid tert-butyl amide was prepared from 4-(4-chloro-phenyl)-2-(2-chloro-pyridin-4-yl)-6-trifluoromethyl-pyrimidine (example E.5) (0.37 g, 1.0 mmol) and N-tert-butyl-5-(4,4,5,5-tetramethyl-1,3,2-dioxaborolan-2-yl)-thiophene-2-sulfonamide (example F.1) (0.41 g, 1.2 mmol) according to the general procedure VI. Obtained as a light brown solid (0.25 g), which was subsequently deprotected.

2) To a cooled and stirred solution of 5-{4-[4-(4-chloro-phenyl)-6-trifluoromethyl-pyrimidin-2-yl]-pyridin-2-yl}-thiophene-2-sulfonic acid tert-butyl amide (0.25 g) in dichloromethane (6 mL) was added TFA (6 mL) and the reaction mixture was allowed to stir at room temperature for 15 h. The mixture was evaporated to dryness and purified by flash chromatography (heptane/ethyl acetate) and crystallization (THF/hexane) to yield the title compound as a white solid (0.13 g, 26%). MS (ISN) 495.2 [$(M-H)^-$]; mp 290° C.

EXAMPLE 171

5-{1-[4-(4-Chloro-phenyl)-6-trifluoromethyl-pyrimidin-2-yl]-1H-imidazol-4-yl}-thiophene-2-sulfonic acid amide 1) 5-{1-[4-(4-Chloro-phenyl)-6-trifluoromethyl-pyrimidin-2-yl]-1H-imidazol-4-yl}-thiophene-2-sulfonic acid tert-butyl amide was prepared from 4-(4-chloro-phenyl)-2-(4-iodo-imidazol-1-yl)-6-trifluoromethyl-pyrimidine (example E.70) (0.68 g, 1.5 mmol) and N-tert-butyl-5-(4,4,5,5-tetramethyl-1,3,2-dioxaborolan-2-yl)-thiophene-2-sulfonamide (example F.1) (0.62 g, 1.8 mmol) according to the general procedure VI. Obtained as a light brown solid (0.52 g), which was subsequently deprotected.

2) To a cooled and stirred solution of 5-{1-[4-(4-chloro-phenyl)-6-trifluoromethyl-pyrimidin-2-yl]-1H-imidazol-4-yl}-thiophene-2-sulfonic acid tert-butyl amide (0.52 g) in dichloromethane (6 mL) was added TFA (6 mL) and the reaction mixture was allowed to stir at room temperature for 15 h. The mixture was evaporated to dryness and saturated $NaHCO_3$ solution (4 mL), diethyl ether and heptane were added. The mixture was stirred at room temperature for 1 h, the precipitate was collected by filtration and further purified by flash chromatography (heptane/ethyl acetate) and crystallization (THF/hexane) to yield the title compound as a light yellow solid (0.045 g, 6%). MS (ISN) 484.2 [$(M-H)^-$]; mp 284° C.

EXAMPLE 172

5-{3-[4-Methyl-6-(4-trifluoromethyl-phenyl)-pyrimidin-2-yl]-phenyl}-thiophene-2-sulfonic acid amide 1) N-tert-Butyl-5-{3-[4-methyl-6-(4-trifluoromethyl-phenyl)-pyrimidin-2-yl]-phenyl}-thiophene-2-sulfonic acid amide was prepared from 2-(3-bromo-phenyl)-6-methyl-4-(4-trifluoromethyl-phenyl)-pyrimidine (example E.47) (0.39 g, 1.0 mmol) and N-tert-butyl-5-(4,4,5,5-tetramethyl-1,3,2-dioxaborolan-2-yl)-thiophene-2-sulfonamide (example F.1) (0.41 g, 1.2 mmol) according to the general procedure VI. Obtained as a light yellow solid (0.16 g), which was subsequently deprotected.

2) To a cooled and stirred solution of N-tert-butyl-5-{3-[4-methyl-6-(4-trifluoromethylphenyl)-pyrimidin-2-yl]-phenyl}-thiophene-2-sulfonic acid amide (0.16 g) in dichloromethane (3 mL) was added TFA (3 mL) and the reaction mixture was allowed to stir at room temperature for 15 h. The mixture was evaporated to dryness and saturated $NaHCO_3$ solution (4 mL), diethyl ether and heptane were added. The mixture was stirred at room temperature for 1 h, the precipitate was collected by filtration, further purified by flash chromatography (heptane/ethyl acetate) and crystallization (dichloromethane/heptane) to yield the title compound as an off-white solid (0.098 g, 21%). MS (ISP) 476.0 [$(M+H)^+$]; mp 225° C.

EXAMPLE 173

5-{3-[4-(4-Chloro-phenyl)-6-methyl-pyrimidin-2-yl]-phenyl}-thiophene-2-sulfonic acid amide 1) N-tert-Butyl-5-{3-[6-(4-chloro-phenyl)-4-methyl-pyrimidin-2-yl]-phenyl}-thiophene-2-sulfonic acid amide was prepared from 2-(3-bromo-phenyl)-4-(4-chloro-phenyl)-6-methyl-pyrimidine (example E.44) (0.36 g, 1.0 mmol) and N-tert-butyl-5-(4,4,5,5-tetramethyl-1,3,2-dioxaborolan-2-yl)-thiophene-2-sulfonamide (example F.1) (0.41 g, 1.2 mmol) according to the general procedure VI. Obtained as a light yellow solid (0.14 g), which was subsequently deprotected.

2) To a cooled and stirred solution of N-tert-butyl-5-{3-[6-(4-chloro-phenyl)-4-methyl-pyrimidin-2-yl]-phenyl}-thiophene-2-sulfonic acid amide (0.14 g) in dichloromethane (3 mL) was added TFA (3 mL) and the reaction mixture was allowed to stir at room temperature for 15 h. The mixture was evaporated to dryness and saturated $NaHCO_3$ solution (4 mL), diethyl ether and heptane were added. The mixture was stirred at room temperature for 1 h, the precipitate was collected by filtration and further purified by flash chromatography (heptane/ethyl acetate) and crystallization (dichloromethane/heptane) to yield the title compound as an off-white solid (0.087 g, 20%). MS (ISP) 442.4 [$(M+H)^+$]; mp 227° C.

EXAMPLE 174

5-{3-[4-(4-Chloro-phenyl)-6-trifluoromethyl-pyrimidin-2-yl]-phenyl}-thiophene-2-sulfonic acid amide To a cooled and stirred solution of 5-{3-[4-(4-chloro-phenyl)-6-trifluoromethyl-pyrimidin-2-yl]-phenyl}-thiophene- 2-sulfonic acid tert-butylamide (example 169) (0.175 g, 0.32 mmol) in dichloromethane (4 mL) was added TFA (5 mL) and the reaction mixture was allowed to stir at room temperature for 15 h. The mixture was evaporated to dryness and saturated $NaHCO_3$ solution (4 mL), diethyl ether and heptane were added. The mixture was stirred at room temperature for 1 h, the precipitate was collected by filtration, washed with water and heptane and dried to yield the title compound as a white solid (0.12 g, 75%). MS (ISN) 494.1 [$(M-H)^-$]; mp 226° C.

EXAMPLE 175

4-{1-[4-(4-Chloro-phenyl)-6-trifluoromethyl-pyrimidin-2-yl]-1H-imidazol-4-yl}-benzenesulfonamide 1) N-tert-Butyl-4-{1-[6-(4-chloro-phenyl)-4-trifluoromethyl-pyrimidin-2-yl]-1H-imidazol-4-yl}-benzenesulfonamide was prepared from 4-(4-chloro-phenyl)-2-(4-iodo-imidazol-1-yl)-6-trifluoromethyl-pyrimidine (example E.70) (0.68 g, 1.5 mmol) and commercially available 4-(tert.-butylsulfamoyl)-phenylboronic acid (0.46 g, 1.8 mmol) according to the general procedure VI. Obtained as a light yellow solid (0.26 g) which was subsequently deprotected.

2) To a cooled and stirred solution of N-tert-butyl-4-{1-[6-(4-chloro-phenyl)-4-trifluoromethyl-pyrimidin-2-yl]-1H-imidazol-4-yl}-benzenesulfonamide (0.26 g) in dichloromethane (6 mL) was added TFA 1. (6 mL) and the reaction mixture was allowed to stir at room temperature for 15 h. The mixture was evaporated to dryness and saturated $NaHCO_3$ solution (3 mL), diethyl ether and heptane were added. The mixture was stirred at room temperature for 1 h, the precipitate was collected by filtration, washed with water and heptane and dried to yield the title compound as an off-white solid (0.073 g, 10%). MS (ISN) 478.0 [$(M-H)^-$]; mp 324° C.

EXAMPLE 176

3-{1-[4-(4-Chloro-phenyl)-6-methyl-pyrimidin-2-yl]-1H-imidazol-4-yl}-benzenesulfonamide 1) N-tert-Butyl-3-{1-[6-(4-chloro-phenyl)-4-methyl-pyrimidin-2-yl]-1H-imidazol-4-yl}-benzenesulfonamide was prepared from 4-(4-chloro-phenyl)-2-(4-iodo-imidazol-1-yl)-6-methyl-pyrimidine (example E.69) (0.40 g, 1.0 mmol) and commercially available 3-(tert.-butylsulfamoyl)-phenylboronic acid (0.39 g, 1.5 mmol) according to the general procedure VI. Obtained as a light yellow solid (0.103 g) which was subsequently deprotected.

2) To a cooled and stirred solution of N-tert-butyl-3-{1-[6-(4-chloro-phenyl)-4-methyl-pyrimidin-2-yl]-1H-imidazol-4-yl}-benzenesulfonamide (0.103 g) in dichloromethane (3 mL) was added TFA (3 mL) and the reaction mixture was allowed to stir at room temperature for 15 h. The mixture was evaporated to dryness and saturated $NaHCO_3$ solution (3 mL), diethyl ether and heptane were added. The mixture was stirred at room temperature for 1 h, the precipitate was collected by filtration, washed with water and heptane and dried to yield the title compound as a white solid (0.046 g, 11%). MS (ISP) 426.0 [$(M+H)^+$]; mp 275° C.

EXAMPLE 177

3-{1-[4-(4-Chloro-phenyl)-6-trifluoromethyl-pyrimidin-2-yl]-1H-imidazol-4-yl}-benzenesulfonamide 1) N-tert-Butyl-3-{1-[6-(4-chloro-phenyl)-4-trifluoromethyl-pyrimidin-2-yl]-1H-imidazol-4-yl}-benzenesulfonamide was prepared from 4-(4-chloro-phenyl)-2-(4-iodo-imidazol-1-yl)-6-trifluoromethyl-pyrimidine (example E.70) (0.68 g, 1.5 mmol) and commercially available 3-(tert.-butylsulfamoyl)-phenylboronic acid (0.46 g, 1.8 mmol) according to the general procedure VI. Obtained as a light yellow solid (0.34 g) which was subsequently deprotected.

2) To a cooled and stirred solution of N-tert-butyl-3-{1-[6-(4-chloro-phenyl)-4-trifluoromethyl-pyrimidin-2-yl]-1H-imidazol-4-yl}-benzenesulfonamide (0.34 g) in dichloromethane (6 mL) was added TFA (6 mL) and the reaction mixture was allowed to stir at room temperature for 15 h. The mixture was evaporated to dryness and saturated $NaHCO_3$ solution (3 mL), diethyl ether and heptane were added. The mixture was stirred at room temperature for 1 h, the precipitate was collected by filtration, washed with water and heptane and dried to yield the title compound as an off-white solid (0.24 g, 34%). MS (ISN) 478.0 [$(M-H)^-$]; mp 225° C.

EXAMPLE 178

3'-[4-(4-Chloro-phenyl)-6-trifluoromethyl-pyrimidin-2-yl]-biphenyl-3-sulfonic acid amide 1) 3'-[4-(4-Chloro-phenyl)-6-trifluoromethyl-pyrimidin-2-yl]-biphenyl-3-sulfonic acid tert-butylamide was prepared from 2-(3-bromo-phenyl)-4-(4-chloro-phenyl)-6-trifluoromethyl-pyrimidine (example E.4) (0.41 g, 1.0 mmol) and commercially available 3-(tert.-butylsulfamoyl)-phenylboronic acid (0.31 g, 1.2 mmol) according to the general procedure VI. Obtained as white foam (0.47 g), which was subsequently deprotected.

2) To a cooled and stirred solution of 3'-[4-(4-chloro-phenyl)-6-trifluoromethyl-pyrimidin-2-yl]-biphenyl-3-sulfonic acid tert-butylamide (0.47 g) in dichloromethane (6 mL) was added TFA (6 mL) and the reaction mixture was allowed to stir at room temperature for 15 h. The mixture was evaporated to dryness and saturated $NaHCO_3$ solution (5 mL), diethyl ether and heptane were added. The mixture was stirred at room temperature for 1 h, the precipitate was collected by filtration, washed with water and heptane and dried to yield the title compound as an white solid (0.31 g, 63%). MS (ISN) 488.1 [$(M-H)^-$]; mp 165° C.

EXAMPLE 179

3-{4-[4-(4-Chloro-phenyl)-6-trifluoromethyl-pyrimidin-2-yl]-pyridin-2-yl}-benzenesulfonamide 1) 3-{4-[4-(4-Chloro-phenyl)-6-trifluoromethyl-pyrimidin-2-yl]-pyridin-2-yl}-benzenesulfonic acid tert-butylamide was prepared from 4-(4-chloro-phenyl)-2-(2-chloro-pyridin-4-yl)-6-trifluoromethyl-pyrimidine (example E.5) (0.37 g, 1.0 mmol) and commercially available 3-(tert.-butylsulfamoyl)-phenylboronic acid (0.31 g, 1.2 mmol) according to the general procedure VI. Obtained as a light brown solid (0.41 g), which was subsequently deprotected.

2) To a cooled and stirred solution of 3-{4-[4-(4-chloro-phenyl)-6-trifluoromethyl-pyrimidin-2-yl]-pyridin-2-yl}-benzenesulfonic acid tert-butylamide (0.41 g) in dichloromethane (6 mL) was added TFA (6 mL) and the reaction mixture was allowed to stir at room temperature for 15 h. The mixture was evaporated to dryness and saturated $NaHCO_3$ solution (5 mL), diethyl ether and heptane were added. The mixture was stirred at room temperature for 1 h, the precipitate was collected by filtration, washed with water and heptane and dried to yield the title compound as an off-white solid (0.31 g, 63%). MS (ISN) 489.1 [$(M-H)^-$]; mp 182° C.

EXAMPLE 180

4-{1-[4-(4-Chloro-phenyl)-6-methyl-pyrimidin-2-yl]-1H-imidazol-4-yl}-benzenesulfonamide 1) N-tert-Butyl-4-{1-[6-(4-chloro-phenyl)-4-methyl-pyrimidin-2-yl]-1H-imidazol-4-yl}-benzenesulfonamide was prepared from 4-(4-chloro-phenyl)-2-(4-iodo-imidazol-1-yl)-6-methyl-pyrimidine (example E.69) (0.40 g, 1.0 mmol) and commercially available 4-(tert.-butylsulfamoyl)-phenylboronic acid (0.39 g, 1.5 mmol) according to the general procedure VI. Obtained as a light brown solid (0.64 g) which was subsequently deprotected.

2) To a cooled and stirred solution of N-tert-butyl-4-{1-[6-(4-chloro-phenyl)-4-methyl-pyrimidin-2-yl]-1H-imidazol-4-yl}-benzenesulfonamide (0.64 g) in dichloromethane (7 mL) was added TFA (7 mL) and the reaction mixture was allowed to stir at room temperature for 15 h. The mixture was evaporated to dryness and saturated $NaHCO_3$ solution (5 mL), diethyl ether and heptane were added. The mixture was stirred at room temperature for 1 h, the precipitate was collected by filtration, washed with water and heptane and dried to yield the title compound as an off-white solid (0.051 g, 12%). MS (ISP) 426.1 [$(M+H)^+$]; mp 312° C.

EXAMPLE 181

2-{1-[4-Trifluoromethyl-6-(4-trifluoromethyl-phenyl)-pyrimidin-2-yl]-1H-imidazol-4-yl}-thiazole-5-sulfonic acid amide 1) A stirred mixture of 2-(4-tributylstannanyl-imidazol-1-yl)-4-trifluoromethyl-6-(4-trifluoromethyl-phenyl)-pyrimidine (Example G.1) (0.265 g, 0.41 mmol), 2-chloro-thiazole-5-sulfonic acid tert-butylamide (Example H.1) (0.115 g, 0.45 mmol), tetrakis(triphenylphosphine)palladium (0.028 g, 0.024 mmol) in toluene (5 mL) was heated under reflux conditions for 15 h. The mixture was poured into saturated potassiumfluoride solution (5 mL), water (20 mL) was added and the water layer was extracted with ethyl acetate (2×30 mL). The combined organic layers were washed with brine (30 mL), dried ($MgSO_4$) and evaporated. The crude product was purified by flash chromatography (heptane/ethyl acetate) and crystallization (THF/hexane) to yield N-tert-butyl-2-{1-[4-trifluoromethyl-6-(4-trifluoromethyl-phenyl)pyrimidin-2-yl]-1H-imidazol-4-yl}-thiazole-5-sulfonamide (0.081) as a light brown solid. Mp 281° C.

2) To a cooled and stirred solution of N-tert-butyl-2-{1-[4-trifluoromethyl-6-(4-trifluoromethyl-phenyl)-pyrimidin-2-yl]-1H-imidazol-4-yl}-thiazole-5-sulfonamide (0.075 g) in dichloromethane (3 mL) was added TFA (3 mL) and the reaction mixture was allowed to stir at room temperature for 15 h. The mixture was evaporated to dryness and purified by flash-chromatography on silica gel (ethyl acetate/hexane) and crystallization (THF/hexane) to yielded the title compound as a light brown solid (0.037 g, 18%). MS (ISN) 519.0 [$(M-H)^-$]; mp 264° C.

EXAMPLE 182

2-{1-[4-(4-Chloro-phenyl)-6-trifluoromethyl-pyridin-2-yl]-1H-imidazol-4-yl}-thiazole-5-sulfonic acid amide 1) A stirred mixture of 4-(4-chloro-phenyl)-2-(4-tributylstannanyl-imidazol-1-yl)-6-trifluoromethyl-pyrimidine (Example G.2) (0.28 g, 0.46 mmol), 2-chloro-thiazole-5-sulfonic acid tert-butylamide (Example H.1) (0.128 g, 0.5 mmol), tetrakis(triphenyl-phosphine)palladium (0.032 g, 0.028 mmol) in toluene (5 mL) was heated under reflux conditions for 15 h. The mixture was poured into saturated potassiumfluoride solution (5 mL), water (20 mL) was added and the water layer was extracted with ethyl acetate (2×30 mL). The combined organic layers were washed with brine (30 mL), dried ($MgSO_4$) and evaporated. The crude product was purified by flash chromatography (heptane/ethyl acetate) and crystallization (THF/hexane) to yield N-tert-butyl-2-{1-[4-(4-chloro-phenyl)-6-trifluoromethyl-pyrimidin-2-yl]-1H-imidazol-4-yl}-thiazole-5-sulfonamide (0.094) as a light brown solid. Mp 261° C.

2) To a cooled and stirred solution of N-tert-butyl-2-{1-[4-(4-chloro-phenyl)-6-trifluoromethyl-pyrimidin-2-yl]-1H-imidazol-4-yl}-thiazole-5-sulfonamide (0.088 g) in dichloromethane (3 mL) was added TFA (3 mL) and the reaction mixture was allowed to stir at room temperature for 15 h. The mixture was evaporated to dryness and purified by flash-chromatography on silica gel (ethyl acetate/hexane) and crystallization (THF/hexane) to yielded the title compound as a light brown solid (0.03 g, 14%). MS (ISN) 485.2 [$(M-H)^-$]; mp 263° C.

EXAMPLE 183

4-{1-[4-Methyl-6-(4-trifluoromethyl-phenyl)-pyrimidin-2-yl]-1H-imidazol-4-yl}-benzenesulfonamide 1) N-tert-Butyl-4-{1-[4-methyl-6-(4-trifluoromethyl-phenyl)-pyrimidin-2-yl]-1H-imidazol-4-yl}-benzenesulfonamide was prepared from 2-(4-iodo-imidazol-1-yl)-6-methyl-4-(4-trifluoromethyl-phenyl)-pyrimidine (example E.71) (0.43 g, 1.0 mmol) and commercially available 4-(tert.-butylsulfamoyl)-phenylboronic acid (0.39 g, 1.5 mmol) according to the general procedure VI. Obtained as a light brown solid (0.2 g) which was subsequently deprotected.

2) To a cooled and stirred solution of N-tert-butyl-4-{1-[4-methyl-6-(4-trifluoromethylphenyl)-pyrimidin-2-yl]-1H-imidazol-4-yl}-benzenesulfonamide (0.2 g) in dichloromethane (4 mL) was added TFA (4 mL) and the reaction mixture was allowed to stir at room temperature for 15 h. The mixture was evaporated to dryness and saturated $NaHCO_3$ solution (2 mL), diethyl ether and heptane were added. The mixture was stirred at room temperature for 1 h, the precipitate was collected by filtration, washed with water and heptane and dried to yield the title compound as an off-white solid (0.075 g, 16%). MS (ISP) 460.1 [$(M+H)^+$]; mp 323° C.

EXAMPLE 184

3-{1-[4-Methyl-6-(4-trifluoromethyl-phenyl)-pyrimidin-2-yl]-1H-imidazol-4-yl}-benzenesulfonamide 1) N-tert-Butyl-3-{1-[4-methyl-6-(4-trifluoromethyl-phenyl)-pyrimidin-2-yl]-1H-imidazol-4-yl}-benzenesulfonamide was prepared from 2-(4-iodo-imidazol-1-yl)-6-methyl-4-(4-trifluoromethyl-phenyl)-pyrimidine (example E.71) (0.43 g, 1.0 mmol) and commercially available 3-(tert.-butylsulfamoyl)-phenylboronic acid (0.39 g, 1.5 mmol) according to the general procedure VI. Obtained as a light yellow solid (0.19 g) which was subsequently deprotected.

2) To a cooled and stirred solution of N-tert-butyl-3-{1-[4-methyl-6-(4-trifluoromethylphenyl)-pyrimidin-2-yl]-1H-imidazol-4-yl}-benzenesulfonamide (0.19 g) in dichloromethane (4 mL) was added TFA (4 mL) and the reaction mixture was allowed to stir at room temperature for 15 h. The mixture was evaporated to dryness and saturated $NaHCO_3$ solution (3 mL), diethyl ether and heptane were added. The mixture was stirred at room temperature for 1 h, the precipitate was collected by filtration, washed with water and heptane and dried to yield the title compound as an off-white solid (0.13 g, 28%). MS (ISP) 460.2 [$(M+H)^+$]; mp 186° C.

EXAMPLE 185

3-{1-[4-(3-Chloro-phenyl)-6-trifluoromethyl-pyrimidin-2-yl]-1H-imidazol-4-yl}-benzenesulfonamide 1) N-tert-Butyl-3-{1-[6-(3-chloro-phenyl)-4-trifluoromethyl-pyrimidin-2-yl]-1H-imidazol-4-yl}-benzenesulfonamide was prepared from 4-(3-chloro-phenyl)-2-(4-iodo-imidazol-1-yl)-6-trifluoromethyl-pyrimidine (example E.72) (0.68 g, 1.5 mmol) and commercially available 3-(tert.-butylsulfamoyl)-phenylboronic acid (0.46 g, 1.8 mmol) according to the general procedure VI. Obtained as a light yellow solid (0.2 g) which was subsequently deprotected.

2) To a cooled and stirred solution of N-tert-butyl-3-{1-[6-(3-chloro-phenyl)-4-trifluoromethyl-pyrimidin-2-yl]-1H-imidazol-4-yl}-benzenesulfonamide (0.2 g) in dichloromethane (5 mL) was added TFA (5 mL) and the reaction mixture was allowed to stir at room temperature for 15 h. The mixture was evaporated to dryness and saturated $NaHCO_3$ solution (3 mL), diethyl ether and heptane were added. The mixture was stirred at room temperature for 1 h, the precipitate was collected by filtration, washed with water and heptane and dried to yield the title compound as a white solid (0.1 g, 14%). MS (ISP) 580.2 [$(M+H)^+$]; mp 204.5° C.

EXAMPLE 186

5-{1-[4-(3-Chloro-phenyl)-6-trifluoromethyl-pyrimidin-2-yl]-1H-imidazol-4-yl}-pyridin-2-ylamine The title compound was prepared from 4-(3-chloro-phenyl)-2-(4-iodo-imidazol-1-yl)-6-trifluoromethyl-pyrimidine (example E.72) (0.45 g, 1.0 mmol) and commercially available 2-amino-5-(4,4,5,5-tetramethyl-1,3,2-dioxaborolan-2-yl)pyridine (0.26 g, 1.2 mmol) according to the general procedure VI. Obtained as a yellow solid (0.27 g, 65%). MS (ISP) 417.2 [$(M+H)^+$]; mp 248° C.

EXAMPLE 187

5-{1-[4-(3-Chloro-phenyl)-6-trifluoromethyl-pyrimidin-2-yl]-1H-imidazol-4-yl}-pyrimidin-2-ylamine The title compound was prepared from 4-(3-chloro-phenyl)-2-(4-iodo-imidazol-1-yl)-6-trifluoromethyl-pyrimidine (example E.72) (0.45 g, 1.0 mmol) and commercially available 2-amino-5-(4,4,5,5-tetramethyl-1,3,2-dioxaborolan-2-yl)pyrimidine (0.26 g, 1.2 mmol) according to the general procedure VI. Obtained as a yellow solid (0.27 g, 65%). MS (ISP) 418.1 [$(M+H)^+$]; mp 281° C.

EXAMPLE 188

5-{1-[4-(3-Chloro-phenyl)-6-trifluoromethyl-pyrimidin-2-yl]-1H-imidazol-4-yl}-thiophene-2-sulfonic acid amide 1) 5-{1-[4-(3-Chloro-phenyl)-6-trifluoromethyl-pyrimidin-2-yl]-1H-imidazol-4-yl}-thiophene-2-sulfonic acid tert-butyl amide was prepared from 4-(3-chloro-phenyl)-2-(4-iodo-imidazol-1-yl)-6-trifluoromethyl-pyrimidine (example E.72) (0.68 g, 1.5 mmol) and N-tert-butyl-5-(4,4,5,5-tetramethyl-1,3,2-dioxaborolan-2-yl)-thiophene-2-sulfonamide (example F.1) (0.62 g, 1.8 mmol) according to the general procedure VI. Obtained as a light yellow solid (0.4 g), which was subsequently deprotected.

2) To a cooled and stirred solution of 5-{1-[4-(3-chloro-phenyl)-6-trifluoromethyl-pyrimidin-2-yl]-1H-imidazol-4-yl}-thiophene-2-sulfonic acid tert-butyl amide (0.4 g) in dichloromethane (6 mL) was added TFA (6 mL) and the reaction mixture was allowed to stir at room temperature for 15 h. The mixture was evaporated to dryness and purified by flash chromatography (heptane/ethyl acetate) and crystallization (dichloromethane/MeOH/hexane) to yield the title compound as a white solid (0.036 g, 5%). MS (ISP) 486.2 [$(M+H)^+$]; mp 280° C.

EXAMPLE 189

3-{4-[4-(4-Chloro-phenyl)-6-methyl-pyrimidin-2-yl]-pyridin-2-yl}-benzenesulfonamide 1) 3-{4-[4-(4-Chloro-phenyl)-6-methyl-pyrimidin-2-yl]-pyridin-2-yl}-benzenesulfonic acid tert-butylamide was prepared from 4-(4-chloro-phenyl)-2-(2-chloro-pyridin-4-yl)-6-methyl-pyrimidine (example E.45) (0.32 g, 1.0 mmol) and commercially available 3-(tert.-butylsulfamoyl)-phenylboronic acid (0.31 g, 1.2 mmol) according to the general procedure VI. Obtained as a light brown solid (0.47 g), which was subsequently deprotected.

2) To a cooled and stirred solution of 3-{4-[4-(4-chloro-phenyl)-6-methyl-pyrimidin-2-yl]-pyridin-2-yl}-benzenesulfonic acid tert-butylamide (0.47 g) in dichloromethane (6 mL) was added TFA (6 mL) and the reaction mixture was allowed to stir at room temperature for 15 h. The mixture was evaporated to dryness and saturated $NaHCO_3$ solution (5 mL), diethyl ether and heptane were added. The mixture was stirred at room temperature for 1 h, the precipitate was collected by filtration, washed with water and heptane and dried to yield the title compound as a white solid (0.2, 46%). MS (ISP) 437.1 [$(M+H)^+$]; mp 224° C.

EXAMPLE 190

5-{1-[4-(4-Chloro-phenyl)-6-methyl-pyrimidin-2-yl]-1H-imidazol-4-yl}-thiophene-2-sulfonic acid amide 1) N-tert-Butyl-5-{1-[6-(4-chloro-phenyl)-4-methyl-pyrimidin-2-yl]-1H-imidazol-4-yl}-thiophene-2-sulfonamide was prepared from 4-(4-chloro-phenyl)-2-(4-iodo-imidazol-1-yl)-6-methyl-pyrimidine (example E.69) (0.40 g, 1.0 mmol) and N-tert-butyl-5-(4,4,5,5-tetramethyl-1,3,2-dioxaborolan-2-yl)-thiophene-2-sulfonamide (example F.1) (0.41 g, 1.2 mmol) according to the general procedure VI. Obtained as a light brown solid (0.15 g) which was subsequently deprotected.

2) To a cooled and stirred solution of N-tert-butyl-5-{1-[6-(4-chloro-phenyl)-4-methyl-pyrimidin-2-yl]-1H-imidazol-4-yl}-thiophene-2-sulfonamide (0.15 g) in dichloromethane (4 mL) was added TFA (4 mL) and the reaction mixture was allowed to stir at room temperature for 15 h. The mixture was evaporated to dryness and saturated $NaHCO_3$ solution (5 mL), diethyl ether and heptane were added. The mixture was stirred at room temperature for 1 h, the precipitate was collected by filtration, washed with water and heptane and dried. Further purification by flash-chromatography on silica gel (ethyl acetate/hexane) and crystallization (diethyl ether) yielded the title compound as a light brown solid (0.01 g, 2%). MS (ISP) 432.3 [(M+H)$^+$]; mp 281° C.

EXAMPLE 191

5-{1-[4-Methyl-6-(4-trifluoromethyl-phenyl)-pyrimidin-2-yl]-1H-imidazol-4-yl}-thiophene-2-sulfonic acid amide 1) N-tert-Butyl-5-{1-[4-methyl-6-(4-trifluoromethyl-phenyl)-pyrimidin-2-yl]-1H-imidazol-4-yl}-thiophene-2-sulfonamide was prepared from 2-(4-iodo-imidazol-1-yl)-6-methyl-4-(4-trifluoromethyl-phenyl)-pyrimidine (example E.71) (0.43 g, 1.0 mmol) and N-tert-butyl-5-(4,4,5,5-tetramethyl-1,3,2-dioxaborolan-2-yl)-thiophene-2-sulfonamide (example F.1) (0.45 g, 1.3 mmol) according to the general procedure VI. Obtained as a light yellow solid (0.08 g) which was subsequently deprotected.

2) To a cooled and stirred solution of N-tert-butyl-5-{1-[4-methyl-6-(4-trifluoromethylphenyl)-pyrimidin-2-yl]-1H-imidazol-4-yl}-thiophene-2-sulfonamide (0.08 g) in dichloromethane (3 mL) was added TFA (3 mL) and the reaction mixture was allowed to stir at room temperature for 15 h. The mixture was evaporated to dryness and saturated $NaHCO_3$ solution (3 mL), diethyl ether and heptane were added. The mixture was stirred at room temperature for 1 h, the precipitate was collected by filtration, washed with water and heptane and dried. Further purification by flash-chromatography on silica gel (ethyl acetate/hexane) and crystallization (diethyl ether) yielded the title compound as a white solid (0.014 g, 3%). MS (ISP) 466.1 [(M+H)$^+$]; mp 277° C.

EXAMPLE 192

5-{4-[4-(4-Chloro-phenyl)-6-methyl-pyrimidin-2-yl]-pyridin-2-yl}-thiophene-2-sulfonic acid amide 1) 5-{4-[4-(4-Chloro-phenyl)-6-methyl-pyrimidin-2-yl]-pyridin-2-yl}-thiophene-2-sulfonic acid tert-butylamide was prepared from 4-(4-chloro-phenyl)-2-(2-chloro-pyridin-4-yl)-6-methyl-pyrimidine (example E.45) (0.22 g, 0.7 mmol) and N-tert-butyl-5-(4,4,5,5-tetramethyl-1,3,2-dioxaborolan-2-yl)-thiophene-2-sulfonamide (example F.1) (0.31 g, 0.9 mmol) according to the general procedure VI. Obtained as a light yellow solid (0.12 g) which was subsequently deprotected.

2) To a cooled and stirred solution of 5-{4-[4-(4-chloro-phenyl)-6-methyl-pyrimidin-2-yl]-pyridin-2-yl}-thiophene-2-sulfonic acid tert-butylamide (0.12 g) in dichloromethane (4 mL) was added TFA (4 mL) and the reaction mixture was allowed to stir at room temperature for 15 h. The mixture was evaporated to dryness and saturated $NaHCO_3$ solution (5 mL), diethyl ether and heptane were added. The mixture was stirred at room temperature for 1 h, the precipitate was collected by filtration, washed with water and heptane and dried. Further purification by flash-chromatography on silica gel (ethyl acetate/hexane) and crystallization (diethyl ether) yielded the title compound as a white solid (0.036 g, 12%). MS (ISP) 443.2 [(M+H)$^+$]; mp 232.5° C.

EXAMPLE 193

3'-[4-(3,4-Dichloro-phenyl)-6-methyl-pyrimidin-2-yl]-biphenyl-3-sulfonic acid amide 1) 3'-[4-(3,4-Dichloro-phenyl)-6-methyl-pyrimidin-2-yl]-biphenyl-3-sulfonic acid tert-butylamide was prepared from 2-(3-bromo-phenyl)-4-(3,4-dichloro-phenyl)-6-methyl-pyrimidine (example E.62) (0.39 g, 1.0 mmol) and commercially available 3-(tert.-butylsulfamoyl)-phenylboronic acid (0.31 g, 1.2 mmol) according to the general procedure VI. Obtained as a light brown solid (0.54 g), which was subsequently deprotected.

2) To a cooled and stirred solution of 3'-[4-(3,4-dichloro-phenyl)-6-methyl-pyrimidin-2-yl]-biphenyl-3-sulfonic acid tert-butylamide (0.54 g) in dichloromethane (6 mL) was added TFA (6 mL) and the reaction mixture was allowed to stir at room temperature for 15 h. The mixture was evaporated to dryness and saturated $NaHCO_3$ solution (5 mL), diethyl ether and heptane were added. The mixture was stirred at room temperature for 1 h, the precipitate was collected by filtration, washed with water and heptane and dried. Further purification by flash-chromatography on silica gel (ethyl acetate/hexane) and crystallization (diethyl ether) yielded the title compound as a white solid (0.16, 34%). MS (ISP) 470.1 [(M+H)$^+$]; mp 206.5° C.

EXAMPLE 194

3-{4-[4-(3,4-Dichloro-phenyl)-6-methyl-pyrimidin-2-yl]-pyridin-2-yl}-benzenesulfonamide 1) 3-{4-[4-(3,4-Dichloro-phenyl)-6-methyl-pyrimidin-2-yl]-pyridin-2-yl}-benzenesulfonic acid tert-butylamide was prepared from 4-(3,4-dichloro-phenyl)-2-(2-chloro-pyridin-4-yl)-6-methyl-pyrimidine (example E.63) (0.35 g, 1.0 mmol) and commercially available 3-(tert.-butylsulfamoyl)-phenylboronic acid (0.31 g, 1.2 mmol) according to the general procedure VI. Obtained as a light brown solid (0.54 g), which was subsequently deprotected.

2) To a cooled and stirred solution of 3-{4-[4-(3,4-dichloro-phenyl)-6-methyl-pyrimidin-2-yl]-pyridin-2-yl}-benzenesulfonic acid tert-butylamide (0.54 g) in dichloromethane (6 mL) was added TFA (6 mL) and the reaction mixture was allowed to stir at room temperature for 15 h. The mixture was evaporated to dryness and saturated $NaHCO_3$ solution (5 mL), diethyl ether and heptane were added. The mixture was stirred at room temperature for 1 h, the precipitate was collected by filtration, washed with water and heptane and dried. Further purification by flash-chromatography on silica gel (ethyl acetate/hexane) and crystallization (diethyl ether) yielded the title compound as a white solid (0.175, 37%). MS (ISP) 471.2 [(M+H)$^+$]; mp 202.5° C.

EXAMPLE 195

5-{3-[4-(3,4-Dichloro-phenyl)-6-methyl-pyrimidin-2-yl]-phenyl}-thiophene-2-sulfonic acid amide 1) N-tert-Butyl-5-{3-[6-(3,4-dichloro-phenyl)-4-methyl-pyrimidin-2-yl]-phenyl}-thiophene-2-sulfonic acid amide was prepared from 2-(3-bromo-phenyl)-4-(3,4-dichlorophenyl)-6-methyl-pyrimidine (example E.62) (0.39 g, 1.0 mmol) and N-tert-butyl-5-(4,4,5,5-tetramethyl-1,3,2-dioxaborolan-2-yl)-thiophene-2-sulfonamide (example F.1) (0.45 g, 1.3 mmol) according to the general procedure VI. Obtained as a light yellow solid (0.39 g), which was subsequently deprotected.

2) To a cooled and stirred solution of N-tert-butyl-5-{3-[6-(3,4-dichloro-phenyl)-4-methyl-pyrimidin-2-yl]-phenyl}-thiophene-2-sulfonic acid amide (0.39 g) in dichloromethane (6 mL) was added TFA (6 mL) and the reaction mixture was allowed to stir at room temperature for 15 h. The mixture was evaporated to dryness and saturated $NaHCO_3$ solution (4 mL), diethyl ether and heptane were added. The mixture was stirred at room temperature for 1 h, the precipitate was collected by filtration and further purified by flash chromatography (heptane/ethyl acetate) and crystallization (dichloromethane/heptane) to yield the title compound as a light brown solid (0.054 g, 11%). MS (ISP) 476.0 [$(M+H)^+$]; mp 238° C.

EXAMPLE 196

5-{4-[4-(3,4-Dichloro-phenyl)-6-methyl-pyrimidin-2-yl]-pyridin-2-yl}-thiophene-2-sulfonic acid amide 1) 5-{4-[4-(3,4-Dichloro-phenyl)-6-methyl-pyrimidin-2-yl]-pyridin-2-yl}-thiophene-2-sulfonic acid tert-butylamide was prepared from 2-(2-chloro-pyridin-4-yl)-4-(3,4-dichlorophenyl)-6-methyl-pyrimidine (example E.63) (0.35 g, 1.0 mmol) and N-tert-butyl-5-(4,4,5,5-tetramethyl-1,3,2-dioxaborolan-2-yl)-thiophene-2-sulfonamide (example F.1) (0.45 g, 1.3 mmol) according to the general procedure VI. Obtained as a light yellow solid (0.22 g) which was subsequently deprotected.

2) To a cooled and stirred solution of 5-{4-[4-(2,4-dichloro-phenyl)-6-methyl-pyrimidin-2-yl]-pyridin-2-yl}-thiophene-2-sulfonic acid tert-butylamide (0.22 g) in dichloromethane (6 mL) was added TFA (6 mL) and the reaction mixture was allowed to stir at room temperature for 15 h. The mixture was evaporated to dryness and saturated $NaHCO_3$ solution (5 mL), diethyl ether and heptane were added. The mixture was stirred at room temperature for 1 h, the precipitate was collected by filtration, washed with water and heptane and dried. Further purification by flash-chromatography on silica gel (ethyl acetate/hexane) and crystallization (dichloromethane) yielded the title compound as a white solid (0.024 g, 5%). MS (ISP) 477.1 [$(M+H)^+$]; mp 267° C.

EXAMPLE 197

5-{4-[4-Methyl-6-(4-trifluoromethyl-phenyl)-pyrimidin-2-yl]-pyridin-2-yl}-thiophene-2-sulfonic acid amide 1) 5-{4-[6-Methyl-4-(4-trifluoro-phenyl)-pyrimidin-2-yl]-pyridin-2-yl}-thiophene-2-sulfonic acid tert-butylamide was prepared from 2-(2-chloro-pyridin-4-yl)-6-methyl-4-(4-trifluoro-phenyl)-pyrimidine (example E.46) (0.35 g, 1.0 mmol) and N-tert-butyl-5-(4,4,5,5-tetramethyl-1,3,2-dioxaborolan-2-yl)-thiophene-2-sulfonamide (example F.1) (0.45 g, 1.3 mmol) according to the general procedure VI. Obtained as a light yellow solid (0.21 g) which was subsequently deprotected.

2) To a cooled and stirred solution of 5-{4-[6-methyl-4-(4-trifluoro-phenyl)-pyrimidin-2-yl]-pyridin-2-yl}-thiophene-2-sulfonic acid tert-butylamide (0.21 g) in dichloromethane (3 mL) was added TFA (3 mL) and the reaction mixture was allowed to stir at room temperature for 15 h. The mixture was evaporated to dryness and saturated $NaHCO_3$ solution (5 mL), diethyl ether and heptane were added. The mixture was stirred at room temperature for 1 h, the precipitate was collected by filtration, washed with water and heptane and dried. Further purification by flash-chromatography on silica gel (ethyl acetate/hexane) and crystallization (dichloromethane) yielded the title compound as a white solid (0.073 g, 15%). MS (ISP) 477.1 [$(M+H)^+$]; mp 263.5° C.

EXAMPLE 198

3-{1-[4-(3,4-Dichloro-phenyl)-6-methyl-pyrimidin-2-yl]-1H-imidazol-4-yl}-benzenesulfonamide 1) N-tert-Butyl-3-{1-[6-(3,4-dichloro-phenyl)-4-methyl-pyrimidin-2-yl]-1H-imidazol-4-yl}-benzenesulfonamide was prepared from 4-(3,4-dichloro-phenyl)-2-(4-iodo-imidazol-1-yl)-6-methyl-pyrimidine (example E.74) (0.37 g, 0.86 mmol) and commercially available 3-(tert.-butylsulfamoyl)-phenylboronic acid (0.33 g, 1.29 mmol) according to the general procedure VI. Obtained as a light yellow solid (0.23 g) which was subsequently deprotected.

2) To a cooled and stirred solution of N-tert-butyl-3-{1-[6-(3,4-dichloro-phenyl)-4-methyl-pyrimidin-2-yl]-1H-imidazol-4-yl}-benzenesulfonamide (0.23 g) in dichloromethane (3 mL) was added TFA (3 mL) and the reaction mixture was allowed to stir at room temperature for 15 h. The mixture was evaporated to dryness and saturated $NaHCO_3$ solution (3 mL), diethyl ether and heptane were added. The mixture was stirred at room temperature for 1 h, the precipitate was collected by filtration, washed with water and heptane and dried to yield the title compound as a white solid (0.18 g, 46%). MS (ISP) 460.1 [$(M+H)^+$]; mp 210° C.

EXAMPLE 199

4-{1-[4-(3,4-Dichloro-phenyl)-6-methyl-pyrimidin-2-yl]-1H-imidazol-4-yl}-benzenesulfonamide 1) N-tert-Butyl-4-{1-[6-(3,4-dichloro-phenyl)-4-methyl-pyrimidin-2-yl]-1H-imidazol-4-yl}-benzenesulfonamide was prepared from 4-(3,4-dichloro-phenyl)-2-(4-iodo-imidazol-1-yl)-6-methyl-pyrimidine (example E.74) (0.37 g, 0.86 mmol) and commercially available 4-(tert.-butylsulfamoyl)-phenylboronic acid (0.33 g, 1.29 mmol) according to the general procedure VI. Obtained as a light yellow solid (0.2 g) which was subsequently deprotected.

2) To a cooled and stirred solution of N-tert-butyl-4-{1-[6-(3,4-dichloro-phenyl)-4-methyl-pyrimidin-2-yl]-1H-imidazol-4-yl}-benzenesulfonamide (0.2 g) in dichloromethane (3 mL) was added TFA (3 mL) and the reaction mixture was allowed to stir at room temperature for 15 h. The mixture was evaporated to dryness and saturated $NaHCO_3$ solution (3 mL), diethyl ether and heptane were added. The mixture was stirred at room temperature for 1 h, the precipitate was collected by filtration, washed with water and heptane and dried to yield the title compound as a white solid (0.13 g, 33%). MS (ISP) 460.1 [$(M+H)^+$]; mp 282.5° C.

EXAMPLE 200

2-{1-[4-(4-Chloro-phenyl)-6-methyl-pyrimidin-2-yl]-1H-imidazol-4-yl}-thiazole-5-sulfonic acid amide 1) A stirred mixture of 4-(4-chloro-phenyl)-6-methyl-2-(4-tributylstannanyl-imidazol-1-yl)-pyrimidine (Example G.3) (0.45 g, 0.80 mmol), 2-chloro-thiazole-5-sulfonic acid tert-butylamide (Example H.1) (0.225 g, 0.88 mmol), tetrakis (triphenyl-phosphine)palladium (0.056 g, 0.048 mmol) in toluene (10 mL) was heated under reflux conditions for 15 h. The mixture was poured into saturated potassiumfluoride solution (10 mL), water (40 mL) was added and the water layer was extracted with ethyl acetate (2×60 mL). The combined organic layers were washed with brine (60 mL), dried ($MgSO_4$) and evaporated. The crude product was purified by flash chromatography (heptane/ethyl acetate) and crystallization (THF/hexane) to yield N-tert-butyl-2-{1-[4-(4-chloro-phenyl)-6-methyl-pyrimidin-2-yl]-1H-imidazol-4-yl}-thiazole-5-sulfonamide (0.1 g) as a light brown solid.

2) To a cooled and stirred solution of N-tert-butyl-2-{1-[4-(4-chloro-phenyl)-6-methyl-pyrimidin-2-yl]-1H-imidazol-4-yl}-thiazole-5-sulfonamide (0.1 g) in dichloromethane (2 mL) was added TFA (2 mL) and the reaction mixture was allowed to stir at room temperature for 15 h. The mixture was evaporated to dryness and purified by flash-chromatography on silica gel (ethyl acetate/hexane) and crystallization (dichloromethane) to yielded the title compound as a light brown solid (0.016 g, 5%). MS (ISP) 433.2 [$(M+H)^+$]; mp 255.5° C.

EXAMPLE 201

2-{1-[4-(3,4-Dichloro-phenyl)-6-methyl-pyrimidin-2-yl]-1H-imidazol-4-yl}-thiazole-5-sulfonic acid amide 1) A stirred mixture of 4-(3,4-dichloro-phenyl)-6-methyl-2-(4-tributylstannanyl-imidazol-1-yl)-pyrimidine (Example G.4) (0.55 g, 0.93 mmol), 2-chloro-thiazole-5-sulfonic acid tert-butylamide (Example H.1) (0.26 g, 1.0 mmol), tetrakis (triphenyl-phosphine)palladium (0.064 g, 0.055 mmol) in toluene (10 mL) was heated under reflux conditions for 15 h. The mixture was poured into saturated potassiumfluoride solution (10 mL), water (40 mL) was added and the water layer was extracted with ethyl acetate (2×60 mL). The combined organic layers were washed with brine (60 mL), dried ($MgSO_4$) and evaporated. The crude product was purified by flash chromatography (heptane/ethyl acetate) and crystallization (THF/hexane) to yield N-tert-butyl-2-{1-[4-(3,4-dichloro-phenyl)-6-methyl-pyrimidin-2-yl]-1H-imidazol-4-yl}-thiazole-5-sulfonamide (0.23 g) as a light brown solid.

2) To a cooled and stirred solution of N-tert-butyl-2-{1-[4-(3,4-dichloro-phenyl)-6-methyl-pyrimidin-2-yl]-1H-imidazol-4-yl}-thiazole-5-sulfonamide (0.23 g) in dichloromethane (4 mL) was added TFA (4 mL) and the reaction mixture was allowed to stir at room temperature for 15 h. The mixture was evaporated to dryness and purified by flash-chromatography on silica gel (ethyl acetate/hexane) and crystallization (dichloromethane) to yielded the title compound as a light brown solid (0.028 g, 6%). MS (ISP) 467.1 [$(M+H)^+$]; mp 230° C.

EXAMPLE 202

3'-[4-(3,4-Dichloro-phenyl)-6-trifluoromethyl-pyrimidin-2-yl]-biphenyl-3-sulfonic acid amide 1) 3'-[4-(3,4-Dichloro-phenyl)-6-trifluoromethyl-pyrimidin-2-yl]-biphenyl-3-sulfonic acid tert-butylamide was prepared from 2-(3-bromo-phenyl)-4-(3,4-dichloro-phenyl)-6-trifluoromethyl-pyrimidine (example E.37) (0.40 g, 0.89 mmol) and commercially available 3-(tert.-butylsulfamoyl)-phenylboronic acid (0.275 g, 1.07 mmol) according to the general procedure VI. Obtained as white foam (0.45 g), which was subsequently deprotected.

2) To a cooled and stirred solution of 3'-[4-(3,4-dichloro-phenyl)-6-trifluoromethyl-pyrimidin-2-yl]-biphenyl-3-sulfonic acid tert-butylamide (0.45 g) in dichloromethane (6 mL) was added TFA (6 mL) and the reaction mixture was allowed to stir at room temperature for 15 h. The mixture was evaporated to dryness and saturated $NaHCO_3$ solution (5 mL), diethyl ether and heptane were added. The mixture was stirred at room temperature for 1 h, the precipitate was collected by filtration and further purified by flash chromatography (heptane/ethyl acetate) and crystallization (THF/hexane) to yield the title compound as a white solid (0.34 g, 72%). MS (ISN) 522.2 [$(M-H)^-$]; mp 241° C.

EXAMPLE 203

3-{4-[4-(3,4-Dichloro-phenyl)-6-trifluoromethyl-pyrimidin-2-yl]-pyridin-2-yl}-benzenesulfonamide 1) 3-{4-[4-(3,4-Dichloro-phenyl)-6-trifluoromethyl-pyrimidin-2-yl]-pyridin-2-yl}-benzenesulfonic acid tert-butylamide was prepared from 2-(2-chloro-pyridin-4-yl)-4-(3,4-dichloro-phenyl)-6-trifluoromethyl-pyrimidine (example E.38) (0.4 g, 1.0 mmol) and commercially available 3-(tert.-butylsulfamoyl)-phenylboronic acid (0.31 g, 1.2 mmol) according to the general procedure VI. Obtained as light brown foam (0.41 g), which was subsequently deprotected.

2) To a cooled and stirred solution of 3-{4-[4-(3,4-dichloro-phenyl)-6-trifluoromethyl-pyrimidin-2-yl]-pyridin-2-yl}-benzenesulfonic acid tert-butylamide (0.41 g) in dichloromethane (6 mL) was added TFA (6 mL) and the reaction mixture was allowed to stir at room temperature for 15 h. The mixture was evaporated to dryness and saturated $NaHCO_3$ solution (5 mL), diethyl ether and heptane were added. The mixture was stirred at room temperature for 1 h, the precipitate was collected by filtration and further purified by flash chromatography (heptane/ethyl acetate) and crystallization (THF/hexane) to yield the title compound as an off-white solid (0.28 g, 54%). MS (ISP) 523.1 [$(M-H)^-$]; mp 247° C.

EXAMPLE 204

5-{3-[4-(3,4-Dichloro-phenyl)-6-trifluoromethyl-pyrimidin-2-yl]-phenyl}-thiophene-2-sulfonic acid amide 1) N-tert-Butyl-5-{3-[6-(3,4-dichloro-phenyl)-4-trifluoromethyl-pyrimidin-2-yl]-phenyl}-thiophene-2-sulfonic acid amide was prepared from 2-(3-bromo-phenyl)-4-(3,4-dichloro-phenyl)-6-trifluoromethyl-pyrimidine (example E.37) (0.40 g, 0.89 mmol) and N-tert-butyl-5-(4,4,5,5-tetramethyl-1,3,2-dioxaborolan-2-yl)-thiophene-2-sulfonamide (example F.1) (0.40 g, 1.16 mmol) according to the general procedure VI. Obtained as white foam (0.45 g), which was subsequently deprotected.

2) To a cooled and stirred solution of N-tert-butyl-5-{3-[6-(3,4-dichloro-phenyl)-4-trifluoromethyl-pyrimidin-2-yl]-phenyl}-thiophene-2-sulfonic acid amide (0.39 g) in dichloromethane (6 mL) was added TFA (6 mL) and the reaction mixture was allowed to stir at room temperature for 15 h. The mixture was evaporated to dryness and saturated $NaHCO_3$ solution (4 mL), diethyl ether and heptane were added. The mixture was stirred at room temperature for 1 h, the precipitate was collected by filtration and further purified by flash chromatography (heptane/ethyl acetate) and crystallization (THF/hexane) to yield the title compound as an off-white solid (0.24 g, 51%). MS (ISN) 527.9 [(M−H)$^-$]; mp 203° C.

EXAMPLE 205

5-{4-[4-(3,4-Dichloro-phenyl)-6-trifluoromethyl-pyrimidin-2-yl]-pyridin-2-yl}-thiophene-2-sulfonic acid amide 1) 5-{4-[4-(3,4-Dichloro-phenyl)-6-trifluoromethyl-pyrimidin-2-yl]-pyridin-2-yl}-thiophene-2-sulfonic acid tert-butyl amide was prepared from 2-(2-chloro-pyridin-4-yl)-4-(3,4-dichloro-phenyl)-6-trifluoromethyl-pyrimidine (example E.38) (0.405 g, 1.0 mmol) and N-tert-butyl-5-(4,4,5,5-tetramethyl-1,3,2-dioxaborolan-2-yl)-thiophene-2-sulfonamide (example F.1) (0.45 g, 1.3 mmol) according to the general procedure VI. Obtained as light brown foam (0.41 g), which was subsequently deprotected.

2) To a cooled and stirred solution of 5-{4-[4-(3,4-dichloro-phenyl)-6-trifluoromethyl-pyrimidin-2-yl]-pyridin-2-yl}-thiophene-2-sulfonic acid tert-butyl amide (0.41 g) in dichloromethane (6 mL) was added TFA (6 mL) and the reaction mixture was allowed to stir at room temperature for 15 h. The mixture was evaporated to dryness and saturated $NaHCO_3$ solution (4 mL), diethyl ether and heptane were added. The mixture was stirred at room temperature for 1 h, the precipitate was collected by filtration and further purified by flash chromatography (heptane/ethyl acetate) and crystallization (THF/hexane) to yield the title compound as an off-white solid (0.2 g, 38%). MS (ISN) 528.9 [(M−H)$^-$]; mp 266° C.

EXAMPLE 206

3'-[4-(3-Methyl-4-trifluoromethyl-phenyl)-6-trifluoromethyl-pyrimidin-2-yl]-biphenyl-3-sulfonic acid amide 1) 3'-[4-(3-methyl 4-trifluoromethyl-phenyl)-6-trifluoromethyl-pyrimidin-2-yl]-biphenyl-3-sulfonic acid tert-butylamide was prepared from 2-(3-bromo-phenyl)-4-(3-methyl-4-trifluoromethyl-phenyl)-6-trifluoromethyl-pyrimidine (example E.49) (0.46 g, 1.0 mmol) and commercially available 3-(tert.-butylsulfamoyl)-phenylboronic acid (0.31 g, 1.2 mmol) according to the general procedure VI. Obtained as white foam (0.52 g), which was subsequently deprotected.

2) To a cooled and stirred solution of 3'-[4-(3-methyl-4-trifluoromethyl-phenyl)-6-trifluoromethyl-pyrimidin-2-yl]-biphenyl-3-sulfonic acid tert-butylamide (0.52 g) in dichloromethane (6 mL) was added TFA (6 mL) and the reaction mixture was allowed to stir at room temperature for 15 h. The mixture was evaporated to dryness and saturated $NaHCO_3$ solution (5 mL), diethyl ether and heptane were added. The mixture was stirred at room temperature for 1 h, the precipitate was collected by filtration and further purified by flash chromatography (heptane/ethyl acetate) and crystallization (dichloromethane/MeOH) to yield the title compound as an white solid (0.29 g, 54%). MS (ISP) 536.2 [(M−H)$^-$]; mp 205° C.

EXAMPLE 207

5-{3-[4-(3-Methyl-4-trifluoromethyl-phenyl)-6-trifluoromethyl-pyrimidin-2-yl]-phenyl}-thiophene-2-sulfonic acid amide 1) N-tert-Butyl-5-{3-[6-(3-methyl-4-trifluoromethyl-phenyl)-4-trifluoromethyl-pyrimidin-2-yl]-phenyl}-thiophene-2-sulfonic acid amide was prepared from 2-(3-bromophenyl)-4-(3-methyl-4-trifluoromethyl-phenyl)-6-trifluoromethyl-pyrimidine (example E.49) (0.46 g, 1.0 mmol) and N-tert-butyl-5-(4,4,5,5-tetramethyl-1,3,2-dioxaborolan-2-yl)-thiophene-2-sulfonamide (example F.1) (0.45 g, 1.3 mmol) according to the general procedure VI. Obtained as a light brown solid (0.46 g), which was subsequently deprotected.

2) To a cooled and stirred solution of N-tert-butyl-5-{3-[6-(3-methyl-4-trifluoromethylphenyl)-4-trifluoromethyl-pyrimidin-2-yl]-phenyl}-thiophene-2-sulfonic acid amide (0.46 g) in dichloromethane (6 mL) was added TFA (6 mL) and the reaction mixture was allowed to stir at room temperature for 15 h. The mixture was evaporated to dryness and saturated $NaHCO_3$ solution (5 mL), diethyl ether and heptane were added. The mixture was stirred at room temperature for 1 h, the precipitate was collected by filtration and further purified by flash chromatography (heptane/ethyl acetate) and crystallization (dichloromethane/MeOH) to yield the title compound as an off-white solid (0.21 g, 38%). MS (ISN) 542.1 [(M−H)$^-$]; mp 216° C.

EXAMPLE 208

5-{1-[4-(3,4-Dichloro-phenyl)-6-trifluoromethyl-pyrimidin-2-yl]-1H-imidazol-4-yl}-thiophene-2-sulfonic acid amide 1) A stirred mixture of 4-(3,4-dichloro-phenyl)-2-(4-tributylstannanyl-imidazol-1-yl)-6-trifluoromethyl-pyrimidine (Example G.6) (0.46 g, 0.71 mmol), commercially available 5-bromothiophene-2-N-tert-butylsulfonamide (0.23 g, 0.78 mmol), tetrakis(triphenylphosphine)palladium (0.049 g, 0.042 mmol) in toluene (8 mL) was heated under reflux conditions for 15 h, hexane (10 mL) was added and the mixture was stirred at RT for 1 h. The precipitate was collected by filtration and dried to yield 5-{1-[4-(3,4-dichloro-phenyl)-6-trifluoromethyl-pyrimidin-2-yl]-1H-imidazol-4-yl}-thiophene-2-sulfonic acid tert-butyl amide (0.34 g) as a white solid.

2) To a cooled and stirred solution of 5-{1-[4-(3,4-dichloro-phenyl)-6-trifluoromethyl-pyrimidin-2-yl]-1H-imidazol-4-yl}-thiophene-2-sulfonic acid tert-butyl amide (0.34 g) in dichloromethane (6 mL) was added TFA (6 mL) and the reaction mixture was allowed to stir at room temperature for 15 h. The mixture was evaporated to dryness and purified by column chromatography on silica gel (dichloromethane/MeOH/$NH_4OH$ 80:10:1) and crystallization (MeOH/diethyl ether) to yield the title compound as a light yellow solid (0.23 g, 62%). MS (ISN) 520.3 [(M−H)$^-$]; mp 282° C. (dec.).

EXAMPLE 209

5-{1-[4-(3-Methyl-4-trifluoromethyl-phenyl)-6-trifluoromethyl-pyrimidin-2-yl]-1H-imidazol-4-yl}-thiophene-2-sulfonic acid amide 1) A stirred mixture of 4-(3-methyl-4-trifluoromethyl-phenyl)-2-(4-tributylstannanyl-imidazol-1-yl)-6-trifluoromethyl-pyrimidine (Example G.7) (0.33 g, 0.5 mmol), commercially available 5-bromothiophene-2-N-tert-butylsulfonamide (0.16 g, 0.55 mmol), tetrakis (triphenylphosphine)palladium (0.035 g, 0.03 mmol) in toluene (6 mL) was heated under reflux conditions for 15 h, heptane (10 mL) was added and the mixture was stirred at RT for 1 h. The precipitate was collected by filtration and dried to yield 5-{1-[4-(3-methyl-4-trifluoromethyl-phenyl)-6-trifluoromethyl-pyrimidin-2-yl]-1H-imidazol-4-yl}-thiophene-2-sulfonic acid tert-butyl amide (0.24 g) as a light yellow solid.

2) To a cooled and stirred solution of 5-{1-[4-(3-methyl-4-trifluoromethyl-phenyl)-6-trifluoromethyl-pyrimidin-2-yl]-1H-imidazol-4-yl}-thiophene-2-sulfonic acid tert-butyl amide (0.24 g) in dichloromethane (5 mL) was added TFA (5 mL) and the reaction mixture was allowed to stir at room temperature for 15 h. The mixture was evaporated to dryness and purified by column chromatography on silica gel (dichloromethane/MeOH/$NH_4OH$ 80:10:1) and crystallization (MeOH/diethyl ether) to yield the title compound as a light yellow solid (0.14 g, 52%). MS (ISN) 532.3 [$(M-H)^-$]; mp 260° C.

EXAMPLE 210

4-(4-Chloro-phenyl)-2-[4-(3-methanesulfonyl-phenyl)-imidazol-1-yl]-6-methyl-pyrimidine A stirred mixture of 4-(4-chloro-phenyl)-6-methyl-2-(4-tributylstannanyl-imidazol-1-yl)-pyrimidine (Example G.3) (0.47 g, 0.84 mmol), commercially available 3-bromo-phenylmethyl sulfone (0.22 g, 0.92 mmol), tetrakis(triphenylphosphine)palladium (0.058 g, 0.05 mmol) in toluene (8 mL) was heated under reflux conditions for 15 h. Hexane (10 mL) was added at room temperature and the mixture was stirred for 1 h. The precipitate was collected by filtration, washed with heptane and dried to yield the title compound (0.33 g, 92%) as an off-white solid. MS (ISN) 423.3 [$(M-H)^-$]; mp 233° C.

EXAMPLE 211

4-{1-[4-(3,4-Dichloro-phenyl)-6-trifluoromethyl-pyrimidin-2-yl]-1H-imidazol-4-yl}-benzenesulfonamide 1) N-tert-Butyl-4-{1-[6-(3,4-dichloro-phenyl)-4-trifluoromethyl-pyrimidin-2-yl]-1H-imidazol-4-yl}-benzenesulfonamide was prepared from 4-(3,4-dichloro-phenyl)-2-(4-iodo-imidazol-1-yl)-6-trifluoromethyl-pyrimidine (example E.74) (0.485 g, 1.0 mmol) and commercially available 4-(tert.-butylsulfamoyl)-phenylboronic acid (0.31 g, 1.2 mmol) according to the general procedure VI. Obtained as a light yellow solid (0.08 g) which was subsequently deprotected.

2) To a cooled and stirred solution of N-tert-butyl-4-{1-[6-(3,4-dichloro-phenyl)-4-trifluoromethyl-pyrimidin-2-yl]-1H-imidazol-4-yl}-benzenesulfonamide (0.08 g) in dichloromethane (2 mL) was added TFA (2 mL) and the reaction mixture was allowed to stir at room temperature for 15 h. The mixture was evaporated to dryness and saturated $NaHCO_3$ solution (2.5 mL) and MeOH (2.5 mL) were added. The mixture was stirred at room temperature for 30 min, the precipitate was collected by filtration and washed with water. The crude product was further purified by crystallization (dichloromethane/heptane/MeOH) to yield the title compound as a white solid (0.058 g, 11%). MS (ISN) 512.3 [$(M-H)^-$]; mp 334° C.

EXAMPLE 212

4-{1-[4-(3-Methyl-4-trifluoromethyl-phenyl)-6-trifluoromethyl-pyrimidin-2-yl]-1H-imidazol-4-yl}-benzenesulfonamide 1) N-tert-Butyl-4-{1-[6-(3-methyl-4-trifluoromethyl-phenyl)-4-trifluoromethyl-pyrimidin-2-yl]-1H-imidazol-4-yl}-benzenesulfonamide was prepared from 2-(4-iodo-imidazol-1-yl)-6-(3-methyl-4-trifluoromethyl-phenyl)-4-trifluoromethyl-pyrimidine (example E.73) (0.50 g, 1.0 mmol) and commercially available 4-(tert.-butylsulfamoyl)-phenylboronic acid (0.31 g, 1.2 mmol) according to the general procedure VI. Obtained as a light yellow solid (0.057 g), which was subsequently deprotected.

2) To a cooled and stirred solution of N-tert-butyl-4-{1-[6-(3-methyl-4-trifluoromethylphenyl)-4-trifluoromethyl-pyrimidin-2-yl]-1H-imidazol-4-yl}-benzenesulfonamide (0.057 g) in dichloromethane (2 mL) was added TFA (2 mL) and the reaction mixture was allowed to stir at room temperature for 15 h. The mixture was evaporated to dryness and saturated $NaHCO_3$ solution (2.5 mL) and MeOH (2.5 mL) were added. The mixture was stirred at room temperature for 30 min, the precipitate was collected by filtration and washed with water. The crude product was further purified by crystallization (dichloromethane/heptane/MeOH) to yield the title compound as a white solid (0.038 g, 7%). MS (ISN) 526.5 [$(M-H)^-$]; mp 287° C.

EXAMPLE 213

3-{1-[4-(3-Methyl-4-trifluoromethyl-phenyl)-6-trifluoromethyl-pyrimidin-2-yl]-1H-imidazol-4-yl}-benzenesulfonamide 1) N-tert-Butyl-3-{1-[6-(3-methyl-4-trifluoromethyl-phenyl)-4-trifluoromethyl-pyrimidin-2-yl]-1H-imidazol-4-yl}-benzenesulfonamide was prepared from 2-(4-iodo-imidazol-1-yl)-6-(3-methyl-4-trifluoromethyl-phenyl)-4-trifluoromethyl-pyrimidine (example E.73) (0.50 g, 1.0 mmol) and commercially available 3-(tert.-butylsulfamoyl)-phenylboronic acid (0.31 g, 1.2 mmol) according to the general procedure VI. Obtained as an off white solid (0.118 g), which was subsequently deprotected.

2) To a cooled and stirred solution of N-tert-butyl-3-{1-[6-(3-methyl-4-trifluoromethylphenyl)-4-trifluoromethyl-pyrimidin-2-yl]-1H-imidazol-4-yl}-benzenesulfonamide (0.128 g) in dichloromethane (3 mL) was added TFA (3 mL) and the reaction mixture was allowed to stir at room temperature for 15 h. The mixture was evaporated to dryness and saturated $NaHCO_3$ solution (2.5 mL) and MeOH (2.5 mL) were added. The mixture was stirred at room temperature for 30 min, the precipitate was collected by filtration and washed with water. The crude product was further purified by crystallization (dichloromethane/heptane/MeOH) to yield the title compound as an off-white solid (0.077 g, 15%). MS (ISN) 526.4 [$(M-H)^-$]; mp 180° C.

EXAMPLE 214

4-(3,4-Dichloro-phenyl)-2-[4-(3-methanesulfonyl-phenyl)-imidazol-1-yl]-6-methyl-pyrimidine A stirred mixture of 4-(3,4-dichloro-phenyl)-6-methyl-2-(4-tributylstannanyl-imidazol-1-yl)-pyrimidine (Example G.4) (0.45 g, 0.76 mmol), commercially available 3-bromo-phenylmethyl sulfone (0.20 g, 0.83 mmol), tetrakis(triphenyl-phosphine)palladium (0.053 g, 0.046 mmol) in toluene (8 mL) was heated under reflux conditions for 15 h. Heptane (10 mL) was added at room temperature and the mixture was stirred for 1 h. The precipitate was collected by filtration, washed with heptane and dried to yield the title compound (0.27 g, 78%) as an off-white solid. MS (ISP) 459.2 [$(M+H)^+$]; mp 213° C.

EXAMPLE 215

3-{1-[4-(3,4-Dichloro-phenyl)-6-trifluoromethyl-pyrimidin-2-yl]-1H-imidazol-4-yl}-benzenesulfonamide 1) N-tert-Butyl-3-{1-[6-(3,4-dichloro-phenyl)-4-trifluoromethyl-pyrimidin-2-yl]-1H-imidazol-4-yl}-benzenesulfonamide was prepared from 4-(3,4-dichloro-phenyl)-2-(4-iodo-imidazol-1-yl)-6-trifluoromethyl-pyrimidine (example E.74) (0.485 g, 1.0 mmol) and commercially available 3-(tert.-butylsulfamoyl)-phenylboronic acid (0.31 g, 1.2 mmol) according to the general procedure VI. Obtained as a light yellow solid (0.084 g) which was subsequently deprotected.

2) To a cooled and stirred solution of N-tert-butyl-3-{1-[6-(3,4-dichloro-phenyl)-4-trifluoromethyl-pyrimidin-2-yl]-1H-imidazol-4-yl}-benzenesulfonamide (0.084 g) in dichloromethane (2 mL) was added TFA (2 mL) and the reaction mixture was allowed to stir at room temperature for 15 h. The mixture was evaporated to dryness and saturated $NaHCO_3$ solution (2.5 mL) and MeOH (2.5 mL) were added. The mixture was stirred at room temperature for 30 min, the precipitate was collected by filtration and washed with water. The crude product was further purified by crystallization (dichloromethane/heptane/MeOH) to yield the title compound as an off-white solid (0.054 g, 10%). MS (ISP) 514.2 [$(M+H)^+$]; mp 239° C.

EXAMPLE 216

5-{1-[4-(3,4-Dichloro-phenyl)-6-methyl-pyrimidin-2-yl]-1H-imidazol-4-yl}-thiophene-2-sulfonic acid amide 1) A stirred mixture of 4-(3,4-dichloro-phenyl)-6-methyl-2-(4-tributylstannanyl-imidazol-1-yl)-pyrimidine (Example G.4) (0.45 g, 0.76 mmol), commercially available 5-bromothiophene-2-N-tert-butylsulfonamide (0.25 g, 0.84 mmol), tetrakis(triphenylphosphine)palladium (0.053 g, 0.046 mmol) in toluene (8 mL) was heated under reflux conditions for 15 h, hexane (10 mL) was added and the mixture was stirred at RT for 1 h. The precipitate was collected by filtration and dried to yield 5-{1-[4-(3,4-dichloro-phenyl)-6-methyl-pyrimidin-2-yl]-1H-imidazol-4-yl}-thiophene-2-sulfonic acid tert-butyl amide (0.41 g) as a light brown solid.

2) To a cooled and stirred solution of 5-{1-[4-(3,4-dichloro-phenyl)-6-methyl-pyrimidin-2-yl]-1H-imidazol-4-yl}-thiophene-2-sulfonic acid tert-butyl amide (0.41 g) in dichloromethane (5 mL) was added TFA (5 mL) and the reaction mixture was allowed to stir at room temperature for 15 h. The mixture was evaporated to dryness and saturated $NaHCO_3$ solution (10 mL) was added. The mixture was stirred at room temperature for 30 min, the precipitate was collected by filtration and washed with water. The crude product was further purified by crystallization (MeOH/diethyl ether) to yield the title compound as a light brown solid (0.28 g, 79%). MS (ISP) 466.1 [$(M+H)^+$]; mp 253.5° C.

EXAMPLE 217

2-[4-(3-Methanesulfonyl-phenyl)-imidazol-1-yl]-4-trifluoromethyl-6-(4-trifluoromethylphenyl)-pyrimidine A stirred mixture of 2-(4-tributylstannanyl-imidazol-1-yl)-4-trifluoromethyl-6-(4-trifluoromethyl-phenyl)-pyrimidine (Example G.1) (0.155 g, 0.24 mmol), commercially available 3-bromo-phenylmethyl sulfone (0.062 g, 0.26 mmol), tetrakis(triphenyl-phosphine)palladium (0.017 g, 0.015 mmol) in toluene (5 mL) was heated under reflux conditions for 15 h. Heptane (5 mL) was added at room temperature and the mixture was stirred for 1 h. The precipitate was collected by filtration, washed with heptane and dried. Further purification by flash chromatography on silica gel (ethyl acetate/heptane) and crystallization (dichloromethane/hexane) yielded the title compound (0.078 g, 64%) as a white solid. MS (ISP) 512.9 [$(M+H)^+$]; mp 231° C.

EXAMPLE 218

2-[2-(3-Methanesulfonyl-phenyl)-pyridin-4-yl]-4-trifluoromethyl-6-(4-trifluoromethyl-phenyl)-pyrimidine The title compound was prepared from 2-(2-chloro-pyridin-4-yl)-4-trifluoromethyl-6-(4-trifluoromethyl-phenyl)-pyrimidine (example E.6) (0.404 g, 1.0 mmol) and commercially available 3-methanesulfonyl-phenylboronic acid (0.22 g, 1.1 mmol) according to the general procedure VI. Obtained as a white solid (0.4 g, 77%). MS (ISP) 524.0 [$(M+H)^+$]; mp 238.5° C.

EXAMPLE 219

2-(3'-Methanesulfonyl-biphenyl-3-yl)-4-trifluoromethyl-6-(4-trifluoromethyl-phenyl)-pyrimidine The title compound was prepared from 2-(3-bromo-phenyl)-4-trifluoromethyl-6-(4-trifluoromethyl-phenyl)-pyrimidine (example E.3) (0.45 g, 1.0 mmol) and commercially available 3-methanesulfonyl-phenylboronic acid (0.22 g, 1.1 mmol) according to the general procedure VI. Obtained as a white solid (0.45 g, 86%). MS (ISP) 523.0 [$(M+H)^+$]; mp 183.5° C.

EXAMPLE 220

3'-[4-Trifluoromethyl-6-(4-trifluoromethyl-phenyl)-pyrimidin-2-yl]-biphenyl-3-ylamine 1) 2-(3'-Nitro-biphenyl-3-yl)-4-trifluoromethyl-6-(4-trifluoromethyl-phenyl)pyrimidine was prepared from 2-(3-bromo-phenyl)-4-trifluoromethyl-6-(4-trifluoromethylphenyl)-pyrimidine (example E.3) (1.79 g, 4.0 mmol) and commercially available 3-nitrophenylboronic acid (0.8 g, 4.8 mmol) according to the general procedure VI. Obtained as a light grey solid (1.74 g, 89%). MS (EI) 489.2 [(M)$^+$]; mp 219° C.

2) To a stirred suspension of 2-(3'-nitro-biphenyl-3-yl)-4-trifluoromethyl-6-(4-trifluoromethyl-phenyl)-pyrimidine (1.6 g, 3.27 mmol) in MeOH (40 mL) was added at room temperature Pd—C (10%, 0.16 g) and THF (40 mL). The mixture was stirred at room temperature under $H_2$ atmosphere for 2 h, the catalyst was removed by filtration and the obtained solution evaporated. The crude product was further purified by crystallization from diethyl ether/hexane to yield the title compound as an off-white solid (1.28 g, 85%). MS (ISP) 460.2 [(M+H)$^+$]; mp 156.5° C.

EXAMPLE 221

N-{3'-[4-Trifluoromethyl-6-(4-trifluoromethyl-phenyl)-pyrimidin-2-yl]-biphenyl-3-yl}-sulfamide To a stirred solution of 3'-[4-trifluoromethyl-6-(4-trifluoromethyl-phenyl)-pyrimidin-2-yl]-biphenyl-3-ylamine (example 220) (0.46 g, 1.0 mmol) in dichloromethane (10 mL) was added triethylamine (0.42 mL) and N-Boc-sulfamoyl chloride (0.8M, 3.75 mL, 3.0 mmol), the reaction mixture was allowed to stir at room temperature for 45 h, poured into ice-water (20 mL) and extracted with ethyl acetate (2×30 mL). The combined organic layers were washed with brine (30 mL), dried ($MgSO_4$) and evaporated. Further purification by flash chromatography on silica gel (ethyl acetate/heptane) and crystallization (dichloromethane/MeOH/hexane) yielded a white solid (0.3 g), which was dissolved in TFA (10 mL) and allowed to stir at room temperature for 15 h. The mixture was evaporated to dryness and saturated $NaHCO_3$ solution (10 mL) was added. The mixture was stirred at room temperature for 30 min, the precipitate was collected by filtration and washed with water. The crude product was further purified by crystallization (dichloromethane/MeOH/hexane) to yield the title compound as a white solid (0.21 g, 39%). MS (ISP) 539.3 [(M+H)$^+$]; mp 174° C.

EXAMPLE 222

N-{3'-[4-Trifluoromethyl-6-(4-trifluoromethyl-phenyl)-pyrimidin-2-yl]-biphenyl-3-yl}-N',N'-dimethyl-sulfamide To a stirred solution of 3'-[4-trifluoromethyl-6-(4-trifluoromethyl-phenyl)-pyrimidin-2-yl]-biphenyl-3-ylamine (example 220) (0.23 g, 0.5 mmol) in toluene (5 mL) was added triethylamine (0.21 mL) and dimethylsulfamoyl chloride (0.14 g, 1.0 mmol), the reaction mixture was allowed to stir at 70° C. for 22 h, poured into ice-water (20 mL) and extracted with ethyl acetate (2×30 mL). The combined organic layers were washed with brine (30 mL), dried ($MgSO_4$) and evaporated. Further purification by flash chromatography on silica gel (ethyl acetate/heptane) and crystallization (EtOH/hexane) yielded the title compound (0.104 g, 37%) as an off-white solid. MS (ISP) 567.3 [(M+H)$^+$]; mp 113° C.

EXAMPLE 223

N-{3'-[4-Trifluoromethyl-6-(4-trifluoromethyl-phenyl)-pyrimidin-2-yl]-biphenyl-3-yl}-methane-sulfonamide To a stirred and cooled (ice bath) solution of 3'-[4-trifluoromethyl-6-(4-trifluoromethylphenyl)-pyrimidin-2-yl]-biphenyl-3-ylamine (example 220) (0.23 g, 0.5 mmol) in dichloromethane (5 mL) was added triethylamine (0.21 mL) and methanesulfonyl chloride (0.06 g, 0.52 mmol), the reaction mixture was allowed to stir at room temperature for 1 h, poured into sat. $NaHCO_3$ solution (20 mL) and extracted with ethyl acetate (2×30 mL). The combined organic layers were washed with brine (30 mL), dried ($MgSO_4$) and evaporated. Further purification by flash chromatography on silica gel (ethyl acetate/heptane) and crystallization (dichloromethane/MeOH/hexane) yielded the title compound (0.16 g, 72%) as a white solid. MS (ISP) 538.0 [(M+H)$^+$]; mp 191° C.

EXAMPLE 224

3-{1-[4-(4-Chloro-3-methyl-phenyl)-6-methyl-pyrimidin-2-yl]-1H-imidazol-4-yl}-benzenesulfonamide 1) N-tert-Butyl-3-{1-[6-(4-chloro-3-methyl-phenyl)-4-methyl-pyrimidin-2-yl]-1H-imidazol-4-yl}-benzenesulfonamide was prepared from 4-(4-chloro-3-methyl-phenyl)-2-(4-iodo-imidazol-1-yl)-6-methyl-pyrimidine (example E.76) (0.41 g, 1.0 mmol) and commercially available 3-(tert.-butylsulfamoyl)-phenylboronic acid (0.31 g, 1.2 mmol) according to the general procedure VI. Obtained as a light grey solid (0.53 g) which was subsequently deprotected.

2) To a cooled and stirred solution of N-tert-butyl-3-{1-[6-(4-chloro-3-methyl-phenyl)-4-methyl-pyrimidin-2-yl]-1H-imidazol-4-yl}-benzenesulfonamide (0.53 g) in dichloromethane (5 ml) was added TFA (5 ml) and the reaction mixture was allowed to stir at room temperature for 15 h. The mixture was evaporated to dryness and saturated $NaHCO_3$ solution (10 ml), diethylether and heptane were added. The mixture was stirred at room temperature for 1 h, the precipitate was collected by filtration, washed with water and heptane and dried. Further purification by flash chromatography on silica gel (ethyl acetate/heptane) and crystallization (THF/heptane) yielded the title compound as a white solid (0.3 g, 68%). MS (ISP) 440.1 [(M+H)$^+$]; mp 219° C. (dec.).

EXAMPLE 225

5-{1-[4-(4-Chloro-3-methyl-phenyl)-6-methyl-pyrimidin-2-yl]-1H-imidazol-4-yl}-thiophene-2-sulfonic acid amide 1) A stirred mixture of 4-(4-chloro-3-methyl-phenyl)-6-methyl-2-(4-tributylstannanyl-imidazol-1-yl)-pyrimidine (Example G.8) (0.59 g, 1.03 mmol), commercially available 5-bromothiophene-2-N-tert-butylsulfonamide (0.34 g, 1.13 mmol), tetrakis(triphenylphosphine)palladium (0.071 g, 0.062 mmol) in toluene (8 ml) was heated under reflux conditions for 15 h, heptane (10 ml) was added and the mixture was stirred at RT for 1 h. The precipitate was collected by filtration and dried to yield 5-{1-[4-(4-chloro-3-methyl-phenyl)-6-methyl-pyrimidin-2-yl]-1H-imidazol-4-yl}-thiophene-2-sulfonic acid tert-butyl amide (0.54 g) as a white solid.

2) To a cooled and stirred solution of 5-{1-[4-(4-chloro-3-methyl-phenyl)-6-methyl-pyrimidin-2-yl]-1H-imidazol-4-yl}-thiophene-2-sulfonic acid tert-butyl amide (0.54 g) in dichloromethane (5 ml) was added TFA (5 ml) and the reaction mixture was allowed to stir at room temperature for 15 h. The mixture was evaporated to dryness and saturated $NaHCO_3$ solution (10 ml) was added. The mixture was stirred at room temperature for 30 min, the precipitate was collected by filtration and washed with water. The crude product was further purified by flash chromatography on silica gel (ethyl acetate/heptane) and crystallization (THF/diethyl ether) to yield the title compound as a white solid (0.24 g, 52%). MS (ISP) 445.9 [$(M+H)^+$]; mp 267° C. (dec.).

EXAMPLE 226

5-{1-[4-(4-Chloro-3-methyl-phenyl)-6-methyl-pyrimidin-2-yl]-1H-imidazol-4-yl}-pyridin-2-ylamine The title compound was prepared from 4-(4-chloro-3-methyl-phenyl)-2-(4-iodo-imidazol-1-yl)-6-methyl-pyrimidine (example E.76) (0.41 g, 1.0 mmol) and commercially available 2-amino-5-(4,4,5,5-tetramethyl-1,3,2-dioxaborolan-2-yl)pyridine (0.26 g, 1.2 mmol) according to the general procedure VI. Obtained as a yellow solid (0.14 g, 37%). MS (ISP) 377.3 [$(M+H)^+$]; mp 202° C. (dec.).

EXAMPLE 227

2-Methyl-6-[3-(4-methyl-imidazol-1-yl)-phenyl]-4-(4-trifluoromethyl-phenyl)-pyridine The title compound was prepared from 2-iodo-6-methyl-4-(4-trifluoromethyl-phenyl)pyridine (example A.31) (400 mg, 1.09 mmol) and 4-methyl-1-[3-(4,4,5,5-tetramethyl-[1,3,2]dioxaborolan-2-yl)-phenyl]-1H-imidazole [in situ prepared by the following sequence: Step 1) A mixture of commercially available 3-bromophenylisothiocyanate (10.06 g, 47.0 mmol) and 2-aminopropionaldehyde dimethylacetal (5.96 mL, 47.0 mmol) in EtOH (50 mL) was refluxed for 1 h. Evaporated to dryness to give 1-(3-bromo-phenyl)-3-(2,2-dimethoxy-1-methylethyl)-thiourea as an off-white solid (15.69 g, 100%). Step 2) A mixture of the above prepared 1-(3-bromo-phenyl)-3-(2,2-dimethoxy-1-methyl-ethyl)-thiourea (15.69 g, 47 mmol) in $H_2O$ (85 mL) and 37% HCl (8.5 mL) was refluxed for 4.5 h. Removed from oilbath, added ice and ice water (total volume: 250 mL), the precipitate was filtered off, washed several times with ice water and dried in vacuum at 60° C. to give the 1-(3-bromo-phenyl)-4-methyl-1H-imidazole-2-thiol as a light orange solid (8.71 g, 69%). Step 3) To a suspension of the above prepared 1-(3-bromophenyl)-4-methyl-1H-imidazole-2-thiol (6.00 g, 22 mmol) in acetic acid (20 mL) and water (5 mL) was added dropwise 35% $H_2O_2$ (13.4 mL, 156 mmol) within 15 min keeping the internal temperature below 60° C. Stirred at 23° C. for 30 min, poured onto ice, destroyed excess $H_2O_2$ by addition of sat. $Na_2SO_3$-sol., adjusted pH with 32% NaOH-sol. until pH 9 is reached, extracted with EtOAc (3×100 mL), the combined organic layers were washed with brine and dried over $Na_2SO_4$. Removal of the solvent in vacuum left a red oil, which was purified by silica gel column chromatography with EtOAc to give the 1-(3-bromo-phenyl)-4-methyl-1H-imidazole as a brown oil (3.80 g, 72%). Step 4) A mixture of the above prepared 1-(3-bromo-phenyl)-4-methyl-1H-imidazole (0.313 g, 1.31 mmol), bis(pinacolato)diboron (0.364 g, 1.438 mmol), potassium acetate (0.389 g, 3.96 mmol) and $PdCl_2(PPh_3)_2$ (0.023 g, 3 mol %) in DMF at 100° C. for 2 h; then addition of $Pd(OAc)_2$ (0.007 g, 3 mol %) and dppf (0.018 g, 3 mol %) and stirred at 100° C. overnight. This solution obtained was used directly.] according to the general procedure VI. Obtained as an off-white solid (0.140 g, 32%). MS (ISP) 394.0 [$(M+H)^+$]; mp 126-132° C.

EXAMPLE 228

3'-[6-Methyl-4-(4-trifluoromethyl-phenyl)-pyridin-2-yl]-biphenyl-3-sulfonic acid amide The title compound was prepared from 2-(3-bromo-phenyl)-6-methyl-4-(4-trifluoromethyl-phenyl)-pyridine (example E.21) (0.200 g, 0.51 mmol) and 3-sulfamoyl-benzeneboronic acid (example F.2) (0.102 g, 0.51 mmol) according to the general procedure VI. Obtained as a white solid (0.120 g, 50%). MS (ISP) 467.1 [$(M+H)^+$]; mp 196° C.

EXAMPLE 229

5-{3-[4-(4-Chloro-phenyl)-6-methyl-pyridin-2-yl]-phenyl}-pyridin-2-ylamine

The title compound was prepared from 2-(3-bromo-phenyl)-4-(4-chloro-phenyl)-6-methyl-pyridine (example E.32) (0.15 g, 0.42 mmol) and commercially available 2-amino-5-(4,4,5,5-tetramethyl-1,3,2-dioxaborolan-2-yl)pyridine (0.101 g, 0.46 mmol) according to the general procedure VI. Obtained as a white solid (0.045 g, 29%). MS (ISP) 372.1 [$(M+H)^+$] and 374 [$(M+2+H)^+$]; mp 76-95° C.

EXAMPLE 230

5-{2-[6-Methyl-4-(4-trifluoromethyl-phenyl)-pyridin-2-yl]-thiazol-4-yl}-pyridin-2-ylamine The title compound was prepared from 2-(4-bromo-thiazol-2-yl)-6-methyl-4-(4-trifluoromethyl-phenyl)-pyridine (example E.80) (0.30 g, 0.75 mmol) and commercially available 2-amino-5-(4,4,5,5-tetramethyl-1,3,2-dioxaborolan-2-yl)pyridine (0.248 g, 1.13 mmol) according to the general procedure VI. Obtained as a light yellow solid (0.040 g, 11%). MS (ISP) 413.2 [$(M+H)^+$]; mp 191° C.

EXAMPLE 231

5-{2-[6-Methyl-4-(4-trifluoromethyl-phenyl)-pyridin-2-yl]-thiazol-4-yl}-pyrimidin-2-ylamine The title compound was prepared from 2-(4-bromo-thiazol-2-yl)-6-methyl-4-(4-trifluoromethyl-phenyl)-pyridine (example E.80) (0.20 g, 0.50 mmol) and commercially available 2-amino-5-(4,4,5,5-tetramethyl-1,3,2-dioxaborolan-2-yl)pyrimidine (0.133 g, 0.60 mmol) according to the general procedure VI. Obtained as a white solid (0.100 g, 48%/o). MS (ISP) 414.2 [$(M+H)^+$]; mp>250° C.

EXAMPLE 232

5-{3-[6-Trifluoromethyl-4-(4-trifluoromethyl-phenyl)-pyridin-2-yl]-phenyl}-pyridin-2-ylamine The title compound was prepared from 2-(3-bromo-phenyl)-6-trifluoromethyl-4-(4-trifluoromethyl-phenyl)-pyridine (example E.81) (0.20 g, 0.45 mmol) and commercially available 2-amino-5-(4,4,5,5-tetramethyl-1,3,2-dioxaborolan-2-yl)pyridine (0.109 g, 0.49 mmol) according to the general procedure VI. Obtained as a white solid (0.110 g, 53%). MS (ISP) 460.2 [$(M+H)^+$]; mp 166° C.

EXAMPLE 233

5-{3-[6-Trifluoromethyl-4-(4-trifluoromethyl-phenyl)-pyridin-2-yl]-phenyl}-pyrimidin-2-ylamine The title compound was prepared from 2-(3-bromo-phenyl)-6-trifluoromethyl-4-(4-trifluoromethyl-phenyl)-pyridine (example E.81) (0.20 g, 0.45 mmol) and commercially available 2-amino-5-(4,4,5,5-tetramethyl-1,3,2-dioxaborolan-2-yl)pyrimidine (0.109 g, 0.49 mmol) according to the general procedure VI. Obtained as a light yellow solid (0.160 g, 77%). MS (ISP) 461.2 [$(M+H)^+$]; mp 260° C.

EXAMPLE 234

5-{3-[4-(4-Chloro-phenyl)-6-trifluoromethyl-pyridin-2-yl]-phenyl}-pyrimidin-2-ylamine The title compound was prepared from 2-(3-bromo-phenyl)-4-(4-chloro-phenyl)-6-trifluoromethyl-pyridine (example E.82) (0.20 g, 0.485 mmol) and commercially available 2-amino-5-(4,4,5,5-tetramethyl-1,3,2-dioxaborolan-2-yl)pyrimidine (0.118 g, 0.532 mmol) according to the general procedure VI. Obtained as a white solid (0.110 g, 53%). MS (ISP) 427.1 [$(M+H)^+$] and 429 [$(M+2+H)^+$]; mp 239° C.

EXAMPLE 235

5-{3-[4-(4-Chloro-phenyl)-6-trifluoromethyl-pyridin-2-yl]-phenyl}-pyridin-2-ylamine The title compound was prepared from 2-(3-bromo-phenyl)-4-(4-chloro-phenyl)-6-trifluoromethyl-pyridine (example E.82) (0.30 g, 0.727 mmol) and commercially available 2-amino-5-(4,4,5,5-tetramethyl-1,3,2-dioxaborolan-2-yl)pyridine (0.192 g, 0.873 mmol) according to the general procedure VI. Obtained as a light grey solid (0.200 g, 65%). MS (ISP) 426.0 [$(M+H)^+$] and 428 [$(M+2+H)^+$]; mp 172° C.

EXAMPLE 236

5-{5-[6-Methyl-4-(4-trifluoromethyl-phenyl)-pyridin-2-yl]-[1,2,4]oxadiazol-3-yl}-pyridin-2-ylamine The title compound was prepared from 6-amino-N-hydroxy-nicotinamidine (example C.3) (0.113 g, 0.53 mmol) and 6-methyl-4-(4-trifluoromethyl-phenyl)-pyridine-2-carboxylic acid (example D.11) (0.10 g, 0.36 mmol) according to the general procedure V. Obtained as an off-white solid (0.045 g, 31%). MS (ISP) 398.1 [$(M+H)^+$]; mp 163° C.

EXAMPLE 237

3-{5-[6-Methyl-4-(4-trifluoromethyl-phenyl)-pyridin-2-yl]-[1,2,4]oxadiazol-3-yl}-benzenesulfonamide The title compound was prepared from N-hydroxy-3-sulfamoyl-benzamidine [CAS-No. 9000-88-7] (0.115 g, 0.53 mmol) and 6-methyl-4-(4-trifluoromethyl-phenyl)-pyridine-2-carboxylic acid (example D.11) (0.10 g, 0.36 mmol) according to the general procedure V. Obtained as an off-white solid (0.080 g, 49%). MS (ISP) 461.0 [$(M+H)^+$]; mp 277° C.

EXAMPLE 238

5-{5-[4-Trifluoromethyl-6-(4-trifluoromethyl-phenyl)-pyridin-2-yl]-[1,2,4]oxadiazol-3-yl}-pyridin-2-ylamine The title compound was prepared from 6-amino-N-hydroxy-nicotinamidine (example C.3) (0.128 g, 0.60 mmol) and 4-trifluoromethyl-6-(4-trifluoromethyl-phenyl)-pyridine-2-carboxylic acid (example D.12) (0.135 g, 0.403 mmol) according to the general procedure V. Obtained as a light yellow solid (0.022 g, 12%). MS (ISP) 452.1 [$(M+H)^+$]; mp 229° C.

EXAMPLE 239

5-{4-[6-Methyl-4-(4-trifluoromethyl-phenyl)-pyridin-2-yl]-pyrimidin-2-yl}-pyridin-2-ylamine The title compound was prepared from 2-chloro-4-[6-methyl-4-(4-trifluoromethylphenyl)-pyridin-2-yl]-pyrimidine (example E.83) (0.40 g, 1.14 mmol) and commercially available 2-amino-5-(4,4,5,5-tetramethyl-1,3,2-dioxaborolan-2-yl)pyridine (0.302 g, 1.37 mmol) according to the general procedure VI. Obtained as an off-white solid (0.050 g, 10%). MS (ISP) 408.3 [$(M+H)^+$]; mp 191° C.

EXAMPLE 240

4-[6-Methyl-4-(4-trifluoromethyl-phenyl)-pyridin-2-yl]-[2,5']bipyrimidinyl-2'-ylamine The title compound was prepared from 2-chloro-4-[6-methyl-4-(4-trifluoromethylphenyl)-pyridin-2-yl]-pyrimidine (example E.83) (0.40 g, 1.14 mmol) and commercially available 2-amino-5-(4,4,5,5-tetramethyl-1,3,2-dioxaborolan-2-yl)pyrimidine (0.303 g, 1.37 mmol) according to the general procedure VI. Obtained as a white solid (0.050 g, 10%). MS (ISP) 409.2 [$(M+H)^+$]; mp 264° C.

EXAMPLE 241

5-{2-[6-Methyl-4-(4-trifluoromethyl-phenyl)-pyridin-2-yl]-pyrimidin-4-yl}-pyridin-2-ylamine The title compound was prepared by the following sequence: Step 1) 2-Chloro-4-[6-(2,5-dimethyl-pyrrol-1-yl)-pyridin-3-yl]-pyrimidine: Prepared from 5-bromo-2-(2,5-dimethyl-pyrrol-1-yl)-pyridine [CAS-no. 228710-82-5] (2.76 g, 11.0 mmol) and commercially available 2,4-dichloropyrimidine (1.49 g, 10.0 mmol) with n-BuLi, $ZnCl_2$ and $Pd(PPh_3)_4$ according to the general procedure IVc protocol b. Obtained as a yellow solid (1.39 g, 49%). MS (ISP) 285.1 [$(M+H)^+$] and 287.1 [$(M+2+H)^+$].

Step 2) 4-[6-(2,5-Dimethyl-pyrrol-1-yl)-pyridin-3-yl]-2-[6-methyl-4-(4-trifluoromethylphenyl)-pyridin-2-yl]-pyrimidine: Prepared from the above described 2-chloro-4-[6-(2,5-dimethyl-pyrrol-1-yl)-pyridin-3-yl]-pyrimidine (404 mg, 1.21 mmol) and from 2-iodo-6-methyl-4-(4-trifluoromethyl-phenyl)-pyridine (example A.31) (0.5 g, 1.17 mmol) according to the general procedure IVc protocol b. Obtained as an off-white solid (0.250 g, 44%). MS (ISP) 486.3 [$(M+H)^+$].

Step 3) The title compound was prepared from the above described 4-[6-(2,5-dimethyl-pyrrol-1-yl)-pyridin-3-yl]-2-[6-methyl-4-(4-trifluoromethyl-phenyl)-pyridin-2-yl]-pyrimidine (0.250 g, 1.29 mmol) by heating with hydroxylamine hydrochloride (259 mg, 3.86 mmol) in a mixture of aqueous NaOH (1.5 M, 0.86 mL, 1.29 mmol) in 1-propanol (2.5 mL) in a sealed tube at 120° C. for 4 h. Cooled to rt, added some water and extracted twice with AcOEt, dried over $Na_2SO_4$, filtered off and evaporated totally. The crude material was triturated with ether to give the title compound (0.140 g, 67%) as an off-white solid. MS (ISP) 408.3 [$(M+H)^+$]; mp 258° C.

EXAMPLE 242

3-[6-Methyl-4-(4-trifluoromethyl-phenyl)-pyridin-2-yl]-benzonitrile

The title compound was prepared trifluoro-methane-sulfonic acid 6-methyl-4-(4-trifluoromethyl-phenyl)-pyridin-2-yl ester (example A.32) (5.00 g, 13 mmol) and commercially available 3-cyanophenylboronic acid (1.67 g, 14.3 mmol) according to the general procedure VI. Obtained as a white solid (3.00 g, 68%). MS (ISP) 339.1 [$(M+H)^+$]; mp 140° C.

EXAMPLE 243

3-{5-[4-Trifluoromethyl-6-(4-trifluoromethyl-phenyl)-pyridin-2-yl]-[1,2,4]oxadiazol-3-yl}-benzene-sulfonamide The title compound was prepared from N-hydroxy-3-sulfamoyl-benzamidine [CAS-No. 9000-88-7] (0.230 g, 1.06 mmol) and 4-trifluoromethyl-6-(4-trifluoromethyl-phenyl)-pyridine-2-carboxylic acid (example D.12) (0.30 g, 1.00 mmol) according to the general procedure V. Obtained as a white solid (0.100 g, 22%). MS (ISP) 513.2 [$(M+H)^+$]; mp 211° C.

EXAMPLE 244

3'-[6-Trifluoromethyl-4-(4-trifluoromethyl-phenyl)-pyridin-2-yl]-biphenyl-3-sulfonic acid amide The title compound was prepared from 2-(3-bromo-phenyl)-6-trifluoromethyl-4-(4-trifluoromethyl-phenyl)-pyridine (example E.81) (0.200 g, 0.448 mmol) and 3-sulfamoyl-benzeneboronic acid (example F.2) (0.100 g, 0.488 mmol) according to the general procedure VI. Obtained as a white solid (0.040 g, 15%). MS (ISP) 523.3 [$(M+H)^+$]; mp 187° C.

EXAMPLE 245

5-{3-[6-Trifluoromethyl-4-(4-trifluoromethyl-phenyl)-pyridin-2-yl]-phenyl}-pyridine-3-sulfonic acid amide The title compound was prepared 2-(3-bromo-phenyl)-6-trifluoromethyl-4-(4-trifluoromethyl-phenyl)-pyridine (example E.81) (0.20 g, 0.448 mmol) and 3-sulfamoyl-pyridine-5-boronic acid (example F.3) (0.100 g, 0.488 mmol) according to the general procedure VI. Obtained as a white solid (0.035 g, 15%). MS (ISP) 522.2 [$(M+H)^+$]; mp 240° C.

EXAMPLE 246

5-{1-[4-(3,4-Dichloro-phenyl)-6-methyl-pyridin-2-yl]-1H-imidazol-4-yl}-pyridin-2-ylamine The title compound was prepared from 4-(3,4-dichloro-phenyl)-2-(4-iodo-imidazol-1-yl)-6-methyl-pyridine (example E.84) (0.20 g, 0.47 mmol) and commercially available 2-amino-5-(4,4,5,5-tetramethyl-1,3,2-dioxaborolan-2-yl) pyridine (0.113 g, 0.51 mmol) according to the general procedure VI. Obtained as an off-white solid (0.035 g, 17%). MS (ISP) 396.0 [$(M+H)^+$], 398.1 [$(M+2+H)^+$] and 400 [$(M+4+H)^+$]; mp 245° C.

EXAMPLE 247

4-(3,4-Dichloro-phenyl)-2-imidazol-1-yl-6-methyl-pyridine

The title compound was prepared from 2-chloro-4-(3,4-dichloro-phenyl)-6-methylpyridine (example A.51) (0.5 g, 0.8 mmol) and commercially available imidazole (0.112 g, 1.6 mmol) according to the general procedure IVa. Obtained as a white solid (0.060 g, 24%). MS (ISP) 304.0 [$(M+H)^+$], 306 [$(M+2+H)^+$] and 308 [$(M+4+H)^+$]; mp 227° C.

EXAMPLE 248

5-{3-[6-Methyl-4-(4-trifluoromethyl-phenyl)-pyridin-2-yl]-phenyl}-pyridine-3-sulfonic acid amide The title compound was prepared from 2-(3-bromo-phenyl)-6-methyl-4-(4-trifluoromethyl-phenyl)-pyridine (example E.21) (0.200 g, 0.51 mmol) and 3-sulfamoyl-pyridine-5-boronic acid (example F.3) (0.103 g, 0.51 mmol) according to the general procedure VI. Obtained as a white solid (0.015 g, 6%). MS (ISP) 470.3 [$(M+H)^+$]; mp>250° C.

EXAMPLE 249

5-{3-[4-(3,4-Dichloro-phenyl)-6-methyl-pyridin-2-yl]-phenyl}-pyridin-2-ylamine

The title compound was prepared from 2-(3-bromo-phenyl)-4-(3,4-dichloro-phenyl)-6-methyl-pyridine (example E.85) (0.20 g, 0.509 mmol) and commercially available 2-amino-5-(4,4,5,5-tetramethyl-1,3,2-dioxaborolan-2-yl) pyridine (0.123 g, 0.56 mmol) according to the general procedure VI. Obtained as an off-white solid (0.050 g, 21%). MS (ISP) 406.0 [$(M+H)^+$], 408.1 [$(M+2+H)^+$] and 410 [$(M+4+H)^+$]; mp 99° C. (dec.).

EXAMPLE 250

5-{3-[4-(3,4-Dichloro-phenyl)-6-methyl-pyridin-2-yl]-phenyl}-pyrimidin-2-ylamine The title compound was prepared from 2-(3-bromo-phenyl)-4-(3,4-dichloro-phenyl)-6-methyl-pyridine (example E.85) (0.20 g, 0.509 mmol) and commercially available 2-amino-5-(4,4,5,5-tetramethyl-1,3,2-dioxaborolan-2-yl) pyrimidine (0.124 g, 0.56 mmol) according to the general procedure VI. Obtained as an off-white solid (0.100 g, 48%). MS (ISP) 407.2 [$(M+H)^+$], 409.1 [$(M+2+H)^+$] and 411 [$(M+4+H)^+$]; mp 188° C.

EXAMPLE 251

2-Methyl-6-thiazol-2-yl-4-(4-trifluoromethyl-phenyl)-pyridine

The title compound was prepared from 2-iodo-6-methyl-4-(4-trifluoromethyl-phenyl)-pyridine (example A.31) (4.0 g, 9.36 mmol) and commercially available 2,4-dibromothiazole (2.53 g, 10.4 mmol) according to the general procedure IVc protocol b. Obtained as a side product as a light yellow solid (0.065 g, 2%). MS (ISP) 321.2 [(M+H)$^+$]; mp 103° C.

EXAMPLE 252

5-{5-[6-Methyl-4-(4-trifluoromethyl-phenyl)-pyridin-2-yl]-thiophen-2-yl}-pyridin-2-ylamine The title compound was prepared from 2-(5-bromo-thiophen-2-yl)-6-methyl-4-(4-trifluoromethyl-phenyl)-pyridine (example E.86) (0.27 g, 0.678 mmol) and commercially available 2-amino-5-(4,4,5,5-tetramethyl-1,3,2-dioxaborolan-2-yl)pyridine (0.164 g, 0.745 mmol) according to the general procedure VI. Obtained as a light brown solid (0.100 g, 35%). MS (ISP) 412.2 [(M+H)$^+$]; mp 196° C.

EXAMPLE 253

5-{5-[6-Methyl-4-(4-trifluoromethyl-phenyl)-pyridin-2-yl]-thiophen-2-yl}-pyrimidin-2-ylamine The title compound was prepared from 2-(5-bromo-thiophen-2-yl)-6-methyl-4-(4-trifluoromethyl-phenyl)-pyridine (example E.86) (0.20 g, 0.502 mmol) and commercially available 2-amino-5-(4,4,5,5-tetramethyl-1,3,2-dioxaborolan-2-yl)pyrimidine (0.124 g, 0.552 mmol) according to the general procedure VI. Obtained as a yellow solid (0.045 g, 21%). MS (ISP) 413.2 [(M+H)$^+$]; mp>250° C.

EXAMPLE 254

5-{5-[4-(3,4-Dichloro-phenyl)-6-methyl-pyridin-2-yl]-thiophen-2-yl}-pyridin-2-ylamine The title compound was prepared from 2-(5-bromo-thiophen-2-yl)-4-(3,4-dichlorophenyl)-6-methyl-pyridine (example E.87) (0.25 g, 0.626 mmol) and commercially available 2-amino-5-(4,4,5,5-tetramethyl-1,3,2-dioxaborolan-2-yl)pyridine (0.152 g, 0.689 mmol) according to the general procedure VI. Obtained as a light brown solid (0.055 g, 21%). MS (ISP) 412.1 [(M+H)$^+$], 414.2 [(M+2+H)$^+$] and 416.2 [(M+4+H)$^+$]; mp 180° C.

EXAMPLE 255

5-{5-[4-(3,4-Dichloro-phenyl)-6-methyl-pyridin-2-yl]-thiophen-2-yl}-pyrimidin-2-ylamine The title compound was prepared from 2-(5-bromo-thiophen-2-yl)-4-(3,4-dichlorophenyl)-6-methyl-pyridine (example E.87) (0.25 g, 0.626 mmol) and commercially available 2-amino-5-(4,4,5,5-tetramethyl-1,3,2-dioxaborolan-2-yl)pyrimidine (0.152 g, 0.689 mmol) according to the general procedure VI. Obtained as a yellow solid (0.060 g, 23%). MS (ISP) 413.1 [(M+H)$^+$], 415.2 [(M+2+H)$^+$] and 417 [(M+4+H)$^+$]; mp 237° C.

EXAMPLE 256

5-{5-[6-Methyl-4-(4-trifluoromethyl-phenyl)-pyridin-2-yl]-thiophen-3-yl}-pyridin-2-ylamine The title compound was prepared from 2-(4-bromo-thiophen-2-yl)-6-methyl-4-(4-trifluoromethyl-phenyl)-pyridine (example E.88) (0.20 g, 0.5 mmol) and commercially available 2-amino-5-(4,4,5,5-tetramethyl-1,3,2-dioxaborolan-2-yl)pyridine (0.122 g, 0.55 mmol) according to the general procedure VI. Obtained as a white solid (0.115 g, 55%). MS (ISP) 412.2 [(M+H)$^+$]; mp 175° C.

EXAMPLE 257

5-{3-[6-Methyl-4-(4-trifluoromethyl-phenyl)-pyridin-2-yl]-phenyl}-pyridine-3-sulfonic acid (2-hydroxy-1,1-dimethyl-ethyl)-amide The title compound was prepared from 3-[6-methyl-4-(4-trifluoromethyl-phenyl)-pyridin-2-yl]-benzeneboronic acid (example G.9) (0.20 g, 0.56 mmol) and 5-bromo-pyridine-3-sulfonic acid (2-hydroxy-1,1-dimethyl-ethyl)-amide (example H.2) (0.173 g, 0.56 mmol) according to the general procedure VI. Obtained as a white solid (0.080 g, 26%). MS (ISP) 542.2 [(M+H)$^+$]; mp 105° C. (dec.).

EXAMPLE 258

3'-[6-Methyl-4-(4-trifluoromethyl-phenyl)-pyridin-2-yl]-biphenyl-3-sulfonic acid methoxy-amide The title compound was prepared from 3-[6-methyl-4-(4-trifluoromethyl-phenyl)pyridin-2-yl]-benzeneboronic acid (example G.9) (0.20 g, 0.56 mmol) and 3-bromo-N-methoxy-benzenesulfonamide (example H.3) (0.149 g, 0.56 mmol) according to the general procedure VI. Obtained as a white solid (0.120 g, 43%). MS (ISP) 499.2 [(M+H)$^+$]; mp 181° C.

EXAMPLE 259

3'-[6-Methyl-4-(4-trifluoromethyl-phenyl)-pyridin-2-yl]-biphenyl-3-sulfonic acid (2-hydroxy-1,1-dimethyl-ethyl)-amide The title compound was prepared from 3-[6-methyl-4-(4-trifluoromethyl-phenyl)pyridin-2-yl]-benzeneboronic acid (example G.9) (0.442 g, 1.2 mmol) and 3-bromo-N-(2-hydroxy-1,1-dimethyl-ethyl)-benzenesulfonamide (example H.4) (0.381 g, 1.2 mmol) according to the general procedure VI. Obtained as a white solid (0.150 g, 22%). MS (ISP) 499.2 [(M+H)$^+$]; mp 181° C.

EXAMPLE 260

5-{3-[6-Ethyl-4-(4-trifluoromethyl-phenyl)-pyridin-2-yl]-phenyl}-pyrimidin-2-ylamine The title compound was prepared from 2-(3-bromo-phenyl)-6-ethyl-4-(4-trifluoromethyl-phenyl)-pyridine (example E.89) (0.30 g, 0.739 mmol) and commercially available 2-amino-5-(4,4,5,5-tetramethyl-1,3,2-dioxaborolan-2-yl)pyrimidine (0.180 g, 0.813 mmol) according to the general procedure VI. Obtained as a white solid (0.050 g, 16%). MS (ISP) 421.1 [(M+H)$^+$]; mp 209° C.

EXAMPLE 261

N-tert-Butyl-3-[6'-methyl-4'-(4-trifluoromethyl-phenyl)-[2,2']bipyridinyl-6-yl]-benzenesulfonamide The title compound was prepared from 6'-bromo-6-methyl-4-(4-trifluoromethylphenyl)-[2,2']bipyridinyl (example E.26) (0.65 g, 1.65 mmol) and commercially available 3-(tert-butylsulfamoyl)-benzeneboronic acid (0.468 g, 1.82 mmol) according to the general procedure VI. Obtained as a white solid (0.10 g, 12%) and additional off-white solid (0.57 g, 66%). MS (ISP) 526.2 [(M+H)$^+$]; mp 183° C.

EXAMPLE 262

N-tert-Butyl-3-{4-[6-methyl-4-(4-trifluoromethyl-phenyl)-pyridin-2-yl]-pyrimidin-2-yl}-benzene-sulfonamide The title compound was prepared from 2-chloro-4-[6-methyl-4-(4-trifluoromethylphenyl)-pyridin-2-yl]-pyrimidine (example E.83) (0.5 g, 1.432 mmol) and commercially available 3-(tert-butylsulfamoyl)-benzeneboronic acid (0.404 g, 1.575 mmol) according to the general procedure VI. Obtained as a white solid (0.10 g, 13%) and additional off-white solid (0.48 g, 64%). MS (ISP) 527.2 [(M+H)$^+$]; mp 218° C.

EXAMPLE 263

N-tert-Butyl-3-{2-[6-methyl-4-(4-trifluoromethyl-phenyl)-pyridin-2-yl]-thiazol-4-yl}-benzenesulfonamide The title compound was prepared from 2-(4-bromo-thiazol-2-yl)-6-methyl-4-(4-trifluoromethyl-phenyl)-pyridine (example E.80) (0.5 g, 1.253 mmol) and commercially available 3-(tert-butylsulfamoyl)-benzeneboronic acid (0.354 g, 1.378 mmol) according to the general procedure VI. Obtained as a white solid (0.10 g, 15%) and additional off-white solid (0.40 g, 60%). MS (ISP) 532.1 [(M+H)$^+$]; mp 196° C.

EXAMPLE 264

5-{3-[6-Ethyl-4-(4-trifluoromethyl-phenyl)-pyridin-2-yl]-phenyl}-pyridin-2-ylamine The title compound was prepared from 2-(3-bromo-phenyl)-6-ethyl-4-(4-trifluoromethyl-phenyl)-pyridine (example E.89) (0.30 g, 0.739 mmol) and commercially available 2-amino-5-(4,4,5,5-tetramethyl-1,3,2-dioxaborolan-2-yl)pyridine (0.179 g, 0.813 mmol) according to the general procedure VI. Obtained as a white solid (0.050 g, 16%). MS (ISP) 420.1 [(M+H)$^+$]; mp 74° C.

EXAMPLE 265

3'-[6-Ethyl-4-(4-trifluoromethyl-phenyl)-pyridin-2-yl]-biphenyl-3-sulfonic acid tert-butylamide The title compound was prepared from 2-(3-bromo-phenyl)-6-ethyl-4-(4-trifluoromethyl-phenyl)-pyridine (example E.89) (0.30 g, 0.739 mmol) and commercially available 3-(tert-butylsulfamoyl)-benzeneboronic acid (0.209 g, 0.813 mmol) according to the general procedure VI. Obtained as a white solid (0.10 g, 25%) and additional off-white solid (0.20 g, 50%). MS (ISP) 539.3 [(M+H)$^+$]; mp 169° C.

EXAMPLE 266

3-[6'-Methyl-4'-(4-trifluoromethyl-phenyl)-[2,2']bipyridinyl-6-yl]-benzenesulfonamide To a cooled and stirred solution of N-tert-butyl-3-[6'-methyl-4'-(4-trifluoromethylphenyl)-[2,2']bipyridinyl-6-yl]-benzenesulfonamide (example 261) (0.570 g, 1.085 mmol) in dichloromethane (10 mL) was added TFA (10 mL) and the reaction mixture was allowed to stir at room temperature for 15 h. The mixture was evaporated to dryness and saturated $NaHCO_3$ solution (5 mL), diethyl ether and heptane were added. The mixture was stirred at room temperature for 1 h, the precipitate was collected by filtration, washed with water and heptane/diethyl ether and dried to yield the title compound as a white solid (0.28 g, 55%). MS (ISP) 468.2 [(M+H)$^+$]; mp 250° C.

EXAMPLE 267

3-{4-[6-Methyl-4-(4-trifluoromethyl-phenyl)-pyridin-2-yl]-pyrimidin-2-yl}-benzenesulfonamide To a cooled and stirred solution of N-tert-butyl-3-{4-[6-methyl-4-(4-trifluoromethylphenyl)-pyridin-2-yl]-pyrimidin-2-yl}-benzenesulfonamide (example 262) (0.480 g, 0.912 mmol) in dichloromethane (10 mL) was added TFA (10 mL) and the reaction mixture was allowed to stir at room temperature for 15 h. The mixture was evaporated to dryness and saturated $NaHCO_3$ solution (5 mL), diethyl ether and heptane were added. The mixture was stirred at room temperature for 1 h, the precipitate was collected by filtration, washed with water and heptane/diethyl ether and dried to yield the title compound as a white solid (0.25 g, 46%). MS (ISP) 469.3 [(M+H)$^+$]; mp>250° C.

EXAMPLE 268

3-{2-[6-Methyl-4-(4-trifluoromethyl-phenyl)-pyridin-2-yl]-thiazol-4-yl}-benzenesulfonamide To a cooled and stirred solution of N-tert-butyl-3-{2-[6-methyl-4-(4-trifluoromethylphenyl)-pyridin-2-yl]-thiazol-4-yl}-benzenesulfonamide (example 263) (0.40 g, 0.753 mmol) in dichloromethane (10 mL) was added TFA (10 mL) and the reaction mixture was allowed to stir at room temperature for 15 h. The mixture was evaporated to dryness and saturated $NaHCO_3$ solution (5 mL), diethyl ether and heptane were added. The mixture was stirred at room temperature for 1 h, the precipitate was collected by filtration, washed with water and heptane/diethyl ether and dried to yield the title compound as a white solid (0.20 g, 56%). MS (ISP) 474.1 [(M+H)$^+$]; mp>250° C.

EXAMPLE 269

3'-[6-Ethyl-4-(4-trifluoromethyl-phenyl)-pyridin-2-yl]-biphenyl-3-sulfonic acid amide To a cooled and stirred solution of 3'-[6-ethyl-4-(4-trifluoromethyl-phenyl)-pyridin-2-yl]-biphenyl-3-sulfonic acid tert-butylamide (example 265) (0.40 g, 0.742 mmol) in dichloromethane (10 in L) was added TFA (10 mL) and the reaction mixture was allowed to stir at room temperature for 15 h. The mixture was evaporated to dryness and saturated $NaHCO_3$ solution (5 mL), diethyl ether and heptane were added. The mixture was stirred at room temperature for 1 h, the precipitate was collected by filtration, washed with water and heptane/diethyl ether and dried to yield the title compound as a white solid (0.022 g, 12%). MS (ISP) 481.2 [(M+H)$^+$].

EXAMPLE 270

4,6-Difluoro-3'-[6-methyl-4-(4-trifluoromethyl-phenyl)-pyridin-2-yl]-biphenyl-3-sulfonic acid amide The title compound was prepared from 3-[6-methyl-4-(4-trifluoromethyl-phenyl)pyridin-2-yl]-benzeneboronic acid (example G.9) (0.40 g, 1.1 mmol) and commercially available 5-bromo-2,4-difluoro-benzenesulfonamide (0.635 g, 2.3 mmol) according to the general procedure VI. Obtained as a white solid (0.150 g, 27%). MS (ISP) 505.1 [$(M+H)^+$]; mp 227° C.

EXAMPLE 271

5-{3-[6-Methyl-4-(4-trifluoromethyl-phenyl)-pyridin-2-yl]-phenyl}-thiophene-2-sulfonic acid amide The title compound was prepared from 3-[6-methyl-4-(4-trifluoromethyl-phenyl)pyridin-2-yl]-benzeneboronic acid (example G.9) (0.40 g, 1.1 mmol) and commercially available 5-bromo-thiophene-2-sulfonic acid amide (0.478 g, 2.4 mmol) according to the general procedure VI. Obtained as a white solid (0.180 g, 42%). MS (ISP) 475.2 [$(M+H)^+$]; mp 215° C.

EXAMPLE 272

5-{3-[4-Methyl-6-(4-trifluoromethyl-phenyl)-pyridin-2-yl]-phenyl}-thiophene-2-sulfonic acid tert-butylamide The title compound was prepared from 2-(3-bromo-phenyl)-4-methyl-6-(4-trifluoromethyl-phenyl)-pyridine (example E.90) (0.392 g, 1.0 mmol) and N-tert-butyl-5-(4,4,5,5-tetramethyl-1,3,2-dioxaborolan-2-yl)-thiophene-2-sulfonamide (example F.1) (0.380 g, 1.1 mmol) according to the general procedure VI. Obtained as a white solid (0.409 g, 77%). MS (ISP) 531.3 [$(M+H)^+$]; mp 156° C.

EXAMPLE 273

5-{3-[4-Methyl-6-(4-trifluoromethyl-phenyl)-pyridin-2-yl]-phenyl}-thiophene-2-sulfonic acid amide To 5-{3-[4-methyl-6-(4-trifluoromethyl-phenyl)-pyridin-2-yl]-phenyl}-thiophene-2-sulfonic acid tert-butylamide (example 272) (0.30 g, 0.565 mmol) was added TFA (3 mL) and the reaction mixture was allowed to stir at room temperature for 15 h. The mixture was evaporated to dryness and saturated $NaHCO_3$ solution (5 mL), diethyl ether and heptane were added. The mixture was stirred at room temperature for 1 h, the precipitate was collected by filtration, washed with water and heptane/diethyl ether and dried to yield the title compound as a white solid (0.092 g, 34%). MS (ISP) 475.1 [$(M+H)^+$]; mp 211° C.

EXAMPLE 274

3'-[4-Methyl-6-(4-trifluoromethyl-phenyl)-pyridin-2-yl]-biphenyl-3-sulfonic acid amide The title compound was prepared from 3-[4-methyl-6-(4-trifluoromethyl-phenyl)pyridin-2-yl]-benzeneboronic acid (example G.10) (0.407 g, 1.14 mmol) and commercially available 3-bromobenzenesulfonamide (177 mg, 1.14 mmol) according to the general procedure VI. Obtained as a white solid (0.052 g, 10%). MS (ISP) 469.4 [$(M+H)^+$]; mp 200° C.

EXAMPLE 275

5-{3-[4-Methyl-6-(4-trifluoromethyl-phenyl)-pyridin-2-yl]-phenyl}-pyridine-3-sulfonic acid amide The title compound was prepared from 3-[4-methyl-6-(4-trifluoromethyl-phenyl)pyridin-2-yl]-benzeneboronic acid (example G.10) (0.407 g, 1.14 mmol) and commercially available 5-bromo-pyridine-3-sulfonic acid amide (178 mg, 1.14 mmol) according to the general procedure VI. Obtained as a white solid (0.101 g, 19%). MS (ISP) 470.3 [$(M+H)^+$]; mp 217° C.

EXAMPLE 276

5-[3-(4-Benzo[1,3]dioxol-5-yl-6-methyl-pyridin-2-yl)-phenyl]-pyridin-2-ylamine

The title compound was prepared from 4-benzo[1,3]dioxol-5-yl-2-(3-bromo-phenyl)-6-methyl-pyridine (example E.91) (0.150 g, 0.407 mmol) and commercially available 2-amino-5-(4,4,5,5-tetramethyl-1,3,2-dioxaborolan-2-yl) pyridine (0.099 g, 0.448 mmol) according to the general procedure VI. Obtained as a white solid (0.100 g, 64%). MS (ISP) 382.2 [$(M+H)^+$]; mp 203° C.

EXAMPLE 277

5-{1-[4-Trifluoromethyl-6-(4-trifluoromethyl-phenyl)-pyridin-2-yl]-1H-[1,2,4]triazol-3-yl}-pyridin-2-ylamine The title compound was prepared from 2-(3-chloro-[1,2,4] triazol-1-yl)-4-trifluoromethyl-6-(4-trifluoromethyl-phenyl)-pyridine (example E.92) (0.314 g, 0.8 mmol) and commercially available 2-amino-5-(4,4,5,5-tetramethyl-1,3,2-dioxaborolan-2-yl)pyridine (0.176 g, 0.8 mmol) according to the general procedure VI. Obtained as a white solid (0.027 g, 8%). MS (ISP) 451.2 [$(M+H)^+$].

EXAMPLE 278

5-{1-[4-Trifluoromethyl-6-(4-trifluoromethyl-phenyl)-pyridin-2-yl]-1H-imidazol-4-yl}-thiophene-2-sulfonic acid tert-butylamide The title compound was prepared from 2-(4-iodo-imidazol-1-yl)-4-trifluoromethyl-6-(4-trifluoromethyl-phenyl)-pyridine (example E.23) (0.966 g, 2.0 mmol) and N-tert-butyl-5-(4,4,5,5-tetramethyl-1,3,2-dioxaborolan-2-yl)-thiophene-2-sulfonamide (example F.1) (0.829 g, 2.4 mmol) according to the general procedure VI. Obtained as a white solid (0.158 g, 14%). MS (ISP) 575.2 [$(M+H)^+$].

EXAMPLE 279

5-{1-[4-Trifluoromethyl-6-(4-trifluoromethyl-phenyl)-pyridin-2-yl]-1H-imidazol-4-yl}-thiophene-2-sulfonic acid amide To a cooled and stirred solution of 5-{1-[4-trifluoromethyl-6-(4-trifluoromethylphenyl)-pyridin-2-yl]-1H-imidazol-4-yl}-thiophene-2-sulfonic acid tert-butylamide (example 278) (0.137 g, 0.24 mmol) in dichloromethane (3 mL) was added TFA (3 mL) and the reaction mixture was allowed to stir at room temperature for 15 h. The mixture was evaporated to dryness and saturated $NaHCO_3$ solution (5 mL), diethyl ether and heptane were added. The mixture was stirred at room temperature for 1 h, the precipitate was collected by filtration, washed with water and heptane/diethyl ether and dried to yield the title compound as a white solid (0.100 g, 81%). MS (ISP) 519.2 [$(M+H)^+$].

EXAMPLE 280

N-tert-Butyl-3-{1-[4-trifluoromethyl-6-(4-trifluoromethyl-phenyl)-pyridin-2-yl]-1H-imidazol-4-yl}-benzenesulfonamide The title compound was prepared from 2-(4-iodo-imidazol-1-yl)-4-trifluoromethyl-6-(4-trifluoromethyl-phenyl)-pyridine (example E.23) (0.483 g, 1.0 mmol) and commercially available 3-(tert-butylsulfamoyl)-benzeneboronic acid (0.334 g, 1.3 mmol) according to the general procedure VI. Obtained as a white solid (0.126 g, 22%). MS (ISP) 539.3 [$(M+H)^+$].

EXAMPLE 281

2-{1-[4-Trifluoromethyl-6-(4-trifluoromethyl-phenyl)-pyridin-2-yl]-1H-imidazol-4-yl}-thiazole-5-sulfonic acid tert-butylamide A stirred mixture of 2-(4-tributylstannanyl-imidazol-1-yl)-4-trifluoromethyl-6-(4-trifluoromethyl-phenyl)-pyridine (Example G.11) (0.575 g, 0.76 mmol), 2-chloro-thiazole-5-sulfonic acid tert-butylamide (Example H.1) (0.227 g, 0.85 mmol), tetrakis(triphenylphosphine)palladium (0.051 g, 0.038 mmol) in toluene (5 mL) was heated under reflux conditions for 4 h. Cooled to rt, some precipitate occurred, diluted with toluene (~5 mL), placed in freezer for 30 min, added heptane (total volume: 25 mL), filtered the precipitate off, washed with toluene/heptane (ca. 1:1, 3×10 mL), dried in HV to give the title compound as an off-white solid (305 mg, 70%). MS (ISP) 576.3 [$(M+H)^+$]; mp 236° C.

EXAMPLE 282

3-{1-[4-Trifluoromethyl-6-(4-trifluoromethyl-phenyl)-pyridin-2-yl]-1H-[1,2,4]triazol-3-yl}-benzenesulfonamide 1) The N-tert-butyl-3-{1-[4-trifluoromethyl-6-(4-trifluoromethyl-phenyl)-pyridin-2-yl]-1H-[1,2,4]triazol-3-yl}-benzenesulfonamide was prepared from 2-(4-iodo-imidazol-1-yl)-4-trifluoromethyl-6-(4-trifluoromethyl-phenyl)-pyridine (example E.23) (0.393 g, 0.81 mmol) and commercially available 3-(tert-butylsulfamoyl)-benzeneboronic acid (0.334 g, 1.3 mmol) according to the general procedure VI. Obtained as a white solid (0.021 g, 4%) and additional light brown residue (0.090 g, 16%). MS (ISP) 570.2 [$(M+H)^+$].

2) To a cooled and stirred solution of the above prepared N-tert-butyl-3-{1-[4-trifluoromethyl-6-(4-trifluoromethyl-phenyl)-pyridin-2-yl]-1H-[1,2,4]triazol-3-yl}-benzenesulfonamide (0.090 g, 0.16 mmol) in dichloromethane (3 mL) was added TFA (3 mL) and the reaction mixture was allowed to stir at room temperature for 15 h. The mixture was evaporated to dryness and saturated $NaHCO_3$ solution (5 mL), diethyl ether and heptane were added. The mixture was stirred at room temperature for 1 h, the precipitate was collected by filtration, washed with water and heptane/diethyl ether and dried to yield the title compound as a white solid (0.022 g, 27%). MS (ISP) 514.3 [$(M+H)^+$].

EXAMPLE 283

3-{1-[4-Trifluoromethyl-6-(4-trifluoromethyl-phenyl)-pyridin-2-yl]-1H-imidazol-4-yl}-benzenesulfonamide To a cooled and stirred solution of N-tert-butyl-3-{1-[4-trifluoromethyl-6-(4-trifluoromethyl-phenyl)-pyridin-2-yl]-1H-imidazol-4-yl}-benzenesulfonamide (example 280) (0.110 g, 0.19 mmol) in dichloromethane (3 mL) was added TFA (3 mL) and the reaction mixture was allowed to stir at room temperature for 15 h. The mixture was evaporated to dryness and saturated $NaHCO_3$ solution (5 mL), diethyl ether and heptane were added. The mixture was stirred at room temperature for 1 h, the precipitate was collected by filtration, washed with water and heptane/diethyl ether and dried to yield the title compound as a white solid (0.092 g, 93%). MS (ISP) 513.4 [$(M+H)^+$]; mp>266° C.

EXAMPLE 284

2-{1-[4-Trifluoromethyl-6-(4-trifluoromethyl-phenyl)-pyridin-2-yl]-1H-imidazol-4-yl}-thiazole-5-sulfonic acid amide To 2-{1-[4-trifluoromethyl-6-(4-trifluoromethyl-phenyl)-pyridin-2-yl]-1H-imidazol-4-yl}-thiazole-5-sulfonic acid tert-butylamide (example 281) (0.160 g, 0.28 mmol) was added TFA (5 mL) and the reaction mixture was allowed to stir at room temperature for 24 h. The mixture was evaporated to dryness and saturated $NaHCO_3$ solution (5 mL), diethyl ether and heptane were added. The mixture was stirred at room temperature for 1 h, the precipitate was collected by filtration, washed with water and heptane/diethyl ether and dried to yield the title compound as an off-white solid (0.124 g, 86%). MS (ISP) 520.2 [$(M+H)^+$]; mp>266° C.

EXAMPLE 285

N-tert-Butyl-3-[4-trifluoromethyl-6-(4-trifluoromethyl-phenyl)-[2,4']bipyridinyl-2'-yl]-benzenesulfonamide The title compound was prepared from 2'-chloro-4-trifluoromethyl-6-(4-trifluoromethyl-phenyl)-[2,4']bipyridinyl (example E.27) (0.403 g, 1.0 mmol) and commercially available 3-(tert-butylsulfamoyl)-benzeneboronic acid (0.334 g, 1.3 mmol) according to the general procedure VI. Obtained as a light yellow solid (0.375 g, 65%). MS (ISP) 580.3 [$(M+H)^+$]; mp 196° C.

EXAMPLE 286

3-[4-Trifluoromethyl-6-(4-trifluoromethyl-phenyl)-[2,4']bipyridinyl-2'-yl]-benzenesulfonamide To a stirred and cooled solution of N-tert-butyl-3-[4-trifluoromethyl-6-(4-trifluoromethyl-phenyl)-[2,4']bipyridinyl-2'-yl]-benzenesulfonamide (example 285) (0.248 g, 0.43 mmol) in dichloromethane (3 mL) was added TFA (3 mL) and the reaction mixture was allowed to stir at room temperature for 16 h. The mixture was evaporated to dryness and saturated $NaHCO_3$ solution (5 mL), diethyl ether and heptane were added. The mixture was stirred at room temperature for 1 h, the precipitate was collected by filtration, washed with water and heptane/diethyl ether and dried to yield the title compound as a white solid (0.182 g, 81%). MS (ISP) 524.3 [(M+H)$^+$]; mp 227° C. (dec.).

EXAMPLE 287

N-tert-Butyl-3-[6-methyl-4-(4-trifluoromethyl-phenyl)-[2,4']bipyridinyl-2-yl]-benzenesulfonamide The title compound was prepared from 2'-chloro-6-methyl-4-(4-trifluoromethylphenyl)-[2,4']bipyridinyl (example E.28) (0.200 g, 0.6 mmol) and commercially available 3-(tert-butylsulfamoyl)-benzeneboronic acid (0.177 g, 0.7 mmol) according to the general procedure VI. Obtained as an off-white solid (0.286 g, 95%). MS (ISP) 526.2 [(M+H)$^+$]; mp 189° C.

EXAMPLE 288

N-tert-Butyl-3-[6-methyl-4-(4-trifluoromethyl-phenyl)-[2,3']bipyridinyl-5'-yl]-benzenesulfonamide The title compound was prepared from 5'-bromo-6-methyl-4-(4-trifluoromethylphenyl)-[2,3']bipyridinyl (example E.24) (0.200 g, 0.5 mmol) and commercially available 3-(tert-butylsulfamoyl)-benzeneboronic acid (0.157 g, 0.6 mmol) according to the general procedure VI. Obtained as an off-white solid (0.182 g, 68%). MS (ISP) 526.3 [(M+H)$^+$].

EXAMPLE 289

3-[6-Methyl-4-(4-trifluoromethyl-phenyl)-[2,4']bipyridinyl-2'-yl]-benzenesulfonamide To a stirred and cooled suspension of N-tert-butyl-3-[6-methyl-4-(4-trifluoromethylphenyl)-[2,4']bipyridinyl-2'-yl]-benzenesulfonamide (example 287) (0.239 g, 0.455 mmol) in dichloromethane (1.5 mL) was added TFA (10 mL) and the reaction mixture was allowed to stir at room temperature for 16 h. The mixture was evaporated to dryness and saturated $NaHCO_3$ solution (5 mL), diethyl ether and heptane were added. The mixture was stirred at room temperature for 1 h, the precipitate was collected by filtration, washed with water and heptane/diethyl ether and dried to yield the title compound as a white solid (0.200 g, 94%). MS (ISP) 470.3 [(M+H)$^+$]; mp>250° C.

EXAMPLE 290

5-{1-[4-Trifluoromethyl-6-(4-trifluoromethyl-phenyl)-pyridin-2-yl]-1H-imidazol-4-yl}-pyridine-3-sulfonic acid amide A stirred mixture of 2-(4-tributylstannanyl-imidazol-1-yl)-4-trifluoromethyl-6-(4-trifluoromethyl-phenyl)-pyridine (Example G.11) (0.503 g, 0.7 mmol), commercially available 5-bromo-pyridine-3-sulfonic acid amide (0.183 g, 0.77 mmol), tetrakis(triphenylphosphine)palladium (0.040 g, 0.030 mmol) in toluene (5 mL) was heated under reflux conditions for 18 h. Cooled to rt, some precipitate occurred, diluted with toluene (~5 mL), added heptane, filtered the precipitate off, washed with toluene/heptane, dried in HV to give the title compound as a white solid (258 mg, 72%). MS (ISP) 514.2 [(M+H)$^+$]; mp>250° C.

EXAMPLE 291

N-(2-Hydroxy-1,1-dimethyl-ethyl)-3-{1-[4-trifluoromethyl-6-(4-trifluoromethyl-phenyl)-pyridin-2-yl]-1H-imidazol-4-yl}-benzenesulfonamide A stirred mixture of 2-(4-tributylstannanyl-imidazol-1-yl)-4-trifluoromethyl-6-(4-trifluoromethyl-phenyl)-pyridine (Example G.11) (0.503 g, 0.7 mmol), 3-bromo-N-(2-hydroxy-1,1-dimethyl-ethyl)-benzenesulfonamide (Example H.4) (0.237 g, 0.77 mmol), tetrakis(triphenyl-phosphine)palladium (0.040 g, 0.030 mmol) in toluene (5 mL) was heated under reflux conditions for 18 h. Cooled to rt, some precipitate occurred, diluted with toluene (~5 mL), added heptane, filtered the precipitate off, washed with toluene/heptane, dried in HV to give the title compound as a white solid (268 mg, 66%). MS (ISP) 585.2 [(M+H)$^+$]; mp 150° C. (dec.).

EXAMPLE 292

4-Methyl-2-{1-[4-trifluoromethyl-6-(4-trifluoromethyl-phenyl)-pyridin-2-yl]-1H-imidazol-4-yl}-thiazole-5-sulfonic acid tert-butylamide A stirred mixture of 2-(4-tributylstannanyl-imidazol-1-yl)-4-trifluoromethyl-6-(4-trifluoromethyl-phenyl)-pyridine (Example G.11) (0.718 g, 1.0 mmol), 2-chloro-4-methyl-thiazole-5-sulfonic acid tert-butylamide (Example H.5) (0.295 g, 1.1 mmol), tetrakis(triphenylphosphine)palladium (0.058 g, 0.044 mmol) in toluene (5 mL) was heated under reflux conditions for 18 h. Cooled to rt, some precipitate occurred, diluted with toluene (~5 mL), added heptane, filtered the precipitate off, washed with toluene/heptane, dried in HV to give the title compound as a white solid (384 mg, 59%). MS (ISP) 590.4 [(M+H)$^+$]; mp>250° C.

EXAMPLE 293

N-tert-Butyl-3-{1-[6-trifluoromethyl-4-(4-trifluoromethyl-phenyl)-pyridin-2-yl]-1H-imidazol-4-yl}-benzenesulfonamide The title compound was prepared from 2-(4-iodo-imidazol-1-yl)-6-trifluoromethyl-4-(4-trifluoromethyl-phenyl)-pyridine (example E.93) (0.200 g, 0.41 mmol) and commercially available 3-(tert-butylsulfamoyl)-benzeneboronic acid (0.117 g, 0.46 mmol) according to the general procedure VI. Obtained as a white solid (0.120 g, 51%). MS (ISP) 569.2 [(M+H)$^+$].

EXAMPLE 294

4-Methyl-2-{1-[4-trifluoromethyl-6-(4-trifluoromethyl-phenyl)-pyridin-2-yl]-1H-imidazol-4-yl}-thiazole-5-sulfonic acid amide To a stirred and cooled suspension of 4-methyl-2-{1-[4-trifluoromethyl-6-(4-trifluoromethyl-phenyl)-pyridin-2-yl]-1H-imidazol-4-yl}-thiazole-5-sulfonic acid tert-butylamide (example 292) (0.295 g, 0.50 mmol) in dichloromethane (3 mL) was added TFA (3 mL) and the reaction mixture was allowed to stir at room temperature for 16 h. The mixture was evaporated to dryness and saturated $NaHCO_3$ solution (5 mL), diethyl ether and heptane were added. The mixture was stirred at room temperature for 1 h, the precipitate was collected by filtration, washed with water and heptane/diethyl ether and dried to yield the title compound as a white solid (0.264 g, 99%). MS (ISP) 534.2 [(M+H)$^+$]; mp 187° C. (dec.).

EXAMPLE 295

3-[6-Methyl-4-(4-trifluoromethyl-phenyl)-[2,3']bipyridinyl-5'-yl]-benzenesulfonamide To a stirred and cooled suspension of N-tert-butyl-3-[6-methyl-4-(4-trifluoromethylphenyl)-[2,3']bipyridinyl-5'-yl]-benzenesulfonamide (example 288) (0.150 g, 0.29 mmol) in dichloromethane (0.9 mL) was added TFA (6.3 mL) and the reaction mixture was allowed to stir at room temperature for 16 h. The mixture was evaporated to dryness and saturated $NaHCO_3$ solution (5 mL), diethyl ether and heptane were added. The mixture was stirred at room temperature for 1 h, the precipitate was collected by filtration, washed with water and heptane/diethyl ether and dried to yield the title compound as a white solid (0.130 g, 97%). MS (ISP) 470.3 [(M+H)$^+$]; mp 235° C. (dec.).

EXAMPLE 296

3-{1-[6-Trifluoromethyl-4-(4-trifluoromethyl-phenyl)-pyridin-2-yl]-1H-imidazol-4-yl}-benzenesulfonamide To a stirred and cooled suspension of N-tert-butyl-3-{1-[6-trifluoromethyl-4-(4-trifluoromethyl-phenyl)-pyridin-2-yl]-1H-imidazol-4-yl}-benzenesulfonamide (example 293) (0.110 g, 0.19 mmol) in dichloromethane (0.69 mL) was added TFA (4.3 mL) and the reaction mixture was allowed to stir at room temperature for 16 h. The mixture was evaporated to dryness and saturated $NaHCO_3$ solution (5 mL), diethyl ether and heptane were added. The mixture was stirred at room temperature for 1 h, the precipitate was collected by filtration, washed with water and heptane/diethyl ether and dried to yield after silica gel column chromatography with heptane/EtOAc and trituration with diethyl ether the title compound as a white solid (0.040 g, 40%). MS (ISP) 513.2 [(M+H)$^+$]; mp>250° C.

EXAMPLE 297

N-tert-Butyl-3-[4-methyl-6-(4-trifluoromethyl-phenyl)-[2,4']bipyridinyl-2'-yl]-benzenesulfonamide The title compound was prepared from 2'-chloro-4-methyl-6-(4-trifluoromethylphenyl)-[2,4']bipyridinyl (example E.94) (0.350 g, 1.0 mmol) and commercially available 3-(tert-butylsulfamoyl)-benzeneboronic acid (0.283 g, 1.1 mmol) according to the general procedure VI. Obtained as a white solid (0.426 g, 81%). MS (ISP) 526.2 [(M+H)$^+$]; mp 189° C.

EXAMPLE 298

N-tert-Butyl-3-{1-[6-(4-chloro-phenyl)-4-methyl-pyridin-2-yl]-1H-imidazol-4-yl}-benzenesulfonamide The title compound was prepared from 2-(4-chloro-phenyl)-6-(4-iodo-imidazol-1-yl)-4-methyl-pyridine (example E.95) (0.198 g, 0.5 mmol) and commercially available 3-(tert-butylsulfamoyl)-benzeneboronic acid (0.141 g, 0.55 mmol) according to the general procedure VI. Obtained as a white solid (0.028 g, 12%). MS (ISP) 482.4 [(M+H)$^+$].

EXAMPLE 299

N-tert-Butyl-3-[4'-methyl-6'-(4-trifluoromethyl-phenyl)-[2,2']bipyridinyl-6-yl]-benzenesulfonamide The title compound was prepared from 6'-bromo-4-methyl-6-(4-trifluoromethylphenyl)-[2,2']bipyridinyl (example E.96) (0.393 g, 1.0 mmol) and commercially available 3-(tert-butylsulfamoyl)-benzeneboronic acid (0.283 g, 1.1 mmol) according to the general procedure VI. Obtained as a white solid (0.500 g, 95%). MS (ISP) 526.3 [(M+H)$^+$].

EXAMPLE 300

4-Methyl-2-{1-[6-trifluoromethyl-4-(4-trifluoromethyl-phenyl)-pyridin-2-yl]-1H-imidazol-4-yl}-thiazole-5-sulfonic acid tert-butylamide A stirred mixture of 2-(4-tributylstannanyl-imidazol-1-yl)-6-trifluoromethyl-4-(4-trifluoromethyl-phenyl)-pyridine (Example G.12) (0.570 g, 0.88 mmol), 2-chloro-4-methyl-thiazole-5-sulfonic acid tert-butylamide (Example H.5) (0.266 g, 0.99 mmol), tetrakis(triphenylphosphine)palladium (0.061 g, 0.046 mmol) in toluene (6 mL) was heated under reflux conditions for 16 h. Cooled to rt, some precipitate occurred, diluted with toluene (~5 mL), added heptane, filtered the precipitate off, washed with toluene/heptane, dried in HV to give the title compound as a white solid (130 mg, 25%). MS (ISP) 590.4 [(M+H)$^+$]; mp 260° C.

EXAMPLE 301

5-{1-[6-Trifluoromethyl-4-(4-trifluoromethyl-phenyl)-pyridin-2-yl]-1H-imidazol-4-yl}-thiophene-2-sulfonic acid tert-butylamide A stirred mixture of 2-(4-tributylstannanyl-imidazol-1-yl)-6-trifluoromethyl-4-(4-trifluoromethyl-phenyl)-pyridine (Example G.12) (0.570 g, 0.88 mmol), commercially available 5-bromo-thiophene-2-sulfonic acid tert-butylamide (0.295 g, 0.99 mmol), tetrakis(triphenylphosphine)palladium (0.061 g, 0.046 mmol) in toluene (6 mL) was heated under reflux conditions for 16 h. Cooled to rt, some precipitate occurred, diluted with toluene (~5 mL), added heptane, filtered the precipitate off, washed with toluene/heptane, dried in HV to give the title compound as a white solid (290 mg, 57%). MS (ISP) 575.2 [(M+H)$^+$]; mp>250° C.

EXAMPLE 302

2-{1-[6-Trifluoromethyl-4-(4-trifluoromethyl-phenyl)-pyridin-2-yl]-1H-imidazol-4-yl}-thiazole-5-sulfonic acid tert-butylamide A stirred mixture of 2-(4-tributylstannanyl-imidazol-1-yl)-6-trifluoromethyl-4-(4-trifluoromethyl-phenyl)-pyridine (Example G.12) (0.570 g, 0.88 mmol), 2-chloro-thiazole-5-sulfonic acid tert-butylamide (Example H.1) (0.265 g, 0.99 mmol), tetrakis(triphenylphosphine)palladium (0.061 g, 0.046 mmol) in toluene (6 mL) was heated under reflux conditions for 16 h. Cooled to rt, some precipitate occurred, diluted with toluene (~5 mL), added heptane, filtered the precipitate off, washed with toluene/heptane, dried in HV to give the title compound as a white solid (220 mg, 43%). MS (ISP) 576.3 [(M+H)$^+$]; mp 252° C.

EXAMPLE 303

5-{4-[6-Methyl-4-(4-trifluoromethyl-phenyl)-pyridin-2-yl]-pyrimidin-2-yl}-thiophene-2-sulfonic acid tert-butylamide The title compound was prepared from 2-chloro-4-[6-methyl-4-(4-trifluoromethylphenyl)-pyridin-2-yl]-pyrimidine (example E.83) (0.3 g, 0.858 mmol) and N-tert-butyl-5-(4,4,5,5-tetramethyl-1,3,2-dioxaborolan-2-yl)-thiophene-2-sulfonamide (example F.1) (0.355 g, 1.029 mmol) according to the general procedure VI. Obtained as a white solid (0.220 g, 48%). MS (ISP) 533.2 [(M+H)$^+$]; mp 242° C. (dec.).

EXAMPLE 304

5-[6-Methyl-4-(4-trifluoromethyl-phenyl)-[2,4']bipyridinyl-2'-yl]-thiophene-2-sulfonic acid tert-butylamide The title compound was prepared from 2'-chloro-6-methyl-4-(4-trifluoromethylphenyl)-[2,4']bipyridinyl (example E.28) (0.300 g, 0.86 mmol) and N-tert-butyl-5-(4,4,5,5-tetramethyl-1,3,2-dioxaborolan-2-yl)-thiophene-2-sulfonamide (example F.1) (0.356 g, 1.029 mmol) according to the general procedure VI. Obtained as a white solid (0.110 g, 24%). MS (ISP) 532.1 [(M+H)$^+$]; mp 225° C.

EXAMPLE 305

5-[6'-Methyl-4'-(4-trifluoromethyl-phenyl)-[2,2']bipyridinyl-6-yl]-thiophene-2-sulfonic acid tert-butylamide The title compound was prepared from 6'-bromo-6-methyl-4-(4-trifluoromethylphenyl)-[2,2']bipyridinyl (example E.26) (0.300 g, 0.763 mmol) and N-tert-butyl-5-(4,4,5,5-tetramethyl-1,3,2-dioxaborolan-2-yl)-thiophene-2-sulfonamide (example F.1) (0.316 g, 0.839 mmol) according to the general procedure VI. Obtained as an off-white solid (0.040 g, 10%). MS (ISP) 532.1 [(M+H)$^+$]; mp 227° C.

EXAMPLE 306

6-Methyl-2'-(3-nitro-phenyl)-4-(4-trifluoromethyl-phenyl)-[2,4']bipyridinyl

The title compound was prepared from 2'-chloro-6-methyl-4-(4-trifluoromethylphenyl)-[2,4']bipyridinyl (example E.28) (5.7 g, 16.34 mmol) and commercially available 3-nitrophenylboronic acid (3.274 g, 19.61 mmol) according to the general procedure VI. Obtained as a white solid (6.6 g, 92%). MS (ISP) 436.2 [(M+H)$^+$]; mp 164° C.

EXAMPLE 307

3-[6-Methyl-4-(4-trifluoromethyl-phenyl)-[2,4']bipyridinyl-2'-yl]-phenylamine

A mixture of 6-methyl-2'-(3-nitro-phenyl)-4-(4-trifluoromethyl-phenyl)-[2,4']bipyridinyl (example 306) (6.6 g, 15.15 mmol) in THF-MeOH 1:1 (300 mL) and 10% palladium on carbon (10 mol %) was hydrogenated (1 bar hydrogen) at 23° C. for 2 h. The catalyst was filtered off, washed with MeOH and the filtrate was completely evaporated totally to leave a crude product, which was triturated with diethyl ether and dried in HV to give the title compound as a light brown solid (6.0 g, 97%). MS (ISP) 406.3 [(M+H)$^+$]; mp 162° C. (dec.).

EXAMPLE 308

3-{4-[4-Methyl-6-(4-trifluoromethyl-phenyl)-pyridin-2-yl]-pyrimidin-2-yl}-benzenesulfonamide 1) The N-tert-butyl-3-{4-[4-methyl-6-(4-trifluoromethyl-phenyl)-pyridin-2-yl]-pyrimidin-2-yl}-benzenesulfonamide was prepared from 2-chloro-4-[4-methyl-6-(4-trifluoromethyl-phenyl)-pyridin-2-yl]-pyrimidine (example E.97) (0.350 g, 1.0 mmol) and commercially available 3-(tert-butylsulfamoyl)-benzeneboronic acid (0.283 g, 1.1 mmol) according to the general procedure VI. Obtained as a white solid (0.400 g, 76%). MS (ISP) 527.2 [(M+H)$^+$]; mp 218° C.

2) To the above prepared N-tert-butyl-3-{4-[4-methyl-6-(4-trifluoromethyl-phenyl)pyridin-2-yl]-pyrimidin-2-yl}-benzenesulfonamide (0.110 g, 0.19 mmol) was added TFA (6 mL) and the reaction mixture was stirred at 50° C. for 2 h. The mixture was evaporated to dryness and partitioned between EtOAc and saturated $NaHCO_3$ solution, the organic layer was dried over $Na_2SO_4$. Removal of the solvent in vacuum left a crude product which was triturated with diethyl ether to give the title compound as a white solid (0.235 g, 100%). MS (ISP) 471.2 [(M+H)$^+$]; mp>250° C.

EXAMPLE 309

3-[4-Methyl-6-(4-trifluoromethyl-phenyl)-[2,4']bipyridinyl-2'-yl]-benzenesulfonamide To N-tert-butyl-3-[4-methyl-6-(4-trifluoromethyl-phenyl)-[2,4']bipyridinyl-2'-yl]-benzenesulfonamide (example 297) (0.110 g, 0.19 mmol) was added TFA (6 mL) and the reaction mixture was stirred at 50° C. for 2 h. The mixture was evaporated to dryness and partitioned between EtOAc and saturated $NaHCO_3$ solution, the organic layer was dried over $Na_2SO_4$. Removal of the solvent in vacuum left a crude product which was triturated with diethyl ether to give the title compound as a white solid (0.230 g, 98%). MS (ISP) 470.3 [(M+H)$^+$]; mp 238° C.

EXAMPLE 310

3-[4'-Methyl-6'-(4-trifluoromethyl-phenyl)-[2,2']bipyridinyl-6-yl]-benzenesulfonamide To N-tert-butyl-3-[4'-methyl-6'-(4-trifluoromethyl-phenyl)-[2,2']bipyridinyl-6-yl]-benzenesulfonamide (example 299) (0.450 g, 0.856 mmol) was added TFA (5 mL) and the reaction mixture was stirred at 23° C. for 16 h. The mixture was evaporated to dryness and partitioned between EtOAc and saturated $NaHCO_3$ solution, the organic layer was dried over $Na_2SO_4$. Removal of the solvent in vacuum left a crude product which was triturated with diethyl ether to give the title compound as an off-white solid (0.304 g, 76%). MS (ISP) 470.3 [(M+H)$^+$]; mp 229° C.

EXAMPLE 311

3-{1'-[6-(4-Chloro-phenyl)-4-methyl-pyridin-2-yl]-1H-imidazol-4-yl}-benzenesulfonamide To N-tert-butyl-3-{1-[6-(4-chloro-phenyl)-4-methyl-pyridin-2-yl]-1H-imidazol-4-yl}-benzenesulfonamide (example 298) (0.028 g, 0.058 mmol) was added TFA (2 mL) and the reaction mixture was stirred at 23° C. for 16 h. The mixture was evaporated to dryness and partitioned between EtOAc and saturated $NaHCO_3$ solution, the organic layer was dried over $Na_2SO_4$. Removal of the solvent in vacuum left a crude product which was triturated with diethyl ether to give the title compound as an off-white solid (0.025 g, 101%). MS (ISP) 425.1 [$(M+H)^+$] and 427 [$(M+2+H)^+$].

EXAMPLE 312

4-Methyl-2-{1-[6-trifluoromethyl-4-(4-trifluoromethyl-phenyl)-pyridin-2-yl]-1H-imidazol-4-yl}-thiazole-5-sulfonic acid amide To 4-methyl-2-{1-[6-trifluoromethyl-4-(4-trifluoromethyl-phenyl)-pyridin-2-yl]-1H-imidazol-4-yl}-thiazole-5-sulfonic acid tert-butylamide (example 300) (0.150 g, 0.254 mmol) was added TFA (5 mL) and the reaction mixture was stirred at 23° C. for 16 h. The mixture was evaporated to dryness and partitioned between TBME and saturated $NaHCO_3$ solution, the organic layer was dried over $Na_2SO_4$. Removal of the solvent in vacuum left a crude product which was triturated with diethyl ether to give the title compound as a white solid (0.070 g, 51%). MS (ISP) 534.2 [$(M+H)^+$]; mp 170° C. (dec.).

EXAMPLE 313

2-{1-[6-Trifluoromethyl-4-(4-trifluoromethyl-phenyl)-pyridin-2-yl]-1H-imidazol-4-yl}-thiazole-5-sulfonic acid amide To 2-{1-[6-trifluoromethyl-4-(4-trifluoromethyl-phenyl)-pyridin-2-yl]-1H-imidazol-4-yl}-thiazole-5-sulfonic acid tert-butylamide (example 302) (0.150 g, 0.260 mmol) was added TFA (5 mL) and the reaction mixture was stirred at 23° C. for 16 h. The mixture was evaporated to dryness and partitioned between TBME and saturated $NaHCO_3$ solution, the organic layer was dried over $Na_2SO_4$. Removal of the solvent in vacuum left a crude product which was triturated with diethyl ether to give the title compound as a white solid (0.120 g, 88%). MS (ISP) 520.2 [$(M+H)^+$]; mp>250° C.

EXAMPLE 314

5-{1-[6-Trifluoromethyl-4-(4-trifluoromethyl-phenyl)-pyridin-2-yl]-1H-imidazol-4-yl}-thiophene-2-sulfonic acid amide To 5-{1-[6-trifluoromethyl-4-(4-trifluoromethyl-phenyl)-pyridin-2-yl]-1H-imidazol-4-yl}-thiophene-2-sulfonic acid tert-butylamide (example 301) (0.200 g, 0.348 mmol) was added TFA (5 mL) and the reaction mixture was stirred at 23° C. for 16 h. The mixture was evaporated to dryness and partitioned between TBME and saturated $NaHCO_3$ solution, the organic layer was dried over $Na_2SO_4$. Removal of the solvent in vacuum left a crude product which was triturated with diethyl ether to give the title compound as a white solid (0.170 g, 94%). MS (ISP) 519.2 [$(M+H)^+$]; mp 237° C. (dec.).

EXAMPLE 315

5-{4-[6-Methyl-4-(4-trifluoromethyl-phenyl)-pyridin-2-yl]-pyrimidin-2-yl}-thiophene-2-sulfonic acid amide To 5-{4-[6-methyl-4-(4-trifluoromethyl-phenyl)-pyridin-2-yl]-pyrimidin-2-yl}-thiophene-2-sulfonic acid tert-butylamide (example 303) (0.250 g, 0.469 mmol) was added TFA (5 mL) and the reaction mixture was stirred at 23° C. for 16 h. The mixture was evaporated to dryness and partitioned between TBME and saturated $NaHCO_3$ solution, the organic layer was dried over $Na_2SO_4$. Removal of the solvent in vacuum left a crude product which was triturated with diethyl ether to give the title compound as a white solid (0.200 g, 89%). MS (ISP) 477.1 [$(M+H)^+$]; mp>250° C.

EXAMPLE 316

5-[6-Methyl-4-(4-trifluoromethyl-phenyl)-[2,4']bipyridinyl-2'-yl]-thiophene-2-sulfonic acid amide To 5-[6-methyl-4-(4-trifluoromethyl-phenyl)-[2,4']bipyridinyl-2'-yl]-thiophene-2-sulfonic acid tert-butylamide (example 304) (0.170 g, 0.32 mmol) was added TFA (5 mL) and the reaction mixture was stirred at 23° C. for 16 h. The mixture was evaporated to dryness and partitioned between TBME and saturated $NaHCO_3$ solution, the organic layer was dried over $Na_2SO_4$. Removal of the solvent in vacuum left a crude product which was triturated with diethyl ether to give the title compound as a white solid (0.135 g, 88%). MS (ISP) 476.2 [$(M+H)^+$]; mp>250° C.

EXAMPLE 317

5-[6'-Methyl-4'-(4-trifluoromethyl-phenyl)-[2,2']bipyridinyl-6-yl]-thiophene-2-sulfonic acid amide To 5-[6'-methyl-4'-(4-trifluoromethyl-phenyl)-[2,2']bipyridinyl-6-yl]-thiophene-2-sulfonic acid tert-butylamide (example 305) (0.170 g, 0.32 mmol) was added TFA (5 mL) and the reaction mixture was stirred at 23° C. for 16 h. The mixture was evaporated to dryness and partitioned between TBME and saturated $NaHCO_3$ solution, the organic layer was dried over $Na_2SO_4$. Removal of the solvent in vacuum left a crude product which was triturated with diethyl ether to give the title compound as a white solid (0.130 g, 85%). MS (ISP) 476.2 [$(M+H)^+$]; mp 243° C. (dec.).

EXAMPLE 318

N-{3-[6-Methyl-4-(4-trifluoromethyl-phenyl)-[2,4']bipyridinyl-2'-yl]-phenyl}-methanesulfonamide To a stirred and cooled solution of 3-[6-methyl-4-(4-trifluoromethyl-phenyl)-[2,4']bipyridinyl-2'-yl]-phenylamine (example 307) (0.200 g, 0.493 mmol) in EtOAc (2 mL) and sat. $NaHCO_3$-sol. (1 mL) was added methanesulfonyl chloride (1.0 mL, 13.6 mmol) and the mixture was stirred at 23° C. for 2 h. Diluted with EtOAc, washed with sat. $NaHCO_3$-sol. and water, dried the organic layer over $Na_2SO_4$. Removal of the solvent in vacuum left a crude product which was purified by silica gel column chromatography with EtOAc, followed by trituration with diethyl ether to give the title compound as a white solid (0.070 g, 29%). MS (ISP) 484.4 [$(M+H)^+$]; mp 196° C.

EXAMPLE 319

5-[4-Trifluoromethyl-6-(4-trifluoromethyl-phenyl)-[2,4']bipyridinyl-2'-yl]-thiophene-2-sulfonic acid tert-butylamide The title compound was prepared from 2'-iodo-4-trifluoromethyl-6-(4-trifluoromethylphenyl)-[2,4']bipyridinyl (example E.98) (0.494 g, 1.0 mmol) and N-tert-butyl-5-(4,4,5,5-tetramethyl-1,3,2-dioxaborolan-2-yl)-thiophene-2-sulfonamide (example F.1) (0.380 g, 1.1 mmol) according to the general procedure VI. Obtained as a white solid (0.360 g, 62%). MS (ISP) 586.2 [$(M+H)^+$]; mp 220° C.

EXAMPLE 320

5-[4-Methyl-6-(4-trifluoromethyl-phenyl)-[2,4']bipyridinyl-2'-yl]-thiophene-2-sulfonic acid tert-butylamide The title compound was prepared from 2'-chloro-4-methyl-6-(4-trifluoromethylphenyl)-[2,4']bipyridinyl (example E.94) (0.349 g, 1.0 mmol) and N-tert-butyl-5-(4,4,5,5-tetramethyl-1,3,2-dioxaborolan-2-yl)-thiophene-2-sulfonamide (example F.1) (0.380 g, 1.1 mmol) according to the general procedure VI. Obtained as a light yellow solid (0.267 g, 50%). MS (ISP) 532.1 [$(M+H)^+$]; mp 209° C.

EXAMPLE 321

5-[4-Trifluoromethyl-6-(4-trifluoromethyl-phenyl)-[2,4']bipyridinyl-2'-yl]-thiophene-2-sulfonic acid amide To 5-[4-trifluoromethyl-6-(4-trifluoromethyl-phenyl)-[2,4']bipyridinyl-2'-yl]-thiophene-2-sulfonic acid tert-butylamide (example 319) (0.180 g, 0.307 mmol) was added TFA (3 mL) and the reaction mixture was stirred at 23° C. for 16 h. The mixture was evaporated to dryness and partitioned between EtOAc and saturated $NaHCO_3$ solution, the organic layer was dried over $Na_2SO_4$. Removal of the solvent in vacuum left a crude product which was triturated with diethyl ether to give the title compound as a white solid (0.097 g, 60%). MS (ISP) 530.2 [$(M+H)^+$]; mp 97° C. (dec.).

EXAMPLE 322

4-[6-Methyl-4-(4-trifluoromethyl-phenyl)-pyridin-2-yl]-2-(3-nitro-phenyl)-pyrimidine The title compound was prepared from 2-chloro-4-[6-methyl-4-(4-trifluoromethylphenyl)-pyridin-2-yl]-pyrimidine (example E.83) (3.6 g, 10.29 mmol) and commercially available 3-nitrophenylboronic acid (2.062 g, 12.35 mmol) according to the general procedure VI. Obtained as a light brown solid (2.1 g, 46%). MS (ISP) 437.2 [$(M+H)^+$].

EXAMPLE 323

5-[4-Methyl-6-(4-trifluoromethyl-phenyl)-[2,4']bipyridinyl-2'-yl]-thiophene-2-sulfonic acid amide To 5-[4-methyl-6-(4-trifluoromethyl-phenyl)-[2,4']bipyridinyl-2'-yl]-thiophene-2-sulfonic acid tert-butylamide (example 320) (0.240 g, 0.45 mmol) was added TFA (3 mL) and the reaction mixture was stirred at 23° C. for 16 h. The mixture was evaporated to dryness and partitioned between EtOAc and saturated $NaHCO_3$ solution, the organic layer was dried over $Na_2SO_4$. Removal of the solvent in vacuum left a crude product which was triturated with diethyl ether to give the title compound as a white solid (0.215 g, 100%). MS (ISP) 476.1 [$(M+H)^+$]; mp 228° C. (dec.).

EXAMPLE 324

5-{2-[6-Methyl-4-(4-trifluoromethyl-phenyl)-pyridin-2-yl]-thiazol-4-yl}-thiophene-2-sulfonic acid tert-butylamide The title compound was prepared from 2-(4-bromo-thiazol-2-yl)-6-methyl-4-(4-trifluoromethyl-phenyl)-pyridine (example E.80) (0.150 g, 0.375 mmol) and N-tert-butyl-5-(4,4,5,5-tetramethyl-1,3,2-dioxaborolan-2-yl)-thiophene-2-sulfonamide (example F.1) (0.143 g, 0.413 mmol) according to the general procedure VI. Obtained as a white solid (0.130 g, 64%). MS (ISP) 538.3 [$(M+H)^+$]; mp 171° C.

EXAMPLE 325

5-{2-[6-Methyl-4-(4-trifluoromethyl-phenyl)-pyridin-2-yl]-thiazol-4-yl}-thiophene-2-sulfonic acid amide To 5-{2-[6-methyl-4-(4-trifluoromethyl-phenyl)-pyridin-2-yl]-thiazol-4-yl}-thiophene-2-sulfonic acid tert-butylamide (example 324) (0.100 g, 0.186 mmol) was added TFA (10 mL) and the reaction mixture was stirred at 23° C. for 16 h. The mixture was evaporated to dryness and partitioned between EtOAc and saturated $NaHCO_3$ solution, the organic layer was dried over $Na_2SO_4$. Removal of the solvent in vacuum left a crude product which was triturated with diethyl ether to give the title compound as a white solid (0.075 g, 83%). MS (ISP) 482.3 [$(M+H)^+$].

EXAMPLE 326

3-{4-[6-Methyl-4-(4-trifluoromethyl-phenyl)-pyridin-2-yl]-pyrimidin-2-yl}-phenylamine A mixture of 4-[6-methyl-4-(4-trifluoromethyl-phenyl)-pyridin-2-yl]-2-(3-nitrophenyl)-pyrimidine (example 322) (2.1 g, 4.81 mmol) in THF-EtOH 1:1 (100 mL) and 10% palladium on carbon (1 mol %) was hydrogenated (1 bar hydrogen) at 23° C. for 2 h. The catalyst was filtered off, washed with EtOH and the filtrate was completely evaporated totally to leave a crude product, which was purified by silica gel column chromatography with heptane/EtOAc, followed by trituration with diethyl ether to give the title compound as an off-white solid (1.5 g, 76%). MS (ISP) 407.4 [$(M+H)^+$]; mp 167° C.

EXAMPLE 327

3-[6'-Methyl-4'-(4-trifluoromethyl-phenyl)-[2,2']bipyridinyl-6-yl]-phenylamine

1) The 6-methyl-6'-(3-nitro-phenyl)-4-(4-trifluoromethyl-phenyl)-[2,2']bipyridinyl was prepared from 6'-bromo-6-methyl-4-(4-trifluoromethyl-phenyl)-[2,2']bipyridinyl (example E.26) (5.0 g, 12.71 mmol) and commercially available 3-nitrophenylboronic acid (2.547 g, 15.26 mmol) according to the general procedure VI. Obtained as a white solid (3.7 g, 66%). MS (ISP) 436.2 [$(M+H)^+$].

2) A mixture of the above prepared 6-methyl-6'-(3-nitrophenyl)-4-(4-trifluoromethylphenyl)-[2,2']bipyridinyl (3.4 g, 7.81 mmol) in THF-EtOH 1:1 (100 mL) and 10% palladium on carbon (1 mol %) was hydrogenated (1 bar hydrogen) at 23° C. for 2 h. The catalyst was filtered off, washed with EtOH and the filtrate was completely evaporated totally to leave a crude product, which was purified by silica gel column chromatography with heptane/EtOAc, followed by trituration with diethyl ether to give the title compound as a white solid (2.55 g, 80%). MS (ISP) 406.3 [(M+H)$^+$]; mp 167° C.

EXAMPLE 328

4-{4-[6-Methyl-4-(4-trifluoromethyl-phenyl)-pyridin-2-yl]-pyrimidin-2-yl}-benzenesulfonamide The title compound was prepared from 2-chloro-4-[6-methyl-4-(4-trifluoromethylphenyl)-pyridin-2-yl]-pyrimidine (example E.83) (0.150 g, 0.381 mmol) and commercially available (4-aminosulfonylphenyl)boronic acid [CAS-No. 613660-87-0] (0.130 g, 0.457 mmol) according to the general procedure VI. Obtained as a white solid (0.045 g, 25%). MS (ISP) 471.1 [(M+H)$^+$].

EXAMPLE 329

4-[6-Methyl-4-(4-trifluoromethyl-phenyl)-[2,4']bipyridinyl-2'-yl]-benzenesulfonamide The title compound was prepared from 2'-chloro-6-methyl-4-(4-trifluoromethylphenyl)-[2,4']bipyridinyl (example E.28) (0.150 g, 0.430 mmol) and commercially available (4-aminosulfonylphenyl)boronic acid [CAS-No. 613660-87-0] (0.146 g, 0.516 mmol) according to the general procedure VI. Obtained as a white solid (0.075 g, 37%). MS (ISP) 470.3 [(M+H)$^+$].

EXAMPLE 330

N-(3-{4-[6-Methyl-4-(4-trifluoromethyl-phenyl)-pyridin-2-yl]-pyrimidin-2-yl}-phenyl)methanesulfonamide To a stirred and cooled solution of 3-{4-[6-methyl-4-(4-trifluoromethyl-phenyl)-pyridin-2-yl]-pyrimidin-2-yl}-phenylamine (example 326) (0.150 g, 0.369 mmol) in EtOAc (2 mL) and sat. $NaHCO_3$-sol. (1 mL) was added methanesulfonyl chloride (1.0 mL, 13.6 mmol) and the mixture was stirred at 23° C. for 2 h. Diluted with EtOAc, washed with sat. $NaHCO_3$-sol. and water, dried the organic layer over $Na_2SO_4$. Removal of the solvent in vacuum left a crude product which was purified by silica gel column chromatography with EtOAc, followed by trituration with diethyl ether to give the title compound as a white solid (0.085 g, 47%). MS (ISP) 485.3 [(M+H)$^+$].

EXAMPLE 331

N-(3-{4-[6-Methyl-4-(4-trifluoromethyl-phenyl)-pyridin-2-yl]-pyrimidin-2-yl}-phenyl)acetamide To a stirred and cooled solution of 3-{4-[6-methyl-4-(4-trifluoromethyl-phenyl)-pyridin-2-yl]-pyrimidin-2-yl}-phenylamine (example 326) (0.150 g, 0.369 mmol) in EtOAc (2 mL) and sat. $NaHCO_3$-sol. (1 mL) was added acetyl chloride (0.030 mL, 0.406 mmol) and the mixture was stirred at 23° C. for 1 h. Diluted with EtOAc, washed with sat. $NaHCO_3$-sol. and water, dried the organic layer over $Na_2SO_4$. Removal of the solvent in vacuum left a crude product which was purified by trituration with diethyl ether to give the title compound as a white solid (0.100 g, 60%). MS (ISP) 449.3 [(M+H)$^+$].

EXAMPLE 332

N-{3-[6'-Methyl-4'-(4-trifluoromethyl-phenyl)-[2,2']bipyridinyl-6-yl]-phenyl}-acetamide To a stirred and cooled solution of 3-[6'-methyl-4'-(4-trifluoromethyl-phenyl)-[2,2']bipyridinyl-6-yl]-phenylamine (example 327) (0.400 g, 0.986 mmol) in EtOAc (4 mL) and sat. $NaHCO_3$-sol. (2 mL) was added acetyl chloride (0.080 mL, 1.085 mmol) and the mixture was stirred at 23° C. for 1 h. Diluted with EtOAc, washed with sat. $NaHCO_3$-sol. and water, dried the organic layer over $Na_2SO_4$. Removal of the solvent in vacuum left a crude product which was purified by trituration with diethyl ether to give the title compound as a white solid (0.250 g, 57%). MS (ISP) 484.2 [(M+H)$^+$].

EXAMPLE 333

N-{3-[6'-Methyl-4'-(4-trifluoromethyl-phenyl)-[2,2']bipyridinyl-6-yl]-phenyl}-methanesulfonamide To a stirred and cooled solution of 3-[6'-methyl-4'-(4-trifluoromethyl-phenyl)-[2,2']bipyridinyl-6-yl]-phenylamine (example 327) (0.400 g, 0.986 mmol) in EtOAc (4 mL) and sat. $NaHCO_3$-sol. (2 mL) was added methanesulfonyl chloride (1.08 mL, 14.7 mmol) and the mixture was stirred at 23° C. for 2 h. Diluted with EtOAc, washed with sat. $NaHCO_3$-sol. and water, dried the organic layer over $Na_2SO_4$. Removal of the solvent in vacuum left a crude product which was purified by silica gel column chromatography with EtOAc, followed by trituration with diethyl ether to give the title compound as a white solid (0.090 g, 19%). MS (ISP) 484.4 [(M+H)$^+$].

EXAMPLE 334

N-(tert-Butoxycarbonyl)-N'-{3-[6'-methyl-4'-(4-trifluoromethyl-phenyl)-[2,2']bipyridinyl-6-yl]-phenyl}-sulfamide To a stirred and cooled solution of commercially available chlorosulfonyl isocyanate (0.215 mL, 2.47 mmol) in dichloromethane (5 mL) was added tert-butanol (0.232 mL, 2.47 mmol) and the mixture was stirred at 0° C. for 30 min. Then 3-[6'-methyl-4'-(4-trifluoromethylphenyl)-[2,2']bipyridinyl-6-yl]-phenylamine (example 327) (0.200 g, 0.494 mmol) and triethyl amine (0.42 mL, 2.96 mmol) were added and the mixture was stirred at 23° C. for 0.5 h. Diluted with DCM, washed with sat. $NaHCO_3$-sol. and water, dried the organic layer over $Na_2SO_4$. Removal of the solvent in vacuum left a crude product which was purified by silica gel column chromatography with heptane/EtOAc/THF, followed by trituration with diethyl ether to give the title compound as an off-white solid (0.100 g, 35%). MS (ISP) 585.3 [(M+H)$^+$].

EXAMPLE 335

N-(tert-Butoxycarbonyl)-N'-(3-{4-[6-methyl-4-(4-trifluoromethyl-phenyl)-pyridin-2-yl]-pyrimidin-2-yl}-phenyl)-sulfamide To a stirred and cooled solution of commercially available chlorosulfonyl isocyanate (0.215 mL, 2.47 mmol) in dichloromethane (5 mL) was added tert-butanol (0.232 mL, 2.47 mmol) and the mixture was stirred at 0° C. for 30 min. Then 3-{4-[6-methyl-4-(4-trifluoromethyl-phenyl)-pyridin-2-yl]-pyrimidin-2-yl}-phenylamine (example 326) (0.200 g, 0.494 mmol) and triethyl amine (0.42 mL, 2.96 mmol) were added and the mixture was stirred at 23° C. for 0.5 h. Diluted with DCM, washed with sat. $NaHCO_3$-sol. and water, dried the organic layer over $Na_2SO_4$. Removal of the solvent in vacuum left a crude product which was purified by silica gel column chromatography with heptane/EtOAc/THF, followed by trituration with diethyl ether to give the title compound as an off-white solid (0.100 g, 35%). MS (ISP) 586.2 $[(M+H)^+]$.

EXAMPLE 336

N-tert-Butyl-3-[4-(3-methoxy-4-trifluoromethyl-phenyl)-6-methyl-[2,4']bipyridinyl-2'-yl]-benzenesulfonamide The title compound was prepared from 2'-chloro-4-(3-methoxy-4-trifluoromethylphenyl)-6-methyl-[2,4']bipyridinyl (example E.99) (0.378 g, 1.0 mmol) and commercially available 3-(tert-butylsulfamoyl)-benzeneboronic acid (0.283 g, 1.1 mmol) according to the general procedure VI. Obtained as a white solid (0.390 g, 70%). MS (ISP) 556.5 $[(M+H)^+]$; mp 189° C.

EXAMPLE 337

N-{3-[6'-Methyl-4'-(4-trifluoromethyl-phenyl)-[2,2']bipyridinyl-6-yl]-phenyl}-sulfamide To N-(tert-butoxycarbonyl)-N'-{3-[6'-methyl-4'-(4-trifluoromethyl-phenyl)-[2,2']bipyridinyl-6-yl]-phenyl}-sulfamide (example 334) (0.100 g, 0.171 mmol) was added TFA (5 mL) and the reaction mixture was stirred at 23° C. for 16 h. The mixture was evaporated to dryness and partitioned between EtOAc and saturated $NaHCO_3$ solution, the organic layer was dried over $Na_2SO_4$. Removal of the solvent in vacuum left a crude product which was triturated with diethyl ether to give the title compound as a white solid (0.090 g, 98%). MS (ISP) 485.4 $[(M+H)^+]$.

EXAMPLE 338

N-(3-{4-[6-Methyl-4-(4-trifluoromethyl-phenyl)-pyridin-2-yl]-pyrimidin-2-yl}-phenyl)-sulfamide To N-(tert-butoxycarbonyl)-N'-(3-{4-[6-methyl-4-(4-trifluoromethyl-phenyl)-pyridin-2-yl]-pyrimidin-2-yl}-phenyl)-sulfamide (example 335) (0.100 g, 0.171 mmol) was added TFA (5 mL) and the reaction mixture was stirred at 23° C. for 16 h. The mixture was evaporated to dryness and partitioned between EtOAc and saturated $NaHCO_3$ solution, the organic layer was dried over $Na_2SO_4$. Removal of the solvent in vacuum left a crude product which was triturated with diethyl ether to give the title compound as a white solid (0.065 g, 78%). MS (ISP) 486.3 $[(M+H)^+]$.

EXAMPLE 339

5-[4-(3-Methoxy-4-trifluoromethyl-phenyl)-6-methyl-[2,4']bipyridinyl-2'-yl]-thiophene-2-sulfonic acid tert-butylamide The title compound was prepared from 2'-chloro-4-(3-methoxy-4-trifluoromethylphenyl)-6-methyl-[2,4']bipyridinyl (example E.99) (0.378 g, 1.0 mmol) and N-tert-butyl-5-(4,4,5,5-tetramethyl-1,3,2-dioxaborolan-2-yl)-thiophene-2-sulfonamide (example F.1) (0.380 g, 1.1 mmol) according to the general procedure VI. Obtained as a white solid (0.142 g, 25%). MS (ISP) 562.3 $[(M+H)^+]$; mp 209° C. (dec.).

EXAMPLE 340

3-[4-(3-Methoxy-4-trifluoromethyl-phenyl)-6-methyl-[2,4']bipyridinyl-2'-yl]-benzenesulfonamide To N-tert-butyl-3-[4-(3-methoxy-4-trifluoromethyl-phenyl)-6-methyl-[2,4']bipyridinyl-2'-yl]-benzenesulfonamide (example 336) (0.277 g, 0.5 mmol) was added TFA (3 mL) and the reaction mixture was stirred at 23° C. for 16 h. The mixture was evaporated to dryness and partitioned between EtOAc and saturated $NaHCO_3$ solution, the organic layer was dried over $Na_2SO_4$. Removal of the solvent in vacuum left a crude product which was triturated with diethyl ether to give the title compound as a white solid (0.250 g, 100%). MS (ISP) 500.2 $[(M+H)^+]$; mp 233° C. (dec.).

EXAMPLE 341

5-[4-(3-Methoxy-4-trifluoromethyl-phenyl)-6-methyl-[2,4']bipyridinyl-2'-yl]-thiophene-2-sulfonic acid amide To 5-[4-(3-methoxy-4-trifluoromethyl-phenyl)-6-methyl-[2,4']bipyridinyl-2'-yl]-thiophene-2-sulfonic acid tert-butylamide (example 339) (0.100 g, 0.178 mmol) was added TFA (3 mL) and the reaction mixture was stirred at 23° C. for 16 h. The mixture was evaporated to dryness and partitioned between EtOAc and saturated $NaHCO_3$ solution, the organic layer was dried over $Na_2SO_4$. Removal of the solvent in vacuum left a crude product which was triturated with diethyl ether to give the title compound as a white solid (0.090 g, 100%). MS (ISP) 506.2 $[(M+H)^+]$; mp 261° C. (dec.).

EXAMPLE 342

4-{3-[6-Methyl-4-(4-trifluoromethyl-phenyl)-pyridin-2-yl]-phenyl}-thiazol-2-ylamine 1) N,N-Dimethyl-N'-(4-{3-[6-methyl-4-(4-trifluoromethyl-phenyl)-pyridin-2-yl]-phenyl}-thiazol-2-yl)-formamidine: Prepared from 2-iodo-6-methyl-4-(4-trifluoromethylphenyl)-pyridine (example A.31) (1.5 g, 4.13 mmol) and N'-[4-(3-bromo-phenyl)-thiazol-2-yl]-N,N-dimethyl-formamidine (1.41 g, 4.54 mmol) [prepared from commercially available 4-(3-bromo-phenyl)-thiazol-2-ylamine (4 g, 15.67 mmol) by simple refluxing with DMF-dimethylacetal (6.3 mL, 47.03 mmol) in toluene (10 mL) for 1 h, followed by evaporation to dryness to give a white solid (4.8 g, 99%)] according to the general procedure IVc protocol b. Obtained as a white solid (0.88 g, 46%). MS (ISP) 467.2 $[(M+H)^+]$; mp 174° C.

2) The above described N,N-dimethyl-N'-(4-{3-[6-methyl-4-(4-trifluoromethyl-phenyl)pyridin-2-yl]-phenyl}- thiazol-2-yl)-formamidine (880 mg, 1.886 mmol) was treated with 3 M HCl (20 mL) in THF (20 mL) at 50° C. for 16 h. Added 2 N NaOH until pH 10 was reached, extracted twice with EtOAc, dried combined organic layer over $Na_2SO_4$, filtered off and evaporated totally to give a crude product, which was triturated with ether to give the title compound (750 mg, 53%) as a white solid. MS (ISP) 412.2 [(M+H)$^+$]; mp>250° C.

EXAMPLE 343

2-[4-(3-Methanesulfonyl-phenyl)-imidazol-1-yl]-4-trifluoromethyl-6-(4-trifluoromethylphenyl)-pyridine A stirred mixture of 2-(4-tributylstannanyl-imidazol-1-yl)-4-trifluoromethyl-6-(4-trifluoromethyl-phenyl)-pyridine (Example G.11) (0.718 g, 1.0 mmol), commercially available 3-bromophenylmethyl sulfone (259 mg, 1.1 mmol), tetrakis (triphenyl-phosphine)palladium (0.058 g, 0.050 mmol) in toluene (5 mL) was heated under reflux conditions for 18 h. Cooled to rt, some precipitate occurred, diluted with toluene (~5 mL), placed in freezer for 30 min, added heptane (total volume: 25 mL), filtered the precipitate off, washed with toluene/heptane (ca. 1:1, 3×10 mL), purified by silica gel column chromatography with heptane/ethyl acetate followed by trituration with diethyl ether/heptane to give the title compound as a white solid (0.150 g, 29%). MS (ISP) 512.3 [(M+H)$^+$].

EXAMPLE 344

N-(tert-Butoxycarbonyl)-N'-(4-{3-[6-methyl-4-(4-trifluoromethyl-phenyl)-pyridin-2-yl]-phenyl}-thiazol-2-yl)-sulfamide To a stirred and cooled solution of commercially available chlorosulfonyl isocyanate (0.215 mL, 2.47 mmol) in dichloromethane (5 mL) was added tert-butanol (0.232 mL, 2.47 mmol) and the mixture was stirred at 0° C. for 30 min. Then 4-{3-[6-methyl-4-(4-trifluoromethyl-phenyl)-pyridin-2-yl]-phenyl}-thiazol-2-ylamine (example 342) (0.100 g, 0.243 mmol) and triethyl amine (0.42 mL, 2.96 mmol) were added and the mixture was stirred at 23° C. for 0.5 h. Diluted with DCM, washed with sat. $NaHCO_3$-sol. and water, dried the organic layer over $Na_2SO_4$. Removal of the solvent in vacuum left a crude product which was purified by silica gel column chromatography with heptane/EtOAc/THF, followed by trituration with diethyl ether/heptane to give the title compound as a white solid (0.060 g, 42%). MS (ISP) 591.3 [(M+H)$^+$]; mp 152° C. (dec.).

EXAMPLE 345

3-[6'-Methyl-4'-(4-trifluoromethyl-phenyl)-[2,2']bipyridinyl-6-yl]-benzenesulfonic acid 1) 3-[6'-Methyl-4'-(4-trifluoromethyl-phenyl)-[2,2']bipyridinyl-6-yl]-benzenesulfonic acid 2,2-dimethyl-propyl ester: The ester was prepared from 6'-bromo-6-methyl-4-(4-trifluoromethyl-phenyl)-[2,2']bipyridinyl (example E.26) (7.0 g, 17.8 mmol) and 3-(2,2-dimethyl-propyloxysulfonyl)-benzeneboronic acid (example F.4) (8.159 g, 28.5 mmol) according to the general procedure VI. Obtained as an off-white solid (7.7 g, 80%). MS (ISP) 541.3 [(M+H)$^+$].

2) The title compound was prepared from the above described 3-[6'-methyl-4'-(4-trifluoromethyl-phenyl)-[2,2']bipyridinyl-6-yl]-benzenesulfonic acid 2,2-dimethyl-propyl ester (7.7 g, 14.24 mmol) by refluxing in 1-propanol (15 mL) with sodium propanolate (1.7 M in n-propanol, 20.95 ml, 35.6 mmol) and 2-(diethylamino)ethanthiol (2.48 mL, 16.38 mmol) for 18 h. Cooled to rt, added water (300 mL), added 1 N HCl (ca. 50 mL) until pH 3-4 was reached, stirred for 10 min, filtered the solid off, washed thrice with water, and then with acetone and dried in HV to give the title compound (5.4 g, 81%) as an off-white solid. MS (ISN) 469.1 [(M−H)$^-$].

EXAMPLE 346

6-Methyl-2'-[3-(morpholine-4-sulfonyl)-phenyl]-4-(4-trifluoromethyl-phenyl)-[2,4']bipyridinyl 1) 2'-(3-Iodo-phenyl)-6-methyl-4-(4-trifluoromethyl-phenyl)-[2,4']bipyridinyl: 3-[6-Methyl-4-(4-trifluoromethyl-phenyl)-[2,4']bipyridinyl-2'-yl]-phenylamine (example 307) (5.0 g, 12.58 mmol) was dissolved in $CH_3CN$ (100 mL), then cooled to 0° C. and acetic acid (10 mL) and conc. HCl (5 mL) was added, followed by $NaNO_2$ (903 mg, 13.08 mmol) in water (2 mL), stirred for 5 min, then KI (2.172 g, 13.08 mmol) in water (3 mL) was added, the mixture was heated up to 50° C. and was stirred at 50° C. for 30 min. Poured into sat. $NaHCO_3$-sol. and extracted with OEtOAc, the organic layers were washed with brine and a small amount of $Na_2SO_3$, dried over $Na_2SO_4$, filtered off and evaporated totally to give a crude product which was purified by silica gel column chromatography with n-heptane/EtOAc followed by trituration with diethyl ether/heptane to give the 2'-(3-iodo-phenyl)-6-methyl-4-(4-trifluoromethyl-phenyl)-[2,4']bipyridinyl (2.7 g, 41%) as a white solid. MS (ISP) 517.1 [(M+H)$^+$].

2) 3-[6-Methyl-4-(4-trifluoromethyl-phenyl)-[2,4']bipyridinyl-2'-yl]-benzenesulfonyl chloride: To a stirred solution of the above described 2'-(3-iodo-phenyl)-6-methyl-4-(4-trifluoromethyl-phenyl)-[2,4']bipyridinyl (2.7 g, 5.23 mmol) in THF (70 mL) at −78° C. was added n-BuLi (1.6 M in hexane, 3.27 mL, 5.23 mmol) and the mixture was stirred at −78° C. for 15 min. Then gaseous sulfur dioxide (ca. 2.2 g, 35 mmol) was added causing a 20° C. increase of the internal temperature. The mixture was allowed to warm to rt and stirred for 1 h. To this reaction mixture containing the lithium 3-[6-methyl-4-(4-trifluoromethyl-phenyl)-[2,4']bipyridinyl-2'-yl]-benzenesulfinate MS (ISP) 455.2 [(M+H)$^+$] was added N-chlorosuccinimide (0.768 g, 5.75 mmol) and the mixture was stirred at 23° C. for 16 h to give a solution of the 3-[6-methyl-4-(4-trifluoromethyl-phenyl)-[2,4']bipyridinyl-2'-yl]-benzenesulfonyl chloride, which was splitted and directly used in the next steps.

3) The title compound was prepared from the above described solution of 3-[6-methyl-4-(4-trifluoromethyl-phenyl)-[2,4']bipyridinyl-2'-yl]-benzenesulfonyl chloride (ca. 0.2 g, 0.41 mmol) by treatment with excess morpholine in THF (5 mL) at 50° C. for 16 h. Cooled to rt, diluted with EtOAc, washed with 1 N HCl, dried organic layer over $Na_2SO_4$. Removal of the solvent in vacuum left a crude product, which was purified by silica gel column chromatography with n-heptane/EtOAc followed by trituration with n-heptane/diethyl ether to give the title compound (0.150 g, 68%) as a white solid. MS (ISP) 539.9 [(M+H)$^+$]; mp 115° C.

EXAMPLE 347

6-Methyl-2'-[3-(thiomorpholine-4-sulfonyl)-phenyl]-4-(4-trifluoromethyl-phenyl)-[2,4']bipyridinyl The title compound was prepared from the solution of 3-[6-methyl-4-(4-trifluoromethylphenyl)-[2,4']bipyridinyl- 2'-yl]-benzenesulfonyl chloride (example 346 step 2) (ca. 0.2 g, 0.41 mmol) by treatment with excess thiomorpholine in THF (5 mL) at 50° C. for 16 h. Cooled to rt, diluted with EtOAc, washed with 1 N HCl, dried organic layer over $Na_2SO_4$. Removal of the solvent in vacuum left a crude product, which was purified by silica gel column chromatography with n-heptane/EtOAc followed by trituration with n-heptane/diethyl ether to give the title compound (0.150 g, 66%) as a white solid. MS (ISP) 555.8 [$(M+H)^+$]; mp 156° C. (dec.).

EXAMPLE 348

N-(2-Hydroxy-ethyl)-3-[6-methyl-4-(4-trifluoromethyl-phenyl)-[2,4']bipyridinyl-2'-yl]-benzene-sulfonamide The title compound was prepared from the solution of 3-[6-methyl-4-(4-trifluoromethylphenyl)-[2,4']bipyridinyl-2'-yl]-benzenesulfonyl chloride (example 346 step 2) (ca. 0.2 g, 0.41 mmol) by treatment with excess ethanolamine in THF (5 mL) at 50° C. for 16 h. Cooled to rt, diluted with EtOAc, washed with 1 N HCl, dried organic layer over $Na_2SO_4$. Removal of the solvent in vacuum left a crude product, which was purified by silica gel column chromatography with n-heptane/EtOAc followed by trituration with n-heptane/diethyl ether to give the title compound (0.045 g, 21%) as a white solid. MS (ISP) 514.0 [$(M+H)^+$]; mp 103° C. (dec.).

EXAMPLE 349

N-(2-Hydroxy-1,1-dimethyl-ethyl)-3-[6-methyl-4-(4-trifluoromethyl-phenyl)-[2,4']bipyridinyl-2'-yl]-benzenesulfonamide The title compound was prepared from the solution of 3-[6-methyl-4-(4-trifluoromethylphenyl)-[2,4']bipyridinyl-2'-yl]-benzenesulfonyl chloride (example 346 step 2) (ca. 0.2 g, 0.41 mmol) by treatment with excess 2-amino-2-methyl-1-propanol in THF (5 mL) at 50° C. for 16 h. Cooled to rt, diluted with EtOAc, washed with 1 N HCl, dried organic layer over $Na_2SO_4$. Removal of the solvent in vacuum left a crude product, which was purified by silica gel column chromatography with n-heptane/EtOAc followed by trituration with n-heptane/diethyl ether to give the title compound (0.035 g, 16%) as a white solid. MS (ISP) 542.2 [$(M+H)^+$]; mp 92° C.

EXAMPLE 350

6-Methyl-2'-[3-(4-methyl-piperazine-1-sulfonyl)-phenyl]-4-(4-trifluoromethyl-phenyl)-[2,4']bipyridinyl The title compound was prepared from the solution of 3-[6-methyl-4-(4-trifluoromethylphenyl)-[2,4']bipyridinyl-2'-yl]-benzenesulfonyl chloride (example 346 step 2) (ca. 0.2 g, 0.41 mmol) by treatment with excess N-methylpiperazine in THF (5 mL) at 50° C. for 16 h. Cooled to rt, diluted with EtOAc, washed with 1 N HCl, dried organic layer over $Na_2SO_4$. Removal of the solvent in vacuum left a crude product, which was purified by silica gel column chromatography with n-heptane/EtOAc followed by trituration with n-heptane/diethyl ether to give the title compound (0.085 g, 37%) as a white solid. MS (ISP) 552 8 [$(M+H)^+$]; mp 180° C. (dec.).

EXAMPLE 351

Morpholine-4-sulfonic acid {3-[6'-methyl-4'-(4-trifluoromethyl-phenyl)-[2,2']bipyridinyl-6-yl]-phenyl}-amide To a stirred solution of 3-[6'-methyl-4'-(4-trifluoromethyl-phenyl)-[2,2']bipyridinyl-6-yl]-phenylamine (example 327) (0.200 g, 0.5 mmol) and triethyl amine (0.21 mL, 1.5 mmol) in dichloromethane (5 mL) was added commercially available morpholine-4-sulfonyl chloride (0.101 mg, 0.55 mmol) and the mixture was stirred at 23° C. for 30 min. Diluted with DCM, washed with sat. $NaHCO_3$-sol. and water, dried the organic layer over $Na_2SO_4$. Removal of the solvent in vacuum left a crude product which was purified by silica gel column chromatography with heptane/EtOAc, followed by trituration with heptane/diethyl ether to give the title compound as an off-white solid (0.035 g, 13%). MS (ISP) 555.2 [$(M+H)^+$]; mp 191° C.

EXAMPLE 352

N,N-(Dimethyl)-N'-{3-[6'-methyl-4'-(4-trifluoromethyl-phenyl)-[2,2']bipyridinyl-6-yl]-phenyl}-sulfamide To a stirred solution of 3-[6'-methyl-4'-(4-trifluoromethyl-phenyl)-[2,2']bipyridinyl-6-yl]-phenylamine (example 327) (0.200 g, 0.5 mmol) and triethyl amine (0.21 mL, 1.5 mmol) in dichloromethane (5 µL) was added commercially available dimethylsulfamoyl chloride (0.078 mg, 0.55 mmol) and the mixture was stirred at 23° C. for 30 min. Diluted with DCM, washed with sat. $NaHCO_3$-sol. and water, dried the organic layer over $Na_2SO_4$. Removal of the solvent in vacuum left a crude product which was purified by silica gel column chromatography with heptane/EtOAc, followed by trituration with heptane/diethyl ether to give the title compound as an off-white solid (0.020 g, 8%). MS (ISP) 513.0 [$(M+H)^+$].

EXAMPLE 353

2-(3'-Methanesulfonyl-biphenyl-3-yl)-6-methyl-4-(4-trifluoromethyl-phenyl)-pyridine The title compound was prepared from 3-[6-methyl-4-(4-trifluoromethyl-phenyl)pyridin-2-yl]-benzeneboronic acid (example G.9) (0.357 g, 1.0 mmol) and commercially available 3-bromophenylmethylsulfone (0.235 g, 1.0 mmol) according to the general procedure VI. Obtained as a white solid (0.414 g, 89%). MS (ISP) 468.0 [$(M+H)^+$]; mp 110° C. (dec.).

EXAMPLE 354

3-[6'-Methyl-4'-(4-trifluoromethyl-phenyl)-[2,2']bipyridinyl-6-yl]-N-propionyl-benzenesulfonamide A mixture of 3-[6'-methyl-4'-(4-trifluoromethyl-phenyl)-[2,2']bipyridinyl-6-yl]-benzenesulfonamide (example 266) (470 mg, 1.0 mmol) and propionic anhydride (0.77 mL, 6 mmol) in propionic acid (5 mL) was stirred at 150° C. for 2 days. Cooled to rt, diluted with EtOAc, extracted with sat. $NaHCO_3$-sol., dried over $Na_2SO_4$, filtered off and evaporated totally to give a crude product, which was purified by silica gel column chromatography with n-heptane/ethyl acetate followed by trituration with diethyl ether/n-heptane to give the title compound (350 mg, 66%) as a white solid. MS (ISP) 526.9 [$(M+H)^+$]; mp 173° C.

EXAMPLE 355

2-(3-Methanesulfonyl-phenyl)-4-[6-methyl-4-(4-trifluoromethyl-phenyl)-pyridin-2-yl]-pyrimidine The title compound was prepared from 2-chloro-4-[6-methyl-4-(4-trifluoromethylphenyl)-pyridin-2-yl]-pyrimidine (example E.83) (0.350 g, 1.0 mmol) and commercially available (3-methylsulfonylphenyl)boronic acid (0.220 g, 1.0 mmol) according to the general procedure VI. Obtained as an off-white solid (0.280 g, 59%). MS (ISP) 470.1 [(M+H)$^+$]; mp 208° C.

EXAMPLE 356

6'-(3-Methanesulfonyl-phenyl)-6-methyl-4-(4-trifluoromethyl-phenyl)-[2,2']bipyridinyl The title compound was prepared from 6'-bromo-6-methyl-4-(4-trifluoromethylphenyl)-[2,2']bipyridinyl (example E.26) (0.39 g, 1.1 mmol) and commercially available (3-methylsulfonylphenyl)boronic acid (0.218 g, 1.0 mmol) according to the general procedure VI. Obtained as a white solid (0.420 g, 90%). MS (ISP) 469.1 [(M+H)$^+$]; mp 186° C.

EXAMPLE 357

6-Methyl-6'-(3-methylsulfanyl-phenyl)-4-(4-trifluoromethyl-phenyl)-[2,2']bipyridinyl The title compound was prepared from 6'-bromo-6-methyl-4-(4-trifluoromethylphenyl)-[2,2']bipyridinyl (example E.26) (0.39 g, 1.1 mmol) and commercially available 3-(methylthio)phenylboronic acid (0.183 g, 1.1 mmol) according to the general procedure VI. Obtained as a white solid (0.150 g, 31%). MS (ISP) 437.1 [(M+H)$^+$]; mp 144° C.

EXAMPLE 358

6-Methyl-4-(4-trifluoromethyl-phenyl)-[2,2';6',4"]terpyridin-2"-ylamine 1) 2"-(2,5-Dimethyl-pyrrol-1-yl)-6-methyl-4-(4-trifluoromethyl-phenyl)-[2,2';6',4"]terpyridine: Prepared from 6'-bromo-6-methyl-4-(4-trifluoromethyl-phenyl)-[2,2']bipyridinyl (example E.26) (0.39 g, 1.1 mmol) and 2-(2,5-dimethyl-pyrrol-1-yl)-pyridine-4-boronic acid (example F.5) (0.295 g, 1.1 mmol) according to the general procedure VI. Obtained as a white solid (0.220 g, 45%) and additional light brown gum (270 mg). MS (ISP) 485.2 [(M+H)$^+$]; mp 175° C.

2) A mixture of the above described 2"-(2,5-dimethyl-pyrrol-1-yl)-6-methyl-4-(4-trifluoromethyl-phenyl)-[2,2';6',4"]terpyridine (470 mg, 0.969 mmol), hydroxylamine hydrochloride (337 mg, 4.849 mmol) 1.5 M NaOH-sol. (1.62 mL, 2.43 mmol) in 1-propanole (5 mL) was stirred at 120° C. for 3 h in a sealed tube. Cooled to rt, poured the reaction mixture directly on a silica gel column and chromatographed with EtOAc followed by trituration with diethyl ether/heptane to give the title compound (0.110 g, 27%) as a light yellow solid. MS (ISP) 407.3 [(M+H)$^+$]; mp 160° C.

EXAMPLE 359

N-(2-Hydroxy-ethyl)-3-[6'-methyl-4'-(4-trifluoromethyl-phenyl)-[2,2']bipyridinyl-6-yl]-benzene-sulfonamide The title compound was prepared from 3-[6'-methyl-4'-(4-trifluoromethyl-phenyl)-[2,2']bipyridinyl-6-yl]-benzene-sulfonyl chloride (example 1.2) (0.275 g, 0.5 mmol) by treatment with excess ethanolamine in THF (5 mL) at 23° C. for 16 h. Diluted with EtOAc, washed with 1 N HCl, dried organic layer over $Na_2SO_4$. Removal of the solvent in vacuum left a crude product, which was purified by silica gel column chromatography with n-heptane/EtOAc followed by trituration with n-heptane/diethyl ether to give the title compound (0.110 g, 43%) as a white solid. MS (ISP) 513.9 [(M+H)$^+$]; mp 110° C. (dec.).

EXAMPLE 360

4-{4-[6-Methyl-4-(4-trifluoromethyl-phenyl)-pyridin-2-yl]-pyrimidin-2-yl}-pyridin-2-ylamine 1) 2-[2-(2,5-Dimethyl-pyrrol-1-yl)-pyridin-4-yl]-4-[6-methyl-4-(4-trifluoromethylphenyl)-pyridin-2-yl]-pyrimidine: Prepared from 2-chloro-4-[6-methyl-4-(4-trifluoromethylphenyl)-pyridin-2-yl]-pyrimidine (example E.83) (0.35 g, 1.0 mmol) and 2-(2,5-dimethyl-pyrrol-1-yl)-pyridine-4-boronic acid (example F.5) (0.297 g, 1.1 mmol) according to the general procedure VI. Obtained as a white solid (0.150 g, 31%) and additional light brown gum (190 mg). MS (ISP) 486.1 [(M+H)$^+$]; mp 177° C.

2) A mixture of the above described 2-[2-(2,5-dimethyl-pyrrol-1-yl)-pyridin-4-yl]-4-[6-methyl-4-(4-trifluoromethyl-phenyl)-pyridin-2-yl]-pyrimidine (280 mg, 0.577 mmol), hydroxylamine hydrochloride (200 mg, 2.89 mmol) 1.5 M NaOH-sol. (0.96 mL, 1.44 mmol) in 1-propanole (3 mL) was stirred at 120° C. for 3 h in a sealed tube. Cooled to rt, poured the reaction mixture directly on a silica gel column and chromatographed with EtOAc followed by trituration with diethyl ether/heptane to give the title compound (0.050 g, 27%) as an off-white solid. MS (ISP) 408.4 [(M+H)$^+$]; mp 217° C.

EXAMPLE 361

3-[4-Methyl-6-(4-trifluoromethyl-phenyl)-[2,4']bipyridinyl-2'-yl]-phenylamine

1) The 4-methyl-2'-(3-nitro-phenyl)-6-(4-trifluoromethyl-phenyl)-[2,4']bipyridinyl was prepared from 2'-chloro-4-methyl-6-(4-trifluoromethyl-phenyl)-[2,4']bipyridinyl (example E.94) (1.25 g, 3.6 mmol) and commercially available 3-nitrophenylboronic acid (0.718 g, 4.3 mmol) according to the general procedure VI. Obtained as a light brown solid (1.03 g, 66%). MS (ISP) 436.1 [(M+H)$^+$]; mp 91° C.

2) A mixture of the above prepared 4-methyl-2'-(3-nitro-phenyl)-6-(4-trifluoromethylphenyl)-[2,4']bipyridinyl (1.12 g, 3.0 mmol) in THF-MeOH 1:1 (100 mL) and 10% palladium on carbon (1 mol %) was hydrogenated (1 bar hydrogen) at 23° C. for 2 h. The catalyst was filtered off, washed with MeOH and the filtrate was completely evaporated totally to leave a crude product, which was purified by trituration with diethyl ether to give the title compound as a light brown solid (0.914 g, 88%). MS (ISP) 406.5 [(M+H)$^+$]; mp 87° C. (dec.).

EXAMPLE 362

N-tert-Butyl-3-{6-[4-trifluoromethyl-6-(4-trifluoromethyl-phenyl)-pyrimidin-2-yl]-pyridin-2-yl}-benzenesulfonamide The title compound was prepared from 2-(6-bromo-pyridin-2-yl)-4-trifluoromethyl-6-(4-trifluoromethyl-phenyl)-pyrimidine (example E.100) (0.600 g, 1.34 mmol) and commercially available 3-(tert-butylsulfamoyl)-benzeneboronic acid (0.448 g, 1.74 mmol) according to the general procedure VI. Obtained as a light yellow foam (0.318 g, 41%). MS (ISP) 581.6 [$(M+H)^+$]; mp 75° C.

EXAMPLE 363

N-(2-Hydroxy-1,1-dimethyl-ethyl)-3-[6'-methyl-4'-(4-trifluoromethyl-phenyl)-[2,2']bipyridinyl-6-yl]-benzenesulfonamide The title compound was prepared from 3-[6'-methyl-4'-(4-trifluoromethyl-phenyl)-[2,2']bipyridinyl-6-yl]-benzenesulfonyl chloride (example 1.2) (0.228 g, 0.47 mmol) by treatment with excess 2-amino-2-methyl-1-propanol in THF (10 mL) at 23° C. for 1 h. Diluted with EtOAc, washed with 5% citric acid, sat. $NaHCO_3$-sol. and brine, dried organic layer over $Na_2SO_4$. Removal of the solvent in vacuum left a crude product, which was purified by silica gel column chromatography with n-heptane/EtOAc followed by trituration with n-heptane/diethyl ether to give the title compound (0.158 g, 63%) as a white solid. MS (ISP) 541.9 [$(M+H)^+$]; mp 171° C.

EXAMPLE 364

3-{6-[4-Trifluoromethyl-6-(4-trifluoromethyl-phenyl)-pyrimidin-2-yl]-pyridin-2-yl}-benzenesulfonamide To N-tert-butyl-3-{6-[4-trifluoromethyl-6-(4-trifluoromethyl-phenyl)-pyrimidin-2-yl]-pyridin-2-yl}-benzenesulfonamide (example 362) (0.232 g, 0.40 mmol) was added TFA (3 mL) and the reaction mixture was stirred at 23° C. for 16 h. The mixture was evaporated to dryness and partitioned between EtOAc and saturated $NaHCO_3$ solution, the organic layer was dried over $Na_2SO_4$. Removal of the solvent in vacuum left a crude product which was triturated with diethyl ether to give the title compound as a white solid (0.170 g, 81%). MS (ISP) 524.8 [$(M+H)^+$]; mp 244° C. (dec.).

EXAMPLE 365

N,N-Bis-(2-{2-[2-(2-methoxy-ethoxy)-ethoxy]-ethoxy}-ethyl)-3-[6'-methyl-4'-(4-trifluoromethyl-phenyl)-[2,2']bipyridinyl-6-yl]-benzenesulfonamide The title compound was prepared from 3-[6'-methyl-4'-(4-trifluoromethyl-phenyl)-[2,2']bipyridinyl-6-yl]-benzenesulfonyl chloride (example I.2) (0.258 g, 0.528 mmol) by treatment with bis-[2-[2-[2-(2-methoxy-ethoxy)-ethoxy]-ethoxy]-ethyl]-amine [CAS-no. 123852-08-4] (0.210 g, 0.528 mmol) and $Et_3N$ (0.221 mL, 1.58 mmol) in THF (5 mL) at 23° C. for 1 h. Diluted with EtOAc, washed with 5% citric acid, sat. $NaHCO_3$-sol.+2 M $Na_2CO_3$-sol. and brine, dried organic layer over $Na_2SO_4$. Removal of the solvent in vacuum left a crude product, which was purified by silica gel column chromatography with EtOAc/EtOH gave the title compound (0.158 g, 63%) as a yellow oil. MS (ISP) 850.5 [$(M+H)^+$].

EXAMPLE 366

N,N-Bis-(2-hydroxy-ethyl)-3-[6'-methyl-4'-(4-trifluoromethyl-phenyl)-[2,2']bipyridinyl-6-yl]-benzenesulfonamide The title compound was prepared from 3-[6'-methyl-4'-(4-trifluoromethyl-phenyl)-[2,2']bipyridinyl-6-yl]-benzenesulfonyl chloride (example I.2) (0.210 g, 0.429 mmol) by treatment with excess diethanolamine in THF (5 mL) at 23° C. for 16 h. Diluted with EtOAc, washed with 5% citric acid, sat. $NaHCO_3$-sol. and brine, dried organic layer over $Na_2SO_4$. Removal of the solvent in vacuum left a crude product, which was purified by silica gel column chromatography with EtOAc followed by trituration with n-heptane/diethyl ether to give the title compound (0.120 g, 50%) as a white solid. MS (ISP) 557.6 [$(M+H)^+$]; mp 176° C.

EXAMPLE 367

N-(2-{2-[2-(2-Methoxy-ethoxy)-ethoxy]-ethoxy}-ethyl)-3-[6'-methyl-4'-(4-trifluoromethylphenyl)-[2,2']bipyridinyl-6-yl]-benzenesulfonamide The title compound was prepared from 3-[6'-methyl-4'-(4-trifluoromethyl-phenyl)-[2,2']bipyridinyl-6-yl]-benzenesulfonyl chloride (example I.2) (0.210 g, 0.429 mmol) by treatment with 2-{2-[2-(2-methoxy-ethoxy)-ethoxy]-ethoxy}-ethylamine [CAS-no. 85030-56-4] (0.089 g, 0.429 mmol) and $Et_3N$ (0.180 mL, 1.287 mmol) in THF (5 mL) at 23° C. for 16 h. Diluted with EtOAc, washed with 5% citric acid, sat. $NaHCO_3$-sol. and brine, dried organic layer over $Na_2SO_4$. Removal of the solvent in vacuum left a crude product, which was purified by silica gel column chromatography with EtOAc gave the title compound (0.080 g, 28%) as an orange oil. MS (ISP) 659.7 [$(M+H)^+$].

EXAMPLE 368

6'-[3-(1,1-Dioxo-1λ6-thiomorpholine-4-sulfonyl)-phenyl]-6-methyl-4-(4-trifluoromethylphenyl)-[2,2']bipyridinyl The title compound was prepared from 3-[6'-methyl-4'-(4-trifluoromethyl-phenyl)-[2,2']bipyridinyl-6-yl]-benzenesulfonyl chloride (example 1.2) (0.300 g, 0.613 mmol) by treatment with commercially available thiomorpholine-1,1-dioxide (0.166 g, 1.226 mmol) and $Et_3N$ (0.260 mL, 1.84 mmol) in THF (5 mL) at 23° C. for 16 h. Diluted with EtOAc, washed with 5% citric acid, sat. $NaHCO_3$-sol. and brine, dried organic layer over $Na_2SO_4$. Removal of the solvent in vacuum left a crude product, which was purified by silica gel column chromatography with EtOAc followed by trituration with diethyl ether/heptane to give the title compound (0.170 g, 47%) as a white solid. MS (ISP) 588.1 [$(M+H)^+$]; mp 230° C. (dec.).

EXAMPLE 369

6-Methyl-6'-[3-(pyrrolidine-1-sulfonyl)-phenyl]-4-(4-trifluoromethyl-phenyl)-[2,2']bipyridinyl The title compound was prepared from 3-[6'-methyl-4'-(4-trifluoromethyl-phenyl)-[2,2']bipyridinyl-6-yl]-benzenesulfonyl chloride (example 1.2) (0.300 g, 0.613 mmol) by treatment with pyrrolidine (0.131 mg, 1.84 mmol) in THF (5 mL) at 23° C. for 16 h. Diluted with EtOAc, washed with 5% citric acid, sat. $NaHCO_3$-sol. and brine, dried organic layer over $Na_2SO_4$. Removal of the solvent in vacuum left a crude product, which was purified by silica gel column chromatography with EtOAc followed by trituration with diethyl ether/heptane to give the title compound (0.230 g, 71%) as a white solid. MS (ISP) 524.3 [$(M+H)^+$]; mp 174° C.

EXAMPLE 370

6-Methyl-6'-[3-(4-methyl-piperazine-1-sulfonyl)-phenyl]-4-(4-trifluoromethyl-phenyl)-[2,2']bipyridinyl The title compound was prepared from 3-[6'-methyl-4'-(4-trifluoromethyl-phenyl)-[2,2']bipyridinyl-6-yl]-benzenesulfonyl chloride (example I.2) (0.300 g, 0.613 mmol) by treatment with pyrrolidine (0.184 mg, 1.84 mmol) in THF (5 mL) at 23° C. for 16 h. Diluted with EtOAc, washed with 5% citric acid, sat. $NaHCO_3$-sol. and brine, dried organic layer over $Na_2SO_4$. Removal of the solvent in vacuum left a crude product, which was purified by silica gel column chromatography with EtOAc followed by trituration with diethyl ether/heptane to give the title compound (0.210 g, 62%) as a white solid. MS (ISP) 553.3 [$(M+H)^+$]; mp 167° C. (dec.).

EXAMPLE 371

N-(2-Methoxy-ethyl)-3-[6'-methyl-4'-(4-trifluoromethyl-phenyl)-[2,2']bipyridinyl-6-yl]-benzenesulfonamide The title compound was prepared from 3-[6'-methyl-4'-(4-trifluoromethyl-phenyl)-[2,2']bipyridinyl-6-yl]-benzenesulfonyl chloride (example I.2) (0.300 g, 0.613 mmol) by treatment with commercially available 2-methoxyethylamine (0.138 mg, 1.84 mmol) in THF (5 mL) at 23° C. for 16 h. Diluted with EtOAc, washed with 5% citric acid, sat. $NaHCO_3$-sol. and brine, dried organic layer over $Na_2SO_4$. Removal of the solvent in vacuum left a crude product, which was purified by silica gel column chromatography with EtOAc followed by trituration with diethyl ether/heptane to give the title compound (0.200 g, 62%) as a white solid. MS (ISP) 528.2 [$(M+H)^+$]; mp 126° C.

EXAMPLE 372

N-[2-(2-Hydroxy-ethoxy)-ethyl]-3-[6'-methyl-4'-(4-trifluoromethyl-phenyl)-[2,2']bipyridinyl-6-yl]-benzenesulfonamide The title compound was prepared from 3-[6'-methyl-4'-(4-trifluoromethyl-phenyl)-[2,2']bipyridinyl-6-yl]-benzenesulfonyl chloride (example I.2) (0.300 g, 0.613 mmol) by treatment with commercially available 2-(2-aminoethoxy) ethanol (0.194 mg, 1.84 mmol) in THF (5 mL) at 23° C. for 16 h. Diluted with EtOAc, washed with 5% citric acid, sat. $NaHCO_3$-sol. and brine, dried organic layer over $Na_2SO_4$. Removal of the solvent in vacuum left a crude product, which was purified by silica gel column chromatography with EtOAc followed by trituration with diethyl ether/heptane to give the title compound (0.210 g, 61%) as a white solid. MS (ISP) 558.2 [$(M+H)^+$]; mp 123° C.

EXAMPLE 373

6-Methyl-6'-[3-(morpholine-4-sulfonyl)-phenyl]-4-(4-trifluoromethyl-phenyl)-[2,2']bipyridinyl The title compound was prepared from 3-[6'-methyl-4'-(4-trifluoromethyl-phenyl)-[2,2']bipyridinyl-6-yl]-benzenesulfonyl chloride (example I.2) (0.300 g, 0.613 mmol) by treatment with morpholine (0.160 mg, 1.84 mmol) in THF (5 mL) at 23° C. for 16 h. Diluted with EtOAc, washed with 5% citric acid, sat. $NaHCO_3$-sol. and brine, dried organic layer over $Na_2SO_4$. Removal of the solvent in vacuum left a crude product, which was purified by silica gel column chromatography with EtOAc followed by trituration with diethyl ether/heptane to give the title compound (0.250 g, 75%) as a white solid. MS (ISP) 540.3 [$(M+H)^+$]; mp 216° C.

EXAMPLE 374

N-Propionyl-3-{4-[4-trifluoromethyl-6-(4-trifluoromethyl-phenyl)-pyrimidin-2-yl]-pyridin-2-yl}-benzenesulfonamide A mixture of 3-{4-[4-trifluoromethyl-6-(4-trifluoromethyl-phenyl)-pyrimidin-2-yl]-pyridin-2-yl}-7-benzenesulfonamide (example 158) (0.1 g, 0.19 mmol), propionic acid anhydride (0.45 ml) and propionic acid (2 ml) was stirred at 150° C. for 40 h, poured into saturated $NaHCO_3$ solution (30 ml) and extracted with ethyl acetate (2×50 ml). The combined organic layers were washed with brine (30 ml), dried ($MgSO_4$) and evaporated. The crude product was further purified by flash chromatography on silica gel (ethylacetate/heptane) and crystallization (dichloromethane/MeOH/hexane) to yield the title compound (0.086 g, 78%) as an off-white solid. MS (ISP) 579.2 [$(M-H)^-$]; mp 144° C.

EXAMPLE 375

5-{4-[4-Trifluoromethyl-6-(4-trifluoromethyl-phenyl)-pyrimidin-2-yl]-pyridin-2-yl}-thiophene-2-sulfonic acid propionyl-amide A mixture of 5-{4-[4-trifluoromethyl-6-(4-trifluoromethyl-phenyl)-pyrimidin-2-yl]-pyridin-2-yl}-thiophene-2-sulfonic acid amide (example 164) (0.1 g, 0.19 mmol), propionic acid anhydride (0.45 ml) and propionic acid (2 ml) was stirred at 150° C. for 40 h, poured into saturated $NaHCO_3$ solution (30 ml) and extracted with ethyl. acetate (2×50 ml). The combined organic layers were washed with brine (30 ml), dried ($MgSO_4$) and evaporated. The crude product was further purified by flash chromatography on silica gel (ethylacetate/heptane) and crystallization (dichloromethane/MeOH/hexane) to yield the title compound (0.074 g, 67%) as a light brown solid. MS (ISP) 585.3 [$(M-H)^-$]; mp 257° C.

EXAMPLE 376

5-{3-[4-(4-Chloro-3-methyl-phenyl)-6-methyl-pyrimidin-2-yl]-phenyl}-pyridin-2-ylamine The title compound was prepared from 2-(3-bromo-phenyl)-4-(4-chloro-3-methylphenyl)-6-methyl-pyrimidine (example E.77) (0.37 g, 1.0 mmol) and commercially available 2-amino-5-(4,4,5,5-tetramethyl-1,3,2-dioxaborolan-2-yl)

pyridine (0.24 g, 1.2 mmol) according to the general procedure VI. Obtained as a white solid (0.27 g, 70%). MS (ISP) 387.2 [$(M+H)^+$]; mp 158° C. (dec.).

EXAMPLE 377

4-(3-{4-[4-Trifluoromethyl-6-(4-trifluoromethyl-phenyl)-pyrimidin-2-yl]-pyridin-2-yl}-benzenesulfonyl)-morpholine To a cooled (ice-water bath) and stirred mixture of morpholine (0.063 g, 0.72 mmol), triethylamine (0.07 ml, 0.5 mmol) and THF (1 ml) was added drop wise a solution of 3-{4-[4-trifluoromethyl-6-(4-trifluoromethyl-phenyl)-pyrimidin-2-yl]-pyridin-2-yl}-benzenesulfonyl chloride hydrochloride (example I.1) (0.14 g, 0.24 mmol) in THF (2 ml). The mixture was allowed to stir at room temperature for 16 h. Purification of the reaction mixture by flash chromatography on silica gel (ethyl acetate/hexane) and crystallization (dichloromethane/hexane) yielded the title compound as a white solid (0.13 g, 91%). MS (ISP) 595.2 [$(M+H)^+$]; mp 202° C.

EXAMPLE 378

5-{1-[4-(4-Fluoro-phenyl)-6-trifluoromethyl-pyrimidin-2-yl]-1H-imidazol-4-yl}-pyridin-2-ylamine The title compound was prepared from 4-(4-fluoro-phenyl)-2-(4-iodo-imidazol-1-yl)-6-trifluoromethyl-pyrimidine (example E.79) (0.43 g, 1.0 mmol) and commercially available 2-amino-5-(4,4,5,5-tetramethyl-1,3,2-dioxaborolan-2-yl)pyridine (0.26 g, 1.2 mmol) according to the general procedure VI. Obtained as a light yellow solid (0.13 g, 33%). MS (ISP) 401.3 [$(M+H)^+$]; mp 249.5° C.

EXAMPLE 379

3'-[4-(4-Chloro-3-methyl-phenyl)-6-methyl-pyrimidin-2-yl]-biphenyl-3-sulfonic acid amide 1) 3'-[4-(4-Chloro-3-methyl-phenyl)-6-methyl-pyrimidin-2-yl]-biphenyl-3-sulfonic acid tert-butylamide was prepared from 2-(3-bromo-phenyl)-4-(4-chloro-3-methyl-phenyl)-6-methyl-pyrimidine (example E.77) (0.37 g, 1.0 mmol) and commercially available 3-(tert.-butylsulfamoyl)-phenylboronic acid (0.31 g, 1.2 mmol) according to the general procedure VI. Obtained as white foam (0.45 g), which was subsequently deprotected.

2) To a cooled and stirred solution of 3'-[4-(4-chloro-3-methyl-phenyl)-6-methyl-pyrimidin-2-yl]-biphenyl-3-sulfonic acid tert-butylamide (0.45 g) in dichloromethane (6 ml) was added TFA (6 ml) and the reaction mixture was allowed to stir at room temperature for 15 h. The mixture was evaporated to dryness and saturated $NaHCO_3$ solution (5 ml), diethylether and heptane were added. The mixture was stirred at room temperature for 1 h, the precipitate was collected by filtration, washed with water and heptane. The crude product was further purified by flash chromatography on silica gel (ethylacetate/heptane) and crystallization (dichloromethane/MeOH/hexane) to yield the title compound as a white solid (0.29 g, 65%). MS (ISP) 450.1 [$(M+H)^+$]; mp 201° C.

EXAMPLE 380

5-{3-[4-(4-Chloro-3-methyl-phenyl)-6-methyl-pyrimidin-2-yl]-phenyl}-thiophene-2-sulfonic acid amide 1) N-tert-Butyl-5-{3-[6-(4-chloro-3-methyl-phenyl)-4-methyl-pyrimidin-2-yl]-phenyl}-thiophene-2-sulfonic acid amide was prepared from 2-(3-bromo-phenyl)-4-(4-chloro-3-methylphenyl)-6-methyl-pyrimidine (example E.77) (0.37 g, 1.0 mmol) and N-tert-butyl-5-(4,4,5,5-tetramethyl-1,3,2-dioxaborolan-2-yl)-thiophene-2-sulfonamide (example F.1) (0.45 g, 1.3 mmol) according to the general procedure VI. Obtained as a light yellow oil (0.405 g), which was subsequently deprotected.

2) To a cooled and stirred solution of N-tert-butyl-5-{3-[6-(4-chloro-3-methyl-phenyl)-4-methyl-pyrimidin-2-yl]-phenyl}-thiophene-2-sulfonic acid amide (0.405 g) in dichloromethane (6 ml) was added TFA (6 ml) and the reaction mixture was allowed to stir at room temperature for 15 h. The mixture was evaporated to dryness and saturated $NaHCO_3$ solution (5 ml), diethylether and heptane were added. The mixture was stirred at room temperature for 1 h, the precipitate was collected by filtration and further purified by flash chromatography (heptane/ethyl acetate) and crystallization (diethyl ether/heptane) to yield the title compound as an off-white solid (0.093 g, 20%). MS (ISP) 456.1 [$(M+H)^+$]; mp 240° C.

EXAMPLE 381

N-(2-Hydroxy-ethyl)-3-{4-[4-trifluoromethyl-6-(4-trifluoromethyl-phenyl)-pyrimidin-2-yl]-pyridin-2-yl}-benzenesulfonamide To a cooled (ice-water bath) and stirred mixture of ethanolamine (0.066 g, 1.08 mmol), triethylamine (0.11 ml, 0.76 mmol) and THF (2 ml) was added drop wise a solution of 3-{4-[4-trifluoromethyl-6-(4-trifluoromethyl-phenyl)-pyrimidin-2-yl]-pyridin-2-yl}-benzenesulfonyl chloride hydrochloride (example I.1) (0.21 g, 0.36 mmol) in THF (3 ml). The mixture was allowed to stir at room temperature for 16 h. Purification of the reaction mixture by flash chromatography on silica gel (ethyl acetate/hexane) and crystallization (diethyl ether/hexane) yielded the title compound as a white solid (0.156 g, 76%). MS (ISP) 569.2 [$(M+H)^+$]; mp 192.5° C.

EXAMPLE 382

N-(2-Hydroxy-1,1-dimethyl-ethyl)-3-{4-[4-trifluoromethyl-6-(4-trifluoromethyl-phenyl)pyrimidin-2-yl]-pyridin-2-yl}-benzenesulfonamide To a cooled (ice-water bath) and stirred mixture of 2-amino-2-methyl-1-propanol (0.097 g, 1.09 mmol), triethylamine (0.11 ml, 0.76 mmol) and THF (2 ml) was added drop wise a solution of 3-{4-[4-trifluoromethyl-6-(4-trifluoromethyl-phenyl)-pyrimidin-2-yl]-pyridin-2-yl}-benzenesulfonyl chloride hydrochloride (example I.1) (0.21 g, 0.36 mmol) in THF (3 ml). The mixture was allowed to stir at room temperature for 16 h. Purification of the reaction mixture by flash chromatography on silica gel (ethyl acetate/hexane) and crystallization (diethyl ether/hexane) yielded the title compound as a white solid (0.135 g, 63%). MS (ISP) 597.3 [$(M+H)^+$]; mp 221° C.

EXAMPLE 383

N,N-Bis-(2-hydroxy-ethyl)-3-{4-[4-trifluoromethyl-6-(4-trifluoromethyl-phenyl)-pyrimidin-2-yl]-pyridin-2-yl}-benzenesulfonamide To a cooled (ice-water bath) and stirred mixture of diethanolamine (0.114 g, 1.08 mmol), triethylamine (0.11 ml, 0.76 mmol) and THF (2 ml) was added drop wise a solution of 3-{4-[4-trifluoromethyl-6-(4-trifluoromethyl-phenyl)-pyrimidin-2-yl]-pyridin-2-yl}-benzenesulfonyl chloride hydrochloride (example 1.1) (0.21 g, 0.36 mmol) in THF (3 ml). The mixture was allowed to stir at room temperature for 16 h. Purification of the reaction mixture by flash chromatography on silica gel (ethyl acetate/hexane) and crystallization (diethyl ether/hexane) yielded the title compound as a white solid (0.127 g, 57%). MS (ISP) 613.2 [$(M+H)^+$]; mp 186° C.

EXAMPLE 384

5-{1-[4-(3,4-Difluoro-phenyl)-6-trifluoromethyl-pyrimidin-2-yl]-1H-imidazol-4-yl}-pyridin-2-ylamine The title compound was prepared from 4-(3,4-difluoro-phenyl)-2-(4-iodo-imidazol-1-yl)-6-trifluoromethyl-pyrimidine (example E.78) (0.45 g, 1.0 mmol) and commercially available 2-amino-5-(4,4,5,5-tetramethyl-1,3,2-dioxaborolan-2-yl)pyridine (0.26 g, 1.2 mmol) according to the general procedure VI. Obtained as a yellow solid (0.036 g, 9%). MS (ISP) 419.1 [$(M+H)^+$]; mp 232° C.

EXAMPLE 385

5-{1-[4-(3,4-Difluoro-phenyl)-6-trifluoromethyl-pyrimidin-2-yl]-1H-imidazol-4-yl}-thiophene-2-sulfonic acid amide 1) A stirred mixture of 4-(3,4-difluoro-phenyl)-2-(4-tributylstannanyl-imidazol-1-yl)-6-trifluoromethyl-pyrimidine (Example G.13) (0.21 g, 0.34 mmol), commercially available 5-bromothiophene-2-N-tert-butylsulfonamide (0.11 g, 0.37 mmol), tetrakis(triphenylphosphine)palladium (0.024 g, 0.02 mmol) in toluene (3 ml) was heated under reflux conditions for 15 h, hexane (10 ml) was added and the mixture was stirred at RT for 1 h. The precipitate was collected by filtration and further purified by flash chromatography on silica gel (ethyl acetate/heptane) to yield 5-{1-[4-(3,4-difluoro-phenyl)-6-trifluoromethyl-pyrimidin-2-yl]-1H-imidazol-4-yl}-thiophene-2-sulfonic acid tert-butyl amide (0.24 g) as a white solid.

2) To a cooled and stirred solution of 5-{1-[4-(3,4-difluoro-phenyl)-6-trifluoromethyl-pyrimidin-2-yl]-1H-imidazol-4-yl}-thiophene-2-sulfonic acid tert-butyl amide (0.24 g) in dichloromethane (4 ml) was added TFA (4 ml) and the reaction mixture was allowed to stir at room temperature for 15 h. The mixture was evaporated to dryness, poured into 2N $NaHCO_3$ solution (25 ml) and extracted ethyl acetate (3×50 ml). The combined organic layers were washed with brine (50 ml), dried (MgSO4) and evaporated. Further purification by flash chromatography on silica gel (MeOH/dichloromethane) and crystallization (dichloromethane/heptane) yielded the title compound as a light yellow solid (0.077 g, 46%). MS (ISP) 487.9 [$(M+H)^+$]; mp 228° C.

EXAMPLE 386

5-{1-[4-(4-Fluoro-phenyl)-6-trifluoromethyl-pyrimidin-2-yl]-1H-imidazol-4-yl}-thiophene-2-sulfonic acid amide 1) A stirred mixture of 4-(4-fluoro-phenyl)-2-(4-tributylstannanyl-imidazol-1-yl)-6-trifluoromethyl-pyrimidine (Example G.14) (0.34 g, 0.57 mmol), commercially available 5-bromothiophene-2-N-tert-butylsulfonamide (0.19 g, 0.63 mmol), tetrakis(triphenylphosphine)palladium (0.039 g, 0.033 mmol) in toluene (5 ml) was heated under reflux conditions for 15 h, hexane (10 ml) was added and the mixture was stirred at RT for 1 h. The precipitate was collected by filtration and further purified by flash chromatography on silica gel (ethyl acetate/heptane) to yield 5-{1-[4-(4-fluoro-phenyl)-6-trifluoromethyl-pyrimidin-2-yl]-1H-imidazol-4-yl}-thiophene-2-sulfonic acid tert-butyl amide (0.37 g) as a white solid.

2) To a cooled and stirred solution of 5-{1-[4-(4-fluoro-phenyl)-6-trifluoromethyl-pyrimidin-2-yl]-1H-imidazol-4-yl}-thiophene-2-sulfonic acid tert-butyl amide (0.37 g) in dichloromethane (4 ml) was added TFA (4 ml) and the reaction mixture was allowed to stir at room temperature for 15 h. The mixture was evaporated to dryness, poured into 2N $NaHCO_3$ solution (25 ml) and extracted with ethyl acetate (3×50 ml). The combined organic layers were washed with brine (50 ml), dried ($MgSO_4$) and evaporated. Further purification by crystallization (ethyl acetate/heptane) yielded the title compound as an off-white solid (0.18 g, 67%). MS (ISN) 468.0 [$(M-H)^-$]; mp 244.5° C.

EXAMPLE 387

3-{1-[4-(4-Fluoro-phenyl)-6-trifluoromethyl-pyrimidin-2-yl]-1H-imidazol-4-yl}-benzenesulfonamide 1) N-tert-Butyl-3-{1-[6-(4-fluoro-phenyl)-4-trifluoromethyl-pyrimidin-2-yl]-1H-imidazol-4-yl}-benzenesulfonamide was prepared from 4-(4-fluoro-phenyl)-2-(4-iodo-imidazol-1-yl)-6-trifluoromethyl-pyrimidine (example E.79) (0.25 g, 0.57 mmol) and commercially available 3-(tert.-butylsulfamoyl)-phenylboronic acid (0.175 g, 0.68 mmol) according to the general procedure VI. Obtained as a light yellow solid (0.52 g) which was subsequently deprotected.

2) To a cooled and stirred solution of N-tert-butyl-3-{1-[6-(4-fluoro-phenyl)-4-trifluoromethyl-pyrimidin-2-yl]-1H-imidazol-4-yl}-benzenesulfonamide (0.52 g) in dichloromethane (4 ml) was added TFA (4 ml) and the reaction mixture was allowed to stir at room temperature for 15 h. The mixture was evaporated to dryness, poured into 2N $NaHCO_3$ solution (25 ml) and extracted with ethyl acetate (3×50 ml). The combined organic layers were washed with brine (50 ml), dried ($MgSO_4$) and evaporated. Further purification by flash chromatography on silica gel (dichloromethane/MeOH) and crystallization (ethyl acetate/heptane) yielded the title compound as an off-white solid (0.13 g, 48%). MS (ISN) 462.0 [$(M-H)^-$]; mp 260° C.

EXAMPLE 388

5-{3-[4-(3,4-Difluoro-phenyl)-6-trifluoromethyl-pyrimidin-2-yl]-phenyl}-thiophene-2-sulfonic acid amide 1) N-tert-Butyl-5-{3-[6-(3,4-difluoro-phenyl)-4-trifluoromethyl-pyrimidin-2-yl]-phenyl}-thiophene-2-sulfonic acid amide was prepared from 2-(3-bromo-phenyl)-4-(3,4-difluoro-phenyl)-6-trifluoromethyl-pyrimidine (example E.101) (0.415 g, 1.0 mmol) and N-tert-butyl-5-(4,4,5,5-tetramethyl-1,3,2-dioxaborolan-2-yl)-thiophene-2-sulfonamide (example F.1) (0.414 g, 1.2 mmol) according to the general procedure VI. Obtained as white foam (0.37 g), which was subsequently deprotected.

2) To a cooled and stirred solution of N-tert-butyl-5-{3-[6-(3,4-difluoro-phenyl)-4-trifluoromethyl-pyrimidin-2-yl]-phenyl}-thiophene-2-sulfonic acid amide (0.37 g) in dichloromethane (6 ml) was added TFA (6 ml) and the reaction mixture was allowed to stir at room temperature for 15 h. The mixture was evaporated to dryness, poured into 2N $NaHCO_3$ solution (25 ml) and extracted with ethyl acetate (3×50 ml). The combined organic layers were washed with brine (50 ml), dried ($MgSO_4$) and evaporated. Further purification by flash chromatography on silica gel (ethyl acetate/heptane) and crystallization (ethyl acetate/heptane) yielded the title compound as a white solid (0.11 g, 22%). MS (ISP) 498.1 [$(M+H)^+$]; mp 238° C.

EXAMPLE 389

2-{2-[3-(4-Methyl-piperazine-1-sulfonyl)-phenyl]-pyridin-4-yl}-4-trifluoromethyl-6-(4-trifluoromethyl-phenyl)-pyrimidine To a cooled (ice-water bath) and stirred mixture of N-methyl-piperazine (0.09 g, 0.9 mmol), triethylamine (0.09 ml, 0.63 mmol) and THF (2 ml) was added drop wise a solution of 3-{4-[4-trifluoromethyl-6-(4-trifluoromethyl-phenyl)-pyrimidin-2-yl]-pyridin-2-yl}-benzenesulfonyl chloride hydrochloride (example 1.1) (0.20 g, 0.34 mmol) in THF (3 ml). The mixture was allowed to stir at room temperature for 16 h. Purification of the reaction mixture by flash chromatography on silica gel (ethyl acetate/hexane) and crystallization (dichloromethane/hexane) yielded the title compound as a white solid (0.18 g, 88%). MS (ISP) 607.6 [$(M+H)^+$]; mp 205° C.

EXAMPLE 390

2-{2-[3-(Pyrrolidine-1-sulfonyl)-phenyl]-pyridin-4-yl}-4-trifluoromethyl-6-(4-trifluoromethylphenyl)-pyrimidine To a cooled (ice-water bath) and stirred mixture of pyrrolidine (0.065 g, 0.91 mmol), triethylamine (0.09 ml, 0.63 mmol) and THF (2 ml) was added drop wise a solution of 3-{4-[4-trifluoromethyl-6-(4-trifluoromethyl-phenyl)-pyrimidin-2-yl]-pyridin-2-yl}-benzenesulfonyl chloride hydrochloride (example 1.1) (0.20 g, 0.34 mmol) in THF (3 ml). The mixture was allowed to stir at room temperature for 16 h. Purification of the reaction mixture by flash chromatography on silica gel (ethyl acetate/hexane) and crystallization (dichloromethane/hexane) yielded the title compound as a white solid (0.17 g, 85%). MS (ISP) 578.6 [$(M+H)^+$]; mp 184° C.

EXAMPLE 391

3'-[4-Trifluoromethyl-6-(4-trifluoromethyl-phenyl)-pyrimidin-2-yl]-biphenyl-3-sulfonic acid (2-hydroxy-ethyl)-amide To a cooled (ice-water bath) and stirred mixture of ethanolamine (0.071 g, 1.16 mmol), triethylamine (0.06 ml, 0.42 mmol) and THF (2 ml) was added drop wise a solution of 3'-[4-trifluoromethyl-6-(4-trifluoromethyl-phenyl)-pyrimidin-2-yl]-biphenyl-3-sulfonyl chloride (example 1.3) (0.21 g, 0.39 mmol) in THF (3 ml). The mixture was allowed to stir at room temperature for 16 h. Purification of the reaction mixture by flash chromatography on silica gel (ethyl acetate/heptane) and crystallization (dichloromethane/MeOH/hexane) yielded the title compound as a white solid (0.15 g, 69%). MS (ISP) 567.7 [$(M+H)^+$]; mp 153° C.

EXAMPLE 392

3'-[4-Trifluoromethyl-6-(4-trifluoromethyl-phenyl)-pyrimidin-2-yl]-biphenyl-3-sulfonic acid bis-(2-hydroxy-ethyl)-amide To a cooled (ice-water bath) and stirred mixture of diethanolamine (0.12 g, 1.14 mmol), triethylamine (0.06 ml, 0.42 mmol) and THF (2 ml) was added drop wise a solution of 3'-[4-trifluoromethyl-6-(4-trifluoromethyl-phenyl)-pyrimidin-2-yl]-biphenyl-3-sulfonyl chloride (example 1.3) (0.21 g, 0.39 mmol) in THF (3 ml). The mixture was allowed to stir at room temperature for 16 h. Purification of the reaction mixture by flash chromatography on silica gel (ethyl acetate/heptane) and crystallization (diethyl ether/hexane) yielded the title compound as a white solid (0.125 g, 53%). MS (ISP) 611.6 [$(M+H)^+$]; mp 111.5° C.

EXAMPLE 393

3'-[4-(3,4-Difluoro-phenyl)-6-trifluoromethyl-pyrimidin-2-yl]-biphenyl-3-sulfonic acid amide 1) 3'-[4-(3,4-difluoro-phenyl)-6-trifluoromethyl-pyrimidin-2-yl]-biphenyl-3-sulfonic acid tert-butylamide was prepared from 2-(3-bromo-phenyl)-4-(3,4-difluoro-phenyl)-6-trifluoromethyl-pyrimidine (example E.101) (0.415 g, 1.0 mmol) and commercially available 3-(tert.-butylsulfamoyl)-phenylboronic acid (0.31 g, 1.2 mmol) according to the general procedure VI. Obtained as white foam (0.43 g), which was subsequently deprotected.

2) To a cooled and stirred solution of 3'-[4-(3,4-difluoro-phenyl)-6-trifluoromethyl-pyrimidin-2-yl]-biphenyl-3-sulfonic acid tert-butylamide (0.43 g) in dichloromethane (6 ml) was added TFA (6 ml) and the reaction mixture was allowed to stir at room temperature for 15 h. The mixture was evaporated to dryness, poured into 2N $NaHCO_3$ solution (20 ml) and extracted with ethyl acetate (3×50 ml). The combined organic layers were washed with brine (50 ml), dried ($MgSO_4$) and evaporated. Further purification by crystallization (ethyl acetate/heptane) yielded the title compound as a white solid (0.26 g, 53%). MS (ISP) 492.1 [$(M+H)^+$]; mp 211° C.

EXAMPLE 394

3'-[4-(4-Fluoro-phenyl)-6-trifluoromethyl-pyrimidin-2-yl]-biphenyl-3-sulfonic acid amide 1) 3'-[4-(4-fluoro-phenyl)-6-trifluoromethyl-pyrimidin-2-yl]-biphenyl-3-sulfonic acid tert-butylamide was prepared from 2-(3-bromo-phenyl)-4-(4-fluoro-phenyl)-6-trifluoromethyl-pyrimidine (example E.102) (0.40 g, 1.0 mmol) and commercially available 3-(tert.-butylsulfamoyl)-phenylboronic acid (0.31 g, 1.2 mmol) according to the general procedure VI. Obtained as white foam (0.49 g), which was subsequently deprotected.

2) To a cooled and stirred solution of 3'-[4-(4-fluoro-phenyl)-6-trifluoromethyl-pyrimidin-2-yl]-biphenyl-3-sulfonic acid tert-butylamide (0.49 g) in dichloromethane (6 ml) was added TFA (6 ml) and the reaction mixture was allowed to stir at room temperature for 15 h. The mixture was evaporated to dryness, poured into 2N $NaHCO_3$ solution (20 ml) and extracted with ethyl acetate (3×50 ml). The combined organic layers were washed with brine (50 ml), dried ($MgSO_4$) and evaporated. Further purification by crystallization (ethyl acetate/heptane) yielded the title compound as a white solid (0.37 g, 78%). MS (ISP) 474.0 [$(M+H)^+$]; mp 208° C.

EXAMPLE 395

5-{3-[4-(4-Fluoro-phenyl)-6-trifluoromethyl-pyrimidin-2-yl]-phenyl}-thiophene-2-sulfonic acid amide 1) N-tert-Butyl-5-{3-[6-(4-fluoro-phenyl)-4-trifluoromethyl-pyrimidin-2-yl]-phenyl}-thiophene-2-sulfonic acid amide was prepared from 2-(3-bromo-phenyl)-4-(4-fluoro-phenyl)-6-trifluoromethyl-pyrimidine (example E.102) (0.40 g, 1.0 mmol) and N-tert-butyl-5-(4,4,5,5-tetramethyl-1,3,2-dioxaborolan-2-yl)-thiophene-2-sulfonamide (example F.1) (0.414 g, 1.2 mmol) according to the general procedure VI. Obtained as an off-white foam (0.37 g), which was subsequently deprotected.

2) To a cooled and stirred solution of N-tert-butyl-5-{3-[6-(4-fluoro-phenyl)-4-trifluoromethyl-pyrimidin-2-yl]-phenyl}-thiophene-2-sulfonic acid amide (0.37 g) in dichloromethane (6 ml) was added TFA (6 ml) and the reaction mixture was allowed to stir at room temperature for 15 h. The mixture was evaporated to dryness, poured into 2N $NaHCO_3$ solution (25 ml) and extracted with ethyl acetate (3×50 ml). The combined organic layers were washed with brine (50 ml), dried ($MgSO_4$) and evaporated. Further purification by flash chromatography on silica gel (ethyl acetate/heptane) and crystallization (ethyl acetate/heptane) yielded the title compound as a light yellow solid (0.17 g, 35%). MS (ISP) 480.0 [$(M+H)^+$]; mp 228.5° C.

EXAMPLE 396

3-{1-[4-(3,4-Difluoro-phenyl)-6-trifluoromethyl-pyrimidin-2-yl]-1H-imidazol-4-yl}-benzenesulfonamide 1) N-tert-Butyl-3-{1-[6-(3,4-difluoro-phenyl)-4-trifluoromethyl-pyrimidin-2-yl]-1H-imidazol-4-yl}-benzenesulfonamide was prepared from 4-(3,4-difluoro-phenyl)-2-(4-iodo-imidazol-1-yl)-6-trifluoromethyl-pyrimidine (example E.78) (0.15 g, 0.33 mmol) and commercially available 3-(tert.-butylsulfamoyl)-phenylboronic acid (0.103 g, 0.4 mmol) according to the general procedure VI. Obtained as a light yellow solid (0.16 g) which was subsequently deprotected.

2) To a cooled and stirred solution of N-tert-butyl-3-{1-[6-(3,4-difluoro-phenyl)-4-trifluoromethyl-pyrimidin-2-yl]-1H-imidazol-4-yl}-benzenesulfonamide (0.16 g) in dichloromethane (4 ml) was added TFA (4 ml) and the reaction mixture was allowed to stir at room temperature for 15 h. The mixture was evaporated to dryness, poured into 2N $NaHCO_3$ solution (20 ml) and extracted with ethyl acetate (3×50 ml). The combined organic layers were washed with brine (50 ml), dried ($MgSO_4$) and evaporated. Further purification by flash chromatography on silica gel (dichloromethane/MeOH) and crystallization (ethyl acetate/heptane) yielded the title compound as a white solid (0.019 g, 12%). MS (ISP) 482.1 [$(M+H)^+$]; mp 241.5° C.

EXAMPLE 397

5-{4-[4-(4-Fluoro-phenyl)-6-trifluoromethyl-pyrimidin-2-yl]-pyridin-2-yl}-thiophene-2-sulfonic acid amide 1) 5-{4-[4-(4-fluoro-phenyl)-6-trifluoromethyl-pyrimidin-2-yl]-pyridin-2-yl}-thiophene-2-sulfonic acid tert-butyl amide was prepared from 2-(2-chloro-pyridin-4-yl)-4-(4-fluoro-phenyl)-6-trifluoromethyl-pyrimidine (example E.103) (0.24 g, 0.68 mmol) and N-tert-butyl-5-(4,4,5,5-tetramethyl-1,3,2-dioxaborolan-2-yl)-thiophene-2-sulfonamide (example F.1) (0.28 g, 0.81 mmol) according to the general procedure VI. Obtained as light brown solid (0.27 g), which was subsequently deprotected.

2) To a cooled and stirred solution of 5-{4-[4-(4-fluoro-phenyl)-6-trifluoromethyl-pyrimidin-2-yl]-pyridin-2-yl}-thiophene-2-sulfonic acid tert-butyl amide (0.27 g) in dichloromethane (4 ml) was added TFA (4 ml) and the reaction mixture was allowed to stir at room temperature for 15 h. The mixture was evaporated to dryness, poured into 2N $NaHCO_3$ solution (20 ml) and extracted with ethyl acetate (3×50 ml). The combined organic layers were washed with brine (50 ml), dried ($MgSO_4$) and evaporated. Further purification by crystallization (ethyl acetate/heptane) yielded the title compound as a white solid (0.16 g, 49%). MS (ISP) 480.9 [$(M+H)^+$]; mp 282° C.

EXAMPLE 398

3-{4-[4-(4-Fluoro-phenyl)-6-trifluoromethyl-pyrimidin-2-yl]-pyridin-2-yl}-benzenesulfonamide 1) 3-{4-[4-(4-Fluoro-phenyl)-6-trifluoromethyl-pyrimidin-2-yl]-pyridin-2-yl}-benzenesulfonic acid tert-butylamide was prepared from 2-(2-chloro-pyridin-4-yl)-4-(4-fluorophenyl)-6-trifluoromethyl-pyrimidine (example E.103) (0.24 g, 0.68 mmol) and commercially available 3-(tert.-butylsulfamoyl)-phenylboronic acid (0.21 g, 0.82 mmol) according to the general procedure VI. Obtained as a light brown solid (0.38 g), which was subsequently deprotected.

2) To a cooled and stirred solution of 3-{4-[4-(4-fluoro-phenyl)-6-trifluoromethyl-pyrimidin-2-yl]-pyridin-2-yl}-benzenesulfonic acid tert-butylamide (0.38 g) in dichloromethane (5 ml) was added TFA (5 ml) and the reaction mixture was allowed to stir at room temperature for 15 h. The mixture was evaporated to dryness, poured into 2N $NaHCO_3$ solution (20 ml) and extracted with ethyl acetate (3×50 ml). The combined organic layers were washed with brine (50 ml), dried ($MgSO_4$) and evaporated. Further purification by crystallization (ethyl acetate/heptane) yielded the title compound as a white solid (0.25 g, 78%). MS (ISP) 475.0 [$(M+H)^+$]; mp 239.5° C.

EXAMPLE 399

5-{4-[4-(3,4-Difluoro-phenyl)-6-trifluoromethyl-pyrimidin-2-yl]-pyridin-2-yl}-thiophene-2-sulfonic acid amide 1) 5-{4-[4-(3,4-Difluoro-phenyl)-6-trifluoromethyl-pyrimidin-2-yl]-pyridin-2-yl}-thiophene-2-sulfonic acid tert-butyl amide was prepared from 2-(2-chloro-pyridin-4-yl)-4-(3,4-difluoro-phenyl)-6-trifluoromethyl-pyrimidine (example E.104) (0.25 g, 0.67 mmol) and N-tert-butyl-5-(4,4,5,5-tetramethyl-1,3,2-dioxaborolan-2-yl)-thiophene-2-sulfonamide (example F.1) (0.28 g, 0.81 mmol) according to the general procedure VI. Obtained as light yellow solid (0.29 g), which was subsequently deprotected.

2) To a cooled and stirred solution of 5-{4-[4-(3,4-difluoro-phenyl)-6-trifluoromethyl-pyrimidin-2-yl]-pyridin-2-yl}-thiophene-2-sulfonic acid tert-butyl amide (0.29 g) in dichloromethane (4 ml) was added TFA (4 ml) and the reaction mixture was allowed to stir at room temperature for 15 h. The mixture was evaporated to dryness, poured into 2N $NaHCO_3$ solution (20 ml) and extracted with ethyl acetate (3×50 ml). The combined organic layers were washed with brine (50 ml), dried ($MgSO_4$) and evaporated. Further purification crystallization (ethyl acetate/heptane) yielded the title compound as a white solid (0.08 g, 24%). MS (ISP) 499.1 [$(M+H)^+$]; mp 281° C.

EXAMPLE 400

3-{4-[4-(3,4-Difluoro-phenyl)-6-trifluoromethyl-pyrimidin-2-yl]-pyridin-2-yl}-benzenesulfonamide 1) 3-{4-[4-(3,4-Difluoro-phenyl)-6-trifluoromethyl-pyrimidin-2-yl]-pyridin-2-yl}-benzenesulfonic acid tert-butylamide was prepared from 2-(2-chloro-pyridin-4-yl)-4-(3,4-difluoro-phenyl)-6-trifluoromethyl-pyrimidine (example E.104) (0.25 g, 0.67 mmol) and commercially available 3-(tert.-butylsulfamoyl)-phenylboronic acid (0.21 g, 0.82 mmol) according to the general procedure VI. Obtained as a light yellow solid (0.25 g), which was subsequently deprotected.

2) To a cooled and stirred solution of 3-{4-[4-(3,4-difluoro-phenyl)-6-trifluoromethyl-pyrimidin-2-yl]-pyridin-2-yl}-benzenesulfonic acid tert-butylamide (0.25 g) in dichloromethane (4 ml) was added TFA (4 ml) and the reaction mixture was allowed to stir at room temperature for 15 h. The mixture was evaporated to dryness, poured into 2N $NaHCO_3$ solution (20 ml) and extracted with ethyl acetate (3×50 ml). The combined organic layers were washed with brine (50 ml), dried ($MgSO_4$) and evaporated. Further purification by crystallization (ethyl acetate/heptane) yielded the title compound as a white solid (0.16 g, 48%). MS (ISP) 492.9 [$(M+H)^+$]; mp 233.5° C.

EXAMPLE 401

N,N-Dimethyl-3-{4-[4-trifluoromethyl-6-(4-trifluoromethyl-phenyl)-pyrimidin-2-yl]-pyridin-2-yl}-benzenesulfonamide To a cooled (ice-water bath) and stirred mixture of dimethylamine solution (60% in water) (0.27 ml, 3.21 mmol), triethylamine (0.29 ml, 2.1 mmol) and THF (4 ml) was added drop wise a solution of 3-{4-[4-trifluoromethyl-6-(4-trifluoromethyl-phenyl)-pyrimidin-2-yl]-pyridin-2-yl}-benzenesulfonyl chloride hydrochloride (example I.1) (0.58 g, 1.0 mmol) in THF (6 ml). The mixture was allowed to stir at room temperature for 16 h. Purification of the reaction mixture by flash chromatography on silica gel (ethyl acetate/heptane) and crystallization (dichloromethane/MeOH/hexane) yielded the title compound as a white solid (0.5 g, 97%). MS (ISP) 552.7 [$(M+H)^+$]; mp 225° C.

EXAMPLE 402

N-Methyl-3-{4-[4-trifluoromethyl-6-(4-trifluoromethyl-phenyl)-pyrimidin-2-yl]-pyridin-2-yl}-benzenesulfonamide To a cooled (ice-water bath) and stirred mixture of methylamine solution (2M in THF) (1.5 ml, 3.0 mmol), triethylamine (0.29 ml, 2.1 mmol) and THF (4 ml) was added drop wise a solution of 3-{4-[4-trifluoromethyl-6-(4-trifluoromethyl-phenyl)-pyrimidin-2-yl]-pyridin-2-yl}-benzenesulfonyl chloride hydrochloride (example 1.1) (0.58 g, 1.0 mmol) in THF (6 ml). The mixture was allowed to stir at room temperature for 16 h. Purification of the reaction mixture by flash chromatography on silica gel (ethyl acetate/heptane) and crystallization (dichloromethane/MeOH/hexane) yielded the title compound as a white solid (0.46 g, 92%). MS (ISP) 538.8 [$(M+H)^+$]; mp 174° C.

EXAMPLE 403

N-Isobutyl-N-methyl-3-{4-[4-trifluoromethyl-6-(4-trifluoromethyl-phenyl)-pyrimidin-2-yl]-pyridin-2-yl}-benzenesulfonamide To a cooled (ice-water bath) and stirred mixture of N-methylisobutylamine (0.26 g, 3.0 mmol), triethylamine (0.29 ml, 2.1 mmol) and THF (4 ml) was added drop wise a solution of 3-{4-[4-trifluoromethyl-6-(4-trifluoromethyl-phenyl)-pyrimidin-2-yl]-pyridin-2-yl}-benzenesulfonyl chloride hydrochloride (example I.1) (0.58 g, 1.0 mmol) in THF (6 ml). The mixture was allowed to stir at room temperature for 16 h. Purification of the reaction mixture by flash chromatography on silica gel (ethyl acetate/heptane) and crystallization (dichloromethane/MeOH/hexane) yielded the title compound as a white solid (0.45 g, 80%). MS (ISP) 594.7 [$(M+H)^+$]; mp 144° C.

EXAMPLE 404

N-Methyl-N-propyl-3-{4-[4-trifluoromethyl-6-(4-trifluoromethyl-phenyl)-pyrimidin-2-yl]-pyridin-2-yl}-benzenesulfonamide To a cooled (ice-water bath) and stirred mixture of N-methylpropylamine (0.23 g, 3.0 mmol), triethylamine (0.29 ml, 2.1 mmol) and THF (4 ml) was added drop wise a solution of 3-{4-[4-trifluoromethyl-6-(4-trifluoromethyl-phenyl)-pyrimidin-2-yl]-pyridin-2-yl}-benzenesulfonyl chloride hydrochloride (example I.1) (0.58 g, 1.0 mmol) in THF (6 ml). The mixture was allowed to stir at room temperature for 16 h. Purification of the reaction mixture by flash chromatography on silica gel (ethyl acetate/heptane) and crystallization (dichloromethane/MeOH/hexane) yielded the title compound as a white solid (0.47 g, 86%). MS (ISP) 580.6 [$(M+H)^+$]; mp 144° C.

EXAMPLE 405

N-Benzyl-3-{4-[4-trifluoromethyl-6-(4-trifluoromethyl-phenyl)-pyrimidin-2-yl]-pyridin-2-yl}-benzenesulfonamide To a cooled (ice-water bath) and stirred mixture of benzylamine (0.32 g, 3.0 mmol), triethylamine (0.29 ml, 2.1 mmol) and THF (4 ml) was added drop wise a solution of 3-{4-[4-trifluoromethyl-6-(4-trifluoromethyl-phenyl)-pyrimidin-2-yl]-pyridin-2-yl}-benzenesulfonyl chloride hydrochloride (example I.1) (0.58 g, 1.0 mmol) in THF (6 ml). The mixture was allowed to stir at room temperature for 16 h. Purification of the reaction mixture by flash chromatography on silica gel (ethyl acetate/heptane) and crystallization (dichloromethane/MeOH/hexane) yielded the title compound as a white solid (0.49 g, 85%). MS (ISP) 614.8 [$(M+H)^+$]; mp 202.5° C.

EXAMPLE 406

N-Phenethyl-3-{4-[4-trifluoromethyl-6-(4-trifluoromethyl-phenyl)-pyrimidin-2-yl]-pyridin-2-yl}-benzenesulfonamide To a cooled (ice-water bath) and stirred mixture of phenethylamine (0.36 g, 3.0 mmol), triethylamine (0.29 ml, 2.1 mmol) and THF (4 ml) was added drop wise a solution of 3-{4-[4-trifluoromethyl-6-(4-trifluoromethyl-phenyl)-pyrimidin-2-yl]-pyridin-2-yl}-benzenesulfonyl chloride hydrochloride (example I.1) (0.58 g, 1.0 mmol) in THF (6 ml). The mixture was allowed to stir at room temperature for 16 h. Purification of the reaction mixture by flash chromatography on silica gel (ethyl acetate/heptane) and crystallization (dichloromethane/MeOH/hexane) yielded the title compound as a white solid (0.57 g, 97%). MS (ISP) 628.8 [$(M+H)^+$]; mp 201° C.

EXAMPLE 407

(RS)-1-(3-{4-[4-Trifluoromethyl-6-(4-trifluoromethyl-phenyl)-pyrimidin-2-yl]-pyridin-2-yl}-benzenesulfonyl)-pyrrolidin-3-ol To a cooled (ice-water bath) and stirred mixture of (RS)-3-pyrrolidinol (0.27 g, 3.0 mmol), triethylamine (0.29 ml, 2.1 mmol) and THF (4 ml) was added drop wise a solution of 3-{4-[4-trifluoromethyl-6-(4-trifluoromethyl-phenyl)-pyrimidin-2-yl]-pyridin-2-yl}-benzenesulfonyl chloride hydrochloride (example I.1) (0.58 g, 1.0 mmol) in THF (6 ml). The mixture was allowed to stir at room temperature for 16 h. Purification of the reaction mixture by flash chromatography on silica gel (ethyl acetate/heptane) and crystallization (dichloromethane/MeOH/hexane) yielded the title compound as a white solid (0.49 g, 88%). MS (ISP) 594.6 [$(M+H)^+$]; mp 234° C.

EXAMPLE 408

N-Cyclopropylmethyl-3-{4-[4-trifluoromethyl-6-(4-trifluoromethyl-phenyl)-pyrimidin-2-yl]-pyridin-2-yl}-benzenesulfonamide To a cooled (ice-water bath) and stirred mixture of cyclopropylmethylamine (0.21 g, 2.96 mmol), triethylamine (0.28 ml, 2.0 mmol) and THF (4 ml) was added drop wise a solution of 3-{4-[4-trifluoromethyl-6-(4-trifluoromethyl-phenyl)-pyrimidin-2-yl]-pyridin-2-yl}-benzenesulfonyl chloride hydrochloride (example I.1) (0.56 g, 0.96 mmol) in THF (6 ml). The mixture was allowed to stir at room temperature for 16 h. Purification of the reaction mixture by flash chromatography on silica gel (ethyl acetate/heptane) and crystallization (dichloromethane/MeOH/hexane) yielded the title compound as a white solid (0.51 g, 97%). MS (ISP) 578.6 [$(M+H)^+$]; mp 133.5° C.

EXAMPLE 409

N-Cyclopropyl-3-{4-[4-trifluoromethyl-6-(4-trifluoromethyl-phenyl)-pyrimidin-2-yl]-pyridin-2-yl}-benzenesulfonamide To a cooled (ice-water bath) and stirred mixture of phenethylamine (0.165 g, 3.0 mmol), triethylamine (0.28 ml, 2.0 mmol) and THF (4 ml) was added drop wise a solution of 3-{4-[4-trifluoromethyl-6-(4-trifluoromethyl-phenyl)-pyrimidin-2-yl]-pyridin-2-yl}-benzenesulfonyl chloride hydrochloride (example I.1) (0.56 g, 0.96 mmol) in THF (6 ml). The mixture was allowed to stir at room temperature for 16 h. Purification of the reaction mixture by flash chromatography on silica gel (ethyl acetate/heptane) and crystallization (dichloromethane/MeOH/hexane) yielded the title compound as a white solid (0.49 g, 96%). MS (ISP) 564.7 [$(M+H)^+$]; mp 195.5° C.

EXAMPLE 410

3'-[4-(2,4-Dichloro-phenyl)-6-trifluoromethyl-pyrimidin-2-yl]-biphenyl-3-sulfonic acid amide 1) 3'-[4-(2,4-dichloro-phenyl)-6-trifluoromethyl-pyrimidin-2-yl]-biphenyl-3-sulfonic acid tert-butylamide was prepared from 2-(3-bromo-phenyl)-4-(2,4-dichloro-phenyl)-6-trifluoromethyl-pyrimidine (example E.106) (0.45 g, 1.0 mmol) and commercially available 3-(tert.-butylsulfamoyl)-phenylboronic acid (0.31 g, 1.2 mmol) according to the general procedure VI. Obtained as an off-white solid (0.36 g), which was subsequently deprotected.

2) To a cooled and stirred solution of 3'-[4-(2,4-dichloro-phenyl)-6-trifluoromethyl-pyrimidin-2-yl]-biphenyl-3-sulfonic acid tert-butylamide (0.36 g) in dichloromethane (6 ml) was added TFA (6 ml) and the reaction mixture was allowed to stir at room temperature for 15 h. The mixture was evaporated to dryness, poured into 2N $Na_2CO_3$ solution (20 ml) and extracted with ethyl acetate (3×50 ml). The combined organic layers were washed with brine (50 ml), dried ($MgSO_4$) and evaporated. Further purification by crystallization (ethyl acetate/heptane) yielded the title compound as a white solid (0.25 g, 48%). MS (ISP) 524.2 [$(M+H)^+$]; mp 202° C.

EXAMPLE 411

5-{3-[4-(2,4-Dichloro-phenyl)-6-trifluoromethyl-pyrimidin-2-yl]-phenyl}-thiophene-2-sulfonic acid amide 1) N-tert-Butyl-5-{3-[6-(2,4-dichloro-phenyl)-4-trifluoromethyl-pyrimidin-2-yl]-phenyl}-thiophene-2-sulfonic acid amide was prepared from 2-(3-bromo-phenyl)-4-(2,4-dichloro-phenyl)-6-trifluoromethyl-pyrimidine (example E.106) (0.45 g, 1.0 mmol) and N-tert-butyl-5-(4,4,5,5-tetramethyl-1,3,2-dioxaborolan-2-yl)-thiophene-2-sulfonamide (example F.1) (0.414 g, 1.2 mmol) according to the general procedure VI. Obtained as an off-white solid (0.4 g), which was subsequently deprotected.

2) To a cooled and stirred solution of N-tert-butyl-5-{3-[6-(2,4-dichloro-phenyl)-4-trifluoromethyl-pyrimidin-2-yl]-phenyl}-thiophene-2-sulfonic acid amide (0.4 g) in dichloromethane (6 ml) was added TFA (6 ml) and the reaction mixture was allowed to stir at room temperature for 15 h. The mixture was evaporated to dryness, poured into 2N $Na_2CO_3$ solution (25 ml) and extracted with ethyl acetate (3×50 ml). The combined organic layers were washed with brine (50 ml), dried ($MgSO_4$) and evaporated. Further purification by flash chromatography on silica gel (ethyl acetate/heptane) and crystallization (ethyl acetate/heptane) yielded the title compound as an off-white solid (0.13 g, 25%). MS (ISP) 530.0 [$(M+H)^+$]; mp 237.5° C.

EXAMPLE 412

3'-[4-(2-Fluoro-4-trifluoromethyl-phenyl)-6-trifluoromethyl-pyrimidin-2-yl]-biphenyl-3-sulfonic acid amide 1) 3'-[4-(2-fluoro-4-trifluoromethyl-phenyl)-6-trifluoromethyl-pyrimidin-2-yl]-biphenyl-3-sulfonic acid tert-butylamide was prepared from 2-(3-bromo-phenyl)-4-(2-fluoro-4-trifluoromethyl-phenyl)-6-trifluoromethyl-pyrimidine (example E.105) (0.465 g, 1.0 mmol) and commercially available 3-(tert.-butylsulfamoyl)-phenylboronic acid (0.31 g, 1.2 mmol) according to the general procedure VI. Obtained as light yellow foam (0.54 g), which was subsequently deprotected.

2) To a cooled and stirred solution of 3'-[4-(2-fluoro-4-trifluoromethyl-phenyl)-6-trifluoromethyl-pyrimidin-2-yl]-biphenyl-3-sulfonic acid tert-butylamide (0.54 g) in dichloromethane (6 ml) was added TFA (6 ml) and the reaction mixture was allowed to stir at room temperature for 15 h. The mixture was evaporated to dryness, poured into 2N $Na_2CO_3$ solution (25 ml) and extracted with ethyl acetate (3×50 ml). The combined organic layers were washed with brine (50 ml), dried ($MgSO_4$) and evaporated. Further purification by crystallization (ethyl acetate/heptane) yielded the title compound as a white solid (0.39 g, 72%). MS (ISP) 542.1 [$(M+H)^+$]; mp 224.5° C.

EXAMPLE 413

5-{3-[4-(2-Fluoro-4-trifluoromethyl-phenyl)-6-trifluoromethyl-pyrimidin-2-yl]-phenyl}-thiophene-2-sulfonic acid amide 1) N-tert-Butyl-5-{3-[6-(2-fluoro-4-trifluoromethyl-phenyl)-4-trifluoromethyl-pyrimidin-2-yl]-phenyl}-thiophene-2-sulfonic acid amide was prepared from 2-(3-bromophenyl)-4-(2-fluoro-4-trifluoromethyl-phenyl)-6-trifluoromethyl-pyrimidine (example E.105) (0.465 g, 1.0 mmol) and N-tert-butyl-5-(4,4,5,5-tetramethyl-1,3,2-dioxaborolan-2-yl)thiophene-2-sulfonamide (example F.1) (0.414 g, 1.2 mmol) according to the general procedure VI. Obtained as an off-white solid (0.43 g), which was subsequently deprotected.

2) To a cooled and stirred solution of N-tert-butyl-5-{3-[6-(2-fluoro-4-trifluoromethylphenyl)-4-trifluoromethyl-pyrimidin-2-yl]-phenyl}-thiophene-2-sulfonic acid amide (0.43 g) in dichloromethane (6 ml) was added TFA (6 ml) and the reaction mixture was allowed to stir at room temperature for 15 h. The mixture was evaporated to dryness, poured into 2N $Na_2CO_3$ solution (25 ml) and extracted with ethyl acetate (3×50 ml). The combined organic layers were washed with brine (50 ml), dried ($MgSO_4$) and evaporated. Further purification by crystallization (ethyl acetate/heptane) yielded the title compound as an off-white solid (0.23 g, 42%). MS (ISP) 548.1 [$(M+H)^+$]; mp 192° C.

EXAMPLE 414

5-{4-[4-(4-Chloro-3-methyl-phenyl)-6-trifluoromethyl-pyrimidin-2-yl]-pyridin-2-yl}-thiophene-2-sulfonic acid amide 1) 5-{4-[4-(4-Chloro-3-methyl-phenyl)-6-trifluoromethyl-pyrimidin-2-yl]-pyridin-2-yl}-thiophene-2-sulfonic acid tert-butyl amide was prepared from 4-(4-chloro-3-methylphenyl)-2-(2-chloro-pyridin-4-yl)-6-trifluoromethyl-pyrimidine (example E.43) (0.14 g, 0.36 mmol) and N-tert-butyl-5-(4,4,5,5-tetramethyl-1,3,2-dioxaborolan-2-yl)-thiophene-2-sulfonamide (example F.1) (0.15 g, 0.43 mmol) according to the general procedure VI. Obtained as a light brown solid (0.14 g), which was subsequently deprotected.

2) To a cooled and stirred solution of 5-{4-[4-(4-chloro-3-methyl-phenyl)-6-trifluoromethyl-pyrimidin-2-yl]-pyridin-2-yl}-thiophene-2-sulfonic acid tert-butyl amide (0.14 g) in dichloromethane (4 ml) was added TFA (4 ml) and the reaction mixture was allowed to stir at room temperature for 15 h. The mixture was evaporated to dryness, poured into 2N $Na_2CO_3$ solution (25 ml) and extracted with ethyl acetate (3×50 ml). The combined organic layers were washed with brine (50 ml), dried ($MgSO_4$) and evaporated. Further purification by crystallization (ethyl acetate/heptane) yielded the title compound as a white solid (0.048 g, 26%). MS (ISP) 511.1 [$(M+H)^+$]; mp 280° C.

EXAMPLE 415

3-{4-[4-(4-Chloro-3-methyl-phenyl)-6-trifluoromethyl-pyrimidin-2-yl]-pyridin-2-yl}-benzenesulfonamide 1) 3-{4-[4-(4-Chloro-3-methyl-phenyl)-6-trifluoromethyl-pyrimidin-2-yl]-pyridin-2-yl}-benzenesulfonic acid tert-butylamide was prepared from 2-(2-chloro-pyridin-4-yl)-4-(4-chloro-3-methyl-phenyl)-6-trifluoromethyl-pyrimidine (example E.43) (0.14 g, 0.36 mmol) and commercially available 3-(tert.-butylsulfamoyl)-phenylboronic acid (0.11 g, 0.43 mmol) according to the general procedure VI. Obtained as light brown solid (0.17 g), which was subsequently deprotected.

2) To a cooled and stirred solution of 3-{4-[4-(4-chloro-3-methyl-phenyl)-6-trifluoromethyl-pyrimidin-2-yl]-pyridin-2-yl}-benzenesulfonic acid tert-butylamide (0.17 g) in dichloromethane (4 ml) was added TFA (4 ml) and the reaction mixture was allowed to stir at room temperature for 15 h. The mixture was evaporated to dryness, poured into 2N $Na_2CO_3$ solution (25 ml) and extracted with ethyl acetate (3×50 ml). The combined organic layers were washed with brine (50 ml), dried ($MgSO_4$) and evaporated. Further purification by crystallization (ethyl acetate/heptane) yielded the title compound as an off-white solid (0.1 g, 55%). MS (ISP) 505.1, 507.1 [$(M+H)^+$]; mp 234° C.

EXAMPLE 416

3'-[4-Methyl-6-(3-methyl-4-trifluoromethyl-phenyl)-pyrimidin-2-yl]-biphenyl-3-sulfonic acid amide 1) 3'-[4-Methyl-6-(3-methyl-4-trifluoromethyl-phenyl)-pyrimidin-2-yl]-biphenyl-3-sulfonic acid tert-butylamide was prepared from 2-(3-bromo-phenyl)-4-(4-trifluoromethylphenyl)-6-methyl-pyrimidine (example E.53) (0.21 g, 0.52 mmol) and commercially available 3-(tert.-butylsulfamoyl)-phenylboronic acid (0.16 g, 0.62 mmol) according to the general procedure VI. Obtained as a light yellow solid (0.21 g), which was subsequently deprotected.

2) To a cooled and stirred solution of 3'-[4-methyl-6-(3-methyl-4-trifluoromethylphenyl)-pyrimidin-2-yl]-biphenyl-3-sulfonic acid tert-butylamide (0.21 g) in dichloromethane (4 ml) was added TFA (4 ml) and the reaction mixture was allowed to stir at room temperature for 15 h. The mixture was evaporated to dryness, poured into 2N $Na_2CO_3$ solution (20 ml) and extracted with ethyl acetate (3×50 ml). The combined organic layers were washed with brine (50 ml), dried ($MgSO_4$) and evaporated. Further purification by crystallization (ethyl acetate/heptane) yielded the title compound as a white solid (0.17 g, 68%). MS (ISP) 484.2 [$(M+H)^+$]; mp 222.5° C.

EXAMPLE 417

5-{3-[4-Methyl-6-(3-methyl-4-trifluoromethyl-phenyl)-pyrimidin-2-yl]-phenyl}-thiophene-2-sulfonic acid amide 1) N-tert-Butyl-5-{3-[4-methyl-6-(3-methyl-4-trifluoromethyl-phenyl)-pyrimidin-2-yl]-phenyl}-thiophene-2-sulfonic acid amide was prepared from 2-(3-bromo-phenyl)-6-methyl-4-(3-methyl-4-trifluoromethyl-phenyl)-pyrimidine (example E.53) (0.21 g, 0.52 mmol) and N-tert-butyl-5-(4,4,5,5-tetramethyl-1,3,2-dioxaborolan-2-yl)-thiophene-2-sulfonamide (example F.1) (0.21 g, 0.62 mmol) according to the general procedure VI. Obtained as a light yellow solid (0.15 g), which was subsequently deprotected.

2) To a cooled and stirred solution of N-tert-butyl-5-{3-[4-methyl-6-(3-methyl-4-trifluoromethyl-phenyl)-pyrimidin-2-yl]-phenyl}-thiophene-2-sulfonic acid amide (0.15 g) in dichloromethane (3 ml) was added TFA (3 ml) and the reaction mixture was allowed to stir at room temperature for 15 h. The mixture was evaporated to dryness, poured into 2N $Na_2CO_3$ solution (25 ml) and extracted with ethyl acetate (3×50 ml). The combined organic layers were washed with brine (50 ml), dried ($MgSO_4$) and evaporated. Further purification by crystallization (ethyl acetate/heptane) yielded the title compound as a light brown solid (0.064 g, 25%). MS (ISP) 490.1 [$(M+H)^+$]; mp 242° C.

EXAMPLE 418

N-tert-Butyl-3-{6-[4-methyl-6-(4-trifluoromethyl-phenyl)-pyrimidin-2-yl]-pyridin-2-yl}-benzenesulfonamide A stirred mixture of trifluoro-methanesulfonic acid 4-methyl-6-(4-trifluoromethylphenyl)-pyrimidin-2-yl ester (Example A.62) (0.418 g, 1.08 mmol), N-tert-butyl-3-(6-tributylstannanyl-pyridin-2-yl)-benzenesulfonamide (Example F.6) (0.570 g, 0.98 mmol), tetrakis(triphenyl-phosphine)palladium (0.057 g, 5 mol %) in toluene (5 mL) was heated under reflux conditions for 18 h. Cooled to rt, extracted with ethyl acetate and water, dried the organic layer over Na2SO4. Removal of the solvent in vacuum left a crude product which was purified by silica gel column chromatography with n-heptane/ethyl acetate to give the title compound after trituration with diethyl ether as a white solid (260 mg, 50%). MS (ISP) 527.3 [$(M+H)^+$]; mp>250° C.

EXAMPLE 419

3-{6-[4-Methyl-6-(4-trifluoromethyl-phenyl)-pyrimidin-2-yl]-pyridin-2-yl}-benzenesulfonamide To N-tert-butyl-3-{6-[4-methyl-6-(4-trifluoromethyl-phenyl)-pyrimidin-2-yl]-pyridin-2-yl}-benzenesulfonamide (Example 418) (0.250 g, 0.475 mmol) was added TFA (3 mL) and the reaction mixture was stirred at 23° C. for 3 h. The mixture was partitioned between EtOAc and saturated $NaHCO_3$ solution, the organic layer was dried over $MgSO_4$. Removal of the solvent in vacuum left a crude product which was triturated with diethyl ether to give the title compound as a white solid (0.223 g, 100%). MS (ISP) 471.2 [$(M+H)^+$]; mp 239° C. (dec.).

EXAMPLE 420

N-[2-(2-Methoxy-ethoxy)-ethyl]-3-[6'-methyl-4'-(4-trifluoromethyl-phenyl)-[2,2']bipyridinyl-6-yl]-benzenesulfonamide The title compound was prepared from 3-[6'-methyl-4'-(4-trifluoromethyl-phenyl)-[2,2']bipyridinyl-6-yl]-benzenesulfonyl chloride (example I.2) (0.200 g, 0.409 mmol) by treatment with commercially available 2-(2-methoxy-ethoxy)-ethylamine [CAS-no. 31576-51-9] (0.244 mg, 2.04 mmol) in THF (5 mL) at 23° C. for 16 h. Diluted with EtOAc, washed with 5% citric acid, sat. $NaHCO_3$-sol. and brine, dried organic layer over $Na_2SO_4$. Removal of the solvent in vacuum left a crude product, which was purified by silica gel column chromatography with EtOAc followed by trituration with diethyl ether/heptane to give the title compound (0.160 g, 68%) as a light yellow oil. MS (ISP) 572.2 [$(M+H)^+$].

EXAMPLE 421

N-{2-[2-(2-Methoxy-ethoxy)-ethoxy]-ethyl}-3-[6'-methyl-4'-(4-trifluoromethyl-phenyl)-[2,2']bipyridinyl-6-yl]-benzenesulfonamide The title compound was prepared from 3-[6'-methyl-4'-(4-trifluoromethyl-phenyl)-[2,2']bipyridinyl-6-yl]-benzenesulfonyl chloride (example I.2) (0.200 g, 0.409 mmol) by treatment with 2-[2-(2-methoxy-ethoxy)-ethoxy]-ethylamine [CAS-no. 74654-07-2] (0.334 mg, 2.04 mmol) in THF (5 mL) at 23° C. for 16 h. Diluted with EtOAc, washed with 5% citric acid, sat. $NaHCO_3$-sol. and brine, dried organic layer over $Na_2SO_4$. Removal of the solvent in vacuum left a crude product, which was purified by silica gel column chromatography with EtOAc followed by trituration with diethyl ether/heptane to give the title compound (0.180 g, 71%) as a light yellow oil. MS (ISP) 616.2 [$(M+H)^+$].

EXAMPLE 422

N-Methyl-3-[6'-methyl-4'-(4-trifluoromethyl-phenyl)-[2,2']bipyridinyl-6-yl]-benzenesulfonamide The title compound was prepared from 3-[6'-methyl-4'-(4-trifluoromethyl-phenyl)-[2,2']bipyridinyl-6-yl]-benzenesulfonyl chloride (example I.2) (0.200 g, 0.409 mmol) by treatment with commercially available methylamine (2 M in THF, 2.05 ml, 4.1 mmol) in THF (5 mL) at 23° C. for 16 h. Diluted with EtOAc, washed with 5% citric acid, sat. $NaHCO_3$-sol. and brine, dried organic layer over $Na_2SO_4$. Removal of the solvent in vacuum left a crude product, which was purified by silica gel column chromatography with EtOAc followed by trituration with diethyl ether/heptane to give the title compound (0.130 g, 65%) as a white solid. MS (ISP) 484.2 [(M+H)$^+$]; mp 176° C.

EXAMPLE 423

N,N-Dimethyl-3-[6'-methyl-4'-(4-trifluoromethyl-phenyl)-[2,2']bipyridinyl-6-yl]-benzenesulfonamide The title compound was prepared from 3-[6'-methyl-4'-(4-trifluoromethyl-phenyl)-[2,2']bipyridinyl-6-yl]-benzene-sulfonyl chloride (example I.2) (0.200 g, 0.409 mmol) by treatment with commercially available dimethylamine (40% in water, 0.52 ml, 4.1 mmol) in THF (5 mL) at 23° C. for 16 h. Diluted with EtOAc, washed with 5% citric acid, sat. $NaHCO_3$-sol. and brine, dried organic layer over $Na_2SO_4$. Removal of the solvent in vacuum left a crude product, which was purified by silica gel column chromatography with EtOAc followed by trituration with diethyl ether/heptane to give the title compound (0.110 g, 54%) as a white foam. MS (ISP) 498.3 [(M+H)$^+$]; mp 155° C.

EXAMPLE 424

N-Cyclopropyl-3-[6'-methyl-4'-(4-trifluoromethyl-phenyl)-[2,2']bipyridinyl-6-yl]-benzenesulfonamide The title compound was prepared from 3-[6'-methyl-4'-(4-trifluoromethyl-phenyl)-[2,2']bipyridinyl-6-yl]-benzene-sulfonyl chloride (example I.2) (0.200 g, 0.409 mmol) by treatment with commercially available cyclopropylamine (0.14 ml, 2.05 mmol) in THF (5 mL) at 23° C. for 16 h. Diluted with EtOAc, washed with 5% citric acid, sat. $NaHCO_3$-sol. and brine, dried organic layer over $Na_2SO_4$. Removal of the solvent in vacuum left a crude product, which was purified by silica gel column chromatography with EtOAc followed by trituration with diethyl ether/heptane to give the title compound (0.090 g, 43%) as a white solid. MS (ISP) 510.2 [(M+H)$^+$]; mp 150° C.

EXAMPLE 425

N-Cyclopropyl-N-methyl-3-[6'-methyl-4'-(4-trifluoromethyl-phenyl)-[2,2']bipyridinyl-6-yl]-benzene-sulfonamide The title compound was prepared from 3-[6'-methyl-4'-(4-trifluoromethyl-phenyl)-[2,2']bipyridinyl-6-yl]-benzene-sulfonyl chloride (example I.2) (0.200 g, 0.409 mmol) by treatment with commercially available N-cyclopropyl-N-methylamine [CAS-no. 5163-20-2] (0.16 ml, 2.05 mmol) in THF (5 mL) at 23° C. for 16 h. Diluted with EtOAc, washed with 5% citric acid, sat. $NaHCO_3$-sol. and brine, dried organic layer over $Na_2SO_4$. Removal of the solvent in vacuum left a crude product, which was purified by silica gel column chromatography with EtOAc followed by trituration with diethyl ether/heptane to give the title compound (0.110 g, 51%) as a white solid. MS (ISP) 524.3 [(M+H)$^+$]; mp 157° C.

EXAMPLE 426

6'-[3-(Azetidine-1-sulfonyl)-phenyl]-6-methyl-4-(4-trifluoromethyl-phenyl)-[2,2']bipyridinyl The title compound was prepared from 3-[6'-methyl-4'-(4-trifluoromethyl-phenyl)-[2,2']bipyridinyl-6-yl]-benzene-sulfonyl chloride (example I.2) (0.200 g, 0.409 mmol) by treatment with commercially available azetidine [CAS-no. 503-29-7] (0.14 ml, 2.05 mmol) in THF (5 mL) at 23° C. for 16 h. Diluted with EtOAc, washed with 5% citric acid, sat. $NaHCO_3$-sol. and brine, dried organic layer over $Na_2SO_4$. Removal of the solvent in vacuum left a crude product, which was purified by silica gel column chromatography with EtOAc followed by trituration with diethyl ether/heptane to give the title compound (0.110 g, 53%) as a white solid. MS (ISP) 510.2 [(M+H)$^+$]; mp 158° C.

EXAMPLE 427

1-{3-[6'-Methyl-4'-(4-trifluoromethyl-phenyl)-[2,2']bipyridinyl-6-yl]-benzenesulfonyl}-piperidin-4-ol The title compound was prepared from 3-[6'-methyl-4'-(4-trifluoromethyl-phenyl)-[2,2']bipyridinyl-6-yl]-benzene-sulfonyl chloride (example I.2) (0.200 g, 0.409 mmol) by treatment with commercially available 4-hydroxypiperidine [CAS-no. 5382-16-1] (0.207 g, 2.05 mmol) in THF (5 mL) at 23° C. for 16 h. Diluted with EtOAc, washed with 5% citric acid, sat. $NaHCO_3$-sol. and brine, dried organic layer over $Na_2SO_4$. Removal of the solvent in vacuum left a crude product, which was purified by silica gel column chromatography with EtOAc followed by trituration with diethyl ether/heptane to give the title compound (0.130 g, 57%) as a white solid. MS (ISP) 554.3 [(M+H)$^+$]; mp 195° C.

EXAMPLE 428

1-{3-[6'-Methyl-4'-(4-trifluoromethyl-phenyl)-[2,2']bipyridinyl-6-yl]-benzenesulfonyl}-azetidin-3-ol The title compound was prepared from 3-[6'-methyl-4'-(4-trifluoromethyl-phenyl)-[2,2']bipyridinyl-6-yl]-benzene-sulfonyl chloride (example 1.2) (0.200 g, 0.409 mmol) by treatment with commercially available 3-hydroxyazetidine hydrochloride [CAS-no. 18621-18-6] (0.224 mg, 2.05 mmol) and triethylamine (0.57 nil, 4.1 mmol) in THF (5 mL) at 23° C. for 16 h. Diluted with EtOAc, washed with 5% citric acid, sat. $NaHCO_3$-sol. and brine, dried organic layer over $Na_2SO_4$. Removal of the solvent in vacuum left a crude product, which was purified by silica gel column chromatography with EtOAc followed by trituration with diethyl ether/heptane to give the title compound (0.120 g, 55%) as a white solid. MS (ISP) 526.3 [(M+H)$^+$]; mp 205° C.

EXAMPLE 429

6'-[3-(4-Methoxy-piperidine-1-sulfonyl)-phenyl]-6-methyl-4-(4-trifluoromethyl-phenyl)-[2,2']bipyridinyl The title compound was prepared from 3-[6'-methyl-4'-(4-trifluoromethyl-phenyl)-[2,2']bipyridinyl-6-yl]-benzene-sulfonyl chloride (example I.2) (0.200 g, 0.409 mmol) by treatment with commercially available 4-methoxypiperidine [CAS-no. 4045-24-3] (0.236 g, 2.05 mmol) in THF (5 mL) at 23° C. for 16 h. Diluted with EtOAc, washed with 5% citric acid, sat. $NaHCO_3$-sol. and brine, dried organic layer over $Na_2SO_4$. Removal of the solvent in vacuum left a crude product, which was purified by silica gel column chromatography with EtOAc followed by trituration with diethyl ether/heptane to give the title compound (0.090 g, 39%) as a white foam. MS (ISP) 568.3 [$(M+H)^+$]; mp 107° C.

EXAMPLE 430

2-(1-{3-[6'-Methyl-4'-(4-trifluoromethyl-phenyl)-[2,2']bipyridinyl-6-yl]-benzenesulfonyl}-piperidin-4-yloxy)-ethanol The title compound was prepared from 3-[6'-methyl-4'-(4-trifluoromethyl-phenyl)-[2,2']bipyridinyl-6-yl]-benzene-sulfonyl chloride (example I.2) (0.200 g, 0.409 mmol) by treatment with 4-(2-hydroxyethoxy)piperidine [CAS-no. 40256-14-2] (0.297 g, 2.05 mmol) in THF (5 mL) at 23° C. for 16 h. Diluted with EtOAc, washed with 5% citric acid, sat. $NaHCO_3$-sol. and brine, dried organic layer over $Na_2SO_4$. Removal of the solvent in vacuum left a crude product, which was purified by silica gel column chromatography with EtOAc followed by trituration with diethyl ether/heptane to give the title compound (0.120 g, 49%) as a white foam. MS (ISP) 598.3 [$(M+H)^+$].

EXAMPLE 431

N-Benzyl-3-[6'-methyl-4'-(4-trifluoromethyl-phenyl)-[2,2']bipyridinyl-6-yl]-benzenesulfonamide The title compound was prepared from 3-[6'-methyl-4'-(4-trifluoromethyl-phenyl)-[2,2']bipyridinyl-6-yl]-benzene-sulfonyl chloride (example I.2) (0.200 g, 0.409 mmol) by treatment with commercially available benzylamine (0.22 ml, 2.05 mmol) in THF (5 mL) at 23° C. for 16 h. Diluted with EtOAc, washed with 5% citric acid, sat. $NaHCO_3$-sol. and brine, dried organic layer over $Na_2SO_4$. Removal of the solvent in vacuum left a crude product, which was purified by silica gel column chromatography with EtOAc followed by trituration with diethyl ether/heptane to give the title compound (0.100 g, 49%) as a white solid. MS (ISP) 560.2 [$(M+H)^+$]; mp 168° C.

EXAMPLE 432

N-(4-Methoxy-benzyl)-3-[6'-methyl-4'-(4-trifluoromethyl-phenyl)-[2,2']bipyridinyl-6-yl]-benzene-sulfonamide The title compound was prepared from 3-[6'-methyl-4'-(4-trifluoromethyl-phenyl)-[2,2']bipyridinyl-6-yl]-benzene-sulfonyl chloride (example I.2) (0.200 g, 0.409 mmol) by treatment with commercially available 4-methoxybenzylamine (0.27 ml, 2.05 mmol) in THF (5 mL) at 23° C. for 16 h. Diluted with EtOAc, washed with 5% citric acid, sat. $NaHCO_3$-sol. and brine, dried organic layer over $Na_2SO_4$. Removal of the solvent in vacuum left a crude product, which was purified by silica gel column chromatography with EtOAc followed by trituration with diethyl ether/heptane to give the title compound (0.130 g, 53%) as a white solid. MS (ISP) 590.2 [$(M+H)^+$]; mp 126° C. (dec.).

EXAMPLE 433

N-(4-Fluoro-benzyl)-3-[6'-methyl-4'-(4-trifluoromethyl-phenyl)-[2,2']bipyridinyl-6-yl]-benzene-sulfonamide The title compound was prepared from 3-[6'-methyl-4'-(4-trifluoromethyl-phenyl)-[2,2']bipyridinyl-6-yl]-benzene-sulfonyl chloride (example I.2) (0.200 g, 0.409 mmol) by treatment with commercially available 4-fluorobenzylamine (0.23 ml, 2.05 mmol) in THF (5 mL) at 23° C. for 16 h. Diluted with EtOAc, washed with 5% citric acid, sat. $NaHCO_3$-sol. and brine, dried organic layer over $Na_2SO_4$. Removal of the solvent in vacuum left a crude product, which was purified by silica gel column chromatography with EtOAc followed by trituration with diethyl ether/heptane to give the title compound (0.110 g, 46%) as a white solid. MS (ISP) 578.2 [$(M+H)^+$]; mp 175° C.

EXAMPLE 434

6-Methyl-6'-{3-[4-(pyridin-4-yloxy)-piperidine-1-sulfonyl]-phenyl}-4-(4-trifluoromethylphenyl)-[2,2']bipyridinyl The title compound was prepared from 3-[6'-methyl-4'-(4-trifluoromethyl-phenyl)-[2,2']bipyridinyl-6-yl]-benzene-sulfonyl chloride (example I.2) (0.200 g, 0.409 mmol) by treatment with 4-(piperidin-4-yloxy)-pyridine [CAS-no. 224178-65-8] (0.365 g, 2.05 mmol) in THF (5 mL) at 23° C. for 16 h. Diluted with EtOAc, washed with 5% citric acid, sat. $NaHCO_3$-sol. and brine, dried organic layer over $Na_2SO_4$. Removal of the solvent in vacuum left a crude product, which was purified by silica gel column chromatography with EtOAc followed by trituration with diethyl ether/heptane to give the title compound (0.130 g, 50%) as a white foam. MS (ISP) 631.3 [$(M+H)^+$].

EXAMPLE 435

6-Methyl-6'-{3-[4-(pyrimidin-2-yloxy)-piperidine-1-sulfonyl]-phenyl}-4-(4-trifluoromethylphenyl)-[2,2']bipyridinyl The title compound was prepared from 3-[6'-methyl-4'-(4-trifluoromethyl-phenyl)-[2,2']bipyridinyl-6-yl]-benzene-sulfonyl chloride (example I.2) (0.200 g, 0.409 mmol) by treatment with commercially available 2-(piperidin-4-yloxy)-pyrimidine [CAS-no. 499240-48-1] (0.367 g, 2.05 mmol) in THF (5 mL) at 23° C. for 16 h. Diluted with EtOAc, washed with 5% citric acid, sat. $NaHCO_3$-sol. and brine, dried organic layer over $Na_2SO_4$. Removal of the solvent in vacuum left a crude product, which was purified by silica gel column chromatography with EtOAc followed by trituration with diethyl ether/heptane to give the title compound (0.140 g, 54%) as a white foam. MS (ISP) 632.3 [$(M+H)^+$]; mp 134° C. (dec.).

EXAMPLE 436

N-tert-Butyl-3-[6'-methyl-4'-(4-trifluoromethoxy-phenyl)-[2,2']bipyridinyl-6-yl]-benzenesulfonamide A stirred mixture of trifluoro-methanesulfonic acid 6-methyl-4-(4-trifluoromethoxyphenyl)-pyridin-2-yl ester (Example A.63) (0.221 g, 0.55 mmol), N-tert-butyl-3-(6-tributylstannanyl-pyridin-2-yl)-benzenesulfonamide (Example F.6) (0.290 g, 0.50 mmol), tetrakis(triphenyl-phosphine)palladium (0.032 g, 5 mol %) in toluene (5 mL) was heated under reflux conditions for 18 h. Cooled to rt, extracted with ethyl acetate and water, dried the organic layer over Na2SO4. Removal of the solvent in vacuum left a crude product which was purified by silica gel column chromatography with n-heptane/ethyl acetate to give the title compound after trituration with diethyl ether as a white solid (100 mg, 34%). MS (ISP) 542.8 [$(M+H)^+$]; mp 148° C.

EXAMPLE 437

3-[6'-Methyl-4'-(4-trifluoromethoxy-phenyl)-[2,2']bipyridinyl-6-yl]-benzenesulfonamide To N-tert-butyl-3-{6-[4-methyl-6-(4-trifluoromethyl-phenyl)-pyrimidin-2-yl]-pyridin-2-yl}-benzenesulfonamide (Example 436) (0.100 g, 0.185 mmol) was added TFA (3 mL) and the reaction mixture was stirred at 23° C. for 3 h. The mixture was partitioned between EtOAc and saturated $NaHCO_3$ solution, the organic layer was dried over $MgSO_4$. Removal of the solvent in vacuum left a crude product which was triturated with diethyl ether to give the title compound as an off-white solid (0.068 g, 76%). MS (ISP) 486.0 [$(M+H)^+$]; mp 231° C. (dec.).

EXAMPLE 438

N-tert-Butyl-3-[6'-methyl-4'-(3-methyl-4-trifluoromethyl-phenyl)-[2,2']bipyridinyl-6-yl]-benzenesulfonamide A stirred mixture of trifluoro-methanesulfonic acid 6-methyl-4-(3-methyl-4-trifluoromethyl-phenyl)-pyridin-2-yl ester (Example A.64) (0.250 g, 0.626 mmol), N-tert-butyl-3-(6-tributylstannanyl-pyridin-2-yl)-benzenesulfonamide (Example F.6) (0.363 g, 0.626 mmol), tetrakis(triphenyl-phosphine)palladium (0.036 g, 5 mol %) in toluene (5 mL) was heated under reflux conditions for 18 h. Removal of the solvent in vacuum left a crude product which was purified by silica gel column chromatography with n-heptane/ethyl acetate to give the title compound after trituration with diethyl ether as a white solid (300 mg, 88%). MS (ISP) 539.8 [$(M+H)^+$]; mp 150° C. (dec.).

EXAMPLE 439

3-[6'-Hydroxymethyl-4'-(4-trifluoromethyl-phenyl)-[2,2']bipyridinyl-6-yl]-benzenesulfonamide 1) N-tert-Butyl-3-[6'-(tetrahydro-pyran-2-yloxymethyl)-4'-(4-trifluoromethyl-phenyl)-[2,2']bipyridinyl-6-yl]-benzenesulfonamide: A stirred mixture of 2-bromo-6-(tetrahydro-pyran-2-yloxymethyl)-4-(4-trifluoromethyl-phenyl)-pyridine (Example A.65) (0.400 g, 0.894 mmol), N-tert-butyl-3-(6-tributylstannanyl-pyridin-2-yl)-benzenesulfonamide (Example F.6) (0.518 g, 0.894 mmol), tetrakis(triphenyl-phosphine)palladium (0.052 g, 5 mol %) in toluene (5 mL) was heated under reflux conditions for 18 h. After cooling to rt, the reaction mixture was directly subjected to silica gel column chromatography with n-heptane/ethyl acetate to give the N-tert-butyl-3-[6'-(tetrahydro-pyran-2-yloxymethyl)-4'-(4-trifluoromethyl-phenyl)-[2,2']bipyridinyl-6-yl]-benzenesulfonamide (550 mg, 98%) as a light yellow oil. MS (ISP) 626.0 [$(M+H)^+$].

2) To the above described N-tert-butyl-3-[6'-(tetrahydro-pyran-2-yloxymethyl)-4'-(4-trifluoromethyl-phenyl)-[2,2']bipyridinyl-6-yl]-benzenesulfonamide (0.550 g, 0.88 mmol) was added TFA (5 mL) and the reaction mixture was stirred at 23° C. for 18 h. The mixture was poured into 3 N NaOH-solution (100 ml) and stirred at 23° C. for 15 min, then partitioned between EtOAc and water, the organic layer was washed with saturated $NaHCO_3$ solution and dried over $MgSO_4$. Removal of the solvent in vacuum left a crude product which was triturated with diethyl ether to give the title compound as an off-white solid (0.100 g, 23%). MS (ISP) 486.0 [$(M+H)^+$]; mp 213° C. (dec.).

EXAMPLE 440

3-[6'-Methyl-4'-(3-methyl-4-trifluoromethyl-phenyl)-[2,2']bipyridinyl-6-yl]-benzenesulfonamide To N-tert-butyl-3-[6'-methyl-4'-(3-methyl-4-trifluoromethyl-phenyl)-[2,2']bipyridinyl-6-yl]-benzenesulfonamide (Example 438) (0.300 g, 0.556 mmol) was added TFA (5 mL) and the reaction mixture was stirred at 23° C. for 16 h. The mixture was partitioned between EtOAc and saturated $NaHCO_3$ solution, the organic layer was dried over $Na_2SO_4$. Removal of the solvent in vacuum left a crude product which was triturated with diethyl ether to give the title compound as an off-white solid (0.090 g, 33%). MS (ISP) 484.1 [$(M+H)^+$]; mp>250° C.

EXAMPLE 441

N-tert-Butyl-3-{6-[4-(4-cyano-phenyl)-6-methyl-pyrimidin-2-yl]-pyridin-2-yl}-benzenesulfonamide 1) 4-(3-Oxo-but-1-ynyl)-benzonitrile: To a solution of commercially available 4-(3-hydroxy-but-1-ynyl)-benzonitrile [CAS-no. 893748-15-7] (380 mg, 2.22 mmol) in diethyl ether (5 ml) at 23° C. was added Jones reagent solution (0.625 M $CrO_3$ in 1.5 M sulfuric acid, 8.9 ml, 5.55 mmol) and the mixture was stirred at 23° C. for 18 h. To the reaction mixture was added 2-propanol (2 ml), stirring was continued at 23° C. for 10 min, then the reaction mixture was extracted with diethyl ether and water, the organic layer was washed with saturated $NaHCO_3$-sol., dried over $MgSO_4$, filtered and the solvents were evaporated to give the 4-(3-oxo-but-1-ynyl)-benzonitrile (260 mg, 69%) as an off-white solid, which was used without further purification.

2) A mixture of the above described 4-(3-oxo-but-1-ynyl)-benzonitrile (85 mg, 0.5 mmol), 6-(3-tert-butylsulfamoyl-phenyl)-pyridine-2-carboxamidinium acetate (236 mg, 0.6 mmol) and sodium carbonate (127 mg, 1.2 mmol) in acetonitrile (2 ml) was treated by microwave irradiation for 60 min at 120° C. The reaction mixture was extracted with ethyl acetate and water, the organic layers were combined, dried over $MgSO_4$, filtered and the solvents evaporated to leave a crude product, which was purified by silica gel flash chromatography with n-heptane and ethyl acetate to give the title compound (98 mg, 41%) as a light brown foam (cf. *Synlett* 2003, (2), 259). MS (ISP) 484.2 [$(M+H)^+$].

EXAMPLE 442

3-{6-[4-(4-Cyano-phenyl)-6-methyl-pyrimidin-2-yl]-pyridin-2-yl}-benzenesulfonamide To N-tert-butyl-3-{6-[4-(4-cyano-phenyl)-6-methyl-pyrimidin-2-yl]-pyridin-2-yl}-benzenesulfonamide (Example 441) (0.080 g, 0.165 mmol) was added TFA (2 mL) and the reaction mixture was stirred at 23° C. for 3 h. The mixture was partitioned between EtOAc and saturated $NaHCO_3$ solution, the organic layer was dried over $Na_2SO_4$. Removal of the solvent in vacuum left a crude product which was triturated with diethyl ether to give the title compound as a light brown solid (0.047 g, 67%). MS (ISP) 428.1 [$(M+H)^+$]; mp 255° C.

EXAMPLE 443

N-Acetyl-3-[6'-methyl-4'-(4-trifluoromethyl-phenyl)-[2,2']bipyridinyl-6-yl]-benzenesulfonamide A mixture of 3-[6'-methyl-4'-(4-trifluoromethyl-phenyl)-[2,2']bipyridinyl-6-yl]-benzenesulfonamide (example 266) (300 mg, 0.639 mmol) and acetic anhydride (2.42 mL, 25.6 mmol) in acetic acid (5 mL) was stirred at 130° C. for 3 days. Cooled to rt, diluted with EtOAc, extracted with sat. $NaHCO_3$-sol., dried over $Na_2SO_4$, filtered off and evaporated totally to give a crude product, which was purified by silica gel column chromatography with n-heptane/ethyl acetate followed by trituration with diethyl ether/n-heptane to give the title compound (290 mg, 88%) as a white solid. MS (ISP) 512.0 [$(M+H)^+$]; mp 244° C.

EXAMPLE 444

3-[6'-Methyl-4'-(4-trifluoromethyl-phenyl)-[2,2']bipyridinyl-6-yl]-N-(tetrahydro-pyran-4-yl)benzenesulfonamide The title compound was prepared from 3-[6'-methyl-4'-(4-trifluoromethyl-phenyl)-[2,2']bipyridinyl-6-yl]-benzenesulfonyl chloride (example 1.2) (0.465 g, 0.951 mmol) by treatment with commercially available 4-aminotetrahydropyran [CAS-no. 38041-19-9] (0.192 g, 1.9 mmol) in THF (5 ml) at 23° C. for 16 h. Diluted with EtOAc, washed with 5% citric acid, sat. $NaHCO_3$-sol. and brine, dried organic layer over $Na_2SO_4$. Removal of the solvent in vacuum left a crude product, which was purified by silica gel column chromatography with EtOAc followed by trituration with diethyl ether/heptane to give the title compound (0.460 g, 87%) as an off-white solid. MS (ISP) 554.2 [$(M+H)^+$]; mp 163° C. (dec.).

EXAMPLE 445

3-[6'-Methyl-4'-(4-trifluoromethyl-phenyl)-[2,2']bipyridinyl-6-yl]-N-(2,2,2-trifluoro-ethyl)-benzenesulfonamide The title compound was prepared from 3-[6'-methyl-4'-(4-trifluoromethyl-phenyl)-[2,2']bipyridinyl-6-yl]-benzenesulfonyl chloride (example I.2) (0.465 g, 0.951 mmol) by treatment with commercially available 2,2,2-trifluorethylamine [CAS-no. 753-90-2] (0.15 ml, 1.9 mmol) and triethylamine (1.33 ml, 9.51 mmol) in THF (5 ml) at 23° C. for 16 h. Diluted with EtOAc, washed with 5% citric acid, sat. $NaHCO_3$-sol. and brine, dried organic layer over $Na_2SO_4$. Removal of the solvent in vacuum left a crude product, which was purified by silica gel column chromatography with EtOAc followed by trituration with diethyl ether/heptane to give the title compound (0.220 g, 46%) as an off-white solid. MS (ISP) 552.2 [$(M+H)^+$]; mp 198° C.

EXAMPLE 446

N-Ethyl-3-[6'-methyl-4'-(4-trifluoromethyl-phenyl)-[2,2']bipyridinyl-6-yl]-benzenesulfonamide The title compound was prepared from 3-[6'-methyl-4'-(4-trifluoromethyl-phenyl)-[2,2']bipyridinyl-6-yl]-benzenesulfonyl chloride (example I.2) (0.465 g, 0.951 mmol) by treatment with commercially available ethylamine (2 M in THF, 2.38 ml, 4.76 mmol) and triethylamine (1.33 ml, 9.51 mmol) in THF (5 ml) at 23° C. for 16 h. Diluted with EtOAc, washed with 5% citric acid, sat. $NaHCO_3$-sol. and brine, dried organic layer over $Na_2SO_4$. Removal of the solvent in vacuum left a crude product, which was purified by silica gel column chromatography with EtOAc followed by trituration with diethyl ether/heptane to give the title compound (0.260 g, 55%) as an off-white solid. MS (ISP) 498.3 [$(M+H)^+$]; mp 135° C.

EXAMPLE 447

3'-{4-[3-(2,2,2-Trifluoro-ethoxy)-4-trifluoromethyl-phenyl]-6-trifluoromethyl-pyrimidin-2-yl}-biphenyl-3-sulfonic acid amide 1) 3'-{4-[3-(2,2,2-Trifluoro-ethoxy)-4-trifluoromethyl-phenyl]-6-trifluoromethyl-pyrimidin-2-yl}-biphenyl-3-sulfonic acid tert-butylamide was prepared from 2-(3-bromophenyl)-4-[3-(2,2,2-trifluoro-ethoxy)-4-trifluoromethyl-phenyl]-6-trifluoromethyl-pyrimidine (example E.55) (0.38 g, 0.69 mmol) and commercially available 3-(tert.-butylsulfamoyl)phenylboronic acid (0.23 g, 0.89 mmol) according to the general procedure VI. Obtained as light yellow solid (0.45 g), which was subsequently deprotected.

2) To a cooled and stirred solution of 3'-{4-[3-(2,2,2-trifluoro-ethoxy)-4-trifluoromethyl-phenyl]-6-trifluoromethyl-pyrimidin-2-yl}-biphenyl-3-sulfonic acid tert-butylamide (0.45 g) in dichloromethane (6 ml) was added TFA (6 ml) and the reaction mixture was allowed to stir at room temperature for 15 h. The mixture was evaporated to dryness, poured into saturated $NaHCO_3$ solution (20 ml) and extracted with ethyl acetate (2×30 ml). The combined organic layers were washed with brine (20 ml), dried ($MgSO_4$) and evaporated. Further purification by crystallization (dischloromethane/MeOH/hexane) yielded the title compound as a white solid (0.25 g, 59%). MS (ISP) 622.2 [$(M+H)^+$]; mp 188° C.

EXAMPLE 448

3-(4-{4-[3-(2,2,2-Trifluoro-ethoxy)-4-trifluoromethyl-phenyl]-6-trifluoromethyl-pyrimidin-2-yl}-pyridin-2-yl)-benzenesulfonamide 1) 3-(4-{4-[3-(2,2,2-Trifluoro-ethoxy)-4-trifluoromethyl-phenyl]-6-trifluoromethyl-pyrimidin-2-yl}-pyridin-2-yl)-benzenesulfonic acid tert-butylamide was prepared from 2-(2-chloro-pyridin-4-yl)-4-[3-(2,2,2-trifluoro-ethoxy)-4-trifluoromethyl-phenyl]-6-trifluoromethyl-pyrimidine (example E.56) (0.16 g, 0.32 mmol) and commercially available 3-(tert.-butylsulfamoyl)-phenylboronic acid (0.11 g, 0.41 mmol) according to the general procedure VI. Obtained as a light yellow solid (0.21 g), which was subsequently deprotected.

2) To a cooled and stirred solution of 3-(4-{4-[3-(2,2,2-trifluoro-ethoxy)-4-trifluoromethyl-phenyl]-6-trifluoromethyl-pyrimidin-2-yl}-pyridin-2-yl)-benzenesulfonic acid tert-butylamide (0.21 g) in dichloromethane (5 ml) was added TFA (5 ml) and the reaction mixture was allowed to stir at room temperature for 15 h. The mixture was evaporated to dryness, poured into saturated $NaHCO_3$ solution (20 ml) and extracted with ethyl acetate (2×30 ml). The combined organic layers were washed with brine (20 ml), dried ($MgSO_4$) and evaporated. Further purification by crystallization (diethyl ether) yielded the title compound as an off-white solid (0.15 g, 77%). MS (ISP) 623.2 [(M+H)$^+$]; mp 211° C.

EXAMPLE 449

3-{4-[4-Trifluoromethyl-6-(3-trifluoromethyl-phenyl)-pyrimidin-2-yl]-pyridin-2-yl}-benzenesulfonamide 1) N-tert-Butyl-3-{4-[4-trifluoromethyl-6-(3-trifluoromethyl-phenyl)-pyrimidin-2-yl]-pyridin-2-yl}-benzenesulfonamide was prepared from 2-(2-chloro-pyridin-4-yl)-4-trifluoromethyl-6-(3-trifluoromethyl-phenyl)-pyrimidine (example E.59) (0.17 g, 0.42 mmol) and commercially available 3-(tert.-butylsulfamoyl)-phenylboronic acid (0.14 g, 0.54 mmol) according to the general procedure VI. Obtained as an off-white solid (0.22 g), which was subsequently deprotected.

2) To a cooled and stirred solution of N-tert-butyl-3-{4-[4-trifluoromethyl-6-(3-trifluoromethyl-phenyl)-pyrimidin-2-yl]-pyridin-2-yl}-benzenesulfonamide (0.22 g) in dichloromethane (5 ml) was added TFA (5 ml) and the reaction mixture was allowed to stir at room temperature for 15 h. The mixture was evaporated to dryness, poured into saturated $NaHCO_3$ solution (20 ml) and extracted with ethyl acetate (2×30 ml). The combined organic layers were washed with brine (20 ml), dried ($MgSO_4$) and evaporated. Further purification by crystallization (diethyl ether) yielded the title compound as an off-white solid (0.14 g, 65%). MS (ISP) 525.2 [(M+H)$^+$]; mp 244° C.

EXAMPLE 450

3-{4-[4-(2-Fluoro-4-trifluoromethyl-phenyl)-6-trifluoromethyl-pyrimidin-2-yl]-pyridin-2-yl}-benzenesulfonamide 1) N-tert-Butyl-3-{4-[6-(2-fluoro-4-trifluoromethyl-phenyl)-4-trifluoromethyl-pyrimidin-2-yl]-pyridin-2-yl}-benzenesulfonamide was prepared from 2-(2-chloro-pyridin-4-yl)-6-(2-fluoro-4-trifluoromethyl-phenyl)-4-trifluoromethyl-pyrimidine (example E.107) (0.32 g, 0.76 mmol) and commercially available 3-(tert.-butylsulfamoyl)-phenylboronic acid (0.23 g, 0.91 mmol) according to the general procedure VI. Obtained as an off-white solid (0.24 g), which was subsequently deprotected.

2) To a cooled and stirred solution of N-tert-butyl-3-{4-[6-(2-fluoro-4-trifluoromethylphenyl)-4-trifluoromethyl-pyrimidin-2-yl]-pyridin-2-yl}-benzenesulfonamide (0.24 g) in dichloromethane (6 ml) was added TFA (6 ml) and the reaction mixture was allowed to stir at room temperature for 15 h. The mixture was evaporated, poured into 2N $Na_2CO_3$ solution (20 ml) and extracted with ethyl acetate (3×50 ml). The combined organic layers were washed with brine (20 ml), dried ($MgSO_4$) and evaporated. Further purification by crystallization (ethyl acetate/heptane) yielded the title compound as a white solid (0.2 g, 49%). MS (ISP) 543.1 [(M+H)$^+$]; mp 210° C.

EXAMPLE 451

5-{4-[4-(2-Fluoro-4-trifluoromethyl-phenyl)-6-trifluoromethyl-pyrimidin-2-yl]-pyridin-2-yl}-thiophene-2-sulfonic acid amide 1) N-tert-Butyl-5-{3-[6-(2-fluoro-4-trifluoromethyl-phenyl)-4-trifluoromethyl-pyrimidin-2-yl]-phenyl}-thiophene-2-sulfonic acid amide was prepared from 2-(3-bromophenyl)-4-(2-fluoro-4-trifluoromethyl-phenyl)-6-trifluoromethyl-pyrimidine (example E.107) (0.32 g, 0.76 mmol) and N-tert-butyl-5-(4,4,5,5-tetramethyl-1,3,2-dioxaborolan-2-yl)-thiophene-2-sulfonamide (example F.1) (0.314 g, 0.91 mmol) according to the general procedure VI. Obtained as an off-white foam (0.37 g), which was subsequently deprotected.

2) To a cooled and stirred solution of N-tert-butyl-5-{3-[6-(2-fluoro-4-trifluoromethylphenyl)-4-trifluoromethyl-pyrimidin-2-yl]-phenyl}-thiophene-2-sulfonic acid amide (0.37 g) in dichloromethane (6 ml) was added TFA (6 ml) and the reaction mixture was allowed to stir at room temperature for 15 h. The mixture was evaporated to dryness, poured into 2N $Na_2CO_3$ solution (20 ml) and extracted with ethyl acetate (3×50 ml). The combined organic layers were washed with brine (50 ml), dried ($MgSO_4$) and evaporated. Further purification by flash chromatography on silica gel (ethyl acetate/heptane) and crystallization (ethyl acetate/heptane) yielded the title compound as a white solid (0.18 g, 43%). MS (ISP) 549.1 [(M+H)$^+$]; mp 228° C.

EXAMPLE 452

3-{4-[4-(3-Ethoxy-4-trifluoromethyl-phenyl)-6-trifluoromethyl-pyrimidin-2-yl]-pyridin-2-yl}-benzenesulfonamide 1) N-tert-Butyl-3-{4-[6-(3-ethoxy-4-trifluoromethyl-phenyl)-4-trifluoromethyl-pyrimidin-2-yl]-pyridin-2-yl}-benzenesulfonamide was prepared from 2-(2-chloro-pyridin-4-yl)-6-(3-ethoxy-4-trifluoromethyl-phenyl)-4-trifluoromethyl-pyrimidine (example E.108) (0.185 g, 0.41 mmol) and commercially available 3-(tert.-butylsulfamoyl)-phenylboronic acid (0.13 g, 0.50 mmol) according to the general procedure VI. Obtained as an off-white solid (0.24 g), which was subsequently deprotected.

2) To a cooled and stirred solution of N-tert-butyl-3-{4-[6-(3-ethoxy-4-trifluoromethylphenyl)-4-trifluoromethyl-pyrimidin-2-yl]-pyridin-2-yl}-benzenesulfonamide (0.24 g) in dichloromethane (6 ml) was added TFA (6 ml) and the reaction mixture was allowed to stir at room temperature for 15 h. The mixture was evaporated to dryness, poured into saturated $Na_2CO_3$ solution (20 ml) and extracted with ethyl acetate (3×50 ml). The combined organic layers were washed with brine (50 ml), dried ($MgSO_4$) and evaporated. Further purification by crystallization (ethyl acetate/heptane) yielded the title compound as a white solid (0.17 g, 72%). MS (ISP) 569.2 [(M+H)$^+$]; mp 223.5° C.

EXAMPLE 453

5-{4-[4-(3-Ethoxy-4-trifluoromethyl-phenyl)-6-trifluoromethyl-pyrimidin-2-yl]-pyridin-2-yl}-thiophene-2-sulfonic acid amide 1) N-tert-Butyl-5-{3-[6-(2-ethoxy-4-trifluoromethyl-phenyl)-4-trifluoromethyl-pyrimidin-2-yl]-phenyl}-thiophene-2-sulfonic acid amide was prepared from 2-(3-bromophenyl)-4-(2-ethoxy-4-trifluoromethyl-phenyl)-6-trifluoromethyl-pyrimidine (example E.108) (0.185 g, 0.41 mmol) and N-tert-butyl-5-(4,4,5,5-tetramethyl-1,3,2-dioxaborolan-2-yl)thiophene-2-sulfonamide (example F.1) (0.17 g, 0.49 mmol) according to the general procedure VI. Obtained as an off-white foam (0.18 g), which was subsequently deprotected.

2) To a cooled and stirred solution of N-tert-butyl-5-{3-[6-(2-ethoxy-4-trifluoromethylphenyl)-4-trifluoromethyl-pyrimidin-2-yl]-phenyl}-thiophene-2-sulfonic acid amide (0.18 g) in dichloromethane (6 ml) was added TFA (6 ml) and the reaction mixture was allowed to stir at room temperature for 15 h. The mixture was evaporated to dryness, poured into 2N $Na_2CO_3$ solution (20 ml) and extracted with ethyl acetate (3×50 ml). The combined organic layers were washed with brine (50 ml), dried ($MgSO_4$) and evaporated. Further purification by flash chromatography on silica gel (ethyl acetate/heptane) and crystallization (ethyl acetate/heptane) yielded the title compound as an off-white solid (0.08 g, 34%). MS (ISP) 575.1 [$(M+H)^+$]; mp 237.5° C.

EXAMPLE 454

N-Butyryl-3-[6'-methyl-4'-(4-trifluoromethyl-phenyl)-[2,2']bipyridinyl-6-yl]-benzenesulfonamide A mixture of 3-[6'-methyl-4'-(4-trifluoromethyl-phenyl)-[2,2']bipyridinyl-6-yl]-benzenesulfonamide (example 266) (300 mg, 0.639 mmol) and n-butyric anhydride (1.05 mL) was stirred at 150° C. for 6 h. Cooled to 80° C., diluted with n-heptane, cooled to rt overnight, the precipitate was filtered off, washed with n-heptane and dried in high vacuum to give the title compound (300 mg, 87%) as a white solid. MS (ISP) 539.8 [$(M+H)^+$]; mp 188° C.

EXAMPLE 455

N-Isobutyryl-3-[6'-methyl-4'-(4-trifluoromethyl-phenyl)-[2,2']bipyridinyl-6-yl]-benzenesulfonamide A mixture of 3-[6'-methyl-4'-(4-trifluoromethyl-phenyl)-[2,2']bipyridinyl-6-yl]-benzenesulfonamide (example 266) (300 mg, 0.639 mmol) and isobutyric anhydride (1.06 mL) was stirred at 150° C. for 6 h. Cooled to 80° C., diluted with n-heptane, cooled to rt overnight, the precipitate was filtered off, washed with n-heptane and dried in high vacuum to give the title compound (250 mg, 73%) as a white solid. MS (ISP) 539.8 [$(M+H)^+$]; mp 190° C.

EXAMPLE 456

3'-[4-Difluoromethyl-6-(4-trifluoromethyl-phenyl)-pyrimidin-2-yl]-biphenyl-3-sulfonic acid amide 1) 3'-[4-Difluoromethyl-6-(4-trifluoromethyl-phenyl)-pyrimidin-2-yl]-biphenyl-3-sulfonic acid tert-butylamide was prepared from 2-(3-bromo-phenyl)-4-difluoromethyl-6-(4-trifluoromethyl-phenyl)-pyrimidine (example E.8) (0.39 g, 0.9 mmol) and commercially available 3-(tert.-butylsulfamoyl)-phenylboronic acid (0.31 g, 1.2 mmol) according to the general procedure VI. Obtained as an off-white solid (0.51 g), which was subsequently deprotected.

2) To a cooled and stirred solution of 3'-[4-difluoromethyl-6-(4-trifluoromethylphenyl)-pyrimidin-2-yl]-biphenyl-3-sulfonic acid tert-butylamide (0.51 g) in dichloromethane (6 ml) was added TFA (6 ml) and the reaction mixture was allowed to stir at room temperature for 15 h. The mixture was evaporated to dryness, poured into 2N $Na_2CO_3$ solution (20 ml) and extracted with ethyl acetate (3×50 ml). The combined organic layers were washed with brine (50 ml), dried ($MgSO_4$) and evaporated. Further purification by flash chromatography on silica gel (ethyl acetate/heptane) and crystallization (ethyl acetate/heptane) yielded the title compound as a white solid (0.21 g, 42%). MS (ISP) 506.1 [$(M+H)^+$]; mp 204° C.

EXAMPLE 457

3-{4-[4-Difluoromethyl-6-(4-trifluoromethyl-phenyl)-pyrimidin-2-yl]-pyridin-2-yl}-benzenesulfonamide 1) N-tert-Butyl-3-{4-[4-difluoromethyl-6-(4-trifluoromethyl-phenyl)-pyrimidin-2-yl]-pyridin-2-yl}-benzenesulfonamide was prepared from 2-(2-chloro-pyridin-4-yl)-4-difluoromethyl-6-(4-trifluoromethyl-phenyl)-pyrimidine (example E.10) (0.43 g, 1.11 mmol) and commercially available 3-(tert.-butylsulfamoyl)-phenylboronic acid (0.31 g, 1.21 mmol) according to the general procedure VI. Obtained as a light brown solid (0.37 g), which was subsequently deprotected.

2) To a cooled and stirred solution of N-tert-butyl-3-{4-[4-difluoromethyl-6-(4-trifluoromethyl-phenyl)-pyrimidin-2-yl]-pyridin-2-yl}-benzenesulfonamide (0.37 g) in dichloromethane (5 ml) was added TFA (5 ml) and the reaction mixture was allowed to stir at room temperature for 15 h. The mixture was evaporated to dryness, poured into 2N $Na_2CO_3$ solution (20 ml) and extracted with ethyl acetate (3×50 ml). The combined organic layers were washed with brine (50 ml), dried ($MgSO_4$) and evaporated. Further purification by flash chromatography (heptane/ethyl acetate) and crystallization (dichloromethane/MeOH/hexane) yielded the title compound as an off-white solid (0.17 g, 34%). MS (ISP) 507.2 [$(M+H)^+$]; mp 233.5° C.

EXAMPLE 458

5-{4-[4-Difluoromethyl-6-(4-trifluoromethyl-phenyl)-pyrimidin-2-yl]-pyridin-2-yl}-thiophene-2-sulfonic acid amide 1) 5-{4-[4-Difluoromethyl-6-(4-trifluoromethyl-phenyl)-pyrimidin-2-yl]-pyridin-2-yl}-thiophene-2-sulfonic acid tert-butylamide was prepared from 2-(2-chloro-pyridin-4-yl)-4-difluoromethyl-6-(4-trifluoro-phenyl)-pyrimidine (example E.10) (0.43 g, 1.11 mmol) and N-tert-butyl-5-(4,4,5,5-tetramethyl-1,3,2-dioxaborolan-2-yl)-thiophene-2-sulfonamide (example F.1) (0.41 g, 1.19 mmol) according to the general procedure VI. Obtained as a light yellow solid (0.24 g), which was subsequently deprotected.

2) To a cooled and stirred solution of 5-{4-[4-difluoromethyl-6-(4-trifluoromethylphenyl)-pyrimidin-2-yl]-pyridin-2-yl}-thiophene-2-sulfonic acid tert-butylamide (0.24 g) in dichloromethane (5 ml) was added TFA (5 ml) and the reaction mixture was allowed to stir at room temperature for 15 h. The mixture was evaporated to dryness, poured into 2N $Na_2CO_3$ solution (20 ml) and extracted with ethyl acetate (3×50 ml). The combined organic layers were washed with brine (50 ml), dried ($MgSO_4$) and evaporated. Further purification by flash-chromatography on silica gel (ethyl acetate/hexane) and crystallization (dichloromethane) yielded the title compound as an off-white solid (0.1 g, 20%). MS (ISP) 513.3 [$(M+H)^+$]; mp 242° C.

EXAMPLE 459

5-{3-[4-Difluoromethyl-6-(4-trifluoromethyl-phenyl)-pyrimidin-2-yl]-phenyl}-thiophene-2-sulfonic acid amide 1) N-tert-Butyl-5-{3-[4-difluoromethyl-6-(4-trifluoromethyl-phenyl)-pyrimidin-2-yl]-phenyl}-thiophene-2-sulfonic acid amide was prepared from 2-(3-bromo-phenyl)-4- difluoromethyl-6-(4-trifluoromethyl-phenyl)-pyrimidine (example E.8) (0.385 g, 0.9 mmol) and N-tert-butyl-5-(4,4,5,5-tetramethyl-1,3,2-dioxaborolan-2-yl)-thiophene-2-sulfonamide (example F.1) (0.41 g, 1.19 mmol) according to the general procedure VI. Obtained as a light yellow solid (0.4 g), which was subsequently deprotected.

2) To a cooled and stirred solution of N-tert-butyl-5-{3-[4-difluoromethyl-6-(4-trifluoromethyl-phenyl)-pyrimidin-2-yl]-phenyl}-thiophene-2-sulfonic acid amide (0.4 g) in dichloromethane (7 ml) was added TFA (7 ml) and the reaction mixture was allowed to stir at room temperature for 15 h. The mixture was evaporated to dryness, poured into 2N $Na_2CO_3$ solution (20 ml) and extracted with ethyl acetate (3×50 ml). The combined organic layers were washed with brine (50 ml), dried ($MgSO_4$) and evaporated. Further purification by flash-chromatography on silica gel (ethyl acetate/hexane) and crystallization (dichloromethane) yielded the title compound as a white solid (0.064 g, 13%). MS (ISP) 512.3 [$(M+H)^+$]; mp 240.5° C.

EXAMPLE 460

3'-[4-(3-Fluoro-4-trifluoromethyl-phenyl)-6-trifluoromethyl-pyrimidin-2-yl]-biphenyl-3-sulfonic acid amide 1) 3'-[4-(3-Fluoro-4-trifluoromethyl-phenyl)-6-trifluoromethyl-pyrimidin-2-yl]-biphenyl-3-sulfonic acid tert-butylamide was prepared from 2-(3-bromo-phenyl)-4-(3-fluoro-4-trifluoromethyl-phenyl)-6-trifluoromethyl-pyrimidine (example E.109) (0.465 g, 1.0 mmol) and commercially available 3-(tert.-butylsulfamoyl)-phenylboronic acid (0.31 g, 1.2 mmol) according to the general procedure VI. Obtained as light yellow solid (0.47 g), which was subsequently deprotected.

2) To a cooled and stirred solution of 3'-[4-(3-fluoro-4-trifluoromethyl-phenyl)-6-trifluoromethyl-pyrimidin-2-yl]-biphenyl-3-sulfonic acid tert-butylamide (0.47 g) in dichloromethane (6 ml) was added TFA (6 ml) and the reaction mixture was allowed to stir at room temperature for 15 h. The mixture was evaporated to dryness, poured into 2N $Na_2CO_3$ solution (25 ml) and extracted with ethyl acetate (3×50 ml). The combined organic layers were washed with brine (50 ml), dried ($MgSO_4$) and evaporated. Further purification by crystallization (ethyl acetate/heptane) yielded the title compound as a white solid (0.27 g, 50%). MS (ISP) 542.1 [$(M+H)^+$]; mp 227.5° C.

EXAMPLE 461

5-{3-[4-(3-Fluoro-4-trifluoromethyl-phenyl)-6-trifluoromethyl-pyrimidin-2-yl]-phenyl}-thiophene-2-sulfonic acid amide 1) N-tert-Butyl-5-{3-[6-(3-fluoro-4-trifluoromethyl-phenyl)-4-trifluoromethyl-pyrimidin-2-yl]-phenyl}-thiophene-2-sulfonic acid amide was prepared from 2-(3-bromophenyl)-4-(3-fluoro-4-trifluoromethyl-phenyl)-6-trifluoromethyl-pyrimidine (example E.109) (0.465 g, 1.0 mmol) and N-tert-butyl-5-(4,4,5,5-tetramethyl-1,3,2-dioxaborolan-2-yl)thiophene-2-sulfonamide (example F.1) (0.414 g, 1.2 mmol) according to the general procedure VI. Obtained as an off-white solid (0.32 g), which was subsequently deprotected.

2) To a cooled and stirred solution of N-tert-butyl-5-{3-[6-(3-fluoro-4-trifluoromethylphenyl)-4-trifluoromethyl-pyrimidin-2-yl]-phenyl}-thiophene-2-sulfonic acid amide (0.32 g) in dichloromethane (6 ml) was added TFA (6 ml) and the reaction mixture was allowed to stir at room temperature for 15 h. The mixture was evaporated to dryness, poured into 2N $Na_2CO_3$ solution (20 ml) and extracted with ethyl acetate (3×50 ml). The combined organic layers were washed with brine (50 ml), dried ($MgSO_4$) and evaporated. Further purification by crystallization (ethyl acetate/heptane) yielded the title compound as an off-white solid (0.071 g, 13%). MS (ISP) 548.0 [$(M+H)^+$]; mp 213.5° C.

EXAMPLE 462

N-(2-Methoxy-acetyl)-3-[6'-methyl-4'-(4-trifluoromethyl-phenyl)-[2,2']bipyridinyl-6-yl]-benzene-sulfonamide A mixture of 3-[6'-methyl-4'-(4-trifluoromethyl-phenyl)-[2,2']bipyridinyl-6-yl]-benzenesulfonamide (example 266) (300 mg, 0.639 mmol), N-ethyldiisopropylamine (0.22 ml, 1.278 mmol) and methoxyacetyl chloride (0.067 ml, 0.639 mmol) in dichloromethane (3 ml) was stirred at 23° C. for 16 h. Diluted with dichloromethane, washed with water, dried the organic layer over $MgSO_4$. Removal of the solvent in vacuum left a crude product, which was purified by silica gel column chromatography with n-heptane/EtOAc, followed by trituration with diethyl ether to give the title compound (46 mg, 13%) as a white solid. MS (ISP) 542.7 [$(M+H)^+$]; mp 188° C.

Preparation of Pharmaceutical Compositions Comprising Compounds of the Invention:

EXAMPLE I

Tablets of the following composition are produced in a conventional manner:

| | mg/Tablet |
|---|---|
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE II

Tablets of the following composition are produced in a conventional manner:

| | mg/Tablet |
|---|---|
| Active ingredient | 200 |
| Powdered. lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE III

Capsules of the following composition are produced:

| | mg/Capsule |
|---|---|
| Active ingredient | 50 |
| Crystalline. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatin capsules of suitable size.

The invention claimed is:

1. A compound of formula (Ia):

(Ia)

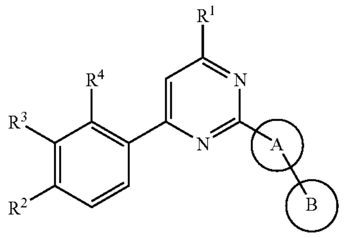

wherein

A is 5 or 6 membered heteroaryl selected from the group consisting of imidazolyl, oxadiazolyl, pyrazolyl, pyridyl, pyrimidinyl, pyrrolyl, and triazolyl each of which is optionally substituted by $C_{1-6}$-alkyl;

B is cyano, or an optionally substituted aryl or an optionally substituted 5 or 6 membered heteroaryl wherein the aryl and heteroaryl group are selected from the group consisting of phenyl, pyridyl, pyrimidinyl, thiazolyl, and thiophenyl, wherein the substituents are selected from the group consisting of:

-halo,

-nitro,

—$C_{1-6}$-alkyl optionally substituted by hydroxy,

—$NR^aR^b$, wherein $R^a$ and $R^b$ are independently H, $C_{1-6}$-alkyl or —(CO)—$C_{1-6}$-alkyl, —S—$C_{1-6}$-alkyl,

—($SO_2$)—OH,

—($SO_2$)—$C_{1-6}$-alkyl,

—($SO_2$)—$NR^cR^d$, wherein $R^c$ and $R^d$ are independently:

H, $C_{1-6}$-alkyl optionally substituted by hydroxy, $C_{1-6}$-haloalkyl, or $C_{1-6}$-alkoxy, —(CO)$C_{1-6}$-alkyl optionally substituted by $C_{1-6}$-alkoxy, —$(CH_2CH_2O)_n$ $CHR^e$, wherein Ris H or $CH_2OH$ and n is 1, 2, 3, 4, 5, 6, 7, 8, 9 or 10, $(CH_2)_m$-aryl, wherein m is 1 or 2 and the aryl is optionally substituted by halo or $C_{1-6}$-alkoxy, —$(CH_2)_p$-$C_{3-6}$-cycloalkyl, wherein p is 0 or 1, -5 or 6-membered heterocycloalkyl, —($SO_2$)—$NR^fR^g$, wherein $R^f$ and $R^g$ together with the nitrogen atom to which they are attached form a 4, 5 or 6 membered heterocycloalkyl ring optionally containing a further heteroatom selected from nitrogen, oxygen, sulphur and an $SO_2$ group, wherein said 4, 5 or 6 membered heterocycloalkyl ring is optionally substituted by a substituent selected from the group consisting of hydroxy, $C_{1-6}$-alkyl, $C_{1-6}$-alkoxy optionally substituted by hydroxy, and 5 or 6 membered heteroaryloxy, —$NHSO_2$—$C_{1-6}$-alkyl, and —$NHSO_2$—$NR^hR^i$ wherein $R^h$ and $R^i$ are independently H, $C_{1-6}$-alkyl, —(CO)O—$C_{1-6}$-alkyl, or $R^h$ and $R^i$ together with the nitrogen atom to which they are attached form a 4, 5 or 6 membered heterocycloalkyl ring optionally containing a further heteroatom selected from nitrogen, oxygen and sulphur, wherein said 4, 5 or 6 membered heterocycloalkyl ring is optionally substituted by $C_{1-6}$-alkyl;

$R^1$ is H, halogen, $C_{1-6}$-alkyl optionally substituted by hydroxy, $C_{1-6}$-alkoxy, $C_{1-6}$-haloalkyl, or $C_{3-6}$-cycloalkyl;

$R^2$ is H, cyano, halogen, $C_{1-6}$-haloalkyl, $C_{1-6}$-alkoxy, $C_{1-6}$-haloalkoxy, $C_{1-6}$-alkyl or $C_{3-6}$-cycloalkyl;

$R^3$ is halogen, H, $C_{1-6}$-alkoxy, $C_{1-6}$-haloalkyl, $C_{1-6}$-alkyl, $C_{3-6}$-cycloalkyl, $C_{1-6}$-haloalkoxy, or is $NR^jR^k$ wherein $R^j$ and $R^k$ are independently selected from the group consisting of:

H, $C_{3-8}$-cycloalkyl, aryl, heteroaryl having from 5 to 12 ring atoms, and $C_{1-6}$-alkyl each of which is optionally substituted by one or more substituent(s) selected from the group consisting of halogen, hydroxy, $C_{3-8}$-cycloalkyl, aryl, heteroaryl having from 5 to 12 ring atoms, and —$NR^lR^m$, wherein $R^l$ and $R^m$ are independently selected from the group consisting of H and $C_{1-6}$-alkyl;

or $R^j$ and $R^k$ can, together with the nitrogen atom to which they are attached, form an optionally substituted heterocyclic group comprising 5 to 12 ring atoms optionally containing a further heteroatom selected from nitrogen, oxygen and sulphur, wherein said heteroaryl group is optionally substituted by one, two, three, four or five substituents selected from the group consisting of halogen, hydroxy, $C_{1-6}$-alkyl and $C_{1-6}$-haloalkyl;

$R^4$ is H or halo;

or a pharmaceutically acceptable salt thereof.

2. The compound of claim 1, wherein B is cyano.

3. The compound of claim 1, wherein:

B is an optionally substituted aryl or an optionally substituted 5 or 6 membered heteroaryl wherein the aryl and heteroaryl group are selected from the group consisting of phenyl, pyridyl, pyrimidinyl, thiazolyl, and thiophenyl, wherein the substituents are selected from the group consisting of:

-halo,

-nitro,

—$C_{1-6}$-alkyl optionally substituted by hydroxy,

—$NR^aR^b$, wherein $R^a$ and $R^b$ are independently H or —(CO)—$C_{1-6}$-alkyl, —S—C1 6-alkyl,

—($SO_2$)—OH,

—($SO_2$)—$C_{1-6}$-alkyl,

—($SO_2$)—$NR^cR^d$, wherein $R^c$ and $R^d$ are independently:

H, $C_{1-6}$-alkyl optionally substituted by hydroxy, $C_{1-6}$-haloalkyl, or $C_{1-6}$-alkoxy, —(CO)$C_{1-6}$-alkyl optionally substituted by $C_{1-6}$-alkoxy, —$(CH_2CH_2O)_nCHR^e$, wherein $R^e$ is H or $CH_2OH$ and n is 1, 2, 3, 4, 5, 6, 7, 8, 9 or 10, $(CH_2)_m$-aryl, wherein m is 1 or 2 and the aryl is optionally substituted by halo or $C_{1-6}$-alkoxy, —$(CH_2)_p$-$C_{3-6}$-cycloalkyl, wherein p is 0 or 1, -5 or 6-membered heterocycloalkyl, —$(SO_2)$—$NR^fR^g$, wherein $R^f$ and $R^g$ together with the nitrogen atom to which they are attached form a 4, 5 or 6 membered heterocycloalkyl ring optionally containing a further heteroatom selected from nitrogen, oxygen, sulphur and an $SO_2$ group, wherein said 4, 5 or 6 membered heterocycloalkyl ring is optionally substituted by a substituent selected from the group consisting of hydroxy, $C_{1-6}$-alkyl, $C_{1-6}$-alkoxy optionally substituted by hydroxy, and 5 or 6 membered heteroaryloxy, —$NHSO_2$-$C_{1-6}$-alkyl, and —$NHSO_2$-$NR^hR^i$ wherein $R^h$ and $R^i$ are independently H, $C_{1-6}$-alkyl, —(CO)O—$C_{1-6}$-alkyl, or $R^h$ and $R^i$ together with the nitrogen atom to which they are attached form a 4, 5 or 6 membered heterocycloalkyl ring optionally containing a further heteroatom selected from nitrogen, oxygen and sulphur, wherein said 4, 5 or 6 membered heterocycloalkyl ring is optionally substituted by $C_{1-6}$-alkyl.

4. The compound of claim 1, having the formula (Ia):

(Ia)

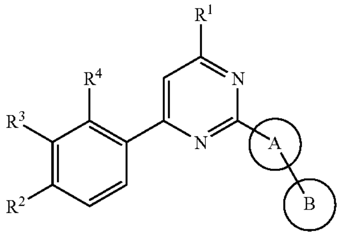

wherein

A is 5 or 6 membered heteroaryl selected from the group consisting of imidazolyl, oxadiazolyl, pyrazolyl, pyridyl, pyrimidinyl, pyrrolyl, and triazolyl;

B is an optionally substituted aryl or an optionally substituted 5 or 6 membered heteroaryl wherein the aryl and heteroaryl group are selected from the group consisting of phenyl, pyridyl, pyrimidinyl, thiazolyl, and thiophenyl, wherein the substituents are selected from the group consisting of:

—$C_{1-6}$-alkyl,

—$NR^aR^b$wherein $R^a$ and $R^b$ are independently H, $C_{1-6}$-alkyl, or —(CO)—$C_{1-6}$-alkyl, and —$(SO_2)$—$NR^cR^d$ wherein RC and Rd are independently H, $C_{1-6}$-alkyl, or —(CO)—$C_{1-6}$-alkyl;

$R^1$ is H, halogen, $C_{1-6}$-alkyl, $C_{1-6}$-alkoxy, $C_{1-6}$-haloalkyl, or $C_{3-6}$-cycloalkyl;

$R^2$ is H, halogen, $C_{1-6}$-haloalkyl, $C_{1-6}$-alkyl or $C_{3-6}$-cycloalkyl;

$R^3$ is halogen, H, $C_{1-6}$-alkoxy, $C_{1-6}$-haloalkyl, $C_{1-6}$-alkyl, $C_{3-6}$-cycloalkyl, $C_{1-6}$-haloalkoxy, or is $NR^jR^k$ wherein $R^j$ and $R^k$ are independently selected from the group consisting of:

H, $C_{3-8}$-cycloalkyl, aryl, heteroaryl having from 5 to 12 ring atoms, and $C_{1-6}$-alkyl each of which is optionally substituted by one or more substituent(s) selected from the group consisting of halogen, hydroxy, $C_{3-8}$-cycloalkyl, aryl, heteroaryl having from 5 to 12 ring atoms, and —$NR^lR^m$, wherein $R^l$ and $R^m$ are independently selected from the group consisting of H and $C_{1-6}$-alkyl;

or $R^j$ and $R^k$ can, together with the nitrogen atom to which they are attached, form an optionally substituted heterocyclic group comprising 5 to 12 ring atoms, wherein the substituents are selected from the group consisting of halogen, hydroxy, $C_{1-6}$-alkyl and $C_{1-6}$-haloalkyl;

or a pharmaceutically acceptable salt thereof.

5. The compound of claim 1, wherein:

A is 5 or 6 membered heteroaryl selected from the group consisting of imidazolyl, oxadiazolyl, pyrazolyl, pyridyl, pyrimidinyl, pyrrolyl, and triazolyl, each of which is optionally substituted by $C_{1-6}$-alkyl;

B is cyano;

$R^1$ is $C_{1-6}$-alkyl or $C_{1-6}$-haloalkyl;

$R^2$ is halogen or $C_{1-6}$-haloalkyl;

$R^3$ is H, halogen, $C_{1-6}$-alkoxy, $C_{1-6}$-haloalkyl, $C_{1-6}$-alkyl or $C_{1-6}$-haloalkoxy;

$R^4$ is H or halo;

or a pharmaceutically acceptable salt thereof.

6. The compound of claim 1, wherein:

A is 5 or 6 membered heteroaryl selected from the group consisting of imidazolyl, oxadiazolyl, pyrazolyl, pyridyl, pyrimidinyl, pyrrolyl, and triazolyl;

B is an optionally substituted aryl or an optionally substituted 5 or 6 membered heteroaryl wherein the aryl and heteroaryl group are selected from the group consisting of phenyl, pyridyl, pyrimidinyl, thiazolyl, and thiophenyl, wherein the substituents are selected from the group consisting of:

—$C_{1-6}$-alkyl optionally substituted by hydroxy,

—$NR^aR^b$, wherein $R^a$ and $R^b$ are independently H or —(CO)—$C_{1-6}$-alkyl, —$(SO_2)$—$C_{1-6}$-alkyl, —$(SO_2)$—$NR^cR^d$, wherein $R^c$ and $R^d$ are independently:

H, or $C_{1-6}$-alkyl optionally substituted by hydroxy,

—(CO)$C_{1-6}$-alkyl optionally substituted by $C_{1-6}$-alkoxy,

—$(CH_2CH_2O)_nCHR^e$, wherein $R^e$ is H or $CH_2OH$ and n is 1, 2, 3, 4, 5, 6, 7, 8, 9 or 10, —$(CH_2)_m$-aryl, wherein m is 1 or 2, —$(CH_2)_p$-$C_{3-6}$-cycloalkyl, wherein p is 0 or 1, —$(SO_2)$—$NR^fR^g$, wherein $R^f$ and $R^g$ together with the nitrogen atom to which they are attached form a 4, 5 or 6 membered heterocycloalkyl ring optionally containing a further heteroatom selected from nitrogen, oxygen, sulphur and an $SO_2$ group, wherein said 4, 5 or 6 membered heterocycloalkyl ring is optionally substituted by a substituent selected from the group consisting of hydroxyl or $C_{1-6}$-alkyl, —$NHSO_2$-$C_{1-6}$-alkyl, and —$NHSO_2NR^hR^i$ wherein $R^h$ and $R^i$ are independently H or $C_{1-6}$-alkyl;

$R_1$ is $C_{1-6}$-alkyl or $C_{1-6}$-haloalkyl;

$R_2$ is halogen or $C_{1-6}$-haloalkyl;

$R_3$ is H, halogen, $C_{1-6}$-alkoxy, $C_{1-6}$-haloalkyl, $C_{1-6}$-alkyl or $C_{1-6}$-haloalkoxy;

$R_4$ is H or halo;

or a pharmaceutically acceptable salt thereof.

7. The compound of claim 1, having formula (Ia2):

(Ia2)

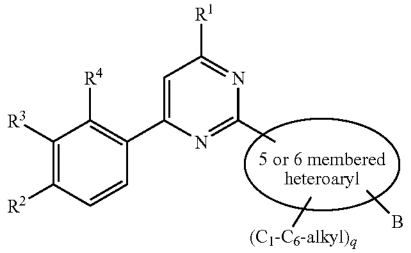

wherein q is 0, 1, 2 or 3.

8. The compound of claim 7, wherein:

B is cyano;

$R^1$ is $C_{1-6}$-alkyl or $C_{1-6}$-haloalkyl;

$R^2$ is halogen or $C_{1-6}$-haloalkyl;

$R^3$ is H, halogen, $C_{1-6}$-alkoxy, $C_{1-6}$-haloalkyl, $C_{1-6}$-alkyl or $C_{1-6}$-haloalkoxy;

$R^4$ is H or halo;

or a pharmaceutically acceptable salt thereof.

9. The compound of claim 7, wherein B is an optionally substituted aryl or an optionally substituted 5 or 6 membered heteroaryl wherein the aryl and heteroaryl group are selected from the group consisting of phenyl, pyridyl, pyrimidinyl, thiazolyl, and thiophenyl, wherein the substituents are selected from the group consisting of:

—$C_{1-6}$-alkyl optionally substituted by hydroxy,

—$NR^aR^b$, wherein $R^a$ and $R^b$ are independently H or —(CO)—$C_{1-6}$-alkyl, —$(SO_2)$—$C_{1-6}$-alkyl, —$(SO_2)$—$NR^cR^d$, wherein $R^c$ and $R^d$ are independently:

H, or $C_{1-6}$-alkyl optionally substituted by hydroxy,

—(CO)$C_{1-6}$-alkyl optionally substituted by $C_{1-6}$-alkoxy,

—$(CH_2CH_2O)_nCHR^e$, wherein $R^e$is H or $CH_2OH$ and n is 1, 2, 3, 4, 5, 6, 7, 8, 9 or 10, $(CH_2)_m$-aryl, wherein m is 1 or 2, —$(CH_2)_p$-$C_{3-6}$-cycloalkyl, wherein p is 0 or 1, and —$(SO_2)$—$NR^fR^g$, wherein $R^f$ and $R^g$ together with the nitrogen atom to which they are attached form a 4, 5 or 6 membered heterocycloalkyl ring optionally containing a further heteroatom selected from nitrogen, oxygen, sulphur and an $SO_2$ group, wherein said 4, 5 or 6 membered heterocycloalkyl ring is optionally substituted by a substituent selected from the group consisting of hydroxy and $C_{1-6}$-alkyl;

$R^1$ is $C_{1-6}$-alkyl or $C_{1-6}$-haloalkyl;

$R^2$ is halogen or $C_{1-6}$-haloalkyl;

$R^3$ is H, halogen, $C_{1-6}$-alkoxy, $C_{1-6}$-haloalkyl, $C_{1-6}$-alkyl or $C_{1-6}$-haloalkoxy;

$R^4$ is H or halo;

or a pharmaceutically acceptable salt thereof.

10. The compound of claim 9, selected from the group consisting of:

2-(4-Pyridin-3-yl-imidazol-1-yl)-4-trifluoromethyl-6-(4-trifluoromethyl-phenyl)-pyrimidine;

4-(4-Chloro-phenyl)-2-(4-pyridin-3-yl-imidazol-1-yl)-6-trifluoromethyl-pyrimidine;

4-(4-Chloro-phenyl)-2-(4-pyridin-4-yl-imidazol-1-yl)-6-trifluoromethyl-pyrimidine;

4-(4-Chloro-phenyl)-2-(3-pyridin-4-yl-[1,2,4]oxadiazol-5-yl)-6-trifluoromethyl-pyrimidine;

4-(4-Chloro-phenyl)-2-(3-pyridin-3-yl-[1,2,4]oxadiazol-5-yl)-6-trifluoromethyl-pyrimidine;

4-(4-Chloro-phenyl)-6-methyl-2-(4-pyridin-3-yl-imidazol-1-yl)-pyrimidine;

4-Methyl-2-(4-pyridin-3-yl-imidazol-1-yl)-6-(4-trifluoromethyl-phenyl)-pyrimidine;

4-[4-Trifluoromethyl-6-(4-trifluoromethyl-phenyl)-pyrimidin-2-yl]-[2,3']bipyridinyl;

4-[4-(4-Chloro-phenyl)-6-trifluoromethyl-pyrimidin-2-yl]-[2,4']bipyridinyl;

2-(3-Pyridin-4-yl-[1,2,4]triazol-1-yl)-4-trifluoromethyl-6-(4-trifluoromethyl-phenyl)-pyrimidine; and 2-(3-Pyridin-3-yl-[1,2,4]triazol-1-yl)-4-trifluoromethyl-6-(4-trifluoromethyl-phenyl)-pyrimidine.

11. The compound of claim 9, wherein B is optionally substituted aryl or an optionally substituted 5 or 6 membered heteroaryl wherein the aryl and heteroaryl group are selected from the group consisting of phenyl, pyridyl, pyrimidinyl, thiazolyl, and thiophenyl, wherein the substituent is $NR^aR^b$, wherein $R^a$ and $R^b$ are independently H or —(CO)—$C_{1-6}$-alkyl.

12. The compound of claim 11, selected from the group consting of:

4-{5-[4-(4-Chloro-phenyl)-6-trifluoromethyl-pyrimidin-2-yl]-[1,2,4]oxadiazol-3-yl}-pyridin-2-ylamine;

5-{5-[4-(4-Chloro-phenyl)-6-trifluoromethyl-pyrimidin-2-yl]-[1,2,4]oxadiazol-3-yl}-pyridin-2-ylamine;

5-{5-[4-Trifluoromethyl-6-(4-trifluoromethyl-phenyl)-pyrimidin-2-yl]-[1,2,4]oxadiazol-3-yl}-pyridin-2-ylamine;

4-{5-[4-Trifluoromethyl-6-(4-trifluoromethyl-phenyl)-pyrimidin-2-yl]-[1,2,4]oxadiazol-3-yl}-pyridin-2-ylamine;

5-{1-[4-Trifluoromethyl-6-(4-trifluoromethyl-phenyl)-pyrimid in-2-yl]-1H-imidazol-4-yl}-pyridin-2-ylamine;

5-{1-[4-(4-Chloro-phenyl)-6-trifluoromethyl-pyrimidin-2-yl]-1H-imidazol-4-yl}-pyridin-2-ylamine;

5-{1-[4-Trifluoromethyl-6-(4-trifluoromethyl-phenyl)-pyrimidin-2-yl]-1H-pyrazol-4-yl}-pyridin-2-ylamine;

5-{5-[4-Trifluoromethyl-6-(4-trifluoromethyl-phenyl)-pyrimidin-2-yl]-[1,2,4]oxadiazol-3-yl}-pyrimidin-2-ylamine;

5-{3-[4-Trifluoromethyl-6-(4-trifluoromethyl-phenyl)-pyrimidin-2-yl]-[1,2,4]oxadiazol-5-yl}-pyridin-2-ylamine; and 5-{3-[4-(4-Chloro-phenyl)-6-trifluoromethyl-pyrimidin-2-yl]-[1,2,4]oxadiazol-5-yl}-pyridin-2-yl amine.

13. The compound of claim 11, selected from the group consting of:

4-[4-(4-Chloro-phenyl)-6-trifluoromethyl-pyrimidin-2-yl]-[2,3']bipyridinyl-6'-ylamine;

4-[4-Trifluoromethyl-6-(4-trifluoromethyl-phenyl)-pyrimidin-2-yl]-[2,3']bipyrid inyl-6'-ylamine;

5-{1-[4-Difluoromethyl-6-(4-trifluoromethyl-phenyl)-pyrimidin-2-yl]-1H-imidazol-4-yl}-pyridin-2-ylamine;

5-{5-[4-Difluoromethyl-6-(4-trifluoromethyl-phenyl)-pyrimidin-2-yl]-[1,2,4]oxadiazol-3-yl}-pyridin-2-ylamine;

5-{1-[4-(4-Chloro-phenyl)-6-methyl-pyrimidin-2-yl]-1H-imidazol-4-yl}-pyridin-2-ylamine;

5-{1-[4-(4-Chloro-phenyl)-6-methyl-pyrimidin-2-yl]-1H-imidazol-4-yl}-pyrimidin-2-ylamine;

5-{1-[4-Methyl-6-(4-trifluoromethyl-phenyl)-pyrimidin-2-yl]-1H-imidazol-4-yl}-pyridin-2-ylamine;

5-{1-[4-Methyl-6-(4-trifluoromethyl-phenyl)-pyrimidin-2-yl]-1H-imidazol-4-yl}-pyrimidin-2-ylamine; and 5-{1-[4-(4-Chloro-phenyl)-6-cyclopropyl-pyrimidin-2-yl]-1H-imidazol-4-yl}-pyridin-2-ylamine.

14. The compound of claim 11 selected from the group consting of:

5-{1-[4-(4-Chloro-phenyl)-6-cyclopropyl-pyrimidin-2-yl]-1H-imidazol-4-yl}-pyrimidin-2-ylamine;

5-{1-[4-(4-Chloro-phenyl)-pyrimidin-2-yl]-1H-imidazol-4-yl}-pyridin-2-ylamine;

5-{1-[4-Trifluoromethyl-6-(3-trifluoromethyl-phenyl)-pyrimid in-2-yl]-1H-imidazol-4-yl}-pyridin-2-ylamine;

5-{1-[4-(3-Ethoxy-4-trifluoromethyl-phenyl)-6-trifluoromethyl-pyrimidin-2-yl]-1H-imidazol-4-yl}-pyridin-2-ylamine;

4-[4-Difluoromethyl-6-(4-trifluoromethyl-phenyl)-pyrimidin-2-yl]-[2,3']bipyridinyl-6'-ylamine;

5-{5-[4-(3-Ethoxy-4-trifluoromethyl-phenyl)-6-trifluoromethyl-pyrimidin-2-yl]-[1,2,4]oxadiazol-3-yl}-pyridin-2-ylamine;

4-[4-(3-Ethoxy-4-trifluoromethyl-phenyl)-6-trifluoromethyl-pyrimidin-2-yl]-[2,3']bipyridinyl-6'-ylamine;

5-{1-[4-(3-Fluoro-4-trifluoromethyl-phenyl)-6-trifluoromethyl-pyrimidin-2-yl]-1H-imidazol-4-yl}-pyridin-2-ylamine; and N-(5-{1-[4-Trifluoromethyl-6-(4-trifluoromethyl-phenyl)-pyrimidin-2-yl]-1H-imidazol-4-yl}-pyridin-2-yl)-acetamide.

15. The compound of claim 11, selected from the group consting of:

5-{5-[4-(3,4-Dichloro-phenyl)-6-trifluoromethyl-pyrimidin-2-yl]-[1,2,4]oxadiazol-3-yl}-pyridin-2-ylamine;

5-[6-Trifluoromethyl-4-(4-trifluoromethyl-phenyl)-[2,4']bipyrimidinyl-2'-yl]-pyridin-2-ylamine;

5-{1-[4-(3,4-Dichloro-phenyl)-6-trifluoromethyl-pyrimidin-2-yl]-1H-imidazol-4-yl}-pyridin-2-ylamine;

4-[4-(3,4-Dichloro-phenyl)-6-trifluoromethyl-pyrimidin-2-yl]-[2,3']bipyridinyl-6'-ylamine;

5-{1-[4-(4-Chloro-3-methyl-phenyl)-6-trifluoromethyl-pyrimidin-2-yl]-1H-imidazol-4-yl}-pyridin-2-ylamine;

5-{5-[4-(4-Chloro-3-methyl-phenyl)-6-trifluoromethyl-pyrimidin-2-yl]-[1,2,4]oxadiazol-3-yl }-pyridin-2-ylamine;

4-[4-(4-Chloro-3-methyl-phenyl)-6-trifluoromethyl-pyrimidin-2-yl]-[2,3']bipyrid inyl-6'-ylamine;

4-{1-[4-Trifluoromethyl-6-(4-trifluoromethyl-phenyl)-pyrimid in-2-yl]-1H-imidazol-4-yl}-phenylamine; and 4-[4-(4-Chloro-phenyl)-6-methyl-pyrimidin-2-yl]-[2,3']bipyridinyl-6'-ylamine.

16. The compound of claim 11, selected from the group consisting of:

4-[4-Methyl-6-(4-trifluoromethyl-phenyl)-pyrimidin-2-yl]-[2,3']bipyrid inyl-6'-ylamine;

5-{1-[4-(3-Methyl-4-trifluoromethyl-phenyl)-6-trifluoromethyl-pyrimidin-2-yl]-1H-imidazol-4-yl}-pyridin-2-ylamine;

4-[4-(3-Methyl-4-trifluoromethyl-phenyl)-6-trifluoromethyl-pyrimidin-2-yl]-[2,3']bipyridinyl-6'-ylamine;

5-{1-[4-Methyl-6-(3-methyl-4-trifluoromethyl-phenyl)-pyrimidin-2-yl]-1H-imidazol-4-yl}-pyridin-2-ylamine;

5-{1-[4-Methyl-6-(3-methyl-4-trifluoromethyl-phenyl)-pyrimidin-2-yl]-1H-imidazol-4-yl}-pyrimidin-2-ylamine;

5-{1-[4-(3-Methyl-4-trifluoromethyl-phenyl)-6-trifluoromethyl-pyrimidin-2-yl]-1H-imidazol-4-yl}-pyrimidin-2-ylamine;

5-{5-[4-Methyl-6-(4-trifluoromethyl-phenyl)-pyrimidin-2-yl]-[1,2,4]oxadiazol-3-yl}-pyridin-2-ylamine;

5-{5-[4-(3-Methyl-4-trifluoromethyl-phenyl)-6-trifluoromethyl-pyrimidin-2-yl]-[1,2,4]oxadiazol-3-yl}-pyridin-2-ylamine; and 4-[4-Methyl-6-(3-methyl-4-trifluoromethyl-phenyl)-pyrimid in-2-yl]-[2,3']bipyrid inyl-6'-ylamine.

17. The compound of claim 11, selected from the group consting of:

5-(1-{4-[3-(2,2,2-Trifluoro-ethoxy)-4-trifluoromethyl-phenyl]-6-trifluoromethyl-pyrimidin-2-yl }-1H-imidazol-4-yl)-pyridin-2-ylamine;

4-{4-[3-(2,2,2-Trifluoro-ethoxy)-4-trifluoromethyl-phenyl]-6-trifluoromethyl-pyrimidin-2-yl}-[2,3']bipyridinyl-6'-ylamine;

5-{5-[4-(4-Chloro-phenyl)-6-methyl-pyrimidin-2-yl]-[1,2,4]oxadiazol-3-yl}-pyridin-2-ylamine;

5-{1-[4-Trifluoromethyl-6-(3-trifluoromethyl-phenyl)-pyrimid in-2-yl]-1H-imidazol-4-yl}-pyrimidin-2-ylamine;

4-[4-Trifluoromethyl-6-(3-trifluoromethyl-phenyl)-pyrimid in-2-yl]-[2,3']bipyrid inyl-6'-ylamine;

5-{2-Methyl-1-[4-trifluoromethyl-6-(4-trifluoromethyl-phenyl)-pyrimidin-2-yl]-1H-imidazol-4-yl}-pyridin-2-ylamine;

5-{2-Methyl-1-[4-trifluoromethyl-6-(4-trifluoromethyl-phenyl)-pyrimidin-2-yl]-1H-imidazol-4-yl}-pyrimidin-2-ylamine;

5-{1-[4-(3,4-Dichloro-phenyl)-6-methyl-pyrimidin-2-yl]-1H-imidazol-4-yl}-pyrimidin-2-ylamine; and 5-{1-[4-(3,4-Dichloro-phenyl)-6-methyl-pyrimidin-2-yl]-1H-imidazol-4-yl}-pyridin-2-ylamine;

4-[4-(3,4-Dichloro-phenyl)-6-methyl-pyrimidin-2-yl]-[2,3']bipyridinyl-6'-ylamine;.

18. The compound of claim 11, selected from the group consting of:

5-{2-Methyl-1-[4-methyl-6-(4-trifluoromethyl-phenyl)-pyrimidin-2-yl]-1H-imidazol-4-yl}-pyridin-2-ylamine;

5-{1-[4-Methyl-6-(4-trifluoromethyl-phenyl)-pyrimidin-2-yl]-1H-[1,2,4]triazol-3-yl}-pyridin-2-ylamine;

5-{1-[4-Isopropyl-6-(4-trifluoromethyl-phenyl)-pyrimidin-2-yl]-1H-imidazol-4-yl}-pyridin-2-ylamine;

5-{1-[4-Isopropyl-6-(4-trifluoromethyl-phenyl)-pyrimidin-2-yl]-1H-imidazol-4-yl}-pyrimidin-2-ylamine;

5-{5-Methyl-1-[4-trifluoromethyl-6-(4-trifluoromethyl-phenyl)-pyrimidin-2-yl]-1H-imidazol-4-yl}-pyrid in-2-ylamine;

5-{1-[4-(3-Chloro-phenyl)-6-trifluoromethyl-pyrimidin-2-yl]-1H-imidazol-4-yl}-pyridin-2-ylamine;

5-{1-[4-(3-Chloro-phenyl)-6-trifluoromethyl-pyrimidin-2-yl]-1H-imidazol-4-yl}-pyrimidin-2-ylamine;

5-{1-[4-(4-Fluoro-phenyl)-6-trifluoromethyl-pyrimidin-2-yl]-1H-imidazol-4-yl}-pyridin-2-ylamine 5-{1-[4-(4-Chloro-3-methyl-phenyl)-6-methyl-pyrimidin-2-yl]-1H-imidazol-4-yl}-pyridin-2-ylamine; and 5-{1-[4-(3,4-Difluoro-phenyl)-6-trifluoromethyl-pyrimidin-2-yl]-1H-imidazol-4-yl}-pyridin-2-ylamine.

19. The compound of claim 9, wherein B is an optionally substituted aryl or an optionally substituted 5 or 6 membered heteroaryl wherein the aryl and heteroaryl group are selected from the group consisting of phenyl, pyridyl, pyrimidinyl, thiazolyl, and thiophenyl, wherein the substituent is —$(SO_2)$—$C_{1-6}$-alkyl.

20. The compound of claim 19, selected from the group consisting of:

4-(4-Chloro-phenyl)-2-[4-(3-methanesulfonyl-phenyl)-imidazol-1-yl]-6-methyl-pyrimidine;

4-(3,4-Dichloro-phenyl)-2-[4-(3-methanesulfonyl-phenyl)-imidazol-1-yl]-6-methyl-pyrimidine;

2-[4-(3-Methanesulfonyl-phenyl)-imidazol-1-yl]-4-trifluoromethyl-6-(4-trifluoromethyl-phenyl) -pyrimidine; and 2-[2-(3-Methanesulfonyl-phenyl)-pyrid in-4-yl]-4-trifluoromethyl-6-(4-trifluoromethyl-phenyl)-pyrimidine.

21. The compound of claim 9, wherein B is optionally substituted aryl or an optionally substituted 5 or 6 membered heteroaryl, wherein the substituent is —$(SO_2)$—$NR^cR^d$, wherein $R^c$ and $R^d$ are independently:

—H,

—$C_{1-6}$-alkyl optionally substituted by hydroxy,

—$(CO)C_{1-6}$-alkyl optionally substituted by $C_{1-6}$-alkoxy,

—$(CH_2CH_2O)_nCHR^e$, wherein $R^e$is H or $CH_2OH$ and n is 1, 2, 3, 4, 5, 6, 7, 8, 9 or 10, —$(CH_2)_m$-aryl, wherein m is 1 or 2, or —$(CH_2)_p$-$C_{3-6}$-cycloalkyl, wherein p is 0 or 1.

22. The compound of claim 21, from the group consisting of:

3-{3-[4-(4-Chloro-phenyl)-6-trifluoromethyl-pyrimidin-2-yl]-[1,2,4]oxadiazol-5-yl}-benzenesulfonamide;

3-{3-[4-Trifluoromethyl-6-(4-trifluoromethyl-phenyl)-pyrimidin-2-yl]-[1,2,4]oxadiazol-5-yl}-benzenesulfonamide;

4-{5-[4-Trifluoromethyl-6-(4-trifluoromethyl-phenyl)-pyrimidin-2-yl]-[1,2,4]oxadiazol-3-yl}-benzenesulfonamide;

3-{5-[4-Trifluoromethyl-6-(4-trifluoromethyl-phenyl)-pyrimidin-2-yl]-[1,2,4]oxadiazol-3-yl}-benzenesulfonamide;

4-{5-[4-(4-Chloro-phenyl)-6-trifluoromethyl-pyrimidin-2-yl]-[1,2,4]oxadiazol-3-yl}-benzenesulfonamide;

3-{5-[4-(4-Chloro-phenyl)-6-trifluoromethyl-pyrimidin-2-yl]-[1,2,4]oxadiazol-3-yl}-benzenesulfonamide;

5-{3-[4-Trifluoromethyl-6-(4-trifluoromethyl-phenyl)-pyrimidin-2-yl]-[1,2,4]oxadiazol-5-yl}-thiophene-2-sulfonic acid amide;

5-{3-[4-(4-Chloro-phenyl)-6-trifluoromethyl-pyrimidin-2-yl]-[1,2,4]oxadiazol-5-yl}-thiophene-2-sulfonic acid amide;

4-{5-[4-Difluoromethyl-6-(4-trifluoromethyl-phenyl)-pyrimidin-2-yl]-[1,2,4]oxadiazol-3-yl}-benzenesulfonamide; and 3-{5-[4-Difluoromethyl-6-(4-trifluoromethyl-phenyl)-pyrimidin-2-yl]-[1,2,4]oxadiazol-3-yl}-benzenesulfonamide.

23. The compound of claim 21, from the group consisting of:

4-{5-[4-(3-Ethoxy-4-trifluoromethyl-phenyl)-6-trifluoromethyl-pyrimidin-2-yl]-[1,2,4]oxadiazol-3-yl}-benzenesulfonamide;

3-{5-[4-(3-Ethoxy-4-trifluoromethyl-phenyl)-6-trifluoromethyl-pyrimidin-2-yl]-[1,2,4]oxadiazol-3-yl}-benzenesulfonamide;

4-{5-[4-(3,4-Dichloro-phenyl)-6-trifluoromethyl-pyrimidin-2-yl]-[1,2,4]oxadiazol-3-yl}-benzenesulfonamide;

3-{5-[4-(3,4-Dichloro-phenyl)-6-trifluoromethyl-pyrimidin-2-yl]-[1,2,4]oxadiazol-3-yl}-benzenesulfonamide;

3-{5-[4-(4-Chloro-3-methyl-phenyl)-6-trifluoromethyl-pyrimidin-2-yl]-[1,2,4]oxadiazol-3-yl }-benzenesulfonamide;

4-{5-[4-Methyl-6-(4-trifluoromethyl-phenyl)-pyrimidin-2-yl]-[1,2,4]oxadiazol-3-yl}-benzenesulfonamide;

3-{5-[4-Methyl-6-(4-trifluoromethyl-phenyl)-pyrimidin-2-yl]-[1,2,4]oxadiazol-3-yl}-benzenesulfonamide;

4-{5-[4-(3-Methyl-4-trifluoromethyl-phenyl)-6-trifluoromethyl-pyrimidin-2-yl]-[1,2,4]oxadiazol-3-yl}-benzenesulfonamide;

3-{5-[4-(3-Methyl-4-trifluoromethyl-phenyl)-6-trifluoromethyl-pyrimidin-2-yl]-[1,2,4]oxadiazol-3-yl}-benzenesulfonamide; and 4-{5-[4-(4-Chloro-phenyl)-6-methyl-pyrimidin-2-yl]-[1,2,4]oxadiazol-3-yl}-benzenesulfonamide.

24. The compound of claim 21, from the group consisting of:

N-tert-Butyl-3-{4-[4-trifluoromethyl-6-(4-trifluoromethyl-phenyl)-pyrimidin-2-yl]-pyridin-2-yl }-benzenesulfonamide;

3-{4-[4-Trifluoromethyl-6-(4-trifluoromethyl-phenyl)-pyrimidin-2-yl]-pyridin-2-yl}-benzenesulfonamide;

4-{1-[4-Trifluoromethyl-6-(4-trifluoromethyl-phenyl)-pyrimid in-2-yl]-1H-imidazol-4-yl}-benzenesulfonamide;

3-{1-[4-Trifluoromethyl-6-(4-trifluoromethyl-phenyl)-pyrimidin-2-yl]-1H-imidazol-4-yl}-benzenesulfonamide;

5-{4-[4-Trifluoromethyl-6-(4-trifluoromethyl-phenyl)-pyrimidin-2-yl]-pyrid i n-2-yl}-thiophene-2-sulfonic acid tert-butylamide;

5-{1-[4-Trifluoromethyl-6-(4-trifluoromethyl-phenyl)-pyrimid in-2-yl]-1H-imidazol-4-yl}-thiophene-2-sulfonic acid amide;

5-{4-[4-Trifluoromethyl-6-(4-trifluoromethyl-phenyl)-pyrimidin-2-yl]-pyridin-2-yl}-thiophene-2-sulfonic acid amide;

3-{4-[4-Methyl-6-(4-trifluoromethyl-phenyl)-pyrimidin-2-yl]-pyridin-2-yl}-benzenesulfonamide;

5-{4-[4-(4-Chloro-phenyl)-6-trifluoromethyl-pyrimidin-2-yl]-pyridin-2-yl}-thiophene-2-sulfonic acid amide; and 5-{1-[4-(4-Chloro-phenyl)-6-trifluoromethyl-pyrimidin-2-yl]-1H-imidazol-4-yl}-thiophene-2-sulfonic acid amide.

25. The compound of claim 21, from the group consisting of:

4-{1-[4-(4-Chloro-phenyl)-6-trifluoromethyl-pyrimidin-2-yl]-1H-imidazol-4-yl}-benzenesulfonamide;

3-{1-[4-(4-Chloro-phenyl)-6-methyl-pyrimidin-2-yl]-1H-imidazol-4-yl}-benzenesulfonamide;

3-{1-[4-(4-Chloro-phenyl)-6-trifluoromethyl-pyrimidin-2-yl]-1H-imidazol-4-yl}-benzenesulfonamide;

3-{4-[4-(4-Chloro-phenyl)-6-trifluoromethyl-pyrimid in-2-yl]-pyrid in-2-yl}-benzenesulfonamide;

4-{1-[4-(4-Chloro-phenyl)-6-methyl-pyrimidin-2-yl]-1H-imidazol-4-yl}-benzenesulfonamide;

2-{1-[4-Trifluoromethyl-6-(4-trifluoromethyl-phenyl)-pyrimid in-2-yl]-1H-imidazol-4-yl}-thiazole-5-sulfonic acid amide;

2-{1-[4-(4-Chloro-phenyl)-6-trifluoromethyl-pyrimidin-2-yl]-1H-imidazol-4-yl}-thiazole-5-sulfonic acid amide;

4-{1-[4-Methyl-6-(4-trifluoromethyl-phenyl)-pyrimidin-2-yl]-1H-imidazol-4-yl}-benzenesulfonamide;

3-{1-[4-Methyl-6-(4-trifluoromethyl-phenyl)-pyrimidin-2-yl]-1H-imidazol-4-yl}-benzenesulfonamide; and 3-{1-[4-(3-Chloro-phenyl)-6-trifluoromethyl-pyrimidin-2-yl]-1H-imidazol-4-yl}-benzenesulfonamide.

26. The compound of claim 21, from the group consisting of:

5-{1-[4-(3-Chloro-phenyl)-6-trifluoromethyl-pyrimidin-2-yl]-1H-imidazol-4-yl}-thiophene-2-sulfonic acid amide;

3-{4-[4-(4-Chloro-phenyl)-6-methyl-pyrimidin-2-yl]-pyridin-2-yl}-benzenesulfonamide;

5-{1-[4-(4-Chloro-phenyl)-6-methyl-pyrimidin-2-yl]-1H-imidazol-4-yl}-thiophene-2-sulfonic acid amide;

5-{1-[4-Methyl-6-(4-trifluoromethyl-phenyl)-pyrimidin-2-yl]-1H-imidazol-4-yl}-thiophene-2-sulfonic acid amide;

5-{4-[4-(4-Chloro-phenyl)-6-methyl-pyrimidin-2-yl]-pyridin-2-yl}-thiophene-2-sulfonic acid amide;

3-{4-[4-(3,4-Dichloro-phenyl)-6-methyl-pyrimidin-2-yl]-pyridin-2-yl}-benzenesulfonamide;

5-{4-[4-(3,4-Dichloro-phenyl)-6-methyl-pyrimidin-2-yl]-pyridin-2-yl}-thiophene-2-sulfonic acid amide;

5-{4-[4-Methyl-6-(4-trifluoromethyl-phenyl)-pyrimidin-2-yl]-pyridin-2-yl}-thiophene-2-sulfonic acid amide;

3-{1-[4-(3,4-Dichloro-phenyl)-6-methyl-pyrimidin-2-yl]-1H-imidazol-4-yl}-benzenesulfonamide; and 4-{1-[4-(3,4-Dichloro-phenyl)-6-methyl-pyrimidin-2-yl]-1H-imidazol-4-yl}-benzenesulfonamide.

27. The compound of claim 21, from the group consisting of:

2-{1-[4-(4-Chloro-phenyl)-6-methyl-pyrimidin-2-yl]-1H-imidazol-4-yl}-thiazole-5-sulfonic acid amide;

2-{1-[4-(3,4-Dichloro-phenyl)-6-methyl-pyrimidin-2-yl]-1H-imidazol-4-yl}-thiazole-5-sulfonic acid amide;

3-{4-[4-(3,4-Dichloro-phenyl)-6-trifluoromethyl-pyrimidin-2-yl]-pyrid in-2-yl}-benzenesulfonamide;

5-{4-[4-(3,4-Dichloro-phenyl)-6-trifluoromethyl-pyrimidin-2-yl]-pyrid in-2-yl}-thiophene-2-sulfonic acid amide;

5-{1-[4-(3,4-Dichloro-phenyl)-6-trifluoromethyl-pyrimidin-2-yl]-1H-imidazol-4-yl}-thiophene-2-sulfonic acid amide;

5-{1-[4-(3-Methyl-4-trifluoromethyl-phenyl)-6-trifluoromethyl-pyrimidin-2-yl]-1H-imidazol-4-yl}-thiophene-2-sulfonic acid amide;

4-{1-[4-(3,4-Dichloro-phenyl)-6-trifluoromethyl-pyrimidin-2-yl]-1H-imidazol-4-yl}-benzenesulfonamide;

4-{1-[4-(3-Methyl-4-trifluoromethyl-phenyl)-6-trifluoromethyl-pyrimidin-2-yl]-1H-imidazol-4-yl}-benzenesulfonamide;

3-{1-[4-(3-Methyl-4-trifluoromethyl-phenyl)-6-trifluoromethyl-pyrimidin-2-yl]-1H-imidazol-4-yl}-benzenesulfonamide; and 3-{1-[4-(3,4-Dichloro-phenyl)-6-trifluoromethyl-pyrimidin-2-yl]-1H-imidazol-4-yl}-benzenesulfonamide.

28. The compound of claim 21, selected from the group consisting of:

5-{1-[4-(3,4-Dichloro-phenyl)-6-methyl-pyrimidin-2-yl]-1H-imidazol-4-yl}-thiophene-2-sulfonic acid amide;

3-{1-[4-(4-Chloro-3-methyl-phenyl)-6-methyl-pyrimidin-2-yl]-1H-imidazol-4-yl}-benzenesulfonamide;

5-{1-[4-(4-Chloro-3-methyl-phenyl)-6-methyl-pyrimidin-2-yl]-1H-imidazol-4-yl}-thiophene-2-sulfonic acid amide;

N-tert-Butyl-3-{6-[4-trifluoromethyl-6-(4-trifluoromethyl-phenyl)-pyrimidin-2-yl]-pyridin-2-yl }-benzenesulfonamide;

3-{6-[4-Trifluoromethyl-6-(4-trifluoromethyl-phenyl)-pyrimidin-2-yl]-pyrid i n-2-yl}-benzenesulfonamide;

N-Propionyl-3-{4-[4-trifluoromethyl-6-(4-trifluoromethyl-phenyl)-pyrimidin-2-yl]-pyridin-2-yl }-benzenesulfonamide; and 5-{4-[4-Trifluoromethyl-6-(4-trifluoromethyl-phenyl)-pyrimidin-2-yl]-pyridin-2-yl}-thiophene-2-sulfonic acid propionyl-amide.

29. The compound of claim 21, from the group consisting of:

N-(2-Hydroxy-ethyl)-3-{4-[4-trifluoromethyl-6-(4-trifluoromethyl-phenyl)-pyrimidin-2-yl]-pyridin-2-yl}-benzenesulfonamide;

N-(2-Hydroxy-1,1 -dimethyl-ethyl)-3-{4-[4-trifluoromethyl-6-(4-trifluoromethyl-phenyl)-pyrimidin-2-yl]-pyridin-2-yl}-benzenesulfonamide;

N,N-Bis-(2-hydroxy-ethyl)-3-{4-[4-trifluoromethyl-6-(4-trifluoromethyl-phenyl)-pyrimidin-2-yl]-pyridin-2-yl}-benzenesulfonamide;

5-{1-[4-(3,4-Difluoro-phenyl)-6-trifluoromethyl-pyrimidin-2-yl]-1H-imidazol-4-yl}-thiophene-2-sulfonic acid amide;

5-{1-[4-(4-Fluoro-phenyl)-6-trifluoromethyl-pyrimidin-2-yl]-1H-imidazol-4-yl}-thiophene-2-sulfonic acid amide;

3-{1-[4-(4-Fluoro-phenyl)-6-trifluoromethyl-pyrimidin-2-yl]-1H-imidazol-4-yl}-benzenesulfonamide;

3-{1-[4-(3,4-Difluoro-phenyl)-6-trifluoromethyl-pyrimidin-2-yl]-1H-imidazol-4-yl}-benzenesulfonamide;

5-{4-[4-(4-Fluoro-phenyl)-6-trifluoromethyl-pyrimidin-2-yl]-pyridin-2-yl}-thiophene-2-sulfonic acid amide;

3-{4-[4-(4-Fluoro-phenyl)-6-trifluoromethyl-pyrimidin-2-yl]-pyridin-2-yl}-benzenesulfonamide;

5-{4-[4-(3,4-Difluoro-phenyl)-6-trifluoromethyl-pyrimid in-2-yl]-pyridin-2-yl}-thiophene-2-sulfonic acid amide; and 3-{4-[4-(3,4-Difluoro-phenyl)-6-trifluoromethyl-pyrimidin-2-yl]-pyrid in-2-yl}-benzenesulfonamide.

30. The compound of claim 21, from the group consisting of:

N,N-Dimethyl-3-{4-[4-trifluoromethyl-6-(4-trifluoromethyl-phenyl)-pyrimidin-2-yl]-pyridin-2-yl}-benzenesulfonamide;

N-Methyl-3-{4-[4-trifluoromethyl-6-(4-trifluoromethyl-phenyl)-pyrimidin-2-yl]-pyrid in-2-yl}-benzenesulfonamide;

N-Isobutyl-N-methyl-3-{4-[4-trifluoromethyl-6-(4-trifluoromethyl-phenyl)-pyrimid in-2-yl]-pyridin-2-yl}-benzenesulfonamide;

N-Methyl-N-propyl-3-{4-[4-trifluoromethyl-6-(4-trifluoromethyl-phenyl)-pyrimidin-2-yl]-pyridin-2-yl}-benzenesulfonamide;

N-Benzyl-3-{4-[4-trifluoromethyl-6-(4-trifluoromethyl-phenyl)-pyrimidin-2-yl]-pyrid in-2-yl}-benzenesulfonamide;

N-Phenethyl-3-{4-[4-trifluoromethyl-6-(4-trifluoromethyl-phenyl)-pyrimidin-2-yl]-pyridin-2-yl }-benzenesulfonamide;

N-Cyclopropylmethyl-3-{4-[4-trifluoromethyl-6-(4-trifluoromethyl-phenyl)-pyrimidin-2-yl]-pyridin-2-yl}-benzenesulfonamide;

N-Cyclopropyl-3-{4-[4-trifluoromethyl-6-(4-trifluoromethyl-phenyl)-pyrimidin-2-yl]-pyridin-2-yl}-benzenesulfonamide;

5-{4-[4-(4-Chloro-3-methyl-phenyl)-6-trifluoromethyl-pyrimidin-2-yl]-pyridin-2-yl}-thiophene-2-sulfonic acid amide;

3-{4-[4-(4-Chloro-3-methyl-phenyl)-6-trifluoromethyl-pyrimidin-2-yl]-pyridin-2-yl}-benzenesulfonamide; and N-tert-Butyl-3-{6-[4-methyl-6-(4-trifluoromethyl-phenyl)-pyrimidin-2-yl]-pyridin-2-yl}-benzenesulfonamide.

31. The compound of claim 21, from the group consisting of:

3-{6-[4-Methyl-6-(4-trifluoromethyl-phenyl)-pyrimidin-2-yl]-pyridin-2-yl}-benzenesulfonamide;

N-tert-Butyl-3-{6-[4-(4-cyano-phenyl)-6-methyl-pyrimidin-2-yl]-pyridin-2-yl}-benzenesulfonamide;

3-{6-[4-(4-Cyano-phenyl)-6-methyl-pyrimid in-2-yl]-pyridin-2-yl}-benzenesulfonamide;

3-(4-{4-[3-(2,2,2-Trifluoro-ethoxy)-4-trifluoromethyl-phenyl]-6-trifluoromethyl-pyrimidin-2-yl }-pyridin-2-yl)-benzenesulfonamide;

3-{4-[4-Trifluoromethyl-6-(3-trifluoromethyl-phenyl)-pyrimidin-2-yl]-pyridin-2-yl}-benzenesulfonamide;

3-{4-[4-(2-Fluoro-4-trifluoromethyl-phenyl)-6-trifluoromethyl-pyrimidin-2-yl]-pyridin-2-yl}-benzenesulfonamide;

5-{4-[4-(2-Fluoro-4-trifluoromethyl-phenyl)-6-trifluoromethyl-pyrimidin-2-yl]-pyridin-2-yl}-thiophene-2-sulfonic acid amide;

3-{4-[4-(3-Ethoxy-4-trifluoromethyl-phenyl)-6-trifluoromethyl-pyrimidin-2-yl]-pyridin-2-yl}-benzenesulfonamide;

5-{4-[4-(3-Ethoxy-4-trifluoromethyl-phenyl)-6-trifluoromethyl-pyrimid in-2-yl]-pyrid in-2-yl}-thiophene-2-sulfonic acid amide;

3-{4-[4-Difluoromethyl-6-(4-trifluoromethyl-phenyl)-pyrimidin-2-yl]-pyridin-2-yl}-benzenesulfonamide; and 5-{4-[4-Difluoromethyl-6-(4-trifluoromethyl-phenyl)-pyrimidin-2-yl]-pyridin-2-yl}-thiophene-2-sulfonic acid amide.

32. The compound of claim 9, wherein B is optionally substituted aryl or an optionally substituted 5 or 6 membered heteroaryl wherein the aryl and heteroaryl group are selected from the group consisting of phenyl, pyridyl, pyrimidinyl, thiazolyl, and thiophenyl, wherein the substituent is —($SO_2$)—$NR^fR^g$ wherein $R^f$ and $R^g$ together with the nitrogen atom to which they are attached form a 4, 5 or 6 membered heterocycloalkyl ring optionally containing a further heteroatom selected from nitrogen, oxygen, sulphur and an $SO_2$ group, wherein said 4, 5 or 6 membered heterocycloalkyl ring is optionally substituted by hydroxy or $C_{1-6}$-alkyl.

33. The compound of claim 32, selected from the group consisting of:

4-(3-{4-[4-Trifluoromethyl-6-(4-trifluoromethyl-phenyl)-pyrimidin-2-yl]-pyridin-2-yl}-benzenesulfonyl)-morpholine;

2-{2-[3-(4-Methyl-piperazine-1-sulfonyl)-phenyl]-pyridin-4-yl}-4-trifluoromethyl-6-(4-trifluoromethyl-phenyl) -pyrimidine;

2-{2-[3-(Pyrrolidine-1-sulfonyl)-phenyl]-pyridin-4-yl}-4-trifluoromethyl-6-(4-trifluoromethyl-phenyl) -pyrimidine; and (RS)-1-(3-{4-[4-Trifluoromethyl-6-(4-trifluoromethyl-phenyl)-pyrimidin-2-yl]-pyridin-2-yl}-benzenesulfonyl) -pyrrolidin-3-ol.

34. The pharmaceutical composition comprising a compound of formula (Ia)

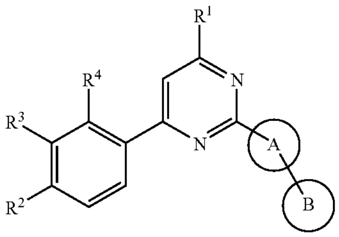

(Ia)

wherein

A is 5 or 6 membered heteroaryl selected from the group consisting of imidazolyl, oxadiazolyl, pyrazolyl, pyridyl, pyrimidinyl, pyrrolyl, and triazolyl each of which is optionally substituted by $C_{1-6}$-alkyl;

B is cyano, or an optionally substituted aryl or an optionally substituted 5 or 6 membered heteroaryl wherein the aryl and heteroaryl group are selected from the group consisting of phenyl, pyridyl, wherein the substituents are selected from the group consisting of:

-halo,

-nitro,

—$C_{1-6}$-alkyl optionally substituted by hydroxy,

—$NR^aR^b$, wherein $R^a$ and $R^b$ are independently H, $C_{1-6}$-alkyl or —(CO)—$C_{1-6}$-alkyl, —S—$C_{1-6}$-alkyl,

—($S_2$)—OH,

—($SO_2$)—$C_{1-6}$-alkyl,

—($SO_2$)—$NR^cR^d$, wherein $R^c$ and $R^d$ are independently:

H, $C_{1-6}$-alkyl optionally substituted by hydroxy, $C_{1-6}$-haloalkyl, or $C_{1-6}$-alkoxy, —(CO)$C_{1-6}$-alkyl optionally substituted by $C_{1-6}$-alkoxy, —$(CH_2CH_2O)_nCHR^e$, wherein $R^e$is H or $CH_2OH$ and n is 1, 2, 3, 4, 5, 6, 7, 8, 9 or 10, $(CH_2)_m$-aryl, wherein m is 1 or 2 and the aryl is optionally substituted by halo or $C_{1-6}$-alkoxy, —$(CH_2)_p$-$C_{3-6}$-cycloalkyl, wherein p is 0 or 1, -5 or 6-membered heterocycloalkyl, —($SO_2$)—$NR^fR^g$, wherein $R^f$ and $R^g$ together with the nitrogen atom to which they are attached form a 4, 5 or 6 membered heterocycloalkyl ring optionally containing a further heteroatom selected from nitrogen, oxygen, sulphur and an $SO_2$ group, wherein said 4, 5 or 6 membered heterocycloalkyl ring is optionally substituted by a substituent selected from the group consisting of hydroxy, $C_{1-6}$-alkyl, $C_{1-6}$-alkoxy optionally substituted by hydroxy, and 5 or 6 membered heteroaryloxy, —$NHSO_2$—$C_{1-6}$-alkyl, and —$NHSO_2NR^hR^i$ wherein $R^h$ and $R^i$ are independently H, $C_{1-6}$-alkyl, —(CO)O—$C_{1-6}$-alkyl, or $R^h$ and $R^i$ together with the nitrogen atom to which they are attached form a 4, 5 or 6 membered heterocycloalkyl ring optionally containing a further heteroatom selected from nitrogen, oxygen and sulphur, wherein said 4, 5 or 6 membered heterocycloalkyl ring is optionally substituted by $C_{1-6}$-alkyl;

$R^1$ is H, halogen, $C_{1-6}$-alkyl optionally substituted by hydroxy, $C_{1-6}$-alkoxy, $C_{1-6}$-haloalkyl, or $C_{3-6}$-cycloalkyl;

$R^2$ is H, cyano, halogen, $C_{1-6}$-haloalkyl, $C_{1-6}$-alkoxy, $C_{1-6}$-haloalkoxy, $C_{1-6}$-alkyl or $C_{3-6}$-cycloalkyl;

$R^3$ is halogen, H, $C_{1-6}$-alkoxy, $C_{1-6}$-haloalkyl, $C_{1-6}$-alkyl, $C_{3-6}$-cycloalkyl, $C_{1-6}$-haloalkoxy, or is $NR^jR^k$ wherein $R^j$ and $R^k$ are independently selected from the group consisting of:

H, C38-cycloalkyl, aryl, heteroaryl having from 5 to 12 ring atoms, and $C_{1-6}$-alkyl each of which is optionally substituted by one or more substituent(s) selected from the group consisting of halogen, hydroxy, $C_{3-8}$-cycloalkyl, aryl, heteroaryl having from 5 to 12 ring atoms, and —$NR^lR^m$, wherein $R^l$ and $R^m$ are independently selected from the group consisting of H and $C_{1-6}$-alkyl;

or $R^j$ and $R^k$ can, together with the nitrogen atom to which they are attached, form an optionally substituted heterocyclic group comprising 5 to 12 ring atoms optionally containing a further heteroatom selected from nitrogen, oxygen and sulphur, wherein said heteroaryl group is optionally substituted by one, two, three, four or five substituents selected from the group consisting of halogen, hydroxy, $C_{1-6}$-alkyl and $C_{1-6}$-haloalkyl;

or $R^2$ and $R^3$ can together form a dioxo bridge;

$R^4$ is H or halo;

or a pharmaceutically acceptable salt thereof and a pharmaceutically acceptable carrier.

35. The compound of claim 1, wherein A is optionally substituted pyridyl.

36. The compound of claim 35, wherein the pyridyl is 2-pyridyl or 4-pyridyl.

37. The compound of claim 1 wherein B is optionally substituted phenyl.

38. The compound of claim 37 wherein B is phenyl substituted by $SO_2NR^cR^d$, wherein $R^c$ and $R^d$ both are H.

39. The compound of claim 1, wherein $R^1$ is $CF_3$ or methyl; $R^2$ is $CF_3$; $R^3$ is H; and $R^4$ is H.

* * * * *